United States Patent
Lou et al.

(10) Patent No.: US 11,154,563 B2
(45) Date of Patent: Oct. 26, 2021

(54) IMMUNOPROTEASOME INHIBITORS

(71) Applicant: Principia Biopharma Inc., South San Francisco, CA (US)

(72) Inventors: Yan Lou, Pleasanton, CA (US); Timothy Duncan Owens, Redwood City, CA (US); Kenneth Albert Brameld, Menlo Park, CA (US); David Michael Goldstein, Redwood City, CA (US)

(73) Assignee: Principia Biopharma Inc., South San Francisco, CA (US)

( * ) Notice: Subject to any disclaimer, the term of this patent is extended or adjusted under 35 U.S.C. 154(b) by 0 days.

(21) Appl. No.: 16/478,788

(22) PCT Filed: Jan. 16, 2018

(86) PCT No.: PCT/US2018/013823
§ 371 (c)(1),
(2) Date: Jul. 17, 2019

(87) PCT Pub. No.: WO2018/136401
PCT Pub. Date: Jul. 26, 2018

(65) Prior Publication Data
US 2019/0336515 A1    Nov. 7, 2019

Related U.S. Application Data

(60) Provisional application No. 62/508,771, filed on May 19, 2017, provisional application No. 62/447,717, filed on Jan. 18, 2017.

(51) Int. Cl.
*A61K 31/69* (2006.01)
*A61K 47/00* (2006.01)

(52) U.S. Cl.
CPC .............. *A61K 31/69* (2013.01); *A61K 47/00* (2013.01)

(58) Field of Classification Search
CPC ................................ A61K 31/69; A61K 47/00
USPC .......................................................... 514/64
See application file for complete search history.

(56) References Cited

FOREIGN PATENT DOCUMENTS

| WO | 9509634 A1 | 4/1995 |
|----|---|---|
| WO | WO 2005/021558 | 3/2005 |
| WO | WO 2016/050358 | 4/2016 |
| WO | 2019099576 A1 | 5/2019 |
| WO | 2019099582 A1 | 5/2019 |

OTHER PUBLICATIONS

International Search Report and Written Opinion dated Jun. 26, 2018 for PCT Application No. PCT/US2018/013823, filed Jan. 16, 2018.
Communication dated May 6, 2020 for EP Application No. 18716009.8, Filed Jan. 16, 2018.
International Preliminary Report on Patentability dated Aug. 1, 2019 for PCT Application No. PCT/US2018/013823, filed Jan. 16, 2018.
Examination Report dated Jun. 14, 2019 for PK Application No. 0036/2018, filed Jan. 16, 2018.
International Preliminary Report on Patentability dated May 19, 2020 and Written Opinion dated Feb. 14, 2019 tor PCT Application No. PCT/US2018/061132 filed Nov. 14, 2018.
International Preliminary Report on Patentability dated May 19, 2020 and Written Opinion dated Jan. 25, 2019 for PCT Application No. PCT/US2018/061140 filed Nov. 14, 2018.
International Search Report for PCT Application No. PCT/US2018/061132 filed Nov. 14, 2018, dated Feb. 14, 2019.
International Search Report for PCT Application No. PCT/US2018/061140 filed Nov. 14, 2018, dated Jan. 25, 2019.
Pending U.S. Appl. No. 16/764,136, filed May 14, 2020 (not enclosed).
Pending U.S. Appl. No. 16/764,199, filed May 14, 2020 (not enclosed).

*Primary Examiner* — Kahsay Habte
(74) *Attorney, Agent, or Firm* — McNeill Baur PLLC

(57) ABSTRACT

Provided herein are compounds, such as a compound of Formula (I), as described herein, or a pharmaceutically acceptable salt thereof, that are immunoproteasome (such as LMP2 and LMP7) inhibitors. The compounds described herein can be useful for the treatment of diseases treatable by inhibition of immunoproteasomes. Also provided herein are pharmaceutical compositions containing such compounds and processes for preparing such compounds.

28 Claims, No Drawings

IMMUNOPROTEASOME INHIBITORS

RELATED APPLICATIONS

This application is a 371 U.S. National Phase of PCT International Application PCT/US2018/13823, filed on Jan. 16, 2018, which claims the benefit of U.S. Provisional Application Ser. No. 62/447,717 filed on Jan. 18, 2017, and U.S. Provisional Application Ser. No. 62/508,771 filed on May 19, 2017, each of which is incorporated by reference herein in its entirety.

BACKGROUND OF THE DISCLOSURE

In eukaryotes, protein degradation is mediated through the ubiquitin pathway in which proteins targeted for destruction are ligated to the 76 amino acid polypeptide ubiquitin. Ubiquitinated proteins then serve as substrates for the 26S proteasome, a multicatalytic protease, which cleaves proteins into short peptides through the action of its three major proteolytic activities. Proteasome-mediated degradation plays a key role in many processes such as antigen presentation in the context of the major histocompatibility complex (MHC) class I, apoptosis and cell viability, antigen processing, NF-KB activation, and transduction of pro-inflammatory signals.

The 20S proteasome is a 700 kDa cylinder-shaped multicatalytic protease complex comprised of 28 subunits, classified as alpha- and beta-type, that are arranged in 4 stacked heptameric rings. In yeast and other eukariotes, 7 different subunits form the outer rings and 7 different subunits comprise the inner rings. The alpha subunits serve as binding sites for the 19S and 11S regulatory complexes, as well as a physical barrier for the inner proteolytic chamber formed by the two subunit rings. Thus, in vivo, the proteasome is believed to exist as a 26S particle. In vivo experiments have shown that inhibition of the 20S form of the proteasome can be readily correlated to inhibition of the 26S proteasome.

In addition to the constitutive proteasome, which is ubiquitously expressed, there is an alternative complex, the immunoproteasomrne, which can be found in immune cells and/or in cells exposed to inflammatory cytokines, such as IFN-γ and TNF-α. The immunoproteasome differs from the constitutive proteasome in its subunit composition. It contains subunits with chymotrypsin-like (β5i/LMP7), caspase-like (β1i/LMP2) and trypsin-like (β2i) protease activity that replace their counterparts in the constitutive proteasome (β5c, β1c, and β2c respectively). When all three IFN-γ-inducible subunits are present, the proteasome is referred to as the "immunoproteasome." Thus, eukaryotic cells can possess two forms of proteasomes in varying ratios. The immunoproteasome plays an essential role in the generation of antigenic peptide repertoire and shaping MHC class I restricted CD8+ T cell response (see Basler et al. Immnunoproteasomes down-regulate presentation of a subdominant T cell epitope from lymphocytic choriomeningitis virus. *J. Immunol* 173:3925-3934 (2004); Moebius, J., M. et al. 2010. Immunoproteasomes are essential for survival and expansion of T cells in virus-infected mice. Eur J Immunol 40:3439-3449).

The immunoproteasome function is not only limited to MHC class I presentation, but it is also involved in a number of pathological disorders including hematological malignancies, inflammatory and autoimmune diseases. The commercially available proteasome inhibitors Bortezomib and Carfilzomib, which have been validated in multiple myeloma and other diseases, appear to target both the constitutive and immunoproteasomes indiscriminately. This lack of specificity may, in part, explain some of the side effects of these agents. It may, however, be possible to keep the therapeutic efficacies (such as antilymphoma and antimyeloma efficacies) of these immunoproteasomes unchanged, and at the same time, increase the therapeutic index, by selectively targeting the immunoproteasome. Therefore, inhibitors which selectively inhibit the immunoproteasome are of interest.

LMP7/β5i is an essential subunit of the immunoproteasome. It regulates inflammatory cytokine production and immune cell functions beyond its role in the generation of MHC class I-restricted epitopes. A small molecule LMP7 inhibitor, PR-957, has been shown to potently block both human and mouse Th1/17 differentiation (see Muchamuel, T., et al. 2009. A selective inhibitor of the immunoproteasome subunit LMP7 blocks cytokine production and attenuates progression of experimental arthritis. Nat Med 15:781-787; Kalim, K. W., et al. 2012. Immunoproteasome Subunit LMP7 Deficiency and Inhibition Suppresses Th1 and Th17 but Enhances Regulatory T Cell Differentiation. J. Immunol. 189:4182-4293), and B cell effector functions and production of proinflammatory cytokines (IL-6, TNF-αu, IL-23) (see Basler, M., et al. 2010. Prevention of experimental colitis by a selective inhibitor of the immunoproteasome. J Immunol 185:634-641). In addition, LMP7 inhibition with PR-957 has been demonstrated to produce therapeutic benefits in several preclinical autoimmune disease models. For example, PR-957 was shown to significantly inhibit disease activity in murine collagen-induced arthritis, including significant reduction of inflammation and bone erosion (see Muchamuel, T., et al. 2009. A selective inhibitor of the immunoproteasome subunit LMP7 blocks cytokine production and attenuates progression of experimental arthritis. Nat Med 15:781-787). PR-957 also reduced plasma cell numbers and anti-dsDNA IgG levels in the MRL/lpr lupus model, and prevented disease progression. (see Ichikawa, H. T., et al. 2012. Beneficial effect of novel proteasome inhibitors in murine lupus via dual inhibition of type I interferon and autoantibody-secreting cells. Arthritis Rheum 64:493-503). In addition, PR-957 reduced inflammation and tissue destruction in a murine DSS-induced colitis model (see Basler, M., et al. 2010. Prevention of experimental colitis by a selective inhibitor of the immunoproteasome. J Immunol 185:634-641). Also, PR-957 has been shown to be efficacious in an autoantibody-driven Hashimoto's thyroiditis model (see Nagayama, Y., et al. 2012. Prophylactic and therapeutic efficacies of a selective inhibitor of the immunoproteasome for Hashimoto's thyroiditis, but not for Graves' hyperthyroidism, in mice. Clin Exp Immunol. 168: 268-273). In addition, LMP7 knockout mice are protected from disease in IBD models (see Basler, M., et al. 2010. Prevention of experimental colitis by a selective inhibitor of the immunoproteasome. J. Immunol. 185:634-641; Kalim, K. W., et al. 2012. Immunoproteasome Subunit LMP7 Deficiency and Inhibition Suppresses Th1 and Th17 but Enhances Regulatory T Cell Differentiation. J Immunol. 189:4182-4293; Schmidt, N., et al. 2010. Targeting the proteasome: partial inhibition of the proteasome by bortezomib or deletion of the immunosubunit LMP7 attenuates experimental colitis. Gut 59:896-906). Additionally, inhibition of LMP7 with the selective inhibitor PR-924 has been shown to inhibit growth of multiple myeloma cell lines and primary patient tumor cells, including those resistant to conventional and novel prior therapies (see Singh, A. V., et al. 2011. PR-924, a Selective Inhibitor of the Immunoproteasome Subunit LMP-7, Blocks Multiple Myeloma Cell Growth both in Vitro and in Vivo. Br J Haematol. 2011 January; 152(2): 155-163).

An additional immunoproteasome subunit LMP2/β1i has been shown to regulate antiviral and innate immune responses in addition to its contribution to antigen processing (see Hensley, S. E., et al. 2010. Unexpected role for the immunoproteasome subunit LMP2 in antiviral humoral and innate immune responses. J. Immunol 184:4115-4122). A small molecule inhibitor, ISPI-001, which preferentially targets LMP2/β1i, inhibited in vitro proliferation of peripheral blood mononuclear cells (PBMC) isolated from myeloma patients (see Kuhn, D. J., et al. 2009. Targeted inhibition of the immunoproteasome is a potent strategy against models of multiple myeloma that overcomes resistance to conventional drugs and nonspecific immunoproteasome inhibitors. Blood 113:4667-4676). An additional small molecule inhibitor, UK-101, which selectively targets LMP2/β1i, induced apoptosis of an prostate PC-3 cell line in vitro and significantly suppressed tumor growth in vivo (Wehenkel, M., et al. 2012. A selective inhibitor of the immunoproteasome subunit LMP2 induced apoptosis in PC-3 cells and suppresses tumor growth in nude mice. Br J Cancer 107:53-62).

WO 2016/050358 A1 discloses inhibitors of LMP7, which are boronic acid derivatives, that can be used for the treatment of autoimmune disorder or hematological malignancies.

WO 2015/195950 A1 discloses inhibitors of LMP7, and methods of treating various diseases using these inhibitors.

SUMMARY OF THE DISCLOSURE

Some embodiments provided herein are directed to a compound of Formula (I):

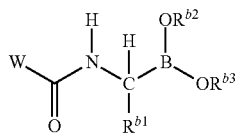

(I)

and/or a pharmaceutically acceptable salt thereof, wherein:
W can be —O—P-Q-C($R^{8b}$)=C($R^{8b}$)($R^{8c}$) or a group of formula

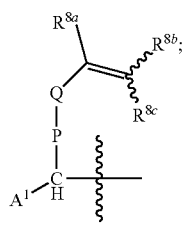

$A^1$ can be hydrogen, hydroxy, optionally substituted alkyl, optionally substituted aryl, optionally substituted heteroaryl, optionally substituted heterocyclyl, or —S(=O)$_2$-alkyl, wherein said alkyl of said —S(=O)$_2$-alkyl is optionally substituted;
P can be -alkyl-N(R)—, -alkyl-($C_3$-$C_6$)cycloalkyl-N(R)—, -alkyl-O-alkyl-N(R)—,

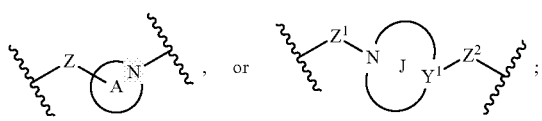

Z and Z' can independently be a covalent bond, -alkyl-, -alkyl-O—, -alkyl-N(R)—, or -alkyl-O-alkyl-, with the proviso that Z is connected to ring A at a carbon atom adjacent to the ring nitrogen atom;
ring A with the ring nitrogen atom shown can be an optionally saturated mono- or multicyclic 4 to 10 membered heterocyclyl;
ring J with the ring nitrogen atom and ring $Y^1$ atom shown can be a saturated 4 to 10 membered heterocyclyl;
Y can be C or N;
$Z^2$ can be a covalent bond or N(R), with the proviso that when $Y^1$ in ring J is nitrogen, then $Z^2$ is a covalent bond;
each R can be independently hydrogen or alkyl;
Q can be —C(=O)— or —S(=O)$_2$—;
$R^{8a}$ can be hydrogen, halogen, or cyano;
$R^{8b}$ can be hydrogen, optionally substituted alkyl, optionally substituted cycloalkyl, optionally substituted heteroaryl, or optionally substituted heterocyclyl; or
$R^{8a}$ and $R^{8b}$ can be taken together to form a bond; and
$R^{8c}$ can be hydrogen or optionally substituted alkyl;
$R^{b1}$ can be optionally substituted alkyl, optionally substituted aryl, optionally substituted heteroaryl, optionally substituted cycloalkyl, or optionally substituted heterocyclyl; and
$R^{b2}$ and $R^{b3}$ can independently be hydrogen or optionally substituted alkyl; or
$R^{b2}$ and $R^{b3}$ together with the boron atom to which they are shown attached can form a cyclic boronic ester.

Some embodiments described herein also provides a pharmaceutical composition comprising a compound of Formula (1) (or any of the embodiments thereof described herein), and/or a pharmaceutically acceptable salt thereof; and a pharmaceutically acceptable excipient.

Some embodiments described herein also provides a method of treating a disease (such as an autoimmune disease, an inflammatory disease, and/or a hematological disorder), treatable by inhibition of LMP2 and/or LMP7 in a patient which method comprises administering to the patient in need thereof, a therapeutically effective amount of a compound of Formula (I) (or any of the embodiments thereof described herein) and/or a pharmaceutically acceptable salt thereof.

DETAILED DESCRIPTION OF THE DISCLOSURE

Definitions

Unless otherwise stated, the following terms used in the specification and claims are defined for the purposes of this Application and have the following meaning. All undefined technical and scientific terms used in this Application have the meaning as commonly understood by one of ordinary skill in the art to which this disclosure belongs.

As used herein, "a" or "an" entity refers to one or more of that entity; for example, a compound refers to one or more compounds or at least one compound unless stated otherwise. As such, the terms "a" (or "an"), "one or more", and "at least one" can be used interchangeably herein.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 5%.

"Patient" includes both human and animals. "Patient" and "subject" are used interchangeably herein.

"Mammal" means humans and other mammalian animals.

"P" in Formula (I) is read left to right, wherein the right side of "P" is attached to "Q".

"Z" and "$Z^1$" in Formula (I) are read left to right, wherein the right side of "Z" is attached to "ring A" and wherein the right side of "$Z^1$" is attached to "ring J".

"Alkyl" means an aliphatic hydrocarbon group which may be straight or branched and comprising 1 to 20 carbon atoms in the chain. Preferred alkyl groups contain 1 to 12 carbon atoms in the chain. More preferred alkyl groups contain 1 to 6 carbon atoms in the chain. Branched means that one or more lower alkyl groups, such as methyl, ethyl or propyl, are attached to a linear alkyl chain. "Lower alkyl" means a group having 1 to 6 carbon atoms in the chain which may be straight or branched. "Optionally substituted alkyl" means an alkyl group that can be optionally substituted by one or more (e.g., one, two, or three) substituents which may be the same or different, each substituent being independently chosen from halo, optionally substituted aryl, optionally substituted heterocyclyl, optionally substituted heterocyclenyl, optionally substituted heteroaryl, optionally substituted cycloalkyl, optionally substituted cycloalkenyl, cyano, hydroxy, alkoxy, aryloxy, —O-alkyl-O-alkyl, heteroaryloxy, cycloalkyloxy, acyl, carboxy, —SH, alkylthio, amino, oxime (e.g., =N—OH), —NH(alkyl), —NH(haloalkyl), —NH(alkyl-O-alkyl), —NH(aryl), —N(alkyl)(aryl), —NH(heteroaryl), —N(alkyl)(heteroaryl), —N(alkyl)(heterocyclyl), NH(cycloalkyl), —N(alkyl)(haloalkyl), —N(alkyl)(cycloalkyl), —N(cycloalkyl)(heterocyclyl), —N(alkyl)$_2$, NH—C(=O)-alkyl, —N(alkyl)-C(=O)-alkyl, —NH—C(=O)-aryl, —N(alkyl)-C(=O)-aryl, —NH—C(=O)-cycloalkyl, —N(alkyl)-C(=O)-cycloalkyl, —O—C(O)-alkyl, —O—C(O)-aryl, —O—C(O)-cycloalkyl, —SF, carboxy and —C(O)O— alkyl. Non-limiting examples of suitable alkyl groups include methyl, ethyl, n-propyl, iso-propyl, n-butyl, iso-butyl, and t-butyl.

"Alkenyl" means an aliphatic hydrocarbon group containing at least one carbon-carbon double bond and which may be straight or branched and comprising 2 to 15 carbon atoms in the chain. Preferred alkenyl groups have 2 to 12 carbon atoms in the chain; and more preferably 2 to 6 carbon atoms in the chain. Branched means that one or more lower alkyl groups, such as methyl, ethyl or propyl, are attached to a linear alkenyl chain. "Lower alkenyl" means 2 to 6 carbon atoms in the chain which may be straight or branched. "Optionally substituted alkenyl" means an alkenyl group that can be optionally substituted by one or more (e.g., one, two or three) substituents which may be the same or different, each substituent being independently chosen from halo, optionally substituted aryl, optionally substituted cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond, which may be straight or branched, and comprising 2 to 15 carbon atoms in the chain. Preferred alkynyl groups have 2 to 12 carbon atoms in the chain; and more preferably 2 to 4 carbon atoms in the chain. Branched means that one or more lower alkyl groups, such as methyl, ethyl or propyl, are attached to a linear alkynyl chain. "Lower alkynyl" means 2 to 6 carbon atoms in the chain which may be straight or branched. "Optionally substituted alkynyl" means an alkynyl group which can be optionally substituted by one or more (e.g., one or two) substituents which may be the same or different, each substituent being independently chosen from aryl and cycloalkyl. Non-limiting examples of suitable alkynyl groups include ethynyl, propynyl, 2-butynyl and 3-methylbutynyl.

",Aryl" means an aromatic monocyclic or multicyclic (e.g., bicyclic, tricyclic) ring system comprising 6 to 14 carbon atoms, preferably 6 to 10 carbon atoms. "Optionally substituted aryl" means an aryl group which can be optionally substituted with one or more (e.g., one, two, three, or four) "ring system substituents" which may be the same or different, and are as defined herein. Non-limiting examples of suitable aryl groups include phenyl and naphthyl.

"Heteroaryl" means an aromatic monocyclic or multicyclic (e.g., bicyclic, tricyclic) ring system comprising 5 to 14 ring atoms, preferably 5 to 10 ring atoms, in which one or more of the ring atoms is an element other than carbon, for example, nitrogen, oxygen or sulfur, alone or in combination. Preferred heteroaryls contain 5 to 6 ring atoms. "Optionally substituted heteroaryl" means a heteroaryl group which can be optionally substituted by one or more (e.g., one, two, three, or four) "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. "Heteroaryl" also includes a heteroaryl ring as described above wherein an oxo (=O) group is also part of the ring, provided the ring is aromatic. For example, tautomers of heteroaryl rings (such as 2-pyridone, which is the tautomer of pyridin-2-ol):

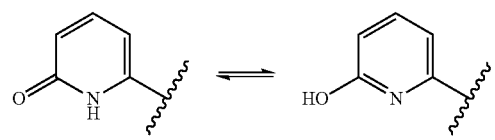 [SMILES: *c1cccc(=O)[nH]1 ; *c1cccc(O)n1]

are also considered heteroaryl groups.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Cycloalkyl" means a non-aromatic mono- or multicyclic (e.g., bicyclic, tricyclic) ring system comprising 3 to 10 carbon atoms, preferably 5 to 10 carbon atoms. Preferred cycloalkyl rings contain t 5 to 7 ring atoms. "Optionally substituted cycloalkyl" means a cycloalkyl group which can be optionally substituted with one or more (e.g., one, two, three, or four) "ring system substituents" which may be the same or different, and are as defined herein. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkenyl" means a non-aromatic mono or multicyclic (e.g., bicyclic, tricyclic) ring system comprising 3 to 10 carbon atoms, preferably 5 to 10 carbon atoms which contains at least one carbon-carbon double bond. Preferred cycloalkenyl rings contain 5 to 7 ring atoms. "Optionally substituted cycloalkenyl" means a cycloalkenyl group which can be optionally substituted with one or more (e.g., one, two, three, or four) "ring system substituents" which may be the same or different, and are as defined herein. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Halogen" or "Halo" means fluorine, chlorine, bromine, or iodine. Preferred are fluorine, chlorine and bromine.

"Haloalkyl" means alkyl radical as defined above, which is substituted with one or more halogen atoms, preferably one to five halogen atoms, preferably fluorine or chlorine, including those substituted with different halogens, e.g., —$CH_2Cl$, —$CF_3$, —$CHF_2$, —$CH_2CF_3$, —$CF_2CF_3$, —$CF(CH_3)_2$, and the like. When the alkyl is substituted with only fluoro, it can be referred to in this Application as fluoroalkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Cycloalkyloxy" means a cycloalkyl-O— group in which the cycloalkyl group is as previously described. Non-limiting examples of suitable cycloalkyloxy groups include cyclopentyloxy and cyclohexyloxy. The bond to the parent moiety is through the ether oxygen.

"Heteroaryloxy" means a heteroaryl-O— group in which the heteroaryl group is as previously described. Non-limiting examples of suitable heteroaryloxy groups include pyridyloxy and thiophenyloxy. The bond to the parent moiety is through the ether oxygen.

"Heterocyclyloxy" means a heterocyclyl-O— group in which the heterocyclyl group is as described herein. Non-limiting examples of suitable heterocyclyloxy groups include piperazinyloxy and morpholinyloxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-$S(O_2)$— group. Preferred groups are those in which the alkyl group is lower alkyl. The bond to the parent moiety is through the sulfonyl.

"Arylsulfonyl" means an aryl-$S(O_2)$— group. The bond to the parent moiety is through the sulfonyl.

"Cyclic boronic ester" (also known as "cyclic boronate ester") as disclosed herein can be formed, for example, by reaction between a boronic acid and an alcohol. The cyclic boronic ester can have between 2 and 20 carbon atoms, preferably between 2 and 10 carbon atoms. The boronic ester optionally can contains one or two additional cyclic heteroatoms chosen from N, O and S.

"Ring system substituent" means a substituent attached to an aromatic or non-aromatic ring system (for example, cycloalkyl, cycloalkenyl, aryl, heteroaryl, heterocyclyl, heterocyclenyl) which, for example, replaces an available hydrogen on the ring system. Ring system substituents may be the same or different, each being independently chosen from alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, alkoxyalkyl, aryloxy, aralkoxy, acyl, aroyl, halo, haloalkyl, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —SH, —$SF_5$, —$OSF_5$ (for aryl), —O— alkyl-O-alkyl, —O—C(O)-alkyl, —O—C(O)-aryl, —O—C(O)-cycloakyl, —C(=N—CN)—$NH_2$, —C(=NH)—$NH_2$, —C(=NH)—NH(alkyl), oxime (e.g., =N—OH), —$NY_1Y_2$, -alkyl-N$Y_2$, —C(O)$NY_1Y_2$, —$SO_2NY_1Y_2$ and —$SO_2NY_1Y_2$, wherein $Y_1$ and $Y_2$ can be the same or different and are independently chosen from hydrogen, alkyl, -alkyl-O-alkyl, aryl, cycloalkyl, heterocyclyl, and aralkyl. "Ring system substituent" may also mean a single moiety which simultaneously replaces two available hydrogens on two adjacent carbon atoms (one H on each carbon, and form a fused ring) or replaces two available hydrogens on a single carbon atom (i.e., a spiro ring) on a ring system. Examples of the former, i.e., a moiety replacing two hydrogens on adjacent carbon atoms are methylenedioxy, ethylenedioxy, —C(CH$_3$)$_2$— and the like which form moieties such as, for example:

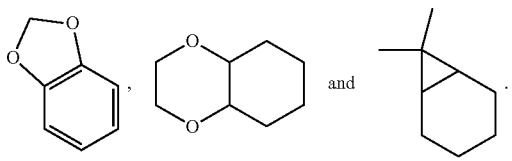

An example of the latter, i.e., a moiety replacing two hydrogens on a single carbon atom (i.e., spiro ring) is

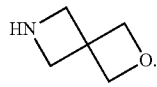

"Heterocyclyl" means a non-aromatic saturated monocyclic or multicyclic (e.g., bicyclic, tricyclic) ring system comprising 3 to 10 ring atoms, preferably 4 to 7 ring atoms, or 5 to 10 ring atoms, in which one or more of the atoms in the ring system is an element other than carbon, for example, nitrogen, oxygen or sulfur, alone or in combination. There are no adjacent oxygen and/or sulfur atoms present in the ring system. Preferred heterocyclyls contain 4 to 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; and are part of the heterocyclyl. "Optionally substituted heterocyclyl" means a heterocyclyl group which can be optionally substituted by one or more (e.g., one, two, three, or four) "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidinyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes heterocyclyl rings as described above wherein =O replaces two available hydrogens on the same ring carbon atom.

"Heterocyclenyl" means a non-aromatic monocyclic or multicyclic (e.g., bicyclic, tricyclic) ring system comprising 3 to 10 ring atoms, preferably 5 to 10 ring atoms, in which one or more of the atoms in the ring system is an element other than carbon, for example, nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain 5 to 6 ring atoms. The prefix aza, oxa or thia before the heterocyclenyl root name means that at least a nitrogen, oxygen or sulfur respectively is present as a ring atom. "Optionally substituted heterocyclenyl" means a hetero-cyclenyl group which can be optionally substituted by one or more (e.g., one, two, three, or four) ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes heterocyclenyl rings as described above wherein =O replaces two available hydrogens on the same ring carbon atom.

It should be noted that in hetero-atom containing ring systems described herein, there are no hydroxyl groups on carbon atoms adjacent to a N, O or S, as well as there are no N or S groups on carbon adjacent to another heteroatom. Thus, for example, in the ring:

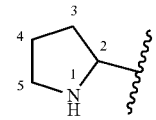

there is no —OH attached directly to carbons marked 2 and 5.

It should also be noted that tautomeric forms such as, for example, the moieties:

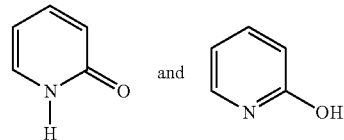 [SMILES: O=c1cccc[nH]1 ; Oc1ccccn1]

are considered equivalent unless otherwise specified.

As used herein, the structure

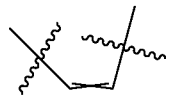 [SMILES: *C=C*]

indicates that the configuration of groups on the double bond can be either E or Z. Thus, for example,

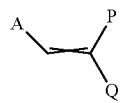

has the same meaning as

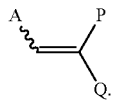

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution (i.e., unsubstituted or substituted) with the specified groups, radicals or moieties. When a list of optional substituents is not explicitly provided, the optional substituents provided in the definitions of various terms (such as "alkyl", "cycloalkyl", "heterocyclyl", "aryl", and "heteroaryl") are to be used.

Unless otherwise specified, reference to an Embodiment number refers to all the subparts of the Embodiment. Thus for example, reference to "Embodiment 12", refers to Embodiment 12, as well as Embodiments 12A-12B. However, this construction does not apply to a subpart within an Embodiment.

As used herein, the term "composition" is intended to encompass a product comprising the specified ingredients in the specified amounts, as well as any product which results, directly or indirectly, from combination of the specified ingredients in the specified amounts.

"Effective amount" or "therapeutically effective amount" is meant to describe an amount of compound or a composition described herein that is effective in inhibiting the above-noted diseases and thus producing the desired therapeutic, ameliorative, inhibitory and/or preventative effect.

EMBODIMENTS

Examples of embodiments of the present application include the following:

Embodiment 1

A compound of Formula (I):

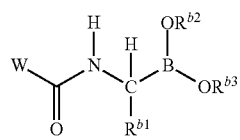

(I)

and/or a pharmaceutically acceptable salt thereof, wherein:

W is —O—P-Q-C($R^{8a}$)=C($R^{8b}$)($R^{8c}$) or a group of formula

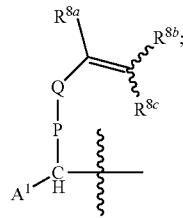

$A^1$ is hydrogen, hydroxy, optionally substituted alkyl, optionally substituted aryl, optionally substituted heteroaryl, optionally substituted heterocyclyl, or —S(=O)$_2$-alkyl, wherein said alkyl of said —S(=O)$_2$-alkyl is optionally substituted;

P is -alkyl-N(R)—, -alkyl-($C_3$-$C_6$)cycloalkyl-N(R)—, -alkyl-O-alkyl-N(R)—,

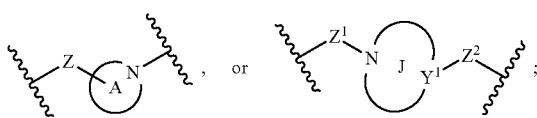

Z and $Z^1$ are independently a covalent bond, -alkyl-, -alkyl-O—, -alkyl-N(R)—, or -alkyl-O-alkyl-, with the proviso that Z is connected to ring A at a carbon atom adjacent to the ring nitrogen atom;

ring A with the ring nitrogen atom shown is an optionally substituted saturated mono- or multicyclic 4 to 10 membered heterocyclyl;

ring J with the ring nitrogen atom and ring $Y^1$ atom shown is a saturated 4 to 10 membered heterocyclyl;

$Y^1$ is C or N;

$Z^2$ is a covalent bond or N(R), with the proviso that when $Y^1$ in ring J is nitrogen, then $Z^2$ is a covalent bond each R is independently hydrogen or alkyl;

Q is —C(=O)— or —S(=O)$_2$—;

$R^{8a}$ is hydrogen, halogen, or cyano;

$R^{8b}$ is hydrogen, optionally substituted alkyl, optionally substituted cycloalkyl, optionally substituted heteroaryl, or optionally substituted heterocyclyl; or $R^{8a}$ and $R^{8b}$ are taken together to form a bond; and $R^{8c}$ is hydrogen or optionally substituted alkyl;

$R^{b1}$ is optionally substituted alkyl, optionally substituted aryl, optionally substituted heteroaryl, optionally substituted cycloalkyl, or optionally substituted heterocyclyl; and $R^{b2}$ and $R^{b3}$ are independently hydrogen or optionally substituted alkyl; or $R^{b2}$ and $R^{b3}$ together with the boron atom to which they are shown attached form a cyclic boronic ester.

Embodiment 1A

The compound and/or a pharmaceutically acceptable salt thereof of embodiment 1, wherein:

W is —O—P-Q-C($R^{8a}$)=C($R^{8b}$)($R^{8c}$) or a group of formula

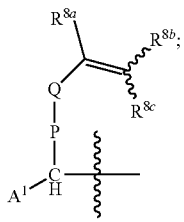

$A^1$ is hydrogen;
P is

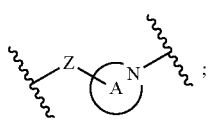

Z is -alkyl- or -alkyl-O-alkyl-, with the proviso that Z is connected to ring A at a carbon atom adjacent to the ring nitrogen atom;

ring A with the ring nitrogen atom shown is an optionally substituted saturated mono- or multicyclic 4 to 10 membered heterocyclyl;

Q is —C(=O)—;

$R^{8a}$ is hydrogen, halogen, or cyano;

$R^{8b}$ is hydrogen; alkyl which is optionally substituted with 1-2 substituents chosen from a —N(alkyl)(haloalkyl), —N(alkyl)$_2$, and heterocyclyl, wherein the heterocyclyl is optionally substituted with 1-3 substituents chosen from halo, alkyl, and —C(=O)-alkyl; and heterocyclyl, which is optionally substituted with 1-2 substituents chosen from halo, alkyl, alkoxy, haloalkyl, cyano, and —S(=O)$_2$-alkyl; or $R^{8a}$ and $R^{8b}$ are taken together to form a bond; and $R^{8c}$ is hydrogen or alkyl;

$R^{b1}$ is alkyl which is optionally substituted with 1-2 substituents chosen from aryl and heteroaryl, each of which is optionally substituted with 1-3 substituents independently chosen from halo, alkyl, alkoxy, haloalkyl, cyano, and —S(=O))$_2$-alkyl; and $R^{b2}$ and $R^{b3}$ are each hydrogen.

Embodiment 2

The compound and/or a pharmaceutically acceptable salt thereof of embodiment 1, wherein W is

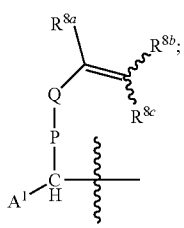

i.e., the compound of Formula (I) is a compound of Formula (Ia)

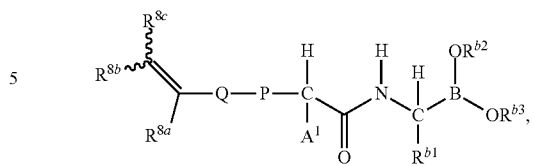

wherein the variables $A^1$, $R^{b1}$, $R^{b2}$, $R^{b3}$, $R^{8a}$, $R^{8b}$, $R^{8c}$, P, and Q are as defined in Formula (I).

Embodiment 2A

The compound and/or a pharmaceutically acceptable salt thereof of Embodiment 2, wherein $A^1$ is H.

Embodiment 3

The compound and/or a pharmaceutically acceptable salt thereof of Embodiment 1, wherein W is —O—P-Q-C($R^a$)=C($R^{8b}$)($R^{8c}$) i.e., the compound of Formula (I) is a compound of Formula (Ib)

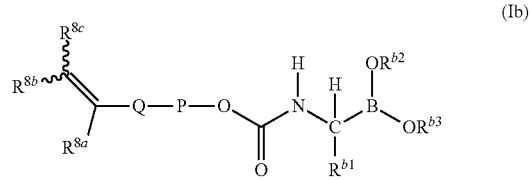

wherein the variables $R^{b1}$, $R^{b2}$, $R^{b3}$, $R^{8a}$, $R^{8b}$, $R^{8c}$, P, and Q are as defined in Formula (I).

Embodiment 4

The compound and/or a pharmaceutically acceptable salt thereof of any of Embodiments 1-3, wherein:
said -alkyl-N(R)— of P is:

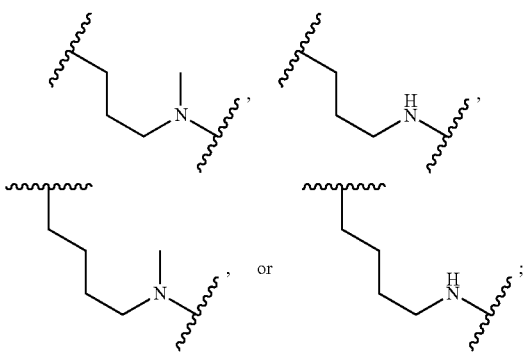

said -alkyl-O-alkyl-N(R)— of P is:

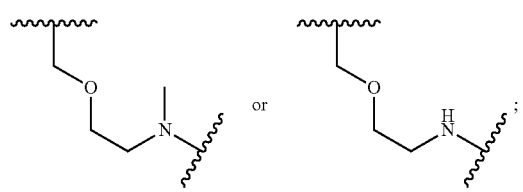

said of P is:
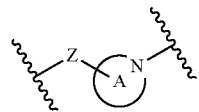
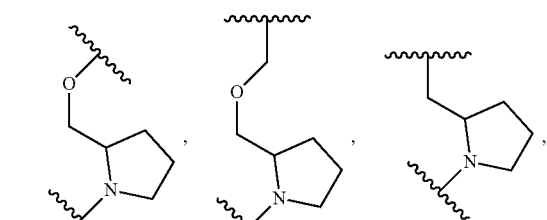
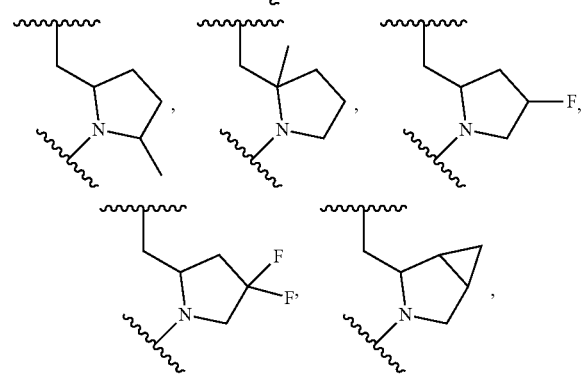
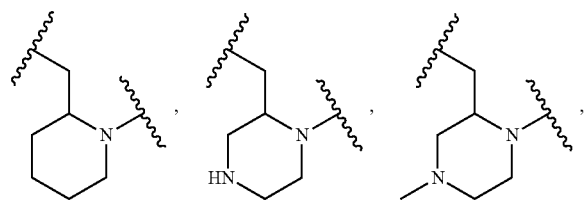
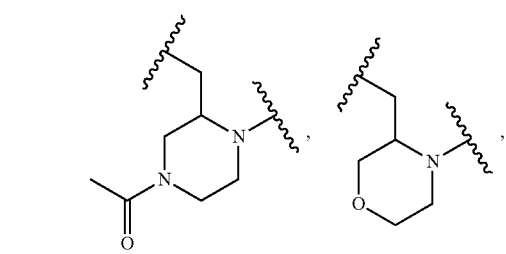
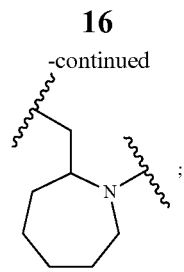
-continued
and said
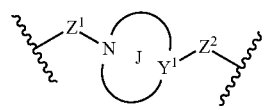
of P is:
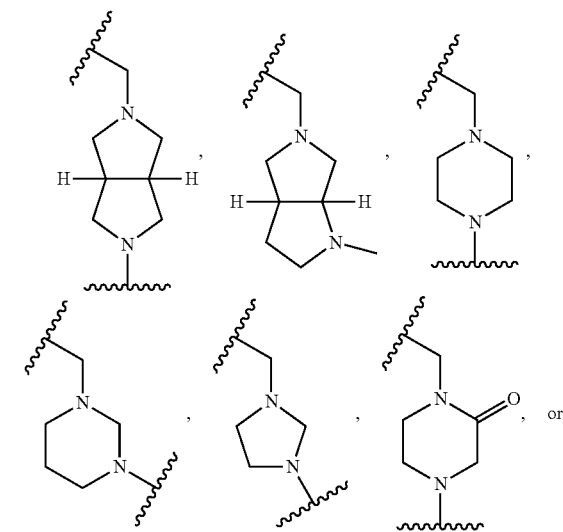
Embodiment 5
The compound and/or a pharmaceutically acceptable salt thereof of Embodiments 1-4, wherein P is
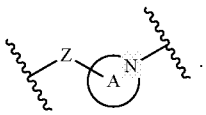

Embodiment 6

The compound and/or a pharmaceutically acceptable salt thereof of Embodiment 5, wherein ring A of P with the ring nitrogen atom shown is:

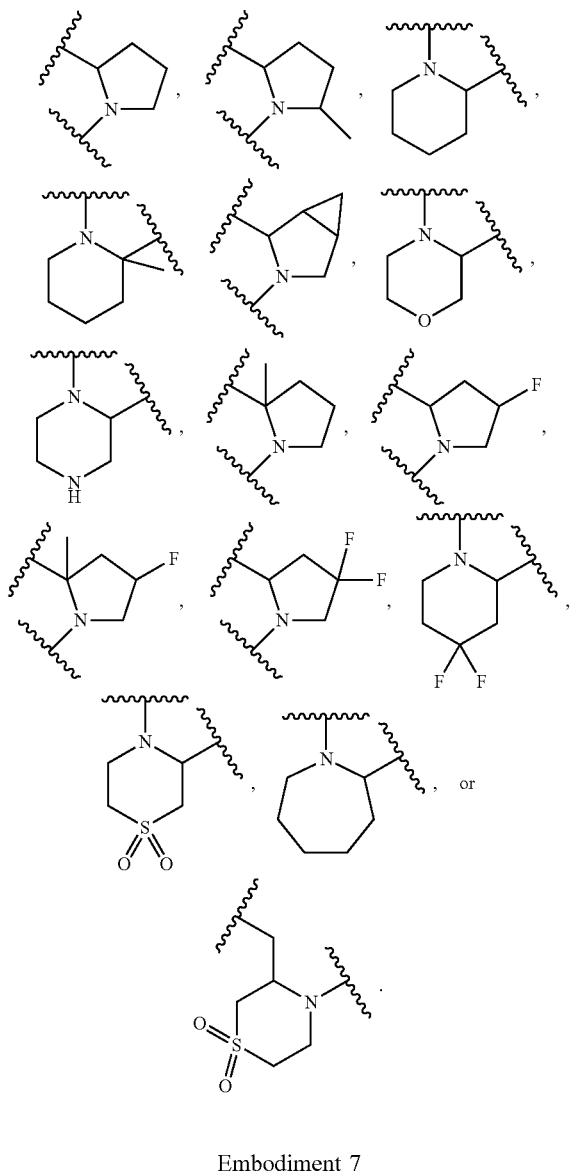

Embodiment 7

The compound and/or a pharmaceutically acceptable salt thereof of Embodiment 1-2, wherein Z of

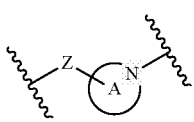

of P is -alkyl-O-alkyl- or -alkyl-.

Embodiment 7A

The compound and/or a pharmaceutically acceptable salt thereof of Embodiment 7, wherein:
said -alkyl-O-alkyl of Z is $-(CH_2)_{1-4}-O-(CH_2)_{1-4}$; and
said -alkyl- of Z is $-(CH_2)_{1-4}-$.

Embodiment 7B

The compound and/or a pharmaceutically acceptable salt thereof of Embodiment 7 or 7A, wherein:
said -alkyl-O-alkyl of Z is $-(CH_2)_2-O-(CH_2)_2$; and
said -alkyl- of Z is $-(CH_2)_2-$.

Embodiment 8

The compound and/or a pharmaceutically acceptable salt thereof of Embodiment 5, wherein Z is -alkyl-.

Embodiment 8A

The compound and/or a pharmaceutically acceptable salt thereof of Embodiment 8, wherein said -alkyl- of Z is $-(CH_2)-$.

Embodiment 9

The compound and/or a pharmaceutically acceptable salt thereof of any of Embodiments 1-8, wherein Q is $-C(=O)-$.

Embodiment 10

The compound and/or a pharmaceutically acceptable salt thereof of any of Embodiments 1-9 wherein $R^{8a}$ is hydrogen or cyano.

Embodiment 10A

The compound and/or a pharmaceutically acceptable salt thereof of Embodiment 10, wherein $R^{8a}$ is cyano.

Embodiment 11

The compound and/or a pharmaceutically acceptable salt thereof of any of Embodiments 1-10 wherein said optionally substituted alkyl of $R^{8b}$ is chosen from:

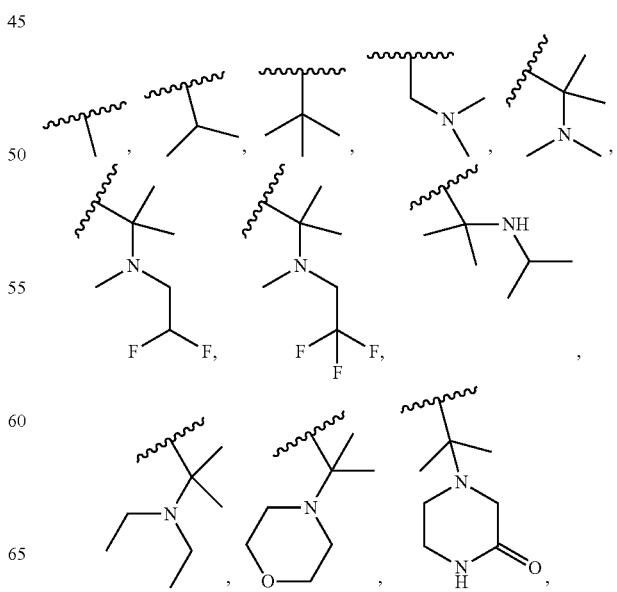

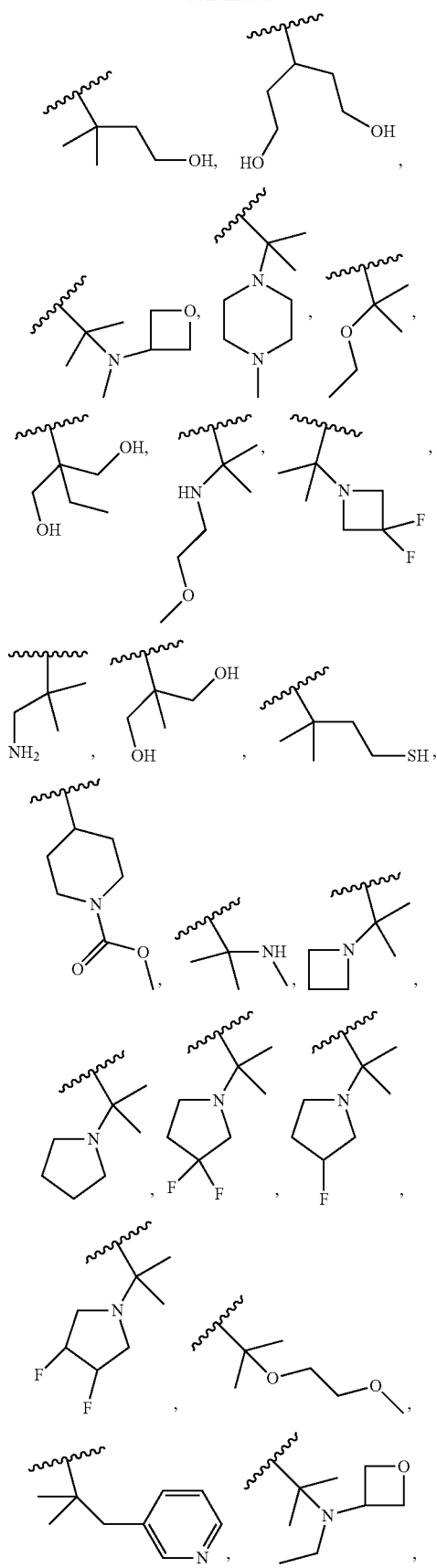
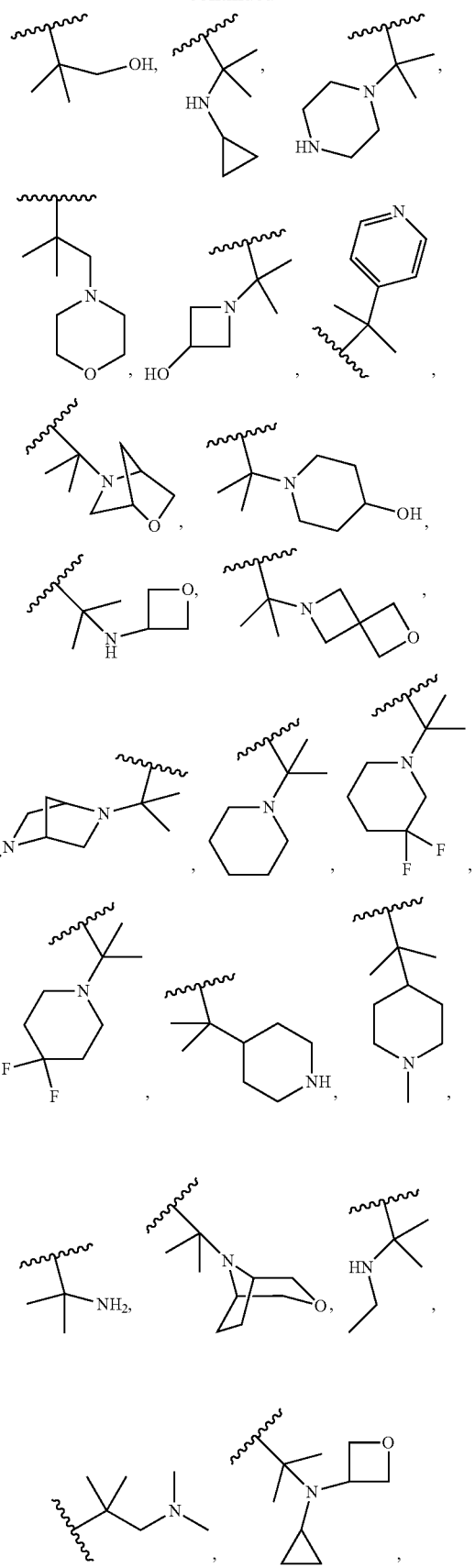

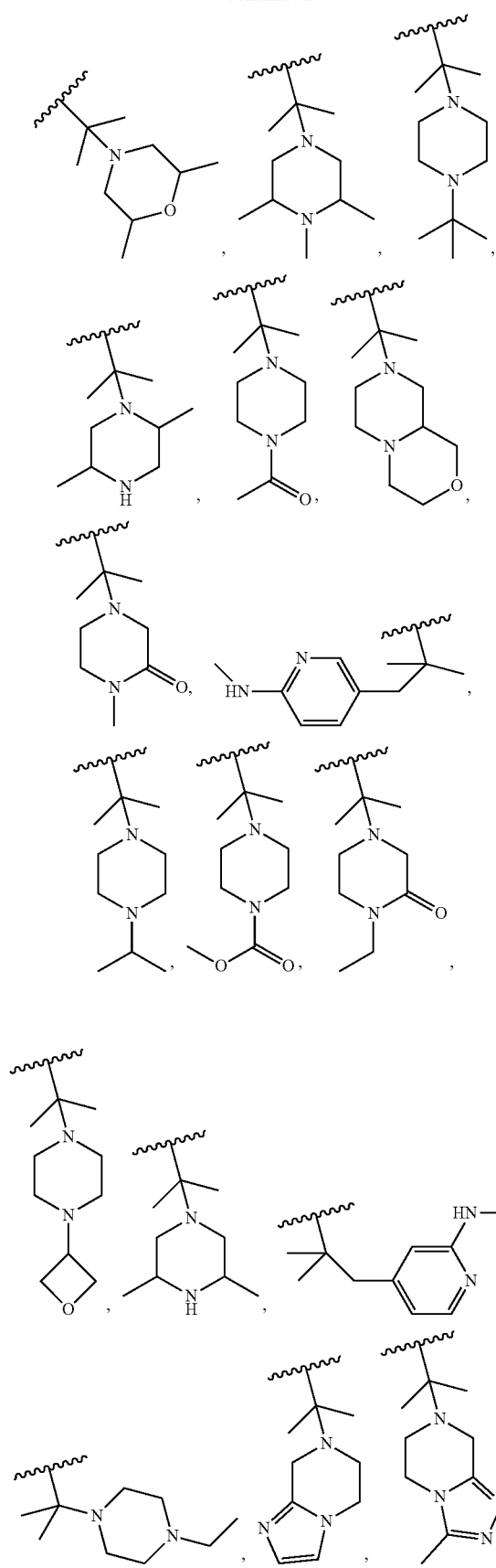
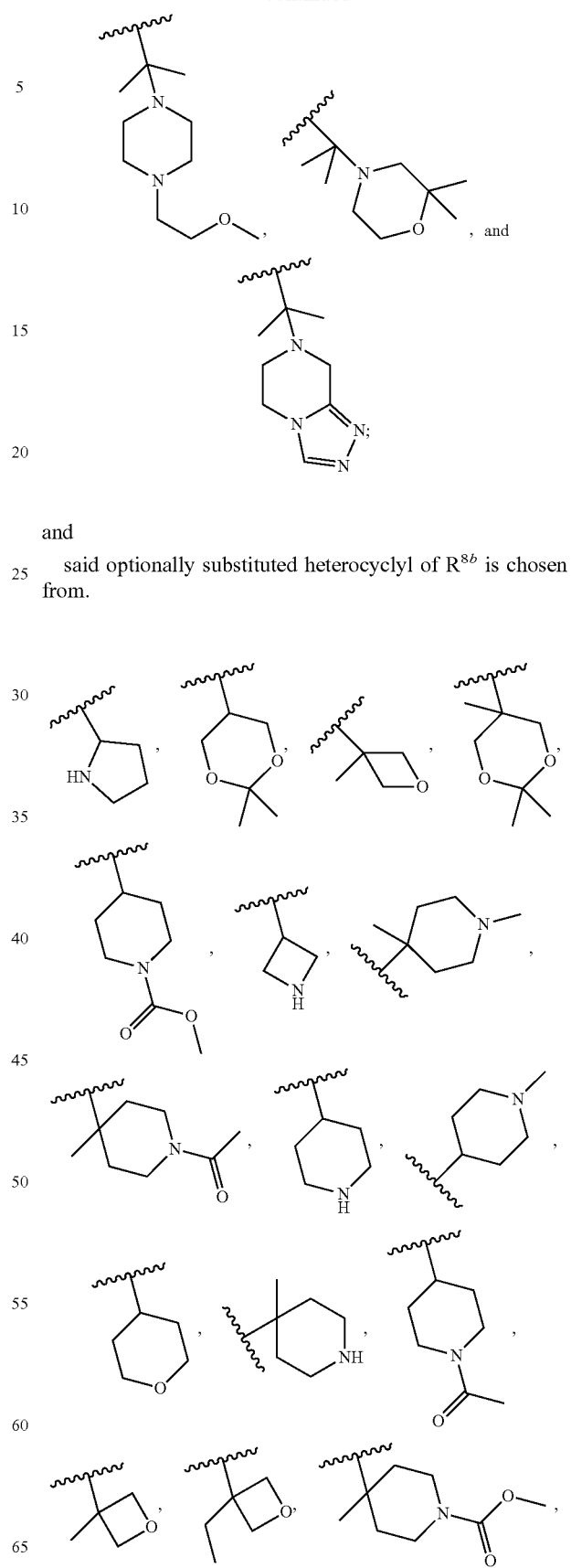
and said optionally substituted heterocyclyl of $R^{8b}$ is chosen from.

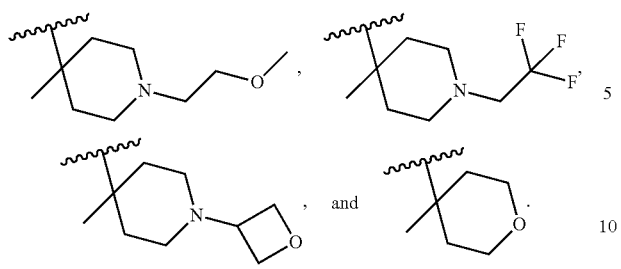

Embodiment 12

The compound and/or a pharmaceutically acceptable salt thereof of any of Embodiments 1-11, wherein:

$R^{8b}$ is H; an alkyl which is optionally substituted with 1-2 substituents chosen from —N(alkyl)(haloalkyl), —N(alkyl)$_2$, and optionally substituted heterocyclyl; or an optionally substituted heterocyclyl; and $R^{8c}$ is H.

Embodiment 12A

The compound and/or a pharmaceutically acceptable salt thereof of Embodiment 12, wherein $R^{8b}$ is an unsubstituted or substituted alkyl chosen from isopropyl, t-butyl, —C(CH$_3$)$_2$—N(CH$_3$)—CH$_2$CF$_3$, —CH$_2$—N(CH$_3$)$_2$, —C(CH$_3$)$_2$—N(CH$_3$)—CH$_2$—CHF$_2$,

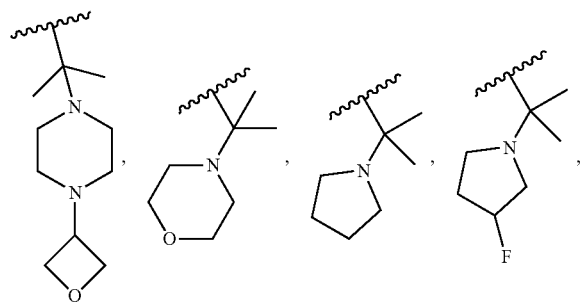

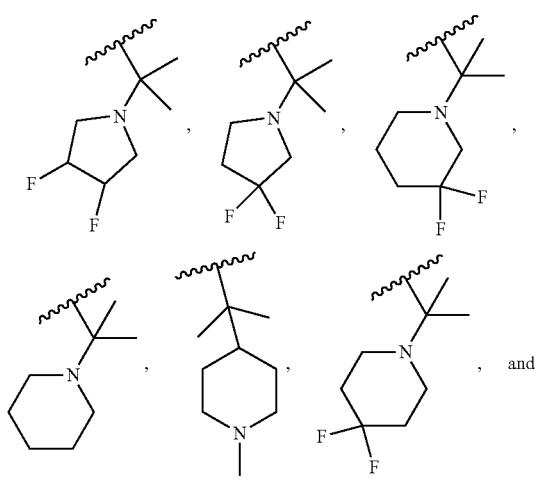

Embodiment 12B

The compound and/or a pharmaceutically acceptable salt thereof of Embodiment 12, wherein $R^{8b}$ is an optionally substituted heterocyclyl, that is

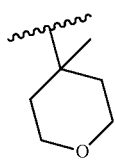

Embodiment 13

The compound and/or a pharmaceutically acceptable salt thereof of any of Embodiments 1-12, wherein $R^{b1}$ is optionally substituted alkyl, wherein the optional substituents are 1-2 substituents chosen from aryl and heteroaryl, each of which is optionally substituted with 1-3 substituents independently chosen from halo, alkyl, alkoxy, haloalkyl, cyano, and —S(=O)$_2$-alkyl.

Embodiment 13A

The compound and/or a pharmaceutically acceptable salt thereof of Embodiment 13, wherein said $R^{b1}$ is an unsubstituted alkyl or a substituted alkyl of the formula —(CH$_2$)$_{1-2}$—R" wherein R" is aryl or heteroaryl, each of which is optionally substituted with 1-3 substituents independently chosen from halo, alkyl, alkoxy, haloalkyl, cyano, and —S(=O)$_2$-alkyl.

Embodiment 13B

The compound and/or a pharmaceutically acceptable salt thereof of Embodiment 13A, wherein said $R^{b1}$ is chosen from —CH$_2$CH(CH$_3$)$_2$, —CH$_2$C(CH$_3$)$_3$, —CH$_2$-phenyl, —CH$_2$CH$_2$-phenyl, —CH$_2$— tolyl, —CH$_2$-methoxyphenyl, —CH$_2$-chlorophenyl, —CH$_2$-fluorophenyl, —CH$_2$-trifluoromethylphenyl, —CH$_2$— benzofuranyl, —CH$_2$-naphthyl, —CH$_2$-cyanophenyl, —CH$_2$-difluorophenyl, and —CH$_2$-phenyl-S(=O)$_2$—CH$_3$

Embodiment 14

The compound and/or a pharmaceutically acceptable salt thereof of any of Embodiments 1-13, wherein $R^{b2}$ and $R^{b3}$ are each H.

Embodiment 15

The compound and/or a pharmaceutically acceptable salt thereof of any of Embodiments 2, 4-7, and 9-14, wherein the compound is chosen from:

((R)-1-(3-(((R)-1-(2-cyano-4-methylpent-2-enoyl)pyrrolidin-2-yl)methoxy)propanamido)-2-phenylethyl)boronic acid;

((1R)-1-(3-(1-(2-cyano-4-methylpent-2-enoyl)pyrrolidin-2-yl)propanamido)-2-phenylethyl)boronic acid; and ((1R)-1-(3-(1-(2-cyano-4-methylpent-2-enoyl)piperidin-2-yl)propanamido)-2-phenylethyl)boronic acid;

an individual E or Z isomer thereof, and/or a pharmaceutically acceptable salt of any of the foregoing compounds.

Embodiment 16

The compound and/or a pharmaceutically acceptable salt thereof of any of Embodiments 3, 4-6, 8, and 9-14, wherein the compound is chosen from:

((R)-1-(((((R)-1-(2-cyano-4-methylpent-2-enoyl)piperidin-2-yl)methoxy)carbonyl)amino)-2-phenylethyl)boronic acid;

((R)-1-(((((R)-1-(2-cyano-4-methylpent-2-enoyl)pyrrolidin-2-yl)methoxy)carbonyl)amino)-2-phenylethyl)boronic acid;

((R)-1-(((((R)-1-acryloylpiperidin-2-yl)methoxy)carbonyl)amino)-2-phenylethyl)boronic acid;

((R)-1-(((((S)-1-((E)-2-cyano-4,4-dimethylpent-2-enoyl)piperidin-2-yl)methoxy)carbonyl)amino)-2-phenylethyl)boronic acid;

((R)-1-(((((R)-1-(2-cyano-4,4-dimethylpent-2-enoyl)pyrrolidin-2-yl)methoxy)carbonyl)amino)-2-phenylethyl)boronic acid;

((R)-1-(((((S)-1-acryloylpiperidin-2-yl)methoxy)carbonyl)amino)-2-phenylethyl)boronic acid;

((R)-1-(((((S)-1-(2-cyano-4-methylpent-2-enoyl)pyrrolidin-2-yl)methoxy)carbonyl)amino)-2-phenylethyl)boronic acid;

((R)-1-(((((S)-1-(2-cyano-4-methylpent-2-enoyl)piperidin-2-yl)methoxy)carbonyl)amino)-2-phenylethyl)boronic acid;

((R)-1-(((((R)-1-acryloylpyrrolidin-2-yl)methoxy)carbonyl)amino)-2-phenylethyl)boronic acid;

((R)-1-(((((R)-1-(2-cyano-4,4-dimethylpent-2-enoyl)piperidin-2-yl)methoxy)carbonyl)amino)-2-phenylethyl)boronic acid;

((R)-2-(benzofuran-3-yl)-1-(((((R)-1-(2-cyano-4-methylpent-2-enoyl)pyrrolidin-2-yl)methoxy)carbonyl)amino)ethyl)boronic acid;

((R)-1-(((((R)-1-(2-cyano-4-methyl-4-(4-(oxetan-3-yl)piperazin-1-yl)pent-2-enoyl)pyrrolidin-2-yl)methoxy)carbonyl)amino)-2-phenylethyl)boronic acid;

((R)-1-(((((R)-1-(2-cyano-4,4-dimethylpent-2-enoyl)pyrrolidin-2-yl)methoxy)carbonyl)amino)-2-(p-tolyl)ethyl)boronic acid;

((R)-1-(((((R)-1-acryloylpyrrolidin-2-yl)methoxy)carbonyl)amino)-2-(p-tolyl)ethyl)boronic acid;

((R)-1-(((((R)-1-(2-cyano-4-methyl-4-(piperidin-1-yl)pent-2-enoyl)pyrrolidin-2-yl)methoxy)carbonyl)amino)-2-phenylethyl)boronic acid;

((R)-1-(((((R)-1-(2-cyano-4-(4,4-difluoropiperidin-1-yl)-4-methylpent-2-enoyl)pyrrolidin-2-yl)methoxy)carbonyl)amino)-2-phenylethyl)boronic acid ((R)-1-(((((1R,2S,5 S)-3-(2-cyano-4,4-dimethylpent-2-enoyl)-3-azabicyclo[3.1.0]hexan-2-yl)methoxy)carbonyl)amino)-2-phenylethyl)boronic acid, ((R)-1-(((((R)-1-(2-cyano-4-methyl-4-morpholinopent-2-enoyl)pyrrolidin-2-yl)methoxy)carbonyl)amino)-2-phenylethyl)boronic acid, ((R)-1-(((((R)-1-(2-cyano-4,4-dimethylpent-2-enoyl)piperidin-2-yl)methoxy)carbonyl)amino)-2-(p-tolyl)ethyl)boronic acid;

((R)-2-(benzofuran-3-yl)-1-(((((R)-1-(2-cyano-4,4-dimethylpent-2-enoyl)piperidin-2-yl)methoxy)carbonyl)amino)ethyl)boronic acid;

((R)-1-(((((1S,2R,5R)-3-(2-cyano-4,4-dimethylpent-2-enol)-3-azabicyclo[3.1.0]hexan-2-yl)methoxy)carbonyl)amino)-2-phenylethyl)boronic acid;

((R)-1-(((((R)-1-(2-cyano-4-methyl-4-(pyrrolidin-1-yl)pent-2-enoyl)piperidin-2-yl)methoxy)carbonyl)amino)-2-phenylethyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-2-phenylethyl)boronic acid;

((R)-1-(((((R)-1-(2-cyano-4-methyl-4-morpholinopent-2-enoyl)piperidin-2-yl)methoxy)carbonyl)amino)-2-phenylethyl)boronic acid;

((R)-1-(((((R)-1-(2-cyano-4-methyl-4-(piperidin-1-yl)pent-2-enol 1)piperidin-2-yl)methoxy)carbonyl)amino)-2-phenylethyl)boronic acid;

((R)-1-(((((R)-1-(2-cyano-4-(4,4-difluoropiperidin-1-yl)-4-methylpent-2-enoyl)piperidin-2-yl)methoxy)carbonyl)amino)-2-phenylethyl)boronic acid;

((R)-1-(((((R)-1-(2-cyano-4,4-dimethylpent-2-enoyl)azepan-2-yl)methoxy)carbonyl)amino)-2-(p-tolyl)ethyl)boronic acid;

((R)-1-(((W(S)-1-(2-cyano-4,4-dimethylpent-2-enoyl)azepan-2-yl)methoxy)carbonyl)amino)-2-(p-tolyl)ethyl)boronic acid;

((R)-1-(((((R)-1-(2-cyano-4-methyl-4-(pyrrolidin-1-yl)pent-2-enoyl)pyrrolidin-2-yl)methoxy)carbonyl)amino)-2-phenylethyl)boronic acid;

((R)-1-(((((R)-11-(2-cyano-4-(3,3-difluoropyrrolidin-1-yl)-4-methylpent-2-enoyl)pyrrolidin-2-yl)methoxy)carbonyl)amino)-2-phenylethyl)boronic acid;

((R)-1-(((((R)-1-acryloylpyrrolidin-2-yl)methoxy)carbonyl)amino)-2-benzofuran-3-yl)ethyl)boronic acid;

((R)-1-(((((1R,2R,5 S)-3-(2-cyano-4,4-dimethylpent-2-enoyl)-3-azabicyclo[3.1.0]hexan-2-yl)methoxy)carbonyl)amino)-2-phenylethyl)boronic acid;

((R)-1-(((((1S,2S,5R)-3-(2-cyano-4,4-dimethylpent-2-enoyl)-3-azabicyclo[3.1.0]hexan-2-yl)methoxy)carbonyl)amino)-2-phenylethyl)boronic acid;

((R)-2-(benzofuran-3-yl)-1-(((((R)-1-(2-cyano-4,4-dimethylpent-2-enoyl)pyrrolidin-2-yl)methoxy)carbonyl)amino)ethyl)boronic acid;

((R)-2-(benzofuran-3-yl)-1-(((((R)-1-(2-cyano-4-methyl-4-morpholinopent-2-enoyl)pyrrolidin-2-yl)methoxy)carbonyl)amino)ethyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-2-(p-tolyl)ethyl)boronic acid;

((R)-2-(benzofuran-3-yl)-1-(((((R)-1-(2-cyano-4-(3,3-difluoropyrrolidin-1-yl)-4-methylpent-2-enoyl)pyrrolidin-2-yl)methoxy)carbonyl)amino)ethyl)boronic acid;

((R)-2-(benzofuran-3-yl)-1-(((((R)-4-(2-cyano-4,4-dimethylpent-2-enoyl)morpholin-3-yl)methoxy)carbonyl)amino)ethyl)boronic acid;

((R)-2-(benzofuran-3-yl)-1-(((((R)-1-(2-cyano-4-methyl-4-(4-(oxetan-3-v 1)piperazin-1-yl)pent-2-enoyl)pyrrolidin-2-yl)methoxy)carbonyl)amino)ethyl)boronic acid;

((R)-1-(((((R)-1-(2-cyano-4-methyl-4-morpholinopent-2-enoyl)piperidin-2-yl)methoxy)carbonyl)amino)-2-(p-tolyl)ethyl)boronic acid;

((R)-2-(benzofuran-3-yl)-1-(((((R)-1-(2-cyano-4-methyl-4-morpholinopent-2-enoyl)piperidin-2-yl)methoxy)carbonyl)amino)ethyl)boronic acid;

((R)-2-benzofuran-3-yl)-1-(((((R)-1-(2-cyano-4-(3,3-difluoropyrrolidin-1-yl)-4-methylpent-2-enoyl)piperidin-2-yl)methoxy)carbonyl)amino)ethyl)boronic acid;

((R)-2-(benzofuran-3-yl)-1-(((((1S,2R,5R)-3-(2-cyano-4,4-dimethylpent-2-enoyl)-3-azabicyclo[3.1.0]hexan-2-yl)methoxy)carbonyl)amino)ethyl)boronic acid;

((R)-2-(benzofuran-3-yl)-1-((((R)-1-((E)-4-(dimethylamino)but-2-enoyl)pyrrolidin-2-yl)methoxy)carbonyl)amino)ethyl)boronic acid;

((R)-1-(((((R)–1-(2-cyano-4,4-dimethylpent-2-enoyl)piperidin-2-yl)methoxy)carbonyl)amino)-3-phenylpropyl)boronic acid;

((R)-2-benzofuran-3-yl)-1-(((((1S,2R,5R)-3-(2-cyano-4-methyl-4-morpholinopent-2-enoyl)-3-azabicyclo[3.1.0]hexan-2-yl)methoxy)carbonyl)amino)ethyl)boronic acid;

((R)-1-(((1S,2R,5R)-3-acryloyl-3-azabicyclo[3.1.0]hexan-2-yl)methoxy)carbonyl)amino)-2-(benzofuran-3-yl)ethyl)boronic acid;

((R)-1-(((((R)-1-(4-(4-acetylpiperazin-1-yl)-2-cyano-4-methylpent-2-enoyl)pyrrolidin-2-yl)methoxy)carbonyl)amino)-2-(benzofuran-3-yl)ethyl)boronic acid.

((R)-2-(benzofuran-3-yl)-1-(((((1S,2R,5R)-3-(2-cyano-4-(3,3-difluoropyrrolidin-1-yl)-4-methylpent-2-enoyl)-3-azabicyclo[3.1.0]hexan-2-yl)methoxy)carbonyl)amino)ethyl)boronic acid;

((R)-2-(benzofuran-3-yl)-1-(((((R)-1-(2-cyano-4-methyl-4-(4-methylpiperazin-1-yl)pent-2-enoyl)pyrrolidin-2-yl)methoxy)carbonyl)amino)ethyl)boronic acid, ((R)-2-(benzofuran-3-yl)-1-(((((R)-1-(2-cyano-4-methyl-4-morpholinopent-2-enoyl)-4,4-difluoropyrrolidin-2-yl)methoxy)carbonyl)amino)ethyl)boronic acid;

((R)-2-(benzofuran-3-yl)-1-(((((2R,5S)-1-(2-cyano-4-methyl-4-morpholinopent-2-enoyl)-5-methylpyrrolidin-2-yl)methoxy)carbonyl)amino)ethyl)boronic acid;

((R)-2-(benzofuran-3-yl)-1 (((((R)-4-(2-cyano-4-methyl-4-morpholinopent-2-enoyl)morpholin-3-yl)methoxy)carbonyl)amino)ethyl)boronic acid;

((R)-2-(benzofuran-3-yl)-1-(((((R)-1-(2-cyano-3-(4-methyltetrahydro-2H-pyran-yl)acryloyl)piperidin-2-yl)methoxy)carbonyl)amino)ethyl)boronic acid;

((R)-2-(benzofuran-3-yl)-1-(((((R)-1-(2-cyano-4-methyl-4-(4-(oxetan-3-yl)piperazin-1-yl)pent-2-enoyl)piperidin-2-yl)methoxy)carbonyl)amino)ethyl)boronic acid;

((R)-1-(((((R)-1-((E)-2-cyano-4,4-dimethylpent-2-enoyl)-4,4-difluoropyrrolidin-2-yl)methoxy)carbonyl)amino)-2-phenylethyl)boronic acid;

((R)-2-(benzofuran-3-yl)-1-(((((R)-1-(2-cyano-4-(3,3-difluoropiperidin-1-yl)-4-methylpent-2-enoyl)piperidin-2-yl)methoxy)carbonyl)amino)ethyl)boronic acid;

((R)-2-(benzofuran-3-yl)-1-(((((R)-1-(2-cyano-4-methyl-4-morpholinopent-2-enoyl)azepan-2-yl)methoxy)carbonyl)amino)ethyl)boronic acid;

((R)-2-benzofuran-3-yl)-1-(((((S)-1-(2-cyano-1-methyl-4-morpholinopent-2-enoyl)azepan-2-yl)methoxy)carbonyl)amino)ethyl)boronic acid;

((R)-2-(benzofuran-3-yl)-1-(((((R)-4-(2-cyano-4-(3,3-difluoropyrrolidin-1-yl)-4-methylpent-2-enoyl)morpholin-3-yl)methoxy)carbonyl)amino)ethyl)boronic acid;

((R)-2-(benzofuran-3-yl)-1-(((((R)-1-(2-cyano-4-(4,4-difluoropiperidin-1-yl)-4-methylpent-2-enoyl)piperidin-2-yl)methoxy)carbonyl)amino)ethyl)boronic acid;

((R)-1-(((((1S,2R,5R)-3-(2-cyano-4-methyl-4-morpholinopent-2-enoyl)-3-azabicyclo[3.1.0]hexan-2-yl)methoxy)carbonyl)amino)-2-phenylethyl)boronic acid;

((R)-2-benzofuran-3-yl)-1-(((((S)-1-(2-cyano-4-(3,3-difluoropyrrolidin-1-yl)-4-methylpent-2-enoyl)azepan-2-yl)methoxy)carbonyl)amino)ethyl)boronic acid;

((R)-1-(((((R)-4-(2-cyano-4,4-dimethylpent-2-enoyl)morpholin-3-yl)methoxy)carbonyl)amino)-2-phenylethyl)boronic acid;

((R)-1-(((((R)-1-(2-cyano-4,4-dimethylpent-2-enoyl)piperidin-2-yl)methoxy)carbonyl)amino)-2-(4-methoxyphenyl)ethyl)boronic acid;

((R)-2-(benzofuran-3-yl)-1-(((((R)-1-(2-cyano-4-methyl-4-morpholinopent-2-enoyl)-2-methylpyrrolidin-2-yl)methoxy)carbonyl)amino)ethyl)boronic acid;

((R)-2-(benzofuran-3-yl)-1-(((((R)-1-(2-cyano-4-(3,3-difluoropyrrolidin-1-yl)-4-methylpent-2-enoyl)azepan-2-yl)methoxy)carbonyl)amino)ethyl)boronic acid;

((R)-1 ((R)-4-(2-cyano-4,4-dimethylpent-2-enoyl)morpholin-3-yl)methoxy)carbonyl)amino)-2-(p-tolyl)ethyl)boronic acid;

((R)-1-(((((1S,2R,5R)-3-(2-cyano-4-(3,3-difluoropyrrolidin-1-yl)-4-methylpent-2-enoyl)-3-azabicyclo[3.1.0]hexan-2-yl)methoxy)carbonyl)amino)-2-phenylethyl)boronic acid;

((R)-1-(((((1S,2R,5R)-3-(2-cyano-4-methyl-4-morpholinopent-2-enoyl)-3-azabicyclo[3.1.0]hexan-2-yl)methoxy)carbonyl)amino)-2-(p-tolyl)ethyl)boronic acid;

((R)-1-(((((1S,2R,5R)-3-(2-cyano-4,4-dimethylpent-2-enoyl)-3-azabicyclo[3.1.0]hexan-2-yl)methoxy)carbonyl)amino)-2-(p-tolyl)ethyl)boronic acid;

((R)-1-(((((R)-1-(2-cyano-4,4-dimethylpent-2-enoyl)piperidin-2-yl)methoxy)carbonyl)amino)-2-(3-methoxyphenyl)ethyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-2-(4-methoxyphenyl)ethyl)boronic acid;

((R)-2-(4-chlorophenyl)-1-((((R)-1-(2-cyano-4-(3,3-difluoropyrrolidin-1-yl)-4-methylpent-2-enoyl)piperidin-2-yl)methoxy)carbonyl)amino)ethyl)boronic acid;

((R)-1-(((((R)-1-(2-cyano-4-((2,2-difluoroethyl)(methyl)amino)-4-methylpent-2-enoyl)piperidin-2-yl)methoxy)carbonyl)amino)-2-phenylethyl)boronic acid;

((R)-1-(((((S)-1-(2-cyano-4-(3,3-difluoropyrrolidin-1-yl)-4-methylpent-2-enoyl)azepan-2-yl)methoxy)carbonyl)amino)-2-(p-tolyl)ethyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-2-(4-fluorophenyl)ethyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-2-(4-(trifluoromethyl)phenyl)ethyl)boronic acid;

((R)-1-(((((R)-1-(2-cyano-4-(3,3-difluoropyrrolidin-1-yl)-4-methylpent-2-enoyl)azepan-2-yl)methoxy)carbonyl)amino)-2-(p-tolyl)ethyl)boronic acid;

((R)-1-(((((R)-1-(2-cyano-4-(3,3-difluoropyrrolidin-1-yl)-4-methylpent-2-enoyl)-2-methylpyrrolidin-2-yl)methoxy)carbonyl)amino)-2-phenylethyl)boronic acid;

((R)-1-(((((R)-4-(2-cyano-4-(3,3-difluoropyrrolidin-1-yl)-4-methylpent-2-enoyl)morpholin-3-yl)methoxy)carbonyl)amino)-2-p-tolyl)ethyl)boronic acid;

((R)-2-(benzofuran-3-yl)-1-(((((1S,2R,5R)-3-((E)-4-(dimethylamino)but-2-enoyl)-3-azabicyclo[3.1.0]hexan-2-yl)methoxy)carbonyl)amino)ethyl)boronic acid;

((R)-2-(benzofuran-3-yl)-1-(((((1S,2R,5R)-3-(but-2-ynoyl)-3-azabicyclo[3.1.0]hexan-2-yl)methoxy)carbonyl)amino)ethyl)boronic acid;

((R)-1-(((((2R,4R)-1-acryloyl-4-fluoropyrrolidin-2-yl)methoxy)carbonyl)amino)-2-phenylethyl)boronic acid;

((R)-1-(((((2R,4R)-1-((E)-2-cyano-4,4-dimethylpent-2-enoyl)-4-fluoropyrrolidin-2-yl)methoxy)carbonyl)amino)-2-phenylethyl)boronic acid;

((R)-1-(((((R)-1-acryloyl-4,4-difluoropyrrolidin-2-yl)methoxy)carbonyl)amino)-2-(benzofuran-3-yl)ethyl)boronic acid;

((R)-1-(((((1S,2R,5R)-3-(2-cyano-3-(4-methyltetrahydro-2H-pyran-4-yl)acryloyl)-3-azabicyclo[3.1.0]hexan-2-yl)methoxy)carbonyl)amino)-2-(p-tolyl)ethyl)boronic acid;

((R)-1-((((R)-4-acryloylmorpholin-3-yl)methoxy)carbonyl)amino)-2-(benzofuran-3-yl)ethyl)boronic acid;

((R)-1-(((((R)-4-(2-cyano-4-(3,3-difluoropyrrolidin-1-yl)-4-methylpent-2-enoyl)morpholin-3-yl)methoxy)carbonyl)amino)-2-phenylethyl)boronic acid;

((R)-1-(((((1S,2R,5R)-3-acryloyl-3-azabicyclo[3.1.0]hexan-2-yl)methoxy)carbonyl)amino)-2-(p-tolyl)ethyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-2-(3-methoxyphenyl)ethyl)boronic acid;

((R)-1-(((((R)-1-(2-cyano-4-methyl-4-(methyl(2,2,2-trifluoroethyl)amino)pent-2-enoyl)piperidin-2-yl)methoxy)carbonyl)amino)-2-phenylethyl)boronic acid;

((R)-1-((((R)-4-(2-cyano-4-(3,3-difluoropyrrolidin-1-yl)-4-methylpent-2-enoyl)morpholin-3-yl)methoxy)carbonyl)amino)-3-phenylpropyl)boronic acid;

((R)-1-(((S,2R,5R)-3-acryloyl-3-azabicyclo[3.1.0]hexan-2-yl)methoxy)carbonyl)amino)-2-phenylethyl)boronic acid;

((R)-1-(((((2R,4S)-1-acryloyl-4-fluoropyrrolidin-2-yl)methoxy)carbonyl)amino)-2-phenylethyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-3-phenylpropyl)boronic acid;

((R)-1-(((((2R,4S)-1 (E)-2-cyano-4,4-dimethylpent-2-enoyl)-4-fluoropyrrolidin-2-yl)methoxy)carbonyl)amino)-2-phenylethyl)boronic acid;

((R)-1-(((((R)-1-((Z)-2-cyano-4-(3,3-difluoropyrrolidin-1-yl)-4-methylpent-2-enoyl)piperidin-2-yl)methoxy)carbonyl)amino)-2-phenylethyl)boronic acid;

((R)-1-(((1S,2R,5R)-3-(2-cyano-4-(3,3-difluoropyrrolidin-1-yl)-4-methylpent-2-enoyl)-3-azabicyclo[3.1.0]hexan-2-yl)methoxy)carbonyl)amino)-3-phenylpropyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-3-methylbutyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-2-(naphthalen-1-yl)ethyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-2-(2-cyanophenyl)ethyl)boronic acid;

((R)-1-(((((1S,2R,5R)-3-(2-cyano-4-(3,3-difluoropyrrolidin-1-yl)-4-methylpent-2-enoyl)-3-azabicyclo[3.1.0]hexan-2-yl)methoxy)carbonyl)amino)-2-(4-fluorophenyl)ethyl)boronic acid;

((R)-1-(((((1S,2R,5R)-3-acryloyl-3-azabicyclo[3.1.0]hexan-2-yl)methoxy)carbonyl)amino)-2-(4-fluorophenyl)ethyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-2-(2-trifluoromethyl)phenyl)ethyl)boronic acid;

((R)-1-(((((S)-4-acryloyl-1,1-dioxidothiomorpholin-3-yl)methoxy)carbonyl)amino)-2-(benzofuran-3-yl)ethyl)boronic acid;

((R)-1-(((((R)-1 acryloyl-4,4-difluoropiperidin-2-yl)methoxy)carbonyl)amino)-2-(benzofuran-3-yl)ethyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-2-(2,4-difluorophenyl)ethyl)boronic acid;

((R)-1-(((((1S,2R,5R)-3-(2-cyano-4-methyl-4-morpholinopent-2-enoyl)-3-azabicyclo[3.1.0]hexan-2-yl)methoxy)carbonyl)amino)-2-(4-(trifluoromethyl)phenyl)ethyl)boronic acid;

((R)-1-(((((1S,2R,5R)-3-acryloyl-3-azabicyclo[3.1.0]hexan-2-yl)methoxy)carbonyl)amino)-2-(4-(trifluoromethyl)phenyl)ethyl)boronic acid;

((R)-1-((((S,2R,5R)-3-(2-cyano-4-(3,3-difluoropyrrolidin-1-yl)-4-methylpent-2-enoyl)-3-azabicyclo[3.1.0]hexan-2-yl)methoxy)carbonyl)amino)-2-p-tolyl)ethyl)boronic acid;

((R)-2-(benzofuran-3-yl)-1-(((((R)-1-(2-cyano-4-(3,3-difluoropyrrolidin-1-yl)-4-methylpent-2-enoyl)-2-methylpyrrolidin-2-yl)methoxy)carbonyl)amino)ethyl)boronic acid;

((R)-1-(((((R)-1-(2-cyano-4-(3,3-difluoropyrrolidin-1-yl)-4-methylpent-2-enoyl)-2-methylpyrrolidin-2-yl)methoxy)carbonyl)amino)-3,3-dimethylbutyl)boronic acid;

((R)-1-(((((1S,2R,5R)-3-(2-cyano-3-(4-methyltetrahydro-2H-pyran-4-yl)acryloyl)-3-azabicyclo[3.1.0]hexan-2-yl)methoxy)carbonyl)amino)-2-(4-fluorophenyl)ethyl)boronic acid;

((R)-1-(((((R)-11-(2-cyano-4-(3,3-difluoropyrrolidin-1-yl)-4-methylpent-2-enoyl)-2-methylpyrrolidin-2-yl)methoxy)carbonyl)amino)-2-(4-fluorophenyl)ethyl)boronic acid;

((R)-1-(((((R)-1-(2-fluoroacryloyl)-2-methylpyrrolidin-2-yl)methoxy)carbonyl)amino)-2-(4-fluorophenyl)ethyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-2-(4-cyanophenyl)ethyl)boronic acid;

((R)-1-(((((1S,2R,5R)-3-(2-cyano-4-methyl-4-morpholinopent-2-enoyl)-3-azabicyclo[3.1.0]hexan-2-yl)methoxy)carbonyl)amino)-2-(4-fluorophenyl)ethyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-2-(4-(methylsulfonyl)phenyl)ethyl)boronic acid;

((R)-1-(((((R)-1-(2-cyano-4-(4-(methoxycarbonyl)piperazin-1-yl)-4-methylpent-2-enoyl)piperidin-2-yl)methoxy)carbonyl)amino)-2-phenylethyl)boronic acid;

((R)-1-(((((R)-1-(2-cyano-4-methyl-4-(4-(oxetan-3-yl)piperazin-1-yl)pent-2-enoyl)piperidin-2-yl)methoxy)carbonyl)amino)-2-phenylethyl)boronic acid;

((R)-1-(((((R)-1-(2-cyano-4-methyl-4-(4-(oxetan-3-yl)piperazin-1-yl)pent-2-enoyl)piperidin-2-yl)methoxy)carbonyl)amino)-2-(4-fluorophenyl)ethyl)boronic acid;

((R)-1-(((((R)-1 (E)-2-cyano-4,4-dimethylpent-2-enoyl)piperazin-2-yl)methoxy)carbonyl)amino)-2-phenylethyl)boronic acid;

((R)-1-(((((R)-1-(2-cyano-4-(3,3-difluoropyrrolidin-1-yl)-4-methylpent-2-enoyl)-2-methylpiperidin-2-yl)methoxy)carbonyl)amino)-2-phenylethyl)boronic acid;

((R)-1-(((((R)-1-(2-cyano-4-methyl-4-morpholinopent-2-enoyl)-2-methylpiperidin-2-yl)methoxy)carbonyl)amino)-2-phenylethyl)boronic acid;

((R)-1-(((((2R,4S)-1-(2-cyano-4-methyl-4-morpholinopent-2-enoyl)-4-fluoropyrrolidin-2-yl)methoxy)carbonyl)amino)-2-phenylethyl)boronic acid;

((R)-1-(((((2R,4S)-1-(2-cyano-4-(3,3-difluoropyrrolidin-1-yl)-4-methylpent-2-enoyl)-4-fluoropyrrolidin-2-yl)methoxy)carbonyl)amino)-2-phenylethyl)boronic acid;

((R)-1-(((((2R,4S)-1-acryloyl-4-fluoropyrrolidin-2-yl)methoxy)carbonyl)amino)-2-(benzofuran-3-yl)ethyl)boronic acid;

((R)-2-(benzofuran-3-yl)-1-(((((2R,4S)-1-(2-cyano-4-(3,3-difluoropyrrolidin-1-yl)-4-methylpent-2-enoyl)-4-fluoropyrrolidin-2-yl)methoxy)carbonyl)amino)ethyl)boronic acid;

((R)-1-(((((2R,4S)-1-(2-cyano-4-(3,3-difluoropyrrolidin-1-)yl)-4-methylpent-2-enoyl)-4-fluoropyrrolidin-2-yl)methoxy)carbonyl)amino)-2-(4-fluorophenyl)ethyl)boronic acid;

((R)-2-benzofuran-3-yl)-1-(((((2R,4S)-1-(2-cyano-4-methyl-4-morpholinopent-2-enoyl)-4-fluoropyrrolidin-2-yl)methoxy)carbonyl)amino)ethyl)boronic acid;

((R)-1-(((((2R,4S)-1-(2-cyano-4-methyl-4-morpholinopent-2-enoyl)-4-fluoropyrrolidin-2-yl)methoxy)carbonyl)amino)-2-(4-fluorophenyl)ethyl)boronic acid;

((R)-1-(((((2R,4S)-1-acryloyl-4-fluoropyrrolidin-2-yl)methoxy)carbonyl)amino)-2-(4-fluorophenyl)ethyl)boronic acid;

((R)-1-(((((R)-1-(2-cyano-4-((R)-3-fluoropyrrolidin-1-yl)-4-methylpent-2-enoyl)-2-methylpyrrolidin-2-yl)methoxy)carbonyl)amino)-2-phenylethyl)boronic acid;

((R)-1-(((((R)-1-(2-cyano-4-((S)-3-fluoropyrrolidin-1-yl)-4-methylpent-2-enoyl)-2-methylpyrrolidin-2-yl)methoxy)carbonyl)amino)-2-phenylethyl)boronic acid;

((R)-1-(((((R)-1-(2-cyano-4-((3 S,4R)-3,4-difluoropyrrolidin-1-yl)-4-methylpent-2-enoyl)-2-methylpyrrolidin-2-yl)methoxy)carbonyl)amino)-2-phenylethyl)boronic acid;

((R)-1-(((((R)-1-(2-cyano-4-((1R)-3-fluoropyrrolidin-1-yl)-4-methylpent-2-enoyl)-2-methylpyrrolidin-2-yl)methoxy)carbonyl)amino)-2-(4-fluorophenyl)ethyl)boronic acid;

((R)-1-(((((R)-1-(2-cyano-4-((S)-3-fluoropyrrolidin-1-yl)-4-methylpent-2-enoyl)-2-methylpyrrolidin-2-yl)methoxy)carbonyl)amino)-2-(4-fluorophenyl)ethyl)boronic acid;

((R)-1-(((((R)-1-(2-cyano-4-((3S,4R)-3,4-difluoropyrrolidin-1-yl)-4-methylpent-2-enoyl)-2-methylpyrrolidin-2-yl)methoxy)carbonyl)amino)-2-(4-fluorophenyl)ethyl)boronic acid;

((R)-1-(((((R)-1-(2-cyano-4-((R)-3-fluoropyrrolidin-1-yl)-4-methylpent-2-enoyl)piperidin-2-yl)methoxy)carbonyl)amino)-2-phenylethyl)boronic acid;

((R)-1-(((((R)-1-(2-cyano-4-((S)-3-fluoropyrrolidin-1-yl)-4-methylpent-2-enoyl)piperidin-2-yl)methoxy)carbonyl)amino)-2-phenylethyl)boronic acid;

((R)-1-(((((R)-1-(2-cyano-4-((3S,4R)-3,4-difluoropyrrolidin-1-yl)-4-methylpent-2-enoyl)piperidin-2-yl)methoxy)carbonyl)amino)-2-phenylethyl)boronic acid;

((R)-1-(((((R)-1-(2-cyano-4-((R)-3-fluoropyrrolidin-1-yl)-4-methylpent-2-enoyl)piperidin-2-yl)methoxy)carbonyl)amino)-2-(4-fluorophenyl)ethyl)boronic acid;

((R)-1-(((((R)-1-(2-cyano-4-((S)-3-fluoropyrrolidin-1-yl)-4-methylpent-2-enoyl)piperidin-2-yl)methoxy)carbonyl)amino)-2-(4-fluorophenyl)ethyl)boronic acid;

((R)-1-(((((R)-1-(2-cyano-4-((3S,4R)-3,4-difluoropyrrolidin-1-yl)-4-methylpent-2-enoyl)piperidin-2-yl)methoxy)carbonyl)amino)-2-(4-fluorophenyl)ethyl)boronic acid;

((R)-1-(((((R)-1-(2-cyano-4-methyl-4-morpholinopent-2-enoyl)-2-methylpyrrolidin-2-yl)methoxy)carbonyl)amino)-2-(4-fluorophenyl)ethyl)boronic acid;

((R)-1-(((((R)-1-(2-cyano-4-methyl-4-morpholinopent-2-enoyl)-2-methylpyrrolidin-2-yl)methoxy)carbonyl)amino)-2-phenylethyl)boronic acid;

((R)-1-(((((2R,4S)-1-(2-cyano-4-(3,3-difluoropyrrolidin-1-yl)-4-methylpent-2-enoyl)-4-fluoro-2-methylpyrrolidin-2-yl)methoxy)carbonyl)amino)-2-(4-fluorophenyl)ethyl)boronic acid;

((R)-1-(((((2R,4S)-1-(2-cyano-4-((S)-3-fluoropyrrolidin-1-yl)-4-methylpent-2-enoyl)-4-fluoro-2-methylpyrrolidin-2-yl)methoxy)carbonyl)amino)-2-(4-fluorophenyl)ethyl)boronic acid;

((R)-1-(((((2R,4S)-1-(2-cyano-4-((R)-3-fluoropyrrolidin-1-yl)-4-methylpent-2-enoyl)-4-fluoro-2-methylpyrrolidin-2-yl)methoxy)carbonyl)amino)-2-(4-fluorophenyl)ethyl)boronic acid;

((R)-1-(((((2R,4S)-1-acryloyl-4-fluoro-2-methylpyrrolidin-2-yl)methoxy)carbonyl)amino)-2-(4-fluorophenyl)ethyl)boronic acid;

((R)-1-(((((2R,4S)-1-(2-cyano-4-(3,3-difluoropyrrolidin-1-yl)-4-methylpent-2-enoyl)-4-fluoro-2-methylpyrrolidin-2-yl)methoxy)carbonyl)amino)-2-phenylethyl)boronic acid;

((R)-1-(((((2R,4S)-1-(2-cyano-4-((S)-3-fluoropyrrolidin-1-yl)-4-methylpent-2-enoyl)-4-fluoro-2-methylpyrrolidin-2-yl)methoxy)carbonyl)amino)-2-phenylethyl)boronic acid;

((R)-1-(((((2R,4S)-1-(2-cyano-4-((R)-3-fluoropyrrolidin-1-yl)-4-methylpent-2-enoyl)-4-fluoro-2-methylpyrrolidin-2-yl)methoxy)carbonyl)amino)-2-phenylethyl)boronic acid;

((R)-1-(((((2R,4S)-1-acryloyl-4-fluoro-2-methylpyrrolidin-2-yl)methoxy)carbonyl)amino)-2-phenylethyl)boronic acid;

((R)-1-(((((R)-1-(2-cyano-4-(3,3-difluoropyrrolidin-1-yl)-4-methylpent-2-enoyl)-2-methylpiperidin-2-yl)methoxy)carbonyl)amino)-2-(4-fluorophenyl)ethyl)boronic acid; and ((R)-1-(((((R)-1-(2-cyano-4-methyl-4-morpholinopent-2-enoyl)-2-methylpiperidin-2-yl)methoxy)carbonyl)amino)-2-(4-fluorophenyl)ethyl)boronic acid;

an individual E or Z isomer thereof; and/or a pharmaceutically acceptable salt of any of the foregoing compounds.

As shown in the above embodiments, combinations of embodiments are clearly contemplated herein. For example, Embodiment 2A combines certain features of Embodiment 1 (W is

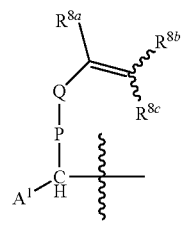

(as set forth in Embodiment 2)) with other features of Embodiment 1 ($A^1$ is H). Similarly, selective combinations of many other embodiments are also possible.

Embodiment 17

In certain embodiments of Formula (Ib) (Embodiment 3), P is

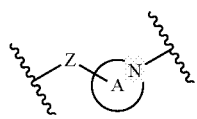

(Embodiment 5); Z of P is —(CH$_2$)— (Embodiment 8A); Q is —C(=O)— (Embodiment 9), R$^{b1}$ is a substituted alkyl of the formula —(CH$_2$)—R″ wherein R″ is optionally substituted aryl (Embodiment 13A); and R$^{b2}$ and R$^{b3}$ are each H (Embodiment 14); such that the compound of formula (Ib) is a compound of Formula (Ib-(i)):

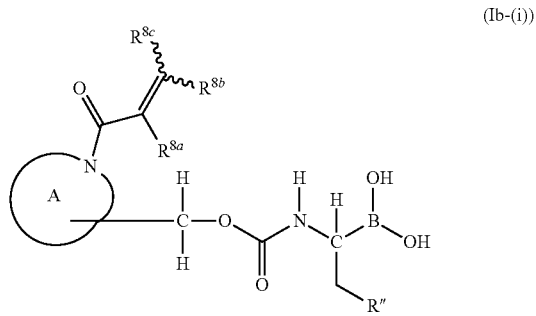

(Ib-(i))

or a pharmaceutically acceptable salt thereof, wherein:

ring A with the ring N atom shown is

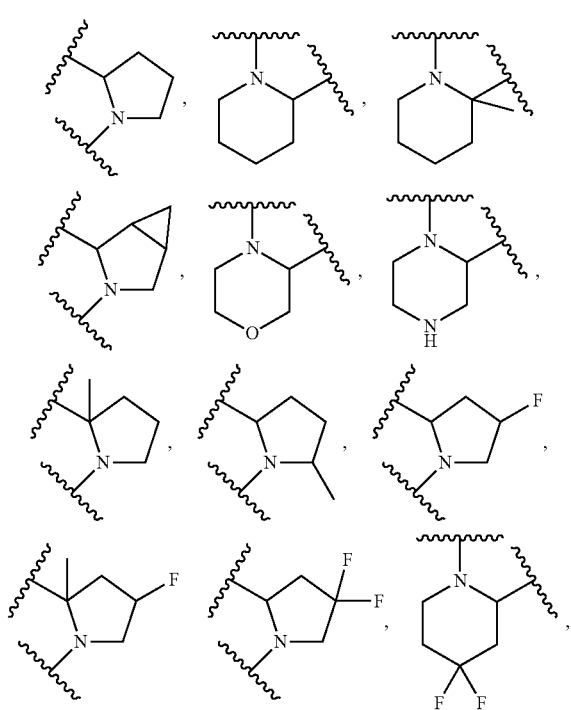

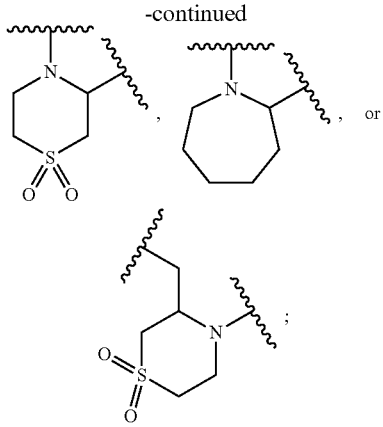

R″ is phenyl or benzofuranyl, each of which is optionally substituted with 1-2 substituents chosen from halo, alkyl, alkoxy, haloalkyl, cyano, and —S(=O)$_2$-alkyl;

R$^{8a}$ is hydrogen or cyano:

R$^{8b}$ is hydrogen; alkyl which is optionally substituted with 1-2 substituents chosen from a —N(alkyl)(haloalkyl), —N(alkyl)$_2$, and heterocyclyl, wherein the heterocyclyl is optionally substituted with 1-3 substituents chosen from halo, alkyl, and —C(=O)-alkyl; and heterocyclyl which is optionally substituted with 1-2 substituents chosen from halo, alkyl, alkoxy, haloalkyl, cyano, and —S(=O)$_2$-alkyl; and R$^{8c}$ is hydrogen or alkyl.

Embodiment 17A

The compound and/or a pharmaceutically acceptable salt of Embodiment 17, wherein in Formula (Ib-(i)), ring A with the ring nitrogen atom shown is

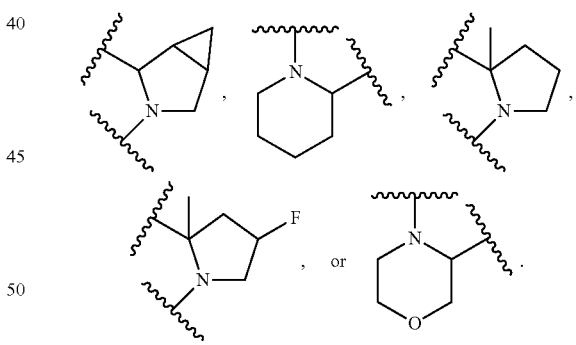

Embodiment 17B

The compound and/or a pharmaceutically acceptable salt of Embodiment 17 A or 17B, wherein in Formula (Ib-(i)), R″ is phenyl or benzofuranyl, each of which is optionally substituted with a halo or alkyl.

Embodiment 17C

The compound and/or a pharmaceutically acceptable salt of any of Embodiments 17, and 17A-B, wherein in Formula (Ib-(i)):

R$^{8a}$ is hydrogen or cyano:

$R^{8b}$ is hydrogen; alkyl which is optionally substituted with a heterocyclyl, wherein the heterocyclyl is optionally substituted with 1-2 halo substituents; and $R^{8c}$ is hydrogen or alkyl.

Embodiment 17D

The compound and/or a pharmaceutically acceptable salt of any of Embodiments 17, and 17A-C, wherein the compound of Formula (Ib-(i)) is the E-isomer.

Embodiment 17E

The compound and/or a pharmaceutically acceptable salt of any of Embodiments 17, and 17A-C, wherein the compound of Formula (Ib-(i)) is the Z-isomer.

Embodiment 17F

The compound and/or a pharmaceutically acceptable salt of any of Embodiments 17, and 17A-F, wherein the compound of Formula (Ib-(i)) is chosen from:
((R)-1-(((((R)-1-(2-cyano-4-(3,3-difluoropyrrolidin-1-yl)-4-methylpent-2-enoyl)piperidin-2-yl)methoxy)carbonyl)amino)-2-phenylethyl)boronic acid;
((R)-1-(((((R)-1-(2-cyano-4-(3,3-difluoropyrrolidin-1-yl)-4-methylpent-2-enoyl)piperidin-2-yl)methoxy)carbonyl)amino)-2-(p-tolyl)ethyl)boronic acid;
((R)-1-(((((R)-1-(2-cyano-4-methyl-4-morpholinopent-2-enoyl)piperidin-2-yl)methoxy)carbonyl)amino)-2-(p-tolyl)ethyl)boronic acid;
((R)-1-(((((1S,2R,5R)-3-acryloyl-3-azabicyclo[3.1.0]hexan-2-yl)methoxy)carbonyl)amino)-2-(benzofuran-3-yl)ethyl)boronic acid;
((R)-1-(((1S,2R,5R)-3-(2-cyano-4-methyl-4-morpholinopent-2-enoyl)-3-azabicyclo[3.1.0]hexan-2-yl)methoxy)carbonyl)amino)-2-phenylethyl)boronic acid;
((R)-1-(((1S,2R,5R)-3-(2-cyano-4-(3,3-difluoropyrrolidin-1-yl)-4-methylpent-2-enoyl)-3-azabicyclo[3.1.0]hexan-2-yl)methoxy)carbonyl)amino)-2-phenylethyl)boronic acid;
((R)-1-(((((1S,2R,5R)-3-(2-cyano-4-methyl-4-morpholinopent-2-enoyl)-3-azabicyclo[3.1.0]hexan-2-yl)methoxy)carbonyl)amino)-2-(p-tolyl)ethyl)boronic acid;
((R)-1-(((((R)-1-(2-cyano-4-(3,3-difluoropyrrolidin-1-yl)-4-methylpent-2-enoyl)piperidin-2-yl)methoxy)carbonyl)amino)-2-(4-fluorophenyl)ethyl)boronic acid;
((R)-1-(((((R)-1-(2-cyano-4-(3,3-difluoropyrrolidin-1-yl)-4-methylpent-2-enoyl)-2-methylpyrrolidin-2-yl)methoxy)carbonyl)amino)-2-phenylethyl)boronic acid;
((R)-1-(((R)-4-(2-cyano-4-(3,3-difluoropyrrolidin-1-yl)-4-methylpent-2-enoyl)morpholin-3-yl)methoxy)carbonyl)amino)-2-(p-tolyl)ethyl)boronic acid,
((R)-1-(((((2R,4S)-1-acryloyl-4-fluoropyrrolidin-2-yl)methoxy)carbonyl)amino)-2-phenylethyl)boronic acid;
((R)-1-(((((1S,2R,5R)-3-(2-cyano-4-(3,3-difluoropyrrolidin-1-yl)-4-methylpent-2-enoyl)-3-azabicyclo[3.1.0]hexan-2-yl)methoxy)carbonyl)amino)-2-(4-fluorophenyl)ethyl)boronic acid;
((R)-1-(((((1S,2R,5R)-3-acryloyl-3-azabicyclo[3.1.0]hexan-2-yl)methoxy)carbonyl)amino)-2-(4-fluorophenyl)ethyl)boronic acid;
((R)-1-(((((1S,2R,5R)-3-(2-cyano-4-(3,3-difluoropyrrolidin-1-yl)-4-methylpent-2-enoyl)-3-azabicyclo[3.1.0]hexan-2-yl)methoxy)carbonyl)amino)-2-p-tolyl)ethyl)boronic acid;
((R)-1-(((((R)-1-(2-cyano-4-(3,3-difluoropyrrolidin-1-yl)-4-methylpent-2-enoyl)-2-methylpyrrolidin-2-yl)methoxy)carbonyl)amino)-2-(4-fluorophenyl)ethyl)boronic acid; and
((R)-1-(((((1S,2R,5R)-3-(2-cyano-4-methyl-4-morpholinopent-2-enoyl)-3-azabicyclo[3.1.0]hexan-2-yl)methoxy)carbonyl)amino)-2-(4-fluorophenyl)ethyl)boronic acid;
an individual E or Z isomer thereof, and/or
a pharmaceutically acceptable salt of any of the foregoing compounds.

Embodiment 18

A pharmaceutical composition comprising at least one compound of any of Embodiments 1-17, and/or a pharmaceutical acceptable salt thereof, and a pharmaceutically acceptable excipient.

Embodiment 19

A method of inhibiting Large Multifunctional Protease 2 (LMP2) and/or Large Multifunctional Protease 7 (LMP7) in a subject comprising administering to said subject in need of said inhibition a therapeutically effective amount of a compound of any one of Embodiments 1-17 and/or a pharmaceutically acceptable salt thereof.

Embodiment 19A

Use of a compound of any one of Embodiments 1-17 and/or a pharmaceutically acceptable salt thereof, in the preparation of a medicament for inhibiting Large Multifunctional Protease 2 (LMP2) and/or Large Multifunctional Protease 7 (LMP7).

Embodiment 20

A method of treating a disease chosen from an autoimmune disorder, an inflammatory disorder, and a hematological disorder in a patient in need of such treatment, comprising administering to the patient a therapeutically effective amount of a compound of any one of Embodiments 1-17 and/or a pharmaceutically acceptable salt thereof.

Embodiment 20A

Use of a compound of any one of Embodiments 1-17 and/or a pharmaceutically acceptable salt thereof, in the preparation of a medicament for treating a disease chosen from an autoimmune disorder, an inflammatory disorder, and a hematological disorder.

Embodiment 21

The method of Embodiment 20, wherein the disease is chosen from lupus, rheumatoid arthritis, scleroderma, ankylosing spondylitis, Duchene muscular dystrophy (DMD), Becker muscular dystrophy (BMD), idiopathic inflammatory myopathies (IIMs), polymyositis, sporadic inclusion body myositis, dermatomyositis, immune-mediated necrotizing myopathies (IMNM), psoriasis, multiple sclerosis, inflammatory bowel disease, Behçet's disease, ulcerative colitis, Crohn's disease, Sjogren's Syndrome, bronchitis, conjunctivitis, pancreatitis, cholecstitis, bronchiectasis, aortic valve stenosis, restenosis, fibrosis, infection, ischemia, cardiovascular disease, hepatitis, cirrhosis, steatohepatitis, chronic liver inflammation, Alzheimer's Disease (AD), amyotrophic lateral sclerosis (ALS), Huntington's disease, body myositis, myofibrilar myopathy, GVHD, and multiple myeloma.

The use of Embodiment 20A, wherein the disease is chosen from lupus, rheumatoid arthritis, scleroderma, ankylosing spondylitis, Duchene muscular dystrophy (DMD), Becker muscular dystrophy (BMD), idiopathic inflammatory myopathies (IIMs), polymyositis, sporadic inclusion body myositis, dermatomyositis, immune-mediated necrotizing myopathies (IMNM), psoriasis, multiple sclerosis, inflammatory bowel disease, Behçet's disease, ulcerative colitis, Crohn's disease, Sjogren's Syndrome, bronchitis, conjunctivitis, pancreatitis, cholecstitis, bronchiectasis, aortic valve stenosis, restenosis, fibrosis, infection, ischemia, cardiovascular disease, hepatitis, cirrhosis, steatohepatitis, chronic liver inflammation, Alzheimer's Disease (AD), amyotrophic lateral sclerosis (ALS), Huntington's disease, body myositis, myofibrilar myopathy, GVHD, and multiple myeloma.

The compounds of Formula (I), (I(a)), (I(b)) or (I(b)-(i)) can form salts. Reference to a compound of Formula (I), (I(a)), (I(b)) or (I(b)-(i)) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I), (I(a)), (I(b)) or (I(b)-(i)) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula (I), (I(a)), (I(b)) or (I(b)-(i)) may be formed, for example, by reacting a compound of Formula (I), (I(a)), (I(b)) or (I(b)-(i)) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additional exemplary acids are those generally considered suitable for the formation of pharmaceutically useful salts from basic pharmaceutical compounds, and are discussed, for example, by P. Stahl et al. Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986), 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts, and all acid and base salts are considered equivalent to the free forms of the corresponding compounds (for example, a compound of Formula (I), (I(a)), (I(b)) or (I(b)-(i)).

Compounds described herein may contain asymmetric or chiral centers, and, therefore, exist in different stereoisomeric forms. It is intended that all stereoisomeric forms of a compound describe herein (such as a compound of Formula (I), (I(a)), (I(b)) or (I(b)-(i)) as well as mixtures thereof, including racemic mixtures, form part of the described compound. In addition, all geometric and positional isomers are included in a compound described herein. For example, if a compound of Formula (I), (I(a)), (I(b)) or (I(b)-(i)) incorporates a double bond or a fused ring, both the cis- and trans-forms, as well as mixtures, are embraced.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Enantiomers can also be separated by use of chiral HPLC column. Also, some of the compounds of Formula (I), (I(a)), (I(b)) or (I(b)-(i)) may be atropisomers (e.g., substituted biaryls) and are considered as part of Formula (I), (I(a)), (I(b)) or (I(b)-i)).

It is also possible that compounds described herein (for example, a compound of Formula (I), (I(a)), (I(b)) or (I(b)-(i)) may exist in different tautomeric forms, and all such forms are embraced. Also, for example, all keto-enol and imine-enamine forms of the compounds described herein are included.

All stereoisomers (for example, geometric isomers, optical isomers and the like) of the compounds described herein (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the compounds described herein, as are positional isomers (such as, for example, 4-pyridyl and 3-pyridyl). (For example, if a compound of Formula (I), (I(a)), (I(b)) or (I(b)-(i)) incorporates a double bond or a fused ring, both the cis- and trans-forms, as well as mixtures) are embraced. Individual stereoisomers of the compounds described herein, for example, may be substantially free of other isomers, or may be admixed, for example, as racemates or with all other, or other selected, stereoisomers. The chiral centers can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the compounds described herein.

Isotopically-labelled compounds of the compounds described herein which are identical to those recited herein, but for the fact that one or more atoms are replaced by an atom having an atomic mass or mass number different from the atomic mass or mass number usually found in nature are also embraced. Examples of isotopes that can be incorporated into compounds described herein include isotopes of hydrogen, carbon, nitrogen, oxygen, phosphorus, fluorine and chlorine and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$ and $^{123}I$, respectively.

Certain isotopically-labelled compounds of Formula (I), (I(a)), (I(b)) or (I(b)-(i)) (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Certain isotopically-labelled compounds of Formula (I), (I(a)), (I(b)) or (I(b)-(i)) can be useful for medical imaging purposes, for example, those labeled with positron-emitting isotopes like $^{11}C$ or $^{18}F$ can be useful for application in Positron Emission Tomography (PET) and those labeled with gamma ray emitting isotopes like $^{123}I$ can be useful for application in Single photon emission computed tomography (SPECT). Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Further, substitution with heavier isotopes such as deuterium (i.e., $^{2}H$) may afford certain therapeutic advantages resulting from greater metabolic stability (e.g., increased in vivo half-life or reduced dosage requirements), and hence, may be preferred in some circumstances. Additionally, isotopic substitution at a site where epimerization occurs may slow or reduce the epimerization process and thereby retain the more active or efficacious form of the compound for a longer period of time. Isotopically labeled compounds of Formula (I), (I(a)), (I(b)) or (I(b)-(i)), in particular those containing isotopes with longer half-lives ($T_{1/2}>1$ day), can generally be prepared by following procedures analogous to those disclosed in the Examples herein below, by substituting an appropriate isotopically labeled reagent for a non-isotopically labeled reagent.

Utility

Given the evidence that immunoproteasomes (e.g., LMP-2 and/or LMP-7) are important in the regulation of various immune responses and the selective expression of LMP-2 and/or LMP-7 in tissues that contain the immunoproteasome, inhibitors of LMP-2 and/or LMP-7 can be used for the treatment of autoimmune disorders. Autoimmune disorders are characterized by inappropriate reaction of the immune system to the host's healthy organs and tissues. Examples of autoimmune disorders that could be treated with an LMP-2 and/or LMP-7 inhibitors include but are not limited to lupus, rheumatoid arthritis, scleroderma, ankylosing spondylitis, dermatomyositis, psoriasis, multiple sclerosis and inflammatory bowel disease (such as ulcerative colitis and Crohn's disease). Another example of an autoimmune disease is Sjogren's Syndrome (SS), which is characterized by infiltration and focal accumulation of lymphocytes in the exocrine glands. It has been shown that there is a significant up-regulation of LMP7 in the salivary glands of Sjogren's patients (see Egerer et al, 2006. Tissue-specific up-regulation of the proteasome subunit beta5i (LMP7) in Sjögren's syndrome. Arthritis Rheum 54:1501-8). Thus, treatment of SS patients with an immunoproteasome inhibitor can mitigate the symptoms of the disease. In addition to autoimmune diseases, tissue/organ transplant rejection occurs when the immune system attacks therapeutic cells that are introduced to the host's body. Graft versus host disease (GVHD), resulting from allogenic transplantation, arises when the immune cells from the donor tissue attack the host's tissues. Therefore, GVHD is another potential utility of treatment with an immunoproteasome inhibitor.

In addition to autoimmune diseases, immunoproteasome inhibitors can be used in circumstances when chronic or acute inflammation leads to tissue damage or loss of function. Proteasome inhibitors have been shown to have anti-inflammatory activity (see Elliot et al. Proteasome inhibition: a new anti-inflammatory strategy. 2003. J Mol Med. 81:235-245). Examples of inflammatory diseases in which treatment with an immunoproteasome inhibitor may have utility include acute conditions (e.g., bronchitis, conjunctivitis, pancreatitis) and chronic conditions (e.g., chronic cholecstitis, hepatitis, bronchiectasis, aortic valve stenosis, restenosis, Behçet's disease, psoriasis and arthritis), along with conditions associated with inflammation (such as fibrosis, infection and ischemia). Behçet's disease (BD) is a chronic, relapsing, inflammatory multisystem disease of unknown etiology. Oral ulcers, genital ulcers, cutaneous lesions, and ocular and articular involvement are the most frequent features of the disease. Accordingly, immunoproteasome inhibitors may be used to treat one or more of oral ulcers, genital ulcers, cutaneous lesions, and ocular and articular involvement.

Upregulation of the immunoproteasome has been detected in response to cardiovascular inflammation potentially resulting in vascular cell apoptosis (see Zang et al. 2009. Cardiovascular inflammation and lesion cell apoptosis: a novel connection via the interferon-inducible immunoproteasome. Arterioscler Thromb Vase Biol. 29:1213-1219), thus, providing utility in cardiovascular disease. Upregulation of the immunoproteasome has also been detected in liver biopsies of patients with chronic active hepatitis, cirrhosis and steatohepatitis (see French, et al. The immunoproteasome in steatohepatitis: Its role in Mallory-Denk body formation. 2011, Experimental and Molecular Pathology 90: 252-256), thus, providing utility in treating chronic liver inflammation. Another chronic inflammatory condition characterized by tissue damage is Alzheimer's Disease (AD) in which microglia, the resident macrophages in the brain, are stimulated to release various proinflammatory cytokines. Increased expression of the immunoproteasome has been found in brain tissue from AD patients compared to control elderly adults not exhibiting symptoms of dementia (see Mishto et al. Immunoproteasome and LMP2 polymorphism in aged and Alzheimer's disease brains. 2006. Neurobiol Aging 27:54-66). In addition, inclusion body myositis and myofibrilar myopathy are muscle diseases that show protein accumulation and increased immunoproteasome expression (see Ferrer et al. 2004. Proteasomal expression, induction of immunoproteasome subunits and local MHC class I presentation in myofibrillar myopathy and inclusion body myositis. J Neuropathol Exp Neurol. 63:484-498). Therefore, treatment of AD patients or other neurodegenerative conditions (such as amyotrophic lateral sclerosis (ALS), and Huntington's disease resulting from chronic inflammation in response to accumulation of protein aggregates) with an immunoproteasome inhibitor constitute additional potential utilities.

Duchene muscular dystrophy (DMD) is an inherited disease, characterized by progressive muscle degeneration and weakness. The disease is caused by a mutation of the DMD gene which leads to deficiency of dystrophin, a protein found throughout the cyctoplasmic face of the plasma membrane in both skeletal and cardiac muscle. Becker muscular dystrophy (BMD), a much milder allelic form of the disease is caused by a reduction in the amount, or an alteration in the size, of the dystrophin protein. These diseases may also be treated by the presently disclosed immunoproteasome inhibitors.

Idiopathic inflammatory myopathies (IIMs) are muscle diseases characterized by muscle weakness and specific inflammatory infiltrates in muscle. These diseases can be classified as polymyositis, sporadic inclusion body myositis (sIBM), dermatomyositis (DM) and immune-mediated necrotizing myopathies (IMNM). These diseases may also be treated by the presently disclosed immunoproteasome inhibitors.

Targeted inhibition of immunoproteasome is also a potent strategy against models of multiple myeloma that overcome resistance to conventional drugs and nonspecific proteasome inhibitors. Accordingly multiple myeloma may also be treated by the presently disclosed immunoproteasome inhibitors.

Testing

The immunoproteasome inhibitory activity of the compounds described herein can be tested using the in vitro assays described in Biological Examples below. A determination of the immunoproteasome inhibitory activity by any of those assays is considered to be immunoproteasome inhibitory activity within the scope of this disclosure even if any or all of the other assays do not result in a determination of immunoproteasome inhibitory activity. The residence time of the compound immunoproteasome bound complexes can be tested using the Biological Example 5 and 6 below. The ability of the compounds described herein to form reversible covalent bond with the immunoproteasome can be determined by the assays described in Biological Examples 4-6 below (please confirm if this is correct).

Without being bound to any specific mechanistic theory, when a compound described herein forms a reversible covalent bond with a cysteine of the immunoproteasome, it is believed that the cysteine sulfhydryl group and a carbon atom forming part of the carbon-carbon double bond in the Y group of Formula (I) where R2 is a group of formula (a) or (b) (see Formula (I)) can form a reversible, i.e., labile, covalent bond, defined herein, such as wherein Cys48 of LMP7 attacks an electron deficient carbon atom of the carbon-carbon double bond in the group of formula (a) or (b) in the compound of Formula (I) to form a thiol adduct (e.g., Michael reaction with cysteine).

Furthermore, all the subunits of an immunoproteasome contain a catalytic threonine residue which can interact with the boronic acid/boronic esters through labile covalent binding (see for example Reem Smoum eta al., "Boron Containing Compounds as Protease Inhibitors", *Chemical Reviews*, 2012, 112, 4156-4220.) In some embodiments, the electron deficient carbon atom of the olefin is distal to the carbon attached to the cyano group and to the electron withdrawing —$X^1NR^6R^7$ or Het, moiety in the compounds described herein. Therefore, the combination of the cyano, a second electron withdrawing group and the olefinic moiety to which they are bonded in a compound described herein (for example, a compound of Formula (I)) can increase the reactivity of the olefin to form a thiol adduct with the active site cysteine residue in LMP7.

The compounds described herein can bind with the immunoproteasome in several different manners. In addition to the labile covalent binding, discussed above (with respect to the cysteine —SH group and the threonine —OH group), they also can form non-covalent binding (e.g., via van der Waals binding, hydrogen binding, hydrophobic binding, hydrophilic binding, and/or electrostatic charge binding) with the immunoproteasome, the non-covalent binding being sufficient to at least partially inhibit the kinase activity of the immunoproteasome As disclosed herein, with regard to LMP7, one of the labile covalent bindings between compound described herein and the immunoproteasome occurs between the olefin mentioned above in the compound and the thiol (sulfydryl) residue of cysteine 48 of LMP7, at or near the site where the compound has the aforementioned non-covalent binding with the LMP7.

Therefore, a compound described herein, which form a reversible covalent bond with the immunoproteasome, can have both a cysteine-mediated covalent binding (in the case of LMP7) and threonine-mediated covalent binding (for all subunits of immunoproteasome) and a non-covalent binding. This is in contrast with non-covalent reversible inhibitors which inhibit the immunoproteasome only via non-covalent binding and lack the cysteine-mediated and/or the threonine-mediated covalent binding.

The result of the binding of compound described herein (for example, a compound of Formula (I)) with the immunoproteasome in the several different manners as disclosed herein is a reversible covalent inhibitor having a slow off-rate and a protracted duration of action, in some instances comparable to an irreversible covalent inhibitor without forming permanent irreversible protein adducts. The difference between irreversible and reversible covalent inhibitors, particularly the compounds disclosed herein, can be ascertained utilizing assays disclosed herein.

In general, the binding involved in an inhibitor that forms a reversible covalent bond with the immunoproteasome, i.e., the compounds disclosed herein, is stable when the immunoproteasome/immunoproteasome subunit is in certain configurations and susceptible to being broken when the immunoproteasome/immunoproteasome subunit is in different configurations (in both cases under physiologic conditions), whereas the interaction between an inhibitor that forms an irreversible covalent bond is stable under physiologic conditions even when the immunoproteasome/immunoproteasome subunit is in different configurations.

A reversible covalent bond often imparts unique properties related to the residence time of the compound within the cysteine-containing and/or threonine-containing binding site. In this context, residence time refers to the temporal duration of the compound-target complex under different conditions (see Copeland R A, Pompliano D L, Meek T D. Drug-target residence time and its implications for lead optimization. Nat. Rev. Drug Discov. 5(9), 730-739 (2006)).

The presence of a reversible covalent bond in a reversible covalent inhibitor as disclosed herein can lead to an extended residence time when compared to a compound that does not form a covalent bond with the immunoproteasome/immunoproteasome subunit. In some embodiments disclosed herein, a compound described herein (for example, a compound of Formula (I)) that are reversible covalent inhibitors have a residence time of at least about 1 h, Residence time may be measured using wash-out assay in a biochemical or cellular environment (see Biological Examples 4-6 below.) A determination of the binding reversibility of the covalent bond between the cysteine residue and the olefinic bond (in the case of LMP7) and between the threonine residue and the boronic acid/ester (in the case of all immunoproteasome subunits) of the compounds described herein by any of the Biological Examples 4-6 below is considered to be binding reversibility within the scope of this disclosure even if one or the other method does not result in a determination of binding reversibility.

Administration and Pharmaceutical Composition

In general, the compounds described herein will be administered in a therapeutically effective amount by any of the accepted modes of administration for agents that serve similar utilities. Therapeutically effective amounts of a compound described herein may range from about 0.01 to about 500 mg per kg patient body weight per day, which can be administered in single or multiple doses. A suitable dosage level may be from about 0.1 to about 250 mg/kg per day; about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage can be about 0.05 to about 0.5, about 0.5 to about 5 or about 5 to about 50 mg/kg per day. For oral administration, the compositions can be provided in the form of tablets containing about 1.0 to about 1000 milligrams of the active ingredient, particularly about 1, 5, 10, 15, 20, 25, 50, 75, 100, 150, 200, 250, 300, 400, 500, 600, 750, 800, 900, and 1000 milligrams of the active ingredient. The actual amount of the compound, i.e., the active ingredient, will depend upon numerous factors such as the severity of the disease to be treated, the age and relative health of the patient, the potency of the compound being utilized, the route and form of administration, and other factors.

In general, compounds described herein will be administered as pharmaceutical compositions by any one of the following routes: oral, systemic (e.g., transdermal, intranasal or by suppository), parenteral (e.g., intramuscular, intravenous or subcutaneous) or topical (e.g., application to skin) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules, including enteric coated or delayed release tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1.000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound described herein) in combination with at least one pharmaceutically acceptable excipient. Acceptable excipients are non-toxic, aid administration, and do not adversely affect the therapeutic benefit of the compound. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be chosen from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound described herein in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 20th ed., 2000).

The level of the compound in a formulation can vary within the full range employed by those skilled in the art. Typically, the formulation will contain, on a weight percent (wt %) basis, from about 0.01-99.99 wt % of a compound described based on the total formulation, with the balance being one or more suitable pharmaceutical excipients. Preferably, the compound is present at a level of about 1-80 wt %.

A compound described herein may be used in combination with one or more other drugs in the treatment of diseases or conditions for which a compound described herein or the other drugs may have utility, where the combination of the drugs together are safer or more effective than either drug alone. Such other drug(s) may be administered, by a route and in an amount commonly used therefore, contemporaneously or sequentially with a compound described herein. When a compound described herein is used contemporaneously with one or more other drugs, a pharmaceutical composition in unit dosage form containing such other drugs and a compound described herein is preferred. However, the combination therapy may also include therapies in which a compound described herein and one or more other drugs are administered on different overlapping schedules. It is also contemplated that when used in combination with one or more other active ingredients, a compound described herein and the other active ingredients may be used in lower doses than when each is used singly.

Accordingly, a pharmaceutical composition described herein also can include those that contain one or more other active ingredients, in addition to a compound described herein.

SYNTHETIC EXAMPLES

Example 1

((R)-1-(3-(((R)-1-(2-cyano-4-methylpent-2-enoyl)pyrrolidin-2-yl)methoxy)propanamido)-2-phenylethyl)boronic acid

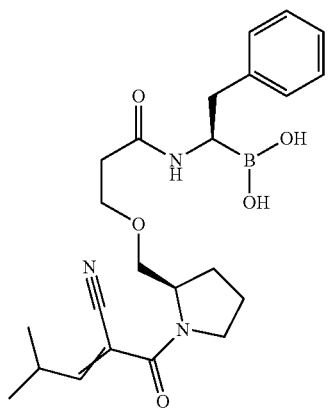 [SMILES: CC(C)C=C(C#N)C(=O)N1CCC[C@@H]1COCCC(=O)N[C@@H](Cc1ccccc1)B(O)O]

Step 1

To a cooled (−50° C.), stirred suspension of NaH (1.6 g, 60% dispersion in mineral oil, 40 mmol) in THF (50 mL) was added (R)-tert-butyl 2-(hydroxymethyl)pyrrolidine-1-carboxylate (4 g, 20 mmol) in THF (15 mL) over 5 min. After stirring for 15 min, methyl acrylate (3.96 g, 46 mmol) was added to the reaction mixture at −50° C. and stirred for additional 15 min. The mixture was warmed up to −40° C. and for 2 h, then acidified with AcOH (1 mL), diluted with ice water and extracted with EtOAc (3×50 mL). The combined organic layer was dried over $Na_2SO_4$ and concentrated. The residue was purified by column chromatography on silica gel, eluting with 15% of EtOAc in petroleum ether to afford (R)-tert-butyl 2-((3-methoxy-3-oxopropoxy)methyl)pyrrolidine-1-carboxylate (1.5 g, 26%) as a yellow oil.

Step 2

A solution of (R)-tert-butyl 2-((3-methoxy-3-oxopropoxy)methyl)pyrrolidine-1-carboxylate (1.5 g, 5.2 mmol) and LiOH (250 mg, 10.4 mmol) in THF (15 mL) and water (5 mL) was stirred 16 h at room temperature (rt). The mixture was concentrated, and the resulting solution was diluted with EtOAc (15 mL) and water (15 mL). The aqueous layer was adjusted to pH=2 with 1 N HCl aqueous solution and extracted with EtOAc (3×15 mL). The combined organic layer was dried over $Na_2SO_4$ and concentrated to afford (R)-3-((1-(tert-butoxycarbonyl)pyrrolidin-2-yl)methoxy)propanoic acid as a yellow solid (1.2 g, 86%), which was used without further purification.

Diisopropylethylamine (1.2 g, 9.68 mmol) was added to stirred solution of (R)-3-((1-(tert-butoxycarbonyl)pyrrolidin-2-yl)methoxy)propanoic acid (1.2 g, 4.4 mmol), (R)-2-phenyl-1-((3aS,4S,6S,7aR)-3a,5,5-trimethylhexahydro-4,6-methanobenzo[d][1,3,2]dioxaborol-2-yl)ethanamine (1.5 mg, 4.4 mmol) and HATU (1.8 g, 4.8 mmol) in DMF (5 mL) at it. The mixture was stirred at it for 2 h, then quenched with water (10 mL) and filtered to afford (R)-tert-butyl 2-((3-oxo-3-(((S)-2-phenyl-1-((3aS,4S,6S,7aR)-3a,5,5-trimethylhexahydro-4,6-methanobenzo[d][1,3,2]dioxaborol-2-yl)ethyl)amino)propoxy)methyl)pyrrolidine-1-carboxylate as a yellow solid (900 mg), which was used without further purification.

Step 4

A solution of (R)-tert-butyl 2-((3-oxo-3-(((S)-2-phenyl-1-((3aS,4S,6S,7aR)-3a,5,5-trimethylhexahydro-4,6-methanobenzo[d][1,3,2]dioxaborol-2-yl)ethyl)amino)propoxy)methyl)pyrrolidine-1-carboxylate (900 mg, crude) and HCl (4 mL, 4 M in dioxane) in dioxane (4 mL) was stirred at rt for 2 h, then concentrated in vacuo. The residue was adjusted to pH=8 with sodium bicarbonate aqueous solution and extracted with EtOAc (20 mL×3). The combined organic layer was dried over $Na_2SO_4$ and concentrated to afford N—((S)-2-phenyl-1-((3aS,4S,6S,7aR)-3a,5,5-trimethylhexahydro-4,6-methanobenzo[d][1,3,2]dioxaborol-2-yl)ethyl)-3-((R)-pyrrolidin-2-ylmethoxy)propanamide as a yellow solid (800 mg), which was used without further purification.

Step 5

DIPEA (500 mg, 3.87 mmol) was added to a stirred solution of N—((S)-2-phenyl-1-((3aS,4S,6S,7aR)-3a,5,5-trimethylhexahydro-4,6-methanobenzo[d][1,3,2]dioxaborol-2-yl)ethyl)-3-((R)-pyrrolidin-2-ylmethoxy)propanamide (800 mg, 1.76 mmol), 2-cyano-4-methylpent-2-enoic acid (245 mg. 1.76 mmol) and BOP (858 mg, 1.94 mmol) in DMF (5 mL) at rt. After stirring at rt for 2 h, the reaction was quenched with water (20 mL) and diluted with EtOAc (40 mL), then washed with brine (2×5 mL), dried over $Na_2SO_4$ and concentrated in vacuo. The crude residue was purified by Prep-HPLC to afford 3-(((R)-1-(2-cyano-4-methylpent-2-enoyl)pyrrolidin-2-yl)methoxy)-N—((S)-2-phenyl-1-((3aS,4S,6S,7aR)-3a,5,5-trimethylhexahydro-4,6-methanobenzo[d][1,3,2]dioxaborol-2-yl)ethyl)propanamide as a white solid (200 mg).

Step 6

To a solution of 3-(((R)-1-(2-cyano-4-methylpent-2-enoyl)pyrrolidin-2-yl)methoxy)-N—((S)-2-phenyl-1-((3aS,4S,6S,7aR)-3a,5,5-trimethylhexahydro-4,6-methanobenzo[d][1,3,2]dioxaborol-2-yl)ethyl)propanamide (200 mg, 0.35 mmol) in MeOH (5 mL) were added hexane (5 mL) and 1N HCl (1 mL), followed by isobutyl boronic acid (106 mg, 1.04 mmol). After stirring at it for 3 h and monitoring by LCMS, the hexane layer was discarded. The methanol layer was diluted with water (10 mL) and freeze dried directly to give a crude product. This crude product was further purified with neutral $Al_2O_3$ column (Methanol/DCM=0-20% as eluent) to afford the title compound as a yellow solid (46 mg). LC-MS m/z: 424.2.

Example 2

((R)-1-(((((R)-1-(2-cyano-4-methylpent-2-enoyl)piperidin-2-yl)methoxy)carbonyl)amino)-2-phenylethyl)boronic acid

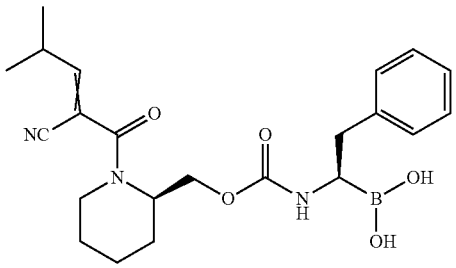 [SMILES: CC(C)C=C(C#N)C(=O)N1CCCC[C@@H]1COC(=O)N[C@@H](Cc1ccccc1)B(O)O]

Step 1

Into a 50-mL round-bottom flask was placed a solution of tert-butyl (2R)-2-(hydroxymethyl)piperidine-1-carboxylate (1 g, 4.6 mmol, 1.0 eq.) in dichloromethane (10 mL), pyridine (900 mg, 11.4 mmol, 2.5 eq.), and 4-nitrophenyl chloroformate (1.03 g, 5.11 mmol, 1.1 eq.). The resulting solution was stirred for 2 h at rt. The reaction was then quenched by the addition of 10 mL of $NH_4Cl$. The mixture was dried over anhydrous sodium sulfate and concentrated under vacuum. The residue was applied onto a silica gel column and eluted with ethyl acetate/petroleum ether (10:90). This gave tert-butyl (2R)-2-[[(4-nitrophenoxycarbonyl)oxy]methyl]piperidine-1-carboxylate (1.4 g) as a yellow solid.

Step 2

Into a 25-mL round-bottom flask was placed a solution of tert-butyl (2R)-2-[[(4-nitrophenoxycarbonyl)oxy]methyl]piperidine-1-carboxylate (150 mg, 0.39 mmol, 1.00 eq.) in dichloromethane (3 mL), followed by DIEA (153 mg, 1.18 mmol, 3.00 eq.), and (R)-2-phenyl-1-((3aS,4S,6S,7aR)-3a,5,5-trimethylhexahydro-4,6-methanobenzo[d][1,3,2]dioxaborol-2-yl)ethanamine hydrochloride (133 mg, 0.40 mmol, 1.00 eq.). The resulting solution was stirred 14 h at rt and then concentrated under vacuum. The residue was applied onto a silica gel column and eluted with petroleum ether: ethyl acetate (4:1). This gave (R)-tert-butyl 2-(((((R)-2-phenyl-1-((3aS,4S,6S,7aR)-3a,5,5-trimethylhexahydro-4,6-methanobenzo[d][1,3,2]dioxaborol-2-yl)ethyl)carbamoyl)oxy)methyl)piperidine-1-carboxylate (40 mg) as a colorless oil.

Step 3

Into a 25-mL round-bottom flask was added a solution of (R)-tert-butyl 2-(((((R)-2-phenyl-1-((3aS,4S,6S,7aR)-3a,5,5-trimethylhexahydro-4,6-methanobenzo[d][1,3,2]dioxaborol-2-yl)ethyl)carbamoyl)oxy)methyl)piperidine-1-carboxylate (130 mg, 0.24 mmol, 1.00 eq.) in dichloromethane (3 mL) and trifluoroacetic acid (1 mL). The resulting solution was stirred for 1 h at it. The resulting mixture was concentrated under vacuum and afforded (R)-piperidin-2-ylmethyl ((R)-2-phenyl-1-((3aS,4S,6S,7aR)-3a,5,5-trimethylhexahydro-4,6-methanobenzo[d][1,3,2]dioxaborol-2-yl)ethyl)carbamate (105 mg) as a brown oil, which was used directly in the next step.

Step 4

Into a 25-mL round-bottom flask was placed a solution of (R)-piperidin-2-ylmethyl ((R)-2-phenyl-1-((3aS,4S,6S,7aR)-3a,5,5-trimethylhexahydro-4,6-methanobenzo[d][1,3,2]dioxaborol-2-yl)ethyl)carbamate (105 mg, 0.24 mmol, 1.00 eq.) in dichloromethane (2 mL), followed by 2-cyano-4-methylpent-2-enoic acid (40 mg. 0.29 mmol. 1.20 eq.), HATU (136 mg, 0.36 mmol, 1.50 eq.), and DIEA (92.4 mg, 0.71 mmol, 3.00 eq.). The resulting solution was stirred for 1 h at rt. The reaction was then quenched by the addition of water (2 mL). The resulting solution was extracted with dichloromethane, and the organic layers combined and washed with brine. The mixture was dried over sodium sulfate and concentrated under vacuum. The resulting material was purified by Prep-HPLC with the following conditions (SHIMADZU): Column. XBridge Prep C18 OBD Column, mobile phase. Water (0.05% $NH_3H_2O$) and ACN (76% ACN up to 77% in 7 min); Detector, UV 254/220 nm. This gave ((R)-1-(2-cyano-4-methylpent-2-enoyl)piperidin-2-yl)methyl ((R)-2-phenyl-1-((3aS,4S,6S,7aR)-3a,5,5-trimethylhexahydro-4,6-methanobenzo[d][1,3,2]dioxaborol-2-yl)ethyl)carbamate (25 mg) as a white solid.

Step 5

Into a 25-mL round-bottom flask was placed a solution of ((R)-1-(2-cyano-4-methylpent-2-enoyl)piperidin-2-yl)methyl ((R)-2-phenyl-1-((3aS,4S,6S,7aR)-3a,5,5-trimethylhexahydro-4,6-methanobenzo[d][1,3,2]dioxaborol-2-yl)ethyl)carbamate (25 mg, 0.04 mmol, 1.00 eq.) in methanol/Hexane (1/1 mL), 1N HCl (0.9 mL. 20.00 eq.), and (2-methylpropyl)boronic acid (14 mg. 0.14 mmol, 3.00 eq.). The resulting solution was stirred for 2 h at it. The hexane layer was discarded. The methanol layer was diluted with water (6 mL), then frozen and lyophilized to afford the crude product (25 mg). The crude product was purified by Prep-HPLC with the following conditions (SHIMADZU): Column, XBridge Prep C18 OBD Column, 19*150 mm 5 um; mobile phase, Water (0.05% TFA) and ACN (36% ACN up to 46% in 8 min); Detector, uv 254 nm. This gave in isolation [(1R)-1-[([[(2R)-1-[2-cyano-2-(2-methylpropylidene)acetyl]piperidin-2-yl]methoxy]carbonyl)amino]-2-phenylethyl]boronic acid (6.1 mg) as a light yellow solid. LC-MS m/z: 450 (M+Na$^+$). $^1$H NMR (400 MHz, CD3OD) δ 7.29-7.27 (m, 2H), 7.26-7.20 (m, 3H), 6.76-6.75 (m, 1H), 4.67-4.41 (m, 1H), 4.23-4.00 (m, 1H), 3.29-3.25 (m, 4H), 2.92-2.87 (m, 1H), 2.83-2.81 (m, 2H), 1.80-1.71 (m, 5H). 1.55-1.32 (m, 1H), 1.22-1.06 (m, 6H).

Examples 3 and 4

((1R)-1-(3-(1-(2-cyano-4-methylpent-2-enoyl)pyrrolidin-2-yl)propanamido)-2-phenylethyl)boronic acid

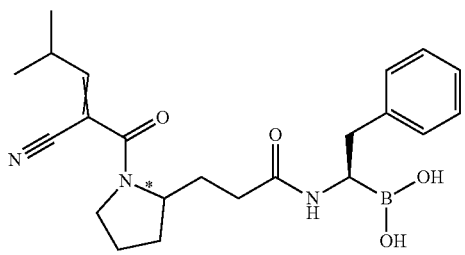

(R)- or (S)- at *C (not assigned)

Step 1

Into a 100-mL round-bottom flask was placed 3-[1-[(tert-butoxy)carbonyl]pyrrolidin-2-yl]propanoic acid (500 mg, 2.06 mmol, 1.00 eq.), (1R)-2-phenyl-1-[(1S,2S,6R,8S)-2,9,9-trimethyl-3,5-dioxa-4-boratricyclo[6.1.1.0^2,6]decan-4-yl]ethan-1-amine hydrochloride (689 mg, 2.05 mmol, 1.00 eq.), EDCI (943 mg, 4.92 mmol, 2.40 eq.), HOBT (667 mg, 4.94 mmol, 2.40 eq.), DIEA (637 mg, 4.93 mmol, 2.40 eq.) and dichloromethane (50 mL). The resulting solution was stirred for 5 h at rt. The resulting solution was extracted with dichloromethane. The organic layers combined, dried over sodium sulfate and concentrated under vacuum. The residue was purified by C18 column with water/MeCN (20%-80% in 30 min). This gave tert-butyl2-(2-[[(1R)-2-phenyl-1-[(1S,2S,6R,8S)-2,9,9-trimethyl-3,5-dioxa-4-boratricyclo[6.1.1.0^[2,6]]decan-4-yl]ethyl]carbamoyl]ethyl)pyrrolidine-1-carboxylate (350 mg) as a yellow oil.

Step 2

Into a 50-mL round-bottom flask was placed tert-butyl 2-(2-[[(1R)-2-phenyl-1-[(1S,2S,6R,8S)-2,9,9-trimethyl-3,5-dioxa-4-boratricyclo[6.1.1.0^[2,6]]decan-4-yl]ethyl]carbamoyl]ethyl)pyrrolidine-1-carboxylate (350 mg, 0.67 mmol, 1.00 eq.), trifluoroacetic acid (2 mL) and dichloromethane (10 mL). The resulting solution was stirred for 2 h at it. The resulting mixture was concentrated under vacuum. The residue was purified by C18 column with water/ACN (20%-80% in min). This resulted N-[(1R)-2-phenyl-1-[(1S,2S,6R,8S)-2,9,9-trimethyl-3,5-dioxa-4-boratricyclo[6.1.1.0^[2,6]]decan-4-yl]ethyl]-3-(pyrrolidin-2-yl)propanamide (280 mg) as a yellow oil.

Step 3

Into a 50-mL round-bottom flask was placed N-[(1R)-2-phenyl-1-[(1S,2S,6R,8S)-2,9,9-trimethyl-3,5-dioxa-4-boratricyclo[6.1.1.0^[2,6]]decan-4-yl]ethyl]-3-(pyrrolidin-2-yl)propanamide (280 mg, 0.66 mmol, 1.00 eq.), 2-cyano-4-methylpent-2-enoic acid (184 mg, 1.32 mmol, 2.00 eq.), HATU (753 mg, 1.98 mmol, 3.00 eq.), DIEA (426 mg, 3.30 mmol, 5.00 eq.) and dichloromethane (15 mL). The resulting solution was stirred for 3 h at rt. The resulting solution was extracted with dichloromethane (3×50 mL). The organic layers combined, dried over anhydrous sodium sulfate and concentrated under vacuum. The crude product was purified by Prep-HPLC with the following conditions (HPLC-SHIMADZU): Column, XBridge Prep C18 OBD Column, 19*150 mm, 5 um; mobile phase, Water (0.05% TFA) and ACN (hold 65.0% ACN in 12 min); Detector, uv 254 nm. This resulted in the separation of two diastereomers. The first eluting fractions afforded 3-(1-(2-cyano-4-methylpent-2-enoyl)pyrrolidin-2-yl)-N—((R)-2-phenyl-1-((3aS,4S,6S,7aR)-3a,5,5-trimethylhexahydro-4,6-methanobenzo[d][1,3,2]dioxaborol-2-yl)ethyl)propanamide (40 mg, 11%, stereochemistry not assigned) as a white solid after the lyophilization. Isolation of the second eluting compound afforded 3-(1-(2-cyano-4-methylpent-2-enoyl)pyrrolidin-2-yl)-N—((R)-2-phenyl-1-((3aS,4S,6S,7aR)-3a,5,5-trimethylhexahydro-4,6-methanobenzo[d][1,3,2]dioxaborol-2-yl) ethyl)propanamide (30 mg, 8%, stereochemistry not assigned) as a white solid after the lyophilization.

Step 4 (Example 3)

The later eluting product 3-(1-(2-cyano-4-methylpent-2-enoyl)pyrrolidin-2-yl)-N—((R)-2-phenyl-1-((3aS,4S,6S,7aR)-3a,5,5-trimethylhexahydro-4,6-methanobenzo[d][1,3,2]dioxaborol-2-yl)ethyl)propanamide (30 mg, 0.05 mmol, 1.00 eq.) was added to a flask followed by (2-methylpropyl)boronic acid (16.8 mg, 0.16 mmol, 3.00 eq.), hydrogen chloride(1N) (0.3 mL), methanol (1.5 mL), and hexane (1.5 mL). The resulting solution was stirred for 3 h at rt. The hexane layer was discarded. The methanol layer was diluted with water (10 mL) and then dried by lyophilization to give a crude product which was purified by Prep-HPLC with the following conditions (HPLC-SHIMADZU): Column, XBridge Prep OBD C18 Column, 19*250 mm, 5 um; mobile phase, Water (0.05% NH$_3$H$_2$O) and ACN (31% ACN up to 51% in 8 min); Detector, uv 220 nm. This resulted ((1R)-1-(3-(1-(2-cyano-4-methylpent-2-enoyl)pyrrolidin-2-yl)propanamido)-2-phenylethyl)boronic acid (11.7 mg, 52%, as a white solid after the lyophilization. LC-MS m/z: 394 (M−17). 1H NMR (300 MHz, Methanol-d4) δ 7.31-7.11 (m, 6H), 6.98 (d, J=10.4 Hz, 1H), 4.06 (s, 1H), 3.63 (s, 2H), 3.57-3.34 (m, 2H), 2.96-2.78 (m, 3H), 2.56 (dd, J=15.8, 11.6 Hz, 1H), 2.42 (t, J=7.7 Hz, 2H), 2.25-1.49 (m, 13H).

Step 4 (Example 4)

The earlier eluting diastereomer 3-(1-(2-cyano-4-methylpent-2-enoyl)pyrrolidin-2-yl)-N—((R)-2-phenyl-1-((3aS,4S,6S,7aR)-3a,5,5-trimethylhexahydro-4,6-methanobenzo[d][1,3,2]dioxaborol-2-yl)ethyl)propanamide (30 mg, 0.05 mmol, 1.00 eq.) was added to a round bottomed flask followed by (2-methylpropyl)boronic acid (17 mg, 0.17 mmol, 3.00 eq.), hydrogen chloride(1N) (1.1 mL, 20.00 eq.), methanol (2 mL) and hexane (2 mL). The resulting solution was stirred for 2 h at rt. The hexane layer was discarded. The methanol layer was diluted with water (10 mL), and then dried by lyophilization to give a crude product. The crude product was purified by Prep-HPLC with the following conditions (SHIMADZU): Column, XBridge Prep C18 OBD Column, 19*150 mm 5 um; mobile phase, Water (10 MMOL/L NH$_4$HCO$_3$+0.1% NH$_3$.H$_2$O) and ACN (30% ACN up to 31% in 7 min); Detector, UV 254/220 nm. This resulted in [(1R)-1-[3-[(2R)-1-[2-cyano-2-(2-methylpropylidene)acetyl]pyrrolidin-2-yl]propanamido]-2-phenylethyl]boronic acid (9.2 mg, 41%, as a white solid after the lyophilization. LC-MS m/z: 394 (M−17) $^1$H NMR (400 MHz. CD3OD) δ 7.29-7.22 (m, 4H), 7.19-7.15 (m, 1H), 7.02-6.99 (m, 1H), 4.18-4.05 (m, 1H). 3.65-3.64 (m, 2H). 2.93-2.86 (m, 3H). 2.59-2.52 (m, 1H). 2.46-2.42 (m, 2H), 2.15-1.99 (m, 3H), 1.91-1.86 (m, 1H), 1.76-1.68 (m, 2H), 1.16-1.13 (m, 6H).

Examples 5 and 6

((1R)-1-(3-(1-(2-cyano-4-methylpent-2-enoyl)piperidin-2-yl)propanamido)-2-phenylethyl)boronic acid

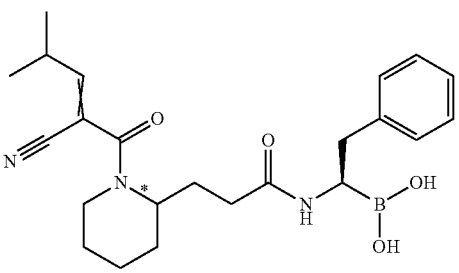

(R)- or (S)- at *C (not assigned)

Step 1

Into a 100-mL round-bottom flask was placed 3-[1-[(tert-butoxy)carbonyl]piperidin-2-yl]propanoic acid (500 mg, 1.94 mmol, 1.00 eq.), (1R)-2-phenyl-1-[(1S,2S,6R,8S)-2,9,9-trimethyl-3,5-dioxa-4-boratricyclo[6.1.1.0^2,6]decan-4-yl]ethan-1-amine hydrochloride (652 mg, 1.94 mmol, 1.00 eq.), EDCI (892 mg, 4.65 mmol, 2.40 eq.), HOBT (630 mg, 4.66 mmol, 2.40 eq.), DIEA (602 mg, 4.66 mmol, 2.40 eq.) and dichloromethane (50 mL). The resulting solution was stirred overnight at rt. The resulting solution was extracted with dichloromethane (3×100 mL) and the organic layers combined. The resulting mixture was washed with saturated sodium chloride (1×100 mL). The mixture was dried over anhydrous sodium sulfate and concentrated under vacuum. The residue was purified by C18 column with water/ACN (20%-100% in 30 min). This resulted in tert-butyl 2-(2-[[(1R)-2-phenyl-1-[(1S,2S,6R,8S)-2,9,9-trimethyl-3,5-dioxa-4-boratricyclo[6.1.1.0^[2.6]]decan-4-yl]ethyl]carbamoyl]ethyl)piperidine-1-carboxylate (460 mg, 44%) as a yellow solid.

Step 2

Into a 100-mL round-bottom flask was placed tert-butyl 2-(2-[[(1R)-2-phenyl-1-[(1S,2S,6R,8S)-2,9,9-trimethyl-3,5-dioxa-4-boratricyclo[6.1.1.0^[2,6]]decan-4-yl]ethyl]carbamoyl]ethyl)piperidine-1-carboxylate (460 mg, 0.85 mmol, 1.00 eq.), trifluoroacetic acid (4 mL) and dichloromethane (20 mL). The resulting solution was stirred for 3 h at rt, and the resulting mixture was concentrated under vacuum. This resulted in N-[(1R)-2-phenyl-1-[(1S,2S,6R,8S)-2,9,9-trimethyl-3,5-dioxa-4-boratricyclo[6.1.1.0^[2,6]]decan-4-yl]ethyl]-3-(piperidin-2-yl)propanamide (370 mg, 99%) as a brown oil, which was used directly in the next step.

Step 3

Into a 50-mL round-bottom flask was placed N-[(1R)-2-phenyl-1-[(1S,2S,6R,8S)-2,9,9-trimethyl-3,5-dioxa-4-boratricyclo[6.1.1.0^[2,6]]decan-4-yl]ethyl]-3-(piperidin-2-yl)propanamide (160 mg, 0.36 mmol. 1.00 eq.). 2-cyano-4-methylpent-2-enoic acid (101 mg, 0.73 mmol. 2.00 eq.), HATU (416 mg, 1.09 mmol, 3.00 eq.), DIEA (236 mg, 1.83 mmol, 5.00 eq.), and dichloromethane (16 mL). The resulting solution was stirred for 3 h at rt. The resulting solution was extracted with dichloromethane (3×50 mL) and the organic layers combined. The resulting mixture was washed with saturated sodium chloride (1×50 mL). The mixture was dried over anhydrous sodium sulfate and concentrated under vacuum. The crude product was purified by Prep-HPLC with the following conditions (SHIMADZU): Column, XBridge Prep C18 OBD Column, 19*150 mm 5 um; mobile phase, Water (0.05% TFA) and ACN (hold 68.0% ACN in 13 min); Detector, uv 254 nm. The first eluting fractions were lyophilized to afford 3-(1-(2-cyano-4-methylpent-2-enoyl)piperidin-2-yl)-N—((R)-2-phenyl-1-((3aS,4S,6S,7aR)-3a,5,5-trimethylhexahydro-4,6-methanobenzo[d][1,3,2]dioxaborol-2-yl)ethyl)propanamide (10 mg, 5%) as a yellow solid. The later eluting fractions were lyophilized to afford 3-(1-(2-cyano-4-methylpent-2-enoyl)piperidin-2-yl)-N—((R)-2-phenyl-1-((3aS,4S,6S,7aR)-3a,5,5-trimethylhexahydro-4,6-methanobenzo[d][1,3,2]dioxaborol-2-yl)ethyl)propanamide (10 mg, 5%) as a yellow solid after the lyophilization.

Step 4 (Example 5)

Into a 8-mL vial, was placed the earlier eluting diastereomer of 3-(1-(2-cyano-4-methylpent-2-enoyl)piperidin-2-yl)-N—((R)-2-phenyl-1-((3aS,4S,6S,7aR)-3a,5,5-trimethylhexahydro-4,6-methanobenzo[d][1,3,2]dioxaborol-2-yl)ethyl)propanamide (10 mg, 0.02 mmol, 1.00 eq.), (2-methylpropyl)boronic acid (5.5 mg, 0.05 mmol, 3.00 eq.), hydrogen chloride(1N) (0.1 mL), methanol (0.5 mL) and hexane (0.5 mL). The resulting solution was stirred for 3 h at rt. The hexane layer was discarded. The methanol layer was diluted water (10 mL) and then dried over lyophylization to give a crude product. The crude product was purified by Prep-HPLC with the following conditions (SHIMADZU): Column, XBridge Prep C18 OBD Column, 19*150 mm 5 um; mobile phase, Water (10 MMOL/L $NH_4HCO_3$+0.1% $NH_3.H_2O$) and ACN (32.0% ACN up to 33.0% in 7 min); Detector, UV 254/220 nm. This resulted in ((1R)-1-(3-(1-(2-cyano-4-methylpent-2-enoyl)piperidin-2-yl)propanamido)-2-phenylethyl)boronic acid (2 mg) as a white solid after the lyophilization. LC-MS m/z: 408 (M−17). $^1$H NMR (300 MHz, $CD_3OD$) δ 7.25-7.12 (m, 6H). 6.76 (d, J=10.2 Hz, 1H), 4.60-4.50 (m, 1H), 3.80-3.60 (m, 1H), 2.90-2.82 (m, 3H), 2.59-2.50 (m, 1H), 2.35-2.31 (m, 2H), 2.23-2.13 (m, 1H), 1.88-1.46 (m, 9H). 1.13-1.03 (m, 7H).

Step 4 (Example 6)

Into a 8-mL vial, was placed the later eluting diastereomer of 3-(1-(2-cyano-4-methylpent-2-enoyl)piperidin-2-yl)-N—((R)-2-phenyl-1-((3aS,4S,6S,7aR)-3a,5,5-trimethylhexahydro-4,6-methanobenzo[d][1,3,2]dioxaborol-2-yl)ethyl)propanamide (10 mg, 0.02 mmol, 1.00 eq.), (2-methylpropyl)boronic acid (5.5 mg, 0.05 mmol, 3.00 eq.), hydrogen chloride(1N) (0.1 mL), methanol (0.5 mL) and hexane (0.5 mL). The resulting solution was stirred for 3 h at rt. The hexane layer was discarded. The methanol layer was diluted with water (10 mL) and then dried via lyophilization to give a crude product. The crude product was purified by Prep-HPLC with the following conditions (SHIMADZU): Column, XBridge Prep C18 OBD Column, 19*150 mm 5 um; mobile phase, Water (10 MMOL/L $NH_4HCO_3$+0.1% $NH_3.H_2O$) and ACN (32.0% ACN up to 33.0% in 7 min); Detector, UV 254/220 nm. This resulted in [(1R)-1-[3-[(2S)-1-[2-cyano-2-(2-methylpropylidene)acetyl]piperidin-2-yl]propanamido]-2-phenylethyl]boronic acid (2 mg, 26%) as a white solid after the lyophilization. LC-MS m/z: 408 (M−17). $^1$H NMR (300 MHz, $CD_3OD$) δ 7.25-7.12 (m, 6H), 6.76 (d, J=10.2 Hz, 1H), 4.60-4.50 (m, 1H), 3.80-3.60 (m, 1H), 2.90-2.79 (m, 3H), 2.61-2.51 (m, 1H), 2.37-2.12 (m, 3H), 1.89-1.26 (m, 9H), 1.13-1.03 (m, 7H).

Example 7

((R)-1-(((((R)-1-(2-cyano-4-methylpent-2-enoyl)pyrrolidin-2-yl)methoxy)carbonyl)amino)-2-phenylethyl)boronic acid

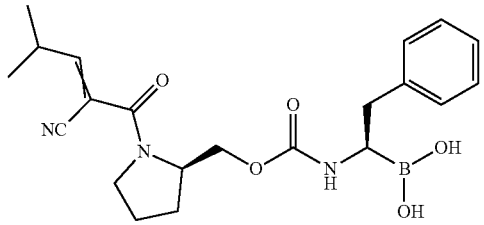 [SMILES: CC(C)C=C(C#N)C(=O)N1CCC[C@@H]1COC(=O)N[C@@H](Cc1ccccc1)B(O)O]

Step 1

Into a 50-mL round-bottom flask was placed tert-butyl (2R)-2-(hydroxymethyl)pyrrolidine-1-carboxylate (1 g, 4.97 mmol, 1.00 eq.), dichloromethane (30 mL), pyridine (982 mg, 12.41 mmol, 2.50 eq.), and 4-nitrophenyl chloroformate (1.10 g, 5.45 mmol, 1.00 eq.). The resulting solution was stirred for overnight at rt. The reaction was then quenched by the addition of NH₄Cl (aq.). The DCM layer was dried over anhydrous sodium sulfate and concentrated under vacuum. The residue was purified by Prep-TLC with ethyl acetate/petroleum ether (1:5). This resulted in tert-butyl (2R)-2-[[(4-nitrophenoxycarbonyl)oxy]methyl]pyrrolidine-1-carboxylate (1.2 g) as a yellow oil.

Step 2

Into a 25-mL round-bottom flask was placed (1R)-2-phenyl-1-[(1S,2S,6R,8S)-2,9,9-trimethyl-3,5-dioxa-4-boratricyclo[6.1.1.0ˆ[2,6]]decan-4-yl]ethan-1-amine hydrochloride (100 mg. 0.30 mmol, 1.00 eq.), N,N-dimethylformamide (5 mL), DIEA (129.3 mg, 1.00 mmol, 3.36 eq.), and tert-butyl (2R)-2-[[(4-nitrophenoxycarbonyl)oxy]methyl]pyrrolidine-1-carboxylate (146.8 mg, 0.40 mmol, 1.35 eq.). The resulting solution was stirred overnight at rt. The reaction was then quenched by the addition of water. The resulting solution was extracted with of ethyl acetate and the organic layers combined. The resulting mixture was washed with sodium chloride (1×20 mL). The mixture was dried over anhydrous sodium sulfate. The residue was purified by Prep-TLC with ethyl acetate/petroleum ether (1:4). This resulted in tert-butyl (2R)-2-[([[(1R)-2-phenyl-1-[(1S,2S,6R,8S)-2,9,9-trimethyl-3,5-dioxa-4-boratricyclo[6.1.1.0ˆ[2,6]]decan-4-yl]ethyl]carbamoyl]oxy)methyl]pyrrolidine-1-carboxylate (0.1 g, 64%) as a yellow oil.

Into a 25-mL round-bottom flask was added tert-butyl (2R)-2-[([[(1R)-2-phenyl-1-[(1S,2S,6R,8S)-2,9,9-trimethyl-3,5-dioxa-4-boratricyclo[6.1.1.0ˆ[2,6]]decan-4-yl]ethyl]carbamoyl]oxy)methyl]pyrrolidine-1-carboxylate (100 mg, 0.19 mmol. 1.00 eq.) followed by dichloromethane (3 mL) and trifluoroacetic acid (1 mL). The resulting solution was stirred for 2 h at rt. The resulting mixture was concentrated under vacuum. This resulted in (2R)-pyrrolidin-2-ylmethyl N-[(1R)-2-phenyl-1-[(1S,2S,6R,8S)-2,9,9-trimethyl-3,5-dioxa-4-boratricyclo[6.1.1.0ˆ[2,6]]decan-4-yl]ethyl]carbamate (0.08 g) as a yellow oil.

Step 4

Into a 25-mL round-bottom flask was placed (2R)-pyrrolidin-2-ylmethyl N-[(1R)-2-phenyl-1-[(1S,2S,6R,8S)-2,9,9-trimethyl-3,5-dioxa-4-boratricyclo[6.1.1.0ˆ[2,6]]decan-4-yl]ethyl]carbamate (30 mg, 0.07 mmol, 1.00 eq.) followed by N,N-dimethylformamide (2 mL), 2-cyano-4-methylpent-2-enoic acid (14.68 mg. 0.11 mmol, 1.50 eq.). DIEA (22.70 mg, 0.18 mmol, 2.50 eq.), and HATU (40 mg, 0.11 mmol, 1.50 eq.). The resulting solution was stirred for 3 h at it. The reaction was then quenched by the addition of water. The resulting solution was extracted with ethyl acetate, and the organic layers combined. The resulting mixture was washed with sodium chloride, dried over anhydrous sodium sulfate and concentrated under vacuum. The crude product was purified by Prep-HPLC with the following conditions (SHIMADZU): Column, XBridge Prep C18 OBD Column, 19*150 mm 5 um; mobile phase, Water (10 MMOL/L $NH_4HCO_3$+0.1% $NH_3 \cdot H_2O$) and ACN (74.0% ACN up to 75.0% in 7 min); Detector, UV 254/220 nm. This resulted in [(2R)-1-[2-cyano-2-(2-methylpropylidene)acetyl]pyrrolidin-2-yl]methyl N-[(1R)-2-phenyl-1-[(1S,2S,6R,8S)-2,9,9-trimethyl-3,5-dioxa-4-boratricyclo[6.1.1.0ˆ[2,6]]decan-4-yl]ethyl]carbamate (6 mg, 16%) as a white solid after lyophilization.

Step 5

Into a 25-mL round-bottom flask was placed [(2R)-1-[2-cyano-2-(2-methylpropylidene)acetyl]pyrrolidin-2-yl]methyl N-[(1R)-2-phenyl-1-[(1S,2S,6R,8S)-2,9,9-trimethyl-3,5-dioxa-4-boratricyclo[6.1.1.0ˆ[2,6]]decan-4-yl]ethyl]carbamate (10 mg, 0.02 mmol, 1.00 eq.), methanol (1.5 mL), (2-methylpropyl)boronic acid (5.6 mg, 0.05 mmol, 3.01 eq.), hexane (1.5 mL) and 1M hydrogen chloride (0.366 mL). The resulting solution was stirred for ~3 h at rt. The hexane layer was discarded. The methanol layer was diluted with water (6 mL), isolated by lyophilization and then purified by Prep-HPLC with the following conditions (SHIMADZU): Column, XBridge Prep C18 OBD Column, 19*150 mm 5 um; mobile phase, Water (10 MMOL/L $NH_4HCO_3$+0.1% $NH_3 \cdot H_2O$) and ACN (33.0% ACN up to 35.0% in 7 min); Detector, UV 254/220 nm. This resulted in [(1R)-1-[([[(2R)-1-[2-cyano-2-(2-methylpropylidene)acetyl]pyrrolidin-2-yl]methoxy]carbonyl)amino]-2-phenylethyl]boronic acid (4.6 mg, 57%) as a solid after lyophilization. LC-MS m/z: 396 (M−17). $^1H$ NMR (300 MHz, Methanol-$d_4$) δ 7.29-6.89 (m, 6H), 4.18-3.88 (d, J=69.8 Hz, 3H), 3.73-3.41 (m, 2H), 3.27-3.12 (d, J=1.5 Hz, 2H), 2.98-2.61 (m, 3H), 1.94 (d, J=43.4 Hz, 4H), 1.24-0.96 (m, 6H).

Example 8

((R)-1-(((((R)-1-acryloylpiperidin-2-yl)methoxy)carbonyl)amino)-2-phenylethyl)boronic acid

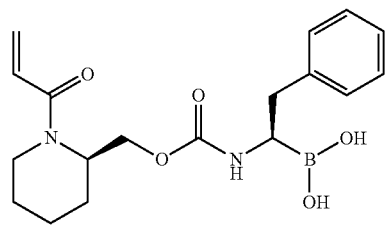 [SMILES: C=CC(=O)N1CCCC[C@@H]1COC(=O)N[C@@H](Cc1ccccc1)B(O)O]

Step 1

To a solution of (R)-piperidin-2-ylmethyl ((R)-2-phenyl-1-((3aS,4S,6S,7aR)-3a,5,5-trimethylhexahydro-4,6-methanobenzo[d][1,3,2]dioxaborol-2-yl)ethyl)carbamate (intermediate from step 3, example 2, 55 mg, 0.12 mmol) and DCM (2 mL) was added acryloyl chloride (0.02 mL, 0.19 mmol). The mixture was stirred at rt for 5 min. The mixture was purified directly by Prep-TLC with 30% EtOAc/Hexane tSHo and gave ((R)-1-acryloylpiperidin-2-yl)methyl ((R)-2-phenyl-1-((3aS,4S,6S,7aR)-3a,5,5-trimethylhexahydro-4,6-methanobenzo[d][1,3,2]dioxaborol-2-yl)ethyl)carbamate (25 mg) as an oil.

Step 2

To a flask charged with ((R)-1-acryloylpiperidin-2-yl)methyl ((R)-2-phenyl-1-((3aS,4S,6S,7aR)-3a,5,5-trimethylhexahydro-4,6-methanobenzo[d][1,3,2]dioxaborol-2-yl)ethyl)carbamate (20 mg, 0.040 mmol), was added methanol (1 mL), hexane (1 mL), 1N HCl (0.5 mL, 0.0400 mmol), and isobutylboronic acid (20.6 mg, 0.200 mmol). The reaction mixture was stirred at rt for 5 h. Hexane layer was removed. The remaining solution was added ACN and water. The mixture was frozen and lyophilized to afford a solid, which was dissolved in minimum amount of DCM and 3 drops of TEA. The solution was purified by Prep-TLC (8% MeOH/DCM) to obtain ((R)-1-(((((R)-1-acryloylpiperidin-2-yl)methoxy)carbonyl)amino)-2-phenylethyl)boronic acid (1.9 mg) after concentration and lyophilization from acetonitrile and water.

Example 9

((R)-1-(((((S)-1-((E)-2-cyano-4,4-dimethylpent-2-enoyl)piperidin-2-yl)methoxy)carbonyl)amino)-2-phenylethyl)boronic acid

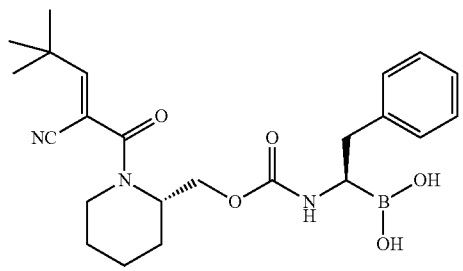 [SMILES: CC(C)(C)/C=C(\C#N)C(=O)N1CCCC[C@H]1COC(=O)N[C@@H](Cc1ccccc1)B(O)O]

Steps 1-3

Following steps 1-3 in synthetic example 2, but replacing (R)-tert-butyl 2-(hydroxymethyl)pyrrolidine-1-carboxylate with (S)-tert-butyl 2-(hydroxymethyl)pyrrolidine-1-carboxylate, afforded (S)-piperidin-2-ylmethyl ((R)-2-phenyl-1-((3aS,4S,6S,7aR)-3a,5,5-trimethylhexahydro-4,6-methanobenzo[d][1,3,2]dioxaborol-2-yl)ethyl)carbamate.

Step 4

To a solution of (S)-piperidin-2-ylmethyl ((R)-2-phenyl-1-((3aS,4S,6S,7aR)-3a,5,5-trimethylhexahydro-4,6-methanobenzo[d][1,3,2]dioxaborol-2-yl)ethyl)carbamate (140 mg. 0.3200 mmol) and (E)-2-cyano-4,4-dimethyl-pent-2-enoic acid (97.39 mg, 0.6400 mmol) in DMF (2 mL) was added DIPEA (0.23 mL, 1.27 mmol). The mixture stirred for 15 min, and HATU was then added (302 mg, 0.790 mmol). After 4 h, additional (E)-2-cyano-4,4-dimethyl-pent-2-enoic acid (1 eq., 50 mg) was added. After 18 h, the mixture was partitioned between DCM (2×50 mL) and water (2×50 mL). The organic layer was dried (MgSO$_4$) and concentrated to an oil, which was purified by silica gel chromatography to collect ((S)-1-(2-cyano-4,4-dimethylpent-2-enoyl)piperidin-2-yl)methyl ((R)-2-phenyl-1-((3aS,4S,6S,7aR)-3a,5,5-trimethylhexahydro-4,6-methanobenzo[d][1,3,2]dioxaborol-2-yl)ethyl)carbamate (140 mg) as a foam.

Step 5

To a solution of ((S)-1-(2-cyano-4,4-dimethylpent-2-enoyl)piperidin-2-yl)methyl ((R)-2-phenyl-1-((3aS,4S,6S,7aR)-3a,5,5-trimethylhexahydro-4,6-methanobenzo[d][1,3,2]dioxaborol-2-yl)ethyl)carbamate (133 mg, 0.23 mmol) in methanol (1.5 mL), hexane (1.5 mL), and 1N HCl (1.0 mL, 0.23 mmol) was added isobutylboronic acid (118 mg, 1.16 mmol). The reaction mixture was stirred at rt for 40 min. The hexane layer was removed, and the remainder purified by Prep-HPLC (MeCN/H$_2$O with 0.1% formic acid). The purified fractions were partitioned between NaHCO$_3$ and DCM. The organic layer concentrated and lyophilized to obtain ((R)-1-(((((S)-1-((E)-2-cyano-4,4-dimethylpent-2-enoyl)piperidin-2-yl)methoxy)carbonyl)amino)-2-phenylethyl)boronic acid 45 mg) as a white powder. LC-MS m/z: 464 (M+23).

Example 10

((R)-1-(((((R)-1-(2-cyano-4,4-dimethylpent-2-enoyl)pyrrolidin-2-yl)methoxy)carbonyl)amino)-2-phenylethyl)boronic acid

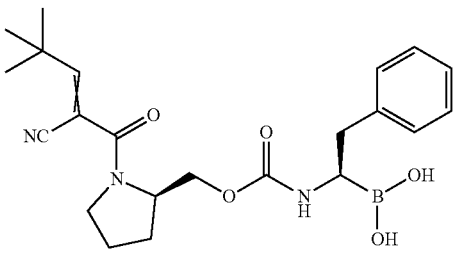 [SMILES: CC(C)(C)C=C(C#N)C(=O)N1CCC[C@@H]1COC(=O)N[C@@H](Cc1ccccc1)B(O)O]

Step 1

Into a 25-mL round-bottom flask was placed tert-butyl (2R)-2-(hydroxymethyl)pyrrolidine-1-carboxylate (500 mg, 2.48 mmol, 1.00 eq.), dichloromethane (10 mL), and DIEA (962 mg, 7.44 mmol, 3.00 eq.), and then dropped in ditrichloromethyl carbonate (365.2 mg, 1.23 mmol, 0.50 eq.)/DCM (5 mL) under 0° C. The resulting solution was stirred for 2-3 h at 0° C. This resultant solution was used directly in the next step.

Step 2

Into a 100-mL round-bottom flask was placed (R)-2-phenyl-1-((3aS,4S,6S,7aR)-3a,5,5-trimethylhexahydro-4,6-methanobenzo[d][1,3,2]dioxaborol-2-yl)ethanamine hydrochloride (693 mg, 2.06 mmol, 1.00 eq.), dichloromethane (24 mL) and DIEA (899.8 mg, 6.96 mmol, 2.00 eq.). The solution of tert-butyl (2R)-2-[[(chlorocarbonyl)oxy]methyl] pyrolidine-1-carboxylate (2.48 mmol, 1.2 eq.) from step 1 was added slowly at 0° C. The resulting solution was stirred for 2-3 h at rt. The resulting mixture was washed with water (1×30 mL) and saturated sodium chloride (1×30 mL). The mixture was dried over anhydrous sodium sulfate and concentrated under vacuum. The residue was applied onto a silica gel column with ethyl acetate/petroleum ether (1:4). This resulted in (R)-tert-butyl 2-((((R)-2-phenyl-1-((3aS,4S,6S,7aR)-3a,5,5-trimethylhexahydro-4,6-methanobenzo[d][1,3,2]dioxaborol-2-yl)ethyl)carbamoyl)oxy)methyl)pyrrolidine-1-carboxylate (0.5 g) as a yellow oil.

Step 3

Into a 25-mL round-bottom flask was placed (R)-tert-butyl 2-(((((R)-2-phenyl-1-((3aS,4S,6S,7aR)-3a,5,5-trimethylhexahydro-4,6-methanobenzo[d][1,3,2]dioxaborol-2-yl)ethyl)carbamoyl)oxy)methyl)pyrrolidine-1-carboxylate (100 mg, 0.19 mmol, 1.00 eq.), dichloromethane (3 mL) and trifluoroacetic acid (1 mL). The resulting solution was stirred for 2 h at rt. The resulting mixture was concentrated under vacuum. This resulted in (R)-pyrrolidin-2-ylmethyl ((R)-2-phenyl-1-((3aS,4S,6S,7aR)-3a,5,5-trimethylhexahydro-4,6-methanobenzo[d][1,3,2]dioxaborol-2-yl)ethyl) carbamate 2,2,2-trifluoroacetate (0.08 mg) as a yellow oil.

Step 4

Into a 50-mL round-bottom flask was placed (R)-pyrrolidin-2-ylmethyl ((R)-2-phenyl-1-((3aS,4S,6S,7aR)-3a,5,5-trimethylhexahydro-4,6-methanobenzo[d][1,3,2]dioxaborol-2-yl)ethyl)carbamate 2,2,2-trifluoroacetate (480 mg, 1.13 mmol. 1.00 eq.), N,N-dimethylformamide (10 mL), DIEA (363.15 mg, 2.81 mmol, 2.50 eq.), 2-cyano-4,4-dimethylpent-2-enoic acid (206.85 mg, 1.35 mmol, 1.20 eq.) and HATU (513.5 mg, 1.35 mmol, 1.20 eq.). The resulting solution was stirred for 3 h at it. The reaction was then quenched by the addition of water. The resulting solution was extracted with ethyl acetate, and the organic layers combined. The resulting mixture was washed with sodium chloride (2×30 mL). The mixture was dried over anhydrous sodium sulfate and concentrated under vacuum. The residue was applied onto a silica gel column with ethyl acetate/petroleum ether (1:1). The crude product was purified by Prep-HPLC with the following conditions (HPLC-SHIMADZU): Column, XBridge Prep C18 OBD Column, 19*150 mm, 5 um, mobile phase, Water (10 MMOL/L NH$_4$HCO$_3$+0.1% NH$_3$H$_2$O) and ACN (72.0% ACN up to 82.0% in 7 min); Detector. UV 254/220 nm. This resulted in ((R)-1-(2-cyano-4,4-dimethylpent-2-enoyl)pyrrolidin-2-yl) methyl ((R)-2-phenyl-1-((3aS,4S,6S,7aR)-3a,5,5-trimethylhexahydro-4,6-methanobenzo[d][1,3,2]dioxaborol-2-yl) ethyl)carbamate (150 mg) as a white solid after lyophilization.

Step 5

Into a 50-mL round-bottom flask was placed ((R)-1-(2-cyano-4,4-dimethylpent-2-enoyl)pyrrolidin-2-yl)methyl ((R)-2-phenyl-1-((3aS,4S,6S,7aR)-3a,5,5-trimethylhexahydro-4,6-methanobenzo[d][1,3,2]dioxaborol-2-yl)ethyl) carbamate (150 mg, 0.27 mmol, 1.00 eq.), methanol (10 mL), (2-methylpropyl)boronic acid (81.84 mg, 0.80 mmol, 3.01 eq.), 1M hydrogen chloride (5.34 mL) and hexane (10 mL). The resulting solution was stirred for ~5 h at rt. After the methanol layer was lyophilized, the crude product was purified by Prep-HPLC with the following conditions (HPLC-SHIMADZU): Column, XBridge Prep C18 OBD Column, 19*150 mm, 5 um; mobile phase, Water (10 MMOL/L NH$_4$HCO$_3$+0.1% NH$_3$.H$_2$O) and ACN (32.0% ACN up to 47.0% in 7 min); Detector, UV 254/220 nm. After lyophilization, ((R)-1-(((((R)-1-(2-cyano-4,4-dimethylpent-2-enoyl)pyrrolidin-2-yl)methoxy)carbonyl)amino)-2-phenylethyl)boronic acid (53.8 mg) was obtained as a white solid. LC-MS m/z: 410 (M−17). $^1$H NMR (300 M-Hz, DMSO-d$_6$) δ 7.71 (d, J=3.3 Hz, 1H), 7.31-6.95 (m, 5H), 6.88 (d, J=5.7 Hz, 1H), 4.04 (dd, J=42.5, 16.3 Hz, 3H), 3.28 (s, 4H), 3.19-2.94 (m, 1H), 2.91-2.56 (m, 2H), 2.01-1.53 (m, 4H), 1.29-1.08 (m, 9H).

Example 11

((R)-1-(((((S)-1-acryloylpiperidin-2-yl)methoxy) carbonyl)amino)-2-phenylethyl)boronic acid

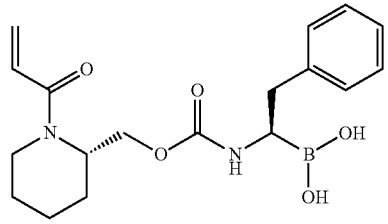 [SMILES: C=CC(=O)N1CCCC[C@H]1COC(=O)N[C@@H](Cc1ccccc1)B(O)O]

The title compound was prepared in the same manner as example 8 by replacing (R)-piperidin-2-ylmethyl ((R)-2-phenyl-1-((3aS,4S,6S,7aR)-3a,5,5-trimethylhexahydro-4,6-methanobenzo[d][1,3,2]dioxaborol-2-yl)ethyl)carbamate in step 1 with the corresponding S-enantiomer.

Example 12

((R)-1-(((((S)-1-(2-cyano-4-methylpent-2-enoyl) pyrrolidin-2-yl)methoxy)carbonyl)amino)-2-phenylethyl)boronic acid

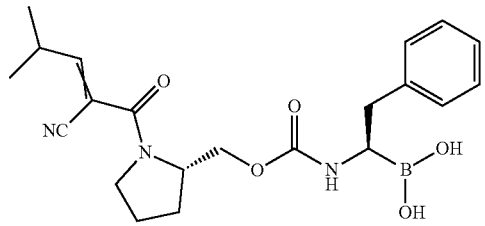 [SMILES: CC(C)C=C(C#N)C(=O)N1CCC[C@H]1COC(=O)N[C@@H](Cc1ccccc1)B(O)O]

The title compound was prepared as in example 7 by replacing tert-butyl (2R)-2-(hydroxymethyl)pyrrolidine-1-carboxylate with tert-butyl (2S)-2-(hydroxymethyl)pyrrolidine-1-carboxylate. LC-MS m/z: 396 (M+1).

Example 13

((R)-1-(((((S)-1 (2-cyano-4-methylpent-2-enoyl)piperidin-2-yl)methoxy)carbonyl)amino)-2-phenylethyl)boronic acid

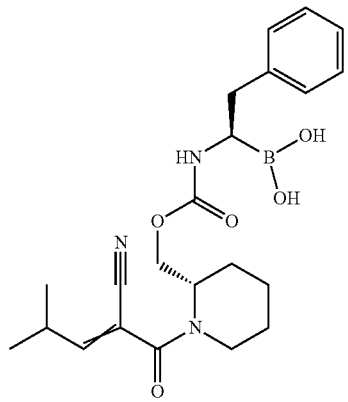 [SMILES: CC(C)C=C(C#N)C(=O)N1CCCC[C@H]1COC(=O)N[C@@H](Cc1ccccc1)B(O)O]

The title compound was prepared in an identical manner to example 2 by replacing tert-butyl (2R)-2-(hydroxymethyl)piperidine-1-carboxylate with tert-butyl (2S)-2-(hydroxymethyl)piperidine-1-carboxylate. LC-MS m/z: 426.2 (M−1).

Example 14

((R)-1-(((((R)-1-acryloylpyrrolidin-2-yl)methoxy)carbonyl)amino)-2-phenylethyl)boronic acid

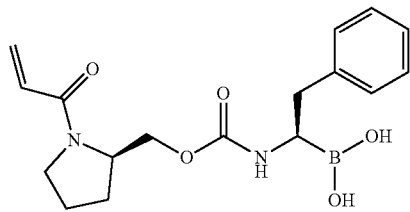 [SMILES: C=CC(=O)N1CCC[C@@H]1COC(=O)N[C@@H](Cc1ccccc1)B(O)O]

Step 1

Into a 50-mL 3-necked round-bottom flask was placed tert-butyl (2R)-2-(hydroxymethyl)pyrrolidine-1-carboxylate (600 mg, 2.98 mmol, 1.00 eq.), dichloromethane (15 mg, 0.18 mmol, 0.06 eq.) and DIPEA (1.16 g, 8.99 mmol, 3.00 eq.). This was followed by the addition of ditrichloromethyl carbonate (438.8 mg, 1.48 mmol, 0.50 eq.) dropwise with stirring at 0° C. The resulting solution was stirred for 3 h at 0° C. The resulting mixture was concentrated under vacuum to give a crude product as a yellow oil, which was used directly to the next step.

Step 2

Into a 100-mL 3-necked round-bottom flask was placed (R)-2-phenyl-1-((3aS,4S,6S,7aR)-3a,5,5-trimethylhexahydro-4,6-methanobenzo[d][1,3,2]dioxaborol-2-yl)ethanamine hydrochloride (900 mg, 3.01 mmol, 0.90 eq.), and dichloromethane (20 mL). DIPEA (693.1 mg, 5.37 mmol, 1.80 eq.). This was followed by the addition of tert-butyl (2R)-2-[[(chlorocarbonyl)oxy]methyl]pyrrolidine-1-carboxylate (785.1 mg, 2.98 mmol, 1.00 eq.) dropwise with stirring at 0° C. The resulting solution was stirred for 90 min at 25° C. The resulting solution was diluted with DCM (100 mL). The resulting mixture was washed with sodium chloride (3×100 mL). The mixture was dried over anhydrous sodium sulfate and concentrated under vacuum. The crude product was purified by Prep-HPLC with the following conditions (SHIMADZU): Column, XBridge Prep C18 OBD Column, 19*150 mm 5 um; mobile phase, Water (10 MMOL/L $NH_4HCO_3$+0.1% $NH_3.H_2O$) and ACN (hold 65.0% ACN in 7 min); Detector, UV 254/220 nm. This resulted in (R)-tert-butyl 2-(((((R)-2-phenyl-1-((3aS,4S,6S,7aR)-3a,5,5-trimethylhexahydro-4,6-methanobenzo[d][1,3,2]dioxaborol-2-yl)ethyl)carbamoyl)oxy)methyl)pyrrolidine-1-carboxylate (530 mg) as a white solid.

Step 3

Into a 250-mL round-bottom flask was placed (R)-tert-butyl 2-(((((R)-2-phenyl-1-((3aS,4S,6S,7aR)-3a,5,5-trimethylhexahydro-4,6-methanobenzo[d][1,3,2]dioxaborol-2-yl)ethyl)carbamoyl)oxy)methyl)pyrrolidine-1-carboxylate (520 mg, 0.99 mmol, 1.00 eq.), dichloromethane (100 mL), and trifluoroacetic acid (10 mL). The resulting solution was stirred for 30 min at rt. The resulting mixture was concentrated under vacuum to give (R)-pyrrolidin-2-ylmethyl ((R)-2-phenyl-1-((3aS,4S,6S,7aR)-3a,5,5-trimethylhexahydro-4,6-methanobenzo[d][1,3,2]dioxaborol-2-yl)ethyl)carbamate, which was used directly in the next step.

Step 4

Into a 50-mL 3-necked round-bottomed flask was placed (R)-pyrrolidin-2-ylmethyl ((R)-2-phenyl-1-((3aS,4S,6S,7aR)-3a,5,5-trimethylhexahydro-4,6-methanobenzo[d][1,3,2]dioxaborol-2-yl)ethyl)carbamate (421 mg, 0.99 mmol, 1.00 eq.), dichloromethane (15 mL), and TEA (299.4 mg. 2.96 mmol, 3.00 eq.). This was followed by the addition of prop-2-enoyl chloride (107.3 mg. 1.19 mmol. 1.20 eq.) dropwise with stirring at 0° C. The resulting solution was stirred for 30 min at 25° C. The resulting mixture was concentrated under vacuum. The crude product was purified by Prep-HPLC with the following conditions (SHIMADZU): Column, XBridge Prep C18 OBD Column, 19*150 mm 5 um; mobile phase, Water (10 MMOL/L $NH_4HCO_3$+0.1% $NH_3.H_2O$) and ACN (hold 65.0% ACN in 7 min); Detector, UV 254/220 nm. This resulted in ((R)-1-acryloylpyrrolidin-2-yl)methyl ((R)-2-phenyl-1-((3aS,4S,6S,7aR)-3a,5,5-trimethylhexahydro-4,6-methanobenzo[d][1,3,2]dioxaborol-2-yl)ethyl)carbamate (220 mg) as a white solid.

Step 5

Into a 100-mL round-bottom flask was placed ((R)-1-acryloylpyrrolidin-2-yl)methyl ((R)-2-phenyl-1-((3aS,4S,6S,7aR)-3a,5,5-trimethylhexahydro-4,6-methanobenzo[d][1,3,2]dioxaborol-2-yl)ethyl)carbamate (220 mg, 0.46 mmol, 1.00 eq.), methanol (9.5 mL), hexane (9.5 mL), (2-methylpropyl)boronic acid (135.6 mg, 1.33 mmol, 2.90 eq.) and 1N HCl (9.2 mL, 20.00 eq.). The resulting solution was stirred for 2 h at it. The resulting mixture was washed with hexane (3×10 mL). The methanol layer was diluted with $H_2O$ (100 mL), then lyophilized to give a crude product which was further purified by Prep-HPLC with the following conditions (SHIMADZU): Column, XBridge Prep C18 OBD Column, 19*150 mm 5 um; mobile phase, Water (10 MMOL/L NH$_4$HCO$_3$+0.1% N H$_3$.H$_2$O) and ACN (5.0% ACN up to 45.0% in 7 min); Detector, UV 254/220 nm. This resulted in ((R)-1-(((((R)-1-acryloylpyrrolidin-2-yl)methoxy)carbonyl)amino)-2-phenylethyl)boronic acid (48 mg) as a white solid after lyophilization. LC-MS m/z: 329 (M+1). $^1$H NMR (300 MHz, Methanol-d4) δ 7.32-7.04 (m, 5H), 6.85-6.45 (m, 1H), 6.24 (m, 1H). 5.69 (m, 1H), 4.43-3.73 (m, 3H), 3.67-3.39 (m, 2H), 3.19 (m, 1H), 2.90-2.60 (m, 2H), 1.94 (m, 4H).

Example 15

((R)-1-(((((R)-1-(2-cyano-4,4-dimethylpent-2-enoyl)piperidin-2-yl)methoxy)carbonyl)amino)-2-phenylethyl)boronic acid

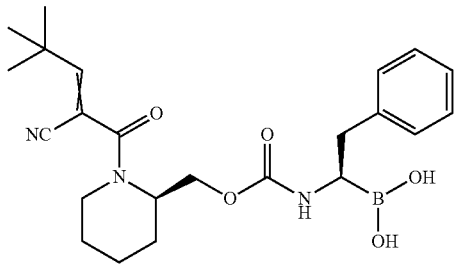

Step 1

Into a 50-mL round-bottom flask was placed tert-butyl (2R)-2-(hydroxymethyl)piperidine-1-carboxylate (16.02 g. 74.42 mmol, 1.0 eq.), pyridine (9.03 mL, 111.6 mmol, 1.5), THF (50 mL) and (4-nitrophenyl) carbonochloridate (18.0 g. 89.3 mmol, 1.2 eq.). The resulting solution was stirred for 18 h at rt. The reaction was then quenched by the addition of NH$_4$Cl (aq.). The DCM layer was dried over anhydrous sodium sulfate and concentrated under vacuum. The residue was purified by silica gel chromatography eluting with ethyl acetate/hexane (1:5). This resulted in (R)-tert-butyl 2-((((4-nitrophenoxy)carbonyl)oxy)methyl)piperidine-1-carboxylate (13.4 g, 47%) as a yellow oil.

Step 2

Into a 25-mL round-bottom flask was placed (R)-tert-butyl 2-((((4-nitrophenoxy)carbonyl)oxy)methyl)piperidine-1-carboxylate (1646 mg, 4.33 mmol, 1.0 eq.). This was dissolved in DCM (10 mL), followed by addition of N,N-Diisopropylethylamine (1.08 mL, 6.49 mmol, 1.5 eq.) and (R)-2-phenyl-1-((3aS,4S,6S,7aR)-3a,5,5-trimethylhexahydro-4,6-methanobenzo[d][1,3,2]dioxaborol-2-yl)ethanamine hydrochloride (1743 mg, 5.19 mmol, 1.2 eq.). The resulting solution was stirred for 3 h at it. The reaction was then quenched by the addition of water. The resulting solution was extracted with of DCM (2×50 mL), and the organic layers combined. The resulting mixture was washed with sodium chloride (20 mL). The mixture was dried over anhydrous sodium sulfate. The residue was purified by Prep-HPLC with the following conditions (SHIMADZU): Column, Higgins Analytical Inc, TARGA C18 10 uL, 250×20 mm, P/N: TS-2520-C181; mobile phase, Water (0.01% formic acid) and ACN (0.01% formic acid in 25 min); Detector, UV 254/220 nm. The pure fractions were made basic with NaHCO$_3$ (sat) and extracted with DCM. The organic was dried with MgSO$_4$, concentrated, frozen and lyophilized. This resulted in (R)-tert-butyl 2-(((((R)-2-phenyl-1-((3aS,4S,6S,7aR)-3a,5,5-trimethylhexahydro-4,6-methanobenzo[d][1,3,2]dioxaborol-2-yl)ethyl)carbamoyl)oxy)methyl)piperidine-1-carboxylate (638 mg, 27%) as a white solid. LC-MS m/z: 541 (M+1).

Step 3

Into a 25-mL round-bottom flask was added (R)-tert-butyl 2-(((((R)-2-phenyl-1-((3aS,4S,6S,7aR)-3a,5,5-trimethylhexahydro-4,6-methanobenzo[d][1,3,2]dioxaborol-2-yl)ethyl)carbamoyl)oxy)methyl)piperidine-1-carboxylate (170 mg, 0.31 mmol) followed by dichloromethane (3 mL) and 4N HCl in dioxane (1.5 mL). The resulting solution was stirred for 1 h at rt. The resulting mixture was concentrated under vacuum resulting in (R)-piperidin-2-ylmethyl ((R)-2-phenyl-1-((3aS,4S,6S,7aR)-3a,5,5-trimethylhexahydro-4,6-methanobenzo[d][1,3,2]dioxaborol-2-yl)ethyl)carbamate (138 mg) as a yellow oil. LC-MS m/z: 441 (M+1).

Step 4

Into a 25-mL round-bottom flask was placed (R)-piperidin-2-ylmethyl ((R)-2-phenyl-1-((3aS,4S,6S,7aR)-3a,5,5-trimethylhexahydro-4,6-methanobenzo[d][1,3,2]dioxaborol-2-yl)ethyl)carbamate (135 mg, 0.31 mmol, 1.0 eq.) followed by DCM (2 mL), (E)-2-cyano-4,4-dimethyl-pent-2-enoic acid (93.9 mg, 0.61 mmol, 2.0 eq.), DIEA (0.22 mL, 1.23 mmol, 4.00 eq.), and HATU (233 mg, 0.613 mmol, 2.00 eq.). The resulting solution was stirred for 3 h at rt. The reaction was then quenched by the addition of water. The resulting solution was extracted with DCM, and the organic layers combined. The resulting mixture was washed with sodium chloride, dried over anhydrous sodium sulfate and concentrated under vacuum. The crude product was purified by Prep-HPLC with the following conditions (SHIMADZU): Column, Higgins Analytical Inc, TARGA C18 10 uL. 250×20 mm, P/N: TS-2520-C181; mobile phase, Water (0.01% formic acid) and ACN (0.01% formic acid in 25 min); Detector, UV 254/220 nm. This resulted in ((R)-1-((E)-2-cyano-4,4-dimethylpent-2-enoyl)piperidin-2-yl) methyl ((R)-2-phenyl-1-((3aS,4S,6S,7aR)-3a,5,5-trimethylhexahydro-4,6-methanobenzo[d][1,3,2]dioxaborol-2-yl)ethyl)carbamate (138 mg, 78%) as a white solid after lyophilization. LC-MS m/z: 574 (M−1).

Step 5

Into a 10-mL round-bottom flask was placed ((R)-1-((E)-2-cyano-4,4-dimethylpent-2-enoyl)piperidin-2-yl)methyl ((R)-2-phenyl-1-((3aS,4S,6S,7aR)-3a,5,5-trimethylhexahydro-4,6-methanobenzo[d][1,3,2]dioxaborol-2-yl)ethyl)carbamate (135.0 mg, 0.23 mmol. 1.00 eq.), methanol (1.5 mL), (2-methylpropyl)boronic acid (119 mg, 1.17 mmol, 5.00 eq.), hexane (1.5 mL) and 1M hydrogen chloride (1.5 mL). The resulting solution was stirred for ~40 min at rt. The hexane layer was discarded. The methanol layer was diluted with water (6 mL), isolated by lyophilization and then purified by Prep-HPLC with the following conditions (SHIMADZU): Column, Higgin Analytical Inc. TARGA C18 10 uL, 250×20 mm, P/N: TS-2520-C181; mobile phase. Water (0.01% formic acid) and ACN (0.01% formic acid in 25 min); Detector, UV 254/220 nm. This resulted in ((R)-1-

(((((R)-1-(2-cyano-4,4-dimethylpent-2-enoyl)piperidin-2-yl)methoxy)carbonyl)amino)-2-phenylethyl)boronic acid (50 mg, 48%) as a solid after lyophilization. LC-MS m/z: 464 (M+23).

Example 16

((R)-2-(benzofuran-3-yl)-1-(((((R)-1-(2-cyano-4-methylpent-2-enoyl)pyrrolidin-2-yl)methoxy)carbonyl)amino)ethyl)boronic acid

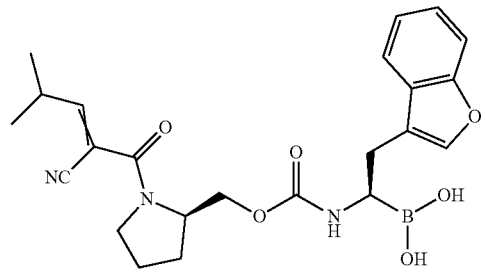 [SMILES: CC(C)C=C(C#N)C(=O)N1CCC[C@@H]1COC(=O)N[C@@H](Cc1coc2ccccc12)B(O)O]

Step 1

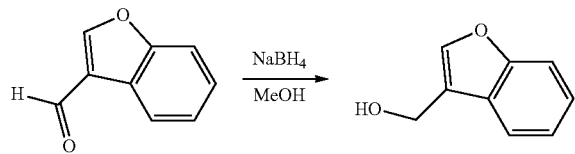 [SMILES: "MeOH" ; O=Cc1coc2ccccc12 ; "NaBH4" ; OCc1coc2ccccc12]

Into a 50-mL round-bottom flask, was placed 1-benzofuran-3-carbaldehyde (5 g, 34.21 mmol, 1.00 eq.), and methanol (50 mL). This was followed by the addition of NaBH₄ (1.96 g, 51.81 mmol, 1.50 eq.) in several batches. The resulting solution was stirred for 1 h at rt. The resulting mixture was concentrated under vacuum. The resulting solution was diluted with 100 mL of DCM. The resulting mixture was washed with 1×50 mL of NH₄Cl. The mixture was dried over anhydrous sodium sulfate and concentrated under vacuum. The residue was applied onto a silica gel column with PE:EA (60:40). This resulted in 4.8 g (95%) of 1-benzofuran-3-ylmethanol as a white solid.

Step 2

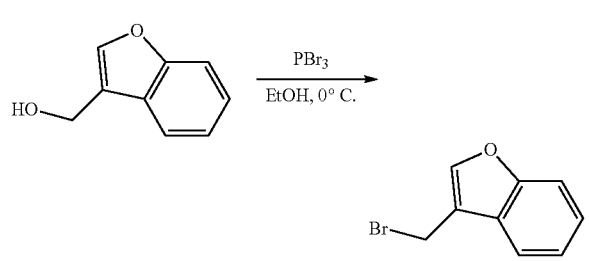

Into a 100-mL 3-necked round-bottom flask, was placed 1-benzofuran-3-ylmethanol (1 g, 6.75 mmol, 1.00 eq.), and ether (10 mL). This was followed by the addition of PBr₃ (730 mg, 2.70 mmol, 0.40 eq.) dropwise with stirring at 0° C. The resulting solution was stirred for 30 min at 0° C. The reaction was then quenched by the addition of water/ice. The resulting solution was extracted with 3×50 mL of ether and the organic layers combined and dried over anhydrous sodium sulfate and concentrated under vacuum. This resulted in 1.3 g (crude) of 3-(bromomethyl)-1-benzofuran as a colorless oil.

Step 3

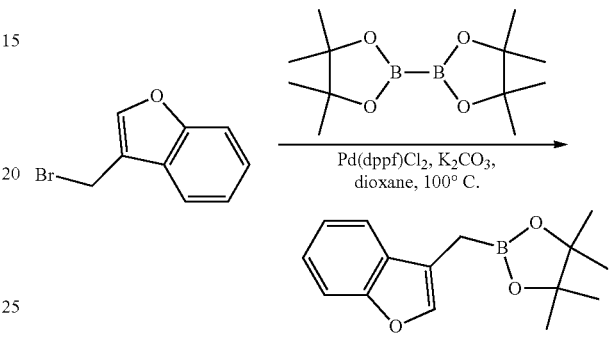

Into a 100-mL round-bottom flask, was placed 3-(bromomethyl)-1-benzofuran (1.3 g, 6.16 mmol, 1.00 eq.), 1,4-dioxane (13 mL), 4,4,5,5-tetramethyl-2-(tetramethyl-1,3,2-dioxaborolan-2-yl)-1,3,2-dioxaborolane (1.88 g, 7.40 mmol, 1.21 eq.), potassium carbonate (2.55 g, 18.48 mmol. 3.00 eq.), and Pd(dppf)Cl₂ (450 mg, 0.62 mmol, 0.10 eq.). The resulting solution was stirred overnight at 100° C. The solids were filtered out. The resulting mixture was concentrated under vacuum. The residue was applied onto a silica gel column with PE:EA (100:0-97:3). This resulted in 490 mg (31%) of 2-(1-benzofuran-3-ylmethyl)-4,4,5,5-tetramethyl-1,3,2-dioxaborolane as light yellow oil.

Step 4

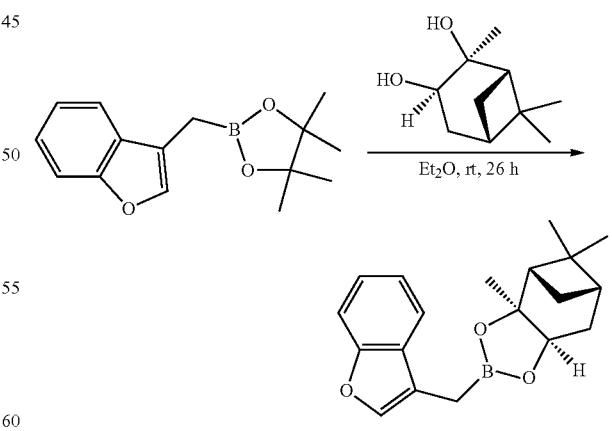

Into a 50-mL round-bottom flask, was placed a solution of 2-(1-benzofuran-3-ylmethyl)-4,4,5,5-tetramethyl-1,3,2-dioxaborolane (490 mg, 1.90 mmol, 1.00 eq.) in ether (5 mL), and (1S,2S,3R,5S)-2,6,6-trimethylbicyclo[3.1.1]heptane-2,3-diol (420 mg, 2.47 mmol, 1.30 eq.). The resulting solution was stirred overnight at rt. The resulting mixture was concentrated under vacuum. The residue was applied onto a silica gel column with ethyl acetate/petroleum ether (3:97). This resulted in 200 mg (34%) of (1S,2S,6R,8S)-4-(1-benzofuran-3-ylmethyl)-2,9,9-trimethyl-3,5-dioxa-4-boratricyclo[6.1.1.0^[2,6]]decane as a yellow oil.

Step 5

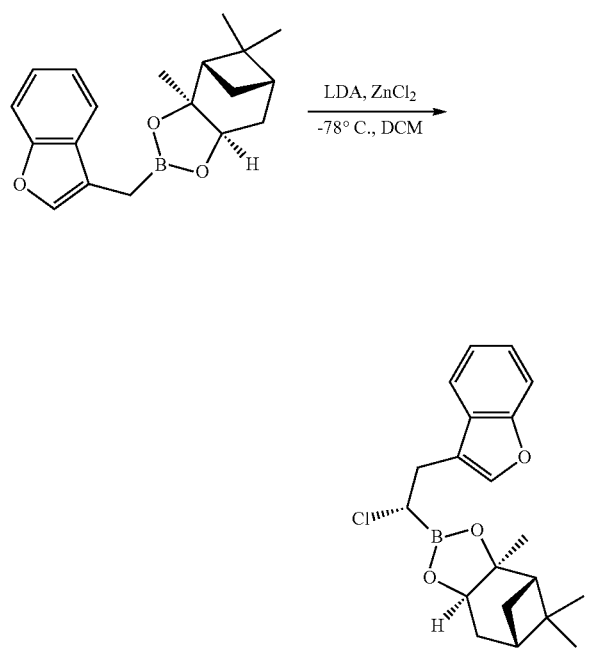

Into a 50-mL 3-necked round-bottom flask, was placed a solution of dichloromethane (617 mg, 7.26 mmol, 3.00 eq.) in tetrahydrofuran (4 mL). This was followed by the addition of LDA (1.6 mL, 1.30 eq.) dropwise with stirring at −78° C. The mixture was stirred for 20 min. at −78° C. To this was added a solution of (1S,2S,6R,8S)-4-(1-benzofuran-3-ylmethyl)-2,9,9-trimethyl-3,5-dioxa-4-boratricyclo[6.1.1.0^[2,6]]decane (750 mg, 2.42 mmol, 1.00 eq.) in tetrahydrofuran (2 mL) dropwise with stirring at −78° C. The mixture was stirred for 10 min at −78° C. To the mixture was added ZnCl$_2$ (5 mL, 1.00 eq., 0.5N) dropwise with stirring at −78° C. The final reaction mixture was stirred for 30 min at −78° C. The resulting solution was allowed to react, with stirring, for an additional 3 h at it. The resulting mixture was concentrated under vacuum. The reaction was then quenched by the addition of 20 mL of NH$_4$Cl. The resulting solution was extracted with 3×20 mL of ether and the organic layers combined and dried over anhydrous sodium sulfate and concentrated under vacuum. The residue was applied onto a silica gel column with ethyl acetate/petroleum ether (3:97). This resulted in 600 mg (69%) of (1S,2S,6R,8S)-4-[(1S)-2-(1-benzofuran-3-yl)-1-chloroethyl]-2,9,9-trimethyl-3,5-dioxa-4-boratricyclo[6.1.1.0^[2,6]]decane as a yellow oil.

Step 6

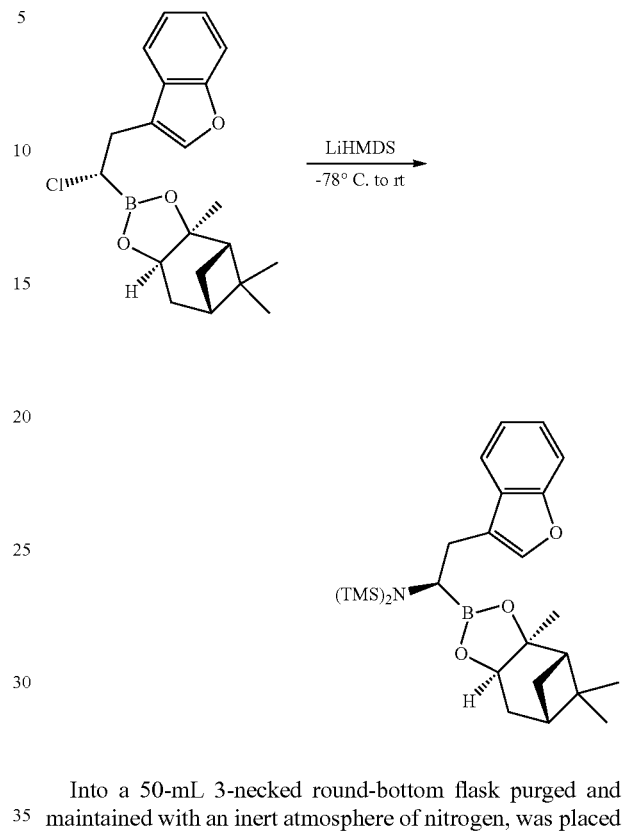

Into a 50-mL 3-necked round-bottom flask purged and maintained with an inert atmosphere of nitrogen, was placed (1S,2S,6R,8S)-4-[(1S)-2-(1-benzofuran-3-yl)-1-chloroethyl]-2,9,9-trimethyl-3,5-dioxa-4-boratricyclo[6.1.1.0^[2,6]]decane (600 mg, 1.67 mmol, 1.00 eq.), and tetrahydrofuran (6 mL). This was followed by the addition of LiHMDS (2 mL, 1.20 eq.) dropwise with stirring at −78° C. The resulting solution was stirred overnight at it. The resulting mixture was concentrated under vacuum. The residue was dissolved in 5 mL of n-hexane. The solids were filtered out. The resulting mixture was concentrated under vacuum. This resulted in 480 mg (59%) of [(1R)-2-(1-benzofuran-3-yl)-1-[(1S,2S,6R,8S)-2,9,9-trimethyl-3,5-dioxa-4-boratricyclo[6.1.1.0^[2,6]]decan-4-yl]ethyl]bis(trimethylsilyl)amine as a yellow oil.

Step 7

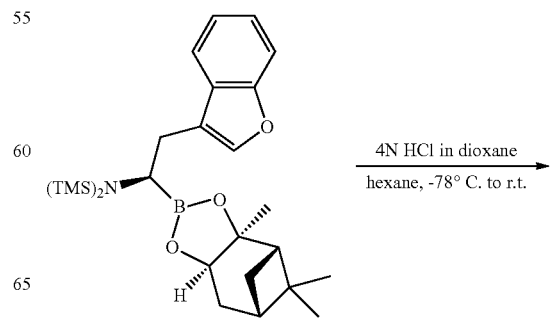

-continued

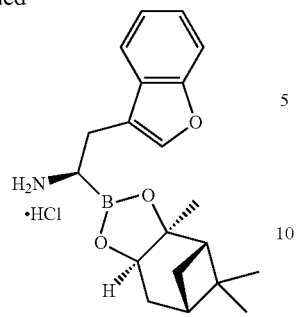

Into a 50-mL 3-necked round-bottom flask purged and maintained with an inert atmosphere of nitrogen, was placed a solution of [(1R)-2-(1-benzofuran-3-yl)-1-[(1S,2S,6R,8S)-2,9,9-trimethyl-3,5-dioxa-4-boratricyclo[6.1.1.0^[2,6]]decan-4-yl]ethyl]bis(trimethylsilyl)amine (480 mg, 0.99 mmol, 1.00 eq.) in n-hexane (10 mL). This was followed by the addition of 4N HCl in dioxane (0.85 mL. 3.00 eq.) at 0° C. The resulting solution was stirred for 2 h at rt. The solids were collected by filtration. This resulted in 230 mg (62%) of (1R)-2-(1-benzofuran-3-yl)-1-[(1S,2S,6R,8S)-2,9,9-trimethyl-3,5-dioxa-4-boratricyclo[6.1.1.0^[2,6]]decan-4-yl]ethan-1-amine hydrochloride as an off-white solid.

Step 8

Into a 50-mL 3-necked round-bottom flask, was placed a solution of tert-butyl (2R)-2-(hydroxymethyl)pyrrolidine-1-carboxylate (100 mg, 0.50 mmol, 1.00 eq.) in dichloromethane (2 mL), and DIEA (193 mg, 1.49 mmol, 3.00 eq.). This was followed by the addition of ditrichloromethyl carbonate (74 mg, 0.25 mmol, 0.50 eq.) dropwise with stirring at 0° C. The resulting solution was stirred for 2 h at 0° C. The resulted solution was used directly to the next step.

Step 9

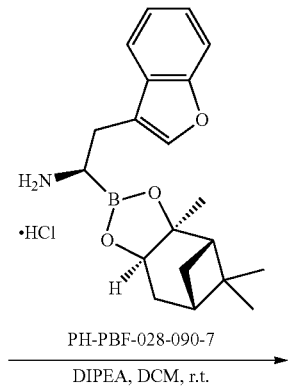

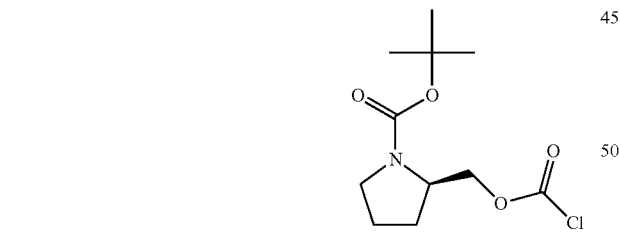

Into a 50-mL 3-necked round-bottom flask, was placed a solution of (1R)-2-(1-benzofuran-3-yl)-1-[(1S,2S,6R,8S)-2,9,9-trimethyl-3,5-dioxa-4-boratricyclo[6.1.1.0^2,6]decan-4-yl]ethan-1-amine hydrochloride (168 mg, 0.45 mmol, 1.00 eq.) in dichloromethane (5 mL), and DIEA (128 mg, 0.99 mmol, 2.00 eq.). This was followed by the addition of a solution of tert-butyl (2R)-2-[[(chlorocarbonyl)oxy]methyl]pyrrolidine-1-carboxylate (130 mg, 0.49 mmol, 1.00 eq.) in dichloromethane (2 mL) dropwise with stirring at 0° C. The resulting solution was stirred for 1 h at it. The reaction was then quenched by the addition of 5 mL of water. The resulting solution was diluted with 10 mL of DCM. The resulting mixture was washed with 1×10 mL of sodium chloride. The mixture was dried over anhydrous sodium sulfate and concentrated under vacuum. This resulted in 280 mg (crude) of tert-butyl (2R)-2-[([[(1R)-2-(1-benzofuran-3-yl)-1-[(1S,2S,6R,8S)-2,9,9-trimethyl-3,5-dioxa-4-boratricyclo[6.1.1.0^[2,6]]decan-4-yl]ethyl]carbamoyl]oxy)methyl]pyrrolidine-1-carboxylate as brown oil.

Step 10

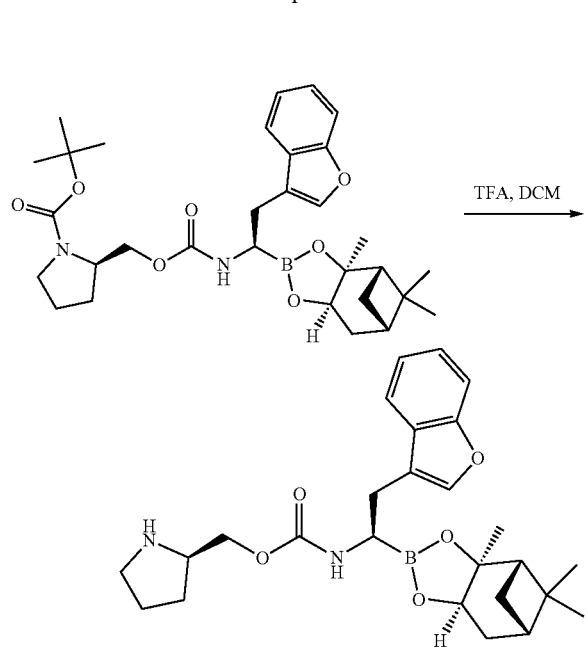

Into a 25-mL round-bottom flask, was placed a solution of tert-butyl (2R)-2-[([[(1R)-2-(1-benzofuran-3-yl)-1-[(1S,2S,6R,8S)-2,9,9-trimethyl-3,5-dioxa-4-boratricyclo[6.1.1.0^[2,6]]decan-4-yl]ethyl]carbamoyl]oxy)methyl]pyrrolidine-1-carboxylate (150 mg, 0.26 mmol. 1.00 eq.) in dichloromethane (3 mL), and trifluoroacetic acid (0.6 mL). The resulting solution was stirred for 1 h at it. The resulting mixture was concentrated under vacuum. This resulted in 120 mg (crude) of (2R)-pyrrolidin-2-ylmethyl N-[(1R)-2-(1-benzofuran-3-yl)-1-[(1S,2S,6R,8S)-2,9,9-trimethyl-3,5-dioxa-4-boratricyclo[6.1.1.0^[2.6]]decan-4-yl]ethyl]carbamate as brown oil.

Step 11

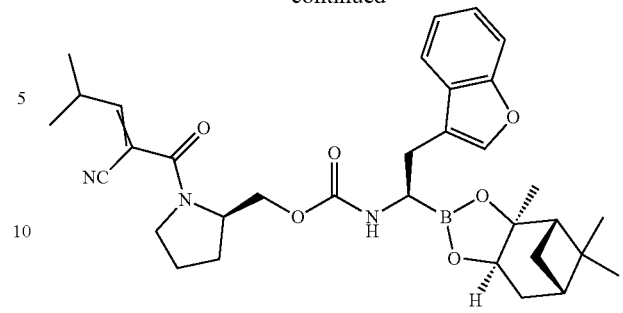

Into a 50-mL round-bottom flask, was placed a solution of (2R)-pyrrolidin-2-ylmethyl N-[(1R)-2-(1-benzofuran-3-yl)-1-[(1S,2S,6R,8S)-2,9,9-trimethyl-3,5-dioxa-4-boratricyclo[6.1.1.0^[2,6]]decan-4-yl]ethyl]carbamate (120 mg, 0.26 mmol, 1.00 eq.) in dichloromethane (3 mL), DIEA (100 mg, 0.77 mmol, 3.00 eq.), HATU (147 mg, 0.39 mmol, 1.50 eq.), and 2-cyano-4-methylpent-2-enoic acid (43 mg, 0.31 mmol, 1.20 eq.). The resulting solution was stirred for 1 h at rt. The reaction was then quenched by the addition of 2 mL of water. The resulting solution was diluted with 10 mL of DCM. The resulting mixture was washed with 1×5 mL of sodium chloride. The mixture was dried over anhydrous sodium sulfate and concentrated under vacuum. The crude product was purified by Prep-HPLC with the following conditions: Column, XBridge Prep C18 OBD Column, 19*150 mm, 5 um; mobile phase, Water (10 MMOL/L NH$_4$HCO$_3$+0.1% NH$_3$.H$_2$O) and ACN (70% ACN up to 85% in 7 min); Detector, UV 254/220 nm. This resulted in 60 mg (40%) of [(2R)-1-[2-cyano-2-(2-methylpropylidene)acetyl]pyrrolidin-2-yl]methyl N-[(1R)-2-(1-(1-benzofuran-3-yl)-1-[(1S,2S,6R,8S)-2,9,9-trimethyl-3,5-dioxa-4-boratricyclo[6.1.1.0^[2,6]]decan-4-yl]ethyl]carbamate as a white solid after the lyophilization.

Step 12

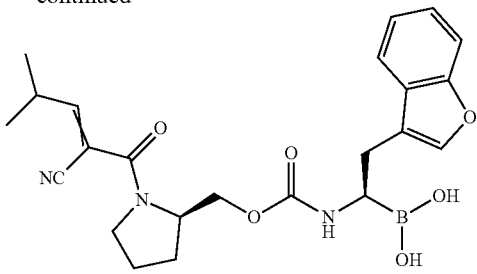

Into a 50-mL round-bottom flask, was placed a solution of [(2R)-1-[2-cyano-2-(2-methylpropylidene)acetyl]pyrrolidin-2-yl]methyl N-[(1R)-2-(1-benzofuran-3-yl)-1-[(1S,2S,6R,8S)-2,9,9-trimethyl-3,5-dioxa-4-boratricyclo[6.1.1.0^[2,6]]decan-4-yl]ethyl]carbamate (60 mg, 0.10 mmol, 1.00 eq.) in methanol/Hexane (1.5/1.5 mL), 1N HCl (2 mL, 20.00 eq.), and (2-methylpropyl)boronic acid (31 mg, 0.30 mmol, 3.00 eq.). The resulting solution was stirred for 2 h at rt. The hexane layer was discarded. The methanol layer was diluted with water (15 mL), then dried over lyophilization to give a crude product. The crude product was purified by Prep-HPLC with the following conditions: Column, XBridge Prep C18 OBD Column, 19*150 mm. 5 um; mobile phase, Water (10 MMOL/L NH$_4$HCO$_3$+0.1% NH$_3$.H$_2$O) and ACN (38.0% ACN up to 42.0% in 7 min); Detector, UV 254/220 nm. This resulted in 15.8 mg (34%) of [(1R)-2-(1-benzofuran-3-yl)-1-[([[(2R)-1-[2-cyano-2-(2-methylpropylidene)acetyl]pyrrolidin-2-yl]methoxy]carbonyl)amino]ethyl]boronic acid as a white solid after the lyophilization. LC-MS m/z: 436 (M−17).

Example 17

((R)-1-(((((R)-1-(2-cyano-4-methyl-4-(4-(oxetan-3-yl)piperazin-1-yl)pent-2-enoyl)pyrrolidin-2-yl)methoxy)carbonyl)amino)-2-phenylethyl)boronic acid

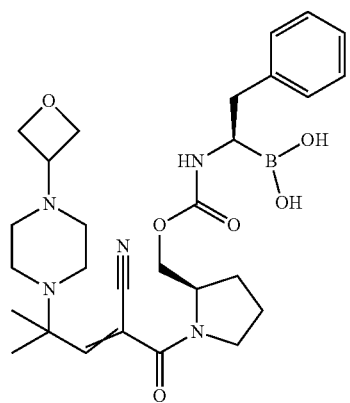 [SMILES: CC(C)(C=C(C#N)C(=O)N1CCC[C@@H]1COC(=O)N[C@@H](Cc1ccccc1)B(O)O)N1CCN(C2COC2)CC1]

Using the method of example 10 and replacing 2-cyano-4,4-dimethylpent-2-enoic acid with 2-cyano-4-methyl-4-(4-(oxetan-3-yl)piperazin-1-yl)pent-2-enoic acid in step 4 afforded the title compound. LC-MS m/z: 554 (M+1).

Example 18

((R)-1-(((((R)-1-(2-cyano-4,4-dimethylpent-2-enoyl)pyrrolidin-2-yl)methoxy)carbonyl)amino)-2-(p-tolyl)ethyl)boronic acid

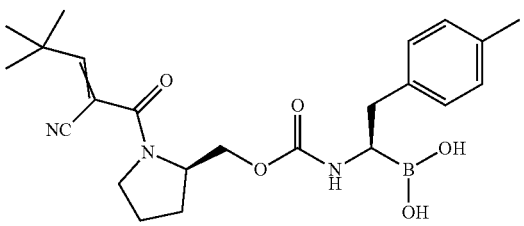 [SMILES: Cc1ccc(C[C@H](NC(=O)OC[C@H]2CCCN2C(=O)C(C#N)=CC(C)(C)C)B(O)O)cc1]

Step 1

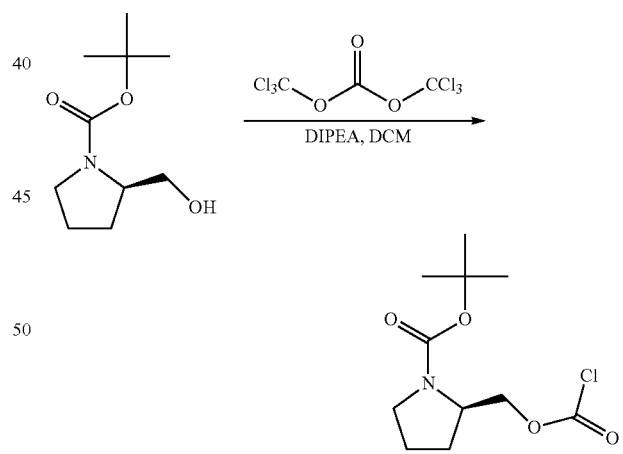

Into a 50-mL 3-necked round-bottom flask purged and maintained with an inert atmosphere of nitrogen, was placed tert-butyl (2R)-2-(hydroxymethyl)pyrrolidine-1-carboxylate (314.8 mg, 1.56 mmol, 1.00 eq.), DIPEA (606.2 mg, 4.70 mmol, 3.00 eq.), and dichloromethane (6 mL). This was followed by the addition of ditrichloromethyl carbonate (230.3 mg. 0.78 mmol, 0.50 eq.) stirring at 0° C. The resulting solution was stirred for 2.5 h at 0° C. The reaction mixture solution was used directly to the next step.

Step 2

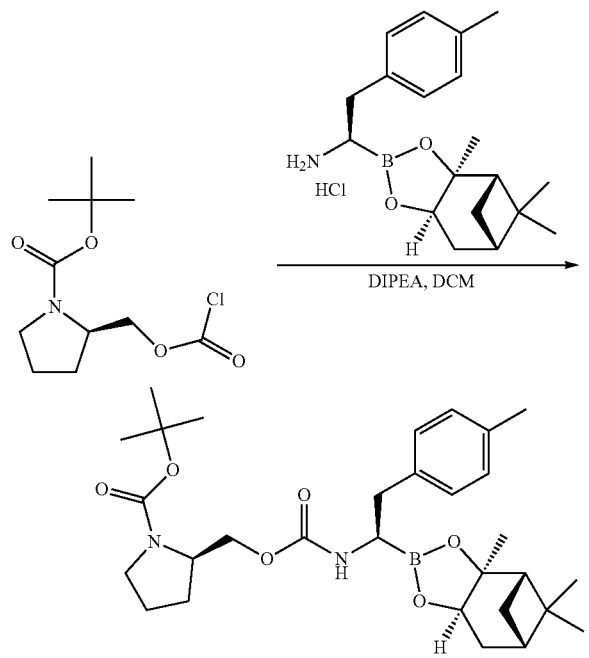

Into a 50-mL 3-necked round-bottom flask, was placed (1R)-2-(4-methylphenyl)-1-[(1S,2S,6R,8S)-2,9,9-trimethyl-3,5-dioxa-4-boratricyclo[6.1.1.0^[2.6]]decan-4-yl]ethan-1-amine hydrochloride (820 mg. 2.34 mmol, 1.50 eq.), DIPEA (404.1 mg, 3.13 mmol, 2.00 eq.), and dichloromethane (15 mL). This was followed by the addition of tert-butyl (2R)-2-[[(chlorocarbonyl)oxy]methyl] pyrrolidine-1-carboxylate (412 mg, 1.56 mmol, 1.00 eq.) stirring at 0° C. The resulting solution was stirred for 60 min at 25° C. The resulting solution was diluted with 100 mL of DCM. The resulting mixture was washed with 3×100 mL of saturated brine. The crude product was purified by Flash-Prep-HPLC with the following conditions: Column, C18 silica gel; mobile phase, $H_2O:CH_3CN=99:1$ increasing to $H_2O:CH_3CN=1:99$; Detector, UV 220 nm. This resulted in 380 mg (45%) of tert-butyl (2R)-2-[([[(1R)-2-(4-methylphenyl)-1-[(1S,2S,6R,8S)-2,9,9-trimethyl-3,5-dioxa-4-boratricyclo[6.1.1.0^[2,6]]decan-4-yl]ethyl]carbamoyl]oxy)methyl]pyrrolidine-1-carboxylate as a yellow solid after the lyophilization.

Step 3

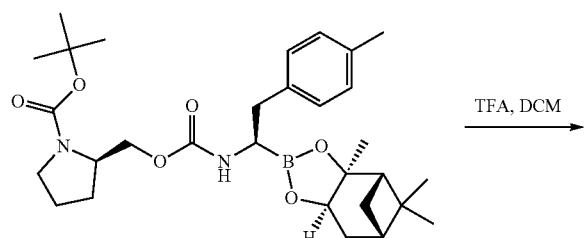

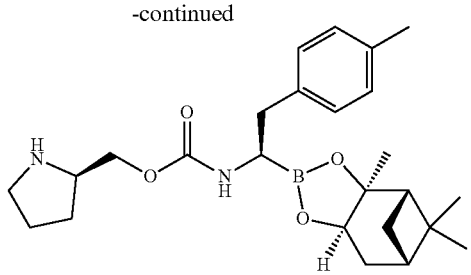

Into a 25-mL round-bottom flask purged and maintained with an inert atmosphere of nitrogen, was placed tert-butyl (2R)-2-[([[(1R)-2-(4-methylphenyl)-1-[(1S,2S,6R,8S)-2,9,9-trimethyl-3,5-dioxa-4-boratricyclo[6.1.1.0^[2,6]]decan-4-yl]ethyl]carbamoyl]oxy)methyl]pyrrolidine-1-carboxylate (60 mg, 0.11 mmol, 1.00 eq.), trifluoroacetic acid (0.2 mL), and dichloromethane (2 mL). The resulting solution was stirred for 30 min at 25° C. The resulting mixture was concentrated under vacuum. The crude product was used directly to the next step.

Step 4

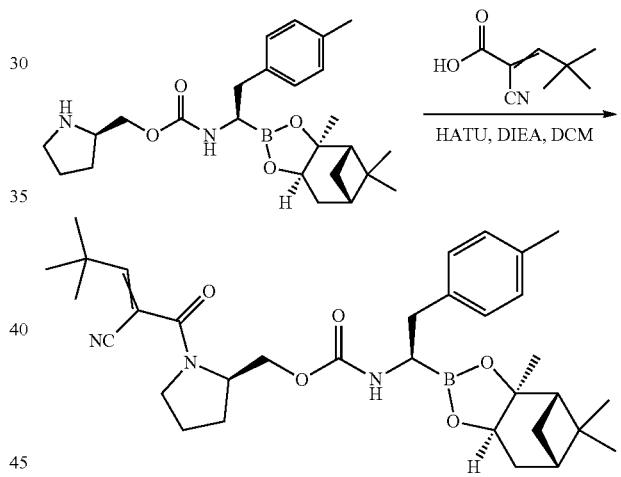

Into a 50-mL round-bottom flask purged and maintained with an inert atmosphere of nitrogen, was placed (2R)-pyrrolidin-2-ylmethyl N-[(1R)-2-(4-methylphenyl)-1-[(1S,2S,6R,8S)-2,9,9-trimethyl-3,5-dioxa-4-boratricyclo[6.1.1.0^[2,6]]decan-4-yl]ethyl]carbamate (48.9 mg, 0.11 mmol, 1.00 eq.), 2-cyano-4,4-dimethylpent-2-enoic acid (20.4 mg, 0.13 mmol, 1.20 eq.), HATU (50.7 mg, 0.13 mmol, 1.20 eq.), DIPEA (35.8 mg, 0.28 mmol, 2.50 eq.), and dichloromethane (1.5 mL). The resulting solution was stirred for 60 min at 25° C. The resulting mixture was concentrated under vacuum. The crude product was purified by Prep-HPLC with the following conditions: Column. XBridge Prep C18 OBD Column, 19*150 mm, 5 um; mobile phase, Water (10 MMOL/L $NH_4HCO_3$+0.1% $NH_3.H_2O$) and ACN (75.0% ACN up to 82.0% in 7 min); Detector, UV 254/220 nm. This resulted in 30 mg (47%) of [(2R)-1-[2-cyano-2-(2,2-dimethylpropylidene)acetyl]pyrrolidin-2-yl]methyl N-[(1R)-2-(4-methylphenyl)-1-[(1S,2S,6R,8S)-2,9,9-trimethyl-3,5-dioxa-4-boratricyclo[6.1.1.0^[2,6]]decan-4-yl]ethyl] carbamate as a white solid after the lyophilization.

Step 5

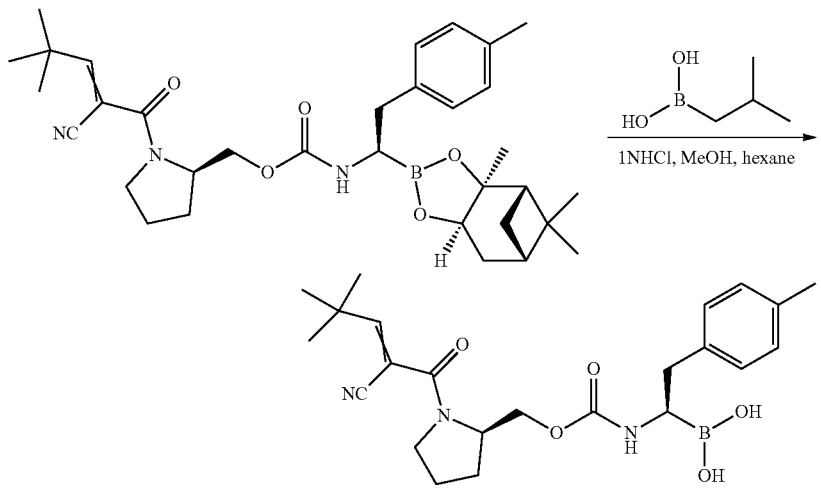

Into a 100-mL round-bottom flask purged and maintained with an inert atmosphere of nitrogen, was placed [(2R)-1-[2-cyano-2-(2,2-dimethylpropylidene)acetyl]pyrrolidin-2-yl]methylN-[(1R)-2-(4-methylphenyl)-1-[(1S,2S,6R,8S)-2,9,9-trimethyl-3,5-dioxa-4-boratricyclo[6.1.1.0^[2.6]]decan-4-yl]ethyl]carbamate (70 mg, 0.12 mmol, 1.00 eq.), methanol (3 mL), hexane (3 mL), (2-methylpropyl)boronic acid (36 mg, 0.35 mmol, 2.90 eq.), and 1N HCl (2.4 mL, 20.00 eq.). The resulting solution was stirred for 2 h at 25° C. The resulting mixture was washed with 3×5 mL of hexane. The methanol layer was diluted with 50 mL of water, and dried over lyophylization to give a crude product which was further purified by Prep-HPLC with the following conditions: Column, XBridge Prep C18 OBD Column, 19*150 mm, 5 um; mobile phase, Water (10 MMOL/L $NH_4HCO_3$+0.1% $NH_3.H_2O$) and ACN (42.0% ACN up to 45.0% in 7 min); Detector, UV 254/220 nm. This resulted in 32.4 mg (60%) of [(1R)-1-[([[(2R)-1-[2-cyano-2-(2,2-dimethylpropylidene)acetyl]pyrrolidin-2-yl]methoxy]carbonyl)amino]-2-(4-methylphenyl)ethyl]boronic acid as a white solid after the lyophilization. LC-MS m/z: 442 (M+1).

Example 19

((R)-1-(((((R)-1-acryloylpyrrolidin-2-yl)methoxy)carbonyl)amino)-2-(p-tolyl)ethyl)boronic acid

Step 1

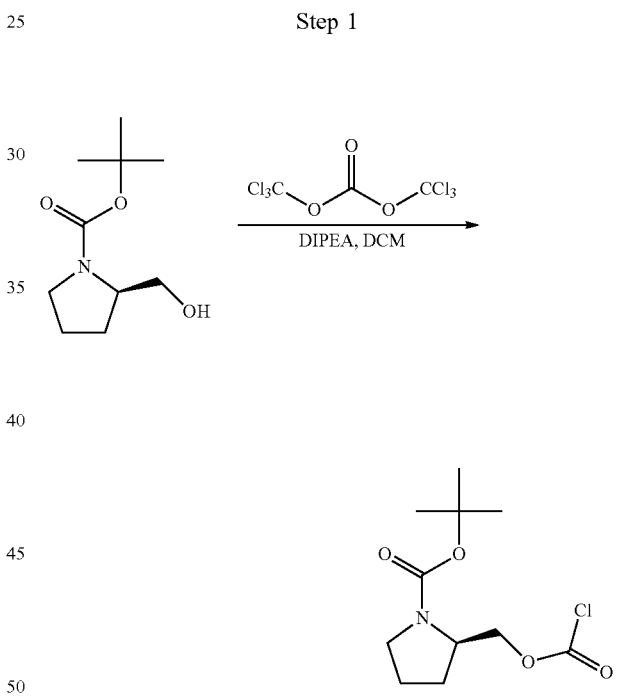

Into a 50-mL 3-necked round-bottom flask purged and maintained with an inert atmosphere of nitrogen, was placed tert-butyl (2R)-2-(hydroxymethyl)pyrrolidine-1-carboxylate (314.8 mg, 1.56 mmol, 1.00 eq.), DIPEA (606.2 mg, 4.70 mmol, 3.00 eq.), and dichloromethane (6 mL). This was followed by the addition of ditrichloromethyl carbonate (230.3 mg, 0.78 mmol, 0.50 eq.) stirring at 0° C. The resulting solution was stirred for 2.5 h at 0° C. The reaction mixture solution was used directly to the next step.

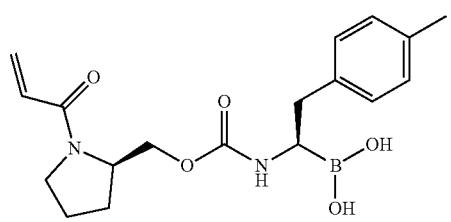 [SMILES: C=CC(=O)N1CCC[C@@H]1COC(=O)N[C@@H](Cc1ccc(C)cc1)B(O)O]

Step 2

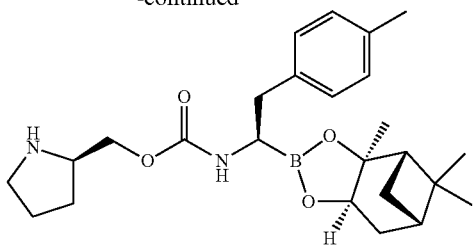

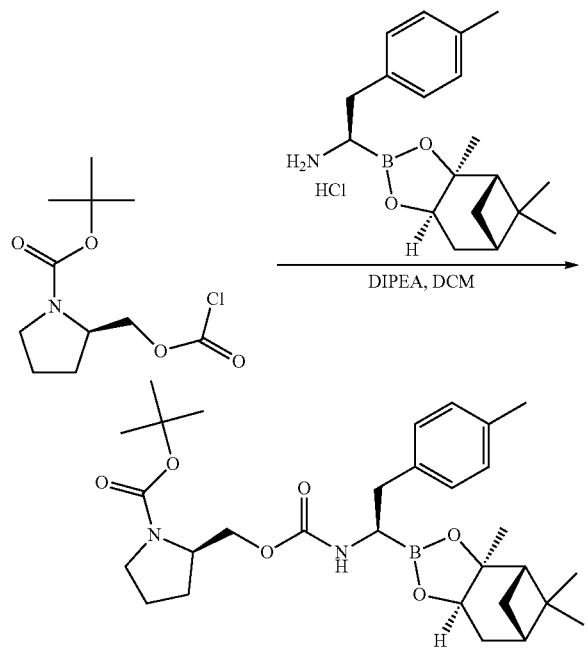

Into a 50-mL 3-necked round-bottom flask, was placed (1R)-2-(4-methylphenyl)-1-[(1S,2S,6R,8S)-2,9,9-trimethyl-3,5-dioxa-4-boratricyclo[6.1.1.0ˆ[2,6]]decan-4-yl]ethan-1-amine hydrochloride (820 mg, 2.34 mmol, 1.50 eq.), DIPEA (404.1 mg, 3.13 mmol, 2.00 eq.), and dichloromethane (15 mL). This was followed by the addition of tert-butyl (2R)-2-[[(chlorocarbonyl)oxy]methyl] pyrrolidine-1-carboxylate (412 mg, 1.56 mmol, 1.00 eq.) stirring at 0° C. The resulting solution was stirred for 60 min. at 25° C. The resulting solution was diluted with 100 mL of DCM. The resulting mixture was washed with 3×100 mL of saturated brine. The resulting mixture was concentrated under vacuum. The crude product was purified by Flash-Prep-HPLC with the following conditions: Column, C18 silica gel; mobile phase, H₂O:CH₃CN=99:1 increasing to H₂O:CH₃CN=1:99; Detector, UV 220 nm. This resulted in 380 mg (45%) of tert-butyl (2R)-2-[([[(1R)-2-(4-methylphenyl)-1-[(1S,2S,6R,8S)-2,9,9-trimethyl-3,5-dioxa-4-boratricyclo[6.1.1.0ˆ[2,6]]decan-4-yl]ethyl]carbamoyl]oxy)methyl]pyrrolidine-1-carboxylate as a yellow solid after the lyophilization.

Step 3

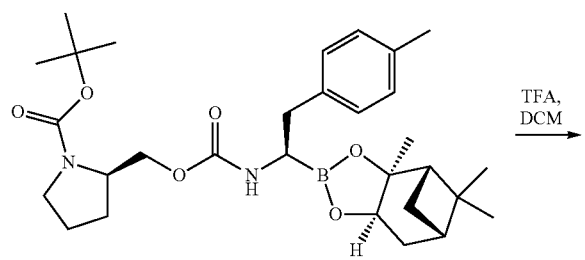

Into a 25-mL round-bottom flask purged and maintained with an inert atmosphere of nitrogen, was placed tert-butyl (2R)-2-[([[(1R)-2-(4-methylphenyl)-1-[(1S,2S,6R,8S)-2,9,9-trimethyl-3,5-dioxa-4-boratricyclo[6.1.1.0ˆ[2,6]]decan-4-yl]ethyl]carbamoyl]oxy)methyl]pyrrolidine-1-carboxylate (60 mg, 0.11 mmol, 1.00 eq.), trifluoroacetic acid (0.2 mL), and dichloromethane (2 mL). The resulting solution was stirred for 30 min at 25° C. The resulting mixture was concentrated under vacuum. The crude product was used directly to the next step.

Step 4

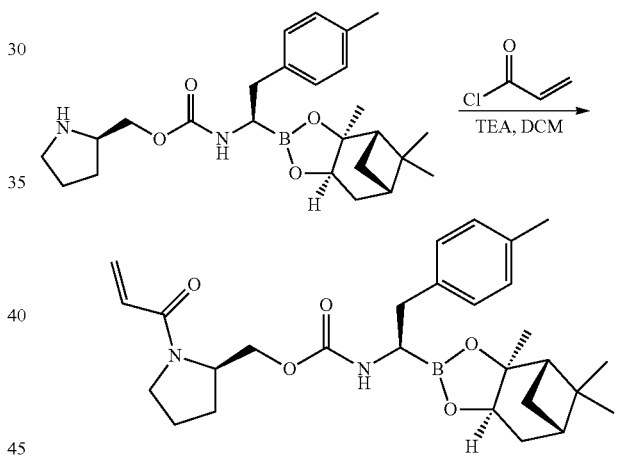

Into a 50-mL 3-necked round-bottom flask purged and maintained with an inert atmosphere of nitrogen, was placed (2R)-pyrrolidin-2-ylmethyl N-[(1R)-2-(4-methylphenyl)-1-[(1S,2S,6R,8S)-2,9,9-trimethyl-3,5-dioxa-4-boratricyclo [6.1.1.0ˆ[2,6]]decan-4-yl]ethyl]carbamate (163 mg, 0.37 mmol, 1.00 eq.), TEA (112.2 mg, 1.11 mmol. 3.00 eq.), and dichloromethane (6 mL). This was followed by the addition of prop-2-enoyl chloride (40.2 mg, 0.44 mmol, 1.20 eq.) dropwise with stirring at 0° C. The resulting solution was stirred for 30 min at 25° C. The resulting mixture was concentrated under vacuum. The crude product was purified by Prep-HPLC with the following conditions: Column, XBridge Prep C18 OBD Column, 19*150 mm, 5 um, mobile phase, Water (10 MMOL/L NH₄HCO₃+0.1% NH₃.H₂O) and ACN (67.0% ACN up to 72.0% in 7 min); Detector, UV 254/220 nm. This resulted in 70 mg (38%) of [(2R)-1-(prop-2-enoyl)pyrrolidin-2-yl]methyl N-[(1R)-2-(4-methylphenyl)-1-[(1S,2S,6R,8S)-2,9,9-trimethyl-3,5-dioxa-4-boratricyclo[6.1.1.0ˆ[2,6]]decan-4-yl]ethyl]carbamate as a white solid after the lyophilization.

Step 5

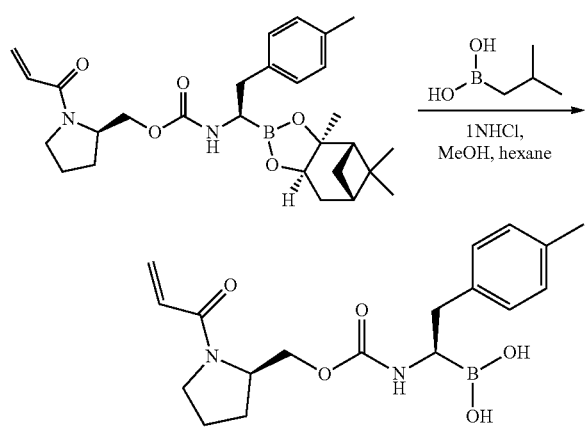

Into a 100-mL round-bottom flask purged and maintained with an inert atmosphere of nitrogen, was placed [(2R)-1-(prop-2-enoyl)pyrrolidin-2-yl]methyl N-[(1R)-2-(4-methylphenyl)-1-[(1S,2S,6R,8S)-2,9,9-trimethyl-3,5-dioxa-4-boratricyclo[6.1.1.0^[2,6]]decan-4-yl]ethyl]carbamate (70 mg, 0.14 mmol, 1.00 eq.), (2-methylpropyl)boronic acid (41.9 mg, 0.41 mmol, 2.90 eq.), hexane (3 mL), methanol (3 mL), and 1N HCl (2.8 mL, 20.00 eq.). The resulting solution was stirred for 2 h at 25° C. The resulting mixture was washed with 3×5 mL of hexane. The methanol layer was diluted with 50 mL of water, and dried over lyophylization to give a crude product which was further purified by Prep-HPLC with the following conditions: Column, XBridge Prep C18 OBD Column, 19*150 mm, 5 um; mobile phase, Water (10 MMOL/L NH$_4$HCO$_3$+0.1% NH$_3$.H$_2$O) and ACN (25.0% ACN up to 31.0% in 7 min); Detector, UV 254/220 nm. This resulted in 26.3 mg (52%) of [(1R)-2-(4-methylphenyl)-1-[([[(2R)-1-(prop-2-enoyl)pyrrolidin-2-yl]methoxy]carbonyl)amino]ethyl]boronic acid as a white solid after the lyophilization. LC-MS m/z: 361 (M+1).

Example 20

((R)-1-(((((R)-1-(2-cyano-4-methyl-4-(piperidin-1l-yl)pent-2-enoyl)pyrrolidin-2-yl)methoxy)carbonyl)amino)-2-phenylethyl)boronic acid

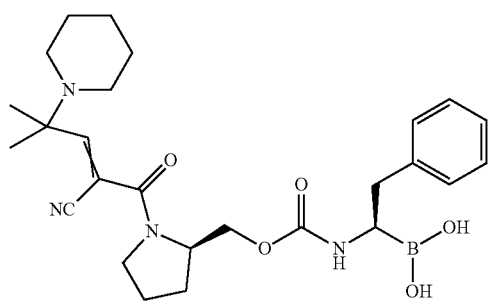 [SMILES: CC(C)(C=C(C#N)C(=O)N1CCC[C@@H]1COC(=O)N[C@@H](Cc1ccccc1)B(O)O)N1CCCCC1]

Step 1

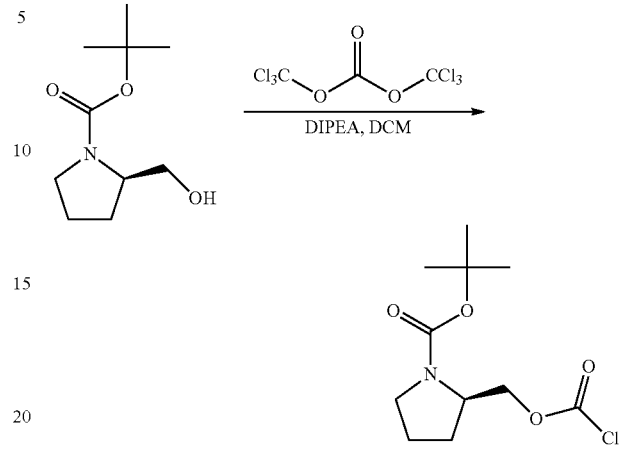

Into a 50-mL 3-necked round-bottom flask, was placed tert-butyl (2R)-2-(hydroxymethyl)pyrrolidine-1-carboxylate (600 mg, 2.98 mmol. 1.00 eq.), dichloromethane (15 mg, 0.18 mmol, 0.06 eq.), and DIPEA (1.16 g, 8.99 mmol, 3.00 eq.). This was followed by the addition of ditrichloromethyl carbonate (438.8 mg, 1.48 mmol, 0.50 eq.) dropwise with stirring at 0° C. The resulting solution was stirred for 3 h at 0° C. The resulting mixture was concentrated under vacuum to give a crude product as a yellow oil which was used directly to the next step.

Step 2

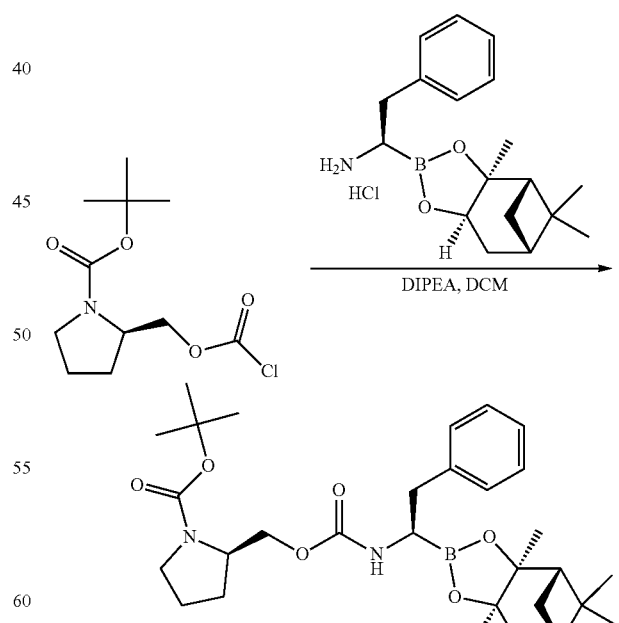

Into a 100-mL 3-necked round-bottom flask, was placed (1R)-2-phenyl-1-[(1S,2S,6R,8S)-2,9,9-trimethyl-3,5-dioxa-4-boratricyclo[6.1.1.0^[2,6]]decan-4-yl]ethan-1-amine (900 mg, 3.01 mmol, 0.90 eq.), dichloromethane (20 mL), and DIPEA (693.1 mg, 5.37 mmol, 1.80 eq.). This was followed by the addition of tert-butyl (2R)-2-[[(chlorocarbonyl)oxy]methyl]pyrrolidine-1-carboxylate (785.1 mg, 2.98 mmol, 1.00 eq.) dropwise with stirring at 0° C. The resulting solution was stirred for 90 min. at 25° C. The resulting solution was diluted with 100 mL of DCM. The resulting mixture was washed with 3×100 mL of sodium chloride. The mixture was dried over anhydrous sodium sulfate and concentrated under vacuum. The crude product was purified by Prep-HPLC with the following conditions: Column, XBridge Prep C18 OBD Column, 19*150 mm, 5 um; mobile phase, Water (10 MMOL/L NH$_4$HCO$_3$+0.1% NH$_3$·H$_2$O) and ACN (hold 65.0% ACN in 7 min); Detector, UV 254/220 nm. This resulted in 530 mg (34%) of tert-butyl (2R)-2-[([[(1R)-2-phenyl-1-((1S,2S,6R,8S)-2,9,9-trimethyl-3,5-dioxa-4-boratricyclo[6.1.1.0ˆ[2,6]]decan-4-yl]ethyl]carbamoyl]oxy)methyl]pyrrolidine-1-carboxylate as a white solid after the lyophilization.

Step 3

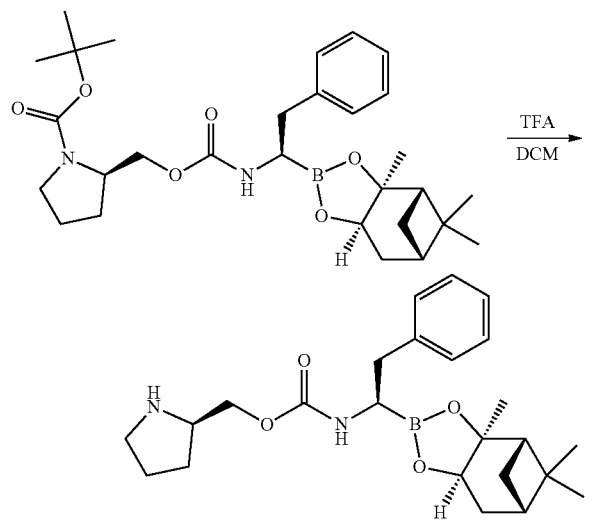

Into a 250-mL round-bottom flask, was placed tert-butyl (2R)-2-[([[(1R)-2-phenyl-1-[(1S,2S,6R,8S)-2,9,9-trimethyl-3,5-dioxa-4-boratricyclo[6.1.1.0ˆ[2,6]]decan-4-yl]ethyl]carbamoyl]oxy)methyl]pyrrolidine-1-carboxylate (520 mg, 0.99 mmol, 1.00 eq.), dichloromethane (100 mL), and trifluoroacetic acid (10 mL). The resulting solution was stirred for 30 min at 25° C. The resulting mixture was concentrated under vacuum to give a crude product which was used directly to the next step.

Step 4

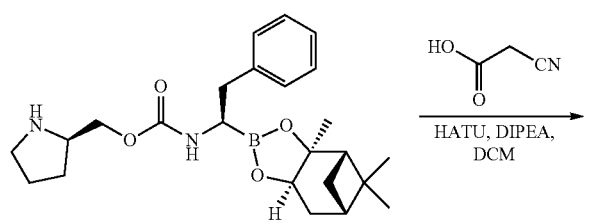

-continued

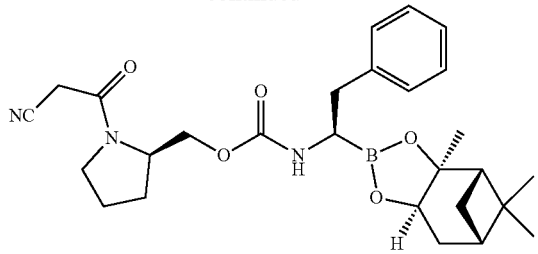

Into a 50-mL round-bottom flask purged and maintained with an inert atmosphere of nitrogen, was placed (2R)-pyrrolidin-2-ylmethyl N-[(1R)-2-phenyl-1-[(1S,2S,6R,8S)-2,9,9-trimethyl-3,5-dioxa-4-boratricyclo[6.1.1.0ˆ[2,6]]decan-4-yl]ethyl]carbamate (372.5 mg, 0.87 mmol, 1.00 eq.), 2-cyanoacetic acid (89.2 mg, 1.05 mmol, 1.20 eq.), HATU (398.8 mg, 1.05 mmol, 1.20 eq.), DIPEA (282 mg, 2.19 mmol, 2.50 eq.), and dichloromethane (15 mL). The resulting solution was stirred for 60 min. at 25° C. The resulting solution was diluted with 100 mL of DCM. The resulting mixture was washed with 3×100 mL of saturated brine. The mixture was dried over anhydrous sodium sulfate and concentrated under vacuum. The crude product was purified by Flash-Prep-HPLC with the following conditions: Column, C18 silica gel, mobile phase, H$_2$O:CH$_3$CN=99:1 increasing to H$_2$O:CH$_3$CN=1:99 within 100 min; Detector, UV 220 nm. This resulted in 280 mg (65%) of [(2R)-1-(2-cyanoacetyl)pyrrolidin-2-yl]methylN-[(1R)-2-phenyl-1-[(1S,2S,6R,8S)-2,9,9-trimethyl-3,5-dioxa-4-boratricyclo[6.1.1.0ˆ[2,6]]decan-4-yl]ethyl]carbamate as a yellow oil.

Step 5

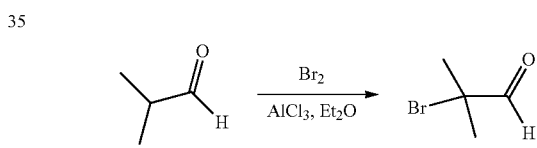

Into a 1L 3-necked round-bottom flask, was placed 2-methylpropanal (50 g. 693.43 mmol, 1.00 eq.), ether (500 mL), and AlCl$_3$ (2.49 g, 0.03 eq.). This was followed by the addition of dibromane (131.34 g, 821.86 mmol, 1.20 eq.) dropwise with stirring at 0° C. in 10 min.; The resulting solution was stirred overnight at rt. The reaction was then quenched by the addition of 100 mL of water/ice. The pH value of the solution was adjusted to 10-12 with sodium carbonate. The resulting solution was extracted with 3×100 mL of ether and the organic layers combined and dried over anhydrous sodium sulfate and concentrated under vacuum. The crude product was purified by distillation under reduced pressure (170 mm Hg) and the fraction was collected at 70-77° C. This resulted in 20 g (19.1%) of 2-bromo-2-methylpropanal as a colorless oil.

Step 6

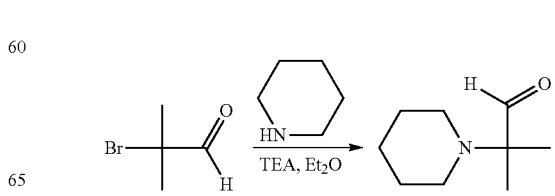

Into a 100-mL round-bottom flask purged and maintained with an inert atmosphere of nitrogen, was placed 2-bromo-2-methylpropanal (1.066 g, 7.06 mmol, 1.20 eq.), ether (25 mL), TEA (1.78 g, 17.59 mmol, 3.00 eq.), and piperidine (500 mg, 5.87 mmol, 1.00 eq.). The resulting solution was stirred overnight at rt. The resulting mixture was washed with 2×20 mL of sodium chloride. The resulting solution was extracted with 3×20 mL of ether and the organic layers combined and dried over anhydrous sodium sulfate and concentrated under vacuum. This resulted in 1.088 g (crude) of 2-methyl-2-(piperidin-1-yl)propanal as a yellow oil.

Step 7

Into a 25-mL round-bottom flask purged and maintained with an inert atmosphere of nitrogen, was placed [(2R)-1-(2-cyanoacetyl)pyrrolidin-2-yl]methyl N-[(1R)-2-phenyl-1-[(1S,2S,6R,8S)-2,9,9-trimethyl-3,5-dioxa-4-boratricyclo[6.1.1.0^[2,6]]decan-4-yl]ethyl]carbamate (100 mg, 0.20 mmol, 1.00 eq.), pyridine (5 mL), 2-methyl-2-(piperidin-1-yl)propanal (50 mg, 0.32 mmol, 1.60 eq.), and pyrrolidine (10 mg, 0.70 eq.). The resulting solution was stirred for 3 h at it. The resulting mixture was concentrated under vacuum. The crude product was purified by Prep-HPLC with the following conditions: Column, XBridge Prep C18 OBD Column, 19*150 mm, 5 um, mobile phase, Water (10 MMOL/L $NH_4HCO_3$+0.1% $NH_3.H_2O$) and ACN (70% ACN up to 95% in 7 min); Detector, UV 254/220 nm. This resulted in 50 mg of [(2R)-1-[2-cyano-2-[2-methyl-2-(piperidin-1-yl)propylidene]acetyl]pyrrolidin-2-yl]methyl-N-[(1R)-2-phenyl-1-[(1S,2S,6R,8S)-2,9,9-trimethyl-3,5-dioxa-4-boratricyclo[6.1.1.0^[2,6]]decan-4-yl]ethyl] carbamate as a white solid after the lyophilization.

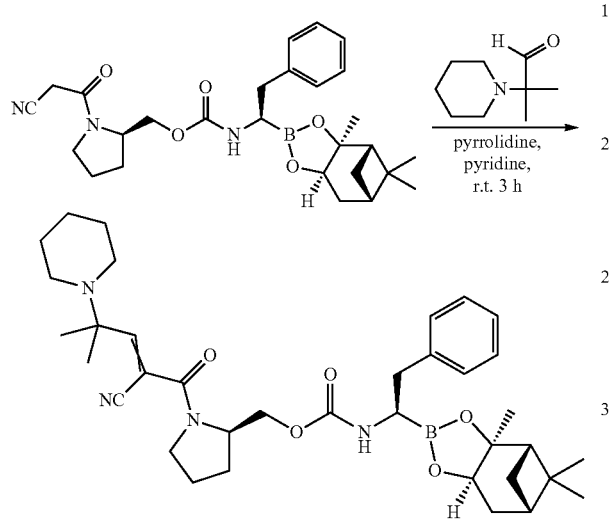

Step 8

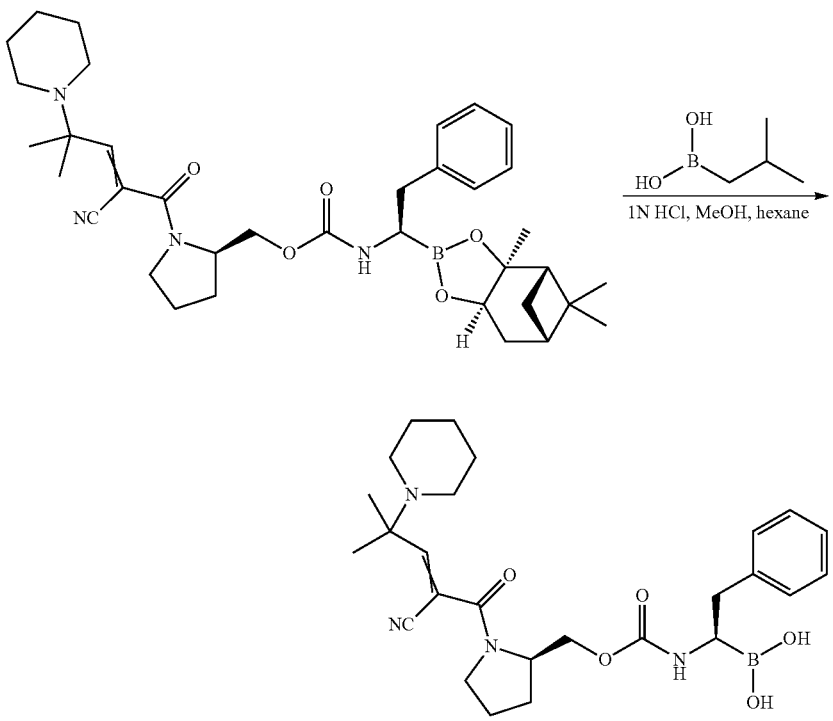

Into a 50-mL round-bottom flask purged and maintained with an inert atmosphere of nitrogen, was placed [(2R)-1-[2-cyano-2-[2-methyl-2-(piperidin-1-yl)propylidene]acetyl]pyrrolidin-2-yl]methyl N-[(1R)-2-phenyl-1-[(1S,2S,6R,8S)-2,9,9-trimethyl-3,5-dioxa-4-boratricyclo[6.1.1.0^[2,6]]decan-4-yl]ethyl]carbamate (50 mg, 0.08 mmol, 1.00 eq.), methanol (2.5 mL), (2-methylpropyl)boronic acid (25 mg, 0.25 mmol, 3.00 eq.), hexane (2.5 mL), and 1N HCl (2.5 mL). The resulting solution was stirred for 2 h at rt. The hexane layer was discarded. The methanol layer was diluted with water (15 mL), then dried over lyophilization to give a crude product. The crude product was purified by Prep-HPLC with the following conditions: Column, XBridge Prep C18 OBD Column, 19*150 mm, 5 um; mobile phase, Water (I MMOL/L $NH_4HCO_3$+0.1% $NH_3.H_2O$) and ACN (70% ACN up to 95% in 7 min); Detector, UV 254/220 nm. This resulted in 11.3 mg (29%) of [(1R)-1-[([[(2R)-1-[2-cyano-2-[2-methyl-2-(piperidin-1-yl)propylidene]acetyl]pyrrolidin-2-yl]methoxy]carbonyl)amino]-2-phenylethyl]boronic acid as a white solid after the lyophilization. LC-MS m/z: 497 (M+1).

Example 21

((R)-1-(((((R)-1-(2-cyano-4-(4,4-difluoropiperidin-1-yl)-4-methylpent-2-enoyl)pyrrolidin-2-yl)methoxy)carbonyl)amino)-2-phenylethyl)boronic acid

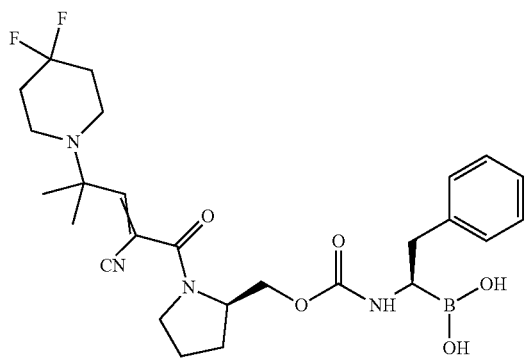 [SMILES: CC(C)(C=C(C#N)C(=O)N1CCC[C@@H]1COC(=O)N[C@@H](Cc1ccccc1)B(O)O)N1CCC(F)(F)CC1]

Step 1

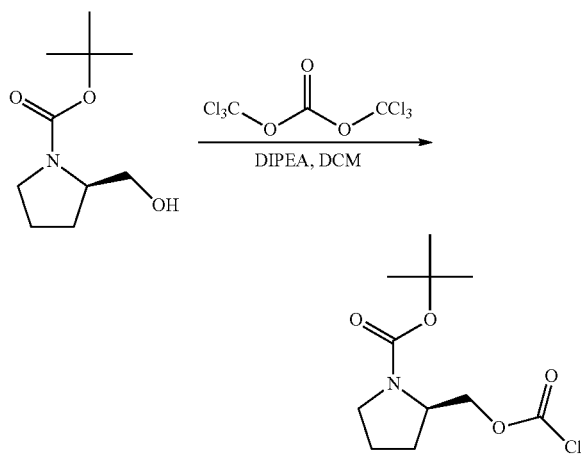

Into a 50-mL 3-necked round-bottom flask, was placed tert-butyl (2R)-2-(hydroxymethyl)pyrrolidine-1-carboxylate (600 mg, 2.98 mmol. 1.00 eq.), dichloromethane (15 mg, 0.18 mmol, 0.06 eq.), and DIPEA (1.16 g, 8.99 mmol, 3.00 eq.). This was followed by the addition of ditrichloromethyl carbonate (438.8 mg, 1.48 mmol, 0.50 eq.) dropwise with stirring at 0° C. The resulting solution was stirred for 3 h at 0° C. The resulting mixture was concentrated under vacuum to give a crude product as a yellow oil which was used directly to the next step.

Step 2

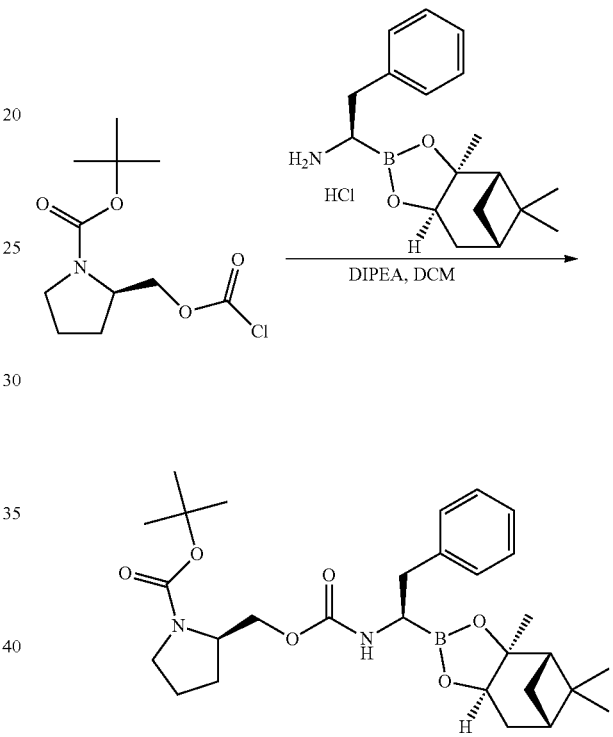

Into a 100-mL 3-necked round-bottom flask, was placed (1R)-2-phenyl-1-[(1S,2S,6R,8S)-2,9,9-trimethyl-3,5-dioxa-4-boratricyclo[6.1.1.0^[2.6]]decan-4-yl]ethan-1-amine (900 mg, 3.01 mmol, 0.90 eq.), dichloromethane (20 mL), and DIPEA (693.1 mg, 5.37 mmol, 1.80 eq.). This was followed by the addition of tert-butyl (2R)-2-[[(chlorocarbonyl)oxy]methyl]pyrrolidine-1-carboxylate (785.1 mg, 2.98 mmol, 1.00 eq.) dropwise with stirring at 0° C. The resulting solution was stirred for 90 min. at 25° C. The resulting solution was diluted with 100 mL of DCM. The resulting mixture was washed with 3×100 mL of sodium chloride. The mixture was dried over anhydrous sodium sulfate and concentrated under vacuum. The crude product was purified by Prep-HPLC with the following conditions: Column, XBridge Prep C18 OBD Column, 19*150 mm, 5 um; mobile phase, Water (10 MMOL/L $NH_4HCO_3$+0.1% $NH_3.H_2O$) and ACN (hold 65.0% ACN in 7 min); Detector, UV 254/220 nm. This resulted in 530 mg (34%) of tert-butyl (2R)-2-[([[(1R)-2-phenyl-1-[(1S,2S,6R,8S)-2,9,9-trimethyl-3,5-dioxa-4-boratricyclo[6.1.1.0^[2,6]]decan-4-yl]ethyl]carbamoyl]oxy)methyl]pyrrolidine-1-carboxylate as a white solid after the lyophilization.

Step 3

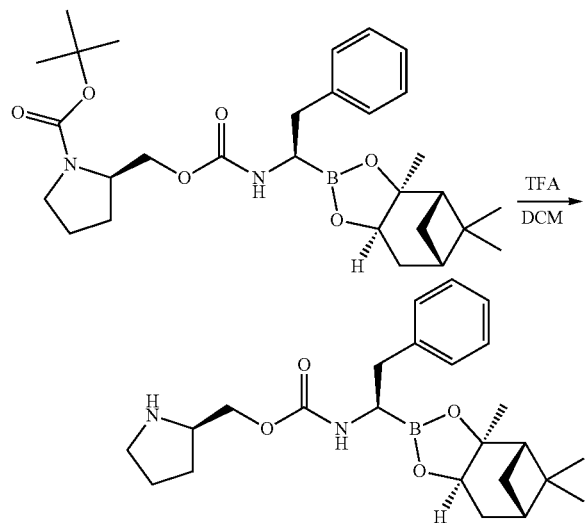

Into a 250-mL round-bottom flask, was placed tert-butyl (2R)-2-[([[(1R)-2-phenyl-1-[(1S,2S,6R,8S)-2,9,9-trimethyl-3,5-dioxa-4-boratricyclo[6.1.1.0^[2,6]]decan-4-yl]ethyl]carbamoyl]oxy)methyl]pyrrolidine-1-carboxylate (520 mg, 0.99 mmol, 1.00 eq.), dichloromethane (100 mL), and trifluoroacetic acid (10 mL). The resulting solution was stirred for 30 min at 25° C. The resulting mixture was concentrated under vacuum to give a crude product which was used directly to the next step.

Step 4

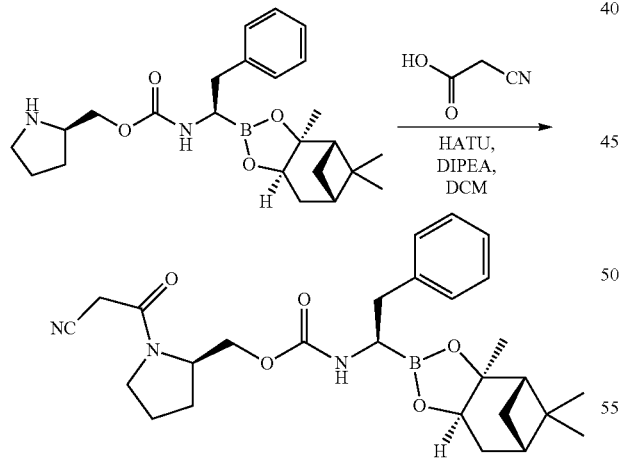

Into a 50-mL round-bottom flask purged and maintained with an inert atmosphere of nitrogen, was placed (2R)-pyrrolidin-2-ylmethyl N-[(1R)-2-phenyl-1-[(1S,2S,6R,8S)-2,9,9-trimethyl-3,5-dioxa-4-boratricyclo[6.1.1.0^[2,6]]decan-4-yl]ethyl]carbamate (372.5 mg, 0.87 mmol, 1.00 eq.), 2-cyanoacetic acid (89.2 mg, 1.05 mmol, 1.20 eq.), HATU (398.8 mg, 1.05 mmol, 1.20 eq.), DIPEA (282 mg, 2.19 mmol, 2.50 eq.), and dichloromethane (15 mL). The resulting solution was stirred for 60 min. at 25° C. The resulting solution was diluted with 100 mL of DCM. The resulting mixture was washed with 3×100 mL of saturated brine. The mixture was dried over anhydrous sodium sulfate and concentrated under vacuum. The crude product was purified by Flash-Prep-HPLC with the following conditions: Column, C18 silica gel, mobile phase, H₂O:CH₃CN=99:1 increasing to H₂O:CH₃CN=1:99 within 100 min; Detector, UV 220 nm. This resulted in 280 mg (65%) of [(2R)-1-(2-cyanoacetyl)pyrrolidin-2-yl]methylN-[(1R)-2-phenyl-1-[(1S,2S,6R,8S)-2,9,9-trimethyl-3,5-dioxa-4-boratricyclo[6.1.1.0^[2,6]]decan-4-yl]ethyl]carbamate as a yellow oil.

Step 5

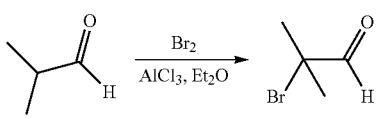

Into a 1L 3-necked round-bottom flask, was placed 2-methylpropanal (50 g. 693.43 mmol, 1.00 eq.), ether (500 mL), and AlCl₃ (2.49 g, 0.03 eq.). This was followed by the addition of dibromane (131.34 g, 821.86 mmol, 1.20 eq.) dropwise with stirring at 0° C. in 10 min. The resulting solution was stirred overnight at rt. The reaction was then quenched by the addition of 100 mL of water/ice. The pH value of the solution was adjusted to 10-12 with sodium carbonate. The resulting solution was extracted with 3×100 mL of ether and the organic layers combined and dried over anhydrous sodium sulfate and concentrated under vacuum. The crude product was purified by distillation under reduced pressure (170 mm Hg) and the fraction was collected at 70-77° C. This resulted in 20 g (19.1%) of 2-bromo-2-methylpropanal as a colorless oil.

Step 6

Into a 100-mL round-bottom flask, was placed 4,4-difluoropiperidine (500 mg, 4.13 mmol, 1.00 eq.), ether (20 mL), TEA (1.25 g, 12.35 mmol, 3.00 eq.), and 2-bromo-2-methylpropanal (750 mg, 4.97 mmol. 1.20 eq.). The resulting solution was stirred overnight at rt. The reaction was then quenched by the addition of 20 mL of ice/salt. The resulting solution was extracted with 2×50 mL of ether and the organic layers combined and dried over anhydrous sodium sulfate and concentrated under vacuum. This resulted in 0.9 g (crude) of 2-(4,4-difluoropiperidin-1-yl)-2-methylpropanal as off-white oil.

Step 7

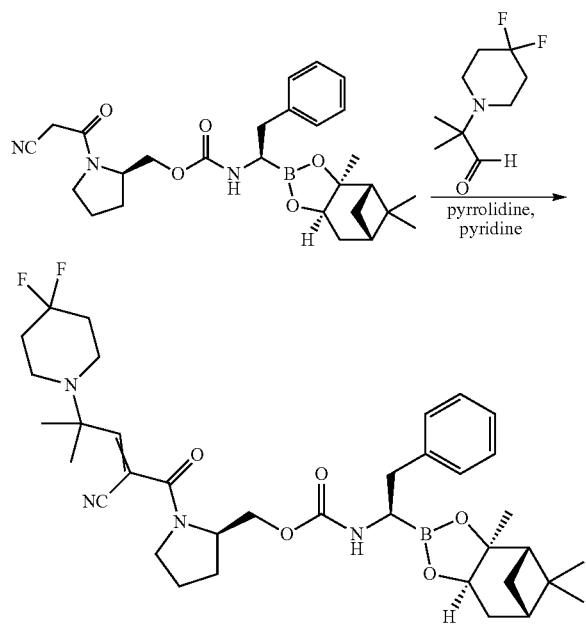

Into a 8-mL sealed tube, was placed [(2R)-1-(2-cyano-acetyl)pyrrolidin-2-yl]methyl N-[(1R)-2-phenyl-1-[(1S,2S,6R,8S)-2,9,9-trimethyl-3,5-dioxa-4-boratricyclo[6.1.1.0^[2,6]]decan-4-yl]ethyl]carbamate (90 mg, 0.18 mmol, 1.00 eq.). 2-(4,4-difluoropiperidin-1-yl)-2-methylpropanal (38 mg, 0.20 mmol, 1.09 eq.), pyrrolidine (13 mg, 0.18 mmol, 1.00 eq.), and pyridine (0.9 mL). The resulting solution was stirred overnight at 25° C. The resulting mixture was concentrated under vacuum. The crude product was purified by Prep-HPLC with the following conditions: Column, XBridge Prep C18 OBD Column, 19*150 mm, 5 um; mobile phase, Water (10 MMOL/L NH$_4$HCO$_3$+0.1% NH$_3$.H$_2$O) and ACN (75.0% ACN up to 83.0% in 7 min); Detector, UV 254/220 nm. This resulted in 18 mg (15%) of [(2R)-1-[2-cyano-2-[2-(4,4-difluoropiperidin-1-yl)-2-methylpropylidene]acetyl]pyrrolidin-2-yl]methylN-[(1R)-2-phenyl-1-[(1S,2S,6R,8S)-2,9,9-trimethyl-3,5-dioxa-4-boratricyclo[6.1.1.0^[2,6]]decan-4-yl]ethyl]carbamate as a white solid after the lyophilization.

Step 8

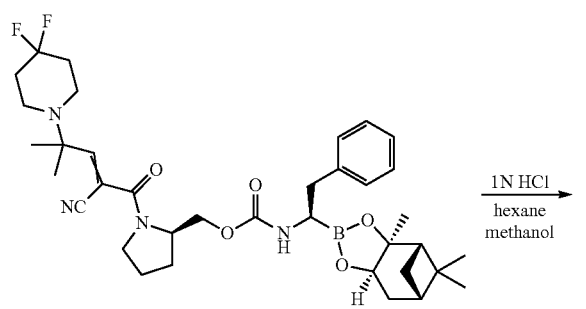

-continued

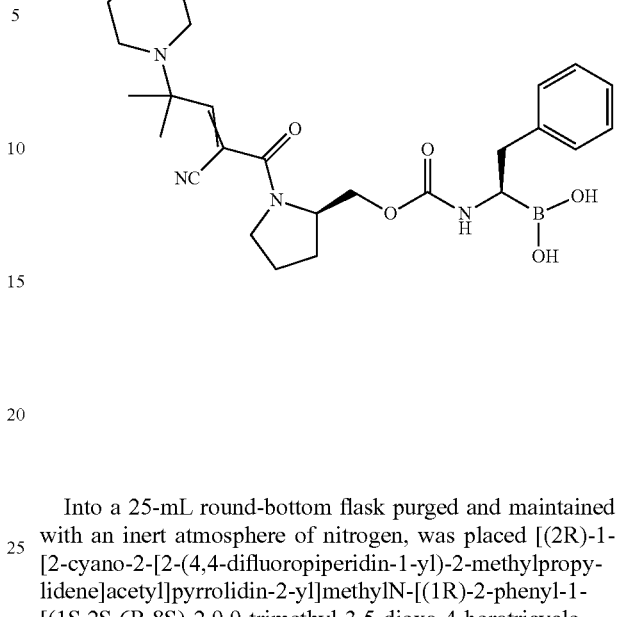

Into a 25-mL round-bottom flask purged and maintained with an inert atmosphere of nitrogen, was placed [(2R)-1-[2-cyano-2-[2-(4,4-difluoropiperidin-1-yl)-2-methylpropylidene]acetyl]pyrrolidin-2-yl]methylN-[(1R)-2-phenyl-1-[(1S,2S,6R,8S)-2,9,9-trimethyl-3,5-dioxa-4-boratricyclo[6.1.1.0^[2,6]]decan-4-yl]ethyl]carbamate (40 mg, 0.06 mmol, 1.00 eq.), (2-methylpropyl)boronic acid (17.8 mg, 0.17 mmol, 2.90 eq.), 1N hydrogen chloride (1.2 mL, 20.00 eq.), hexane (1.7 mL), and methanol (1.7 mL). The resulting solution was stirred for 2 h at 25° C. The resulting mixture was washed with 3×10 mL of hexane. The methanol layer was diluted with 17 mL of H$_2$O, then dried over lyophylization to give a crude product which was further purified by Prep-HPLC with the following conditions: Column, XBridge Prep C18 OBD Column. 19*150 mm, 5 um; mobile phase, Water (10 MMOL/L NH$_4$HCO$_3$+0.1% NH$_3$.H$_2$O) and ACN (40.0% ACN up to 51.0% in 7 min); Detector. UV 254/220 nm. This resulted in 8.4 mg (26%) of [(1R)-1-[([[(2R)-1-[2-cyano-2-[2-(4,4-difluoropiperidin-1-yl)-2-methylpropylidene]acetyl]pyrrolidin-2-yl]methoxy]carbonyl)amino]-2-phenylethyl]boronic acid as a white solid after the lyophilization. LC-MS m/z: 533 (M+1).

Example 22

((R)-1-(((((1R,2S,5S)-3-(2-cyano-4,4-dimethylpent-2-enoyl)-3-azabicyclo[3.1.0]hexan-2-yl)methoxy)carbonyl)amino)-2-phenylethyl)boronic acid

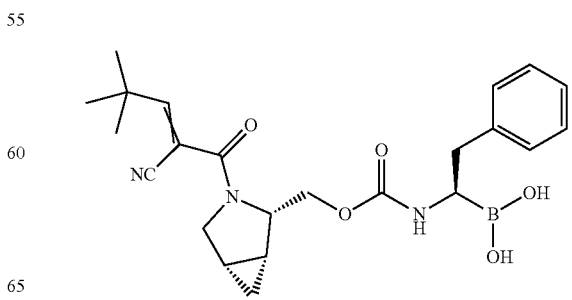

Step 1

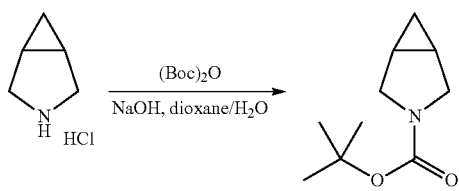

Into a 500-mL round-bottom flask, was placed a solution of 3-azabicyclo[3.1.0]hexane hydrochloride (5 g, 41.81 mmol, 1.00 eq.) in dioxane/$H_2O$ (75/75 mL), 1N NaOH (84 mL, 2.00 eq.), and $(Boc)_2O$ (14 g, 64.15 mmol, 1.50 eq.). The resulting solution was stirred overnight at rt. The resulting mixture was concentrated under vacuum. The resulting solution was extracted with 3×200 mL of petroleum ether and the organic layers combined and dried over anhydrous sodium sulfate and concentrated under vacuum. The residue was applied onto a silica gel column with ethyl acetate/petroleum ether (1:50). This resulted in 6 g (70%) of tert-butyl 3-azabicyclo[3.1.0]hexane-3-carboxylate as light yellow oil.

Step 2

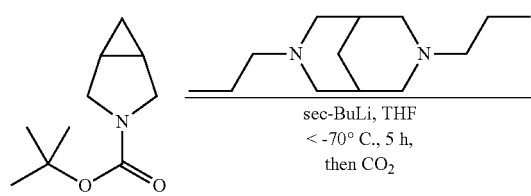

Into a 250-mL 3-necked round-bottom flask, was placed a solution of tert-butyl 3-azabicyclo[3.1.0]hexane-3-carboxylate (4.75 g, 25.92 mmol, 1.00 eq.) in tetrahydrofuran (104 mL), and 3,7-dipropyl-3,7-diazabicyclo[3.3.1]nonane (6.81 g, 32.37 mmol, 1.25 eq.). This was followed by the addition of sec-BuLi (24 mL, 1.20 eq.) dropwise with stirring at −60° C. To this was added dry ice (1 g, 1.00 eq.) at −68° C. The resulting solution was stirred for 1 h at −45° C. The reaction was then quenched by the addition of 60 mL of $H_2O$. The resulting mixture was concentrated under vacuum. The resulting solution was extracted with 2×60 mL of MTBE and the aqueous layers combined. The pH value of the solution was adjusted to 2-3 with $KHSO_4$ (25% g/mL). The resulting solution was extracted with 3×80 mL of MTBE and the organic layers combined and dried over sodium sulfate and concentrated under vacuum. This resulted in 3.9 g (66%) of rac-cis(1S,2R,5R)-3-[(tert-butoxy)carbonyl]-3-azabicyclo[3.1.0]hexane-2-carboxylic acid as a colorless oil.

Step 3

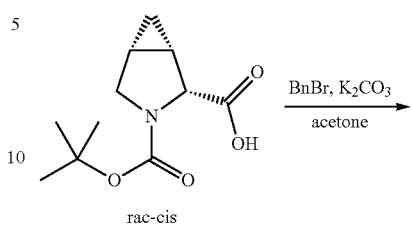

Into a 100-mL round-bottom flask, was placed a solution of rac-cis-(1S,2R,5R)-3-[(tert-butoxy)carbonyl]-3-azabicyclo[3.1.0]hexane-2-carboxylic acid (2 g, 8.80 mmol, 1.00 eq.) in acetone (40 mL), BnBr (1.5 g, 8.77 mmol, 1.00 eq.), and potassium carbonate (1.5 g, 10.85 mmol, 1.25 eq.). The resulting solution was stirred overnight at rt. The solids were filtered out. The resulting mixture was concentrated under vacuum. The residue was applied onto a silica gel column with ethyl acetate/petroleum ether (2:98-5:95). This resulted in 2 g (72%) of rac-cis-2-benzyl 3-tert-butyl (1S,2R,5R)-3-azabicyclo[3.1.0]hexane-2,3-dicarboxylate as a yellow oil.

Step 4

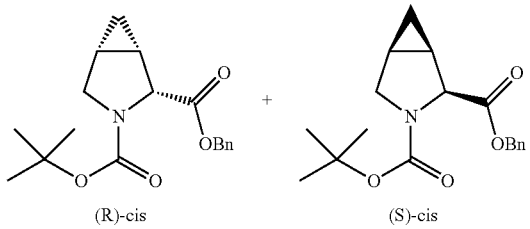

The product rac-cis-2-benzyl 3-tert-butyl (1S,2R,5R)-3-azabicyclo[3.1.0]hexane-2,3-dicarboxylate (1 g) was purified by Chiral-Prep-HPLC with the following conditions: Column, CHIRAL ART Cellulose-SB, 2*25 cm, 5 um; mobile phase, Hex- and ethanol- (hold 7.0% ethanol- in 13 min); Detector, UV 220/254 nm. This resulted in 400 mg (40%) of (R)-cis-2-benzyl 3-tert-butyl (1S,2R,5R)-3-azabicyclo[3.1.0]hexane-2,3-dicarboxylate as a colorless oil ($[\alpha]_{25°\ C.}^{589\ nm}$=103.2 (C 0.5, MeOH)). And 400 mg (40%) of (S)-cis-2-benzyl 3-tert-butyl (1R,2S,5S)-3-azabicyclo[3.1.0]hexane-2,3-dicarboxylate as a colorless oil ([α]$_{25° C.}^{589\ nm}$=−120.8 (C 0.5, MeOH)).

Step 5

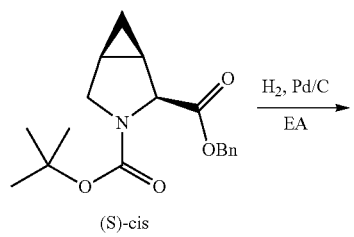

(S)-cis

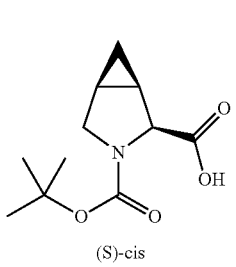

(S)-cis

Into a 50-mL round-bottom flask, was placed a solution of (S)-cis-2-benzyl 3-tert-butyl (1R,2S,5S)-3-azabicyclo[3.1.0]hexane-2,3-dicarboxylate (450 mg, 1.42 mmol, 1.00 eq.) in ethyl acetate (6 mL), and palladium carbon (450 mg, 1.00 eq.). The mixture was introduced in H$_2$. The resulting solution was stirred for 3 h at rt. The solids were filtered out. The resulting mixture was concentrated under vacuum. This resulted in 310 mg (96%) of (1R,2S,5S)-3-[(tert-butoxy)carbonyl]-3-azabicyclo[3.1.0]hexane-2-carboxylic acid as a colorless oil.

Step 6

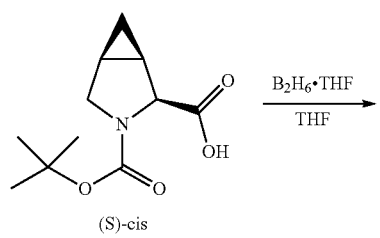

(S)-cis

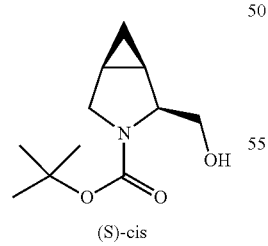

(S)-cis

Into a 25-mL round-bottom flask, was placed a solution of (S)-cis-(1R,2S,5S)-3-[(tert-butoxy)carbonyl]-3-azabicyclo[3.1.0]hexane-2-carboxylic acid (310 mg, 1.36 mmol, 1.00 eq.) in tetrahydrofuran (7 mL). To the mixture was added dropwise BH$_3$.THF (1.7 mL, 1.25 eq., 1N) at 0 degree C. The resulting solution was stirred overnight at rt. The reaction was then quenched by the addition of 10 mL of NH$_4$Cl. The resulting solution was extracted with 2×20 mL of ethyl acetate and the organic layers combined. The resulting mixture was washed with 1×10 mL of water and 1×10 mL of sodium chloride. The mixture was dried over anhydrous sodium sulfate and concentrated under vacuum. The residue was applied onto a silica gel column with ethyl acetate/petroleum ether (1:10). This resulted in 200 mg (69%) of tert-butyl (1R,2S,5S)-2-(hydroxymethyl)-3-azabicyclo[3.1.0]hexane-3-carboxylate as a colorless oil.

Step 7

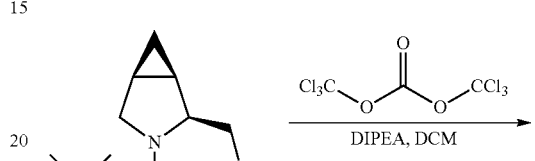

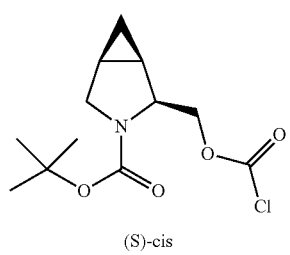

(S)-cis

Into a 50-mL 3-necked round-bottom flask, was placed a solution of tert-butyl (1R,2S,5S)-2-(hydroxymethyl)-3-azabicyclo[3.1.0]hexane-3-carboxylate (200 mg, 0.94 mmol, 1.00 eq.) in dichloromethane (4 mL), and DIEA (363 mg, 2.81 mmol, 3.00 eq.). This was followed by the addition of a solution of ditrichloromethyl carbonate (139 mg, 0.47 mmol, 3.00 eq.) in dichloromethane (3 mL) dropwise with stirring at 0° C. The resulting solution was stirred for 2.5 h at 0° C. The resulted mixture solution was used directly to the next step.

Step 8

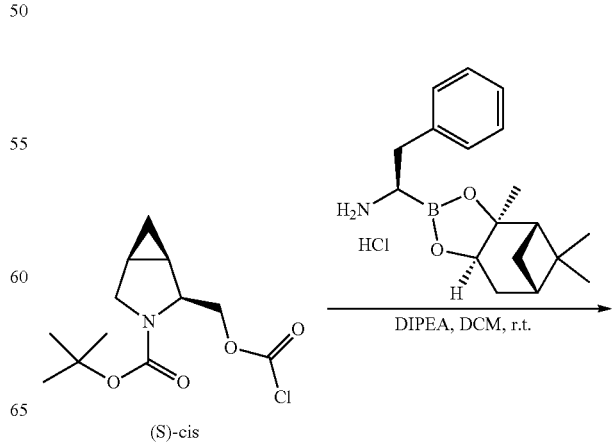

(S)-cis

95

-continued

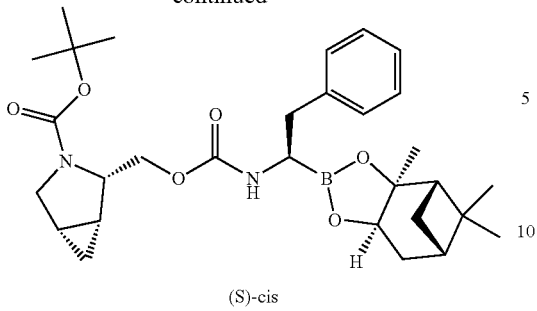

(S)-cis

Into a 50-mL 3-necked round-bottom flask, was placed a solution of (1R)-2-phenyl-1-[(1S,2S,6R,8S)-2,9,9-trimethyl-3,5-dioxa-4-boratricyclo[6.1.1.0^2,6]decan-4-yl] ethan-1-amine hydrochloride (268 mg, 0.80 mmol, 1.00 eq.) in dichloromethane (7 mL), and DIEA (24 mg. 0.19 mmol, 2.00 eq.). This was followed by the addition of a solution of (S)-cis-tert-butyl (1R,2S,5S)-2-[[(chlorocarbonyl)oxy]methyl]-3-azabicyclo[3.1.0]hexane-3-carboxylate (250 mg, 0.91 mmol, 1.00 eq.) in dichloromethane (5 mL) dropwise with stirring at 0° C. The resulting solution was stirred for 1 h at rt. The reaction was then quenched by the addition of 5 mL of water. The resulting solution was diluted with 20 mL of DCM. The resulting mixture was washed with 1×20 mL of sodium chloride. The mixture was dried over anhydrous sodium sulfate and concentrated under vacuum. This resulted in 500 mg (crude) of (S)-cis-tert-butyl (1R,2S,5S)-2-[([[(1R)-2-phenyl-1-[(1S,2S,6R,8S)-2,9,9-trimethyl-3,5-dioxa-4-boratricyclo[6.1.1.0^[2,6]]decan-4-yl]ethyl]carbamoyl]oxy)methyl]-3-azabicyclo[3.1.0.]hexane-3-carboxylate as light yellow oil.

Step 9

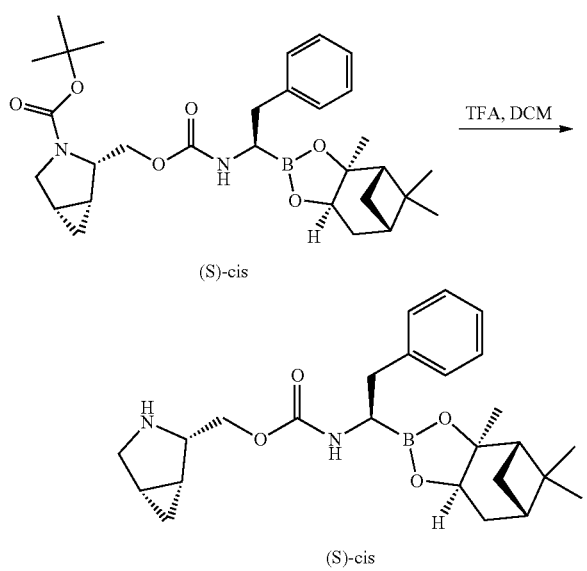

Into a 50-mL round-bottom flask, was placed a solution of (S)-cis-tert-butyl (1R,2S,5S)-2-[([[(1R)-2-phenyl-1-((1S,2S,6R,8S)-2,9,9-trimethyl-3,5-dioxa-4-boratricyclo[6.1.1.0^[2,6]]decan-4-yl]ethyl]carbamoyl]oxy)methyl]-3-azabicyclo[3.1.0]hexane-3-carboxylate (450 mg. 0.84 mmol, 1.00

96 eq.) in dichloromethane (5 mL), and trifluoroacetic acid (1 mL). The resulting solution was stirred for 1 h at rt. The resulting mixture was concentrated under vacuum. This resulted in 360 mg (crude) of (S)-cis-(1R,2S,5S)-3-azabicyclo[3.1.0]hexan-2-ylmethyl N-[(1R)-2-phenyl-1-[(1S,2S,6R,8S)-2,9,9-trimethyl-3,5-dioxa-4-boratricyclo[6.1.1.0^[2,6]]decan-4-yl]ethyl]carbamate as light yellow oil.

Step 10

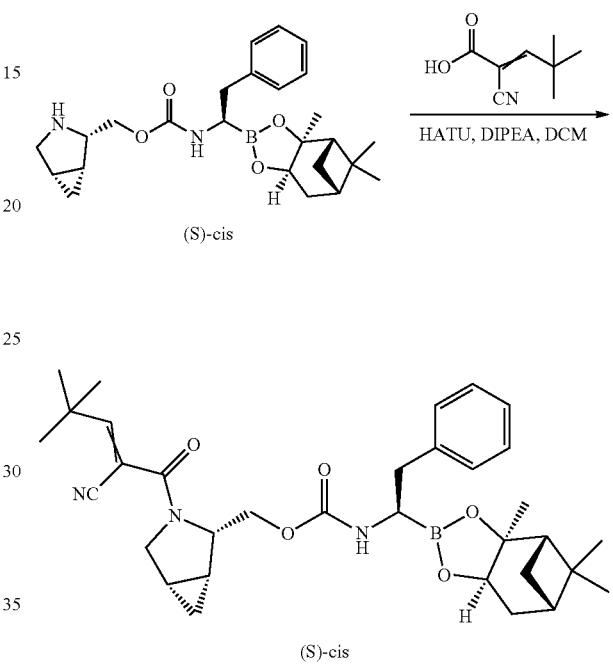

Into a 50-mL round-bottom flask, was placed a solution of (S)-cis-(1R,2S,5S)-3-azabicyclo[3.1.0]hexan-2-ylmethyl N-[(1R)-2-phenyl-1-[(1S,2S,6R,8S)-2,9,9-trimethyl-3,5-dioxa-4-boratricyclo[6.1.1.0^[2,6]]decan-4-yl]ethyl]carbamate (360 mg, 0.82 mmol, 1.00 eq.) in dichloromethane (5 mL), DIEA (318 mg, 2.46 mmol, 3.00 eq.), 2-cyano-4,4-dimethylpent-2-enoic acid (151 mg, 0.99 mmol, 1.20 eq.), and HATU (470 mg, 1.24 mmol, 1.50 eq.). The resulting solution was stirred for 2 h at rt. The reaction was then quenched by the addition of 2 mL of water. The resulting solution was diluted with 10 mL of DCM. The resulting mixture was washed with 1×10 mL of sodium chloride. The mixture was dried over anhydrous sodium sulfate and concentrated under vacuum. The crude product was purified by Prep-HPLC with the following conditions: Column, XBridge Prep C18 OBD Column, 19*150 mm, 5 um, mobile phase, Water (10 MMOL/L NH$_4$HCO$_3$+0.1% NH$_3$.H$_2$O) and ACN (75% ACN up to 80% in 7 min); Detector, UV 254/220 nm. This resulted in 55 mg (12%) of (S)-cis-[(1R,2S,5S)-3-[2-cyano-2-(2,2-dimethylpropylidene)acetyl]-3-azabicyclo[3.1.0]hexan-2-yl]methyl N-[(1R)-2-phenyl-1-[(1S,2S,6R,8S)-2,9,9-trimethyl-3,5-dioxa-4-boratricyclo [6.1.1.0^[2,6]]decan-4-yl]ethyl]carbamate as a white solid after the lyophilization.

Step 11

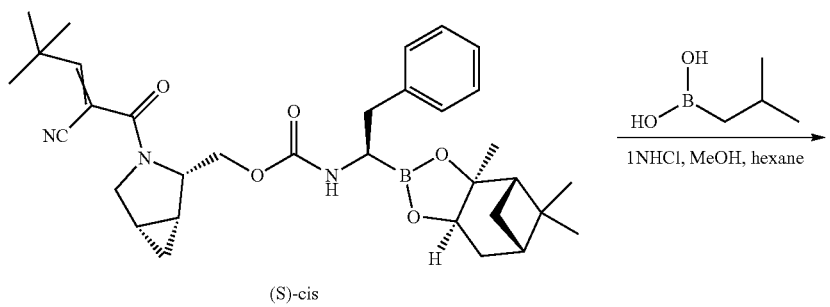

Into a 100-mL round-bottom flask, was placed a solution of (S)-cis-[(1R,2S,5S)-3-[2-cyano-2-(2,2-dimethylpropylidene)acetyl]-3-azabicyclo[3.1.0]hexan-2-yl]methyl N-[(1R)-2-phenyl-1-[(1S,2S,6R,8S)-2,9,9-trimethyl-3,5-dioxa-4-boratricyclo[6.1.1.0^[2,6]]decan-4-yl]ethyl]carbamate (60 mg, 0.10 mmol, 1.00 eq.) in methanol/hexane (2/2 mL), 1NHCl (2 mL, 20.00 eq.), and (2-methylpropyl)boronic acid (20 mg, 0.20 mmol, 3.00 eq.). The resulting solution was stirred for 2 h at rt. The hexane layer was discarded. The methanol layer was diluted with water (15 mL), then dried over lyophilization to give a crude product. The crude product was purified by Prep-HPLC with the following conditions: Column, XBridge Prep C18 OBD Column, 19*150 mm, 5 um; mobile phase, Water (10 MMOL/L NH$_4$HCO$_3$+0.1% NH$_3$.H$_2$O) and ACN (15% ACN up to 76% in 7 min); Detector, UV 254/220 nm. This resulted in 21.1 mg (43%) of [(1R)-1-[([[(1R,2S,5S)-3-[2-cyano-2-(2,2-dimethylpropylidene)acetyl]-3-azabicyclo[3.1.0]hexan-2-yl]methoxy]carbonyl)amino]-2-phenylethyl]boronic acid as a white solid after the lyophilization. LC-MS m/z: 457 (M+18).

Example 23

((R)-1-(((((R)-1-(2-cyano-4-methyl-4-morpholino-pent-2-enoyl)pyrrolidin-2-yl)methoxy)carbonyl) amino)-2-phenylethyl)boronic acid

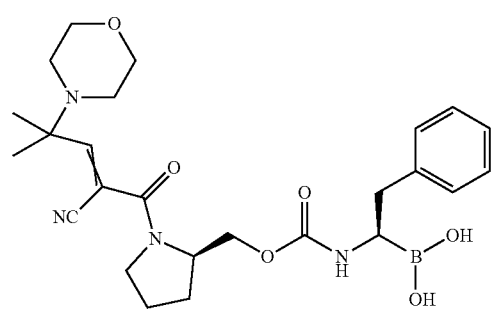 [SMILES: CC(C)(C=C(C#N)C(=O)N1CCC[C@@H]1COC(=O)N[C@@H](Cc1ccccc1)B(O)O)N1CCOCC1]

The title compound was prepared as in example 20 by replacing piperidine with morpholine. LC-MS m/z: 499 (M+1).

Example 24

((R)-1-(((((R)-1-(2-cyano-4,4-dimethylpent-2-enoyl)piperidin-2-yl)methoxy)carbonyl)amino)-2-(p-tolyl)ethyl)boronic acid

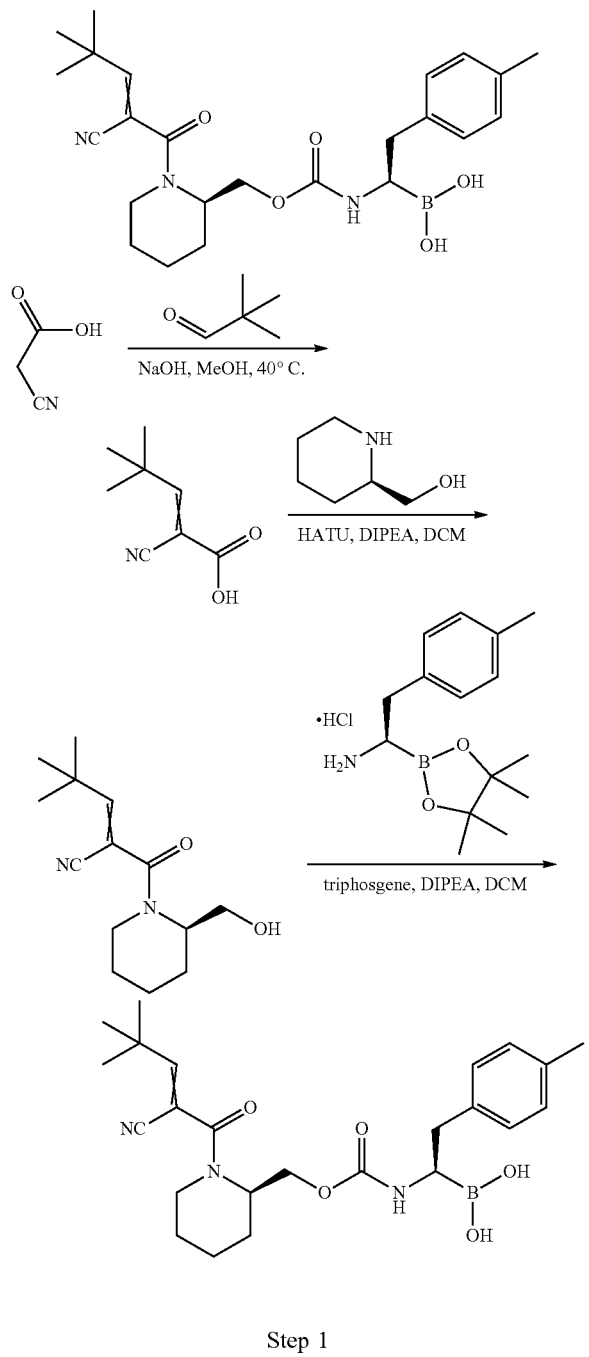

Step 1

To a stirring solution of 2-cyanoacetic acid (9.65 g, 112.7 mmol) in methanol (120 mL) at 0° C. was added portionwise NaOH (9.03 g, 225.4 mmol).Then pivalaldehyde (9.7 g, 112.7 mmol) was added slowly. The mixture was stirred at 40° C. for 16 h, then concentrated to dryness. The residue was dissolved in water (200 mL) and stirred for 5 min, then laid at r.t. for 2 h. The precipitate was collected and rinsed with water, dried over high vacuum to give pure title compound as light yellow crystal (3.5 g, 20%).

Step 2

To a mixture of 2-cyano-4,4-dimethylpent-2-enoic acid (398 mg, 2.6 mmol), (R)-piperidin-2-ylmethanol (300 mg, 2.6 mmol) and DIPEA (874 mg, 6.76 mmol) in DCM (30 mL) was added portionwise HATU (989 mg. 2.6 mmol) at 0° C. The resulted mixture was stirred at rt for 1 h, then concentrated to dryness. The residue was stirred in EtOAc (20 mL) for 5 min, then filtered. The filtration was concentrated in vacuo. The crude residue was purified via silica chromatography and a gradient of 0%-100% EtOAc in hexanes to afford (R)-2-(2-(hydroxymethyl)piperidine-1-carbonyl)-4,4-dimethylpent-2-enenitrile as a colorless solid (340 mg, 52%).

Step 3

Bis(trichloromethyl) carbonate (222 mg. 0.75 mmol) in DCM (1 mL) was added to a stirring solution of (R)-2-(2-(hydroxymethyl)piperidine-1-carbonyl)-4,4-dimethylpent-2-enenitrile (340 mg, 1.36 mmol) and DIPEA (1.05 g, 8.2 mmol) in DCM (5 mL) at 0° C. The mixture was stirred for 2 h at 0° C. This resulted solution was added dropwise into a well-stirred solution of (R)-1-(4,4,5,5-tetramethyl-1,3,2-dioxaborolan-2-yl)-2-p-tolylethanamine hydrochloride (225 mg, 0.75 mmol) and DIPEA (530 mg, 4.1 mmol) in DCM (3 mL) at 0° C. The reaction was stirred at 0° C. for 1 h, then diluted with DCM (25 mL), washed with water (10 mL) and brine (10 mL), dried over Na$_2$SO$_4$, concentrated in vacuo. The residue was dissolved in MeOH (4 mL)/1N HCl aq. (0.8 mL) and stirred at r.t. for 2 h, then diluted with water (15 mL), dried over lyophilization to give a crude product which was purified by prep-HPLC to afford (R)-1-((((R)-1-(2-cyano-4,4-dimethylpent-2-enoyl)piperidin-2-yl)methoxy)carbonylamino)-2-p-tolylethylboronic acid as a light yellow solid (79.1 mg, 23%). LC-MS m/z: 478 (M+23).

Example 25

((R)-2-(benzofuran-3-yl)-1-(((((R)-1-(2-cyano-4,4-dimethylpent-2-enoyl)piperidin-2-yl)methoxy)carbonyl)amino)ethyl)boronic acid

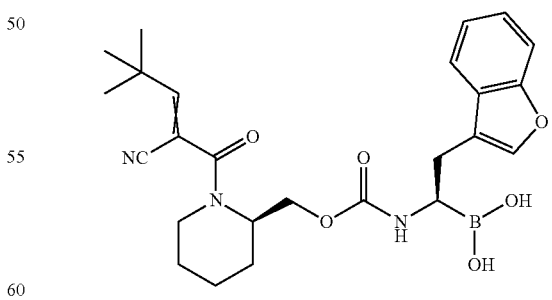

The title compound was prepared as in example 24 by replacing (R)-1-(4,4,5,5-tetramethyl-1,3,2-dioxaborolan-2-yl)-2-p-tolylethanamine hydrochloride with (R)-2-(benzofuran-3-yl)-1-((3aS,4S,6S,7aR)-3a,5,5-trimethylhexahydro-4,6-methanobenzo[d][1,3,2]dioxaborol-2-yl)ethan-1-amine hydrochloride. LC-MS m/z: 504 (M+23).

Example 26

((R)-1-(((((1S,2R,5R)-3-(2-cyano-4,4-dimethylpent-2-enoyl)-3-azabicyclo[3.1.0]hexan-2-yl)methoxy)carbonyl)amino)-2-phenylethyl)boronic acid

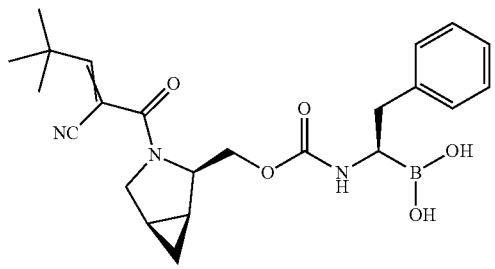 [SMILES: CC(C)(C)C=C(C#N)C(=O)N1C[C@@H]2C[C@@H]2[C@@H]1COC(=O)N[C@@H](Cc1ccccc1)B(O)O]

The title compound was prepared as in example 22 by carrying forward (R)-cis-2-benzyl 3-tert-butyl (1S,2R,5R)-3-azabicyclo[3.1.0]hexane-2,3-dicarboxylate. LC-MS m/z: 462 (M+23).

Example 27

(((R)-1-(((((R)-1-(2-cyano-4-methyl-4-(pyrrolidin-1-yl)pent-2-enoyl)piperidin-2-yl)methoxy)carbonyl)amino)-2-phenylethyl)boronic acid

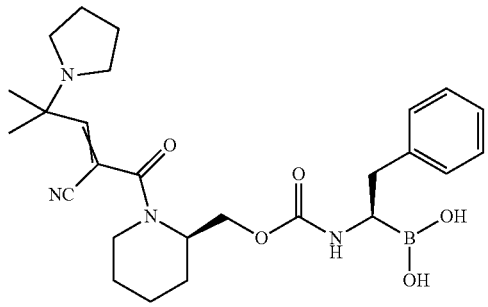 [SMILES: CC(C)(C=C(C#N)C(=O)N1CCCC[C@@H]1COC(=O)N[C@@H](Cc1ccccc1)B(O)O)N1CCCC1]

Step 1

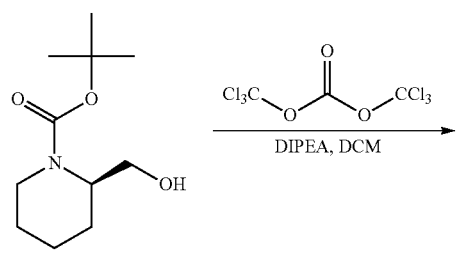

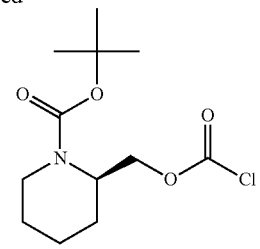

Into a 50-mL 3-necked round-bottom flask purged and maintained with an inert atmosphere of nitrogen, was placed ditrichloromethyl carbonate (500 mg, 1.68 mmol, 1.00 eq.), and dichloromethane (10 mL), DIPEA (900 mg, 3.00 eq.). This was followed by the addition of tert-butyl (2R)-2-(hydroxymethyl)piperidine-1-carboxylate (345 mg, 1.60 mmol, 0.50 eq.) in portions at 0° C. The resulting solution was stirred for 2.5 h at 0° C. The reaction mixture solution was used directly to the next step.

Step 2

Into a 100-mL 3-necked round-bottom flask purged and maintained with an inert atmosphere of nitrogen, was placed (1R)-2-phenyl-1-[(1S,2S,6R,8S)-2,9,9-trimethyl-3,5-dioxa-4-boratricyclo[6.1.1.0^[2,6]]decan-4-yl]ethan-1-amine hydrochloride (500 mg. 1.49 mmol, 1.00 eq.), DCM. (20 mL), and DIPEA (465 mg, 2.00 eq.). This was followed by the addition of tert-butyl (2R)-2-[[(chlorocarbonyl)oxy]methyl]piperidine-1-carboxylate (900 mg, 3.24 mmol, 1.50 eq.) dropwise with stirring at 0° C. The resulting solution was stirred for 1 h at rt. The resulting solution was diluted with 20 mL of $H_2O$. The resulting solution was extracted with 3×20 mL of dichloromethane and the organic layers combined and dried over anhydrous sodium sulfate and concentrated under vacuum. The crude product was purified by Flash-Prep-HPLC with the following conditions: Column, C18 silica gel; mobile phase, H₂O/CH₃CN=99:1 increasing to H₂O/CH₃CN=1:99 within 100 min; Detector, UV 220 nm. This resulted in 820 mg of tert-butyl (2R)-2-[([[(1R)-2-phenyl-1-[(1S,2S,6R,8S)-2,9,9-trimethyl-3,5-dioxa-4-boratricyclo[6.1.1.0ˆ[2,6]]decan-4-yl]ethyl]carbamoyl]oxy)methyl]piperidine-1-carboxylate as a white solid.

Step 3

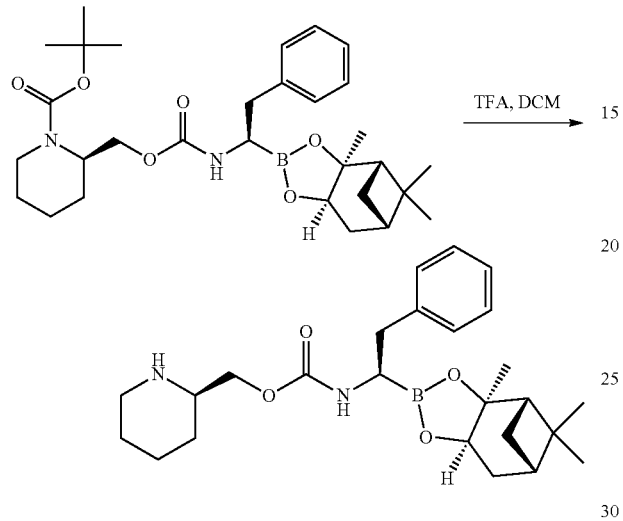

Into a 100-mL round-bottom flask, was placed tert-butyl (2R)-2-[([[(1R)-2-phenyl-1-[(1S,2S,6R,8S)-2,9,9-trimethyl-3,5-dioxa-4-boratricyclo[6.1.1.0ˆ[2,6]]decan-4-yl]ethyl]carbamoyl]oxy)methyl]piperidine-1-carboxylate (820 mg, 1.00 eq.), dichloromethane (20 mL), and trifluoroacetic acid (2.0 mL). The resulting solution was stirred for 1 h at rt. The resulting mixture was concentrated under vacuum. The crude product was purified by Flash-Prep-HPLC with the following conditions: Column, C18 silica gel; mobile phase, H₂O/CH₃CN=99:1 increasing to H₂O/CH₃CN=1:99 within 80 min; Detector, UV 220 nm. This resulted in 525 mg (82%) of (2R)-piperidin-2-ylmethyl N-[(1R)-2-phenyl-1-[(1S,2S,6R,8S)-2,9,9-trimethyl-3,5-dioxa-4-boratricyclo[6.1.1.0ˆ[2,6]]decan-4-yl]ethyl]carbamate as a white solid.

Step 4

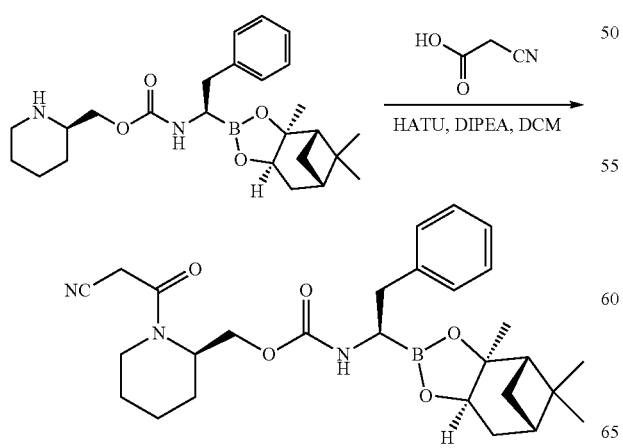

Into a 250-mL round-bottom flask, was placed (2R)-piperidin-2-ylmethyl N-[(1R)-2-phenyl-1-[(1S,2S,6R,8S)-2,9,9-trimethyl-3,5-dioxa-4-boratricyclo[6.1.1.0ˆ[2,6]]decan-4-yl]ethyl]carbamate (330 mg, 0.75 mmol, 1.00 eq.), dichloromethane (50 mL), 2-cyanoacetic acid (1.05 g, 12.34 mmol, 16.00 eq.), HATU (2.25 g, 5.92 mmol, 8.00 eq.), and DIEA (256 mg, 1.98 mmol, 2.60 eq.). The resulting solution was stirred overnight at it. The reaction was then quenched by the addition of 40 mL of water/ice. The resulting solution was extracted with 3×40 mL of dichloromethane and the organic layers combined and dried over anhydrous sodium sulfate and concentrated under vacuum. The crude product was purified by Flash-Prep-HPLC with the following conditions: Column, C18 silica gel, mobile phase, H₂O/CH₃CN=99:1 increasing to H₂O/CH₃CN=1:99 within 60 min; Detector, UV 220 nm. This resulted in 500 mg (82%) of [(2R)-1-(2-cyanoacetyl)piperidin-2-yl]methyl N-[(1R)-2-phenyl-1-[(1S,2S,6R,8S)-2,9,9-trimethyl-3,5-dioxa-4-boratricyclo[6.1.1.0ˆ[2,6]]decan-4-yl]ethyl]carbamate as a white solid.

Step 5

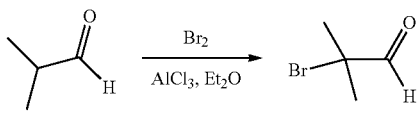

Into a 1L 3-necked round-bottom flask, was placed 2-methylpropanal (50 g, 693.43 mmol, 1.00 eq.), ether (500 mL), and AlCl (2.49 g, 0.03 eq.). This was followed by the addition of dibromane (131.34 g, 821.86 mmol. 1.20 eq.) dropwise with stirring at 0° C. in 10 min. The resulting solution was stirred overnight at rt. The reaction was then quenched by the addition of 100 mL of water/ice. The pH value of the solution was adjusted to 10-12 with sodium carbonate. The resulting solution was extracted with 3×100 mL of ether and the organic layers combined and dried over anhydrous sodium sulfate and concentrated under vacuum. The crude product was purified by distillation under reduced pressure (170 mm Hg) and the fraction was collected at 70-77° C. This resulted in 20 g (19.1%) of 2-bromo-2-methylpropanal as a colorless oil.

Step 6

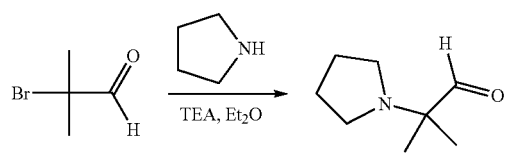

Into a 100-mL round-bottom flask, was placed pyrrolidine (500 mg, 7.03 mmol, 1.00 eq.), ether (25 mL), TEA (2.13 g, 21.05 mmol, 3.00 eq.), and 2-bromo-2-methylpropanal (1.27 g, 8.41 mmol, 1.20 eq.). The resulting solution was stirred for overnight at it. The resulting mixture was washed with 2×20 mL of sodium chloride. The resulting solution was extracted with 3×25 mL of ether and the organic layers combined and dried over anhydrous sodium sulfate and concentrated under vacuum. This resulted in 0.8 g (crude) of 2-methyl-2-(pyrrolidin-1-yl)propanal as a yellow oil.

Step 7

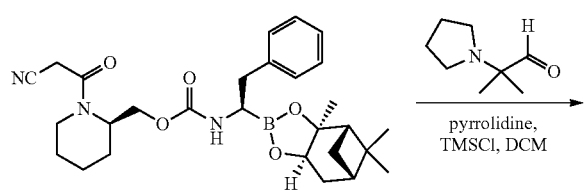

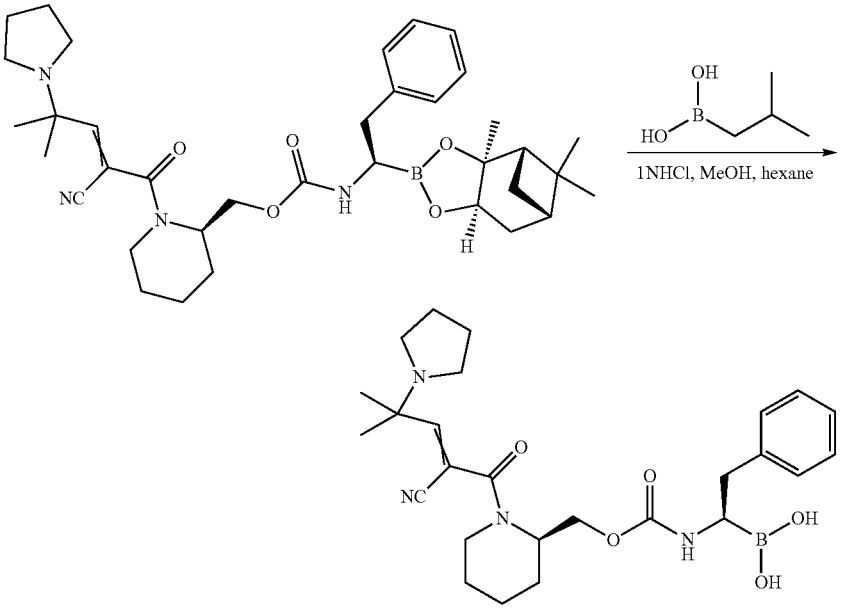

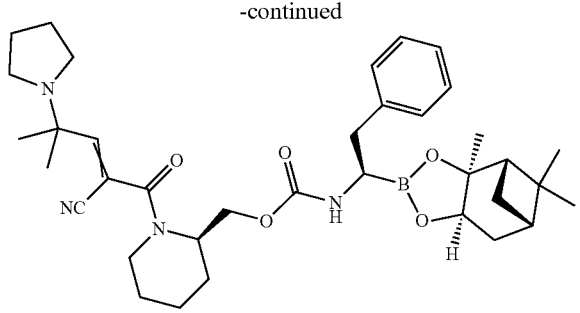

Into a 100-mL round-bottom flask, was placed [(2R)-1-(2-cyanoacetyl)piperidin-2-yl]methyl N-[(1R)-2-phenyl-1-[(1S,2S,6R,8S)-2,9,9-trimethyl-3,5-dioxa-4-boratricyclo[6.1.1.0ˆ[2,6]]decan-4-yl]ethyl]carbamate (85 mg, 0.17 mmol, 1.00 eq.), dichloromethane (15 mL), 2-methyl-2-(pyrrolidin-1-yl)propanal (71 mg. 0.50 mmol, 3.00 eq.), pyrrolidine (60 mg, 5.00 eq.), and TMSCl (90 mg, 0.83 mmol, 5.00 eq.). The resulting solution was stirred overnight at rt. The reaction was then quenched by the addition of 20 mL of ice/salt. The resulting solution was extracted with 3×20 mL of dichloromethane and the organic layers combined and dried over anhydrous sodium sulfate and concentrated under vacuum. The crude product was purified by Prep-HPLC with the following conditions: Column. XBridge Prep C18 OBD Column. 19*150 mm. 5 um; mobile phase, Water (10 MMOL/L NH$_4$HCO$_3$+0.1% NH$_3$.H$_2$O) and ACN (72.0% ACN up to 95.0% in 7 min); Detector, UV 254/220 nm. This resulted in 80 mg (76%) of [(2R)-1-[2-cyano-2-[2-methyl-2-(pyrrolidin-1-yl)propylidene]acetyl] piperidin-2-yl]methyl N-[(1R)-2-phenyl-1-[(1S,2S,6R,8S)-2,9,9-trimethyl-3,5-dioxa-4-boratricyclo[6.1.1.0ˆ[2.6]] decan-4-yl]ethyl]carbamate as an off-white solid after the lyophilzation.

Step 8

Into a 40-mL vial, was placed [(2R)-1-[2-cyano-2-[2-methyl-2-(pyrrolidin-1-yl)propylidene]acetyl]piperidin-2-yl]methyl N-[(1R)-2-phenyl-1-[(1S,2S,6R,8S)-2,9,9-trimethyl-3,5-dioxa-4-boratricyclo[6.1.1.0ˆ[2,6]]decan-4-yl] ethyl]carbamate (80 mg, 0.13 mmol, 1.00 eq.), methanol (3 mL), (2-methylpropyl)boronic acid (29 mg, 0.28 mmol, 2.30 eq.), hexane (3 mL), and 1N hydrogen chloride (1.9 mL). The resulting solution was stirred for 2 h at rt. The resulting mixture was washed with 3×5 mL of hexane. The methanol layer was diluted with 50 mL of water, and dried over lyophylization to give a crude product which was further purified by Prep-HPLC with the following conditions: Column, XBridge Prep C18 OBD Column, 19*150 mm, 5 um; mobile phase, Water (10 MMOL/L NH$_4$HCO$_3$+0.1% NH$_3$.H$_2$O) and ACN (30.0% ACN up to 45.0% in 8 min); Detector, UV 254/220 nm. This resulted in 19.2 mg (30%) of [(1R)-1-[([[(2R)-1-[2-cyano-2-[2-methyl-2-(pyrrolidin-1-yl)propylidene]acetyl]piperidin-2-yl]methoxy]carbonyl) amino]-2-phenylethyl]boronic acid as a white solid after the lyophilization. LC-MS m/z: 497 (M+1).

Example 28

((R)-1-(((((R)-1-(2-cyano-4-(3,3-difluoropyrrolidin-1-yl)-4-methylpent-2-enoyl)piperidin-2-yl)methoxy)carbonyl)amino)-2-phenylethyl)boronic acid

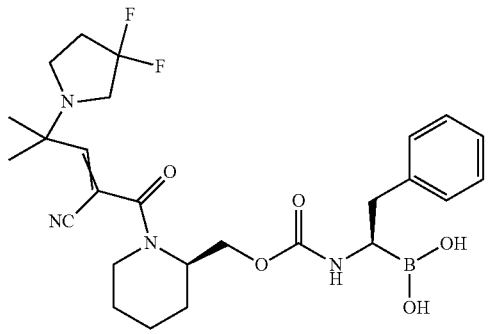 [SMILES: CC(C)(C=C(C#N)C(=O)N1CCCC[C@@H]1COC(=O)N[C@@H](Cc1ccccc1)B(O)O)N1CCC(F)(F)C1]

The title compound was prepared as in example 27 by replacing pyrrolidine with 2,2-difluoropyrrolidine. LC-MS m/z: 533 (M+1).

Example 29

((R)-1-(((((R)-1-(2-cyano-4-methyl-4-morpholino-pent-2-enoyl)piperidin-2-yl)methoxy)carbonyl)amino)-2-phenylethyl)boronic acid

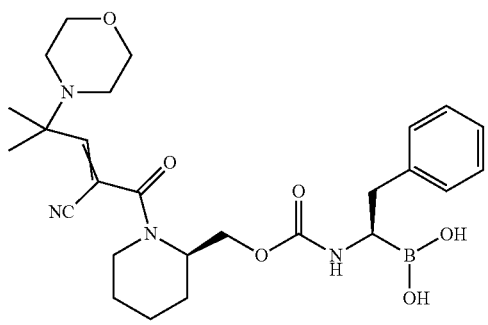 [SMILES: CC(C)(C=C(C#N)C(=O)N1CCCC[C@@H]1COC(=O)N[C@@H](Cc1ccccc1)B(O)O)N1CCOCC1]

The title compound was prepared as in example 27 by replacing pyrrolidine with morpholine. LC-MS m/z: 513 (M+1).

Example 30

((R)-1-(((((R)-1-(2-cyano-4-methyl-4-(piperidin-1-yl)pent-2-enoyl)piperidin-2-yl)methoxy)carbonyl)amino)-2-phenylethyl)boronic acid

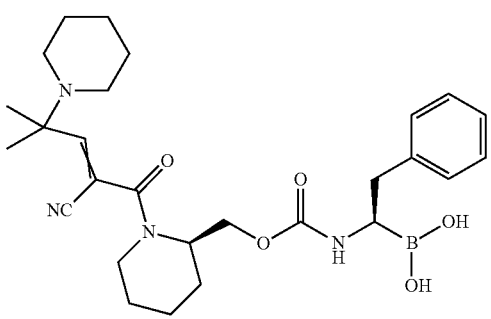 [SMILES: CC(C)(C=C(C#N)C(=O)N1CCCC[C@@H]1COC(=O)N[C@@H](Cc1ccccc1)B(O)O)N1CCCCC1]

The title compound was prepared as in example 27 by replacing pyrrolidine with morpholine. LC-MS m/z: 511 (M+1).

Example 31

((R)-1-(((((R)-1-(2-cyano-4-(4,4-difluoropiperidin-1-yl)-4-methylpent-2-enoyl)piperidin-2-yl)methoxy)carbonyl)amino)-2-phenylethyl)boronic acid

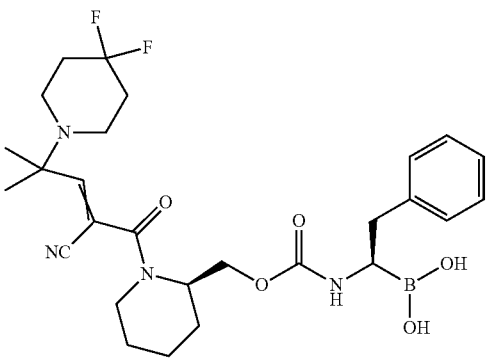 [SMILES: CC(C)(C=C(C#N)C(=O)N1CCCC[C@@H]1COC(=O)N[C@@H](Cc1ccccc1)B(O)O)N1CCC(F)(F)CC1]

The title compound was prepared as in example 27 by replacing pyrrolidine with 3,3-difluoropiperazine. LC-MS m/z: 547 (M+1).

Example 32

((R)-1-(((((R)-1-(2-cyano-4,4-dimethylpent-2-enoyl)azepan-2-yl)methoxy)carbonyl)amino)-2-(p-tolyl)ethyl)boronic acid

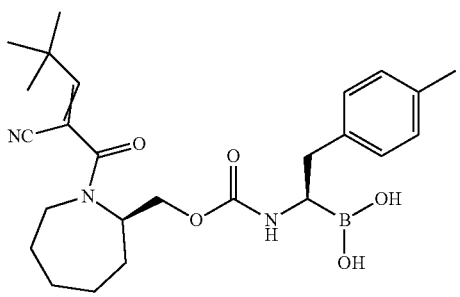 [SMILES: Cc1ccc(C[C@H](NC(=O)OC[C@H]2CCCCCN2C(=O)C(C#N)=CC(C)(C)C)B(O)O)cc1]

Step 1

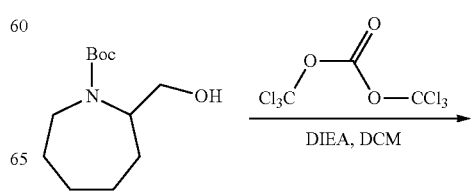

-continued

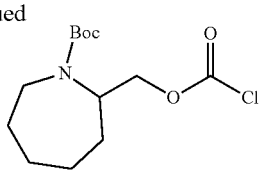

Into a 50-mL 3-necked round-bottom flask, was placed tert-butyl 2-(hydroxymethyl)azepane-1-carboxylate (700 mg, 3.05 mmol, 1.00 eq.), dichloromethane (12 mL), and DIEA (1.177 g, 9.11 mmol, 3.00 eq.). This was followed by the addition of ditrichloromethyl carbonate (448 mg, 1.51 mmol, 0.50 eq.) at 0° C. The resulting solution was stirred for 2 h at 0° C. The reaction mixture solution was used directly to the next step.

Step 2

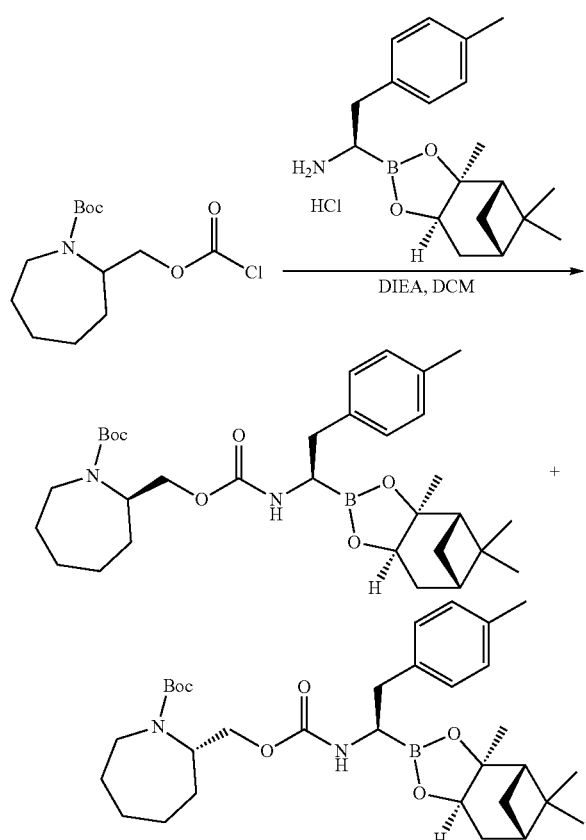

Into a 50-mL 3-necked round-bottom flask, was placed tert-butyl 2-[[(chlorocarbonyl) oxy] methyl] azepane-1-carboxylate (890.62 mg, 3.05 mmol, 1.00 eq.), dichloromethane (10 mL), and DIEA (706 mg, 5.46 mmol, 1.80 eq.). This was followed by the addition of (1R)-2-(4-methylphenyl)-1-[(1S,2S,6R,8S)-2,9,9-trimethyl-3,5-dioxa-4-boratricyclo [6.1.1.0^[2,6]]decan-4-yl]ethan-1-amine hydrochloride (905 mg, 2.59 mmol, 0.85 eq.) at 0° C. The resulting solution was stirred for 1 h at it. The resulting solution was diluted with 100 mL of DCM. The resulting mixture was washed with 3×100 mL of saturated brine. The resulting mixture was concentrated under vacuum. The crude product was purified by Prep-HPLC with the following conditions: Column, XBridge Prep C18 OBD Column, 19*150 mm, 5 um; mobile phase, Water (10 MMOL/L NH₄HCO₃+0.1% NH₃.H₂O) and ACN (82.0% ACN up to 93.0% in 7 min); Detector. UV 254/220 nm. This resulted in 540 mg isomers mixture product after lyophilization; The isomers mixture product was purified by Chiral-Prep-HPLC with the following conditions: Column, (R,R)Whelk-O 1, 21.1*250 mm, 5 um; mobile phase, Hex- and IPA- (hold 10.0% IPA- in 29 min); Detector, UV 220/254 nm. This resulted in 245 mg (14%) of tert-butyl (2R)-2-[([[(1R)-2-(4-methylphenyl)-1-[(1S,2S,6R,8S)-2,9,9-trimethyl-3,5-dioxa-4-boratricyclo[6.1.1.0^[2,6]]decan-4-yl]ethyl]carbamoyl]oxy)methyl]azepane-1-carboxylate (assumed) as a yellow oil. And 250 mg (14%) of tert-butyl (2S)-2-[([[(1R)-2-(4-methylphenyl)-1-[(1S,2S,6R,8S)-2,9,9-trimethyl-3,5-dioxa-4-boratricyclo[6.1.1.0^[2,6]] decan-4-yl]ethyl] carbamoyl]oxy)methyl]azepane-1-carboxylate (assumed) as a yellow oil.

Step 3

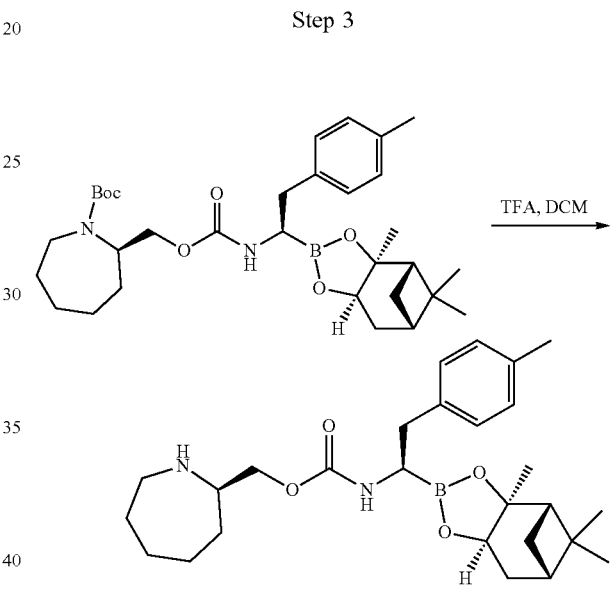

Into a 50-mL round-bottom flask, was placed tert-butyl (2R)-2-[([[(1R)-2-(4-methylphenyl)-1-[(1S,2S,6R,8S)-2,9,9-trimethyl-3,5-dioxa-4-boratricyclo[6.1.1.0^[2,6]]decan-4-yl]ethyl]carbamoyl]oxy)methyl]azepane-1-carboxylate (150 mg, 0.26 mmol, 1.00 eq.), dichloromethane (5 mL), and trifluoroacetic acid (0.76 mL). The resulting solution was stirred for 1 h at 25° C. The resulting mixture was concentrated under vacuum. This resulted in 123 mg (crude) of (2R)-azepan-2-ylmethyl N-[(1R)-2-(4-methylphenyl)-1-[(1S,2S,6R,8S)-2,9,9-trimethyl-3,5-dioxa-4-boratricyclo [6.1.1.0^[2,6]]decan-4-yl]ethyl]carbamate as a yellow oil.

Step 4

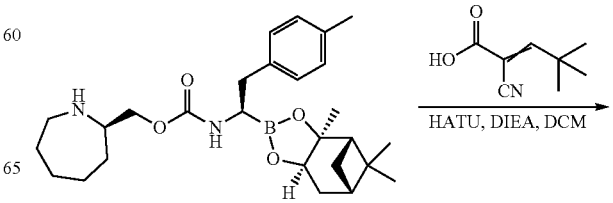

-continued

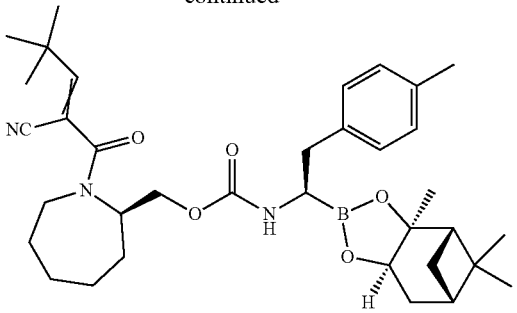

Into a 50-mL round-bottom flask, was placed (2R)-azepan-2-ylmethyl N-[(1R)-2-(4-methylphenyl)-1-[(S,2S,6R,8S)-2,9,9-trimethyl-3,5-dioxa-4-boratricyclo[6.1.1.0^[2,6]]decan-4-yl]ethyl]carbamate (123 mg, 0.26 mmol, 1.00 eq.), dichloromethane (4 mg, 0.05 mmol, 0.18 eq.), 2-cyano-4,4-dimethylpent-2-enoic acid (60 mg, 0.39 mmol, 1.50 eq.), DIEA (50.7 mg, 0.39 mmol, 1.50 eq.), and HATU (299 mg, 0.79 mmol, 3.00 eq.). The resulting solution was stirred for 2 h at 25° C. The resulting solution was diluted with 100 mL of DCM. The resulting mixture was washed with 3×100 mL of saturated brine. The resulted organic layers combined and dried over anhydrous sodium sulfate and concentrated under vacuum. The crude product was purified by Prep-HPLC with the following conditions: Column, XBridge Prep C18 OBD Column, 19*150 mm, 5 um; mobile phase, Water (10 MMOL/L NH$_4$HCO$_3$+0.1% NH$_3$.H$_2$O) and ACN (77.0% ACN up to 95.0% in 8 min); Detector, UV 254/220 nm. This resulted in 60 mg (38%) of [(2R)-1-[2-cyano-2-(2,2-dimethylpropylidene)acetyl] azepan-2-yl] methyl N-[(1R)-2-(4-methylphenyl)-1-[(1S,2S,6R,8S)-2,9,9-trimethyl-3,5-dioxa-4-boratricyclo[6.1.1.0^[2,6]]decan-4-yl] ethyl] carbamate as a white solid after the lyophilization.

Step 5

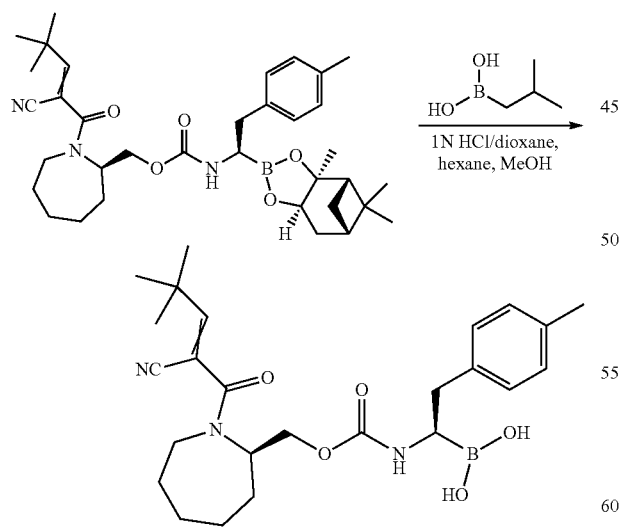

Into a 50-mL round-bottom flask, was placed [(2R)-1-[2-cyano-2-(2,2-dimethylpropylidene) acetyl]azepan-2-yl] methylN-[(1R)-2-(4-methylphenyl)-1-[(1S,2S,6R,8S)-2,9,9-trimethyl-3,5-dioxa-4-boratricyclo[6.1.1.0^[2,6]]decan-4-yl]ethyl]carbamate (60 mg, 0.10 mmol. 1.00 eq.), methanol (5 mL), (2-methylpropyl)boronic acid (30.6 mg, 0.30 mmol, 3.00 eq.), hexane (5 mL), and 1N HC/dioxane (1.98 mL, 20.00 eq.). The resulting solution was stirred for 4 h at 25° C. The resulting mixture was washed with 3×5 mL of hexane. The methanol layer was diluted with 5 mL of water, and dried over lyophylization to give a crude product which was further purified by Prep-HPLC with the following conditions: Column, XBridge Prep C18 OBD Column, 19*150 mm. 5 um; mobile phase. Water (10 MMOL/L NH$_4$HCO$_3$+0.1% NH$_3$.H$_2$O) and ACN (45.0% ACN up to 61.0% in 7 min); Detector, UV 254/220 nm. This resulted in 19.3 mg (41%) of [(1R)-1-[([[(2R)-1-[2-cyano-2-(2,2-dimethylpropylidene)acetyl] azepan-2-yl]methoxy]carbonyl)amino]-2-(4-methylphenyl)ethyl]boronic acid as a white solid after the lyophilization. LC-MS m/z: 492 (M+23).

Example 33

((R)-1-(((((S)-1-(2-cyano-4,4-dimethylpent-2-enoyl)azepan-2-yl)methoxy)carbonyl)amino)-2-(p-tolyl)ethyl)boronic acid

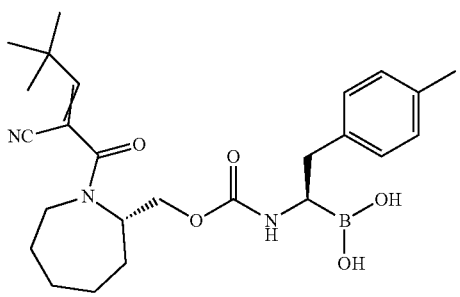 [SMILES: Cc1ccc(C[C@H](NC(=O)OC[C@@H]2CCCCCN2C(=O)C(C#N)=CC(C)(C)C)B(O)O)cc1]

The title compound was prepared as in example 32 by carrying forward tert-butyl (2S)-2-[([[(1R)-2-(4-methylphenyl)-1-[(1S,2S,6R,8S)-2,9,9-trimethyl-3,5-dioxa-4-boratricyclo[6.1.1.0^[2,6]]decan-4-yl]ethyl] carbamoyl] oxy) methyl]azepane-1-carboxylate. LC-MS m/z: 547 (M+1).

Example 34

((R)-1-(((((R)-1-(2-cyano-4-methyl-4-(pyrrolidin-1-yl)pent-2-enoyl)pyrrolidin-2-yl)methoxy)carbonyl)amino)-2-phenylethyl)boronic acid

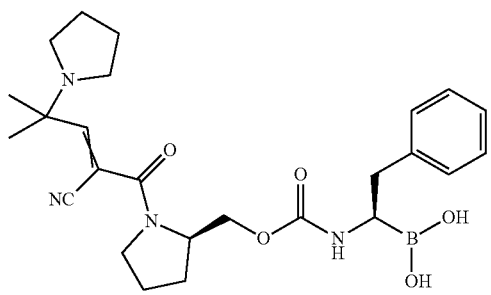 [SMILES: CC(C)(C=C(C#N)C(=O)N1CCC[C@@H]1COC(=O)N[C@@H](Cc1ccccc1)B(O)O)N1CCCC1]

The title compound was prepared as in example 20 by replacing piperidine with pyrrolidine. LC-MS m/z: 483 (M+1).

Example 35

((R)-1-(((((R)-1-(2-cyano-4-(3,3-difluoropyrrolidin-1-yl)-4-methylpent-2-enoyl)pyrrolidin-2-yl)methoxy)carbonyl)amino)-2-phenylethyl)boronic acid

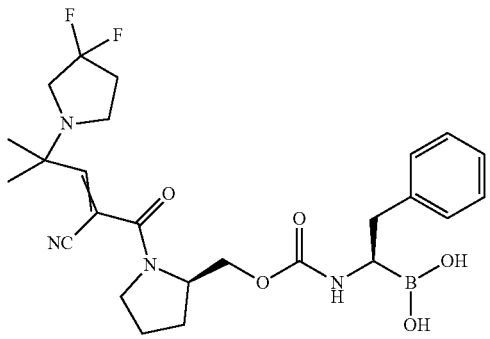 [SMILES: CC(C)(C=C(C#N)C(=O)N1CCC[C@@H]1COC(=O)N[C@@H](Cc1ccccc1)B(O)O)N1CCC(F)(F)C1]

The title compound was prepared as in example 20 by replacing piperidine with 2,2-difluoropyrrolidine. LC-MS m/z: 519 (M+1).

Example 36

((R)-1-(((((R)-1-acryloylpyrrolidin-2-yl)methoxy)carbonyl)amino)-2-(benzofuran-3-yl)ethyl)boronic acid

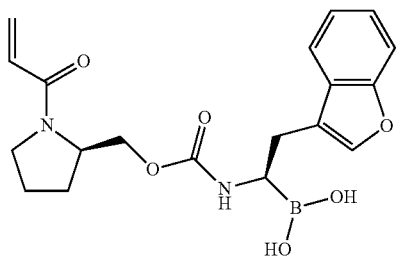 [SMILES: C=CC(=O)N1CCC[C@@H]1COC(=O)N[C@@H](Cc1coc2ccccc12)B(O)O]

Step 1

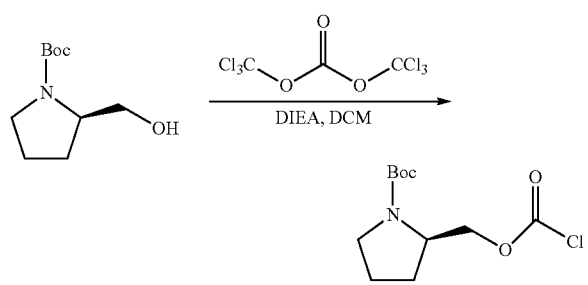

Into a 100-mL 3-necked round-bottom flask, was placed tert-butyl (2R)-2-(hydroxymethyl)pyrrolidine-1-carboxylate (500 mg, 2.48 mmol, 1.00 eq.), dichloromethane (10 mL), and DIEA (965 mg, 7.47 mmol, 3.00 eq.). This was followed by the addition of ditrichloromethyl carbonate (370 mg, 1.25 mmol, 0.50 eq.) at 0° C. The resulting solution was stirred for 2 h at 0° C. The resulted reaction solution was used directly to the next step.

Step 2

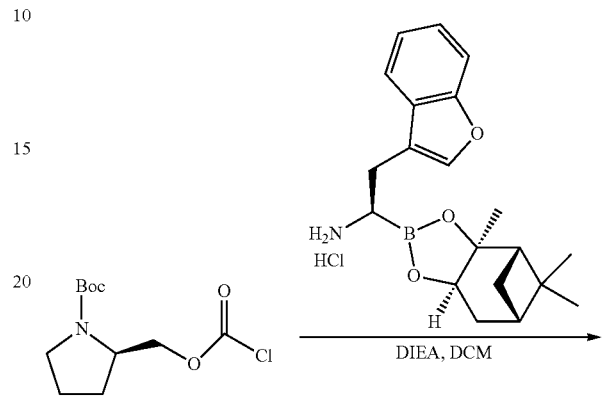

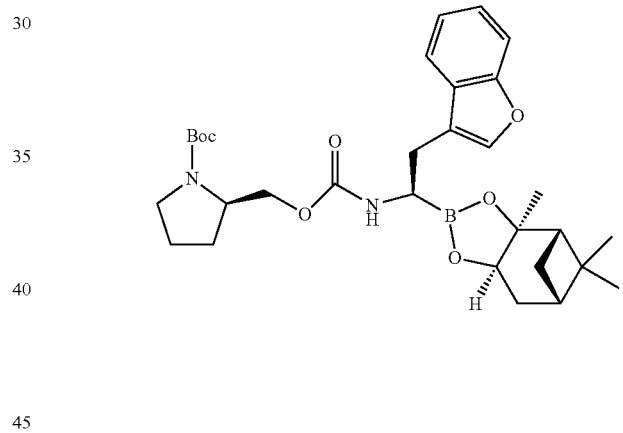

Into a 100-mL 3-necked round-bottom flask, was placed (1R)-2-(1-benzofuran-3-yl)-1-[(1S,2S,6R,8S)-2,9,9-trimethyl-3,5-dioxa-4-boratricyclo[6.1.1.0^[2,6]]decan-4-yl]ethan-1-amine hydrochloride (787.5 mg, 2.10 mmol, 0.85 eq.), dichloromethane (20 mL), and DIEA (640 mg, 4.95 mmol, 2.00 eq.). This was followed by the addition of tert-butyl (2R)-2-[[(chlorocarbonyl)oxy]methyl]pyrrolidine-1-carboxylate (656 mg, 2.49 mmol, 1.00 eq.) at 0° C. The resulting solution was stirred for 1 h at it. The resulting mixture was diluted with 50 mL of brine. The resulting solution was extracted with 3×30 mL of dichloromethane and the organic layers combined and dried over anhydrous sodium sulfate and concentrated under vacuum. The residue was applied onto a silica gel column with ethyl acetate/petroleum ether (1:10). This resulted in 1.1 g (78%) of tert-butyl (2R)-2-[([[(1R)-2-(1-benzofuran-3-yl)-1-[(1S,2S,6R,8S)-2,9,9-trimethyl-3,5-dioxa-4-boratricyclo[6.1.1.0^[2,6]]decan-4-yl]ethyl]carbamoyl]oxy)methyl]pyrrolidine-1-carboxylate as a yellow oil.

Step 3

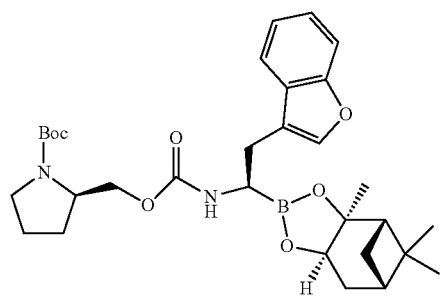

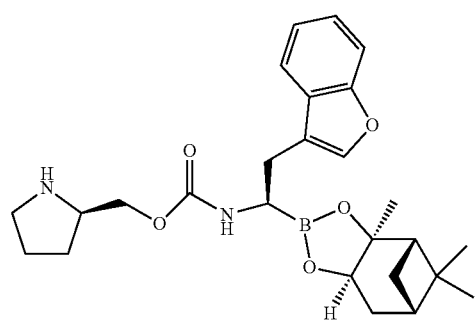

Into a 50-mL round-bottom flask, was placed tert-butyl (2R)-2-[([[(1R)-2-(1-benzofuran-3-yl)-1-[(1S,2S,6R,8S)-2,9,9-trimethyl-3,5-dioxa-4-boratricyclo[6.1.1.0^[2,6]]decan-4-yl]ethyl]carbamoyl]oxy)methyl]pyrrolidine-1-carboxylate (250 mg, 0.44 mmol. 1.00 eq.), dichloromethane (12.5 mL), and trifluoroacetic acid (2.5 mL). The resulting solution was stirred for 1 h at it. The resulting mixture was concentrated under vacuum. This resulted in 206 mg (crude) of (2R)-pyrrolidin-2-ylmethyl N-[(1R)-2-(1-benzofuran-3-yl)-1-[(1S,2S,6R,8S)-2,9,9-trimethyl-3,5-dioxa-4-boratricyclo[6.1.1.0^[2,6]]decan-4-yl]ethyl]carbamate as a yellow oil.

Step 4

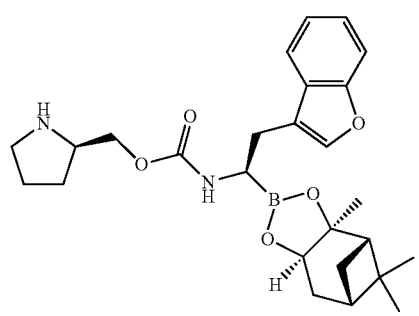

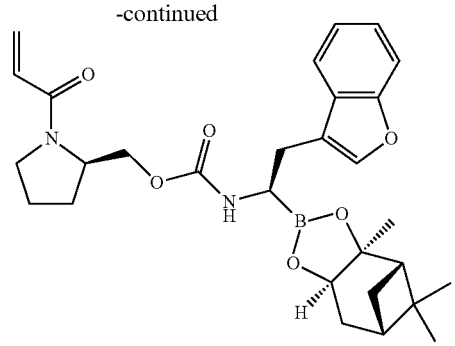

Into a 50-mL round-bottom flask, was placed (2R)-pyrrolidin-2-ylmethyl N-[(1R)-2-(1-benzofuran-3-yl)-1-[(1S,2S,6R,8S)-2,9,9-trimethyl-3,5-dioxa-4-boratricyclo[6.1.1.0^[2,6]]decan-4-yl]ethyl]carbamate (206 mg, 0.44 mmol, 1.00 eq.), dichloromethane (3 mL), TEA (133.8 mg, 1.32 mmol, 3.00 eq.), and prop-2-enoyl chloride (48 mg, 0.53 mmol. 1.20 eq.). The resulting solution was stirred for 2 h at rt. The resulting mixture was diluted with 30 mL of brine. The resulting solution was extracted with 3×20 mL of dichloromethane and the organic layers combined and dried over anhydrous sodium sulfate and concentrated under vacuum. The crude product was purified by Prep-HPLC with the following conditions: Column. XBridge Prep C18 OBD Column, 19*150 mm 5 um; mobile phase, Water (10 MMOL/L $NH_4HCO_3$+0.1% $NH_3.H_2O$) and ACN (60.0% ACN up to 75.0% in 7 min); Detector, UV 254/220 nm. This resulted in 80 mg (35%) of [(2R)-1-(prop-2-enoyl)pyrrolidin-2-yl]methyl N-[(1R)-2-(1-benzofuran-3-yl)-1-[(1S,2S,6R,8S)-2,9,9-trimethyl-3,5-dioxa-4-boratricyclo[6.1.1.0^[2,6]]decan-4-yl]ethyl]carbamate as a white solid after lyophilization.

Step 5

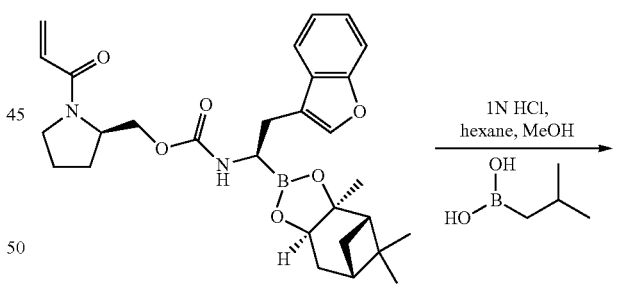

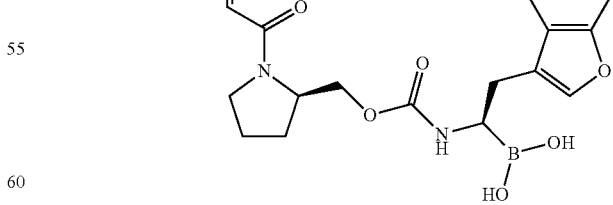

Into a 100-mL round-bottom flask, was placed [(2R)-1-(prop-2-enoyl)pyrrolidin-2-yl]methyl N-[(1R)-2-(1-benzofuran-3-yl)-1-[(1S,2S,6R,8S)-2,9,9-trimethyl-3,5-dioxa-4-boratricyclo[6.1.1.0^[2,6]]decan-4-yl]ethyl]carbamate (90 mg. 0.17 mmol, 1.00 eq.), methanol (8 mL), (2-methylpropyl)boronic acid (53.3 mg, 0.52 mmol, 3.00 eq.), hexane (8 mL), and 1N hydrogen chloride (3.5 mL, 20.00 eq.). The resulting solution was stirred for 3 h at rt. The resulting mixture was washed with 3×10 mL of hexane. The methanol layer was diluted with 15 mL of H₂O, then dried over lyophilization to give a crude product. The crude product was purified by Prep-HPLC with the following conditions: Column. XBridge Prep C18 OBD Column, 19*150 mm 5 um; mobile phase, Water (10 MMOL/L NH₄HCO₃+0.1% NH₃.H₂O) and ACN (18.0% ACN up to 35.0% in 7 min); Detector, UV 254/220 nm. This resulted in 61.9 mg (93%) of [(1R)-2-(1-benzofuran-3-yl)-1-[([[(2R)-1-(prop-2-enoyl)pyrrolidin-2-yl]methoxy]carbonyl) amino]ethyl]boronic acid as a white solid after lyophilization again. LC-MS m/z: 369 (M–17).

Example 37

((R)-1-(((((1R,2R,5S)-3-(2-cyano-4,4-dimethylpent-2-enoyl)-3-azabicyclo[3.1.0]hexan-2-yl)methoxy)carbonyl)amino)-2-phenylethyl)boronic acid

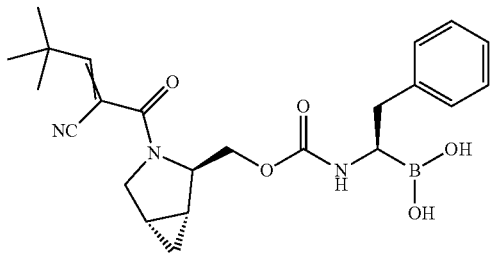 [SMILES: CC(C)(C)C=C(C#N)C(=O)N1C[C@H]2C[C@H]2[C@@H]1COC(=O)N[C@@H](Cc1ccccc1)B(O)O]

Step 1

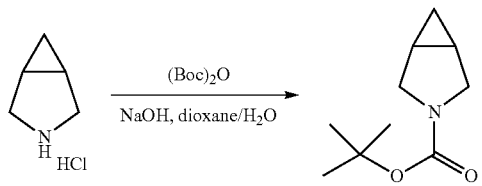

Into a 500-mL round-bottom flask, was placed a solution of 3-azabicyclo[3.1.0]hexane hydrochloride (5 g, 41.81 mmol. 1.00 eq.) in dioxane/H₂O (75/75 mL), 1N NaOH (84 mL, 2.00 eq.), and (Boc)₂O (14 g, 64.15 mmol, 1.50 eq.). The resulting solution was stirred overnight at rt. The resulting mixture was concentrated under vacuum. The resulting solution was extracted with 3×200 mL of petroleum ether and the organic layers combined and dried over anhydrous sodium sulfate and concentrated under vacuum. The residue was applied onto a silica gel column with ethyl acetate/petroleum ether (1:50). This resulted in 6 g (70%) of tert-butyl 3-azabicyclo[3.1.0]hexane-3-carboxylate as light yellow oil.

Step 2

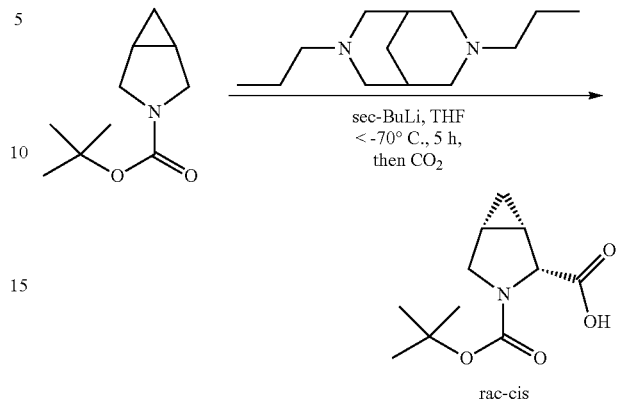

Into a 250-mL 3-necked round-bottom flask, was placed a solution of tert-butyl 3-azabicyclo[3.1.0]hexane-3-carboxylate (4.75 g, 25.92 mmol, 1.00 eq.) in tetrahydrofuran (104 mL), and 3,7-dipropyl-3,7-diazabicyclo[3.3.1]nonane (6.81 g, 32.37 mmol. 1.25 eq.). This was followed by the addition of sec-BuLi (24 mL, 1.20 eq.) dropwise with stirring at –60° C. To this was added dry ice (1 g, 1.00 eq.) at –68° C. The resulting solution was stirred for 1 h at –45° C. The reaction was then quenched by the addition of 60 mL of H₂O. The resulting mixture was concentrated under vacuum. The resulting solution was extracted with 2×60 mL of MTBE and the aqueous layers combined. The pH value of the solution was adjusted to 2-3 with KHSO₄ (25% g/mL). The resulting solution was extracted with 3×80 mL of MTBE and the organic layers combined and dried over sodium sulfate and concentrated under vacuum. This resulted in 3.9 g (66%) of rac-cis(1S,2R,5R)-3-[(tert-butoxy)carbonyl]-3-azabicyclo[3.1.0]hexane-2-carboxylic acid as a colorless oil.

Step 3

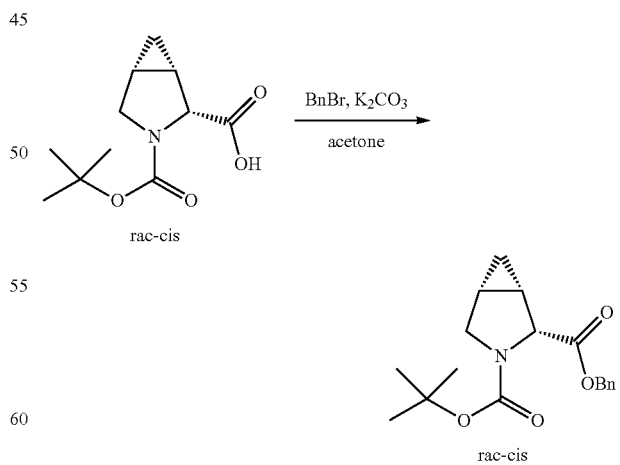

Into a 100-mL round-bottom flask, was placed a solution of rac-cis-(1S,2R,5R)-3-[(tert-butoxy)carbonyl]-3-azabicyclo[3.1.0]hexane-2-carboxylic acid (2 g, 8.80 mmol, 1.00 eq.) in acetone (40 mL), BnBr (1.5 g, 8.77 mmol, 1.00 eq.), and potassium carbonate (1.5 g, 10.85 mmol, 1.25 eq.). The resulting solution was stirred overnight at rt. The solids were filtered out. The resulting mixture was concentrated under vacuum. The residue was applied onto a silica gel column with ethyl acetate/petroleum ether (2:98-5:95). This resulted in 2 g (72%) of rac-cis-2-benzyl 3-tert-butyl (1S,2R,5R)-3-azabicyclo[3.1.0]hexane-2,3-dicarboxylate as a yellow oil.

Step 4

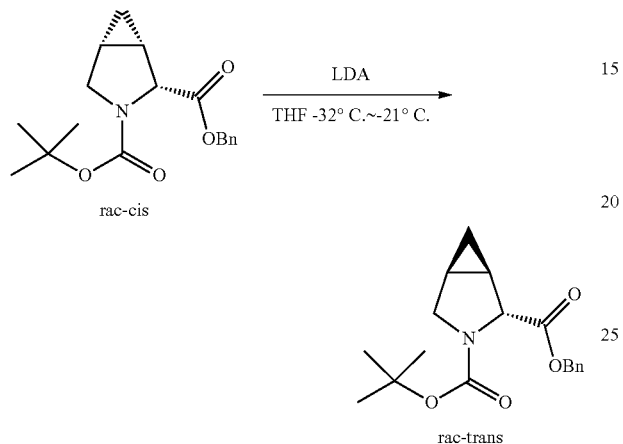

Into a 50-mL 3-necked round-bottom flask purged and maintained with an inert atmosphere of nitrogen, was placed a solution of rac-cis-2-benzyl 3-tert-butyl (1S,2R,5R)-3-azabicyclo[3.1.0]hexane-2,3-dicarboxylate (800 mg, 2.52 mmol, 1.00 eq.) in tetrahydrofuran (13 mL). This was followed by the addition of LDA (2.5 mL, 2.00 eq., 2N) at −32° C. The resulting solution was stirred for 1 min at −32° C. The reaction was then quenched by the addition of 20 mL of sodium bicarbonate. The resulting solution was diluted with 20 mL of $H_2O$. The resulting solution was extracted with 3×50 mL of ethyl acetate and the organic layers combined. The resulting mixture was washed with 1×50 mL of brine. The mixture was dried over sodium sulfate. The crude product was purified by Prep-HPLC with the following conditions: Column, XBridge Prep C18 OBD Column, 19*150 mm 5 um; mobile phase, Water (10 MMOL/L $NH_4HCO_3$+0.1% $NH_3.H_2O$) and ACN (56% ACN up to 57% in 10 min); Detector, UV 254/220 nm. This resulted in 450 mg (56%) of rac-trans-2-benzyl 3-tert-butyl (1R,2R,5S)-3-azabicyclo[3.1.0]hexane-2,3-dicarboxylate as a colorless oil.

Step 5

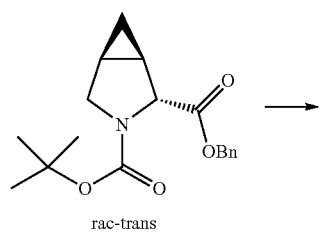

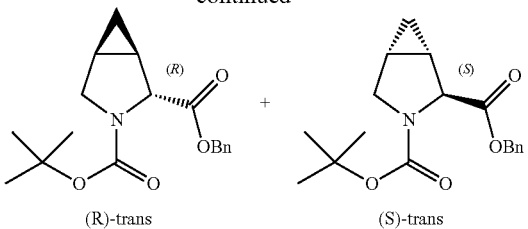

The isomers mixture (rac)-trans-2-benzyl 3-tert-butyl (1R,2R,5S)-3-azabicyclo[3.1.0]hexane-2,3-dicarboxylate (550 mg) was purified by Chiral-Prep-HPLC with the following conditions: Column, Chiralpak ID-2, 2*25 cm, 5 um; mobile phase, Hex-HPLC and IPA-HPLC (hold 5% IPA-HPLC in 15 min); Detector, UV 220/254 nm. This resulted in 200 mg (36%) of (R)-trans-2-benzyl 3-tert-butyl (1R,2R,5S)-3-azabicyclo[3.1.0]hexane-2,3-dicarboxylate as a colorless oil. ($[\alpha]_{17°\ C.}^{589\ nm}$=94.2 (C 0.5, $CHCl_3$)) And 200 mg (36%) of (S)-trans-2-benzyl 3-tert-butyl (1S,2S,5R)-3-azabicyclo[3.1.0]hexane-2,3-dicarboxylate as a colorless oil. ($\alpha_{18.2°\ C.}^{589\ nm}$=−89 (C 0.5, $CHCl_3$))

Step 6

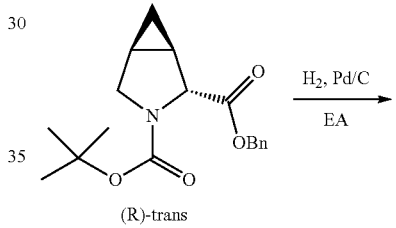

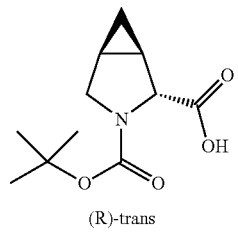

Into a 50-mL round-bottom flask, was placed a solution of (R)-trans-2-benzyl 3-tert-butyl (1R,2R,5S)-3-azabicyclo[3.1.0]hexane-2,3-dicarboxylate (330 mg, 1.04 mmol, 1.00 eq.) in ethyl acetate (5 mL), and palladium carbon (330 mg, 1.00 eq.).To the mixture was introduced in $H_2$ (gas). The resulting solution was stirred for 3 h at it. The solids were filtered out. The resulting mixture was concentrated under vacuum. This resulted in 240 mg (crude) of (R)-trans-(1R,2R,5S)-3-[(tert-butoxy)carbonyl]-3-azabicyclo[3.1.0] hexane-2-carboxylic acid as a white solid.

Step 7

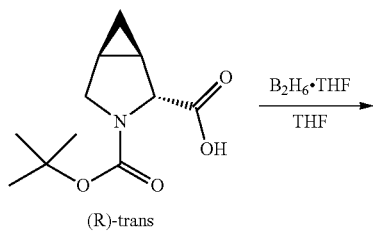

Into a 50-mL round-bottom flask, was placed a solution of (R)-trans-(1R,2R,5S)-3-[(tert-butoxy)carbonyl]-3-azabicyclo[3.1.0]hexane-2-carboxylic acid (240 mg, 1.06 mmol, 1.00 eq.) in tetrahydrofuran (5 mL). This was followed by the addition of B2H6.THF (1.3 mL, 1.25 eq.) dropwise with stirring at 0° C. The resulting solution was stirred overnight at rt. The reaction was then quenched by the addition of 5 mL of NH4Cl. The resulting solution was extracted with 2×10 mL of ethyl acetate and the organic layers combined. The resulting mixture was washed with 1×10 mL of water and 1×10 mL of sodium chloride. The mixture was dried over anhydrous sodium sulfate and concentrated under vacuum. The residue was applied onto a silica gel column with ethyl acetate/petroleum ether (40:60). This resulted in 210 mg (93%) of (R)-trans-tert-butyl (1R,2R,5S)-2-(hydroxymethyl)-3-azabicyclo[3.1.0]hexane-3-carboxylate as a yellow oil.

Step 8

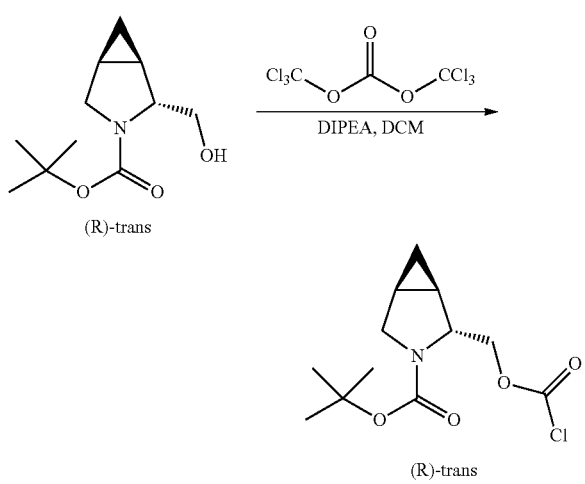

Into a 50-mL 3-necked round-bottom flask, was placed a solution of (R)-trans-tert-butyl(1 R,2R,5S)-2-(hydroxymethyl)-3-azabicyclo[3.1.0]hexane-3-carboxylate (190 mg, 0.89 mmol, 1.00 eq.) in dichloromethane (4 mL), and DIEA (345 mg, 2.67 mmol. 3.00 eq.). This was followed by the addition of ditrichloromethyl carbonate (132 mg, 0.44 mmol, 0.50 eq.) in several batches at 0° C. The resulting solution was stirred for 2 h at 0° C. This resulted solution was to be used directly to the next step.

Step 9

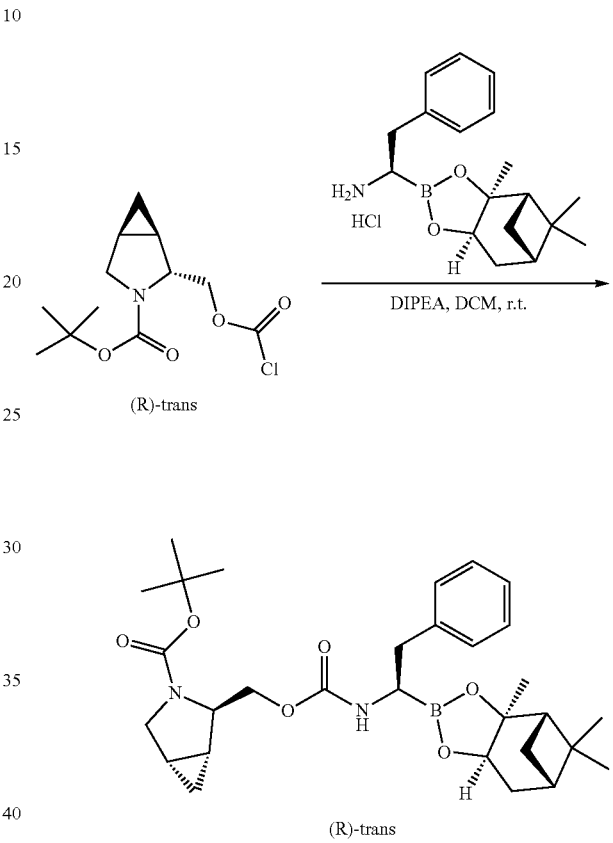

Into a 50-mL 3-necked round-bottom flask, was placed a solution of (1R)-2-phenyl-1-[(1S,2S,6R,8S)-2,9,9-trimethyl-3,5-dioxa-4-boratricyclo[6.1.1.0^2,6]decan-4-yl] ethan-1-amine hydrochloride (239 mg, 0.71 mmol, 1.00 eq.) in dichloromethane (7 mL), and DIEA (230 mg. 1.78 mmol, 2.00 eq.). This was followed by the addition of a solution of (R)-trans-tert-butyl (1R,2R,5S)-2-[[(chlorocarbonyl)oxy] methyl]-3-azabicyclo[3.1.0]hexane-3-carboxylate (240 mg, 0.87 mmol, 1.00 eq.) in dichloromethane (4 mL) dropwise with stirring at 0° C. The resulting solution was stirred for 1 h at rt. The reaction was then quenched by the addition of 2 mL of water. The resulting solution was diluted with 10 mL of DCM. The resulting mixture was washed with 1×10 mL of sodium chloride. The mixture was dried over anhydrous sodium sulfate and concentrated under vacuum. This resulted in 350 mg (75%) of (R)-trans-tert-butyl (1R,2R,5S)-2-[([[(1R)-2-phenyl-1-[(1S,2S,6R,8S)-2,9,9-trimethyl-3,5-dioxa-4-boratricyclo[6.1.1.0^[2,6]]decan-4-yl]ethyl]carbamoyl]oxy)methyl]-3-azabicyclo[3.1.0]hexane-3-carboxylate as a yellow oil.

123

Step 10

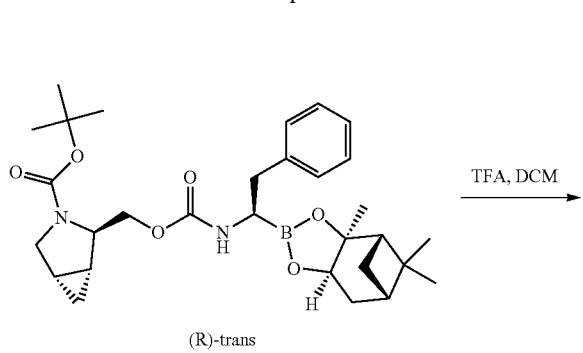
(R)-trans

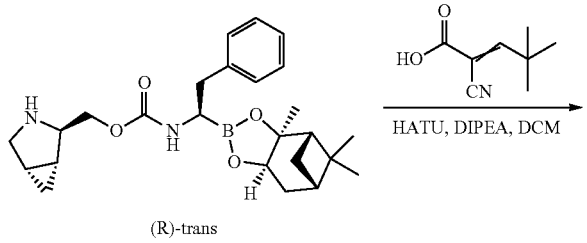
(R)-trans

Into a 50-mL round-bottom flask, was placed a solution of (R)-trans-tert-butyl (1R,2R,5S)-2-[([[(1R)-2-phenyl-1-[(1S,2S,6R,8S)-2,9,9-trimethyl-3,5-dioxa-4-boratricyclo[6.1.1.0^[2,6]]decan-4-yl]ethyl]carbamoyl]oxy)methyl]-3-azabicyclo[3.1.0]hexane-3-carboxylate (350 mg, 0.65 mmol, 1.00 eq.) in dichloromethane (5 mL), and trifluoroacetic acid (0.8 mL). The resulting solution was stirred for 2 h at rt. The resulting mixture was concentrated under vacuum. This resulted in 270 mg (crude) of (R)-trans-(1R,2R,5S)-3-azabicyclo[3.1.0]hexan-2-ylmethyl N-[(1R)-2-phenyl-1-[(1S,2S,6R,8S)-2,9,9-trimethyl-3,5-dioxa-4-boratricyclo[6.1.1.0^[2,6]]decan-4-yl]ethyl]carbamate as brown oil.

Step 11

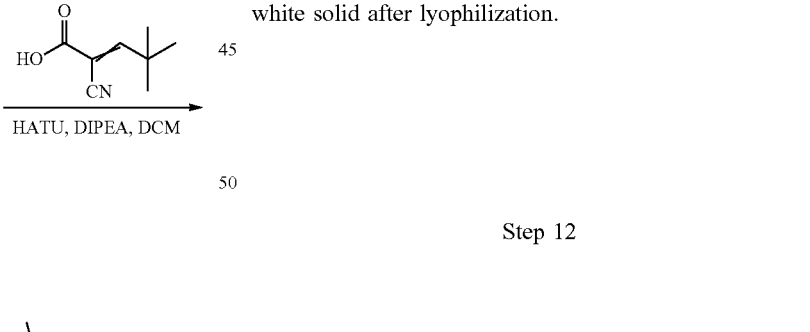
(R)-trans

124
-continued

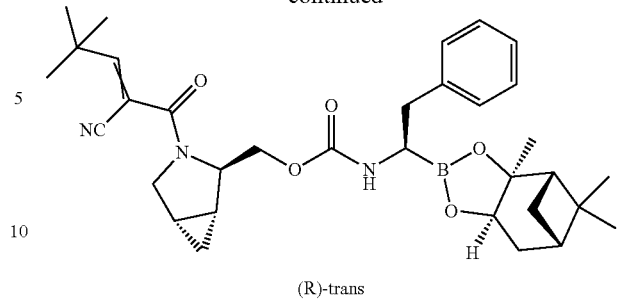
(R)-trans

Into a 50-mL round-bottom flask, was placed a solution of (R)-trans-(1R,2R,5S)-3-azabicyclo[3.1.0]hexan-2-ylmethyl N-[(1R)-2-phenyl-1-[(1S,2S,6R,8S)-2,9,9-trimethyl-3,5-dioxa-4-boratricyclo[6.1.1.0^[2,6]]decan-4-yl]ethyl]carbamate (270 mg, 0.62 mmol, 1.00 eq.) in dichloromethane (5 mL), DIEA (240 mg, 1.86 mmol, 3.00 eq.), 2-cyano-4,4-dimethylpent-2-enoic acid (113 mg, 0.74 mmol, 1.20 eq.), and HATU (351 mg, 0.92 mmol, 1.50 eq.). The resulting solution was stirred for 1 h at rt. The reaction was then quenched by the addition of 2 mL of water. The resulting solution was diluted with 10 mL of DCM. The resulting mixture was washed with 1×10 mL of sodium chloride. The mixture was dried over anhydrous sodium sulfate and concentrated under vacuum. The crude product was purified by Prep-HPLC with the following conditions: Column, XBridge Prep C18 OBD Column, 19*150 mm 5 um; mobile phase, Water (10 MMOL/L NH$_4$HCO$_3$+0.1% NH$_3$.H$_2$O) and ACN (70% ACN up to 90% in 7 min); Detector, UV 254/220 nm. This resulted in 90 mg (25%) of (R)-trans-[(1R,2R,5S)-3-[2-cyano-2-(2,2-dimethylpropylidene)acetyl]-3-azabicyclo[3.1.0]hexan-2-yl]methyl N-[(1R)-2-phenyl-1-[(1S,2S,6R,8S)-2,9,9-trimethyl-3,5-dioxa-4-boratricyclo[6.1.1.0^[2,6]]decan-4-yl]ethyl]carbamate as a white solid after lyophilization.

Step 12

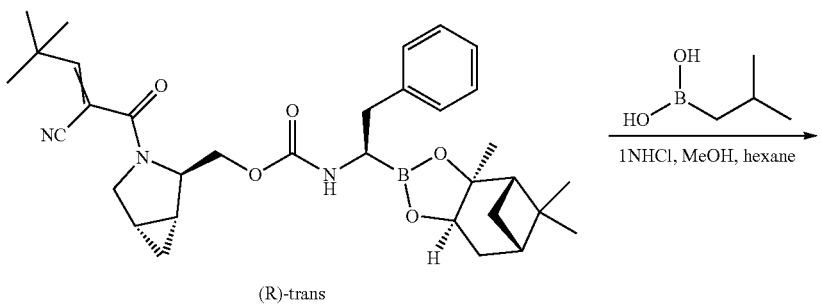
(R)-trans

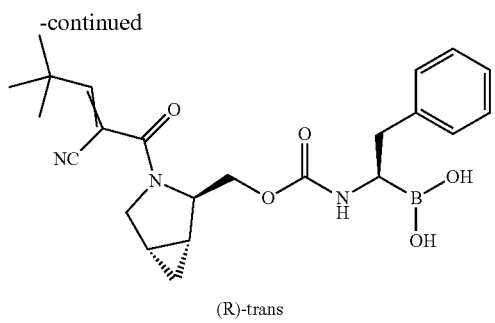

(R)-trans

Into a 100-mL round-bottom flask, was placed a solution of R-trans-[(1R,2R,5S)-3-[2-cyano-2-(2,2-dimethylpropylidene)acetyl]-3-azabicyclo[3.1.0]hexan-2-yl]methyl N-[(1R)-2-phenyl-1-[(1S,2S,6R,8S)-2,9,9-trimethyl-3,5-dioxa-4-boratricyclo[6.1.1.0^[2,6]]decan-4-yl]ethyl]carbamate (90 mg, 0.16 mmol, 1.00 eq.) in methanol/hexane (3/3 mL), 1NHCl (3 mL, 20.00 eq.), and (2-methylpropyl)boronic acid (48 mg, 0.47 mmol, 3.00 eq.). The resulting solution was stirred for 3 h at rt. The hexane layer was discarded. The methanol layer was diluted with water (15 mL), then dried over lyophilization. The crude product was purified by Prep-HPLC with the following conditions: Column, XBridge Prep C18 OBD Column, 19*150 mm 5 um; mobile phase, Water (10 MMOL/L $NH_4HCO_3$+0.1% $NH_3.H_2O$) and ACN (35.0% ACN up to 55.0% in 7 min); Detector, UV 254/220 nm. This resulted in 46.6 mg (66%) of R-trans-[(1R)-1-[([[(1R,2R,5S)-3-[2-cyano-2-(2,2-dimethylpropylidene)acetyl]-3-azabicyclo[3.1.0]hexan-2-yl]methoxy]carbonyl)amino]-2-phenylethyl]boronic acid as a white solid after lyophilization. LC-MS m/z: 422 (M–17).

Example 38

((R)-1-(((((1S,2S,5R)-3-(2-cyano-4,4-dimethylpent-2-enoyl)-3-azabicyclo[3.1.0]hexan-2-yl)methoxy)carbonyl)amino)-2-phenylethyl)boronic acid

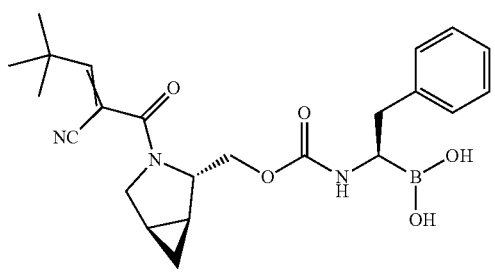 [SMILES: CC(C)(C)C=C(C#N)C(=O)N1C[C@@H]2C[C@@H]2[C@H]1COC(=O)N[C@@H](Cc1ccccc1)B(O)O]

The title compound was prepared as in example 37 by carrying forward (S)-trans-2-benzyl 3-tert-butyl (1S,2S,5R)-3-azabicyclo[3.1.0]hexane-2,3-dicarboxylate. LC-MS m/z: 422 (M+1).

Example 39

((R)-2-(benzofuran-3-yl)-1-(((((R)-1-(2-cyano-4,4-dimethylpent-2-enoyl)pyrrolidin-2-yl)methoxy)carbonyl)amino)ethyl)boronic acid

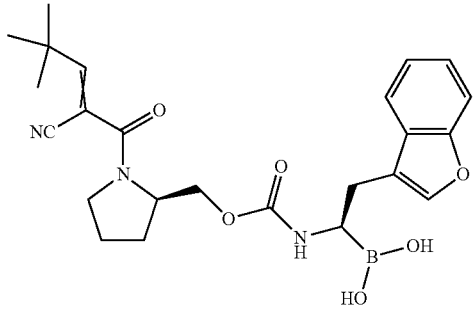 [SMILES: CC(C)(C)C=C(C#N)C(=O)N1CCC[C@@H]1COC(=O)N[C@@H](Cc1coc2ccccc12)B(O)O]

The title compound was prepared as in example 16 by replacing 2-cyano-4-methylpent-2-enoic acid with 2-cyano-4,4-dimethylpent-2-enoic acid. LC-MS m/z: 450 (M–17).

Example 40

((R)-2-(benzofuran-3-yl)-1-(((((R)-(2-cyano-4-methyl-4-morpholinopent-2-enoyl)pyrrolidin-2-yl)methoxy)carbonyl)amino)ethyl)boronic acid

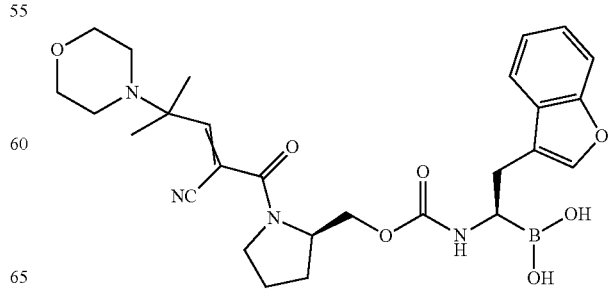

Step 1

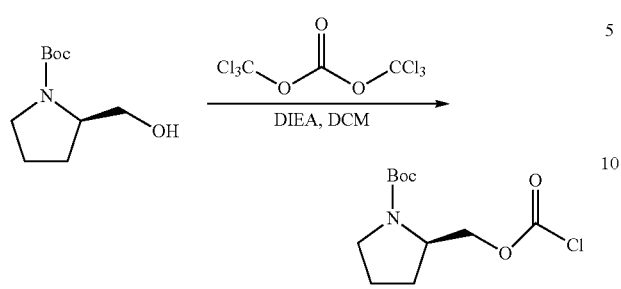

Into a 100-mL 3-necked round-bottom flask, was placed tert-butyl (2R)-2-(hydroxy)methyl)pyrrolidine-1-carboxylate (500 mg, 2.48 mmol, 1.00 eq.), dichloromethane (10 mL), and DIEA (965 mg, 7.47 mmol, 3.00 eq.). This was followed by the addition of ditrichloromethyl carbonate (370 mg, 1.25 mmol, 0.50 eq.) at 0° C. The resulting solution was stirred for 2 h at 0° C. This resulted reaction solution was used directly to the next step.

Step 2

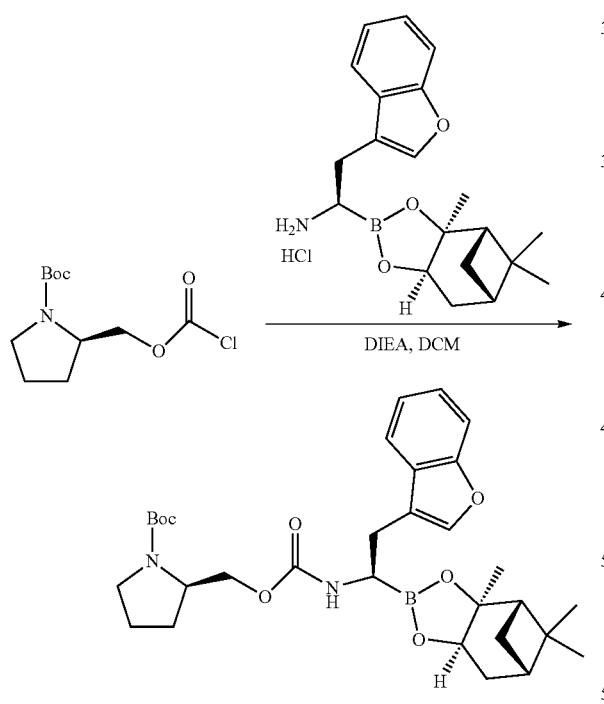

Into a 100-mL 3-necked round-bottom flask, was placed (1R)-2-(1-benzofuran-3-yl)-1-[(1S,2S,6R,8S)-2,9,9-trimethyl-3,5-dioxa-4-boratricyclo[6.1.1.0ˆ[2,6]]decan-4-yl]ethan-1-amine hydrochloride (787.5 mg. 2.10 mmol, 0.85 eq.), dichloromethane (20 mL), and DIEA (640 mg, 4.95 mmol, 2.00 eq.). This was followed by the addition of tert-butyl (2R)-2-[[(chlorocarbonyl)oxy]methyl]pyrrolidine-1-carboxylate (656 mg, 2.49 mmol, 1.00 eq.) at 0° C. The resulting solution was stirred for 1 h at it. The resulting mixture was diluted with 50 mL of brine. The resulting solution was extracted with 3×30 mL of dichloromethane and the organic layers combined and dried over anhydrous sodium sulfate and concentrated under vacuum. The residue was applied onto a silica gel column with ethyl acetate/petroleum ether (1:10). This resulted in 1.1 g (78%) of tert-butyl (2R)-2-[([[(1R)-2-(1-benzofuran-3-yl)-1-[(1S,2S,6R,8S)-2,9,9-trimethyl-3,5-dioxa-4-boratricyclo[6.1.1.0ˆ[2,6]]decan-4-yl]ethyl]carbamoyl]oxy)methyl]pyrrolidine-1-carboxylate as a yellow oil.

Step 3

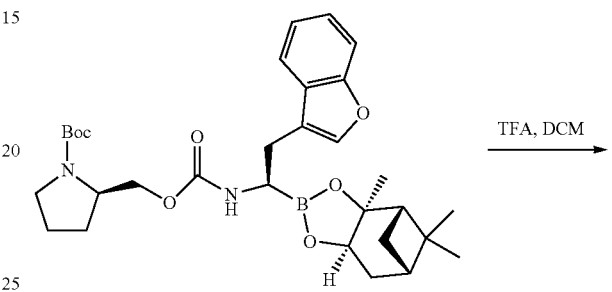

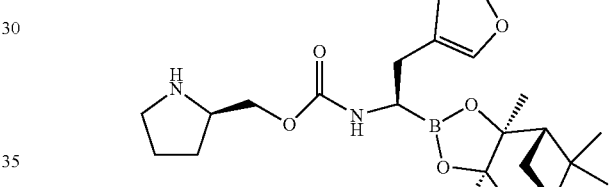

Into a 100-mL round-bottom flask, was placed tert-butyl (2R)-2-[([[(1R)-2-(1-benzofuran-3-yl)-1-[(1S,2S,6R,8S)-2,9,9-trimethyl-3,5-dioxa-4-boratricyclo[6.1.1.0ˆ[2,6]]decan-4-yl]ethyl]carbamoyl]oxy)methyl]pyrrolidine-1-carboxylate (300 mg, 0.53 mmol, 1.00 eq.), dichloromethane (10 mL), and trifluoroacetic acid (2 mL). The resulting solution was stirred for 1 h at it. The resulting mixture was concentrated under vacuum. This resulted in 247 mg (crude) of (2R)-pyrrolidin-2-ylmethyl N-[(1R)-2-(1-benzofuran-3-yl)-1-[(1S,2S,6R,8S)-2,9,9-trimethyl-3,5-dioxa-4-boratricyclo[6.1.1.0ˆ[2,6]]decan-4-yl]ethyl]carbamate as a yellow oil.

Step 4

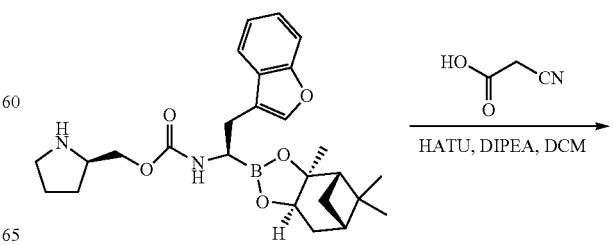

-continued

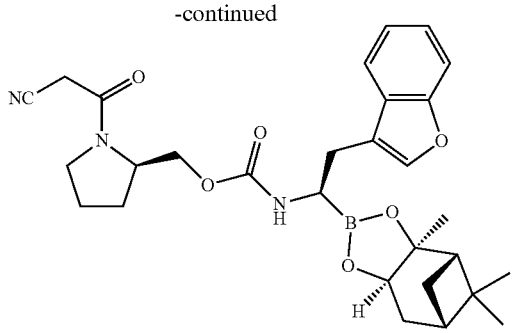

Step 6

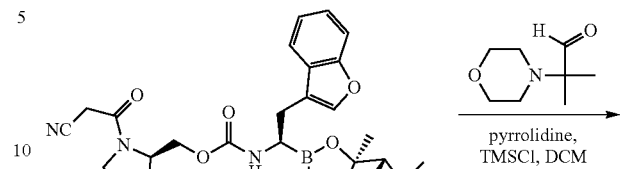

Into a 100-mL round-bottom flask, was placed (2R)-pyrrolidin-2-ylmethyl N-[(1R)-2-(1-benzofuran-3-yl)-1-[(1S,2S,6R,8S)-2,9,9-trimethyl-3,5-dioxa-4-boratricyclo[6.1.1.0^[2,6]]decan-4-yl]ethyl]carbamate (247 mg, 0.53 mmol, 1.00 eq.), dichloromethane (10 mL), 2-cyanoacetic acid (67 mg, 0.79 mmol, 1.50 eq.), DIEA (204 mg, 1.58 mmol, 3.00 eq.), and HATU (300 mg, 0.79 mmol, 1.50 eq.). The resulting solution was stirred for 2 h at rt. The resulting mixture was diluted with 50 mL of brine. The resulting solution was extracted with 3×20 mL of dichloromethane and the organic layers combined and dried over anhydrous sodium sulfate and concentrated under vacuum. The residue was applied onto a silica gel column with ethyl acetate/petroleum ether (1:5). This resulted in 150 mg (53%) of [(2R)-1-(2-cyanoacetyl)pyrrolidin-2-yl]methyl N-[(1R)-2-(1-benzofuran-3-yl)-1-[(1S,2S,6R,8S)-2,9,9-trimethyl-3,5-dioxa-4-boratricyclo[6.1.1.0^[2,6]]decan-4-yl]ethyl]carbamate as a yellow oil.

Step 5

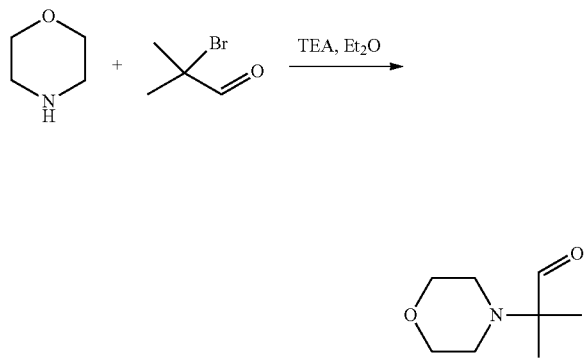

Into a 250-mL round-bottom flask, was placed ether (50 mL), morpholine (2 g, 22.96 mmol, 1.00 eq.), 2-bromo-2-methylpropanal (4 g, 26.49 mmol, 1.20 eq.), and TEA (4 g, 39.53 mmol, 2.00 eq.). The resulting solution was stirred overnight at rt. The resulting mixture was concentrated under vacuum. The residue was applied onto a silica gel column with ethyl acetate/petroleum ether (1:10). This resulted in 3.25 g (90%) of 2-methyl-2-(morpholin-4-yl)propanal as a yellow oil.

Into a 50-mL round-bottom flask, was placed [(2R)-1-(2-cyanoacetyl)pyrrolidin-2-yl]methyl N-[(1R)-2-(1-benzofuran-3-yl)-1-[(1S,2S,6R,8S)-2,9,9-trimethyl-3,5-dioxa-4-boratricyclo[6.1.1.0^[2,6]]decan-4-yl]ethyl]carbamate (100 mg, 0.19 mmol, 1.00 eq.), dichloromethane (6.87 mL), and 2-methyl-2-(morpholin-4-yl)propanal (100 mg, 0.64 mmol, 3.00 eq.). This was followed by the addition of pyrrolidine (67 mg, 0.94 mmol, 5.00 eq.) dropwise with stirring. To this was added TMSCl (101 mg, 0.93 mmol, 5.00 eq.) dropwise with stirring. The resulting solution was stirred for 1 h at rt. The resulting mixture was diluted with 15 mL of brine. The resulting solution was extracted with 3×10 mL of dichloromethane and the organic layers combined and dried over anhydrous sodium sulfate and concentrated under vacuum. The crude product was purified by Prep-HPLC with the following conditions: Column, XBridge Prep C18 OBD Column, 19*150 mm 5 um, mobile phase, Water (10 MMOL/L $NH_4HCO_3$+0.1% $NH_3.H_2O$) and ACN (60.0% ACN up to 87.0% in 7 min); Detector, UV 254/220 nm. This resulted in 100 mg (79%) of [(2R)-1-[2-cyano-2-[2-methyl-2-(morpholin-4-yl) propylidene]acetyl]pyrrolidin-2-yl]methylN-[(1R)-2-(1-benzofuran-3-yl)-1-[(1S,2S,6R,8S)-2,9,9-trimethyl-3,5-dioxa-4-boratricyclo[6.1.1.0^[2,6]]decan-4-yl]ethyl]carbamate as a white solid after lyophilization.

Step 7

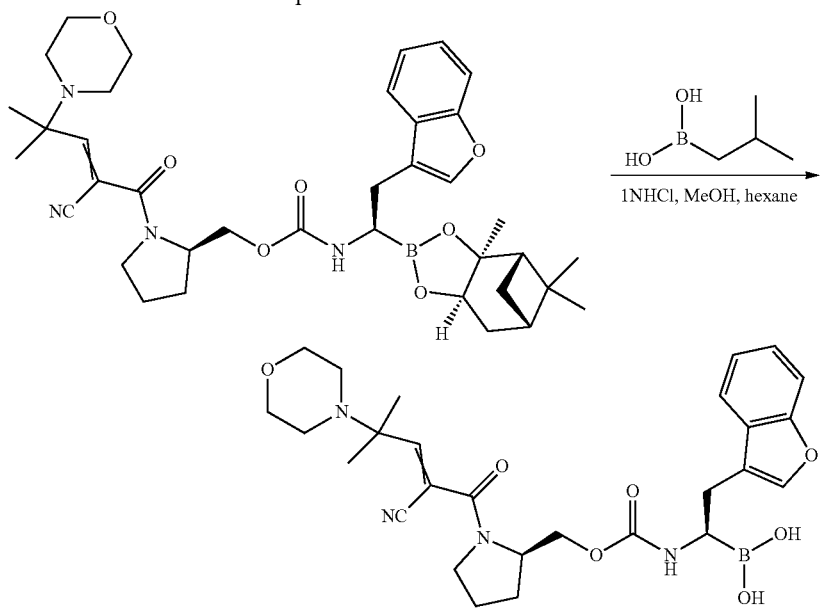

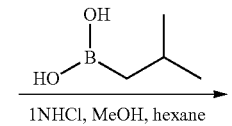

Into a 50-mL round-bottom flask, was placed [(2R)-1-[2-cyano-2-[2-methyl-2-(morpholin-4-yl) propylidene]acetyl] pyrrolidin-2-yl]methylN-[(1R)-2-(1-benzofuran-3-yl)-1-[(1S,2S,6R,8S)-2,9,9-trimethyl-3,5-dioxa-4-boratricyclo [6.1.1.0ˆ[2,6]]decan-4-yl]ethyl]carbamate (80 mg, 0.12 mmol, 1.00 eq.), methanol (5 mL), (2-methylpropyl)boronic acid (12.2 mg, 0.12 mmol, 3.00 eq.), hexane (5 mL), and 1N hydrogen chloride (2.37 mL, 20.00 eq.). The resulting solution was stirred for 3 h at rt. The resulting mixture was washed with 3×5 mL of hexane. The methanol layer was diluted with 8 mL of water, and dried over lyophilization to give a crude product which was further purified by Prep-HPLC with the following conditions: Column, XBridge Prep C18 OBD Column, 19*250 mm, 5 um; mobile phase, Water (0.05% NH3H2O) and ACN (27.0% ACN up to 40.0% in 8 min); Detector, uv 220 nm. This resulted in 16.1 mg (25%) of [(1R)-2-(1-benzofuran-3-yl)-1-[((2R)-1-[2-cyano-2-[2-methyl-2-(morpholin-4-yl) propylidene] acetyl] pyrrolidin-2-yl] methoxyl carbonyl)amino]ethyl]boronic acid as a white solid after lyophilization again. LC-MS m/z: 539 (M+1).

Example 41

((R)-1-(((((R)-1-(2-cyano-4-(3,3-difluoropyrrolidin-1-yl)-4-methylpent-2-enoyl)piperidin-2-yl)methoxy)carbonyl)amino)-2-(p-tolyl)ethyl)boronic acid

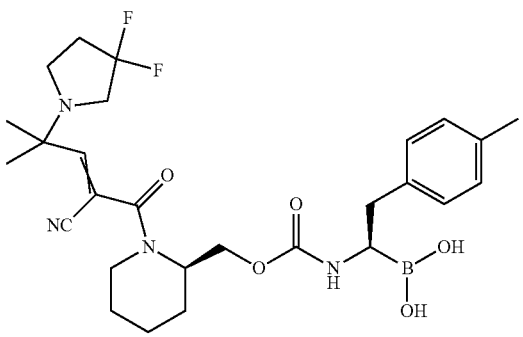 [SMILES: Cc1ccc(C[C@H](NC(=O)OC[C@H]2CCCCN2C(=O)C(C#N)=CC(C)(C)N2CCC(F)(F)C2)B(O)O)cc1]

Step 1

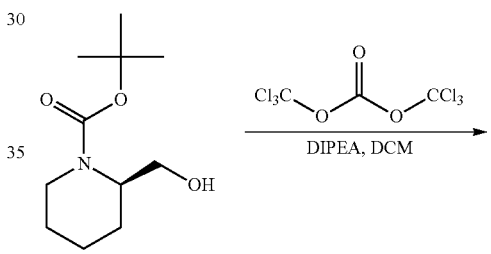

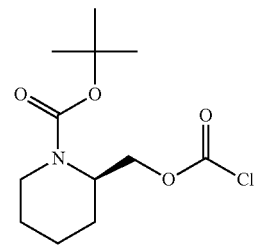

Into a 50-mL 3-necked round-bottom flask, was placed tert-butyl (2R)-2-(hydroxymethyl) piperidine-1-carboxylate (500 mg, 2.32 mmol, 1.00 eq.), dichloromethane (8 mL), and DIEA (599 mg, 4.63 mmol, 2.00 eq.). This was followed by the addition of ditrichloromethyl carbonate (341 mg, 1.15 mmol, 0.50 eq.) at 0° C. The resulting solution was stirred for 2 h at 0° C. This resulted in 645 mg (crude) of tert-butyl (2R)-2-[[(chlorocarbonyl)oxy] methyl]piperidine-1-carboxylate as a yellow oil. The reaction mixture was used directly to the next step.

Step 2

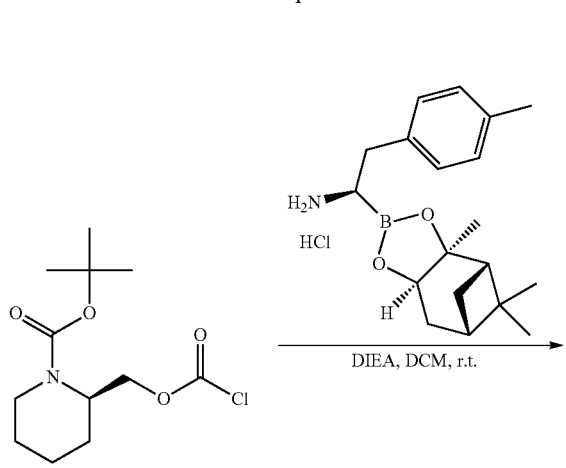

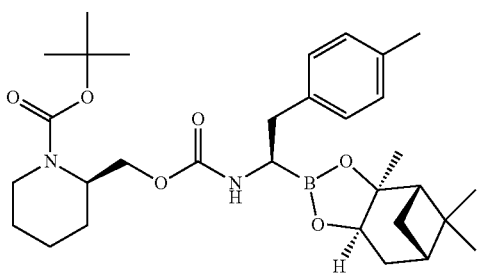

Into a 50-mL 3-necked round-bottom flask, was placed (1R)-2-(4-methylphenyl)-1-[(1S,2S,6R,8S)-2,9,9-trimethyl-3,5-dioxa-4-boratricyclo[6.1.1.0ˆ[2,6]]decan-4-yl]ethan-1-amine hydrochloride (690 mg, 1.97 mmol, 0.85 eq.), dichloromethane (10 mL), and DIEA (599 mg, 4.63 mmol, 2.00 eq.). This was followed by the addition of tert-butyl (2R)-2-[[(chlorocarbonyl)oxy]methyl] piperidine-1-carboxylate (645 mg, 2.32 mmol, 1.00 eq.) at 0° C. The resulting solution was stirred for 2 h at rt. The resulting mixture was diluted with 50 mL of brine. The resulting solution was extracted with 3×20 mL of dichloromethane and the organic layers combined and dried over anhydrous sodium sulfate and concentrated under vacuum. The crude product was purified by Flash-Prep-HPLC with the following conditions: Column, C18 silica gel; mobile phase, H₂O/CH₃CN=99:1 increasing to CH₃CN/H₂O=4:1 within 2 h; Detector, UV 254 nm. This resulted in 420 mg (33%) of tert-butyl (2R)-2-[([[(1R)-2-(4-methylphenyl)-1-[(1S,2S,6R,8S)-2,9,9-trimethyl-3,5-dioxa-4-boratricyclo[6.1.1.0ˆ[2,6]]decan-4-yl]ethyl]carbamoyl]oxy)methyl]piperidine-1-carboxylate as a yellow oil.

Step 3

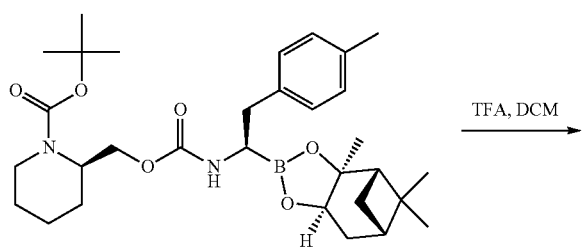

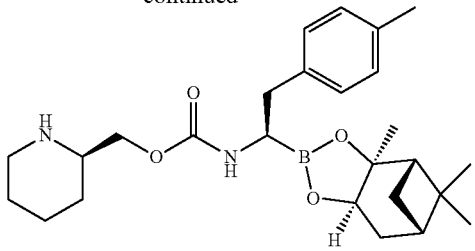

Into a 100-mL round-bottom flask, was placed tert-butyl (2R)-2-[([[(1R)-2-(4-methylphenyl)-1-[(1S,2S,6R,8S)-2,9,9-trimethyl-3,5-dioxa-4-boratricyclo[6.1.1.0ˆ[2,6]]decan-4-yl]ethyl]carbamoyl]oxy)methyl]piperidine-1-carboxylate (728 mg, 1.31 mmol, 1.00 eq.), dichloromethane (22.5 mL), and trifluoroacetic acid (4.5 mL). The resulting solution was stirred for 1 h at rt. The resulting mixture was concentrated under vacuum. The crude product was purified by Flash-Prep-HPLC with the following conditions: Column, C18 silica gel; mobile phase, H₂O:ACN=1:0 increasing to H₂O:ACN=1:3.5 within 100 min.; Detector, UV 254 nm. This resulted in 510 mg (85%) of (2R)-piperidin-2-ylmethyl N-[(1R)-2-(4-methylphenyl)-1-[(1S,2S,6R,8S)-2,9,9-trimethyl-3,5-dioxa-4-boratricyclo[6.1.1.0ˆ[2,6]]decan-4-yl]ethyl]carbamate as a yellow oil.

Step 4

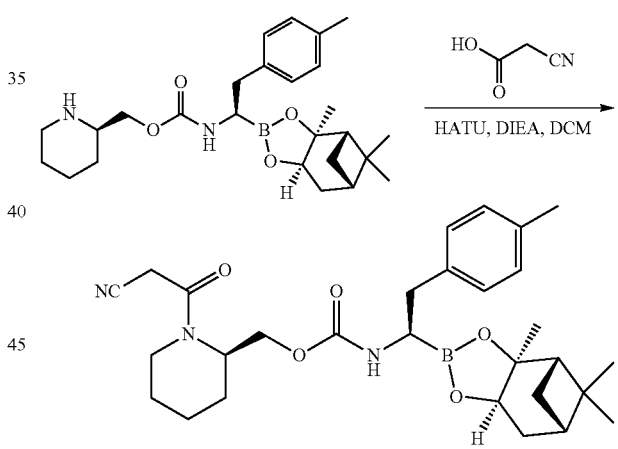

Into a 100-mL round-bottom flask, was placed (2R)-piperidin-2-ylmethyl N-[(1R)-2-(4-methylphenyl)-1-[(1S,2S,6R,8S)-2,9,9-trimethyl-3,5-dioxa-4-boratricyclo[6.1.1.0ˆ[2,6]]decan-4-yl]ethyl]carbamate (510 mg, 1.12 mmol, 1.00 eq.), dichloromethane (20 mL), 2-cyanoacetic acid (143 mg, 1.68 mmol. 1.50 eq.), DIEA (434 mg, 3.36 mmol, 3.00 eq.), and HATU (638.9 mg, 1.68 mmol, 1.50 eq.). The resulting solution was stirred for 1 h at rt. The resulting mixture was diluted with 50 mL of brine. The resulting solution was extracted with 3×30 mL of dichloromethane and the organic layers combined and dried over anhydrous sodium sulfate. The crude product was purified by Flash-Prep-HPLC with the following conditions: Column, C18 silica gel; mobile phase, H₂O:ACN=1:0 increasing to H₂O:ACN=0:1 within 100 min.; Detector, UV 254 nm. This resulted in 334 mg (57%) of [(2R)-1-(2-cyanoacetyl)piperidin-2-yl]methyl N-[(1R)-2-(4-methylphenyl)-1-[(1S,2S,6R,8S)-2,9,9-trimethyl-3,5-dioxa-4-boratricyclo[6.1.1.0^[2,6]]decan-4-yl]ethyl]carbamate as a yellow oil.

Step 5

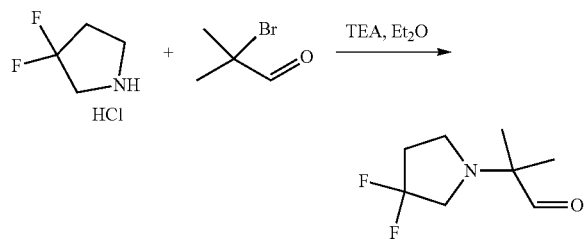

Into a 100-mL round-bottom flask, was placed 3,3-difluoropyrrolidine hydrochloride (500 mg, 3.48 mmol, 1.00 eq.), ether (25 mL), 2-bromo-2-methylpropanal (703 mg, 4.66 mmol, 1.35 eq.), and TEA (1 g, 9.88 mmol, 3.00 eq.). The resulting solution was stirred overnight at it. The resulting mixture was concentrated under vacuum. The residue was applied onto a silica gel column with dichloromethane/methanol (99:1). This resulted in 350 mg (57%) of 2-(3,3-difluoropyrrolidin-1-yl)-2-methylpropanal as a yellow oil.

Step 6

Into a 100-mL round-bottom flask, was placed [(2R)-1-(2-cyanoacetyl)piperidin-2-yl]methyl N-[(1R)-2-(4-methylphenyl)-1-[(1S,2S,6R,8S)-2,9,9-trimethyl-3,5-dioxa-4-boratricyclo[6.1.1.0^[2,6]]decan-4-yl]ethyl]carbamate (305 mg, 0.58 mmol, 1.00 eq.), dichloromethane (21.7 mL), 2-(3,3-difluoropyrrolidin-1-yl)-2-methylpropanal (311 mg, 1.76 mmol, 3.00 eq.), pyrrolidine (206 mg, 2.90 mmol, 5.00 eq.), and TMSCl (315 mg, 2.90 mmol, 5.00 eq.). The resulting solution was stirred for 2 h at rt. The resulting mixture was diluted with 50 mL of brine. The resulting solution was extracted with 3×30 mL of dichloromethane and the organic layers combined and dried over anhydrous sodium sulfate and concentrated under vacuum. The crude product was purified by Prep-HPLC with the following conditions: Column, XBridge Prep C18 OBD Column, 19*150 mm 5 um; mobile phase, Water (10 MMOL/L $NH_4HCO_3$+0.1% $NH_3.H_2O$) and ACN (73.0% ACN up to 90.0% in 7 min); Detector, UV 254/220 nm. This resulted in 260 mg (67%) of [(2R)-1-[2-cyano-2-[2-(3,3-difluoropyrrolidin-1-yl)-2-methylpropylidene]acetyl] piperidin-2-yl]methylN-[(1R)-1-[(1S,2S,6R,8S)-2,9-dimethyl-3,5-dioxa-4-boratricyclo[6.1.1.0^[2,6]]decan-4-yl]-2-(4-methylphenyl)ethyl]carbamate as a white solid after lyophilization.

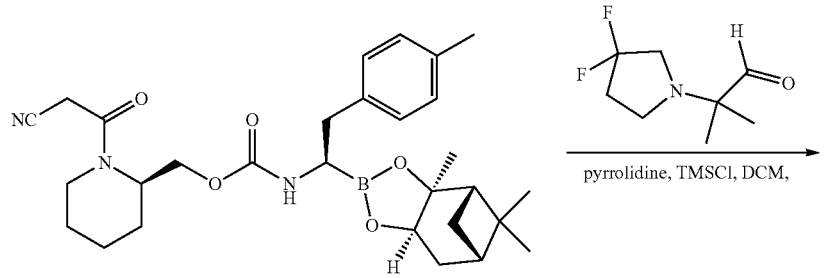

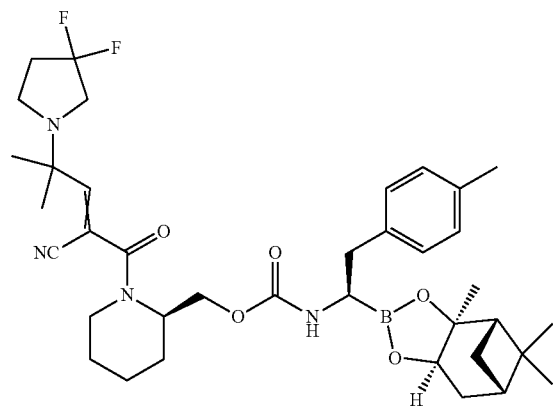

Step 7

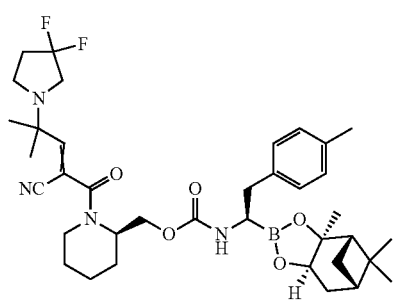
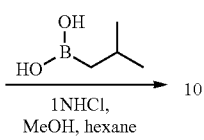
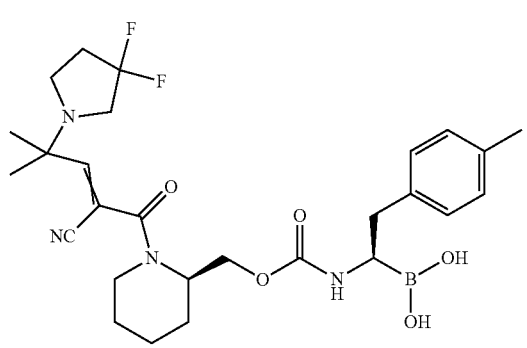

Into a 100-mL round-bottom flask, was placed [(2R)-1-[2-cyano-2-[2-(3,3-difluoropyrrolidin-1-yl)-2-methylpropylidene]acetyl]piperidin-2-yl]methyl N-[(1R)-2-(4-methylphenyl)-1-[(1S,2S,6R,8S)-2,9,9-trimethyl-3,5-dioxa-4-boratricyclo[6.1.1.0^[2.6]]decan-4-yl]ethyl]carbamate (240 mg, 0.35 mmol, 1.00 eq.), methanol (10 mL), (2-methylpropyl)boronic acid (108.8 mg, 1.07 mmol, 3.00 eq.), hexane (10 mL), and 1N hydrogen chloride (7 mL, 20.00 eq.). The resulting solution was stirred for 3 h at it. The resulting mixture was washed with 3×6 mL of hexane. The methanol layer was diluted with 12 mL of water, and dried over lyophilization to give a crude product which was further purified by Prep-HPLC with the following conditions: Column, XBridge Prep OBD C18 Column, 19*250 mm, 5 um; mobile phase, Water (0.05% NH₃H₂O) and ACN (43.0% ACN up to 55.0% in 8 min.); Detector, uv 20 nm. This resulted in 65.8 mg (34%) of [(1R)-1-[([[(2R)-1-[2-cyano-2-[2-(3,3-difluoropyrrolidin-1-yl)-2-methylpropylidene]acetyl]piperidin-2-yl]methoxy]carbonyl)amino]-2-(4-methylphenyl)ethyl]boronic acid as a white solid after lyophilization again. LC-MS m/z: 547 (M+1).

Example 42

((R)-2-(benzofuran-3-yl)-1-(((((R)-1-(2-cyano-4-(3,3-difluoropyrrolidin-1-yl)-4-methylpent-2-enoyl)pyrrolidin-2-yl)methoxy)carbonyl)amino)ethyl)boronic acid

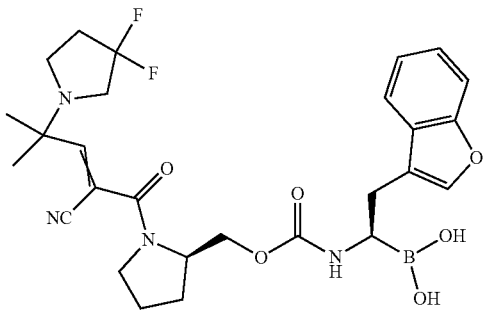 [SMILES: CC(C)(C=C(C#N)C(=O)N1CCC[C@@H]1COC(=O)N[C@@H](Cc1coc2ccccc12)B(O)O)N1CCC(F)(F)C1]

The title compound was prepared as in example 40 by replacing morpholine with 2,2-difluoropyrrolidine. LC-MS m/z: 541 (M−17).

Example 43

((R)-2-(benzofuran-3-yl)-1-(((((R)-4-(2-cyano-4,4-dimethylpent-2-enoyl)morpholin-3-yl)methoxy)carbonyl)amino)ethyl)boronic acid

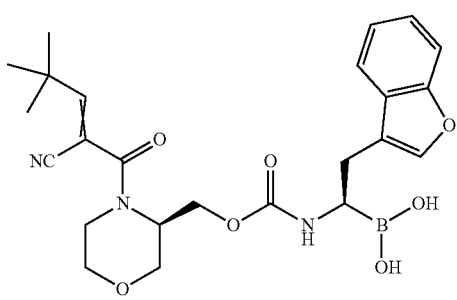 [SMILES: CC(C)(C)C=C(C#N)C(=O)N1CCOC[C@@H]1COC(=O)N[C@@H](Cc1coc2ccccc12)B(O)O]

Step 1

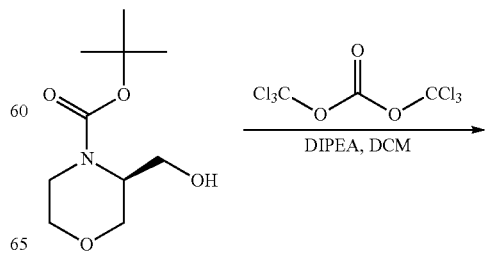

-continued

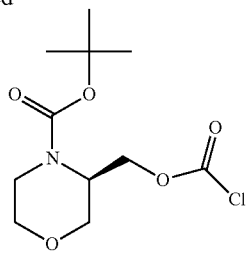

Into a 25-mL 3-necked round-bottom flask purged and maintained with an inert atmosphere of nitrogen, was placed tert-butyl (3S)-3-(hydroxymethyl)morpholine-4-carboxylate (150 mg, 0.69 mmol, 1.00 eq.), dichloromethane (1.5 mL), and DIPEA (267.5 mg, 2.07 mmol, 3.00 eq.). This was followed by the addition of ditrichloromethyl carbonate (102.6 mg, 0.35 mmol, 0.50 eq.) dropwise with stirring at 0° C. The resulting solution was stirred for 3 h at 0° C. The resulted solution was used directly to the next step.

Step 2

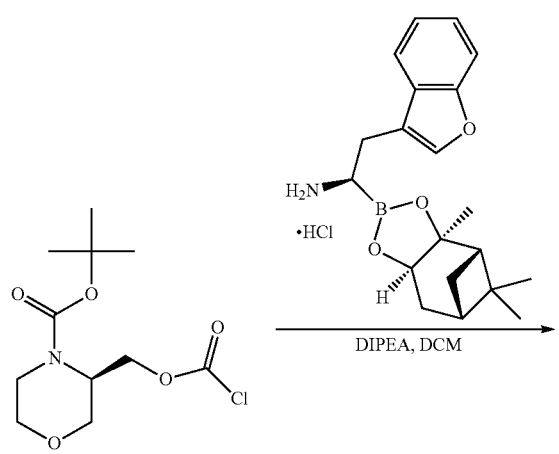

Into a 100-mL 3-necked round-bottom flask purged and maintained with an inert atmosphere of nitrogen, was placed (1R)-2-(1-benzofuran-3-yl)-1-[(1S,2S,6R,8S)-2,9,9-trimethyl-3,5-dioxa-4-boratricyclo[6.1.1.0^[2,6]]decan-4-yl]ethan-1-amine hydrochloride (220.3 mg, 0.59 mmol, 0.85 eq.), dichloromethane (1.5 mL), and DIPEA (178.3 mg, 1.38 mmol, 2.00 eq.). This was followed by the addition of tert-butyl (3R)-3-[[(chlorocarbonyl)oxy]methyl]morpholine-4-carboxylate (192.9 mg, 0.69 mmol, 1.00 eq.) dropwise with stirring at 0° C. The resulting solution was stirred for 60 min. at 25° C. The resulting solution was diluted with 100 mL of DCM. The resulting mixture was washed with 3×100 mL of saturated brine. The mixture was dried over anhydrous sodium sulfate and concentrated under vacuum. The residue was separated by PREP-TLC with ethyl acetate/petroleum ether (1:2). This resulted in 280 mg (70%) of tert-butyl (3R)-3-[([[(1R)-2-(1-benzofuran-3-yl)-1-[(1S,2S,6R,1R)-2,9,9-trimethyl-3,5-dioxa-4-boratricyclo[6.1.1.0^[2,6]]decan-4-yl]ethyl]carbamoyl]oxy)methyl]morpholine-4-carboxylate as a yellow solid.

Step 3

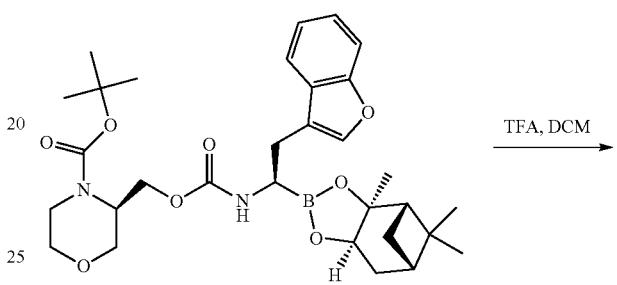

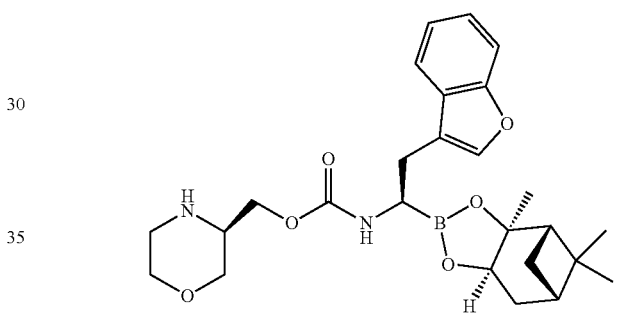

Into a 100-mL round-bottom flask, was placed tert-butyl (3R)-3-[([[(1R)-2-(1-benzofuran-3-yl)-1-[(1S,2S,6R,8S)-2,9,9-trimethyl-3,5-dioxa-4-boratricyclo[6.1.1.0^[2,6]]decan-4-yl]ethyl]carbamoyl]oxy)methyl]morpholine-4-carboxylate (280 mg, 0.48 mmol, 1.00 eq.), dichloromethane (20 mL), and trifluoroacetic acid (2 mL). The resulting solution was stirred for 60 min at 25° C. The resulting mixture was concentrated under vacuum. This resulted in 231.9 mg (crude) product was used directly to the next step.

Step 4

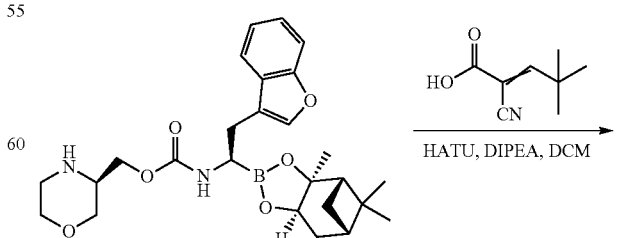

141

-continued

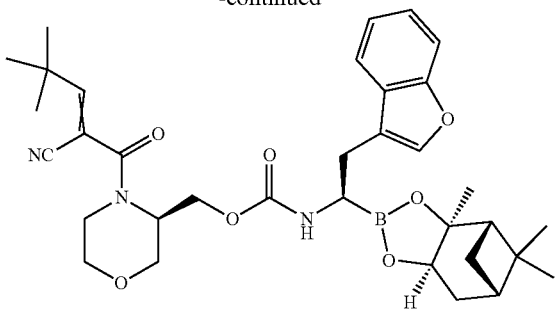

Into a 50-mL round-bottom flask purged and maintained with an inert atmosphere of nitrogen, was placed (3R)-morpholin-3-ylmethyl N-[(1R)-2-(1-benzofuran-3-yl)-1-[(1S,2S,6R,8S)-2,9,9-trimethyl-3,5-dioxa-4-boratricyclo[6.1.1.0ˆ[2,6]]decan-4-yl]ethyl]carbamate (231.9 mg. 0.48 mmol, 1.00 eq.). 2-cyano-4,4-dimethylpent-2-enoic acid (80.2 mg, 0.52 mmol, 1.20 eq.), HATU (219.4 mg, 0.58 mmol, 1.20 eq.), DIPEA (155.2 mg, 1.20 mmol, 2.50 eq.), and dichloromethane (19 mL). The resulting solution was stirred for 60 min. at 25° C. The resulting mixture was concentrated under vacuum. The crude product was purified by Prep-HPLC with the following conditions: Column, XBridge Prep C18 OBD Column, 19*150 mm 5 um; mobile phase, Water (10 MMOL/IL $NH_4HCO_3$+0.1% $NH_3.H_2O$) and ACN (5.0% ACN up to 77.0% in 2 min, up to 80.0% in 5 min); Detector, UV 254/220 nm. This resulted in 50 mg (17%) of [(3R)-4-[2-cyano-2-(2,2-dimethylpropylidene)acetyl]morpholin-3-yl]methylN-[(1R)-2-(1-benzofuran-3-yl)-1-[(1S,2S,6R,8S)-2,9,9-trimethyl-3,5-dioxa-4-boratricyclo[6.1.1.0ˆ[2,6]]decan-4-yl]ethyl]carbamate as a white solid after lyophilization.

Step 5

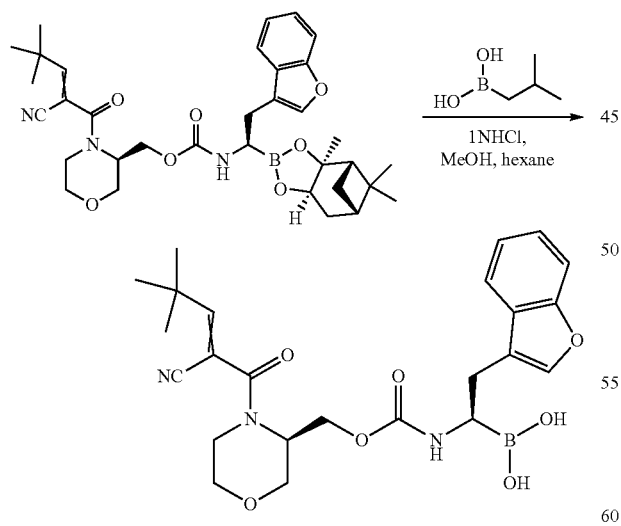

Into a 50-mL round-bottom flask purged and maintained with an inert atmosphere of nitrogen, was placed [(3R)-4-[2-cyano-2-(2,2-dimethylpropylidene)acetyl]morpholin-3-yl]methylN-[(1R)-2-(1-benzofuran-3-yl)-1-[(1S,2S,6R,8S)-2,9,9-trimethyl-3,5-dioxa-4-boratricyclo[6.1.1.0ˆ[2,6]]decan-4-yl]ethyl]carbamate (50 mg, 0.08 mmol, 1.00 eq.),

142 methanol (2.2 mL), (2-methylpropyl)boronic acid (24 mg, 0.24 mmol, 2.90 eq.), hexane (2.2 mL), and 1N HCl (1.61 mL. 20.00 eq.). The resulting solution was stirred for 2 h at 25° C. The resulting mixture was washed with 3×2 mL of hexane. The methanol layer was diluted with 10 mL of $H_2O$, then dried over lyophylization to give a crude product which was further purified by Prep-HPLC with the following conditions: Column, XBridge Prep C18 OBD Column, 19*150 mm 5 um; mobile phase, Water (10 MMOL/L $NH_4HCO_3$+0.1% $NH_3.H_2O$) and ACN (35.0% ACN up to 37.0% in 10 min); Detector, UV 254/220 nm. This resulted in 19.6 mg (50%) of [(1R)-2-(1-benzofuran-3-yl)-1-[([[(3R)-4-[2-cyano-2-(2,2-dimethylpropylidene)acetyl]morpholin-3-yl]methoxy]carbonyl)amino]ethyl]boronic acid as a white solid after lyophilization. LC-MS m/z: 484 (M+1).

Example 44

((R)-2-(benzofuran-3-yl)-1-(((((R)-1-(2-cyano-4-methyl-4-(4-(oxetan-3-yl)piperazin-1-yl)pent-2-enoyl)pyrrolidin-2-yl)methoxy)carbonyl)amino)ethyl)boronic acid

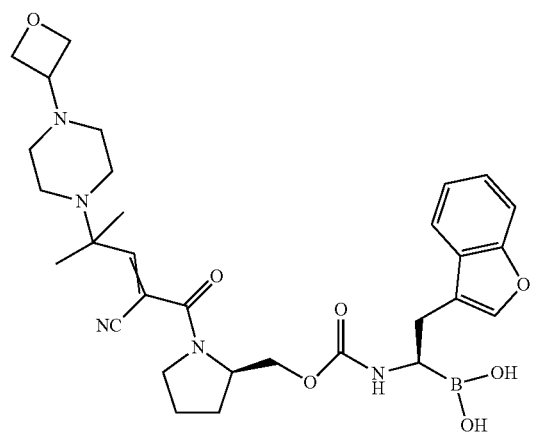 [SMILES: CC(C)(C=C(C#N)C(=O)N1CCC[C@@H]1COC(=O)N[C@@H](Cc1coc2ccccc12)B(O)O)N1CCN(C2COC2)CC1]

The title compound was prepared as in example 40 by replacing morpholine with 4-(oxetan-3-yl)piperazine. LC-MS m/z: 594 (M+1).

Example 45

((R)-1-(((((R)-1-(2-cyano-4-methyl-4-morpholino-pent-2-enoyl)piperidin-2-yl)methoxy)carbonyl)amino)-2-(p-tolyl)ethyl)boronic acid

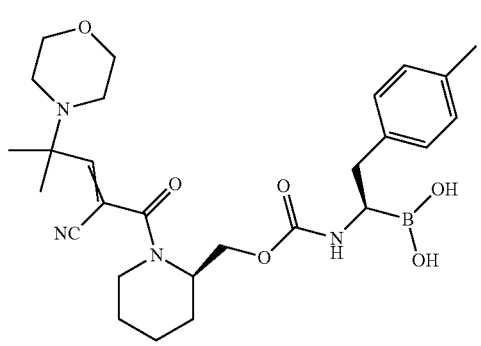 [SMILES: Cc1ccc(C[C@H](NC(=O)OC[C@H]2CCCCN2C(=O)C(C#N)=CC(C)(C)N2CCOCC2)B(O)O)cc1]

The title compound was prepared as in example 41 by replacing 2,2-difluoropyrrolidine with morpholine. LC-MS m/z: 527 (M−17).

Example 46
((R)-2-(benzofuran-3-yl)-1-(((((R)-1-(2-cyano-4-methyl-4-morpholinopent-2-enoyl)piperidin-2-yl)methoxy)carbonyl)amino)ethyl)boronic acid
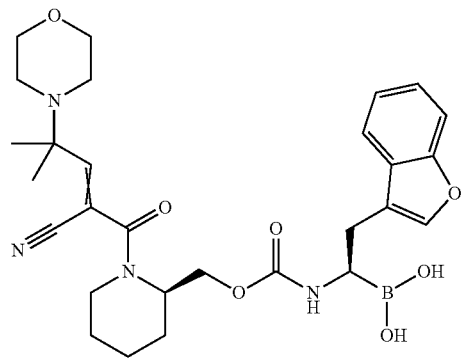
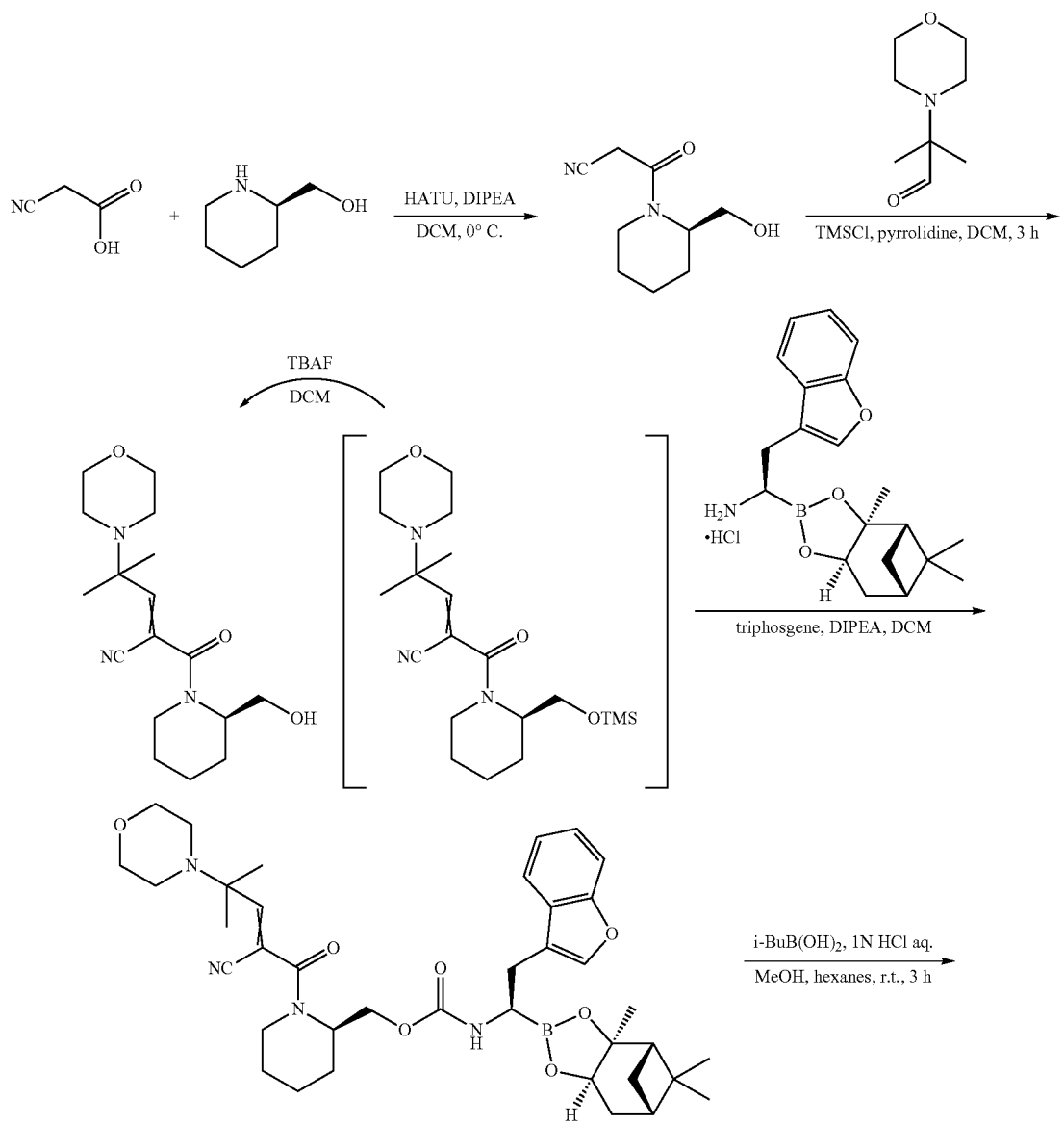

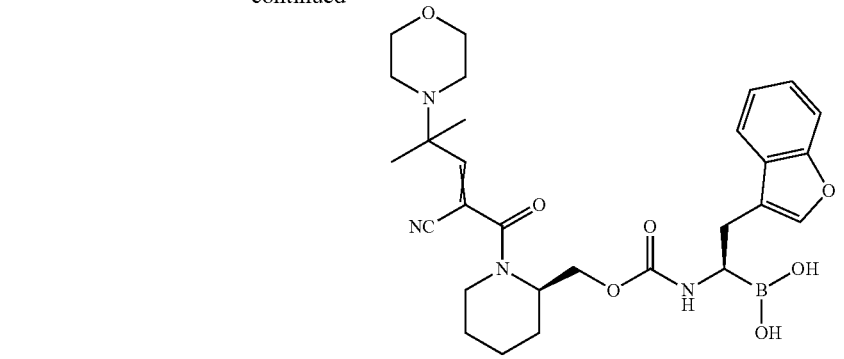

Step 1

To a mixture of 2-cyanoacetic acid (1.48 g, 17.4 mmol), (R)-piperidin-2-ylmethanol (2 g, 17.4 mmol) and DIPEA (5.6 g, 43.6 mmol) in DCM (100 mL) was added portionwise HATU (8 g, 20.8 mmol) at 0° C. The resulted mixture was stirred at 0° C. for 1 h, then concentrated to dryness. The residue was stirred in EtOAc (100 mL) for 5 min, then filtered. The filtration was concentrated in vacuo. The crude residue was purified via silica chromatography and a gradient of 0%-100% EtOAc in hexanes to afford (R)-3-(2-(hydroxymethyl)piperidin-1-yl)-3-oxopropanenitrile as a colorless oil (1.9 g over 900/% purity, 63%).

Step 2

To a solution of (R)-3-(2-(hydroxymethyl)piperidin-1-.l)-3-oxopropanenitrile (1.56 g, 8.6 mmol), 2-methyl-2-morpholinopropanal (1.48 g, 9.4 mmol) and pyrrolidine (2.4 g, 34.4 mmol) in DCM (30 mL) in ice-water bath was added dropwise chloro(trimethyl)silane (1.87 g, 17.2 mmol). The reaction was stirred at 0° C. for 0.5 h, then washed with brine (5 mL). The DCM layer was dried over Na₂SO₄, concentrated to dryness. The crude residue was purified via silica chromatography and a gradient of 0%-100% EtOAc in hexanes to afford (R)-2-(2-(hydroxymethyl)piperidine-1-carbonyl)-4-methyl-4-morpholinopent-2-enenitrile as light yellow oil (400 mg) and (R)-4-methyl-4-morpholino-2-(2-((trimethylsilyloxy)methyl)piperidine-1-carbonyl)pent-2-enenitrile as a colorless oil (1.2 g). (R)-4-methyl-4-morpholino-2-(2-((trimethylsilyloxy)methy)piperidine-1 carbonyl)pent-2-enenitrile (700 mg, 1.78 mmol) was dissolved in DCM (20 mL). TBAF.3H₂O (650 mg, 2.5 mmol) was added. The mixture was stirred at rt for 3 h, then concentrated to dryness. The residue was purified via silica chromatography and a gradient of 50%-100% EtOAc in hexanes to afford (R)-2-(2-(hydroxymethyl)piperidine-1-carbonyl)-4-methyl-4-morpholinopent-2-enenitrile as light yellow oil (290 mg, total 690 mg, 25% yield)

Step 3

Bis(trichloromethyl) carbonate (523 mg, 1.6 mmol) in DCM (1.5 mL) was added dropwise into a stirring solution of (R)-2-(2-(hydroxymethyl)piperidine-1-carbonyl)-4-methyl-4-morpholinopent-2-enenitrile (690 mg, 2.1 mmol) and DIPEA (1.6 g, 12.6 mmol) in DCM (10 mL) at 0° C. The mixture was stirred for 2 h at 0° C. This resulted solution was added dropwise into a well-stirred solution of (R)-2-(benzofuran-3-yl)-1-((3aS,4S,6S,7aR)-3a,5,5-trimethylhexahydro-4,6-methanobenzo[d][1,3,2]dioxaborol-2-yl) ethan-1-amine hydrochloride (805 mg, 2.1 mmol) and DIPEA (812 mg, 6.3 mmol) in DCM (10 mL) at 0° C. The reaction was stirred at 0° C. for 1 h, then diluted with DCM (25 mL), washed with water (10 mL) and brine (10 mL), dried over Na₂SO₄, concentrated in vacuo. The residue was purified via silica chromatography and a gradient of 0%-25% EtOAc in hexanes to afford ((R)-1-(2-cyano-4-methyl-4-morpholinopent-2-enoyl)piperidin-2-yl)methyl ((R)-2-(benzofuran-3-yl)-1-((3aS,4S,6S,7aR)-3a,5,5-trimethylhexahydro-4,6-methanobenzo[d][1,3,2]dioxaborol-2-yl)ethyl)carbamate as light yellow solid (430 mg, 31%).

Step 4

To a solution of ((R)-1-(2-cyano-4-methyl-4-morpholinopent-2-enoyl)piperidin-2-yl)methyl ((R)-2-(benzofuran-3-yl)-1-((3aS,4S,6S,7aR)-3a,5,5-trimethylhexahydro-4,6-methanobenzo[d][1,3,2]dioxaborol-2-yl)ethyl)carbamate (430 mg, 0.62 mmol) in MeOH (4 mL) were added hexanes (4 mL) and 1 N HCl (2 mL), followed by isobutyl boric acid (182 mg, 1.8 mmol). After stirred at rt for 3 h and TLC suggested the reaction was completed, the hexanes layer was discarded. The methanol layer was diluted with water (20 mL), then dried over lyophilization to give a crude product which was purified by prep-HPLC to afford (R)-2-(benzofuran-3-yl)-1-((((R)-1-(2-cyano-4-methyl-4-morpholinopent-2-enoyl)piperidin-2-yl)methoxy)carbonylamino)ethylboronic as a white solid (170 mg, 50%). LC-MS m/z: 553 (M+1).

Example 47

((R)-2-(benzofuran-3-yl)-1-(((((R)-1-(2-cyano-4-(3,3-difluoropyrrolidin-1-yl)-4-methylpent-2-enoyl) piperidin-2-yl)methoxy)carbonyl)amino)ethyl boronic acid

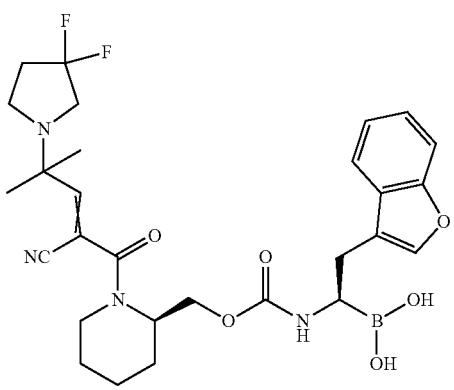 [SMILES: CC(C)(C=C(C#N)C(=O)N1CCCC[C@@H]1COC(=O)N[C@@H](Cc1coc2ccccc12)B(O)O)N1CCC(F)(F)C1]

The title compound was prepared as in example 46 by replacing morpholine with 2,2-difluoropyrrolidine. LC-MS m/z: 595 (M+23).

Example 48

((R)-2-(benzofuran-3-yl)-1-(((((1S,2R,5R)-3-(2-cyano-4,4-dimethylpent-2-enoyl)-3-azabicyclo[3.1.0]hexan-2-yl)methoxy)carbonyl)amino)ethyl)boronic acid

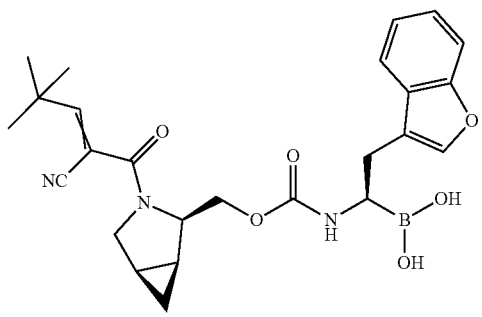 [SMILES: CC(C)(C)C=C(C#N)C(=O)N1C[C@@H]2C[C@@H]2[C@@H]1COC(=O)N[C@@H](Cc1coc2ccccc12)B(O)O]

The title compound was prepared as in example 26 by replacing (1R)-2-phenyl-1-[(1S,2S,6R,8S)-2,9,9-trimethyl-3,5-dioxa-4-boratricyclo[6.1.1.0ˆ[2,6]]decan-4-yl]ethan-1-amine hydrochloride with (1R)-2-(1-benzofuran-3-yl)-1-[(1S,2S,6R,8S)-2,9,9-trimethyl-3,5-dioxa-4-boratricyclo[6.1.1.0ˆ[2,6]]decan-4-yl]ethan-1-amine hydrochloride. LC-MS m/z: 502 (M+23).

Example 49

((R)-2-(benzofuran-3-yl)-1-(((((R)-1-((E)-4-(dimethylamino)but-2-enoyl)pyrrolidin-2-yl)methoxy)carbonyl)amino)ethyl)boronic acid

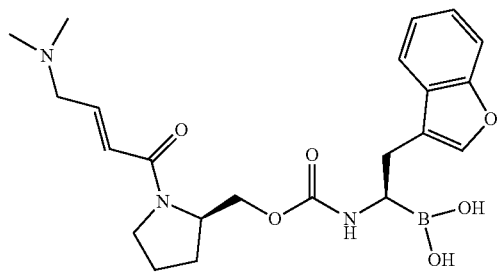 [SMILES: CN(C)C/C=C/C(=O)N1CCC[C@@H]1COC(=O)N[C@@H](Cc1coc2ccccc12)B(O)O]

Step 1

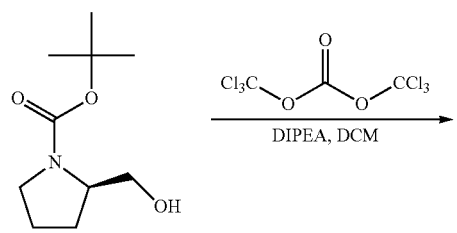

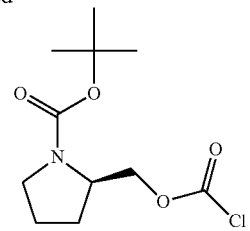

Into a 50-mL 3-necked round-bottom flask, was placed tert-butyl (2R)-2-(hydroxymethyl)pyrrolidine-1-carboxylate (200 mg, 0.99 mmol, 1.00 eq.), dichloromethane (4 mL), and DIEA (386 mg, 2.99 mmol, 3.00 eq.). This was followed by the addition of ditrichloromethyl carbonate (148 mg, 0.50 mmol, 0.50 eq.) at 0° C. The resulting solution was stirred for 2 h at 0° C. in a water/ice bath. The resulting mixture was concentrated under vacuum to give a product 262 mg (crude) of tert-butyl (2R)-2-[[(chlorocarbonyl)oxy]methyl]pyrrolidine-1-carboxylate as a yellow oil which was used directly to the next step.

Step 2

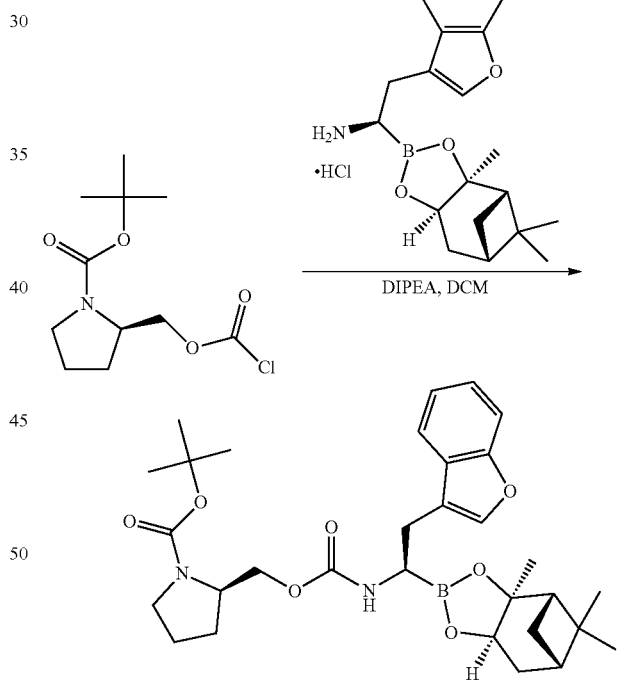

Into a 100-mL 3-necked round-bottom flask purged and maintained with an inert atmosphere of nitrogen, was placed (1R)-2-phenyl-1-[(1S,2S,6R,8S)-2,9,9-trimethyl-3,5-dioxa-4-boratricyclo[6.1.1.0ˆ[2,6]]decan-4-yl]ethan-1-amine hydrochloride (317 mg, 0.845 mmol, 0.85 eq.), DCM (20 mL), and DIPEA (465 mg, 2.00 eq.). This was followed by the addition of tert-butyl (2R)-2-[[(chlorocarbonyl)oxy]methyl]pyrrolidine-1-carboxylate (262 mg, 1.0 mmol, 1 eq.) dropwise with stirring at 0° C. The resulting solution was stirred for 1 h at rt. The resulting solution was diluted with 20 mL of H₂O. The resulting solution was extracted with 3×20 mL of dichloromethane and the organic layers combined and dried over anhydrous sodium sulfate and concentrated under vacuum. The crude product was purified by Flash-Prep-HPLC with the following conditions: Column, C18 silica gel; mobile phase, H$_2$O/CH$_3$CN=99:1 increasing to H$_2$O/CH$_3$CN=1:99 within 100 min.; Detector, UV 220 nm. This resulted in 300 mg (53%) of tert-butyl (2R)-2-[([[(1R)-2-(1-benzofuran-3-yl)-1-[(1S,2S,6R,8S)-2,9,9-trimethyl-3,5-dioxa-4-boratricyclo[6.1.1.0ˆ[2.6]]decan-4-yl]ethyl]carbamoyl]oxy)methyl]pyrrolidine-1-carboxylate as a white solid.

Step 3

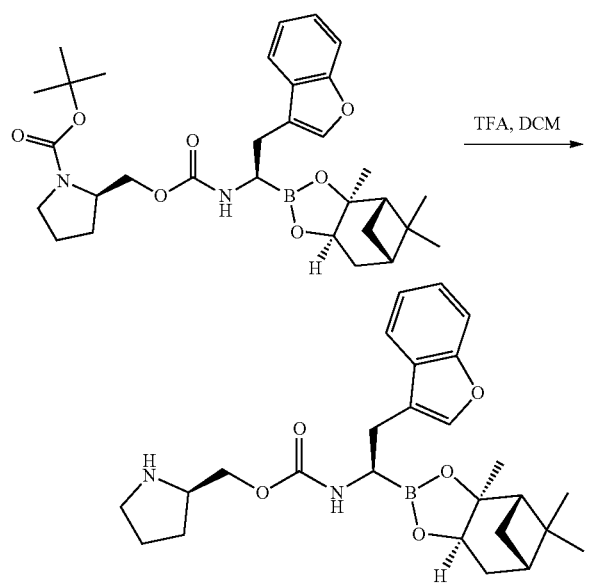

Into a 8-mL vial it was placed tert-butyl (2R)-2-[([[(1R)-2-(1-benzofuran-3-yl)-1-[(1S,2S,6R,8S)-2,9,9-trimethyl-3,5-dioxa-4-boratricyclo[6.1.1.0ˆ[2,6]]decan-4-yl]ethyl]carbamoyl]oxy)methyl]pyrrolidine-1-carboxylate (22 mg, 0.04 mmol, 1.00 eq.), dichloromethane (1 mL), and trifluoroacetic acid (0.4 mL). The resulting solution was stirred for 1 h at rt. The resulting mixture was concentrated under vacuum to give a crude product (18 mg) which was used directly to the next step.

Step 4

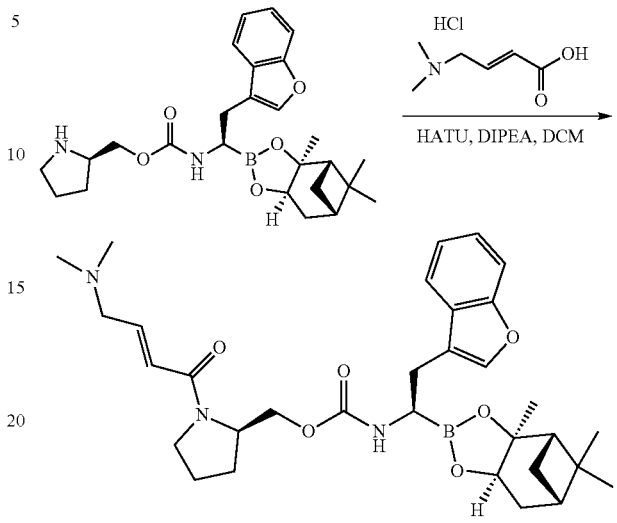

Into a 50-mL round-bottom flask purged and maintained with an inert atmosphere of nitrogen, was placed (2R)-pyrrolidin-2-ylmethyl N-[(1R)-2-(1-benzofuran-3-yl)-1-[(1S,2S,6R,8S)-2,9,9-trimethyl-3,5-dioxa-4-boratricyclo[6.1.1.0ˆ[2,6]]decan-4-yl]ethyl]carbamate (82.3 mg, 0.18 mmol, 1.00 eq.), dichloromethane (7 mL), DIPEA (79.8 mg, 0.62 mmol, 3.50 eq.), HATU (80.6 mg, 0.21 mmol, 1.20 eq.), and (2E)-4-(dimethylamino)but-2-enoic acid hydrochloride (35 mg, 0.21 mmol. 1.20 eq.). The resulting solution was stirred for 60 min at 25° C. The resulting mixture was concentrated under vacuum. The crude product was purified by Prep-HPLC with the following conditions: Column, XBridge Prep C18 OBD Column, 19*150 mm 5 um; mobile phase, Water (10 MMOL/L NH$_4$HCO$_3$+0.1% NH$_3$.H$_2$O) and ACN (5.0% ACN up to 77.0% in 2 min, up to 80.0% in 5 min); Detector, UV 254/220 nm. This resulted in 60 mg (59%) of [(2R)-1-[(2E)-4-(dimethylamino)but-2-enoyl]pyrrolidin-2-yl]methylN-[(1R)-2-(1-benzofuran-3-yl)-1-[(1S,2S,6R,8S)-2,9,9-trimethyl-3,5-dioxa-4-boratricyclo[6.1.1.0ˆ[2,6]]decan-4-yl]ethyl]carbamate as a white solid after lyophilization.

Step 5

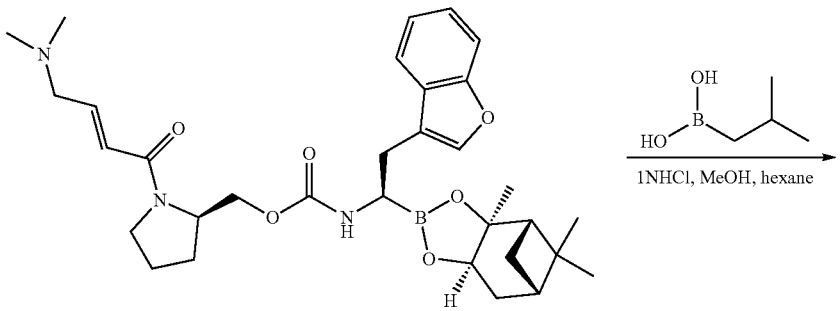

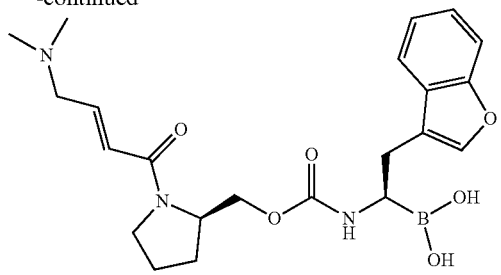

Into a 50-mL round-bottom flask purged and maintained with an inert atmosphere of nitrogen, was placed [(2R)-1-[(2E)-4-(dimethylamino)but-2-enoyl]pyrrolidin-2-yl]methyl N-[(1R)-2-(1-benzofuran-3-yl)-1-[(1S,2S,6R,8S)-2,9,9-trimethyl-3,5-dioxa-4-boratricyclo[6.1.1.0˚[2.6]]decan-4-yl]ethyl]carbamate (85 mg, 0.15 mmol, 1.00 eq.), methanol (3.7 mL), hexane (3.7 mL), (2-methylpropyl)boronic acid (43.6 mg, 0.43 mmol, 2.90 eq.), and 1N HCl (2.9 mL, 20.00 eq.). The resulting solution was stirred for 2 h at 25° C. The resulting mixture was washed with 3×4 mL of hexane. The methanol layer was diluted with 20 mL of $H_2O$, then dried over lyophilization to give a crude product which was purified by Prep-HPLC with the following conditions: Column, XBridge Prep C18 OBD Column, 19*150 mm 5 um; mobile phase, Water (10 MMOL/L $NH_4HCO_3$+0.1% $NH_3.H_2O$) and ACN (18.0% ACN up to 40.0% in 10 min); Detector, UV 220 nm. This resulted in 28.7 mg (44%) of [(1R)-2-(1-benzofuran-3-yl)-1-[([[(2R)-1-[(2E)-4-(dimethylamino)but-2-enoyl]pyrrolidin-2-yl]methoxy]carbonyl)amino]ethyl]boronic acid as a white solid after lyophilization again. LC-MS m/z: 444 (M+1).

Example 50

((R)-1-(((((R)-1-(2-cyano-4,4-dimethylpent-2-enoyl)piperidin-2-yl)methoxy)carbonyl)amino)-3-phenylpropyl)boronic acid

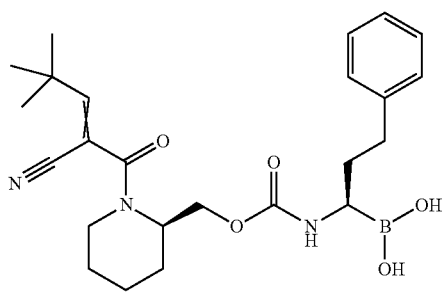 [SMILES: CC(C)(C)C=C(C#N)C(=O)N1CCCC[C@@H]1COC(=O)N[C@@H](CCc1ccccc1)B(O)O]

A suspension of 3-phenylpropanal (25 g, 186.5 mmol), (R)-2-methylpropane-2-sulfinamide (22.6 g, 186.5 mmol), $CuSO_4$ (135 g, 932 mmol) in DCM (300 mL) was stirred at rt under N2 overnight. The reaction was filtered through a silica pad and concentrated to provide 20 g of (R,E)-2-methyl-N-(3-phenylpropylidene)propane-2-sulfinamide. A solution of (R,E)-2-methyl-N-(3-phenylpropylidene)propane-2-sulfinamide (20 g, 84.3 mmol), bis(pinacolato)diboron (23.6 g, 93.8 mmol) and ICyCuOt-Bu (2 g) in benzene (150 mL) was stirred at it overnight. The reaction was filtered and concentrated to dryness to give a residue which solidified on cooling. The solid was collected, washed with petroleum ether to afford 22 g of (R)-2-methyl-N—((S)-3-phenyl-1-(4,4,5,5-tetramethyl-1,3,2-dioxaborolan-2-yl)propyl)propane-2-sulfinamide as a colorless solid.

A solution of compound (R)-2-methyl-N—((S)-3-phenyl-1-(4,4,5,5-tetramethyl-1,3,2-dioxaborolan-2-yl)propyl)propane-2-sulfinamid (22 g, 67 mmol) in 4M HCl/MTBE (150 mL) was stirred at 60° C. for 2 h. The reaction was cooled to give a suspension and filtered. The filter cake was triturated with MTBE and filtered to afford 12 g of (S)-3-phenyl-1-(4,4,5,5-tetramethyl-1,3,2-dioxaborolan-2-yl)propan-1-amine hydrochloride as a colorless solid.

Bis(trichloromethyl) carbonate (306 mg, 1.03 mmol) in DCM (1.5 mL) was added to a stirring solution of (R)-2-(2-(hydroxymethyl)piperidine-1-carbonyl)-4,4-dimethylpent-2-enenitrile (prepared as in example 24, 370 mg, 1.47 mmol) and DIPEA (1.14 g. 8.85 mmol) in DCM (8 mL) at −15° C. The mixture was stirred for 2 h below 0° C. and then added dropwise into a well-stirred solution of (R)-3-phenyl-1-(4,4,5,5-tetramethyl-1,3,2-dioxaborolan-2-yl)propan-1-amine hydrochloride (330 mg, 1.1 mmol) and DIPEA (570 mg, 4.42 mmol) in DCM (5 mL) at 0° C. The reaction was stirred at 0° C. for 1 h, then diluted with DCM (25 mL), washed with water (10 mL) and brine (10 mL), dried over $Na_2SO_4$, and concentrated in vacuo. The residue was dissolved in MeOH (4 mL)/1N HCl aq. (0.8 mL), stirred at rt for 2 h, then diluted with water (15 mL), and dried over lyophilization to give a crude product which was purified by preparative HPLC to afford (R)-1-((((R)-1-(2-cyano-4,4-dimethylpent-2-enoyl)piperidin-2-yl)methoxy)carbonylamino)-3-phenylpropylboronic acid as white solid (128 mg). LC-MS m/z: 478 (M+23).

Example 51

((R)-2-(benzofuran-3-yl)-1-(((((1S,2R,5R)-3-(2-cyano-4-methyl-4-morpholinopent-2-enoyl)-3-azabicyclo[3.1.0]hexan-2-yl)methoxy)carbonyl)amino)ethyl)boronic acid

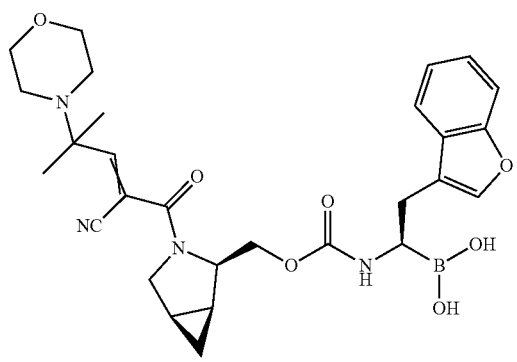 [SMILES: CC(C)(C=C(C#N)C(=O)N1C[C@@H]2C[C@@H]2[C@@H]1COC(=O)N[C@@H](Cc1coc2ccccc12)B(O)O)N1CCOCC1]

Step 1

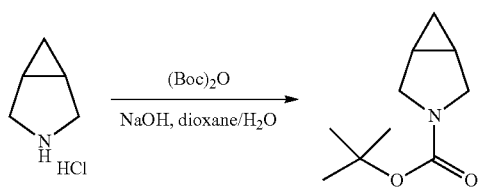

Into a 500-mL round-bottom flask, was placed a solution of 3-azabicyclo[3.1.0]hexane hydrochloride (5 g, 41.81 mmol, 1.00 eq.) in dioxane/H₂O (75/75 mL), and 1N NaOH (84 mL, 2.00 eq.), (Boc)₂O (14 g, 64.15 mmol, 1.50 eq.). The resulting solution was stirred overnight at rt. The resulting mixture was concentrated under vacuum. The resulting solution was extracted with 3×200 mL of petroleum ether and the organic layers combined and dried over anhydrous sodium sulfate and concentrated under vacuum. The residue was applied onto a silica gel column with ethyl acetate/petroleum ether (1:50). This resulted in 6 g (70%) of tert-butyl 3-azabicyclo[3.1.0]hexane-3-carboxylate as light yellow oil.

Step 2

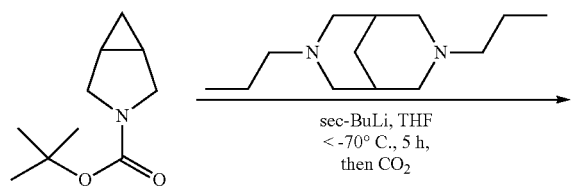

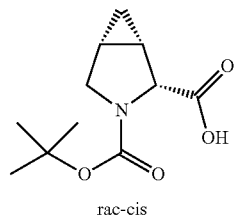

Into a 250-mL 3-necked round-bottom flask, was placed a solution of tert-butyl 3-azabicyclo[3.1.0]hexane-3-carboxylate (4.75 g, 25.92 mmol, 1.00 eq.) in tetrahydrofuran (104 mL), and 3,7-dipropyl-3,7-diazabicyclo[3.3.1]nonane (6.81 g, 32.37 mmol, 1.25 eq.). This was followed by the addition of sec-BuLi (24 mL, 1.20 eq.) dropwise with stirring at −60° C. To this was added dry ice (1 g, 1.00 eq.) at −68° C. The resulting solution was stirred for 1 h at −45° C. The reaction was then quenched by the addition of 60 mL of H₂O. The resulting mixture was concentrated under vacuum. The resulting solution was extracted with 2×60 mL of MTBE and the aqueous layers combined. The pH value of the solution was adjusted to 2-3 with KHSO₄ (25% g/mL). The resulting solution was extracted with 3×80 mL of MTBE and the organic layers combined and dried over sodium sulfate and concentrated under vacuum. This resulted in 3.9 g (66%) of rac-cis(1S,2R,5R)-3-[(tert-butoxy)carbonyl]-3-azabicyclo[3.1.0]hexane-2-carboxylic acid as a colorless oil.

Step 3

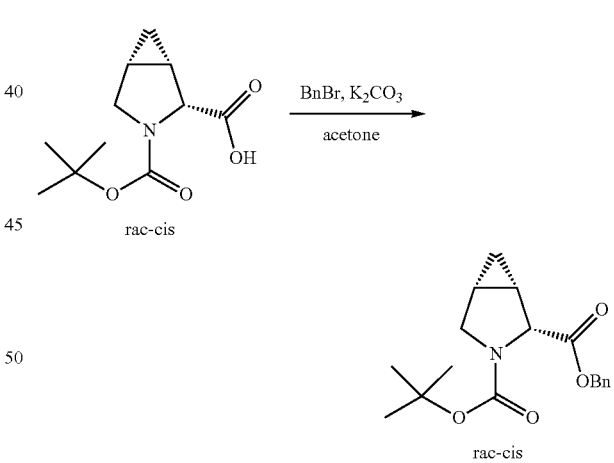

Into a 100-mL round-bottom flask, was placed a solution of rac-cis-(1S,2R,5R)-3-[(tert-butoxy)carbonyl]-3-azabicyclo[3.1.0]hexane-2-carboxylic acid (2 g, 8.80 mmol. 1.00 eq.) in acetone (40 mL), BnBr (1.5 g. 8.77 mmol. 1.00 eq.), and potassium carbonate (1.5 g, 10.85 mmol, 1.25 eq.). The resulting solution was stirred overnight at rt. The solids were filtered out. The resulting mixture was concentrated under vacuum. The residue was applied onto a silica gel column with ethyl acetate/petroleum ether (2:98-5:95). This resulted in 2 g (72%) of rac-cis-2-benzyl 3-tert-butyl (1S,2R,5R)-3-azabicyclo[3.1.0]hexane-2,3-dicarboxylate as a yellow oil.

Step 4

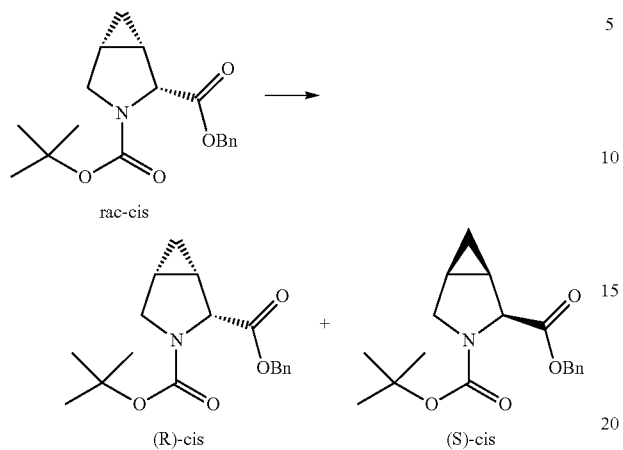

The product rac-cis-2-benzyl 3-tert-butyl (1S,2R,5R)-3-azabicyclo[3.1.0]hexane-2,3-dicarboxylate (1 g) was separated by Chiral-Prep-HPLC with the following conditions: Column, CHIRAL ART Cellulose-SB, 2*25 cm, 5 um; mobile phase, Hex- and ethanol- (hold 7.0% ethanol- in 13 min); Detector, UV 220/254 nm. This resulted in 400 mg (40%) of (R)-cis-2-benzyl 3-tert-butyl (1S,2R,5R)-3-azabicyclo[3.1.0]hexane-2,3-dicarboxylate as a colorless oil ($[\alpha]_{25°\ C.}^{589\ nm}$=103.2 (C 0.5, MeOH)) and 400 mg (40%) of (S)-cis-2-benzyl 3-tert-butyl (1R,2S,5S)-3-azabicyclo[3.1.0]hexane-2,3-dicarboxylate as a colorless oil ($[\alpha]_{25°\ C.}^{589\ nm}$=−120.8 (C 0.5. MeOH)).

Step 5

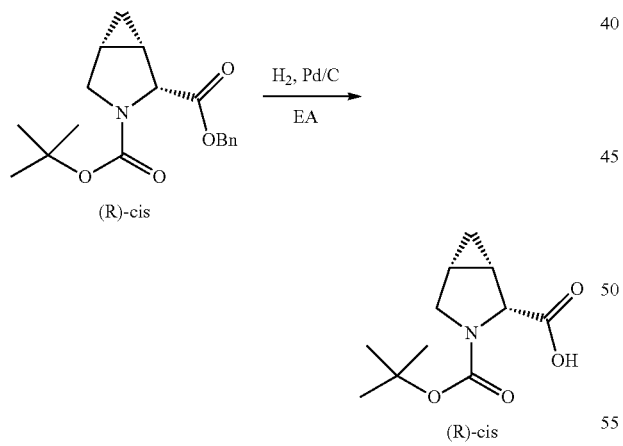

Into a 50-mL round-bottom flask, was placed a solution of (R)-cis-2-benzyl 3-tert-butyl (1S,2R,5R)-3-azabicyclo[3.1.0]hexane-2,3-dicarboxylate (500 mg, 1.58 mmol, 1.00 eq.) in ethyl acetate (6 mL), and palladium carbon (500 mg. 1.00 eq.). To the mixture was introduced in $H_2$. The resulting solution was stirred for 3 h at it. The solids were filtered out. The resulting mixture was concentrated under vacuum. This resulted in 350 mg (98%) of (R)-cis-(1S,2R,5R)-3-[(tert-butoxy)carbonyl]-3-azabicyclo[3.1.0]hexane-2-carboxylic acid as a colorless oil.

Step 6

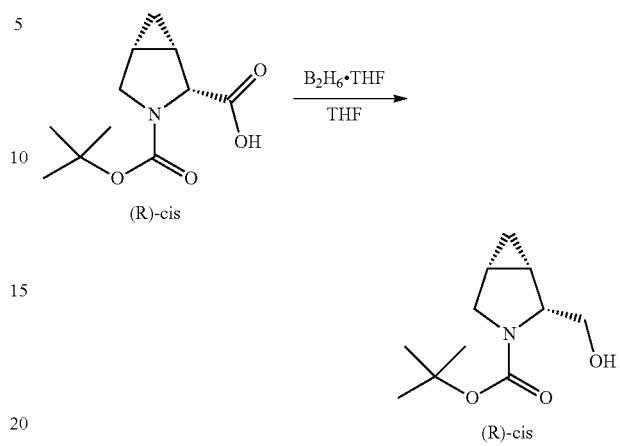

Into a 50-mL round-bottom flask purged and maintained with an inert atmosphere of nitrogen, was placed a solution of (R)-cis-(1 S,2R,5R)-3-[(tert-butoxy)carbonyl]-3-azabicyclo[3.1.0]hexane-2-carboxylic acid (350 mg, 1.54 mmol, 1.00 eq.) in tetrahydrofuran (8 mL). This was followed by the addition of $B_2H_6$·THF (1.9 mL, 1.25 eq., 1M) dropwise with stirring at 0° C. The resulting solution was stirred overnight at rt. The reaction was then quenched by the addition of 10 mL of $NH_4Cl$. The resulting solution was extracted with 2×20 mL of ethyl acetate and the organic layers combined. The resulting mixture was washed with 1×10 mL of brine. The resulting mixture was washed with 1×10 mL of $H_2O$. The mixture was dried over anhydrous sodium sulfate and concentrated under vacuum. The residue was applied onto a silica gel column with ethyl acetate/petroleum ether (1:10). This resulted in 260 mg (79%) of (R)-cis-tert-butyl(1S,2R,5R)-2-(hydroxymethyl)-3-azabicyclo[3.1.0]hexane-3-carboxylate as a colorless oil.

Step 7

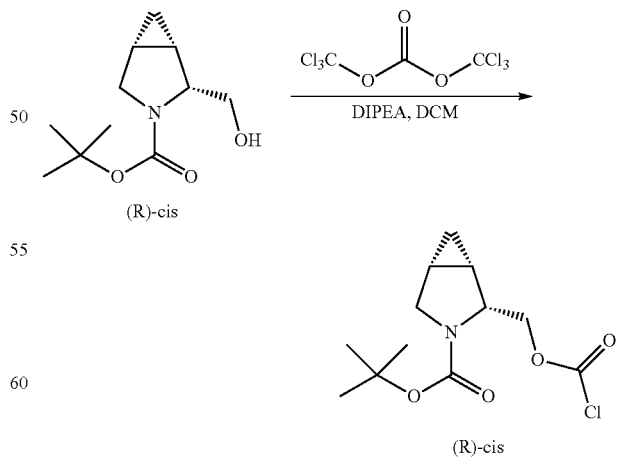

Into a 50-mL 3-necked round-bottom flask, was placed a solution of (R)-cis-tert-butyl (1S,2R,5R)-2-(hydroxymethyl)-3-azabicyclo[3.1.0]hexane-3-carboxylate (260 mg, 1.22 mmol, 1.00 eq.) in dichloromethane (5 mL), and DIEA (472 mg, 3.65 mmol, 3.00 eq.). This was followed by the addition of a solution of ditrichloromethyl carbonate (180 mg, 0.61 mmol, 0.50 eq.) in dichloromethane (2 mL) dropwise with stirring at 0° C. The resulting solution was stirred for 2.5 h at 0° C. The resulted solution was to be used directly with the next step.

Step 8

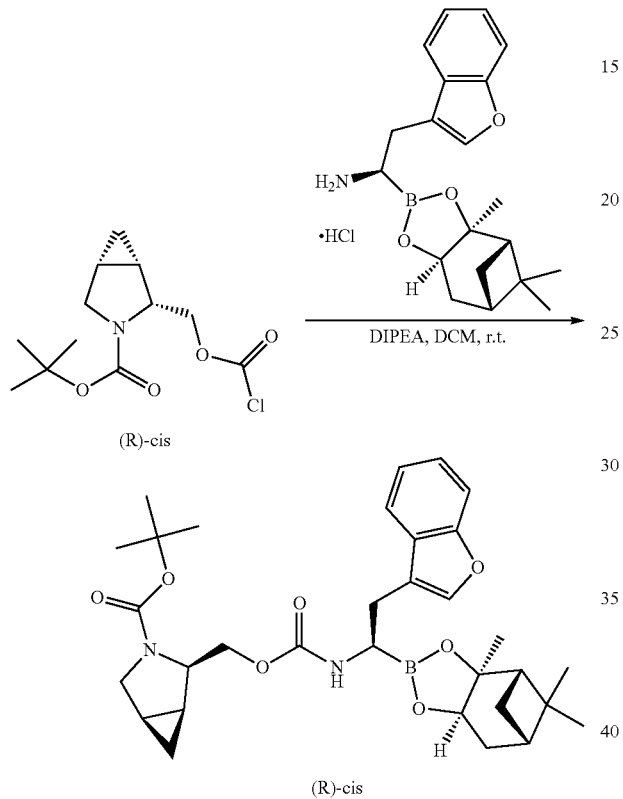

Into a 50-mL round-bottom flask, was placed a solution of (1R)-2-(1-benzofuran-3-yl)-1-[(S,2S,6R,8S)-2,9,9-trimethyl-3,5-dioxa-4-boratricyclo[6.1.1.0^2,6]decan-4-yl]ethan-1-amine hydrochloride (209 mg, 0.56 mmol, 0.85 eq.) in dichloromethane (5 mL), and DIPEA (170 mg, 1.32 mmol, 2.00 eq.). This was followed by the addition of a solution of (R)-cis-tert-butyl (1S,2R,5R)-2-[[(chlorocarbonyl)oxy]methyl]-3-azabicyclo[3.1.0]hexane-3-carboxylate (180 mg, 0.65 mmol, 1.00 eq.) in dichloromethane (3 mL) dropwise with stirring at 0° C. The resulting solution was stirred for 1 h at rt. The resulting mixture was washed with 1×10 mL of brine. The mixture was dried over anhydrous sodium sulfate and concentrated under vacuum. The residue was applied onto a silica gel column with ethyl acetate/petroleum ether (10:90). This resulted in 220 mg (60%) of (R)-cis-tert-butyl (1S,2R,5R)-2-[([[(1R)-2-(1-benzofuran-3-yl)-1-[(1S,6R,8S)-9,9-dimethyl-3,5-dioxa-4-boratricyclo[6.1.1.0^[2,6]]decan-4-yl]ethyl]carbamoyl]oxy)methyl]-3-azabicyclo[3.1.0]hexane-3-carboxylate as a yellow oil.

Step 9

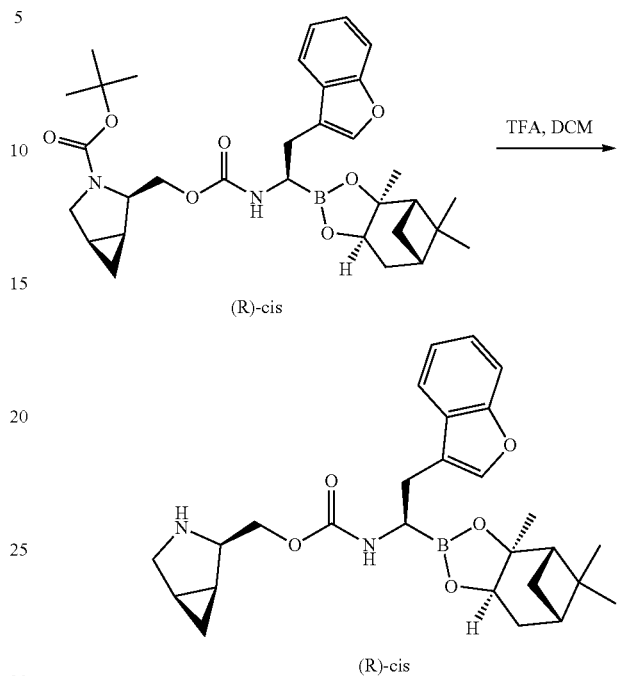

Into a 50-mL round-bottom flask, was placed a solution of (R)-cis-tert-butyl (1S,2R,5R)-2-[([[(1R)-2-(1-benzofuran-3-yl)-1-[(1S,2S,6R,8S)-2,9,9-trimethyl-3,5-dioxa-4-boratricyclo[6.1.1.0^[2,6]]decan-4-yl]ethyl]carbamoyl]oxy)methyl]-3-azabicyclo[3.1.0]hexane-3-carboxylate (220 mg, 0.38 mmol, 1.00 eq.) in dichloromethane (4 mL), and trifluoroacetic acid (1 mL). The resulting solution was stirred for 2 h at rt. The resulting mixture was concentrated under vacuum. This resulted in 180 mg (crude) of (R)-cis-(1S,2R,5R)-3-azabicyclo[3.1.0]hexan-2-ylmethyl N-[(1R)-2-(1-benzofuran-3-yl)-1-[(1S,2S,6R,8S)-2,9,9-trimethyl-3,5-dioxa-4-boratricyclo[6.1.1.0^[2,6]]decan-4-yl]ethyl]carbamate as a yellow oil.

Step 10

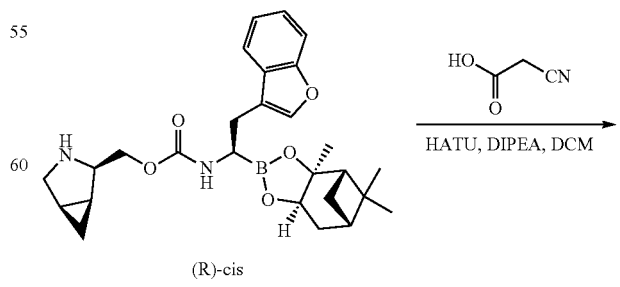

-continued

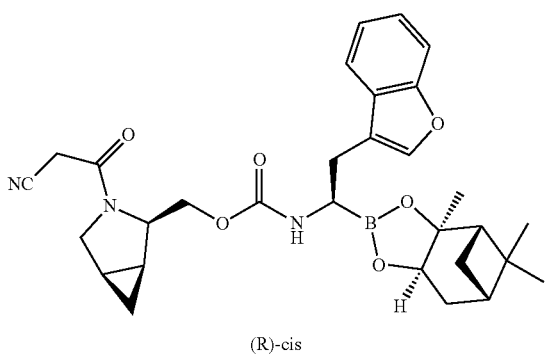

(R)-cis

Into a 50-mL round-bottom flask, was placed a solution of (1S,2R,5R)-3-azabicyclo[3.1.0]hexan-2-ylmethyl N-[(1R)-2-(1-benzofuran-3-yl)-1-[(1S,2S,6R,8S)-2,9,9-trimethyl-3,5-dioxa-4-boratricyclo[6.1.1.0^[2,6]]decan-4-yl]ethyl]carbamate (180 mg, 0.38 mmol, 1.00 eq.) in dichloromethane (2 mL), DIPEA (146 mg, 1.13 mmol, 3.00 eq.), 2-cyanoacetic acid (50 mg, 0.59 mmol, 1.50 eq.), and HATU (216 mg, 0.57 mmol, 1.50 eq.). The resulting solution was stirred for 2 h at rt. The resulting solution was diluted with 10 mL of DCM. The resulting mixture was washed with 1×10 mL of brine. The mixture was dried over anhydrous sodium sulfate and concentrated under vacuum. The residue was applied onto a silica gel column with ethyl acetate/petroleum ether (40:60). This resulted in 140 mg (68%) of [(1S,2R,5R)-3-(2-cyanoacetyl)-3-azabicyclo[3.1.0]hexan-2-yl]methyl N-[(1R)-2-(1-benzofuran-3-yl)-1-[(1S,2S,6R,8S)-2,9,9-trimethyl-3,5-dioxa-4-boratricyclo[6.1.1.0^[2,6]]decan-4-yl]ethyl]carbamate as a yellow oil.

Step 11

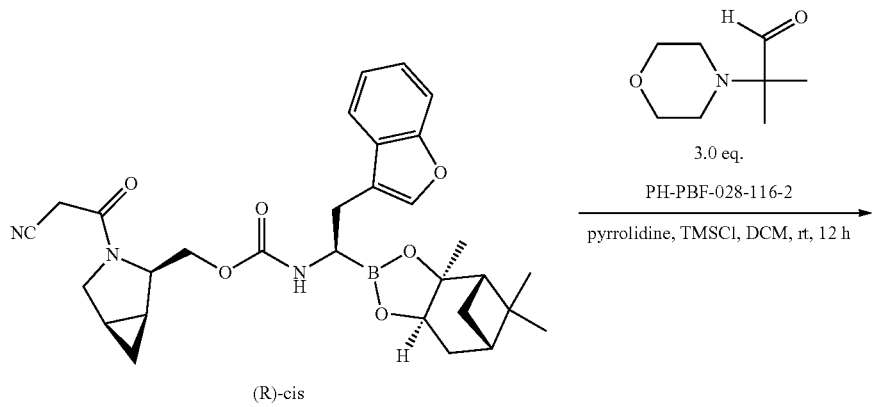

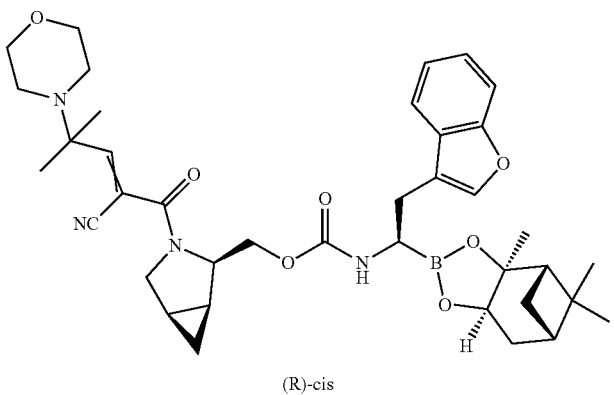

(R)-cis

Into a 50-mL round-bottom flask, was placed a solution of [(1S,2R,5R)-3-(2-cyanoacetyl)-3-azabicyclo[3.1.0]hexan-2-yl]methyl N-[(1R)-2-(1-benzofuran-3-yl)-1-[(1S,2S,6R,8S)-2,9,9-trimethyl-3,5-dioxa-4-boratricyclo[6.1.1.0ˆ[2,6]]decan-4-yl]ethyl]carbamate (80 mg, 0.15 mmol, 1.00 eq.) in dichloromethane (2 mL), 2-methyl-2-(morpholin-4-yl)propanal (70 mg, 0.45 mmol, 3.00 eq.), pyrrolidine (52 mg, 0.73 mmol, 5.00 eq.), and TMSCl (80 mg, 0.74 mmol, 5.00 eq.). The resulting solution was stirred for 2 h at rt. The resulting solution was diluted with 10 mL of DCM. The resulting mixture was washed with 1×10 mL of brine. The mixture was dried over anhydrous sodium sulfate and concentrated under vacuum. The crude product was purified by Prep-HPLC with the following conditions: Column, XBridge Prep C18 OBD Column. 19*150 mm 5 um; mobile phase, Water (10 MMOL/L NH$_4$HCO$_3$+0.1% NH$_3$.H$_2$O) and ACN (62% ACN up to 87% in 7 min); Detector, UV 254/220 nm. This resulted in 40 mg (40%) of [(1S,2R,5R)-3-[2-cyano-2-[2-methyl-2-(morpholin-4-yl)propylidene]acetyl]-3-azabicyclo[3.1.0]hexan-2-yl]methyl N-[(1R)-2-(1-benzofuran-3-yl)-1-[(1S,2S,6R,8S)-2,9,9-trimethyl-3,5-dioxa-4-boratricyclo[6.1.1.0[2,6]]decan-4-yl]ethyl]carbamate as a white solid after lyophilization.

Step 12

Into a 100-mL round-bottom flask, was placed a solution of [(1S,2R,5R)-3-[2-cyano-2-[2-methyl-2-(morpholin-4-yl)propylidene]acetyl-3-azabicyclo[3.1.0]hexan-2-yl]methyl N-[(1R)-2-(1-benzofuran-3-yl)-1-[(1S,2S,6R,8S)-2,9,9-trimethyl-3,5-dioxa-4-boratricyclo[6.1.1.0ˆ[2,6]]decan-4-yl]ethyl]carbamate (50 mg, 0.07 mmol, 1.00 eq.) in methanol/hexane (2/2 mL), 1N HCl (1.5 mL, 20.00 eq.), and (2-methylpropyl)boronic acid (23 mg, 0.23 mmol, 3.00 eq.). The resulting solution was stirred for 3 h at it. The hexane layer was discarded. The methanol layer was diluted with H$_2$O (10 mL), then dried over lyophilization. The crude product was purified by Prep-HPLC with the following conditions: Column, XBridge Prep C18 OBD Column, 19*150 mm 5 um; mobile phase, Water (10 MMOL/L NH$_4$HCO$_5$+0.1% NH$_3$.H$_2$O) and ACN (30.0% ACN up to 45.0% in 7 min); Detector, UV 254/220 nm. This resulted in 18.5 mg (45%) of [(1R)-2-(1-benzofuran-3-yl)-1-[([[(1S,2R,5R)-3-[2-cyano-2-[2-methyl-2-(morpholin-4-yl)propylidene]acetyl]-3-azabicyclo[3.1.0]hexan-2-yl]methoxy]carbonyl)amino]ethyl]boronic acid as a white solid after lyophilization again. LC-MS m/z: 551 (M+1).

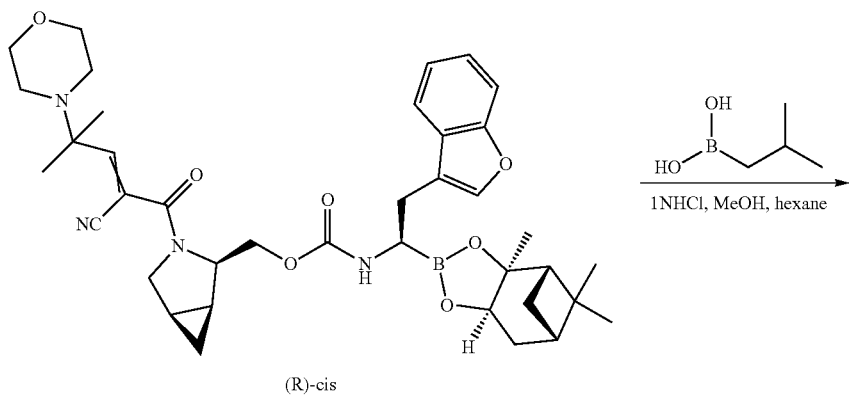

(R)-cis

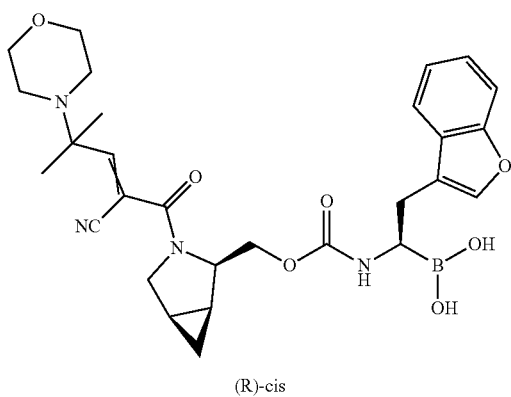

(R)-cis

Example 52

((R)-1-(((((1S,2R,5R)-3-acryloyl-3-azabicyclo[3.1.0]hexan-2-yl)methoxy)carbonyl)amino)-2-(benzofuran-3-yl)ethyl)boronic acid

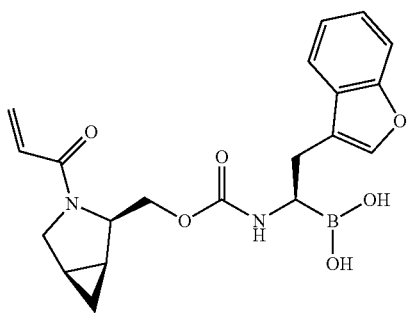 [SMILES: C=CC(=O)N1C[C@@H]2C[C@@H]2[C@@H]1COC(=O)N[C@@H](Cc1coc2ccccc12)B(O)O]

Step 1

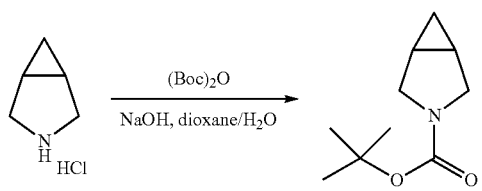

Into a 500-mL round-bottom flask, was placed a solution of 3-azabicyclo[3.1.0]hexane hydrochloride (5 g, 41.81 mmol. 1.00 eq.) in dioxane/H₂O (75/75 mL), 1N NaOH (84 mL, 2.00 eq.), and (Boc)₂O (14 g, 64.15 mmol, 1.50 eq.). The resulting solution was stirred overnight at it. The resulting mixture was concentrated under vacuum. The resulting solution was extracted with 3×200 mL of petroleum ether and the organic layers combined and dried over anhydrous sodium sulfate and concentrated under vacuum. The residue was applied onto a silica gel column with ethyl acetate/petroleum ether (1:50). This resulted in 6 g (70%) of tert-butyl 3-azabicyclo[3.1.0]hexane-3-carboxylate as a light yellow oil.

Step 2

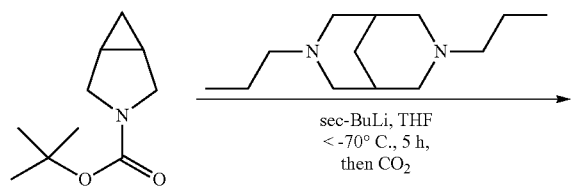

Into a 250-mL 3-necked round-bottom flask, was placed a solution of tert-butyl 3-azabicyclo[3.1.0]hexane-3-carboxylate (4.75 g, 25.92 mmol, 1.00 eq.) in tetrahydrofuran (104 mL), 3,7-dipropyl-3,7-diazabicyclo[3.3.1]nonane (6.81 g, 32.37 mmol, 1.25 eq.). This was followed by the addition of sec-BuLi (24 mL, 1.20 eq.) dropwise with stirring at −60° C. To this was added dry ice (1 g, 1.00 eq.) at −68° C. The resulting solution was stirred for 1h at −45° C. The reaction was then quenched by the addition of 60 mL of H₂O. The resulting mixture was concentrated under vacuum. The resulting solution was extracted with 2×60 mL of MTBE and the aqueous layers combined. The pH value of the solution was adjusted to 2-3 with KHSO₄ (25% g/mL). The resulting solution was extracted with 3×80 mL of MTBE and the organic layers combined and dried over sodium sulfate and concentrated under vacuum. This resulted in 3.9 g (66%) of rac-cis(1S,2R,5R)-3-[(tert-butoxy)carbonyl]-3-azabicyclo[3.1.0]hexane-2-carboxylic acid as a colorless oil.

Step 3

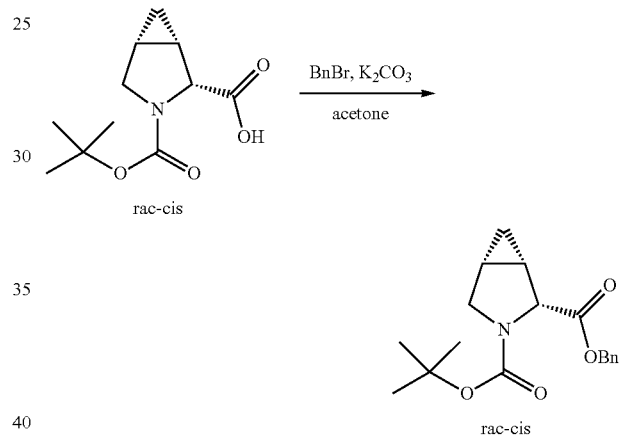

Into a 100-mL round-bottom flask, was placed a solution of rac-cis-(1S,2R,5R)-3-[(tert-butoxy)carbonyl]-3-azabicyclo[3.1.0]hexane-2-carboxylic acid (2 g, 8.80 mmol, 1.00 eq.) in acetone (40 mL), BnBr (1.5 g, 8.77 mmol, 1.00 eq.), and potassium carbonate (1.5 g, 10.85 mmol, 1.25 eq.). The resulting solution was stirred overnight at it. The solids were filtered out. The resulting mixture was concentrated under vacuum. The residue was applied onto a silica gel column with ethyl acetate/petroleum ether (2:98-5:95). This resulted in 2 g (72%) of rac-cis-2-benzyl 3-tert-butyl (1S,2R,5R)-3-azabicyclo[3.1.0]hexane-2,3-dicarboxylate as a yellow oil.

Step 4

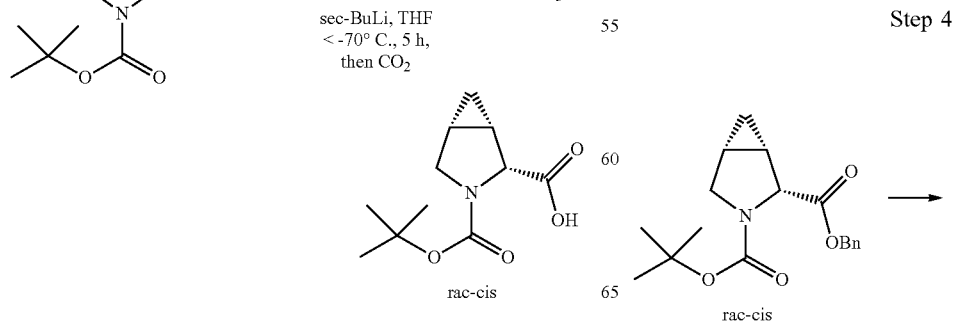

-continued

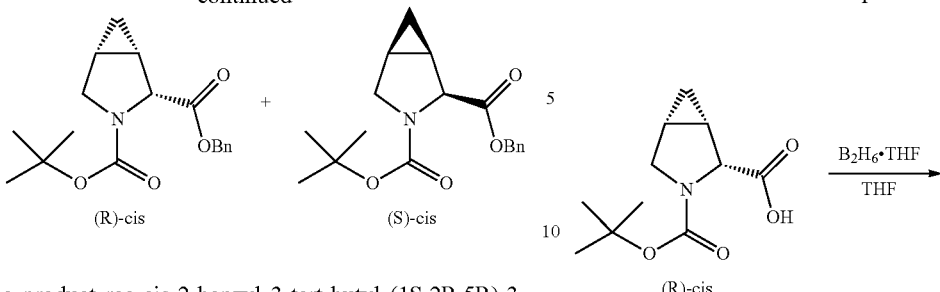

The product rac-cis-2-benzyl 3-tert-butyl (1S,2R,5R)-3-azabicyclo[3.1.0]hexane-2,3-dicarboxylate (1 g) was separated by Chiral-Prep-HPLC with the following conditions: Column, CHIRAL ART Cellulose-SB, 2*25 cm, 5 um; mobile phase, Hex- and ethanol- (hold 7.0% ethanol- in 13 min); Detector, UV 220/254 nm. This resulted in 400 mg (40%) of (R)-cis-2-benzyl 3-tert-butyl (1S,2R,5R)-3-azabicyclo[3.1.0]hexane-2,3-dicarboxylate as a colorless oil ($[\alpha]_{25°\ C.}^{589\ nm}$=103.2 (C 0.5, MeOH)) and 400 mg (40%) of (S)-cis-2-benzyl 3-tert-butyl (1R,2S,5S)-3-azabicyclo[3.1.0]hexane-2,3-dicarboxylate as a colorless oil ($[\alpha]_{25°\ C.}^{589\ nm}$=−120.8 (C 0.5, MeOH)).

Step 5

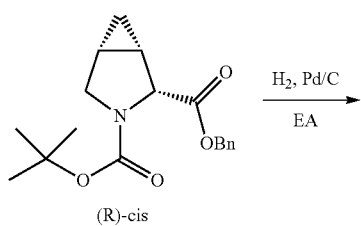

Into a 50-mL round-bottom flask, was placed a solution of (R)-cis-2-benzyl 3-tert-butyl (1S,2R,5R)-3-azabicyclo[3.1.0]hexane-2,3-dicarboxylate (500 mg, 1.58 mmol, 1.00 eq.) in ethyl acetate (6 mL), and palladium carbon (500 mg, 1.00 eq.). To the mixture was introduced in H₂. The resulting solution was stirred for 3 h at rt. The solids were filtered out. The resulting mixture was concentrated under vacuum. This resulted in 350 mg (98%) of (R)-cis-(1S,2R,5R)-3-[(tert-butoxy)carbonyl]-3-azabicyclo[3.1.0]hexane-2-carboxylic acid as a colorless oil.

Step 6

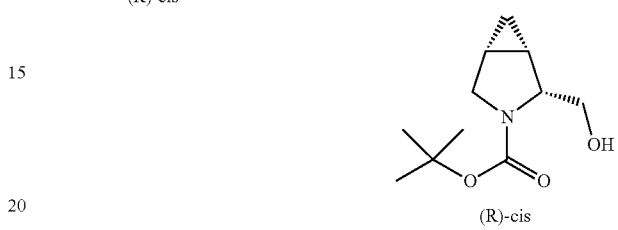

Into a 50-mL round-bottom flask purged and maintained with an inert atmosphere of nitrogen, was placed a solution of (R)-cis-(1S,2R,5R)-3-[(tert-butoxy)carbonyl]-3-azabicyclo[3.1.0]hexane-2-carboxylic acid (350 mg, 1.54 mmol, 1.00 eq.) in tetrahydrofuran (8 mL). This was followed by the addition of B₂H₆.THF (1.9 mL, 1.25 eq., 1M) dropwise with stirring at 0° C. The resulting solution was stirred overnight at rt. The reaction was then quenched by the addition of 10 mL of NH₄Cl. The resulting solution was extracted with 2×20 mL of ethyl acetate and the organic layers combined. The resulting mixture was washed with 1×10 mL of brine. The resulting mixture was washed with 1×10 mL of H₂O. The mixture was dried over anhydrous sodium sulfate and concentrated under vacuum. The residue was applied onto a silica gel column with ethyl acetate/petroleum ether (1:10). This resulted in 260 mg (79%) of (R)-cis-tert-butyl(1S,2R,5R)-2-(hydroxymethyl)-3-azabicyclo[3.1.0]hexane-3-carboxylate as a colorless oil.

Step 7

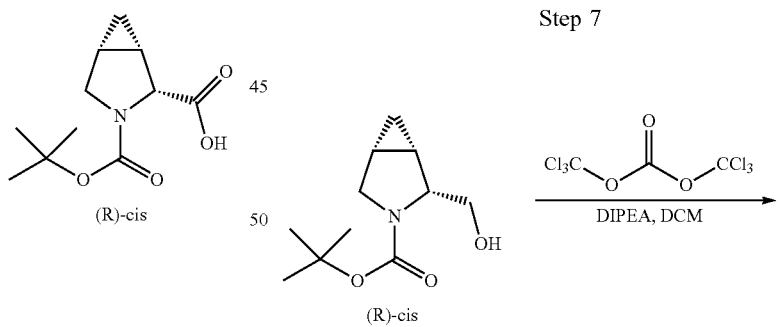

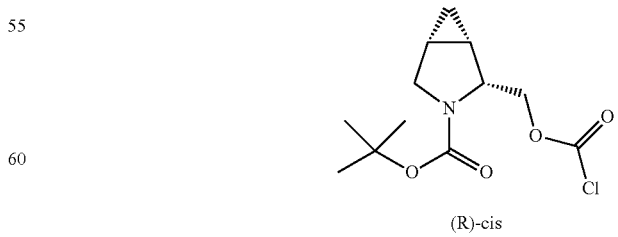

Into a 50-mL 3-necked round-bottom flask, was placed a solution of (R)-cis-tert-butyl (1S,2R,5R)-2-(hydroxymethyl)-3-azabicyclo[3.1.0]hexane-3-carboxylate (260 mg, 1.22 mmol, 1.00 eq.) in dichloromethane (5 mL), and DIEA (472 mg, 3.65 mmol, 3.00 eq.). This was followed by the addition of a solution of ditrichloromethyl carbonate (180 mg, 0.61 mmol, 0.50 eq.) in dichloromethane (2 mL) dropwise with stirring at 0° C. The resulting solution was stirred for 2.5 h at 0° C. The resulted solution was to be used directly with the next step.

Step 8

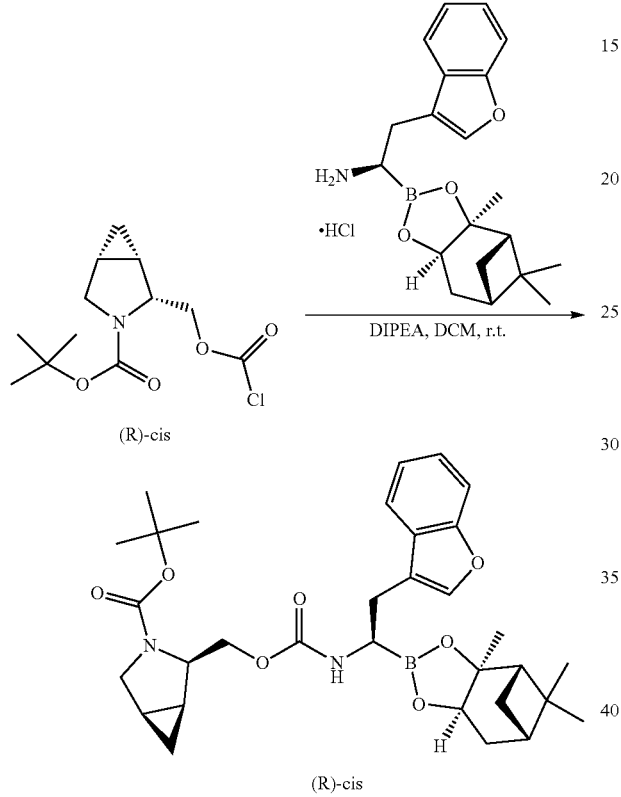

(R)-cis

Into a 50-mL round-bottom flask, was placed a solution of (1R)-2-(1-benzofuran-3-yl)-1-[(1S,2S,6R,8S)-2,9,9-trimethyl-3,5-dioxa-4-boratricyclo[6.1.1.0^2,6]decan-4-yl]ethan-1-amine hydrochloride (209 mg, 0.56 mmol, 0.85 eq.) in dichloromethane (5 mL), and DIPEA (170 mg, 1.32 mmol, 2.00 eq.). This was followed by the addition of a solution of (R)-cis-tert-butyl (1S,2R,5R)-2-[[(chlorocarbonyl)oxy]methyl]-3-azabicyclo[3.1.0]hexane-3-carboxylate (180 mg, 0.65 mmol, 1.00 eq.) in dichloromethane (3 mL) dropwise with stirring at 0° C. The resulting solution was stirred for 1 h at rt. The resulting mixture was washed with 1×10 mL of brine. The mixture was dried over anhydrous sodium sulfate and concentrated under vacuum. The residue was applied onto a silica gel column with ethyl acetate/petroleum ether (10:90). This resulted in 220 mg (60%) of (R)-cis-tert-butyl (1S,2R,5R)-2-[([[(1R)-2-(1-benzofuran-3-yl)-1-[(1S,6R,8S)-9,9-dimethyl-3,5-dioxa-4-boratricyclo[6.1.1.0^[2,6]]decan-4-yl]ethyl]carbamoyl]oxy)methyl]-3-azabicyclo[3.1.0]hexane-3-carboxylate as a yellow oil.

Step 9

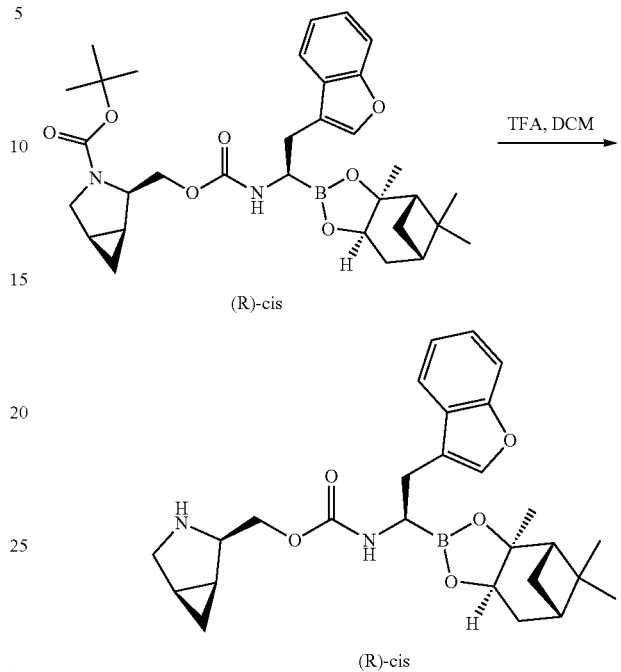

Into a 50-mL round-bottom flask, was placed a solution of (R)-cis-tert-butyl (1S,2R,5R)-2-[([[(1R)-2-(1-benzofuran-3-yl)-1-[(1S,2S,6R,8S)-2,9,9-trimethyl-3,5-dioxa-4-boratricyclo[6.1.1.0^[2,6]]decan-4-yl]ethyl]carbamoyl]oxy)methyl]-3-azabicyclo[3.1.0]hexane-3-carboxylate (220 mg, 0.38 mmol, 1.00 eq.) in dichloromethane (4 mL), and trifluoroacetic acid (1 mL). The resulting solution was stirred for 2 h at rt. The resulting mixture was concentrated under vacuum. This resulted in 180 mg (crude) of (R)-cis-(1S,2R,5R)-3-azabicyclo[3.1.0]hexan-2-ylmethyl N-[(1R)-2-(1-benzofuran-3-yl)-1-[(1S,2S,6R,8S)-2,9,9-trimethyl-3,5-dioxa-4-boratricyclo[6.1.1.0^[2,6]]decan-4-yl]ethyl]carbamate as a yellow oil.

Step 10

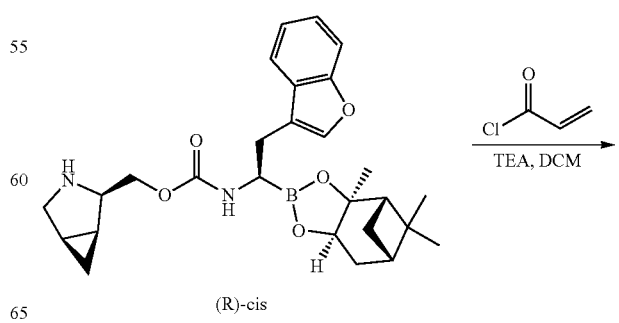

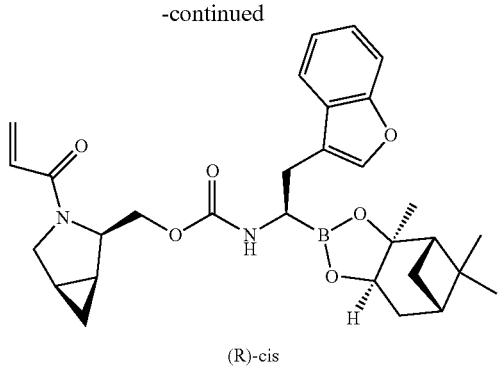

(R)-cis

Into a 50-mL round-bottom flask, was placed a solution of (R)-cis-(1S,2R,5R)-3-azabicyclo[3.1.0]hexan-2-ylmethyl N-[(1R)-2-(1-benzofuran-3-yl)-1-[(1S,2S,6R,8S)-2,9,9-trimethyl-3,5-dioxa-4-boratricyclo[6.1.1.0ˆ[2,6]]decan-4-yl]ethyl]carbamate (140 mg, 0.29 mmol, 1.00 eq.) in dichloromethane (3 mL), TEA (89 mg, 0.88 mmol, 3.00 eq.), and prop-2-enoyl chloride (32 mg, 0.35 mmol, 1.20 eq.). The resulting solution was stirred for 1 h at rt. The resulting solution was diluted with 10 mL of DCM. The resulting mixture was washed with 1×10 mL of brine. The mixture was dried over anhydrous sodium sulfate and concentrated under vacuum. The crude product was purified by Prep-HPLC with the following conditions: Column, XBridge Shield RP 18 OBD Column, 5 um, 19*150 mm, mobile phase, Water (10 MMOL/L NH$_4$HCO$_5$+0.1% NH$_3$.H$_2$O) and ACN (56.0% ACN up to 69.0% in 8 min); Detector, UV 254/220 nm. This resulted in 40 mg (26%) of (R)-cis-[(1S,2R,5R)-3-(prop-2-enoyl)-3-azabicyclo[3.1.0]hexan-2-yl]methyl N-[(1R)-2-(1-benzofuran-3-yl)-1-[(1S,2S,6R,8S)-2,9,9-trimethyl-3,5-dioxa-4-borantricyclo[6.1.1.0ˆ[2,6]]decan-4-yl]ethyl]carbamate as a white solid after lyophilization.

Step 11

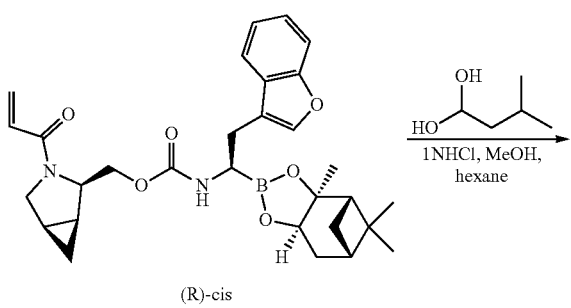

(R)-cis

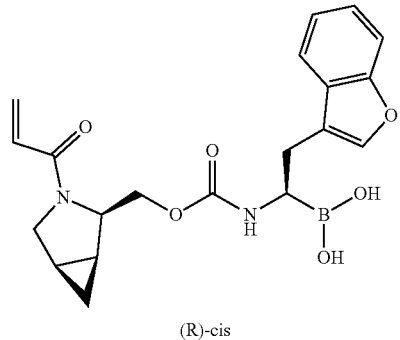

(R)-cis

Into a 100-mL round-bottom flask, was placed a solution of [(1S,2R,5R)-3-(prop-2-enoyl)-3-azabicyclo[3.1.0]hexan-2-yl]methyl N-[(1R)-2-(1-benzofuran-3-yl)-1-[(1S,2S,6R,8S)-2,9,9-trimethyl-3,5-dioxa-4-boratricyclo[6.1.1.0ˆ[2,6]] decan-4-yl]ethyl]carbamate (50 mg, 0.09 mmol, 1.00 eq.) in methanol/hexane (2/2 mL), 1N HCl (1.8 mL, 20.00 eq.), and (2-methylpropyl)boronic acid (29 mg, 0.28 mmol, 3.00 eq.). The resulting solution was stirred for 3 h at it. The hexane layer was discarded. The methanol was diluted with water (10 mL), then dried over lyophilization. The crude product was purified by Prep-HPLC with the following conditions: Column, XBridge Prep C18 OBD Column, 19*150 mm 5 um; mobile phase, Water (10 MMOL/L NH$_4$HCO$_3$+0.1% NH$_3$.H$_2$O) and ACN (22.0% ACN up to 35.0% in 7 min); Detector, UV 254/220 nm. This resulted in 23.6 mg (60%) of [(1R)-2-(1-benzofuran-3-yl)-1-[([[(1S,2R,5R)-3-(prop-2-enoyl)-3-azabicyclo[3.1.0]hexan-2-yl]methoxy]carbonyl) amino]ethyl]boronic acid as a white solid after lyophilization again. LC-MS m/z: 421 (M+23).

Example 53

((R)-1-(((((R)-1-(4-(4-acetylpiperazin-1-yl)-2-cyano-4-methylpent-2-enoyl)pyrrolidin-2-yl)methoxy)carbonyl)amino)-2-(benzofuran-3-yl)ethyl)boronic acid

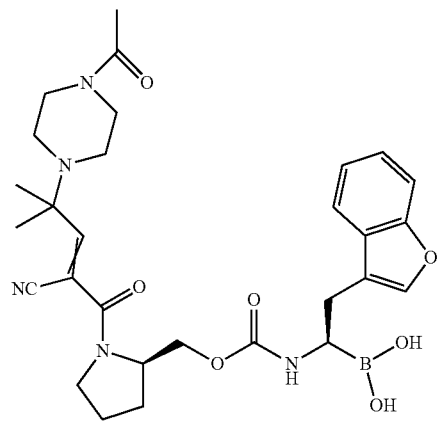 [SMILES: CC(=O)N1CCN(C(C)(C)C=C(C#N)C(=O)N2CCC[C@@H]2COC(=O)N[C@@H](Cc2coc3ccccc23)B(O)O)CC1]

The title compound was prepared as in example 40 by replacing morpholine with 4-acyl piperazine. LC-MS m/z: 580 (M+1).

Example 54

((R)-2-(benzofuran-3-yl)-1-(((((1S,2R,5R)-3-(2-cyano-4-(3,3-difluoropyrrolidin-1-yl)-4-methylpent-2-enoyl)-3-azabicyclo[3.1.0]hexan-2-yl)methoxy)carbonyl)amino)ethyl)boronic acid

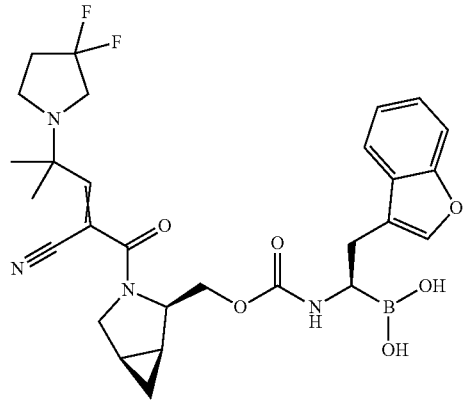 [SMILES: CC(C)(C=C(C#N)C(=O)N1C[C@@H]2C[C@@H]2[C@@H]1COC(=O)N[C@@H](Cc1coc2ccccc12)B(O)O)N1CCC(F)(F)C1]

The title compound was prepared as in example 51 by replacing morpholine with 3,3-difluoropyrrolidine. LC-MS m/z: 571 (M+1).

Example 55

((R)-2-(benzofuran-3-yl)-1-(((((R)-1-(2-cyano-4-methyl-4-(4-methylpiperazin-1-yl)pent-2-enoyl)pyrrolidin-2-yl)methoxy)carbonyl)amino)ethyl)boronic acid

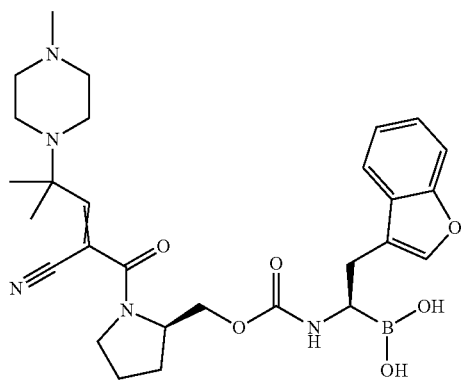 [SMILES: CN1CCN(C(C)(C)C=C(C#N)C(=O)N2CCC[C@@H]2COC(=O)N[C@@H](Cc2coc3ccccc23)B(O)O)CC1]

The title compound was prepared as in example 40 by replacing morpholine with 1-methylpiperazine. LC-MS m/z: 552 (M+1).

Example 56

((R)-2-(benzofuran-3-yl)-1-(((((R)-1-(2-cyano-4-methyl-4-morpholinopent-2-enoyl)-4,4-difluoropyrrolidin-2-yl)methoxy)carbonyl)amino)ethyl)boronic acid

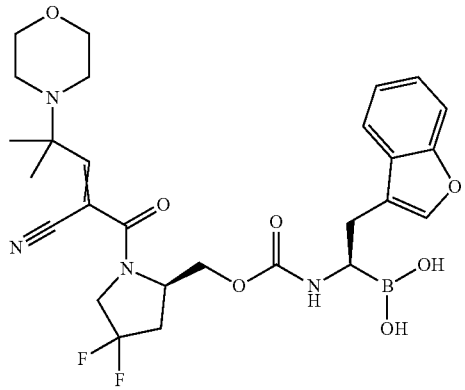 [SMILES: CC(C)(C=C(C#N)C(=O)N1CC(F)(F)C[C@@H]1COC(=O)N[C@@H](Cc1coc2ccccc12)B(O)O)N1CCOCC1]

The title compound was prepared as in example 40 by replacing tert-butyl (2R)-2-(hydroxymethyl)pyrrolidine-1-carboxylate with tert-butyl (2R)-4,4-difluoro-2-(hydroxymethyl)pyrrolidine-1-carboxylate. LC-MS m/z: 575 (M+1).

Example 57

((R)-2-(benzofuran-3-yl)-1-(((((2R,5S)-1-(2-cyano-4-methyl-4-morpholinopent-2-enoyl)-5-methylpyrrolidin-2-yl)methoxy)carbonyl)amino)ethyl)boronic acid

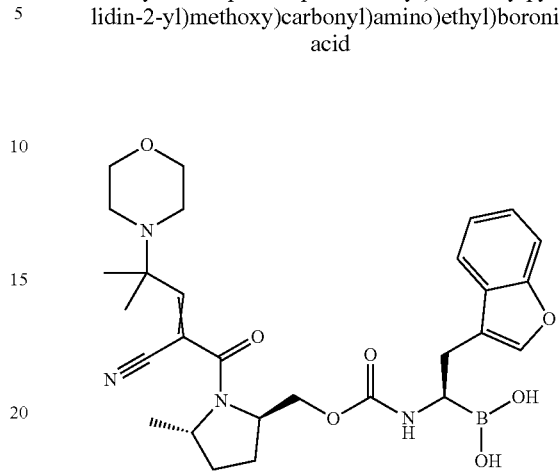

The title compound was prepared as in example 40 by replacing tert-butyl (2R)-2-(hydroxymethyl)pyrrolidine-1-carboxylate with tert-butyl (2R,5S)-2-(hydroxymethyl)-5-methylpyrrolidine-1-carboxylate. LC-MS m/z: 553 (M+1).

tert-Butyl (2R,5S)-2-(hydroxymethyl)-5-methylpyrrolidine-1-carboxylate was synthesized according to below procedure:

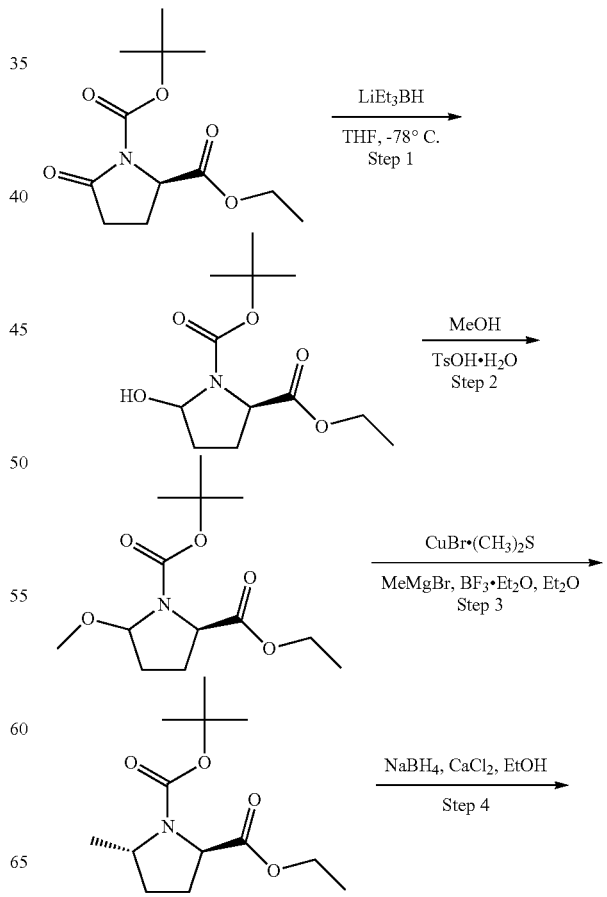

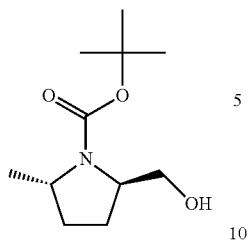

Step 1

Into a 250-mL round-bottom flask, was placed a solution of 1-tert-butyl 2-ethyl (2R)-5-oxopyrrolidine-1,2-dicarboxylate (4 g, 15.55 mmol, 1.00 eq.) in tetrahydrofuran (100 mL). This was followed by the addition of triethyllithium borane (18.7 mL, 1.20 eq., 1 M) dropwise with stirring at −78° C. in 20 min. The resulting solution was allowed to react, with stirring, for an additional 30 min at −78° C. To this was added sodium bicarbonate (40 mL, aq.) and the mixture allowed to warm to 0° C. $H_2O$ (5 mL, 30%) is added. The resulting solution was allowed to react, with stirring, for an additional 30 min at t. The resulting solution was extracted with 3×100 mL of ethyl acetate and the organic layers combined. The resulting mixture was washed with 1×100 mL of water and 1×100 mL of sodium chloride, dried over anhydrous sodium sulfate and evaporated. This resulted in 4 g (crude) of 1-tert-butyl 2-ethyl (2R)-5-hydroxypyrrolidine-1,2-dicarboxylate as a colorless oil.

Step 2

Into a 250-mL round-bottom flask, was placed a solution of 1-tert-butyl 2-ethyl (2R)-5-hydroxypyrrolidine-1,2-dicarboxylate (3.4 g, 13.11 mmol, 1.00 eq.) in methanol (40 mL), and $TsOH.H_2O$ (250 mg, 1.31 mmol, 0.10 eq.). The resulting solution was stirred overnight at it. To the mixture was added sodium bicarbonate (9 mL, aq.). The resulting solution was stirred for 10 mins at rt. The resulting mixture was concentrated under vacuum. The resulting solution was diluted with 20 mL of $H_2O$. The resulting solution was extracted with 2×50 mL of ethyl acetate and the organic layers combined. The resulting mixture was washed with 1×50 mL of sodium chloride (aq.). The mixture was dried over anhydrous sodium sulfate and concentrated under vacuum. The residue was applied onto a silica gel column with ethyl acetate/petroleum ether (8:92). This resulted in 3.2 g (89%) of 1-tert-butyl 2-ethyl (2R)-5-methoxypyrrolidine-1,2-dicarboxylate as a colorless oil.

Into a 250-mL 3-necked round-bottom flask purged and maintained with an inert atmosphere of nitrogen, was placed a solution of $CuBr.(CH_3)_2S$ (3 g, 14.63 mmol, 4.00 eq.) in ether (38 mL). This was followed by the addition of MeMgBr (4.9 mL, 4.00 eq., 3M in ether) dropwise with stirring at −40° C. The resulting solution was stirred for 45 min. at −40° C. To this was added BF3.Et2O (1.84 mL, 4.00 eq.) dropwise with stirring at −78° C. in 30 min. To the mixture was added a solution of 1-tert-butyl 2-ethyl (2R)-5-methoxypyrrolidine-1,2-dicarboxylate (1 g. 3.66 mmol, 1.00 eq.) in ether (50 mL) dropwise with stirring at −78° C. The resulting solution was stirred for 30 min. at −78° C. The resulting solution was stirred for 1 h at it. The reaction was then quenched by the addition of 100 mL of $NH_4CL$. The resulting solution was extracted with 3×100 mL of ether and the organic layers combined. The resulting mixture was washed with 1×50 mL of sodium bicarbonate (aq.). The resulting mixture was washed with 1×50 mL of sodium chloride (aq.). The mixture was dried over anhydrous sodium sulfate and concentrated under vacuum. The residue was applied onto a silica gel column with ethyl acetate/petroleum ether (1:10). This resulted in 500 mg (53%) of 1-tert-butyl 2-ethyl (2R,5S)-5-methylpyrrolidine-1,2-dicarboxylate as a colorless oil.

Step 4

Into a 50-mL 3-necked round-bottom flask, was placed a solution of 1-tert-butyl 2-ethyl (2R,5S)-5-methylpyrrolidine-1,2-dicarboxylate (300 mg, 1.17 mmol, 1.00 eq.) in ethanol (9 mL). This was followed by the addition of $CaCl_2$ (687 mg, 6.19 mmol, 5.30 eq.) in several batches at 0° C. To this was added $NaBH_4$ (444 mg, 11.74 mmol, 10.00 eq.) in several batches at 0° C. The resulting solution was stirred overnight at rt. The reaction was then quenched by the addition of 5 mL of 2M potassium carbonate. The resulting solution was diluted with 10 mL of $H_2O$. The resulting solution was extracted with 2×20 mL of ethyl acetate and the organic layers combined. The resulting mixture was washed with 1×10 mL of NaCl (aq.). The mixture was dried over anhydrous sodium sulfate and concentrated under vacuum. The residue was applied onto a silica gel column with ethyl acetate/petroleum ether (70; 30). This resulted in 230 mg (92%) of tert-butyl (2R,5S)-2-(hydroxymethyl)-5-methylpyrrolidine-1-carboxylate as a yellow oil.

Example 58

((R)-2-(benzofuran-3-yl)-1-(((((R)-4-(2-cyano-4-methyl-4-morpholinopent-2-enoyl)morpholin-3-yl)methoxy)carbonyl)amino)ethyl)boronic acid

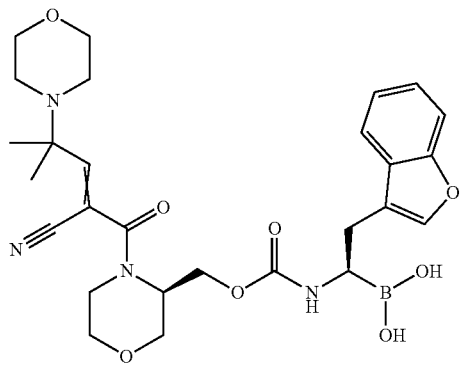 [SMILES: CC(C)(C=C(C#N)C(=O)N1CCOC[C@@H]1COC(=O)N[C@@H](Cc1coc2ccccc12)B(O)O)N1CCOCC1]

The title compound was prepared as in example 40 by replacing tert-butyl (2R)-2-(hydroxymethyl)pyrrolidine-1-carboxylate with tert-butyl (3S)-3-(hydroxymethyl)morpholine-4-carboxylate. LC-MS m/z: 555 (M+1).

Example 59

((R)-2-(benzofuran-3-yl)-1-(((((R)-1-(2-cyano-3-(4-methyltetrahydro-2H-pyran-4-yl)acryloyl)piperidin-2-yl)methoxy)carbonyl)amino)ethyl)boronic acid

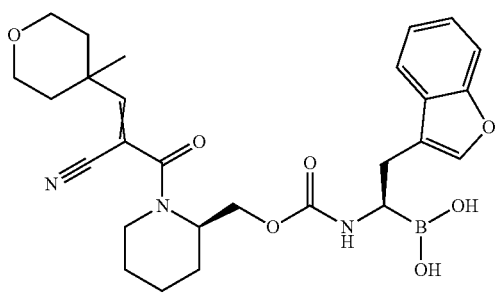 [SMILES: CC1(C=C(C#N)C(=O)N2CCCC[C@@H]2COC(=O)N[C@@H](Cc2coc3ccccc23)B(O)O)CCOCC1]

The title compound was prepared as in example 46 by replacing 2-methyl-2-morpholinopropanal with 4-methyltetrahydro-2H-pyran-4-carbaldehyde. LC-MS m/z: 546 (M+23).

Example 60

((R)-2-(benzofuran-3-yl)-1-(((((R)-1-(2-cyano-4-methyl-4-(4-(oxetan-3-yl)piperazin-1-yl)pent-2-enoyl)piperidin-2-yl)methoxy)carbonyl)amino)ethyl)boronic acid

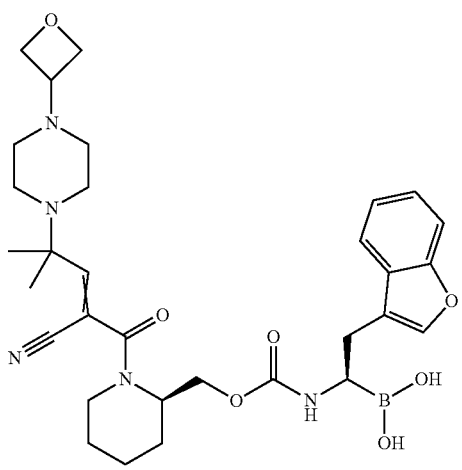 [SMILES: CC(C)(C=C(C#N)C(=O)N1CCCC[C@@H]1COC(=O)N[C@@H](Cc1coc2ccccc12)B(O)O)N1CCN(C2COC2)CC1]

The title compound was prepared as in example 46 by replacing 2-methyl-2-(morpholin-4-yl)propanal with 2-methyl-2-(4-(oxetan-3-yl)piperazin-1-yl)propanal. LC-MS m/z: 608 (M+1).

Example 61

((R)-1-(((((R)-1-((E)-2-cyano-4,4-dimethylpent-2-enoyl)-4,4-difluoropyrrolidin-2-yl)methoxy)carbonyl)amino)-2-phenylethyl)boronic acid

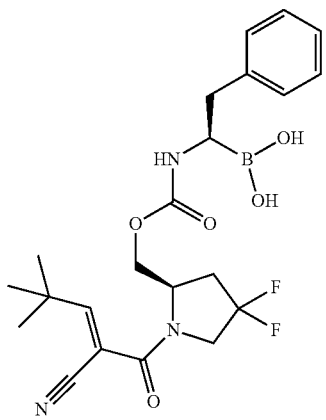 [SMILES: CC(C)(C)/C=C(\C#N)C(=O)N1CC(F)(F)C[C@@H]1COC(=O)N[C@@H](Cc1ccccc1)B(O)O]

Using the method of example 10 and replacing tert-butyl (2R)-2-(hydroxymethyl)pyrrolidine-1-carboxylate with (R)-tert-butyl 4,4-difluoro-2-(hydroxymethyl)pyrrolidine-1-carboxylate afforded the title compound. LC-MS m/z: 463 (M−1).

Example 62

((R)-2-(benzofuran-3-yl)-1-(((((R)-1-(2-cyano-4-(3,3-difluoropiperidin-1-yl)-4-methylpent-2-enoyl)piperidin-2-yl)methoxy)carbonyl)amino)ethyl)boronic acid

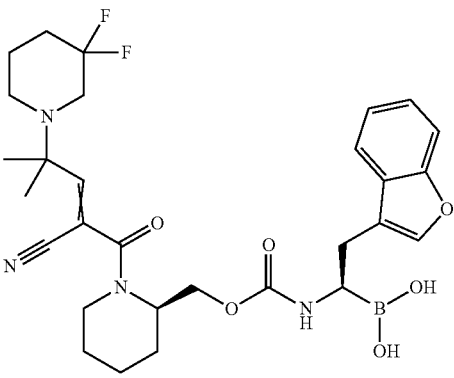 [SMILES: CC(C)(C=C(C#N)C(=O)N1CCCC[C@@H]1COC(=O)N[C@@H](Cc1coc2ccccc12)B(O)O)N1CCCC(F)(F)C1]

The title compound was prepared as in example 46 by replacing morpholine with 3,3-difluoropiperidine. LC-MS m/z: 603 (M+23).

Example 63 and Example 64

((R)-2-(benzofuran-3-yl)-1-(((((R)-1-(2-cyano-4-methyl-4-morpholinopent-2-enoyl)-azepan-2-yl)methoxy)carbonyl)amino)ethyl)boronic acid (Example 63)

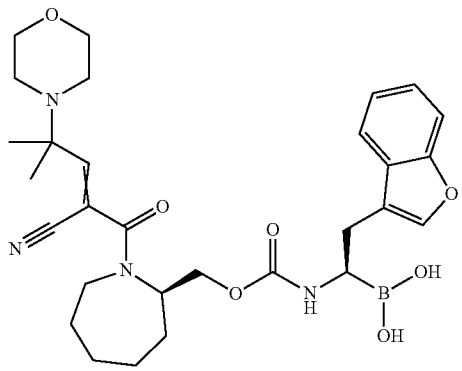 [SMILES: CC(C)(C=C(C#N)C(=O)N1CCCCC[C@@H]1COC(=O)N[C@@H](Cc1coc2ccccc12)B(O)O)N1CCOCC1]

And ((R)-2-(benzofuran-3-yl)-1-(((((S)-1-(2-cyano-4-methyl-4-morpholinopent-2-enoyl)azepan-2-yl)methoxy)carbonyl)amino)ethyl)boronic acid (Example 64)

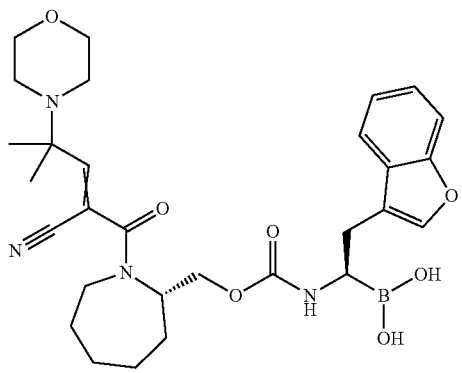 [SMILES: CC(C)(C=C(C#N)C(=O)N1CCCCC[C@H]1COC(=O)N[C@@H](Cc1coc2ccccc12)B(O)O)N1CCOCC1]

The title compounds were prepared as in example 40 by replacing tert-butyl (2R)-2-(hydroxymethyl)pyrrolidine-1-carboxylate with tert-butyl 2-(hydroxymethyl) azepane-1-carboxylate. LC-MS m/z: 567 (M+1).

Example 65

((R)-2-(benzofuran-3-yl)-1-(((((R)-4-(2-cyano-4-(3,3-difluoropyrrolidin-1-yl)-4-methylpent-2-enoyl)morpholin-3-yl)methoxy)carbonyl)amino)ethyl)boronic acid

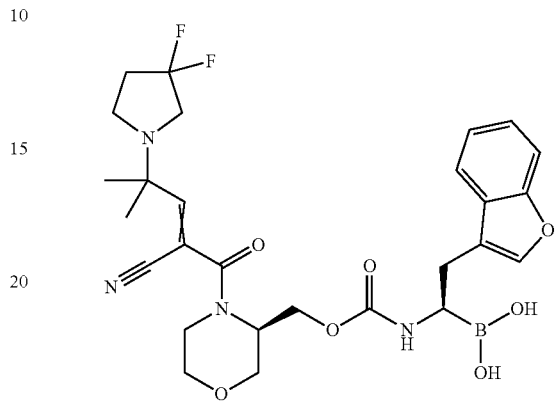

The title compound was prepared as in example 47 by replacing tert-butyl (2R)-2-(hydroxymethyl)pyrrolidine-1-carboxylate with tert-butyl (3S)-3-(hydroxymethyl)morpholine-4-carboxylate. LC-MS m/z: 575 (M+1).

Example 66

((R)-2-(benzofuran-3-yl)-1-(((((R)-1-(2-cyano-4-(4,4-difluoropiperidin-1-yl)-4-methylpent-2-enoyl)piperidin-2-yl)methoxy)carbonyl)amino)ethyl)boronic acid

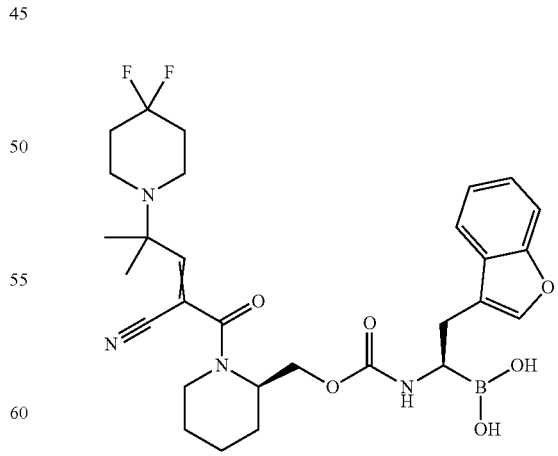

The title compound was prepared as in example 46 by replacing 2-methyl-2-(morpholin-4-yl)propanal with 2-(4,4-difluoropiperidin-1-yl)-2-methylpropanal. LC-MS m/z: 587 (M+1).

Example 67

((R)-1-(((((1S,2R,5R)-3-(2-cyano-4-methyl-4-morpholinopent-2-enoyl)-3-azabicyclo[3.1.0]hexan-2-yl)methoxy)carbonyl)amino)-2-phenylethyl)boronic acid

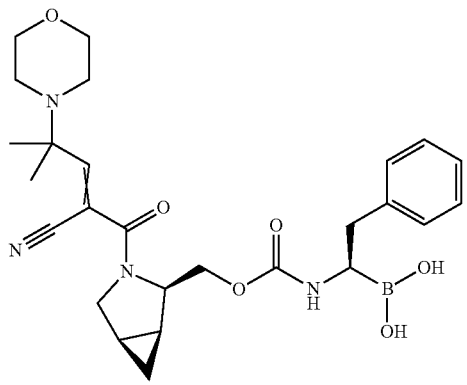 [SMILES: CC(C)(C=C(C#N)C(=O)N1C[C@@H]2C[C@@H]2[C@@H]1COC(=O)N[C@@H](Cc1ccccc1)B(O)O)N1CCOCC1]

The title compound was prepared as in example 51 by replacing (1R)-2-(1-benzofuran-3-yl)-1-[(1S,2S,6R,8S)-2,9,9-trimethyl-3,5-dioxa-4-boratricyclo[6.1.1.0^2,6]decan-4-yl]ethan-1-amine hydrochloride with (1R)-2-phenyl-1-[(1S,2S,6R,8S)-2,9,9-trimethyl-3,5-dioxa-4-boratricyclo[6.1.1.0^2,6]decan-4-yl]ethan-1-amine hydrochloride. LC-MS m/z: 511 (M+1).

Example 68 and Example 72

((R)-2-(benzofuran-3-yl)-1-(((((S)-1-(2-cyano-4-(3,3-difluoropyrrolidin-1-yl)-4-methylpent-2-enoyl)azepan-2-yl)methoxy)carbonyl)amino)ethyl)boronic acid (Example 68)

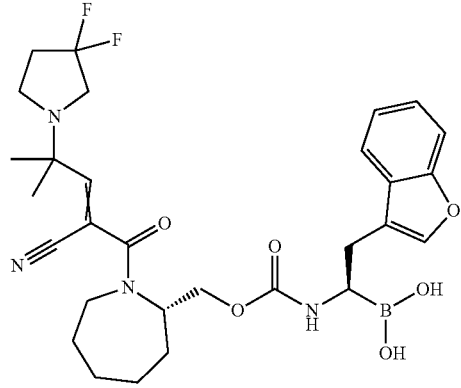 [SMILES: CC(C)(C=C(C#N)C(=O)N1CCCCC[C@H]1COC(=O)N[C@@H](Cc1coc2ccccc12)B(O)O)N1CCC(F)(F)C1]

And ((R)-2-(benzofuran-3-yl)-1-(((((R)-1-(2-cyano-4-(3,3-difluoropyrrolidin-1-yl)-4-methylpent-2-enoyl)azepan-2-yl)methoxy)carbonyl)amino)ethyl)boronic acid (Example 72)

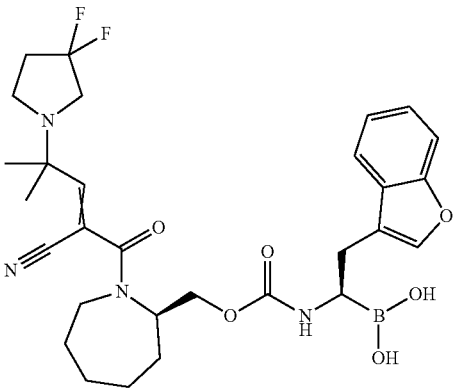 [SMILES: CC(C)(C=C(C#N)C(=O)N1CCCCC[C@@H]1COC(=O)N[C@@H](Cc1coc2ccccc12)B(O)O)N1CCC(F)(F)C1]

The title compounds were prepared as in examples 63 and 64 by replacing morpholine with 3,3-difluoropyrrolidine. LC-MS m/z: 587 (M+1).

Example 69

((R)-1-(((((R)-4-(2-cyano-4,4-dimethylpent-2-enoyl)morpholin-3-yl)methoxy)carbonyl)amino)-2-phenylethyl)boronic acid

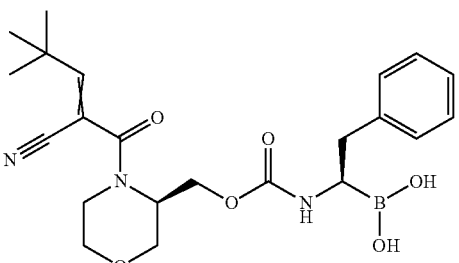

The title compound was prepared as in example 43 by replacing (1R)-2-(1-benzofuran-3-yl)-1-[(1S,2S,6R,8S)-2,9,9-trimethyl-3,5-dioxa-4-boratricyclo[6.1.1.0^2,6]decan-4-yl]ethan-1-amine hydrochloride with (1R)-2-phenyl-1-[(1S,2S,6R,8S)-2,9,9-trimethyl-3,5-dioxa-4-boratricyclo[6.1.1.0^2,6]decan-4-yl]ethan-1-amine hydrochloride. LC-MS m/z: 511 (M+1).

Example 70

((R)-1-(((((R)-1-(2-cyano-4,4-dimethylpent-2-enoyl)piperidin-2-yl)methoxy)carbonyl)amino)-2-(4-methoxyphenyl)ethyl)boronic acid

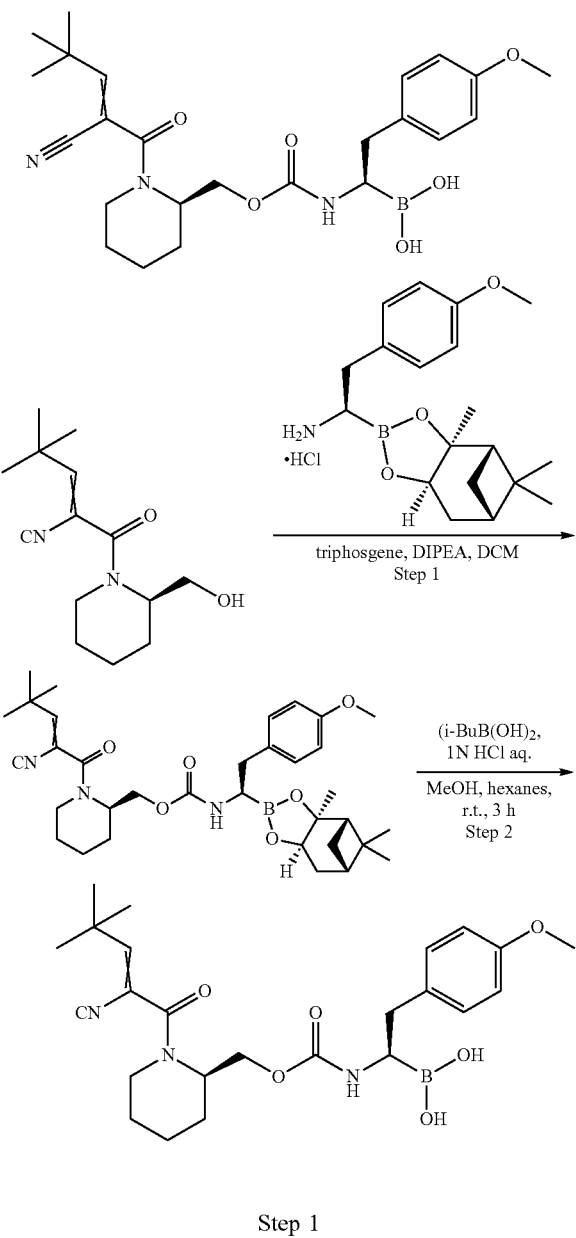

Step 1

Bis(trichloromethyl) carbonate (200 mg, 0.66 mmol) in DCM (1.5 mL) was added dropwise into a stirring solution of (R)-4-(4,4-difluoropiperidin-1-yl)-2-(2-(hydroxymethyl)piperidine-1-carbonyl)-4-methylpent-2-enenitrile (260 mg, 0.73 mmol) and DIPEA (565 mg, 4.38 mmol) in DCM (10 mL) at 0° C. The mixture was stirred for 2 h at 0° C. This resulted solution was added dropwise into a well-stirred solution of (R)-2-(4-methoxyphenyl)-1-((3aS,4S,6S,7aR)-3a,5,5-trimethylhexahydro-4,6-methanobenzo[d][1,3,2]dioxaborol-2-yl)ethan-1-amine hydrochloride (273 mg, 0.73 mmol) and DIPEA (283 mg, 2.19 mmol) in DCM (10 mL) at 0° C. The reaction was stirred at 0° C. for 1 h, then diluted with DCM (25 mL), washed with water (10 mL) and brine (10 mL), dried over $Na_2SO_4$, concentrated in vacuo. The residue was purified via silica chromatography and a gradient of 0%-25% EtOAc in hexanes to afford ((R)-1-(2-cyano-4,4-dimethylpent-2-enoyl)piperidin-2-yl)methyl ((R)-2-(4-methoxyphenyl)-1-((3aS,4S,6S,7aR)-3a,5,5-trimethylhexahydro-4,6-methanobenzo[d][1,3,2]dioxaborol-2-yl)ethyl)carbamate as light yellow solid (85 mg, 16%).

Step 2

To a solution of ((R)-1-(2-cyano-4,4-dimethylpent-2-enoyl)piperidin-2-yl)methyl ((R)-2-(4-methoxyphenyl)-1-((3aS,4S,6S,7aR)-3a,5,5-trimethylhexahydro-4,6-methanobenzo[d][1,3,2]dioxaborol-2-yl)ethyl)carbamate (85 mg. 0.12 mmol) in MeOH (3 mL) were added hexanes (3 mL) and 1 N HCl (1.5 mL), followed by isobutyl boric acid (36 mg. 0.36 mmol). After stirred at rt for 3 h and TLC suggested the reaction was completed, the hexanes layer was discarded. The methanol layer was diluted with water (20 mL), then dried over lyophilization to give a crude product which was purified by prep-HPLC to afford ((R)-2-(benzofuran-3-yl)-1-(((((R)-1-(2-cyano-4-(4,4-difluoropiperidin-1-yl)-4-methylpent-2-enoyl)piperidin-2-yl)methoxy)carbonyl)amino)ethyl)boronic acid as a white solid (26.8 mg, 38%). LC-MS m/z: 494 (M−17).

(R)-2-(benzofuran-3-yl)-1-((3aS,4S,6S,7aR)-3a,5,5-trimethylhexahydro-4,6-methanobenzo[d][1,3,2]dioxaborol-2-yl)ethan-1-amine hydrochloride was prepared according to below sequence:

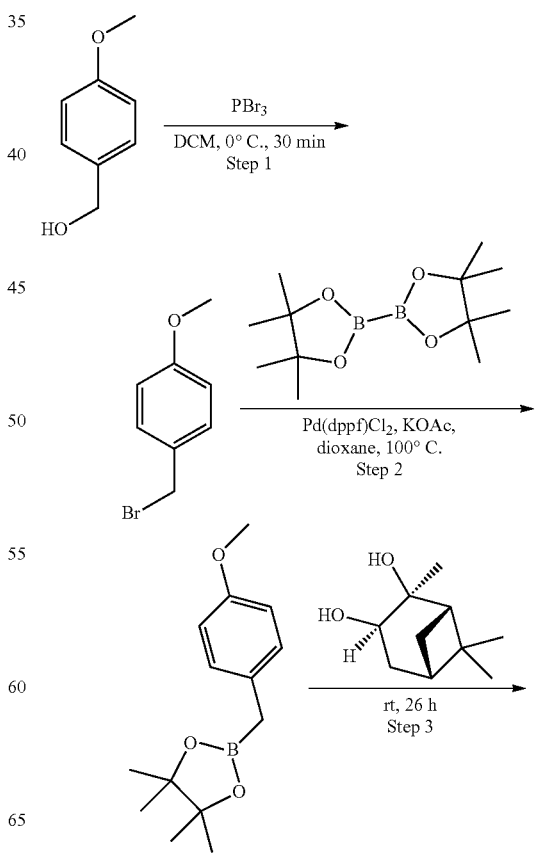

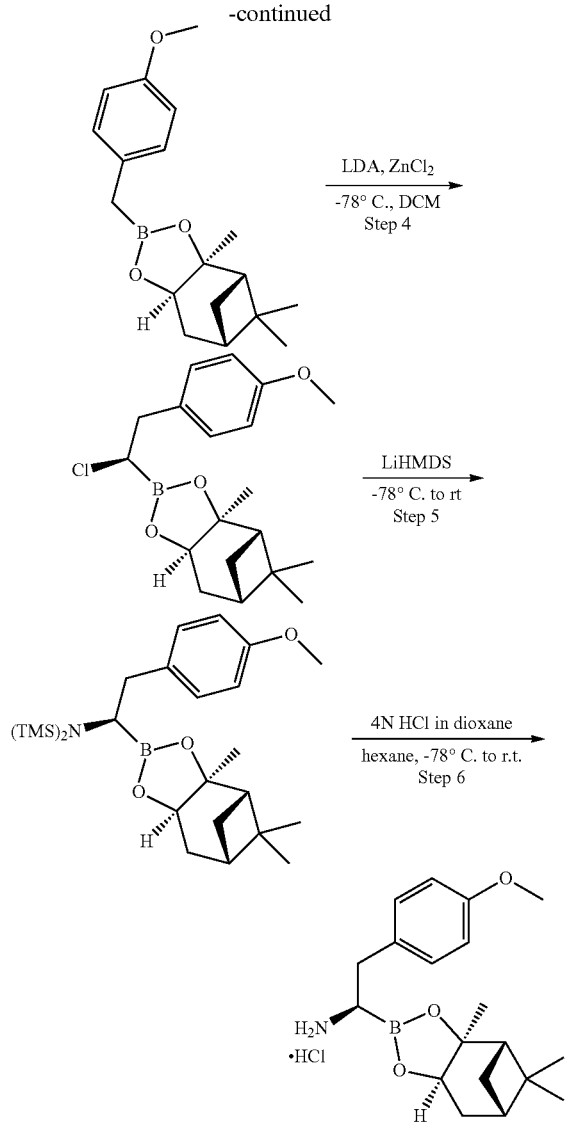

Step 1

A cooled (0° C.) solution of (4-methoxyphenyl)methanol (5 g, 36.23 mmol) in diethyl ether (180 mL) was treated with phosphorus tribromide (2.9 g, 10.8 mmol) and the mixture was stirred at 0° C. for 30 min. The reaction mixture was then poured into ice and extracted with ether. The organic layer was dried over sodium sulfate and concentrated. The crude (6.3 g, 89%) was used without further purification.

Step 2

A solution of 1-(bromomethyl)-4-methoxybenzene (6 g, 30 mmol) in degassed 1,4-dioxane (50 mL) was treated with bis(pinacolato)diboron (11.4 g, 45 mmol), potassium acetate (8.8 g, 90 mmol), Pd(dppf)Cl$_2$ (1.02 g, 1.4 mmol) and the mixture heated at 100° C. for 12 h. The mixture was cooled to rt and filtered. Filtrate was concentrated and the crude was purified by column chromatography on silica gel, eluting with 5% of ethyl acetate in petroleum ether to afford 2-(4-methoxybenzyl)-4,4,5,5-tetramethyl-1,3,2-dioxaborolane (5 g, 60%) as a colorless oil.

Step 3

A solution of (1S,2S,3R,5 S)-2,6,6-trimethylbicyclo[3.1.1]heptane-2,3-diol (4.9 g, 28.8 mmol) in diethyl ether (100 mL) was treated with 2-(4-methoxybenzyl)-4,4,5,5-tetramethyl-1,3,2-dioxaborolane (5 g, 20 mmol), the mixture was stirred at rt for 12 h. Then the mixture was concentrated and the crude was purified by column chromatography on silica gel, eluting with 5% of ethyl acetate in petroleum ether to afford the (3aS,4S,6S,7aR)-2-(4-methoxybenzyl)-3a,5,5-trimethylhexahydro-4,6-methanobenzo[d][1,3,2]dioxaborole (4.5 g, 75%) as a colorless oil.

Step 4

To a cooled (−78° C.) mixture of dichloromethane (10 mL) and anhydrous tetrahydrofuran (20 mL) was added LDA (2 M in tetrahydrofuran, 9.5 mL, 19 mmol). After stirring for 20 min at −78° C., a solution of (3aS,4S,6S,7aR)-2-(4-methoxybenzyl)-3a,5,5-trimethylhexahydro-4,6-methanobenzo[d][1,3,2]dioxaborole (4.4 g, 14.7 mmol) in anhydrous tetrahydrofuran (80 mL) was added over 10 min. Then a solution of zinc chloride (1 M in Diethyl ether, 14.7 mL, 14.7 mmol) was added at −78° C. over 30 min. The mixture was allowed to reach rt and stirred for 3 h. Then the mixture was concentrated. To the resulting oil was added diethyl ether and saturated ammonium chloride. The aqueous layer was extracted with diethyl ether three times and the combined organic layers were dried over anhydrous sodium sulfate and concentrated in vacuo. The crude was purified by column chromatography on silica gel, eluting with 5% of ethyl acetate in petroleum ether to afford (3aS,4S,6S,7aR)-2-((R)-1-chloro-2-(4-methoxyphenyl)ethyl)-3a,5,5-trimethylhexahydro-4,6-methanobenzo[d][1,3,2]dioxaborole (4.27 g, 83%) as a colorless oil.

Step 5

To a cooled (−78° C.) solution of (3aS,4S,6S,7aR)-2-((R)-1-chloro-2-(4-methoxyphenyl)ethyl)-3a,5,5-trimethylhexahydro-4,6-methanobenzo[d][1,3,2]dioxaborole (4.27 g, 12.27 mmol) in anhydrous tetrahydrofuran (50 mL) was added LiHMDS (1 M in tetrahydrofuran, 14.7 mL, 14.7 mmol). The mixture was allowed to it, stirred for 3 h and concentrated to dryness. To the resulting residue was added hexane, and then the precipitated solid was filtered off. The filtrate was used without further purification.

Step 6

A cooled (0° C.) solution of N—((R)-2-(4-methoxyphenyl)-1-((3aS,4S,6S,7aR)-3a,5,5-trimethylhexahydro-4,6-methanobenzo[d][1,3,2]dioxaborol-2-yl)ethyl)-1,1,1-trimethyl-N-(trimethylsilyl)silanamine in anhydrous hexane (50 mL) was treated with 4N HCl in dioxane (9.2 mL. 36.8 mmol) dropwise. The mixture was allowed to rt, stirred for 2 h. Then the solid was filtered to afford (R)-2-(4-methoxyphenyl)-1-((3aS,4S,6S,7aR)-3a,5,5-trimethylhexahydro-4,6-methanobenzo[d][1,3,2]dioxaborol-2-yl)ethan-1-amine as brown solid (2 g, 45% for 2 steps), which was used without further purification.

Example 71

((R)-2-(benzofuran-3-1)-1-(((((R)-1-(2-cyano-4-methyl-4-morpholinopent-2-enoyl)-2-methylpyrrolidin-2-yl)methoxy)carbonyl)amino)ethyl)boronic acid

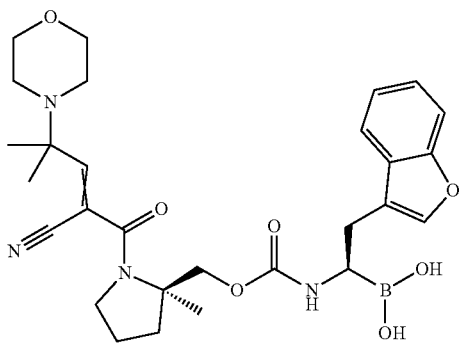 [SMILES: CC(C)(C=C(C#N)C(=O)N1CCC[C@]1(C)COC(=O)N[C@@H](Cc1coc2ccccc12)B(O)O)N1CCOCC1]

The title compound was prepared as in example 40 by replacing tert-butyl (2R)-2-(hydroxymethyl)pyrrolidine-1-carboxylate with tert-butyl (2R)-2-(hydroxymethyl)-2-methylpyrrolidine-1-carboxylate. LC-MS m/z: 553 (M+1).

Example 73

((R)-1-(((((R)-4-(2-cyano-4,4-dimethylpent-2-enoyl)morpholin-3-yl)methoxy)carbonyl)amino)-2-(p-tolyl)ethyl)boronic acid

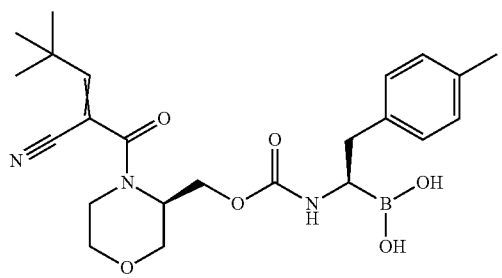 [SMILES: Cc1ccc(C[C@H](NC(=O)OC[C@H]2COCCN2C(=O)C(C#N)=CC(C)(C)C)B(O)O)cc1]

The title compound was prepared as in example 43 by replacing (1R)-2-(1-benzofuran-3-yl)-1-[(1S,2S,6R,8S)-2,9,9-trimethyl-3,5-dioxa-4-boratricyclo[6.1.1.0^2,6]decan-4-yl]ethan-1-amine hydrochloride with (1R)-2-(4-methylphenyl)-1-[(2S,6R)-2,9,9-trimethyl-3,5-dioxa-4-boratricyclo[6.1.1.0^[2,6]]decan-4-yl]ethan-1-amine hydrochloride. LC-MS m/z: 480 (M+23).

Example 74

((R)-1-(((((1S,2R,5R)-3-(2-cyano-4-(3,3-difluoropyrrolidin-1-yl)-4-methylpent-2-enoyl)-3-azabicyclo[3.1.0]hexan-2-yl)methoxy)carbonyl)amino)-2-phenylethyl)boronic acid

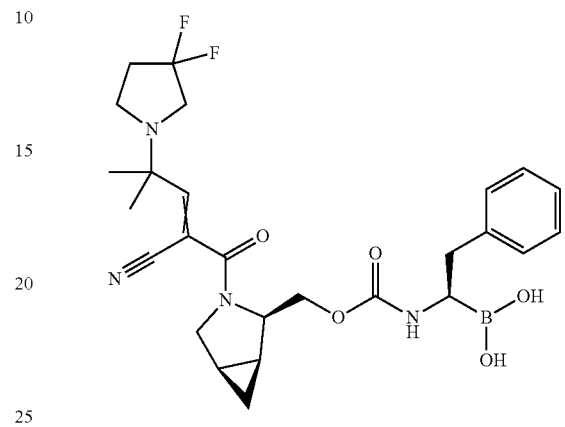

The title compound was prepared as in example 67 by replacing morpholine with 3,3-difluoropyrrolidine. LC-MS m/z: 553 (M+23).

Example 75

((R)-1-(((((1S,2R,5R)-3-(2-cyano-4-methyl-4-morpholinopent-2-no)yl)-3-azabicyclo[3.1.0]hexan-2-yl)methoxy)carbonyl)amino)-2-(p-tolyl)ethyl)boronic acid

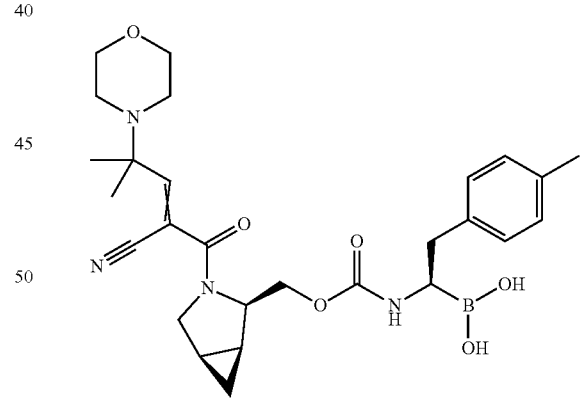

The title compound was prepared as in example 51 by replacing (1R)-2-(1-benzofuran-3-yl)-1-[(1S,2S,6R,8S)-2,9,9-trimethyl-3,5-dioxa-4-boratricyclo[6.1.1.0^2,6]decan-4-yl]ethan-1-amine hydrochloride with (1R)-2-(4-methylphenyl)-1-[(2S,6R)-2,9,9-trimethyl-3,5-dioxa-4-boratricyclo[6.1.1.0^[2,6]]decan-4-yl]ethan-1-amine hydrochloride. LC-MS m/z: 525 (M+1).

Example 76

((R)-1-(((((1S,2R,5R)-3-(2-cyano-4,4-dimethylpent-2-enoyl)-3-azabicyclo[3.1.0]hexan-2-yl)methoxy)carbonyl)amino)-2-(p-tolyl)ethyl)boronic acid

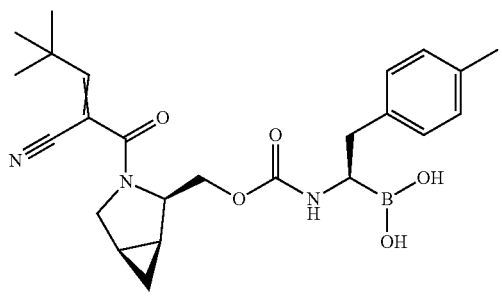 [SMILES: Cc1ccc(C[C@H](NC(=O)OC[C@H]2[C@H]3C[C@H]3CN2C(=O)C(C#N)=CC(C)(C)C)B(O)O)cc1]

The title compound was prepared as in example 26 by replacing (1R)-2-phenyl-1-[(1S,2S,6R,8S)-2,9,9-trimethyl-3,5-dioxa-4-boratricyclo[6.1.1.0^2,6]decan-4-yl]ethan-1-amine hydrochloride with (1R)-2-(4-methylphenyl)-1-[(2S,6R)-2,9,9-trimethyl-3,5-dioxa-4-boratricyclo[6.1.1.0^[2.6]]decan-4-yl]ethan-1-amine hydrochloride. LC-MS m/z: 476 (M+23).

Example 77

((R)-1-(((((R)-1-(2-cyano-4,4-dimethylpent-2-enoyl)piperidin-2-yl)methoxy)carbonyl)amino)-2-(3-methoxyphenyl)ethyl)boronic acid

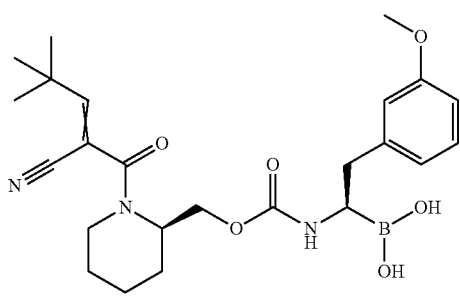 [SMILES: COc1cccc(C[C@H](NC(=O)OC[C@H]2CCCCN2C(=O)C(C#N)=CC(C)(C)C)B(O)O)c1]

The title compound was prepared as in example 70 by replacing (R)-2-(4-methoxyphenyl)-1-((3aS,4S,6S,7aR)-3a,5,5-trimethylhexahydro-4,6-methanobenzo[d][1,3,2]dioxaborol-2-yl)ethan-1-amine hydrochloride with (R)-2-(3-methoxyphenyl)-1-((3aS,4S,6S,7aR)-3a,5,5-trimethylhexahydro-4,6-methanobenzo[d][1,3,2]dioxaborol-2-yl)ethan-1-amine hydrochloride. LC-MS m/z: 494 (M+23).

Example 78

((R)-1-(((((R)-1-(2-cyano-4-(3,3-difluoropyrrolidin-1-yl)-4-methylpent-2-enoyl)piperidin-2-yl)methoxy)carbonyl)amino)-2-(4-methoxyphenyl)ethyl)boronic acid

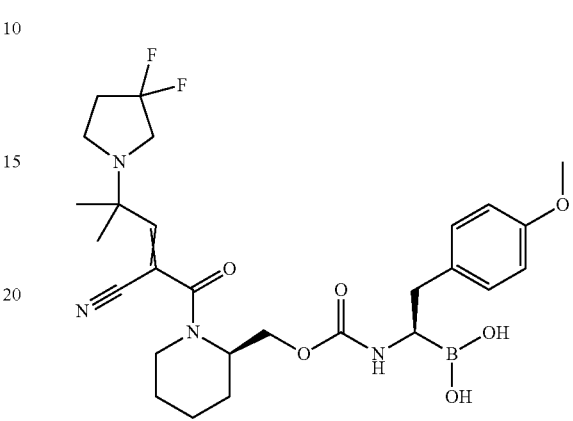

The title compound was prepared as in example 28 by replacing (1R)-2-phenyl-1-[(1S,2S,6R,8S)-2,9,9-trimethyl-3,5-dioxa-4-boratricyclo[6.1.1.0^2,6]decan-4-yl]ethan-1-amine hydrochloride with (R)-2-(4-methoxyphenyl)-1-((3aS,4S,6S,7aR)-3a,5,5-trimethylhexahydro-4,6-methanobenzo[d][1,3,2]dioxaborol-2-yl)ethan-1-amine hydrochloride. LC-MS nm/z: 494 (M+23).

Example 79

((R)-2-(4-chlorophenyl)-1-(((((R)-1-(2-cyano-4-(3,3-difluoropyrrolidin-1-yl)-4-methylpent-2-enoyl)piperidin-2-yl)methoxy)carbonyl)amino)ethyl)boronic acid

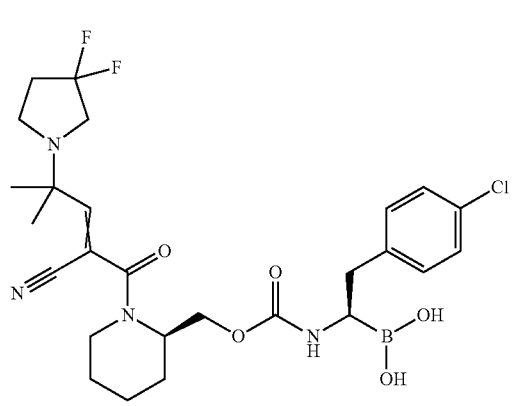 [SMILES: CC(C)(C=C(C#N)C(=O)N1CCCC[C@@H]1COC(=O)N[C@@H](Cc1ccc(Cl)cc1)B(O)O)N1CCC(F)(F)C1]

The title compound was prepared as in example 28 by replacing (1R)-2-phenyl-1-[(1S,2S,6R,8S)-2,9,9-trimethyl-3,5-dioxa-4-boratricyclo[6.1.1.0^2,6]decan-4-yl]ethan-1-amine hydrochloride with (R)-2-(4-chlorophenyl)-1-(4,4,5,5-tetramethyl-1,3,2-dioxaborolan-2-yl)ethanamine hydrochloride. LC-MS m/z: 589 (M+23).

Example 80

((R)-1-(((((R)-1-(2-cyano-4-((2,2-difluoroethyl)(methyl)amino)-4-methylpent-2-enoyl)piperidin-2-yl)methoxy)carbonyl)amino)-2-phenylethyl)boronic acid

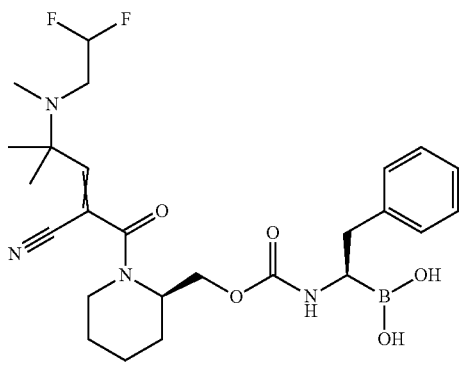 [SMILES: CN(CC(F)F)C(C)(C)C=C(C#N)C(=O)N1CCCC[C@@H]1COC(=O)N[C@@H](Cc1ccccc1)B(O)O]

The title compound was prepared as in example 27 by replacing 2-methyl-2-(pyrrolidin-1-yl)propanal with 2-((2,2-difluoroethyl)(methyl)amino)-2-methylpropanal. LC-MS m/z: 543 (M+23).

2-((2,2-Difluoroethyl)(methyl)amino)-2-methylpropanal was synthesized according to below procedure:

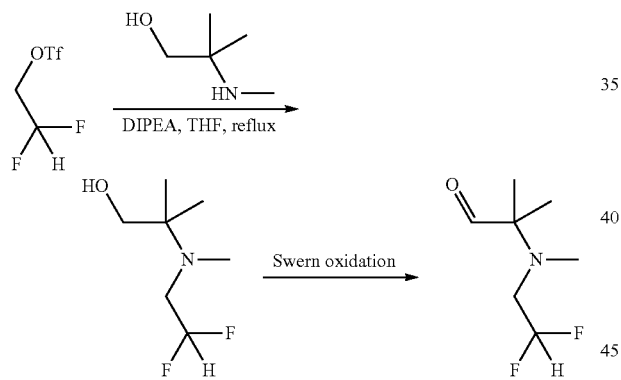

Step 1

To a mixture of 2,2-difluoroethyl trifluoromethanesulfonate (1.0 g, 4.67 mmol), 2-methyl-2-(methylamino)propan-1-ol (0.48 g, 4.67 mmol) in THF (10 mL) was added DIPEA (0.65 g, 4.8 mmol). The resulted mixture was stirred at 70° C. for 18 h, then concentrated to dryness. The residue was stirred in EtOAc (40 mL) for 5 min, then filtered. The filtration was concentrated in vacuo. The crude residue was purified via silica chromatography and a gradient of 10%-100% EtOAc in hexanes to afford 2-((2,2-difluoroethyl)(methyl)amino)-2-methylpropan-1-ol as a colorless oil (0.66 g).

Step 2

To a solution of oxalyl chloride (COCl)$_2$ (0.6 g, 4.65 mmol) in DCM (15 mL) was added dropwise a solution of DMSO (0.4 g, 4.8 mmol) in DCM (5 mL) at −78° C. The resulted mixture was stirred at −78° C. for 0.5 h. A mixture of 2-((2,2-difluoroethyl)(methyl)amino)-2-methylpropan-1-ol (0.66 g, 3.9 mmol) in DCM (10 mL) was added dropwise at −80° C. The resulted mixture was stirred at −80° C. for 1.5 h. Et3N (5 mL) was added dropwise at −80° C. The resulted mixture was stirred at −80° C. for 0.5 h, then warmed to rt slowly and stirred for 2 h. After quenched with NaHCO$_3$ aqueous (8 mL), the DCM layer was separated and washed with brine (8 mL), then dried over Na$_2$SO$_4$, concentrated to dryness. The crude residue was purified via silica chromatography and a gradient of 0%-20% EtOAc in hexanes to afford 2-((2,2-difluoroethyl)(methyl)amino)-2-methylpropanal as a colorless oil (0.29 g, 48%).

Example 81 and Example 84

((R)-1-(((((S)-1-(2-cyano-4-(3,3-difluoropyrrolidin-1-yl)-4-methylpent-2-enoyl)azepan-2-yl)methoxy)carbonyl)amino)-2-(p-tolyl)ethyl)boronic acid (Example 81)

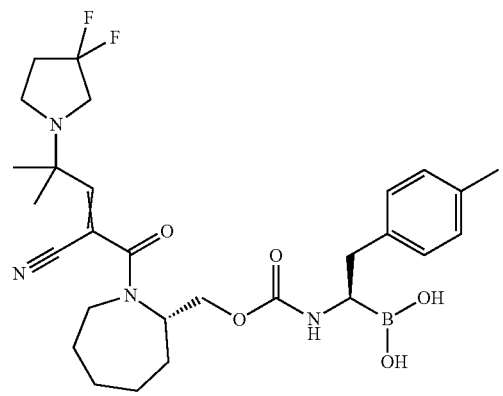 [SMILES: Cc1ccc(C[C@H](NC(=O)OC[C@@H]2CCCCCN2C(=O)C(C#N)=CC(C)(C)N2CCC(F)(F)C2)B(O)O)cc1]

And ((R)-1-(((((R)-1-(2-cyano-4-(3,3-difluoropyrrolidin-1-yl)-4-methylpent-2-enoyl)azepan-2-yl)methoxy)carbonyl)amino)-2-(p-tolyl)ethyl)boronic acid (Example 84)

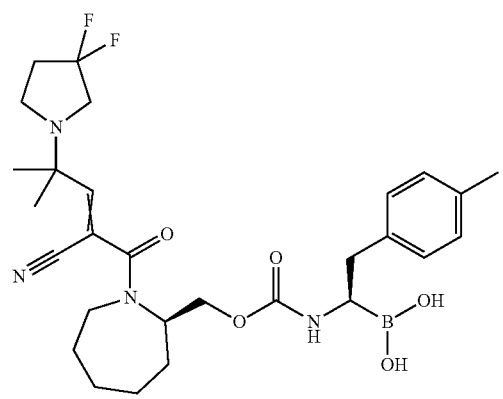 [SMILES: Cc1ccc(C[C@H](NC(=O)OC[C@H]2CCCCCN2C(=O)C(C#N)=CC(C)(C)N2CCC(F)(F)C2)B(O)O)cc1]

The title compounds were prepared as in examples 68 and 72 respectively by replacing (1R)-2-(1-benzofuran-3-yl)-1-

[(1S,2S,6R,8S)-2,9,9-trimethyl-3,5-dioxa-4-boratricyclo[6.1.1.0^2,6]decan-4-yl]ethan-1-amine hydrochloride with (1R)-2-(4-methylphenyl)-1-[(2S,6R)-2,9,9-trimethyl-3,5-dioxa-4-boratricyclo[6.1.1.0^[2,6]]decan-4-yl]ethan-1-amine hydrochloride. LC-MS m/z: 583 (M−17).

Example 82

((R)-1-(((((R)-1-(2-cyano-4-(3,3-difluoropyrrolidin-1-yl)-4-methylpent-2-enoyl)piperidin-2-yl)methoxy)carbonyl)amino)-2-(4-fluorophenyl)ethyl)boronic acid

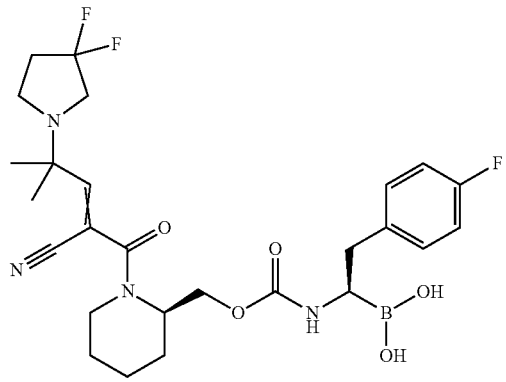 [SMILES: CC(C)(C=C(C#N)C(=O)N1CCCC[C@@H]1COC(=O)N[C@@H](Cc1ccc(F)cc1)B(O)O)N1CCC(F)(F)C1]

The title compound was prepared as in example 28 by replacing (1R)-2-phenyl-1-[(1S,2S,6R,8S)-2,9,9-trimethyl-3,5-dioxa-4-boratricyclo[6.1.1.0^2,6]decan-4-yl]ethan-1-amine hydrochloride with (R)-2-(4-fluorophenyl)-1-((3aS,4S,6S,7aR)-3a,5,5-trimethylhexahydro-4,6-methanobenzo[d][1,3,2]dioxaborol-2-yl)ethan-1-amine hydrochloride. LC-MS m/z: 573 (M+23).

Example 83

((R)-1-(((((R)-1-(2-cyano-4-(3,3-difluoropyrrolidin-1-yl)-4-methylpent-2-enoyl)piperidin-2-yl)methoxy)carbonyl)amino)-2-(4-(trifluoromethyl)phenyl)ethyl)boronic acid

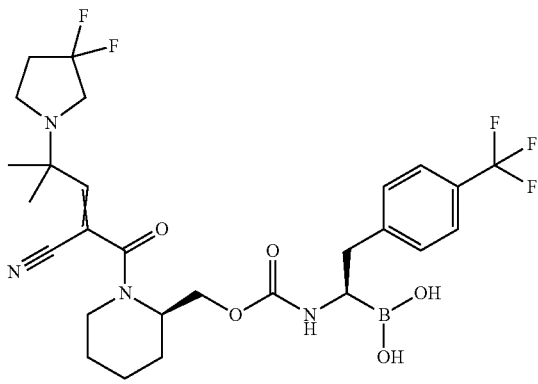 [SMILES: CC(C)(C=C(C#N)C(=O)N1CCCC[C@@H]1COC(=O)N[C@@H](Cc1ccc(C(F)(F)F)cc1)B(O)O)N1CCC(F)(F)C1]

The title compound was prepared as in example 28 by replacing (1R)-2-phenyl-1-[(1S,2S,6R,8S)-2,9,9-trimethyl-3,5-dioxa-4-boratricyclo[6.1.1.0^2,6]decan-4-yl]ethan-1-amine hydrochloride with (R)-2-(4-(trifluoromethyl)phenyl)-1-((3aS,4S,6S,7aR)-3a,5,5-trimethylhexahydro-4,6-methanobenzo[d][1,3,2]dioxaborol-2-yl)ethan-1-amine hydrochloride. LC-MS m/z: 601 (M+1).

Example 85

((R)-1-(((((R)-1-(2-cyano-4-(3,3-difluoropyrrolidin-1-yl)-4-methylpent-2-enoyl)-2-methylpyrrolidin-2-yl)methoxy)carbonyl)amino)-2-phenylethyl)boronic acid

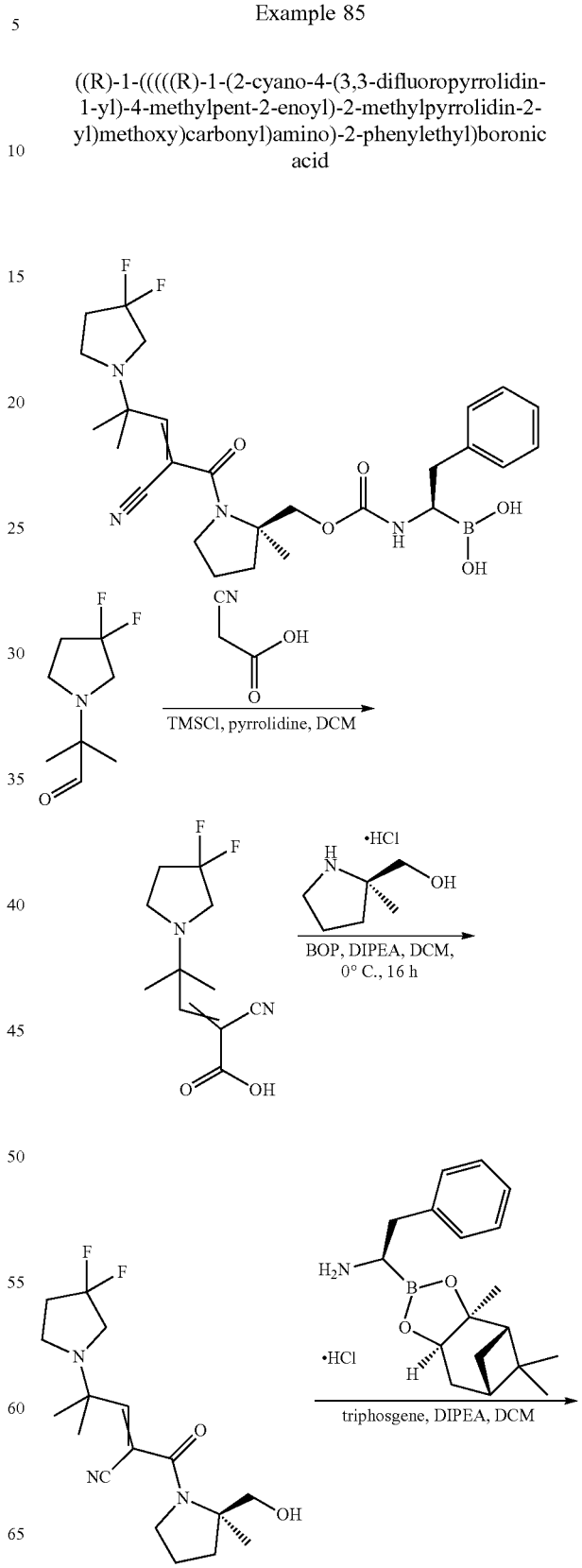

193

-continued

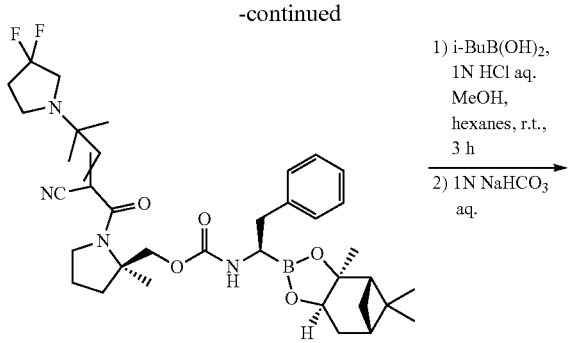

1) i-BuB(OH)₂, 1N HCl aq. MeOH, hexanes, r.t., 3 h
2) 1N NaHCO₃ aq.

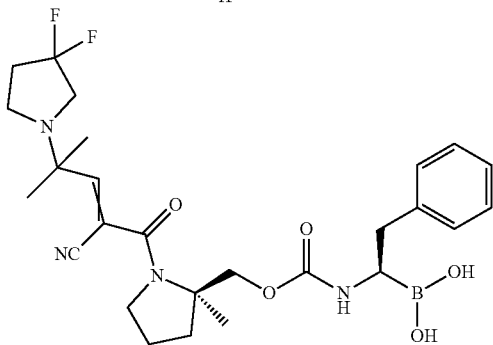

Step 1

To a solution of 2-(3,3-difluoropyrrolidin-1-yl)-2-methylpropanal (2.3 g, 12.98 mmol), 2-cyanoacetic acid (1.10 g, 12.98 mmol) and pyrrolidine (7.39 g, 103.84 mmol) in DCM (30 mL) in ice-water bath was added dropwise chloro (trimethyl)silane (6.58 mL, 51.92 mmol). The reaction was stirred at rt for 2 h, then concentrated in vacuo. The pH of the mixture was adjusted to 5-6 with NaHSO₄ (aq) before extraction with DCM (50 mL×3). The organic layers were combined then washed with brine (50 mL), dried over Na₂SO₄ and concentrated in vacuo. The crude material was purified via silica chromatography to afford the title compound as a yellow solid (800 mg, 25.24%).

Step 2

To a mixture of 2-cyano-4-(3,3-difluoropyrrolidin-1-yl)-4-methylpent-2-enoic acid (342 mg TFA salt, 1.0 mmol), (R)-(2-methylpyrrolidin-2-yl)methanol hydrochloride (152 mg, 1.0 mmol) and DIPEA (780 mg, 6 mmol) in DCM (20 mL) was added portionwise BOP (442 mg, 1 mmol) at 0° C. The resulted mixture was stirred at rt for 12 h, then concentrated to dryness. The crude residue was purified via silica chromatography and a gradient of 0%-100% EtOAc in hexanes to afford (R)-4-(3,3-difluoropyrrolidin-1-yl)-2-(2-(hydroxymethyl)-2-methylpyrrolidine-1-carbonyl)-4-methylpent-2-enenitrile as a colorless oil (230 mg, 67%).

Step 3

Bis(trichloromethyl) carbonate (200 mg, 0.674 mmol) in DCM (1.0 mL) was added dropwise into a stirring solution of (R)-4-(3,3-difluoropyrrolidin-1-yl)-2-(2-(hydroxymethyl)-2-methylpyrrolidine-1-carbonyl)-4-methylpent-2-enenitrile (230 mg, 0.674 mmol) and DIPEA (523 mg, 4 mmol) in DCM (4 mL) at −15° C. The mixture was stirred for 2 h below 0° C. This resulted solution was added dropwise into

194 a well-stirred solution of (R)-2-phenyl-1-((3aS,4S,6S,7aR)-3a,5,5-trimethylhexahydro-4,6-methanobenzo[d][1,3,2]dioxaborol-2-yl)ethanamine hydrochloride (158 mg, 0.472 mmol) and DIPEA (262 mg, 2 mmol) in DCM (3 mL) at 0° C. The reaction was stirred at 0° C. for 1 h, then diluted with DCM (15 mL), washed with brine (5 mL), dried over Na₂SO₄, concentrated in vacuo. The residue was purified by prep-HPLC to afford ((R)-1-(2-cyano-4-(3,3-difluoropyrrolidin-1-yl)-4-methylpent-2-enoyl)-2-methylpyrrolidin-2-yl) methyl ((R)-2-phenyl-1-((3aS,4S,6S,7aR)-3a,5,5-trimethylhexahydro-4,6-methanobenzo[d][1,3,2]dioxaborol-2-yl) ethyl)carbamate as white solid (72 mg, 23%).

Step 4

To a solution of ((R)-1-(2-cyano-4-(3,3-difluoropyrrolidin-1-yl)-4-methylpent-2-enoyl)-2-methylpyrrolidin-2-yl) methyl ((R)-2-phenyl-1-((3aS,4S,6S,7aR)-3a,5,5-trimethylhexahydro-4,6-methanobenzo[d][1,3,2]dioxaborol-2-yl) ethyl)carbamate (72 mg, 0.108 mmol) in MeOH (2.5 mL) were added hexanes (2.5 mL) and 1 N HCl (0.5 mL), followed by isobutyl boric acid (33 mg, 0.324 mmol). After stirred at rt for 3 h and TLC suggested the reaction was completed, the pH of the mixture was adjusted to 7 with NaHCO₃ aq. before the hexanes layer was discarded. The methanol layer was diluted with water (20 mL), then dried over lyophilization to give a crude product which was further purified by Gel column (methanol as eluent) to afford (R)-1-((((R)-1-(2-cyano-4-(3,3-difluoropyrrolidin-1-yl)-4-methylpent-2-enoyl)-2-methylpyrrolidin-2-yl)methoxy)carbonylamino)-2-phenylethylboronic acid as a white solid (26.4 mg, 45%). LC-MS m/z: 555 (M+23).

Example 86

((R)-1-(((((R)-4-(2-cyano-4-(3,3-difluorpyrrolidin-1-yl)-4-methylpent-2-enoyl)morpholin-3-yl)methoxy) carbonyl)amino)-2-(p-tolyl)ethyl)boronic acid

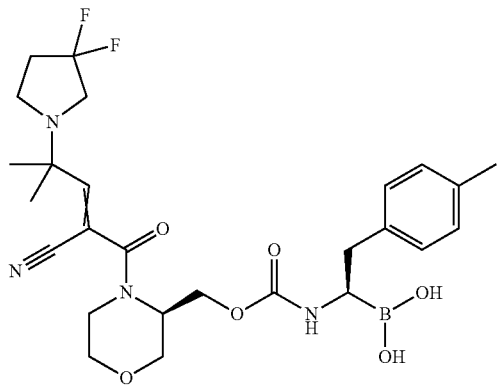 [SMILES: Cc1ccc(C[C@H](NC(=O)OC[C@H]2COCCN2C(=O)C(C#N)=CC(C)(C)N2CCC(F)(F)C2)B(O)O)cc1]

The title compound was prepared as in example 65 by replacing (1R)-2-(1-benzofuran-3-yl)-1-[(1S,2S,6R,8S)-2,9,9-trimethyl-3,5-dioxa-4-boratricyclo[6.1.1.0^2,6]decan-4-yl]ethan-1-amine hydrochloride with (1R)-2-(4-methylphenyl)-1-[(2S,6R)-2,9,9-trimethyl-3,5-dioxa-4-boratricyclo [6.1.1.0^[2,6]]decan-4-yl]ethan-1-amine hydrochloride. LC-MS m/z: 549 (M+1).

Example 87

((R)-2-(benzofuran-3-yl)-1-(((((1S,2R,5R)-3-((E)-4-(dimethylamino)but-2-enoyl)-3-azabicyclo[3.1.0]hexan-2-yl)methoxy)carbonyl)amino)ethyl)boronic acid

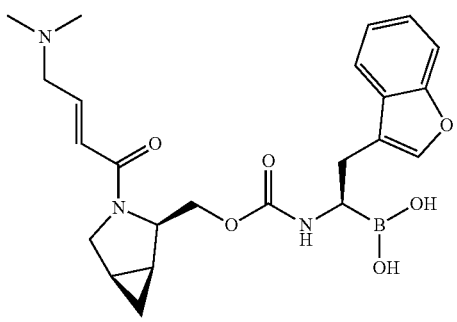 [SMILES: CN(C)C/C=C/C(=O)N1C[C@@H]2C[C@@H]2[C@@H]1COC(=O)N[C@@H](Cc1coc2ccccc12)B(O)O]

The title compound was prepared as in example 52 by replacing prop-2-enoyl chloride with (2E)-4-(dimethylamino)but-2-enoic acid hydrochloride and using HATU as amide coupling reagent. LC-MS m/z: 456 (M+1).

Example 88

((R)-2-(benzofuran-3-yl)-1-(((((1S,2R,5R)-3-(but-2-ynoyl)-3-azabicyclo[3.1.0]hexan-2-yl)methoxy)carbonyl)amino)ethyl)boronic acid

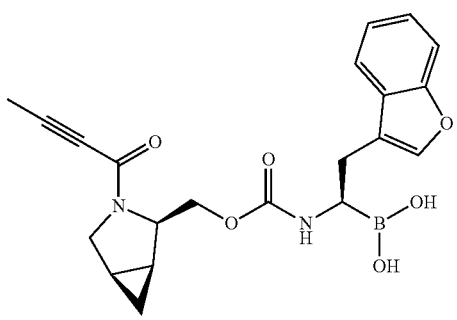 [SMILES: CC#CC(=O)N1C[C@@H]2C[C@@H]2[C@@H]1COC(=O)N[C@@H](Cc1coc2ccccc12)B(O)O]

The title compound was prepared as in example 52 by replacing prop-2-enoyl chloride with but-2-ynoic acid and using HATU as amide coupling reagent. LC-MS m/z: 433 (M+23).

Example 89

((R)-1-(((((2R,4R)-1-acryloyl-4-fluoropyrrolidin-2-yl)methoxy)carbonyl)amino)-2-phenylethyl)boronic acid

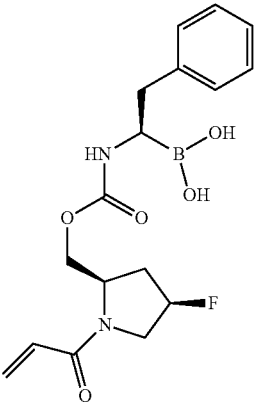 [SMILES: C=CC(=O)N1C[C@H](F)C[C@@H]1COC(=O)N[C@@H](Cc1ccccc1)B(O)O]

Step 1

Into a 100-mL round-bottom flask, was placed a solution of (2R,4R)-1-tert-butyl 2-methyl 4-fluoropyrrolidine-1,2-dicarboxylate (2935 mg, 11.9 mmol), and THF (10 mL) at 0° C. LiBH$_4$ 3 mol/L in THF (5.94 mL. 17.81 mmol) was added slowly for 10 min. The mixture was allowed to warm up to rt and stirred for 20 h. The mixture was cooled to 0° C., dilute acetic acid in water was added, then extracted with EtOAc, followed by washes with saturated NaHCO$_3$ and saturated NaCl. The organic layer was dried with MgSO4, filtered, and concentrated to obtain tert-butyl (2R,4R)-4-fluoro-2-(hydroxymethyl)pyrrolidine-1-carboxylate (2000 mg, 9.12 mmol) as a crude oil.

Step 2

To a solution of (2R,4R)-tert-butyl 4-fluoro-2-(hydroxymethyl)pyrrolidine-1-carboxylate (1.70 g, 7.75 mmol) and triethylamine (3.23 mL, 23.3 mmol) in 70 mL of DCM was added bis(trichloromethyl) carbonate (2761 mg, 9.3 mmol). The mixture was stirred at rt for 10 min and then added to a solution of (R)-2-phenyl-1-((3aS,4S,6S,7aR)-3a,5,5-trimethylhexahydro-4,6-methanobenzo[d][1,3,2]dioxaborol-2-yl)ethanamine hydrochloride (2.00 g, 5.96 mmol) and triethylamine (1.65 mL, 11.9 mmol) in DCM (20 mL) at rt. After stirring 1 h at rt, water and DCM were added, the layers separated, and the organic phase was dried over MgSO$_4$, filtered and concentrated. Purification by column chromatography afforded 544 mg of (2R,4R)-tert-butyl 4-fluoro-2-(((((R)-2-phenyl-1-((3aS,4S,6S,7aR)-3a,5,5-trimethylhexahydro-4,6-methanobenzo[d][1,3,2]dioxaborol-2-yl)ethyl)carbamoyl)oxy)methyl)pyrrolidin-1-carboxylate.

Step 3

Into 25-mL round-bottom flask, was placed (2R,4R)-tert-butyl 4-fluoro-2-(((((R)-2-phenyl-1-((3aS,4S,6S,7aR)-3a,5,5-trimethylhexahydro-4,6-methanobenzo[d][1,3,2]dioxaborol-2-yl)ethyl)carbamoyl)oxy)methyl)pyrrolidine-1-carboxylate (178 mg. 0.330 mmol) which was dissolved in DCM (2 mL). 4N HCl in dioxane (0.7 mL) was added and the reaction mixture stirred at rt for 30 min, then concentrated to oil and placed in high-vacuum overnight. This material was dissolved in DCM (2 mL) and DIPEA (0.2 mL). Acryloyl chloride (0.03 mL, 0.34 mmol) was added. The resulting mixture was stirred for 15 min and then water and DCM were added and the layers separated. The organic layer was dried with MgSO₄ and concentrated to an oil which was purified by preparative HPLC (10-95 water/ACN gradient, 20 min) to obtain 39 mg of ((2R,4S)-1-acryloyl-4-fluoropyrrolidin-2-yl)methyl ((R)-2-phenyl-1-((3aS,4S,6S,7aR)-3a,5,5-trimethylhexahydro-4,6-methanobenzo[d][1,3,2]dioxaborol-2-yl)ethyl)carbamate as a solid.

Step 4

((2R,4S)-1-acryloyl-4-fluoropyrrolidin-2-yl)methyl ((R)-2-phenyl-1-((3aS,4S,6S,7aR)-3a,5,5-trimethylhexahydro-4,6-methanobenzo[d][1,3,2]dioxaborol-2-yl)ethyl)carbamate (39.1 mg, 0.08 mmol) was dissolved in methanol (2 mL) and hexane (2 mL) and 0.1 mL of 1N HCl was added. Isobutylboronic acid (16.02 mg, 0.16 mmol) was then added and the mixture allowed to stir at rt for 2 h. The reaction mixture was concentrated and purified by preparative HPLC (10-95 water/ACN, 20 min). The collected fraction was frozen and lyophilized to obtain the title compound as white solid. LC-MS m/z: 751 (2M+23).

Example 90

((R)-1-(((((2R,4R)-1-((E)-2-cyano-4,4-dimethylpent-2-enoyl)-4-fluoropyrrolidin-2-yl)methoxy)carbonyl)amino)-2-phenylethyl)boronic acid

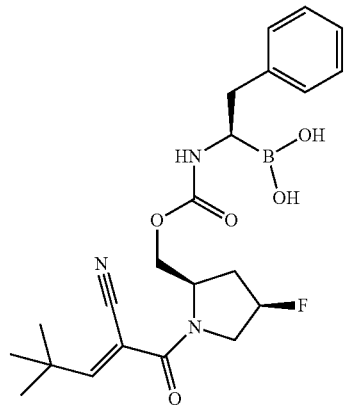 [SMILES: CC(C)(C)/C=C(\C#N)C(=O)N1C[C@H](F)C[C@@H]1COC(=O)N[C@@H](Cc1ccccc1)B(O)O]

The title compound was prepared from ((2R,4S)-4-fluoropyrrolidin-2-yl)methyl ((R)-2-phenyl-1-((3aS,4S,6S,7aR)-3a,5,5-trimethylhexahydro-4,6-methanobenzo[d][1,3,2]dioxaborol-2-yl)ethyl)carbamate as in example 10. LC-MS m/z: 468 (M+23).

Example 91

((R)-1-(((((R)-1-acryloyl-4,4-difluoropyrrolidin-2-yl)methoxy)carbonyl)amino)-2-(benzofuran-3-yl)ethyl)boronic acid

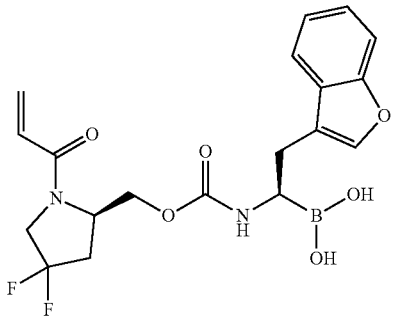 [SMILES: C=CC(=O)N1CC(F)(F)C[C@@H]1COC(=O)N[C@@H](Cc1coc2ccccc12)B(O)O]

The title compound was prepared as in example 36 by replacing tert-butyl (2R)-2-(hydroxymethyl)pyrrolidine-1-carboxylate with tert-butyl (2R)-4,4-difluoro-2-(hydroxymethyl) pyrrolidine-1-carboxylate. LC-MS m/z: 445 (M+23).

Example 92

((R)-1-(((((1S,2R,5R)-3-(2-cyano-3-(4-methyltetrahydro-2H-pyran-4-yl)acryloyl)-3-azabicyclo[3.1.]hexan-2-yl)methoxy)carbonyl)amino)-2-(p-tolyl)ethyl)boronic acid

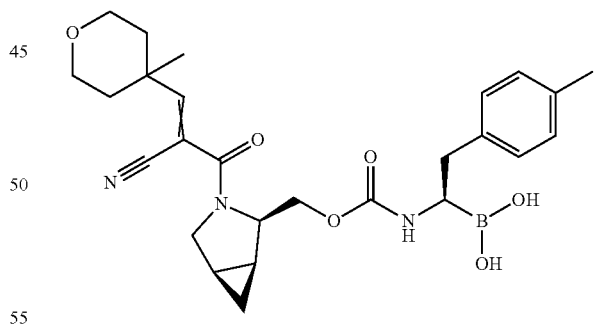

The title compound was prepared as in example 75 by replacing 2-methyl-2-(morpholin-4-yl)propanal with 4-methyloxane-4-carbaldehyde. LC-MS m/z: 518 (M+23).

Example 93

((R)-1-(((((R)-4-acryloylmorpholin-3-yl)methoxy)carbonyl)amino)-2-(benzofuran-3-yl)ethyl)boronic acid

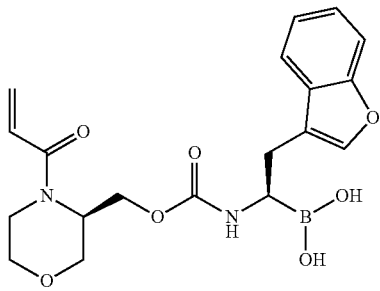 [SMILES: C=CC(=O)N1CCOC[C@@H]1COC(=O)N[C@@H](Cc1coc2ccccc12)B(O)O]

The title compound was prepared as in example 36 by replacing tert-butyl (2R)-2-(hydroxymethyl)pyrrolidine-1-carboxylate with tert-butyl (3S)-3-(hydroxymethyl)morpholine-4-carboxylate. LC-MS m/z: 425 (M+23).

Example 94

((R)-1-(((((R)-4-(2-cyano-4-(3,3-difluoropyrrolidin-1-yl)-4-methylpent-2-enoyl)morpholin-3-yl)methoxy)carbonyl)amino)-2-phenylethyl)boronic acid

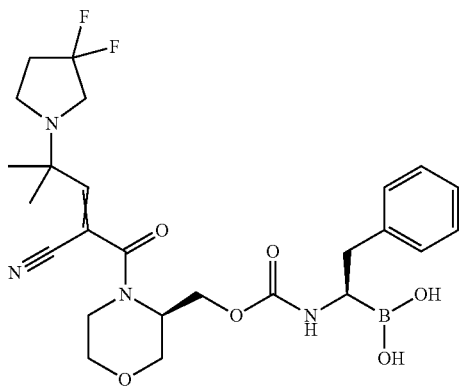 [SMILES: CC(C)(C=C(C#N)C(=O)N1CCOC[C@@H]1COC(=O)N[C@@H](Cc1ccccc1)B(O)O)N1CCC(F)(F)C1]

The title compound was prepared as in example 65 by replacing (1R)-2-(1-benzofuran-3-yl)-1-[(1S,2S,6R,8S)-2,9,9-trimethyl-3,5-dioxa-4-boratricyclo[6.1.1.0^2,6]decan-4-yl]ethan-1-amine hydrochloride with (R)-2-phenyl-1-((3aS,4S,6S,7aR)-3a,5,5-trimethylhexahydro-4,6-methanobenzo[d][1,3,2]dioxaborol-2-yl)ethanamine hydrochloride. LC-MS m/z: 557 (M+23).

Example 95

((R)-1-(((((1S,2R,5R)-3-acryloyl-3-azabicyclo[3.1.0]hexan-2-yl)methoxy)carbonyl)amino)-2-(p-tolyl)ethyl)boronic acid

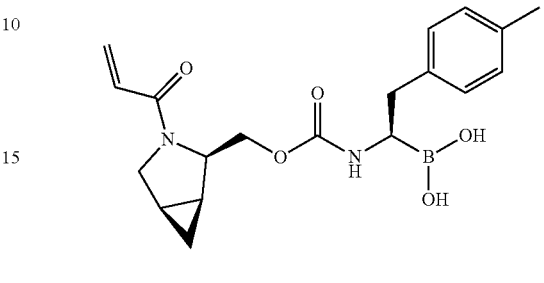

To a 50-mL round-bottom flask, was added (1S,2R,5R)-3-azabicyclo[3.1.0]hexan-2-ylmethyl ((R)-2-(p-tolyl)-1-((3aS,4S,6S,7aR)-3a,5,5-trimethylhexahydro-4,6-methanobenzo[d][1,3,2]dioxaborol-2-yl)ethyl)carbamate hydrochloride (325 mg, 0.72 mmol, 1.00 eq.), prepared as in example 37 but replacing (R)-2-phenyl-1-((3aS,4S,6S,7aR)-3a,5,5-trimethylhexahydro-4,6-methanobenzo[d][1,3,2]dioxaborol-2-yl)ethanamine hydrochloride with (R)-2-(p-tolyl)-1-((3aS,4S,6S,7aR)-3a,5,5-trimethylhexahydro-4,6-methanobenzo[d][1,3,2]dioxaborol-2-yl)ethanamine hydrochloride, dichloromethane (6 mL), TEA (224 mg, 2.21 mmol, 3.00 eq.), and prop-2-enoyl chloride (79 mg, 0.87 mmol, 1.20 eq.). The resulting solution was stirred for 1 h at 25° C. The resulting mixture was washed with 30 mL of brine. The resulting solution was extracted with dichloromethane and the organic layers combined and dried over anhydrous sodium sulfate and concentrated under vacuum. The residue was purified by silica gel chromatography to afford 160 mg (44%) of ((1S,2R,5R)-3-acryloyl-3-azabicyclo[3.1.0]hexan-2-yl)methyl ((R)-2-(p-tolyl)-1-((3aS,4S,6S,7aR)-3a,5,5-trimethylhexahydro-4,6-methanobenzo[d][1,3,2]dioxaborol-2-yl)ethyl)carbamate as a yellow oil.

Into a 50-mL round-bottom flask, was placed ((1S,2R,5R)-3-acryloyl-3-azabicyclo[3.1.0]hexan-2-yl)methyl ((R)-2-(p-tolyl)-1-((3aS,4S,6S,7aR)-3a,5,5-trimethylhexahydro-4,6-methanobenzo[d][1,3,2]dioxaborol-2-yl)ethyl)carbamate (160 mg, 0.32 mmol. 1.00 eq.), methanol (7 mL), (2-methylpropyl)boronic acid (97 mg, 0.95 mmol, 3.00 eq.), hexane (7 mL), and 1N HCl (6.3 mL, 20.0 eq.). The resulting solution was stirred for 1 h at 25° C. The resulting mixture was washed with 3×7 mL of hexane. The methanol layer was diluted with 10 mL of water, and dried over lyophylization to give a crude product which was further purified by Prep-HPLC with the following conditions: Column, XBridge Prep C18 OBD Column, 5 um, 19*150 mm; mobile phase, Water (0.05% TFA) and ACN (35.0% ACN up to 40.0% in 8 min); Detector. UV 254 nm. This resulted in 36.1 mg (31%) of ((R)-1-(((((1S,2R,5R)-3-acryloyl-3-azabicyclo[3.1.0]hexan-2-yl)methoxy)carbonyl)amino)-2-(p-tolyl)ethyl)boronic acid as an off-white solid. LC-MS m/z: 395 (M+23).

Example 96

((R)-1-((((R)-1-(2-cyano-4-(3,3-difluoropyrrolidin-1-yl)-4-methylpent-2-enoyl)piperidin-2-yl)methoxy)carbonyl)amino)-2-(3-methoxyphenyl)ethyl)boronic acid

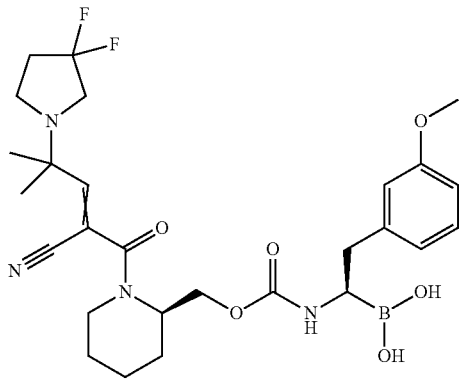 [SMILES: COc1cccc(C[C@H](NC(=O)OC[C@H]2CCCCN2C(=O)C(C#N)=CC(C)(C)N2CCC(F)(F)C2)B(O)O)c1]

The title compound was prepared as in example 46 but starting with (R)-2-(3-methoxyphenyl)-1 (3aS,4S,6S,7aR)-3a,5,5-trimethylhexahydro-4,6-methanobenzo[d][1,3,2]dioxaborol-2-yl)ethanamine which was prepared by the method used in example 16 to prepare (R)-2-(benzofuran-3-yl)-1-((3aS,4S,6S,7aR)-3a,5,5-trimethylhexahydro-4,6-methanobenzo[d][1,3,2]dioxaborol-2-yl)ethanamine hydrochloride but replacing 1-benzofuran-3-ylmethanol with (3-methoxyphenyl)methanol. LC-MS m/z: 585 (M+23).

Example 97

((R)-1-(((((R)-1-(2-cyano-4-methyl-4-(methyl(2,2,2-trifluoroethyl)amino)pent-2-enoyl)piperidin-2-yl)methoxy)carbonyl)amino)-2-phenylethyl)boronic acid

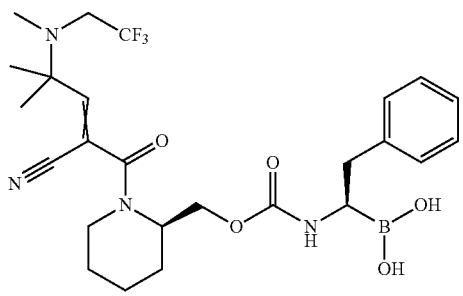 [SMILES: CN(CC(F)(F)F)C(C)(C)C=C(C#N)C(=O)N1CCCC[C@@H]1COC(=O)N[C@@H](Cc1ccccc1)B(O)O]

The title compound was prepared as in example 27 but using 2-methyl-2-(methyl(2,2,2-trifluoroethyl)amino)propanal in place of 2-methyl-2-(pyrrolidin-1-yl)propanal. LC-MS m/z: 561 (M+23).

Example 98

((R)-1-(((((R)-4-(2-cyano-4-(3,3-difluoropyrrolidin-1-yl)-4-methylpent-2-enoyl)morpholin-3-yl)methoxy)carbonyl)amino)-3-phenylpropyl)boronic acid

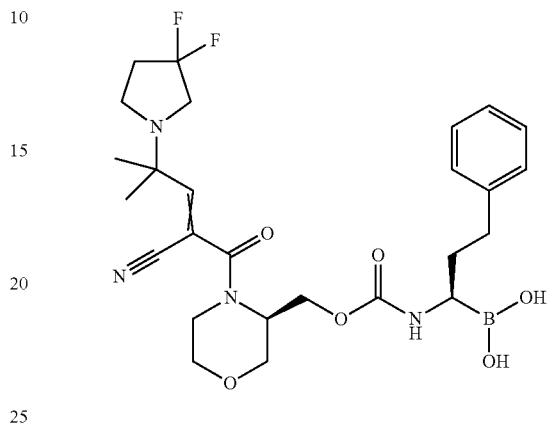

Into a 100-mL 3-necked round-bottom flask purged and maintained with an inert atmosphere of nitrogen, was placed (1R)-3-phenyl-1-tetramethyl-1,3,2-dioxaborolan-2-yl)propan-1-amine hydrochloride (821 mg, 2.76 mmol, 0.90 eq.), dichloromethane (18 mL), and DIEA (1.44 mL. 3.00 eq.). This was followed by the addition of a solution of tert-butyl (3R)-3-[[(chlorocarbonyl)oxy]methyl]morpholine-4-carboxylate (779 mg, 2.78 mmol), prepared as in example 43, in dichloromethane (18 mL) dropwise with stirring at 0° C. The resulting solution was stirred for 1 h at rt, then washed with water and brine. The mixture was dried over anhydrous sodium sulfate, concentrated and purified by silica gel chromatography to afford in 0.65 g of tert-butyl(3R)-3-[([[(1R)-3-phenyl-1-(tetramethyl-1,3,2-dioxaborolan-2-yl)propyl]carbamoyl]oxy)methyl]morpholine-4-carboxylate as light yellow crude oil.

Into a 100-mL round-bottom flask, was placed tert-butyl (3R)-3-[([[(1R)-3-phenyl-1-(tetramethyl-1,3,2-dioxaborolan-2-yl)propyl]carbamoyl]oxy)methyl]morpholine-4-carboxylate (650 mg, 1.29 mmol), ether (10 mL), and (1S,2S,3R,5S)-2,6,6-trimethylbicyclo[3.1.1]heptane-2,3-diol (287 mg, 1.69 mmol). The resulting solution was stirred for 2 days at it, dried over anhydrous sodium sulfate and concentrated under vacuum. The crude product was purified by preparative HPLC to afford 190 mg of (R)-tert-butyl 3-(((((R)-3-phenyl-1-((3aS,4S,6S,7aR)-3a,5,5-trimethylhexahydro-4,6-methanobenzo[d][1,3,2]dioxaborol-2-yl)propyl)carbamoyl)oxy)methyl)morpholine-4-carboxylate as a light yellow solid. Proceeding with this material as in example 28 afforded ((R)-1-(((((R)-4-(2-cyano-4-(3,3-difluoropyrrolidin-1-yl)-4-methylpent-2-enoyl)morpholin-3-yl)methoxy)carbonyl)amino)-3-phenylpropyl)boronic acid. LC-MS m/z: 549 (M+1).

Example 99

((R)-1-(((((1S,2R,5R)-3-acryloyl-3-azabicyclo[3.1.0]hexan-2-yl)methoxy)carbonyl)amino)-2-phenylethyl)boronic acid

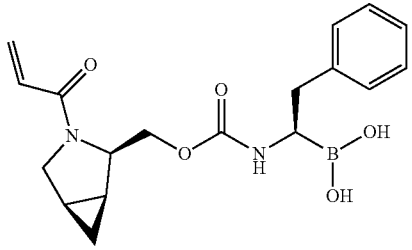 [SMILES: C=CC(=O)N1C[C@@H]2C[C@@H]2[C@@H]1COC(=O)N[C@@H](Cc1ccccc1)B(O)O]

The title compound was prepared as in example 95 but using (1S,2R,5R)-3-azabicyclo[3.1.0]hexan-2-ylmethyl ((R)-3-phenyl-1-((3aS,4S,6S,7aR)-3a,5,5-trimethylhexahydro-4,6-methanobenzo[d][1,3,2]dioxaborol-2-yl)propyl)carbamate, prepared as in example 26.

Example 100

((R)-1-(((((2R,4S)-1-acryloyl-4-fluoropyrrolidin-2-yl)methoxy)carbonyl)amino)-2-phenylethyl)boronic acid

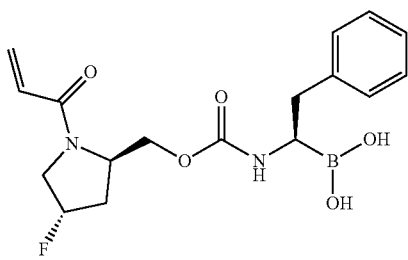 [SMILES: C=CC(=O)N1C[C@@H](F)C[C@@H]1COC(=O)N[C@@H](Cc1ccccc1)B(O)O]

The title compound was prepared as in example 89 but using (2R,4S)-1-tert-butyl 2-methyl 4-fluoropyrrolidine-1,2-dicarboxylate rather than (2R,4R)-1-tert-butyl 2-methyl 4-fluoropyrrolidine-1,2-dicarboxylate as a starting material.

Example 101

((R)-1-(((((R)-1-(2-cyano-4-(3,3-difluoropyrrolidin-1-yl)-4-methylpent-2-enoyl)piperidin-2-yl)methoxy)carbonyl)amino)-3-phenylpropyl)boronic acid

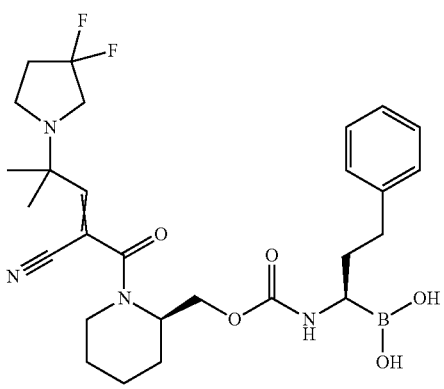 [SMILES: CC(C)(C=C(C#N)C(=O)N1CCCC[C@@H]1COC(=O)N[C@@H](CCc1ccccc1)B(O)O)N1CCC(F)(F)C1]

The title compound was prepared as in example 98 but starting with tert-butyl (2R)-2-[[(chlorocarbonyl)oxy]methyl]piperidine-1-carboxylate in place of tert-butyl (3R)-3-[[(chlorocarbonyl)oxy]methyl]morpholine-4-carboxylate.

Example 102

((R)-1-(((((2R,4S)-1-((E)-2-cyano-4,4-dimethylpent-2-enoyl)-4-fluoropyrrolidin-2-yl)methoxy)carbonyl)amino)-2-phenylethyl)boronic acid

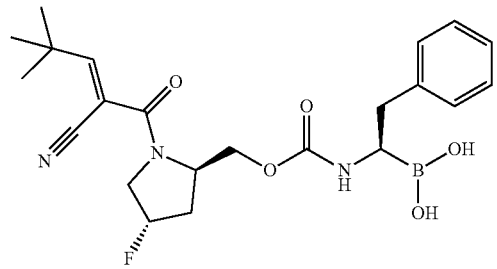 [SMILES: CC(C)(C)/C=C(\C#N)C(=O)N1C[C@@H](F)C[C@@H]1COC(=O)N[C@@H](Cc1ccccc1)B(O)O]

The title compound was prepared as in example 90 but starting with ((2R,4S)-4-fluoropyrrolidin-2-yl)methyl ((R)-2-phenyl-1-((3aS,4S,6S,7aR)-3a,5,5-trimethylhexahydro-4,6-methanobenzo[d][1,3,2]dioxaborol-2-yl)ethyl)carbamate hydrochloride, prepared from as in example 89 from (2R,4S)-1-tert-butyl 2-methyl 4-fluoropyrrolidine-1,2-dicarboxylate.

Example 103

((R)-1-(((((R)-1-((Z)-2-cyano-4-(3,3-difluoropyrrolidin-1-yl)-4-methylpent-2-enoyl)piperidin-2-yl)methoxy)carbonyl)amino)-2-phenylethyl)boronic acid

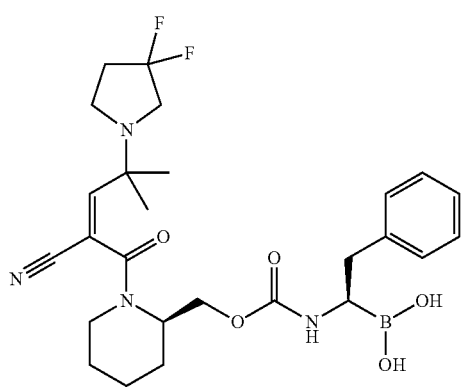 [SMILES: CC(C)(/C=C(/C#N)C(=O)N1CCCC[C@@H]1COC(=O)N[C@@H](Cc1ccccc1)B(O)O)N1CCC(F)(F)C1]

The title compound was prepared as in example 28 as a mixture of isomers. Into a 250-mL round-bottom flask, was placed ((R)-1-(2-cyano-4-(3,3-difluoropyrrolidin-1-yl)-4-methylpent-2-enoyl)piperidin-2-yl)methyl ((R)-2-phenyl-1-((3aS,4S,6S,7aR)-3a,5,5-trimethylhexahydro-4,6-methanobenzo[d][1,3,2]dioxaborol-2-yl)ethyl)carbamate (500 mg, 0.75 mmol), hexane (15 mL), methanol (15 mL), (2-methylpropyl)boronic acid (230 mg, 2.26 mmol), and 1N hydrogen chloride (15 mL). The resulting solution was stirred for 1 h at rt. The resulting mixture was washed with 3×5 mL of hexane. The methanol layer was diluted with 50 mL of water, and dried by lyophylization to give a crude product which was further purified by Prep-HPLC with the following conditions: Column, XBridge Prep C18 OBD Column, 5 um, 19*150 mm; mobile phase, Water (10 mmol/L HCOOH) and ACN (65.0% ACN up to 90.0% in 10 min); Detector, uv 254 nm. This resulted in 302 mg of the major isomer (assigned E) of compound example 28 and 27.6 mg of ((R)-1-(((((R)-1-((Z)-2-cyano-4-3,3-difluoropyrrolidin-1-yl)-4-methylpent-2-enoyl)piperidin-2-yl)methoxy)carbonyl)amino)-2-phenylethyl)boronic acid as a white solid. LC-MS m/z: 533 (M+1).

Example 104

((R)-1-(((((1S,2R,5R)-3-(2-cyano-4-(3,3-difluoropyrrolidin-1-yl)-4-methylpent-2-enoyl)-3-azabicyclo[3.1.0]hexan-2-yl)methoxy)carbonyl)amino)-3-phenylpropyl)boronic acid

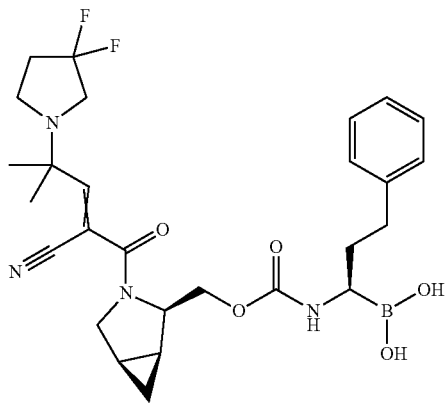 [SMILES: CC(C)(C=C(C#N)C(=O)N1C[C@@H]2C[C@@H]2[C@@H]1COC(=O)N[C@@H](CCc1ccccc1)B(O)O)N1CCC(F)(F)C1]

The title compound was prepared as in example 54 but replacing (R)-2-(benzofuran-3-yl)-1-((3aS,4S,6S,7aR)-3a,5,5-trimethylhexahydro-4,6-methanobenzo[d][1,3,2]dioxaborol-2-yl)ethanamine hydrochloride with (R)-tert-butyl 3-(((((R)-3-phenyl-1-((3aS,4S,6S,7aR)-3a,5,5-trimethylhexahydro-4,6-methanobenzo[d][1,3,2]dioxaborol-2-yl)propyl)carbamoyl)oxy)methyl)morpholine-4-carboxylate as prepared in example 98.

Example 105

((R)-1-(((((R)-1-(2-cyano-4-(3,3-difluoropyrrolidin-1-yl)-4-methylpent-2-enoyl)piperidin-2-yl)methoxy)carbonyl)amino)-3-methylbutyl)boronic acid

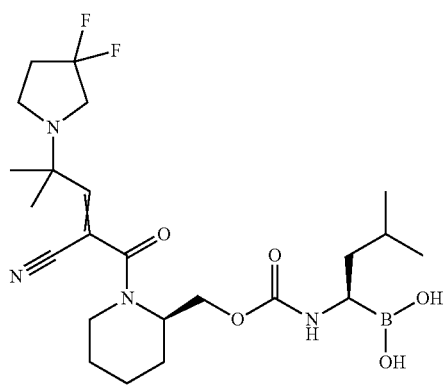 [SMILES: CC(C)C[C@H](NC(=O)OC[C@H]1CCCCN1C(=O)C(C#N)=CC(C)(C)N1CCC(F)(F)C1)B(O)O]

The title compound was prepared as in example 28, but replacing (R)-2-phenyl-1-((3aS,4S,6S,7aR)-3a,5,5-trimethylhexahydro-4,6-methanobenzo[d][1,3,2]dioxaborol-2-yl)ethanamine hydrochloride with (R)-3-methyl-1-((3aS,4S,6S,7aR)-3a,5,5-trimethylhexahydro-4,6-methanobenzo[d][1,3,2]dioxaborol-2-yl)butan-1-amine hydrochloride.

Example 106

((R)-1-(((((R)-1-(2-cyano-4-(3,3-difluoropyrrolidin-1-yl)-4-methylpent-2-enoyl)piperidin-2-yl)methoxy)carbonyl)amino)-2-(naphthalen-1-yl)ethyl)boronic acid

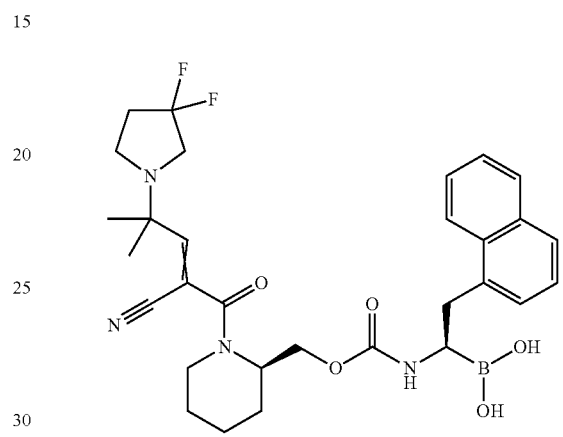

The title compound was prepared as in example 28, but replacing (R)-2-phenyl-1-((3aS,4S,6S,7aR)-3a,5,5-trimethylhexahydro-4,6-methanobenzo[d][1,3,2]dioxaborol-2-yl)ethanamine hydrochloride with (R)-2-(naphthalen-1-yl)-1-((3aS,4S,6S,7aR)-3a,5,5-trimethylhexahydro-4,6-methanobenzo[d][1,3,2]dioxaborol-2-yl)ethanamine hydrochloride.

Example 107

((R)-1-(((((R)-1-(2-cyano-4-(3,3-difluoropyrrolidin-1-yl)-4-methylpent-2-enoyl)piperidin-2-yl)methoxy)carbonyl)amino)-2-(2-cyanophenyl)ethyl)boronic acid

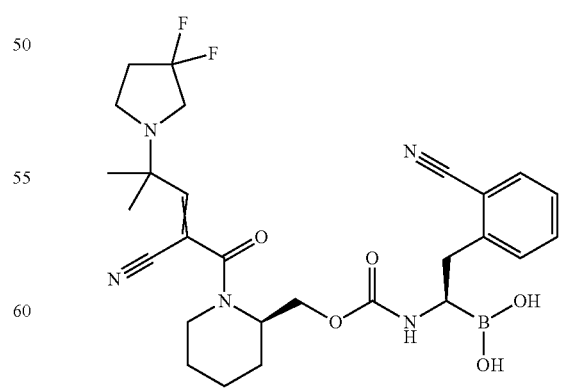

The title compound was prepared as in example 28, but replacing (R)-2-phenyl-1-((3aS,4S,6S,7aR)-3a,5,5-trimethylhexahydro-4,6-methanobenzo[d][1,3,2]dioxaborol-2-yl)

ethanamine hydrochloride with 2-((R)-2-amino-2-((3aS,4S, 6S,7aR)-3a,5,5-trimethylhexahydro-4,6-methanobenzo[d] [1,3,2]dioxaborol-2-yl)ethyl)benzonitrile hydrochloride.

Example 108

((R)-1-(((((1S,2R,5R)-3-(2-cyano-4-(3,3-difluoropyr-rolidin-1-yl)-4-methylpent-2-enoyl)-3-azabicyclo [3.1.0]hexan-2-yl)methoxy)carbonyl)amino)-2-(4-fluorophenyl)ethyl)boronic acid

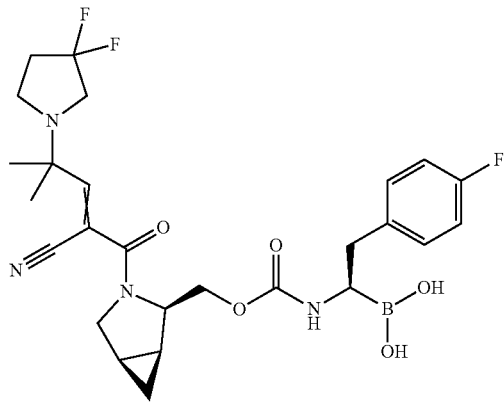 [SMILES: CC(C)(C=C(C#N)C(=O)N1C[C@@H]2C[C@@H]2[C@@H]1COC(=O)N[C@@H](Cc1ccc(F)cc1)B(O)O)N1CCC(F)(F)C1]

The title compound was prepared as in example 74, but replacing (R)-2-phenyl-1-((3aS,4S,6S,7aR)-3a,5,5-trimethylhexahydro-4,6-methanobenzo[d][1,3,2]dioxaborol-2-yl) ethanamine hydrochloride with (R)-2-(4-fluorophenyl)-1-((3aS,4S,6S,7aR)-3a,5,5-trimethylhexahydro-4,6-methanobenzo[d][1,3,2]dioxaborol-2-yl)ethanamine hydrochloride.

Example 109

((R)-1-((((1S,2R,5R)-3-acryloyl-3-azabicyclo[3.1.0] hexan-2-yl)methoxy)carbonyl)amino)-2-(4-fluorophenyl)ethyl)boronic acid

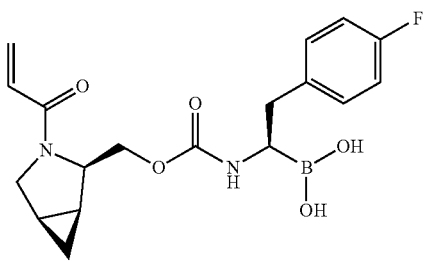 [SMILES: C=CC(=O)N1C[C@@H]2C[C@@H]2[C@@H]1COC(=O)N[C@@H](Cc1ccc(F)cc1)B(O)O]

The title compound was prepared as in example 95, but replacing (R)-2-(p-tolyl)-1-((3aS,4S,6S,7aR)-3a,5,5-trimethylhexahydro-4,6-methanobenzo[d][1,3,2]dioxaborol-2-yl)ethanamine hydrochloride with (R)-2-(4-fluorophenyl)-1-((3aS,4S,6S,7aR)-3a,5,5-trimethylhexahydro-4,6-methanobenzo[d][1,3,2]dioxaborol-2-yl)ethanamine hydrochloride.

Example 110

((R)-1-(((((R)-1-(2-cyano-4-(3,3-difluoropyrrolidin-1-yl)-4-methylpent-2-enoyl)piperidin-2-yl)methoxy) carbonyl)amino)-2-(2-(trifluoromethyl)phenyl)ethyl) boronic acid

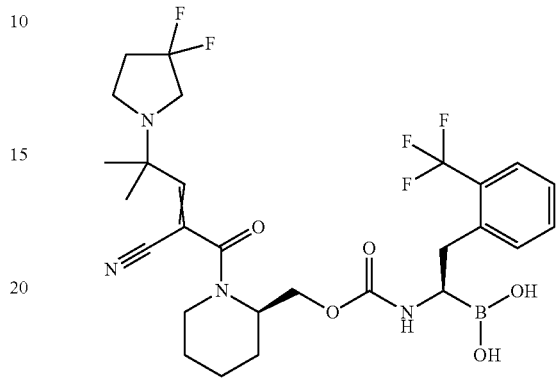

The title compound was prepared as in example 28, but replacing (R)-2-phenyl-1-((3aS,4S,6S,7aR)-3a,5,5-trimethylhexahydro-4,6-methanobenzo[d][1,3,2]dioxaborol-2-yl) ethanamine hydrochloride with (R)-2-(2-(trifluoromethyl) phenyl)-1-((3aS,4S,6S,7aR)-3a,5,5-trimethylhexahydro-4, 6-methanobenzo[d][1,3,2]dioxaborol-2-yl)ethanamine hydrochloride.

Example 111

((R)-1-((((S)-4-acryloyl-1,1-dioxidothiomorpholin-3-yl)methoxy)carbonyl)amino)-2-(benzofuran-3-yl) ethyl)boronic acid

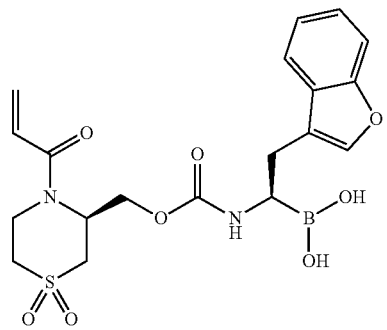 [SMILES: C=CC(=O)N1CCS(=O)(=O)C[C@@H]1COC(=O)N[C@@H](Cc1coc2ccccc12)B(O)O]

Into a 100-mL round-bottom flask, was placed (3S)-thiomorpholine-3-carboxylic acid (500 mg, 3.40 mmol), DCM (15 mL), TEA (1.32 mL, 9.50 mmol), and Boc$_2$O (0.9 g, 4.1 mmol). The resulting solution was stirred for 4 h at rt. The resulting mixture was washed with 1×50 mL of 1M HCl and 1×50 mL of brine, dried over anhydrous sodium sulfate and concentrated. The residue was purified by silica gel chromatography to afford 0.49 g of (3S)-4-[(tert-butoxy) carbonyl]thiomorpholine-3-carboxylic acid as a light yellow solid.

Into a 100-mL round-bottom flask purged and maintained with an inert atmosphere of nitrogen, was placed (3S)-4-[(tert-butoxy)carbonyl]thiomorpholine-3-carboxylic acid (696.9 mg, 2.82 mmol), THF (25 mL), and TEA (0.47 mL, 3.38 mmol). This was followed by the addition of chloro (2-methylpropoxy)methanone (0.402 mL) at −10° C. The resulting solution was stirred for 1 hr at −10° C. The solids were filtered out. To this filtrate was added a solution of NaBH$_4$ (0.427 g, 11.3 mmol) in 1.1 mL of H$_2$O. The resulting solution was stirred for 1 hr at −10° C. then diluted with 50 mL of H$_2$O. The resulting solution was extracted with 50 mL of ethyl acetate and the organic phase washed with 1M HCl and water. The organic phase was dried over anhydrous sodium sulfate and concentrated under vacuum. The residue was purified by silica gel chromatography to afford 0.58 g of tert-butyl (3S)-3-(hydroxymethyl) thiomorpholine-4-carboxylate as an off-white solid.

Into a 100-mL round-bottom flask, was placed tert-butyl (3S)-3-(hydroxymethyl) thiomorpholine-4-carboxylate (0.58 g. 2.49 mmol) and Et$_2$O (20 mL). This was followed by the addition of m-CPBA (0.859 g) at 0° C. The resulting solution was stirred for 3 h at rt before being concentrated. The residue was purified by silica gel chromatography to afford 0.59 g of (S)-tert-butyl 3-(hydroxymethyl)thiomorpholine-4-carboxylate 1,1-dioxide as a white solid.

The title compound was then prepared as in example 36, but replacing tert-butyl (2R)-2-(hydroxymethyl)pyrrolidine-1-carboxylate with (S)-tert-butyl 3-(hydroxymethyl)thiomorpholine-4-carboxylate 1,1-dioxide. LC-MS m/z: 451 (M+1).

Example 112

((R)-1-(((((R)-1-acryloyl-4,4-difluoropiperidin-2-yl) methoxy)carbonyl)amino)-2-(benzofuran-3-yl)ethyl) boronic acid

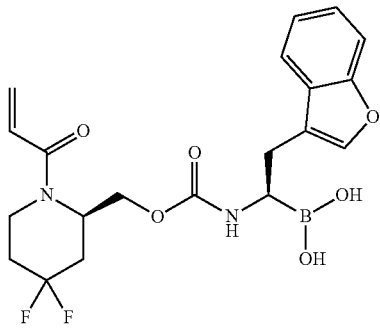 [SMILES: C=CC(=O)N1CCC(F)(F)C[C@@H]1COC(=O)N[C@@H](Cc1coc2ccccc12)B(O)O]

Into a 250-mL round-bottom flask, was placed a solution of 1-tert-butyl 2-methyl (2R)-4-oxopiperidine-1,2-dicarboxylate (2.17 g, 8.43 mmol) in dichloromethane (100 mL). This was followed by the addition of Deoxo-Fluor (7.2 mL) dropwise with stirring at −78° C. The resulting solution was stirred for 3 h at −78° C. than warmed to rt and stirred overnight. The reaction was then quenched by the addition of 20 mL of water/ice. The resulting solution was extracted with dichloromethane and the organic layers combined and dried over anhydrous sodium sulfate and concentrated under vacuum. The residue was purified by silica gel chromatography to afford 1.5 g of 1-tert-butyl 2-methyl (2R)-4,4-difluoropiperidine-1,2-dicarboxylate as a yellow oil.

Into a 50-mL round-bottom flask was added 15 mL of tetrahydrofuran followed by a 2M solution of LiBH$_4$ in THF (5.4 mL, 2.00 eq.). To this was added a 1-tert-butyl 2-methyl (2R)-4,4-difluoropiperidine-1,2-dicarboxylate (1.5 g, 5.37 mmol). The resulting solution was stirred overnight at it, then diluted with 50 mL of EtOAc and washed with 20 mL of water. The mixture was dried over anhydrous sodium sulfate and concentrated under vacuum. The residue as purified by silica gel chromatography to afford 1 g of tert-butyl (2R)-4,4-difluoro-2-(hydroxymethyl)piperidine-1-carboxylate as a white solid.

The title compound was then prepared as in example 36, but replacing tert-butyl (2R)-2-(hydroxymethyl)pyrrolidine-1-carboxylate with tert-butyl (2R)-4,4-difluoro-2-(hydroxymethyl)piperidine-1-carboxylate. LC-MS m/z: 459 (M+23).

Example 113

((R)-1-(((((R)-1-(2-cyano-4-(3,3-difluoropyrrolidin-1-yl)-4-methylpent-2-enoyl)piperidin-2-yl)methoxy) carbonyl)amino)-2-(2,4-difluorophenyl)ethyl)boronic acid

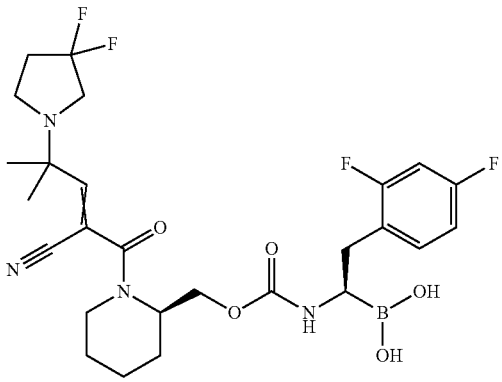 [SMILES: CC(C)(C=C(C#N)C(=O)N1CCCC[C@@H]1COC(=O)N[C@@H](Cc1ccc(F)cc1F)B(O)O)N1CCC(F)(F)C1]

The title compound was prepared as in example 28, but replacing (R)-2-phenyl-1-((3aS,4S,6S,7aR)-3a,5,5-trimethylhexahydro-4,6-methanobenzo[d][1,3,2]dioxaborol-2-yl) ethanamine hydrochloride with (R)-2-(2,4-difluorophenyl)-1-((3aS,4S,6S,7aR)-3a,5,5-trimethylhexahydro-4,6-methanobenzo[d][1,3,2]dioxaborol-2-yl)ethanamine hydrochloride. LC-MS m/z: 591 (M+23).

Example 114

((R)-1-((((1S,2R,5R)-3-(2-cyano-4-methyl-4-morpholinopent-2-enoyl)-3-azabicyclo[3.1.0]hexan-2-yl) methoxy)carbonyl)amino)-2-(4-(trifluoromethyl) phenyl)ethyl)boronic acid

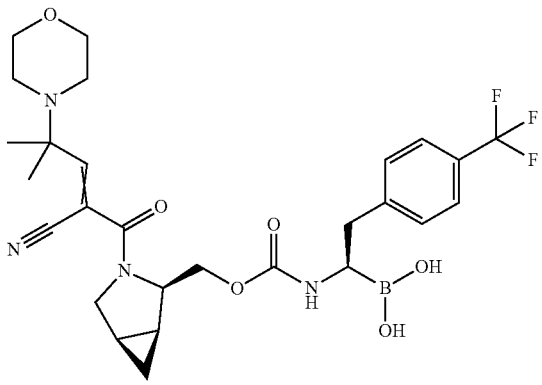 [SMILES: CC(C)(C=C(C#N)C(=O)N1C[C@@H]2C[C@@H]2[C@@H]1COC(=O)N[C@@H](Cc1ccc(C(F)(F)F)cc1)B(O)O)N1CCOCC1]

The title compound was prepared as in example 67 but replacing (R)-2-phenyl-1-((3aS,4S,6S,7aR)-3a,5,5-trimethylhexahydro-4,6-methanobenzo[d][1,3,2]dioxaborol-2-yl)ethanamine hydrochloride with (R)-2-(4-(trifluoromethyl)phenyl)-1-((3aS,4S,6S,7aR)-3a,5,5-trimethylhexahydro-4,6-methanobenzo[d][1,3,2]dioxaborol-2-yl)ethanamine hydrochloride. LC-MS m/z: 579 (M+1).

Example 115

((R)-1-(((((1S,2R,5R)-3-acryloyl-3-azabicyclo[3.1.0]hexan-2-yl)methoxy)carbonyl)amino)-2-(4-(trifluoromethyl)phenyl)ethyl)boronic acid

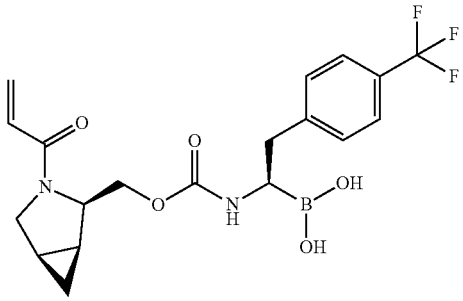 [SMILES: C=CC(=O)N1C[C@@H]2C[C@@H]2[C@@H]1COC(=O)N[C@@H](Cc1ccc(C(F)(F)F)cc1)B(O)O]

The title compound was prepared as in example 52 but replacing (R)-2-phenyl-1-((3aS,4S,6S,7aR)-3a,5,5-trimethylhexahydro-4,6-methanobenzo[d][1,3,2]dioxaborol-2-yl)ethanamine hydrochloride with (R)-2-(4-(trifluoromethyl)phenyl)-1-((3aS,4S,6S,7aR)-3a,5,5-trimethylhexahydro-4,6-methanobenzo[d][1,3,2]dioxaborol-2-yl)ethanamine hydrochloride.

Example 116

((R)-1-(((((1S,2R,5R)-3-(2-cyano-4-(3,3-difluoropyrrolidin-1-yl)-4-methylpent-2-enoyl)-3-azabicyclo[3.1.0]hexan-2-yl)methoxy)carbonyl)amino)-2-(p-tolyl)ethyl)boronic acid

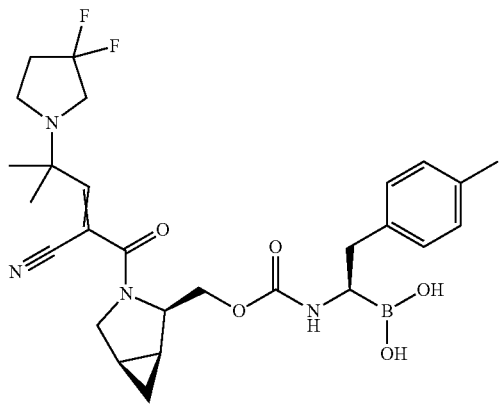 [SMILES: Cc1ccc(C[C@H](NC(=O)OC[C@H]2[C@H]3C[C@H]3CN2C(=O)C(C#N)=CC(C)(C)N2CCC(F)(F)C2)B(O)O)cc1]

The title compound was prepared as in example 54 but replacing (R)-2-(benzofuran-3-yl)-1-((3aS,4S,6S,7aR)-3a,5,5-trimethylhexahydro-4,6-methanobenzo[d][1,3,2]dioxaborol-2-yl)ethanamine hydrochloride with (R)-2-(p-tolyl)-1-((3aS,4S,6S,7aR)-3a,5,5-trimethylhexahydro-4,6-methanobenzo[d][1,3,2]dioxaborol-2-yl)ethanamine hydrochloride. LC-MS m/z: 545 (M+1).

Example 117

((R)-2-(benzofuran-3-yl)-1-(((((R)-1-(2-cyano-4-(3,3-difluoropyrrolidin-1-yl)-4-methylpent-2-enoyl)-2-methylpyrrolidin-2-yl)methoxy)carbonyl)amino)ethyl)boronic acid

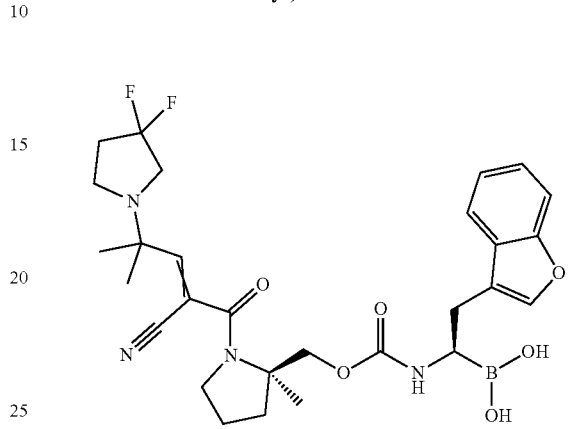

To a solution of 2-(3,3-difluoropyrrolidin-1-yl)-2-methylpropanal (2.3 g, 13 mmol), 2-cyanoacetic acid (1.10 g, 13 mmol) and pyrrolidine (7.39 g, 104 mmol) in DCM (30 mL) in ice-water bath was added dropwise chloro(trimethyl)silane (6.58 mL, 51.9 mmol). The reaction was stirred at rt for 2 h. then concentrated in vacuo. The pH of the mixture was adjusted to 5-6 with $NaHSO_4$ (aq) before extraction with DCM (50 mL×3). The organic layers were combined then washed with brine (50 mL), dried over $Na_2SO_4$ and concentrated in vacuo. The crude material was purified via silica chromatography to afford 2-cyano-4-(3,3-difluoropyrrolidin-1-yl)-4-methylpent-2-enoic acid as a yellow solid (800 mg).

To a mixture of 2-cyano-4-(3,3-difluoropyrrolidin-1-yl)-4-methylpent-2-enoic acid (342 mg TFA salt), (R)-2-methylpyrrolidin-2-yl)methanol hydrochloride (152 mg. 1.0 mmol) and DIPEA (780 mg, 6 mmol) in DCM (20 mL) was added portionwise BOP (442 mg, 1 mmol) at 0° C. The resulting mixture was stirred at rt for 12 h, and then concentrated to dryness. The crude residue was purified via silica chromatography and a gradient of 0%-100% EtOAc in hexanes to afford (R)-4-(3,3-difluoropyrrolidin-1-yl)-2-(2-(hydroxymethyl)-2-methylpyrrolidine-1-carbonyl)-4-methylpent-2-enenitrile as a colorless oil (230 mg).

Bis(trichloromethyl) carbonate (156 mg, 0.53 mmol) in DCM (1.5 mL) was added dropwise into a stirring solution of (R)-4-(3,3-difluoropyrrolidin-1-yl)-2-(2-(hydroxymethyl)-2-methylpyrrolidine-1-carbonyl)-4-methylpent-2-enenitrile (200 mg, 0.59 mmol) and DIPEA (456 mg, 3.54 mmol) in DCM (10 mL) at 0° C. The mixture was stirred for 2 h at 0° C. and added dropwise into a well-stirred solution of (R)-2-(benzofuran-3-yl)-1-((3aS,4S,6S,7aR)-3a,5,5-trimethylhexahydro-4,6-methanobenzo[d][1,3,2]dioxaborol-2-yl)ethan-1-amine hydrochloride (221 mg, 0.59 mmol) and DIPEA (228 mg, 1.77 mmol) in DCM (10 mL) at 0° C. The reaction was stirred at 0° C. for 1 h, then diluted with DCM (25 mL), washed with water (10 mL) and brine (10 mL), dried over $Na_2SO_4$, concentrated in vacuo. The residue was purified via silica chromatography and a gradient of 50%-90% EtOAc in hexanes to afford ((R)-1-(2-cyano-4-(3,3- difluoropyrrolidin-1-yl)-4-methylpent-2-enoyl)-2-methylpyrrolidin-2-yl)methyl ((R)-2-(benzofuran-3-yl)-1-((3aS,4S,6S,7aR)-3a,5,5-trimethylhexahydro-4,6-methanobenzo[d][1,3,2]dioxaborol-2-yl)ethyl)carbamate as white solid (120 mg). Hydrolysis of the boronate as in example 1, step 6, and purification by preparative HPLC, afforded 78 mg of the title compound as a colorless solid. LC-MS m/z: 595 (M+23).

Example 118

((R)-1-(((((R)-1-(2-cyano-4-(3,3-difluoropyrrolidin-1-yl)-4-methylpent-2-enoyl)-2-methylpyrrolidin-2-yl)methoxy)carbonyl)amino)-3,3-dimethylbutyl) boronic acid

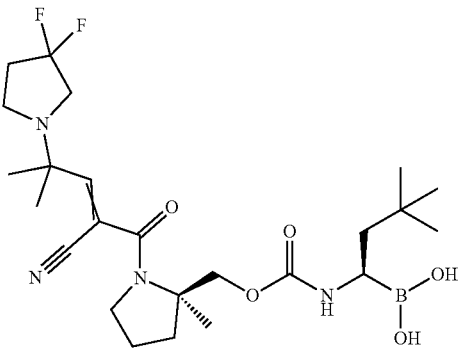 [SMILES: CC(C)(C)C[C@H](NC(=O)OC[C@@]1(C)CCCN1C(=O)C(C#N)=CC(C)(C)N1CCC(F)(F)C1)B(O)O]

The title compound was prepared as in example 117, but replacing (R)-2-(benzofuran-3-yl)-1-((3aS,4S,6S,7aR)-3a,5,5-trimethylhexahydro-4,6-methanobenzo[d][1,3,2]dioxaborol-2-yl)ethanamine hydrochloride with (R)-3,3-dimethyl-1-((3aS,4S,6S,7aR)-3a,5,5-trimethylhexahydro-4,6-methanobenzo[d][1,3,2]dioxaborol-2-yl)butan-1-amine hydrochloride. LC-MS m/z: 535 (M+23).

Example 119

((R)-1-(((((1S,2R,5R)-3-(2-cyano-3-(4-methyltetrahydro-2H-pyran-4-yl)acryloyl)-3-azabicyclo[3.1.0]hexan-2-yl)methoxy)carbonyl)amino)-2-(4-fluorophenyl)ethyl)boronic acid

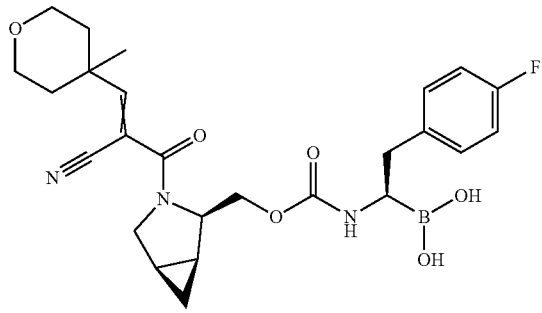 [SMILES: CC1(C=C(C#N)C(=O)N2C[C@@H]3C[C@@H]3[C@@H]2COC(=O)N[C@@H](Cc2ccc(F)cc2)B(O)O)CCOCC1]

The title compound was prepared as in example 108, using 4-methyltetrahydro-2H-pyran-4-carbaldehyde in place of 2-(3,3-difluoropyrrolidin-1-yl)-2-methylpropanal.

Example 120

((R)-1-(((((R)-1-(2-cyano-4-(3,3-difluoropyrrolidin-1-yl)-4-methylpent-2-enoyl)-2-methylpyrrolidin-2-yl)methoxy)carbonyl)amino)-2-(4-fluorophenyl) ethyl)boronic acid

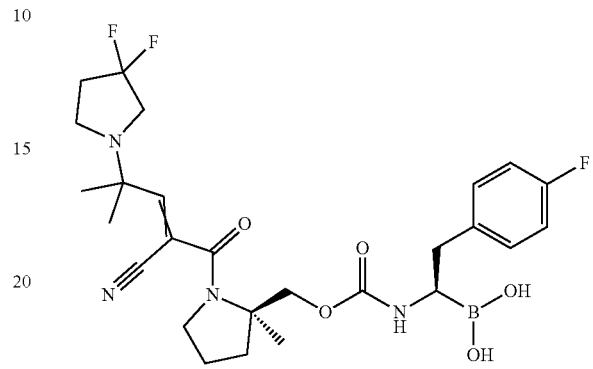

To a suspension of DSC (351 mg, 1.37 mmol) and (R)-4-(3,3-difluoropyrrolidin-1-yl)-2-(2-(hydroxymethyl)-2-methylpyrrolidine-1-carbonyl)-4-methylpent-2-enenitrile (360 mg, 1.05 mmol) in anhydrous acetonitrile (3 mL) was added dropwise DIPEA (407 mg, 3.15 mmol) at 25° C. The mixture was stirred for 2 h at 25° C., then diluted with water (20 mL), extracted with DCM (each 7 mL) twice. The combined organic phase was washed with brine (3 mL), dried over $Na_2SO_4$, concentrated in vacuo. The (R)-(1-(2-cyano-4-(3,3-difluoropyrrolidin-1-yl)-4-methylpent-2-enoyl)-2-methylpyrrolidin-2-yl)methyl (2,5-dioxopyrrolidin-1-yl) carbonate thus obtained was used into next step directly (220 mg).

To a solution of (R)-(1-(2-cyano-4-(3,3-difluoropyrrolidin-1-yl)-4-methylpent-2-enoyl)-2-methylpyrrolidin-2-yl) methyl (2,5-dioxopyrrolidin-1-yl) carbonate (160 mg, 0.33 mmol) in DCM (4 mL) was added dropwise a solution of (R)-2-(4-fluorophenyl)-1-((3aS,4S,6S,7aR)-3a,5,5-trimethylhexahydro-4,6-methanobenzo[d][1,3,2]dioxaborol-2-yl) ethan-1-amine hydrochloride (117 mg, 0.33 mmol) and DIPEA (127 mg, 0.99 mmol) in DCM (1 mL) at 0° C. The resulted mixture was stirred at rt for 1 h, then diluted with DCM (20 mL), washed with brine, dried over $Na_2SO_4$, concentrated in vacuo. The residue was purified via silica chromatography to afford 100 mg of ((R)-1-(2-cyano-4-(3,3-difluoropyrrolidin-1-yl)-4-methylpent-2-enoyl)-2-methylpyrrolidin-2-yl)methyl ((R)-2-(4-fluorophenyl)-1-((3aS,4S,6S,7aR)-3a,5,5-trimethylhexahydro-4,6-methanobenzo[d][1,3,2]dioxaborol-2-yl)ethyl)carbamate as a white solid (100 mg, 44%)

The title compound was prepared as in example 117, but replacing (R)-2-(benzofuran-3-yl)-1-((3aS,4S,6S,7aR)-3a,5,5-trimethylhexahydro-4,6-methanobenzo[d][1,3,2]dioxaborol-2-yl)ethan-1-amine hydrochloride with (R)-2-(4-fluorophenyl)-1-((3aS,4S,6S,7aR)-3a,5,5-trimethylhexahydro-4,6-methanobenzo[d][1,3,2]dioxaborol-2-yl)ethanamine hydrochloride. LC-MS m/z: 573 (M+23). Hydrolysis of the boronate as in example 1, step 6, and purification by preparative HPLC, afforded 43 mg of the title compound as a colorless solid. LC-MS m/z: 573 (M+23).

Example 121

((R)-1-(((((R)-1-(2-fluoroacryloyl)-2-methylpyrrolidin-2-yl)methoxy)carbonyl)amino)-2-(4-fluorophenyl)ethyl)boronic acid

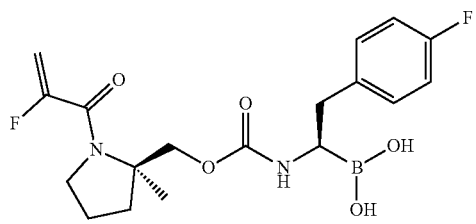 [SMILES: C=C(F)C(=O)N1CCC[C@]1(C)COC(=O)N[C@@H](Cc1ccc(F)cc1)B(O)O]

To a mixture of lithium 2-fluoroacrylate (250 mg, crude), (R)-(2-methylpyrrolidin-2-yl)methanol (300 mg, 2.6 mmol) and DIPEA (1 g, 7.8 mmol) in ACN (8 mL), was added PyBOP (1.62 g, 3.12 mmol) at rt. The mixture was stirred at rt for 1 h. The mixture was concentrated and the crude was purified by silica gel chromatography to afford (R)-2-fluoro-1-(2-(hydroxymethyl)-2-methylpyrrolidin-1-yl)prop-2-en-1-one (252 mg) as a colorless oil. Following the procedure of the final 2 steps in example 117 afforded 84 mg of the title compound as a colorless solid. LC-MS m/z: 419 (M+23).

Example 122

((R)-1-(((((R)-1-(2-cyano-4-(3,3-difluoropyrrolidin-1-yl)-4-methylpent-2-enoyl)piperidin-2-yl)methoxy)carbonyl)amino)-2-(4-cyanophenyl)ethyl)boronic acid

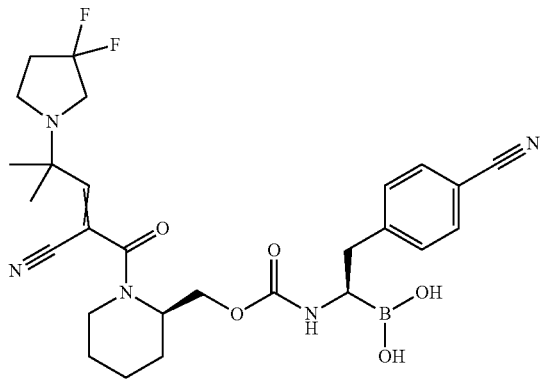 [SMILES: CC(C)(C=C(C#N)C(=O)N1CCCC[C@@H]1COC(=O)N[C@@H](Cc1ccc(C#N)cc1)B(O)O)N1CCC(F)(F)C1]

Following the protocol in example 28 but replacing (R)-2-phenyl-1-((3aS,4S,6S,7aR)-3a,5,5-trimethylhexahydro-4,6-methanobenzo[d][1,3,2]dioxaborol-2-yl)ethanamine hydrochloride with 4-((R)-2-amino-2-((3aS,4S,6S,7aR)-3a,5,5-trimethylhexahydro-4,6-methanobenzo[d][1,3,2]dioxaborol-2-yl)ethyl)benzonitrile hydrochloride (prepared by the method in example 98), the title compound was obtained. LC-MS m/z: 580 (M+23).

Example 123

((R)-1-(((((1S,2R,5R)-3-(2-cyano-4-methyl-4-morpholinopent-2-enoyl)-3-azabicyclo[3.1.0]hexan-2-yl)methoxy)carbonyl)amino)-2-(4-fluorophenyl)ethyl)boronic acid

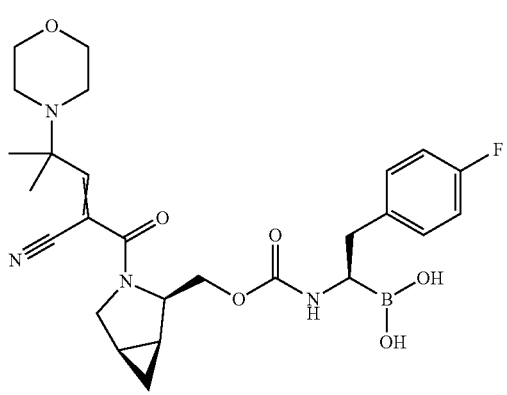 [SMILES: CC(C)(C=C(C#N)C(=O)N1C[C@@H]2C[C@@H]2[C@@H]1COC(=O)N[C@@H](Cc1ccc(F)cc1)B(O)O)N1CCOCC1]

The title compound was prepared as in example 67 but replacing (R)-2-phenyl-1-((3aS,4S,6S,7aR)-3a,5,5-trimethylhexahydro-4,6-methanobenzo[d][1,3,2]dioxaborol-2-yl)ethanamine hydrochloride with (R)-2-(4-fluorophenyl)-1-((3aS,4S,6S,7aR)-3a,5,5-trimethylhexahydro-4,6-methanobenzo[d][1,3,2]dioxaborol-2-yl)ethanamine hydrochloride. LC-MS m/z: 579 (M+1). LC-MS m/z: 529 (M+1).

Example 124

((R)-1-(((((R)-1-(2-cyano-4-(3,3-difluoropyrrolidin-1-yl)-4-methylpent-2-enoyl)piperidin-2-yl)methoxy)carbonyl)amino)-2-(4-(methylsulfonyl)phenyl)ethyl)boronic acid

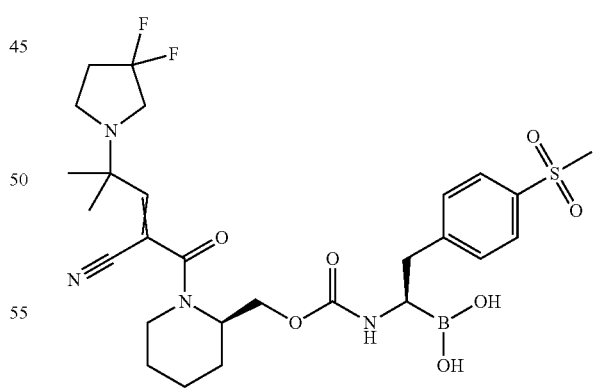

Following the protocol in example 28 but replacing (R)-2-phenyl-1-((3aS,4S,6S,7aR)-3a,5,5-trimethylhexahydro-4,6-methanobenzo[d][1,3,2]dioxaborol-2-yl)ethanamine hydrochloride with (R)-2-(4-(methylsulfonyl)phenyl)-1-((3aS,4S,6S,7aR)-3a,5,5-trimethylhexahydro-4,6-methanobenzo[d][1,3,2]dioxaborol-2-yl)ethanamine hydrochloride (prepared by the method in example 98), the title compound was obtained. LC-MS m/z: 611 (M+1).

Example 125

((R)-1-(((((R)-1-(2-cyano-4-(4-(methoxycarbonyl)piperazin-1-yl)-4-methylpent-2-enoyl)piperidin-2-yl)methoxy)carbonyl)amino)-2-phenylethyl)boronic acid

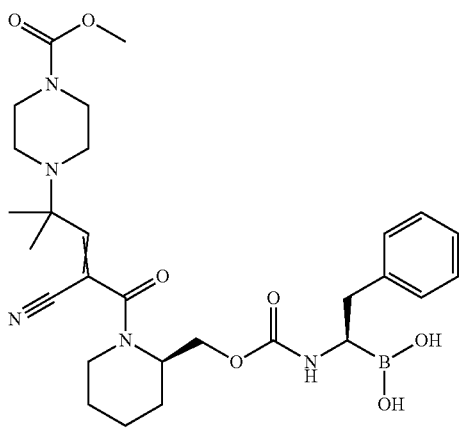 [SMILES: COC(=O)N1CCN(C(C)(C)C=C(C#N)C(=O)N2CCCC[C@@H]2COC(=O)N[C@@H](Cc2ccccc2)B(O)O)CC1]

Following the protocol in example 28 but replacing 3,3-difluoropyrrolidine with methyl piperazine-1-carboxylate, the title compound was obtained. LC-MS m/z: 570 (M+1).

Example 126

((R)-1-(((((R)-1-(2-cyano-4-methyl-4-(4-(oxetan-3-yl)piperazin-1-yl)pent-2-enoyl)piperidin-2-yl)methoxy)carbonyl)amino)-2-phenylethyl)boronic acid

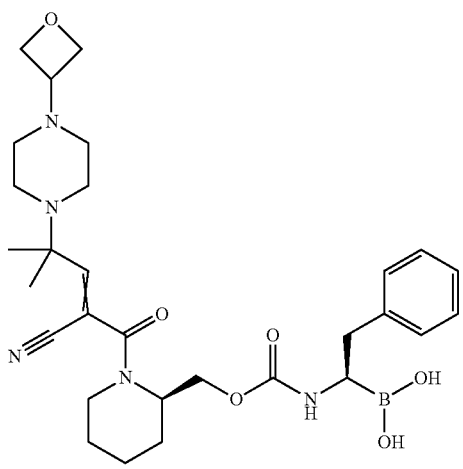 [SMILES: CC(C)(C=C(C#N)C(=O)N1CCCC[C@@H]1COC(=O)N[C@@H](Cc1ccccc1)B(O)O)N1CCN(C2COC2)CC1]

Following the protocol in example 28 but replacing 2-(3,3-difluoropyrrolidin-1-yl)-2-methylpropanal with 2-methyl-2-(4-(oxetan-3-yl)piperazin-1-yl)propanal, the title compound was obtained. LC-MS m/z: 568 (M+1).

Example 127

((R)-1-(((((R)-1-(2-cyano-4-methyl-4-(4-(oxetan-3-yl)piperazin-1-yl)pent-2-enoyl)piperidin-2-yl)methoxy)carbonyl)amino)-2-(4-fluorophenyl)ethyl)boronic acid

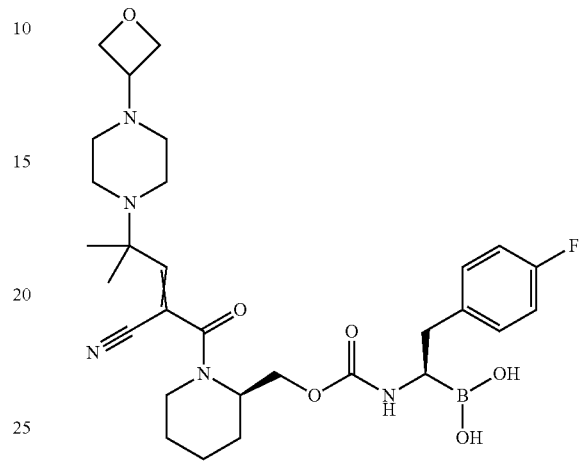

Following the protocol in example 126 but replacing (R)-2-phenyl-1-((3aS,4S,6S,7aR)-3a,5,5-trimethylhexahydro-4,6-methanobenzo[d][1,3,2]dioxaborol-2-yl)ethanamine hydrochloride with (R)-2-(4-fluorophenyl)-1-((3aS,4S,6S,7aR)-3a,5,5-trimethylhexahydro-4,6-methanobenzo[d][1,3,2]dioxaborol-2-yl)ethanamine hydrochloride, the title compound was obtained. LC-MS m/z: 586 (M+1).

Example 128

((R)-1-(((((R)-1-((E)-2-cyano-4,4-dimethylpent-2-enoyl)piperazin-2-yl)methoxy)carbonyl)amino)-2-phenylethyl)boronic acid

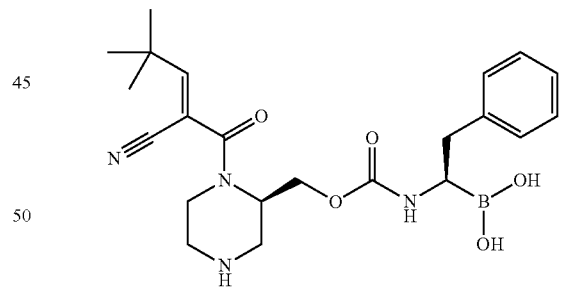

To the solution of tert-butyl (3R)-3-(hydroxymethyl)piperazine-1-carboxylate (1044 mg, 4.83 mmol) in N,N-Diisopropylethylamine (2.57 mL, 14.48 mmol) and DMF (7 mL) was added (E)-2-cyano-4,4-dimethyl-pent-2-enoic acid (1109.1 mg, 7.24 mmol) followed by HATU (486.6 mg, 5.79 mmol). The mixture was stirred at rt for 1 h. The mixture was diluted with DCM and water and partitioned. The organic layer was dried with MgSO$_4$ and concentrated. The crude mixture was purified by column chromatography to obtain tert-butyl (3R)-4-[(E)-2-cyano-4,4-dimethyl-pent-2-enoyl]-3-(hydroxymethyl)piperazine-1-carboxylate (1340 mg) as an oil.

To the solution of tert-butyl (3R)-4-[(E)-2-cyano-4,4-dimethyl-pent-2-enoyl]-3-(hydroxymethyl)piperazine-1- carboxylate (1325 mg, 3.77 mmol) and triethylamine (1.05 mL, 7.54 mmol) in DCM was added bis(2,5-dioxopyrrolidin-1-yl) carbonate (1255 mg. 4.9 mmol). The resulting solution was stirred at rt for 2 h. The mixture was diluted with DCM and water and partitioned. The organic layer was dried with MgSO$_4$ and concentrated. The crude mixture was purified by column chromatography to obtain tert-butyl (3R)-4-[(E)-2-cyano-4,4-dimethyl-pent-2-enoyl]-3-[(2,5-dioxopyrrolidin-1-yl)oxycarbonyloxymethyl]piperazine-1-carboxylate (318 mg) as an oil.

To the solution of (R)-2-phenyl-1-((3aS,4S,6S,7aR)-5,5,7a-trimethylhexahydro-4,6-methanobenzo[d][1,3,2]dioxaborol-2-yl)ethanamine hydrochloride (325.1 mg, 0.97 mmol) and triethylamine (0.27 mL, 1.94 mmol) in DCM (10 mL) was added a mixture of tert-butyl (3R)-4-(R,E)-tert-butyl 4-(2-cyano-4,4-dimethylpent-2-enoyl)-3-(((((2,5-dioxopyrrolidin-1-yl)oxy)carbonyl)oxy)methyl)piperazine-1-carboxylate (318 mg, 0.65 mmol) in DCM (5 mL). The mixture was stirred at t for 1 h. The reaction mixture was washed with water (40 mL) then NaCl (aq) and then the organic layer was dried with MgSO$_4$ and concentrated to oil. The oil was purified by silica gel chromatography to afford (R)-tert-butyl 4-((E)-2-cyano-4,4-dimethylpent-2-enoyl)-3-((((R)-2-phenyl-1-((3aS,4S,6S,7aR)-5,5,7a-trimethylhexahydro-4,6-methanobenzo[d][1,3,2]dioxaborol-2-yl)ethyl)carbamoyl)oxy)methyl)piperazine-1-carboxylate (134 mg) as an oil.

To the solution of (R)-tert-butyl 4-((E)-2-cyano-4,4-dimethylpent-2-enoyl)-3-(((((R)-2-phenyl-1-((3aS,4S,6S,7aR)-5,5,7a-trimethylhexahydro-4,6-methanobenzo[d][1,3,2]dioxaborol-2-yl)ethyl)carbamoyl)oxy)methyl)piperazine-1-carboxylate (135 mg, 0.20 mmol) was added 4N HCl in dioxane (1.5 mL) and DCM (5 mL). After stirring for 1.5 h at rt, the reaction mixture was concentrated. 1N HCl (1.8 mL), methanol (4 mL) and hexane (4 mL) were added followed by isobutylboronic acid (30.5 mg, 0.30 mmol), and the mixture was stirred at rt for 1 h. The mixture was concentrated slightly under reduced pressure and the residual material purified by preparative HPLC to provide after lyophilization, 30 mg of ((R)-1-(((((R)-1 (E)-2-cyano-4,4-dimethylpent-2-enoyl)piperazin-2-yl)methoxy)carbonyl)amino)-2-phenylethyl)boronic acid as a colorless solid. LC-MS m/z: 443 (M+1).

Example 129

((R)-1-(((((R)-1-(2-cyano-4-(3,3-difluoropyrrolidin-1-yl)-4-methylpent-2-enoyl)-2-methylpiperidin-2-yl)methoxy)carbonyl)amino)-2-phenylethyl)boronic acid

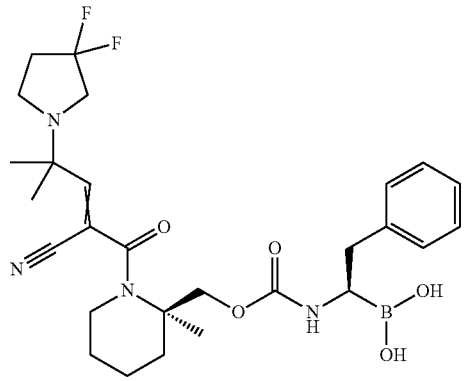 [SMILES: CC(C)(C=C(C#N)C(=O)N1CCCC[C@]1(C)COC(=O)N[C@@H](Cc1ccccc1)B(O)O)N1CCC(F)(F)C1]

Into a 25-mL 3-necked round-bottom flask purged and maintained with an inert atmosphere of nitrogen, was placed (R)-2-phenyl-1-((3aS,4S,6S,7aR)-3a,5,5-trimethylhexahydro-4,6-methanobenzo[d][1,3,2]dioxaborol-2-yl) ethanamine hydrochloride (366 mg, 1.09 mmol), DCM (6 mL, 94 mmol) and Et$_3$N (441 mg, 4.36 mmol). The reaction was cooled to −60° C. This was followed by the addition of a solution of ditrichloromethyl carbonate (129.4 mg, 0.44 mmol) in DCM (3 mL) dropwise with stirring at −60° C. The resulting solution containing (3aS,4S,6S,7aR)-2-((R)-1-isocyanato-2-phenylethyl)-3a,5,5-trimethylhexahydro-4,6-methanobenzo[d][1,3,2]dioxaborole was cooled −60° C. This was followed by the addition of a solution of tert-butyl 2-(hydroxymethyl)-2-methylpiperidine-1-carboxylate (303 mg. 1.32 mmol) in DCM (3 mL) dropwise with stirring at −60° C. The resulting solution was stirred for 1 h at −60° C. The reaction was then quenched by the addition of 3 mL of water. The resulting solution was extracted with 3×3 mL of dichloromethane. The organic layers were combined, washed with sodium carbonate (aq.) and brine, dried over Na$_2$SO$_4$ and concentrated under vacuum. This resulted in 609.4 mg of tert-butyl 2-methyl-2-(((((R)-2-phenyl-l-((3aS,4S,6S,7aR)-3a,5,5-trimethylhexahydro-4,6-methanobenzo[d][1,3,2]dioxaborol-2-yl)ethyl)carbamoyl)oxy)methyl)piperidine-1-carboxylate as a yellow oil. Using the above steps starting with (R)-tert-butyl 2-(hydroxymethyl)-2-methylpiperidine-1-carboxylate and continuing as in example 28 affords the title compound.

Example 130

((R)-1-(((((R)-1-(2-cyano-4-methyl-4-morpholinopent-2-enoyl)-2-methylpiperidin-2-yl)methoxy)carbonyl)amino)-2-phenylethyl)boronic acid

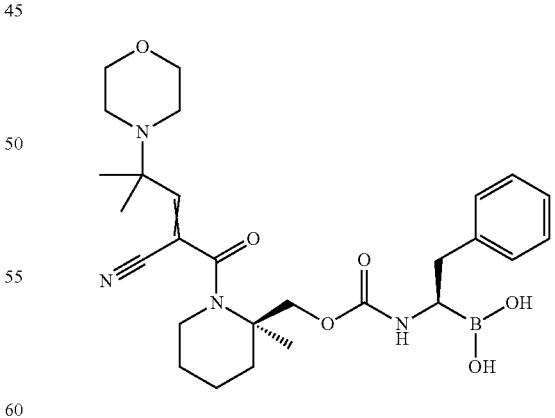

Starting with (R)-tert-butyl 2-methyl-2-(((((R)-2-phenyl-1-((3aS,4S,6S,7aR)-3a,5,5-trimethylhexahydro-4,6-methanobenzo[d][1,3,2]dioxaborol-2-yl)ethyl)carbamoyl)oxy) methyl)piperidine-1-carboxylate prepared by the method described in example 129, and continuing as in ex 67 affords the title compound.

Example 131

((R)-1-(((((2R,4S)-1-(2-cyano-4-methyl-4-morpholinopent-2-enoyl)-4-fluoropyrrolidin-2-yl)methoxy)carbonyl)amino)-2-phenylethyl)boronic acid

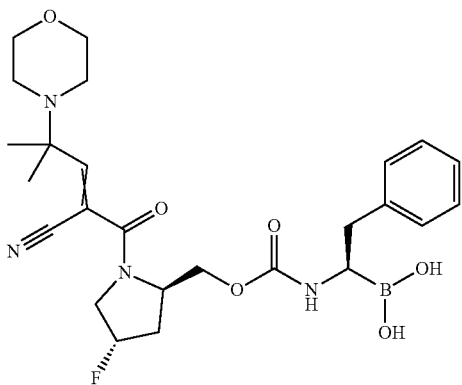 [SMILES: CC(C)(C=C(C#N)C(=O)N1C[C@@H](F)C[C@@H]1COC(=O)N[C@@H](Cc1ccccc1)B(O)O)N1CCOCC1]

Starting with (2R,4S)-tert-butyl 4-fluoro-2-(hydroxymethyl)pyrrolidine-1-carboxylate and continuing as in example 67 affords the title compound. LC-MS m/z: 517 (M+1).

Example 132

((R)-1-(((((2R,4S)-1-(2-cyano-4-(3,3-difluoropyrrolidin-1-yl)-4-methylpent-2-enoyl)-4-fluoropyrrolidin-2-yl)methoxy)carbonyl)amino)-2-phenylethyl)boronic acid

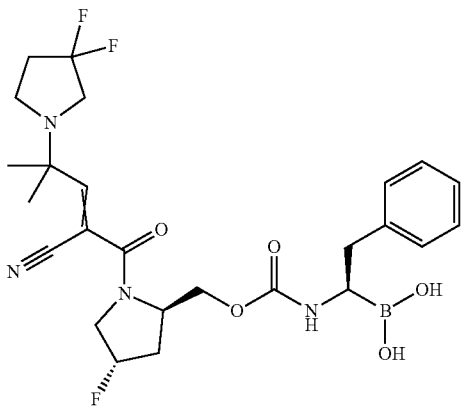 [SMILES: CC(C)(C=C(C#N)C(=O)N1C[C@@H](F)C[C@@H]1COC(=O)N[C@@H](Cc1ccccc1)B(O)O)N1CCC(F)(F)C1]

Starting with (2R,4S)-tert-butyl 4-fluoro-2-(hydroxymethyl)pyrrolidine-1-carboxylate and continuing as in example 28 afforded the title compound. LC-MS m/z: 671 (M+1).

Example 133

((R)-1-(((((2R,4S)-1-acryloyl-4-fluoropyrrolidin-2-yl)methoxy)carbonyl)amino)-2-(benzofuran-3-yl)ethyl)boronic acid

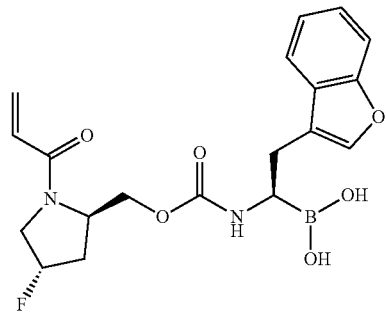 [SMILES: C=CC(=O)N1C[C@@H](F)C[C@@H]1COC(=O)N[C@@H](Cc1coc2ccccc12)B(O)O]

Using the method in example 52 and replacing (1S,2R,5R)-tert-butyl 2-(hydroxymethyl)-3-azabicyclo[3.1.0]hexane-3-carboxylate with (2R,4S)-tert-butyl 4-fluoro-2-(hydroxymethyl)pyrrolidine-1-carboxylate afforded the title compound. LC-MS m/z: 427 (M+23).

Example 134

((R)-2-(benzofuran-3-yl)-1-(((((2R,4S)-1-(2-cyano-4-(3,3-difluoropyrrolidin-1-yl)-4-methylpent-2-enoyl)-4-fluoropyrrolidin-2-yl)methoxy)carbonyl)amino)ethyl)boronic acid

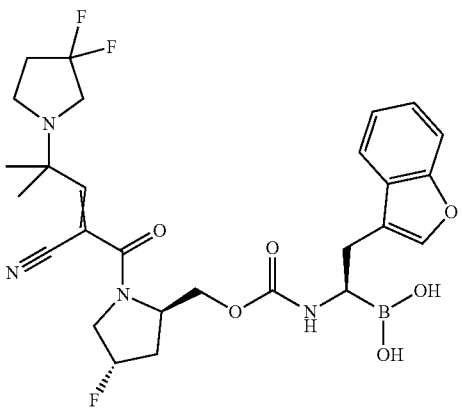 [SMILES: CC(C)(C=C(C#N)C(=O)N1C[C@@H](F)C[C@@H]1COC(=O)N[C@@H](Cc1coc2ccccc12)B(O)O)N1CCC(F)(F)C1]

Using the method in example 42 and replacing (R)-tert-butyl 2-(hydroxymethyl)pyrrolidine-1-carboxylate with (2R,4S)-tert-butyl 4-fluoro-2-(hydroxymethyl)pyrrolidine-1-carboxylate afforded the title compound. LC-MS m/z: 577 (M+1).

Example 135

((R)-1-(((((2R,4S)-1-(2-cyano-4-(3,3-difluoropyrrolidin-1-yl)-4-methylpent-2-enoyl)-4-fluoropyrrolidin-2-yl)methoxy)carbonyl)amino)-2-(4-fluorophenyl)ethyl)boronic acid

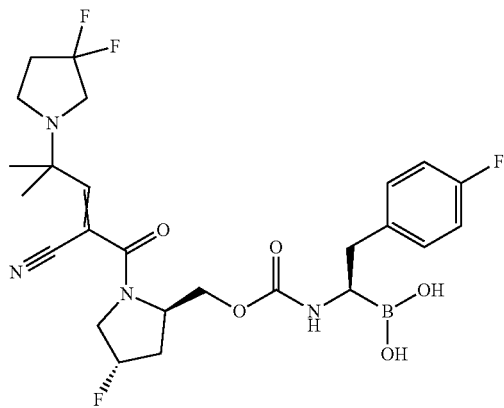 [SMILES: CC(C)(C=C(C#N)C(=O)N1C[C@@H](F)C[C@@H]1COC(=O)N[C@@H](Cc1ccc(F)cc1)B(O)O)N1CCC(F)(F)C1]

Using the method in example 132 and replacing (R)-2-phenyl-1-((3aS,4S,6S,7aR)-3a,5,5-trimethylhexahydro-4,6-methanobenzo[d][1,3,2]dioxaborol-2-yl)ethanamine hydrochloride with (R)-2-(4-fluorophenyl)-1-((3aS,4S,6S,7aR)-3a,5,5-trimethylhexahydro-4,6-methanobenzo[d][1,3,2]dioxaborol-2-yl)ethanamine hydrochloride afforded the title compound. LC-MS m/z: 555 (M+1).

Example 136

((R)-2-(benzofuran-3-yl)-1-(((((2R,4S)-1 (2-cyano-4-methyl-4-morpholinopent-2-enoyl)-4-fluoropyrrolidin-2-yl)methoxy)carbonyl)amino)ethyl)boronic acid

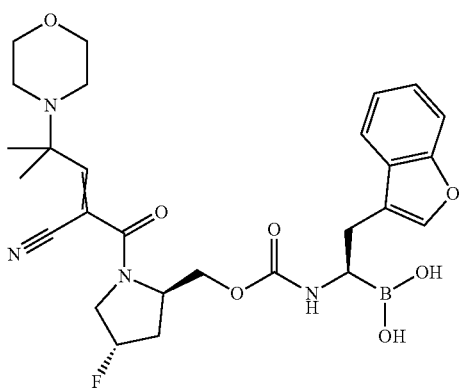 [SMILES: CC(C)(C=C(C#N)C(=O)N1C[C@@H](F)C[C@@H]1COC(=O)N[C@@H](Cc1coc2ccccc12)B(O)O)N1CCOCC1]

Using the method in example 131 and replacing (R)-2-phenyl-1-((3aS,4S,6S,7aR)-3a,5,5-trimethylhexahydro-4,6-methanobenzo[d][1,3,2]dioxaborol-2-yl)ethanamine hydrochloride with R)-2-(benzofuran-3-yl)-1-((3aS,4S,6S,7aR)-3a,5,5-trimethylhexahydro-4,6-methanobenzo[d][1,3,2]dioxaborol-2-yl)ethanamine hydrochloride afforded the title compound. LC-MS m/z: 557 (M+1).

Example 137

((R)-1-(((((2R,4S)-1-(2-cyano-4-methyl-4-morpholinopent-2-enoyl)-4-fluoropyrrolidin-2-yl)methoxy)carbonyl)amino)-2-(4-fluorophenyl)ethyl)boronic acid

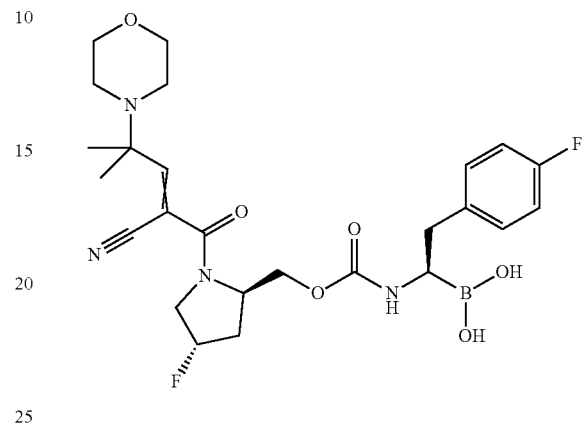

Using the method in example 131 and replacing (R)-2-phenyl-1-((3aS,4S,6S,7aR)-3a,5,5-trimethylhexahydro-4,6-methanobenzo[d][1,3,2]dioxaborol-2-yl)ethanamine hydrochloride with (R)-2-(4-fluorophenyl)-1-((3aS,4S,6S,7aR)-3a,5,5-trimethylhexahydro-4,6-methanobenzo[d][1,3,2]dioxaborol-2-yl)ethanamine hydrochloride afforded the title compound. LC-MS m/z: 535 (M+1).

Example 138

((R)-1-(((((2R,4S)-1-acryloyl-4-fluoropyrrolidin-2-yl)methoxy)carbonyl)amino)-2-(4-fluorophenyl)ethyl)boronic acid

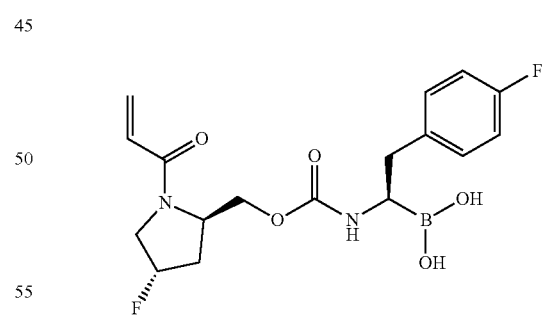

Using the method in example 109 and replacing (1S,2R,5R)-tert-butyl 2-(hydroxymethyl)-3-azabicyclo[3.1.0]hexane-3-carboxylate with (2R,4S)-tert-butyl 4-fluoro-2-(hydroxymethyl)pyrrolidine-1-carboxylate afforded the title compound.

Example 139

((R)-1-(((((R)-1-(2-cyano-4-((R)-3-fluoropyrrolidin-1-yl)-4-methylpent-2-enoyl)-2-methylpyrrolidin-2-yl)methoxy)carbonyl)amino)-2-phenylethyl)boronic acid

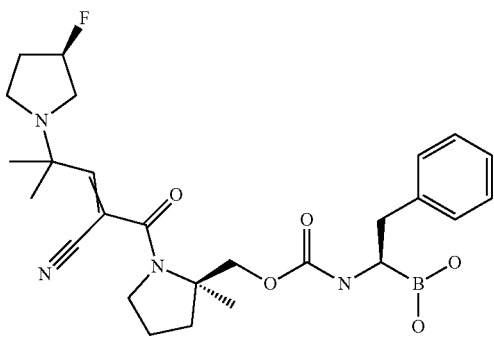 [SMILES: CC(C)(C=C(C#N)C(=O)N1CCC[C@]1(C)COC(=O)N[C@@H](Cc1ccccc1)B(O)O)N1CC[C@@H](F)C1]

Using the method in example 85 and replacing 2-(3,3-difluoropyrrolidin-1-yl)-2-methylpropanal with (R)-2-(3-fluoropyrrolidin-1-yl)-2-methylpropanal affords the title compound.

Example 140

((R)-1-(((((R)-1-(2-cyano-4-((S)-3-fluoropyrrolidin-1-yl)-4-methylpent-2-enoyl)-2-methylpyrrolidin-2-yl)methoxy)carbonyl)amino)-2-phenylethyl)boronic acid

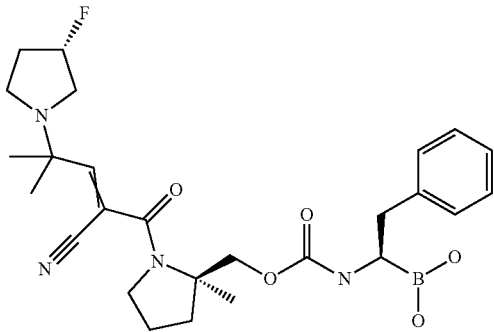 [SMILES: CC(C)(C=C(C#N)C(=O)N1CCC[C@]1(C)COC(=O)N[C@@H](Cc1ccccc1)B(O)O)N1CC[C@H](F)C1]

Using the method in example 85 and replacing 2-(3,3-difluoropyrrolidin-1-yl)-2-methylpropanal with (S)-2-(3-fluoropyrrolidin-1-yl)-2-methylpropanal affords the title compound.

Example 141

((R)-1-(((((R)-1-(2-cyano-4-((3S,4R)-3,4-difluoropyrrolidin-1-yl)-4-methylpent-2-enoyl)-2-methylpyrrolidin-2-yl)methoxy)carbonyl)amino)-2-phenylethyl)boronic acid

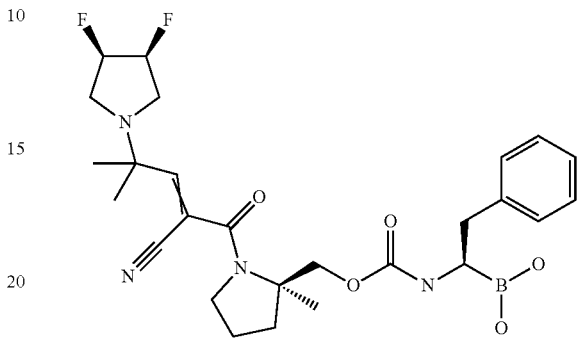

Using the method in example 85 and replacing 2-(3,3-difluoropyrrolidin-1-yl)-2-methylpropanal with (3R,4S)-3,4-difluoropyrrolidine affords the title compound.

Example 142

((R)-1-(((((R)-1-(2-cyano-4-((R)-3-fluoropyrrolidin-1-yl)-4-methylpent-2-enoyl)-2-methylpyrrolidin-2-yl)methoxy)carbonyl)amino)-2-(4-fluorophenyl)ethyl)boronic acid

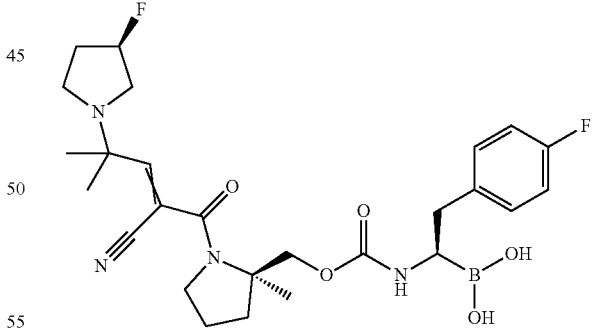

Using the method in example 120 and replacing 2-(3,3-difluoropyrrolidin-1-yl)-2-methylpropanal with (R)-2-(3-fluoropyrrolidin-1-yl)-2-methylpropanal affords the title compound.

Example 143

((R)-1-(((((R)-1-(2-cyano-4-((S)-3-fluoropyrrolidin-1-yl)-4-methylpent-2-enoyl)-2-methylpyrrolidin-2-yl)methoxy)carbonyl)amino)-2-(4-fluorophenyl)ethyl)boronic acid

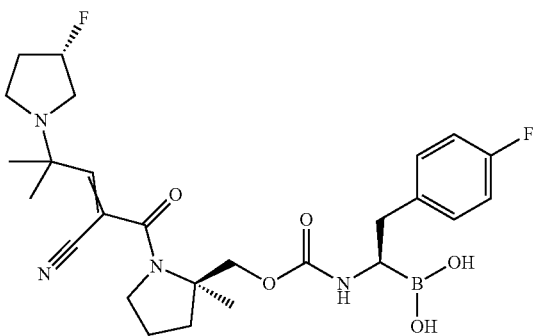 [SMILES: CC(C)(C=C(C#N)C(=O)N1CCC[C@]1(C)COC(=O)N[C@@H](Cc1ccc(F)cc1)B(O)O)N1CC[C@H](F)C1]

Using the method in example 120 and replacing 2-(3,3-difluoropyrrolidin-1-yl)-2-methylpropanal with (R)-2-(3-fluoropyrrolidin-1-yl)-2-methylpropanal affords the title compound.

Example 144

((R)-1-(((((R)-1-(2-cyano-4-((3S,4R)-3,4-difluoropyrrolidin-1-yl)-4-methylpent-2-enoyl)-2-methylpyrrolidin-2-yl)methoxy)carbonyl)amino)-2-(4-fluorophenyl)ethyl)boronic acid

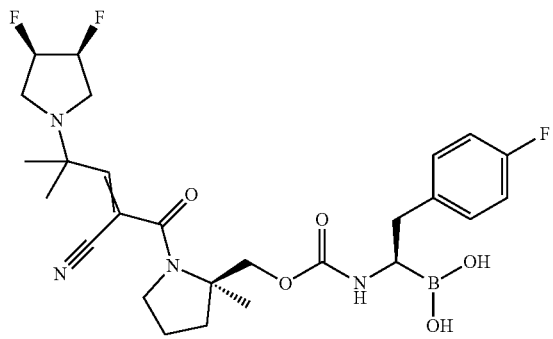 [SMILES: CC(C)(C=C(C#N)C(=O)N1CCC[C@]1(C)COC(=O)N[C@@H](Cc1ccc(F)cc1)B(O)O)N1C[C@@H](F)[C@@H](F)C1]

Using the method in example 120 and replacing 2-(3,3-difluoropyrrolidin-1-yl)-2-methylpropanal with (3R,4S)-3,4-difluoropyrrolidine affords the title compound.

Example 145

((R)-1-(((((R)-1-(2-cyano-4-((R)-3-fluoropyrrolidin-1-yl)-4-methylpent-2-enoyl)piperidin-2-yl)methoxy)carbonyl)amino)-2-phenylethyl)boronic acid

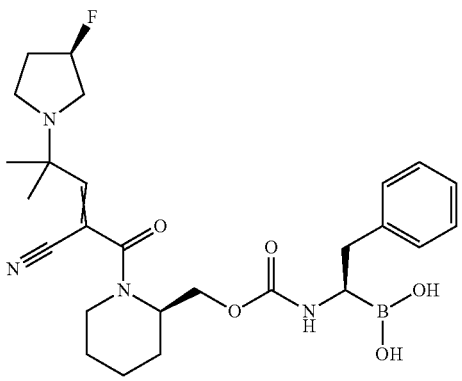 [SMILES: CC(C)(C=C(C#N)C(=O)N1CCCC[C@@H]1COC(=O)N[C@@H](Cc1ccccc1)B(O)O)N1CC[C@@H](F)C1]

Using the method in example 28 and replacing 2-(3,3-difluoropyrrolidin-1-yl)-2-methylpropanal with (R)-2-(3-fluoropyrrolidin-1-yl)-2-methylpropanal affords the title compound.

Example 146

((R)-1-(((((R)-1-(2-cyano-4-((S)-3-fluoropyrrolidin-1-yl)-4-methylpent-2-enoyl)piperidin-2-yl)methoxy)carbonyl)amino)-2-phenylethyl)boronic acid

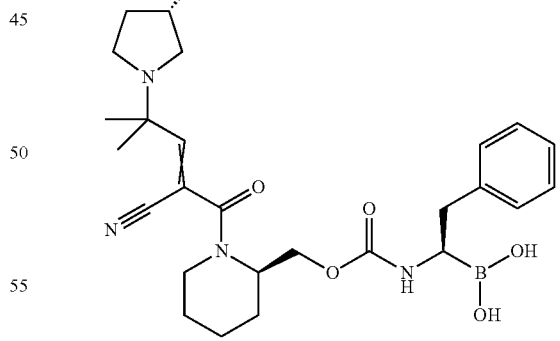

Using the method in example 28 and replacing 2-(3,3-difluoropyrrolidin-1-yl)-2-methylpropanal with (S)-2-(3-fluoropyrrolidin-1-yl)-2-methylpropanal affords the title compound.

Example 147

((R)-1-(((((R)-1-(2-cyano-4-((3S,4R)-3,4-difluoro-pyrrolidin-1-yl)-4-methylpent-2-enoyl)piperidin-2-yl)methoxy)carbonyl)amino)-2-phenylethyl)boronic acid

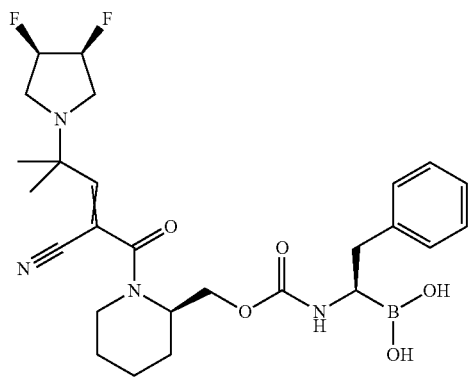 [SMILES: CC(C)(C=C(C#N)C(=O)N1CCCC[C@@H]1COC(=O)N[C@@H](Cc1ccccc1)B(O)O)N1C[C@@H](F)[C@@H](F)C1]

Using the method in example 28 and replacing 2-(3,3-difluoropyrrolidin-1-yl)-2-methylpropanal with (3R,4S)-3,4-difluoropyrrolidine affords the title compound.

Example 148

((R)-1-(((((R)-1-(2-cyano-4-((R)-3-fluoropyrrolidin-1-yl)-4-methylpent-2-enoyl)piperidin-2-yl)methoxy)carbonyl)amino)-2-(4-fluorophenyl)ethyl)boronic acid

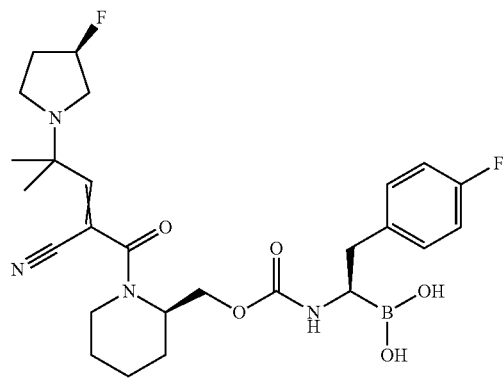 [SMILES: CC(C)(C=C(C#N)C(=O)N1CCCC[C@@H]1COC(=O)N[C@@H](Cc1ccc(F)cc1)B(O)O)N1CC[C@@H](F)C1]

Using the method in example 82 and 2-(3,3-difluoropyrrolidin-1-yl)-2-methylpropanal with (R)-2-(3-fluoropyrrolidin-1-yl)-2-methylpropanal affords the title compound.

Example 149

((R)-1-(((((R)-1-(2-cyano-4-((S)-3-fluoropyrrolidin-1-yl)-4-methylpent-2-enoyl)piperidin-2-yl)methoxy)carbonyl)amino)-2-(4-fluorophenyl)ethyl)boronic acid

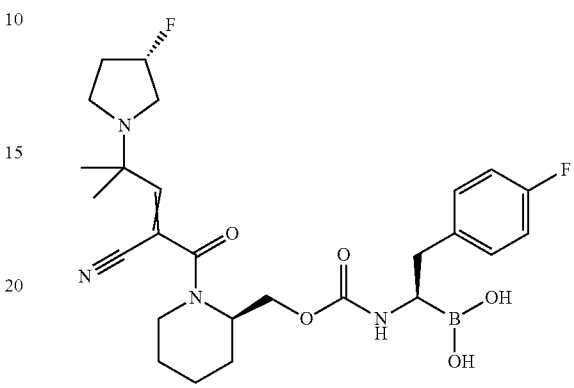

Using the method in example 82 and 2-(3,3-difluoropyrrolidin-1-yl)-2-methylpropanal with (S)-2-(3-fluoropyrrolidin-1-yl)-2-methylpropanal affords the title compound.

Example 150

((R)-1-(((((R)-1-(2-cyano-4-((3S,4R)-3,4-difluoropyrrolidin-1-yl)-4-methylpent-2-enoyl)piperidin-2-yl)methoxy)carbonyl)amino)-2-(4-fluorophenyl)ethyl)boronic acid

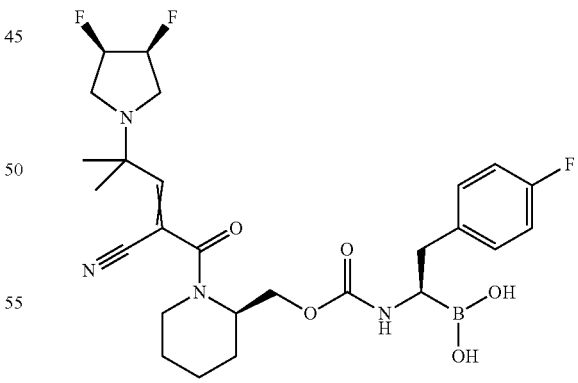

Using the method in example 82 and 2-(3,3-difluoropyrrolidin-1-yl)-2-methylpropanal with (3R,4S)-3,4-difluoropyrrolidine affords the title compound.

Example 151

((R)-1-(((((R)-1-(2-cyano-4-methyl-4-morpholino-pent-2-enoyl)-2-methylpyrrolidin-2-yl)methoxy)carbonyl)amino)-2-(4-fluorophenyl)ethyl)boronic acid

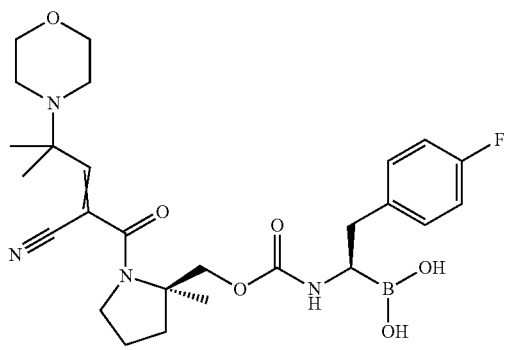 [SMILES: CC(C)(C=C(C#N)C(=O)N1CCC[C@]1(C)COC(=O)N[C@@H](Cc1ccc(F)cc1)B(O)O)N1CCOCC1]

Using the method in example 120 and replacing 2-(3,3-difluoropyrrolidin-1-yl)-2-methylpropanal with 2-methyl-2-morpholinopropanal affords the title compound.

Example 152

((R)-1-(((((R)-1-(2-cyano-4-methyl-4-morpholino-pent-2-enoyl)-2-methylpyrrolidin-2-yl)methoxy)carbonyl)amino)-2-phenylethyl)boronic acid

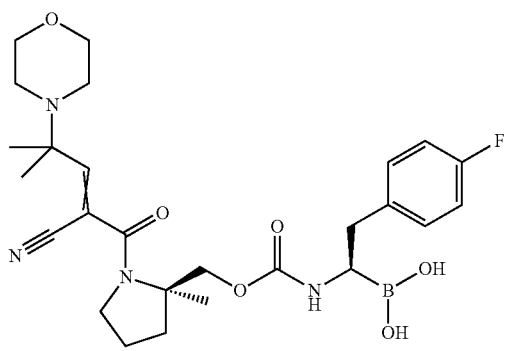 [SMILES: CC(C)(C=C(C#N)C(=O)N1CCC[C@]1(C)COC(=O)N[C@@H](Cc1ccc(F)cc1)B(O)O)N1CCOCC1]

Using the method of the first two steps in example 117 and replacing 2-(3,3-difluoropyrrolidin-1-yl)-2-methylpropanal with 2-methyl-2-morpholinopropanal afforded 2-cyano-4-methyl-4-morpholinopent-2-enoic acid. Starting from this material and proceeding as in example 120 affords the title compound.

Example 153

((R)-1-(((((2R,4S)-1-(2-cyano-4-(3,3-difluoropyrrolidin-1-yl)-4-methylpent-2-enoyl)-4-fluoro-2-methylpyrrolidin-2-yl)methoxy)carbonyl)amino)-2-(4-fluorophenyl)ethyl)boronic acid

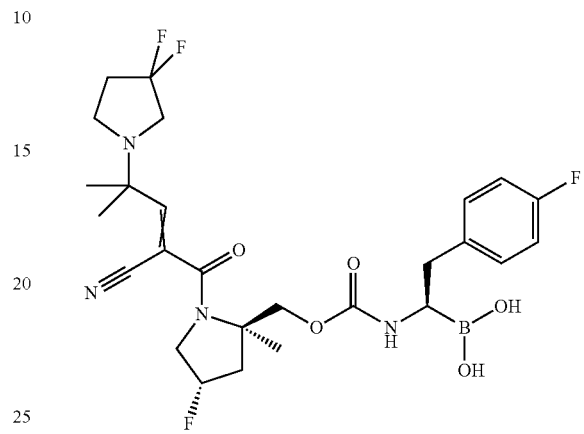

Treating (2R,4R)-1-tert-butyl 2-methyl 4-hydroxy-2-methylpyrrolidine-1,2-dicarboxylate (prepared as described in Org Lett, 2007, 3029-3032) with DAST in DCM affords (2R,4S)-1-tert-butyl 2-methyl 4-fluoro-2-methylpyrrolidine-1,2-dicarboxylate. Reduction of the ester as in example 89 yields (2R,4S)-tert-butyl 4-fluoro-2-(hydroxymethyl)-2-methylpyrrolidine-1-carboxylate and continuing as in example 120 affords the title compound.

Example 154

((R)-1-(((((2R,4S)-1-(2-cyano-4-((S)-3-fluoropyrrolidin-1-yl)-4-methylpent-2-enoyl)-4-fluoro-2-methylpyrrolidin-2-yl)methoxy)carbonyl)amino)-2-(4-fluorophenyl)ethyl)boronic acid

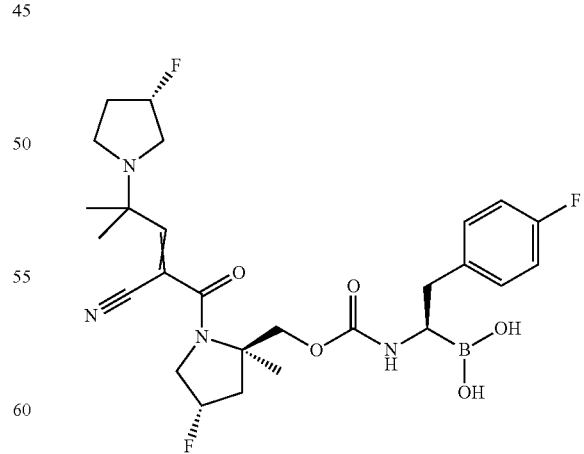

Using the method in example 153 and replacing 2-(3,3-difluoropyrrolidin-1-yl)-2-methylpropanal with (S)-2-(3-fluoropyrrolidin-1-yl)-2-methylpropanal affords the title compound.

Example 155

((R)-1-(((((2R,4S)-1-(2-cyano-4-((R)-3-fluoropyrrolidin-1-yl)-4-methylpent-2-enoyl)-4-fluoro-2-methylpyrrolidin-2-yl)methoxy)carbonyl)amino)-2-(4-fluorophenyl)ethyl)boronic acid

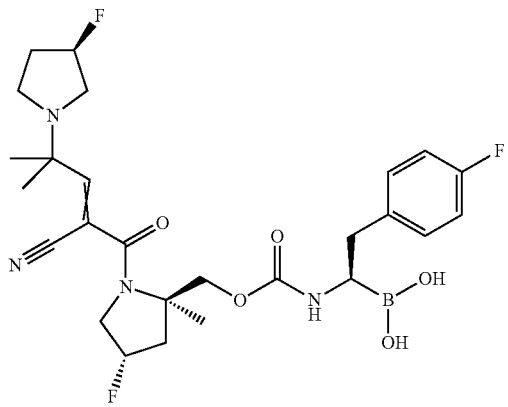 [SMILES: CC(C)(C=C(C#N)C(=O)N1C[C@@H](F)C[C@]1(C)COC(=O)N[C@@H](Cc1ccc(F)cc1)B(O)O)N1CC[C@@H](F)C1]

Using the method in example 153 and replacing 2-(3,3-difluoropyrrolidin-1-yl)-2-methylpropanal with (R)-2-(3-fluoropyrrolidin-1-yl)-2-methylpropanal affords the title compound.

Example 156

((R)-1-(((((2R,4S)-1-acryloyl-4-fluoro-2-methylpyrrolidin-2-yl)methoxy)carbonyl)amino)-2-(4-fluorophenyl)ethyl)boronic acid

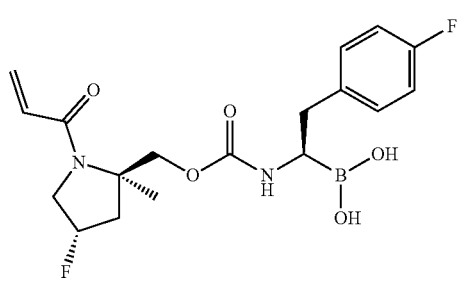 [SMILES: C=CC(=O)N1C[C@@H](F)C[C@]1(C)COC(=O)N[C@@H](Cc1ccc(F)cc1)B(O)O]

Using the method in example 109 and replacing (1S,2R,5R)-tert-butyl 2-(hydroxymethyl)-3-azabicyclo[3.1.0]hexane-3-carboxylate with (2R,4S)-tert-butyl 4-fluoro-2-(hydroxymethyl)-2-methylpyrrolidine-1-carboxylate affords the title compound.

Example 157

((R)-1-(((((2R,4S)-1-(2-cyano-4-(3,3-difluoropyrrolidin-1-yl)-4-methylpent-2-enoyl)-4-fluoro-2-methylpyrrolidin-2-yl)methoxy)carbonyl)amino)-2-phenylethyl)boronic acid

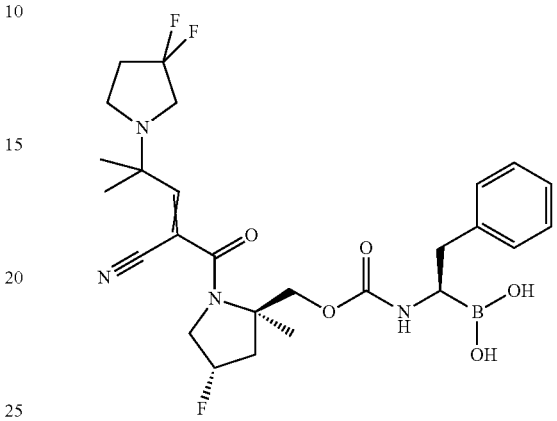

Using the method in example 28 and replacing tert-butyl (2R)-2-(hydroxymethyl)piperidine-1-carboxylate with (2R,4S)-tert-butyl 4-fluoro-2-(hydroxymethyl)-2-methylpyrrolidine-1-carboxylate affords the title compound.

Example 158

((R)-1-(((((2R,4S)-1-(2-cyano-4-((S)-3-fluoropyrrolidin-1-yl)-4-methylpent-2-enoyl)-4-fluoro-2-methylpyrrolidin-2-yl)methoxy)carbonyl)amino)-2-phenylethyl)boronic acid

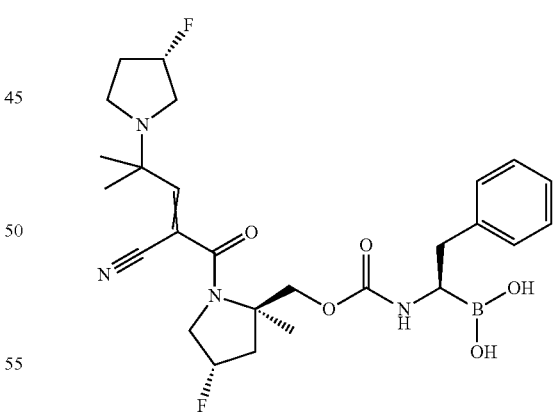

Using the method in example 157 and replacing 2-(3,3-difluoropyrrolidin-1-yl)-2-methylpropanal with (S)-2-(3-fluoropyrrolidin-1-yl)-2-methylpropanal affords the title compound.

Example 159

((R)-1-(((((2R,4S)-1-(2-cyano-4-((R)-3-fluoropyrrolidin-1-yl)-4-methylpent-2-enoyl)-4-fluor-2-methylpyrrolidin-2-yl)methoxy)carbonyl)amino)-2-phenylethyl)boronic acid

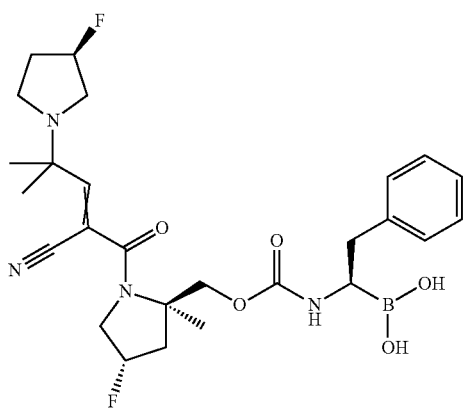 [SMILES: CC(C)(C=C(C#N)C(=O)N1C[C@@H](F)C[C@]1(C)COC(=O)N[C@@H](Cc1ccccc1)B(O)O)N1CC[C@@H](F)C1]

Using the method in example 157 and replacing 2-(3,3-difluoropyrrolidin-1-yl)-2-methylpropanal with (R)-2-(3-fluoropyrrolidin-1-yl)-2-methylpropanal affords the title compound.

Example 160

((R)-1-(((((2R,4S)-1-acryloyl-4-fluoro-2-methylpyrrolidin-2-yl)methoxy)carbonyl)amino)-2-phenylethyl)boronic acid

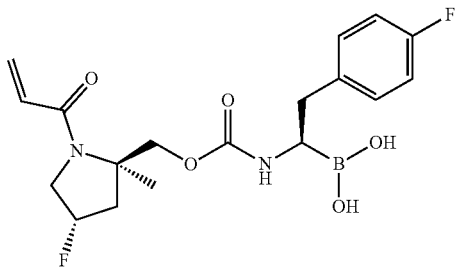 [SMILES: C=CC(=O)N1C[C@@H](F)C[C@]1(C)COC(=O)N[C@@H](Cc1ccc(F)cc1)B(O)O]

Starting with (2R,4S)-tert-butyl 4-fluoro-2-(hydroxymethyl)-2-methylpyrrolidine-1-carboxylate and proceeding as in example 109 produces the title compound.

Example 161

((R)-1-(((((R)-1-(2-cyano-4-(3,3-difluoropyrrolidin-1-yl)-4-methylpent-2-enoyl)-2-methylpiperidin-2-yl)methoxy)carbonyl)amino)-2-(4-fluorophenyl)ethyl)boronic acid

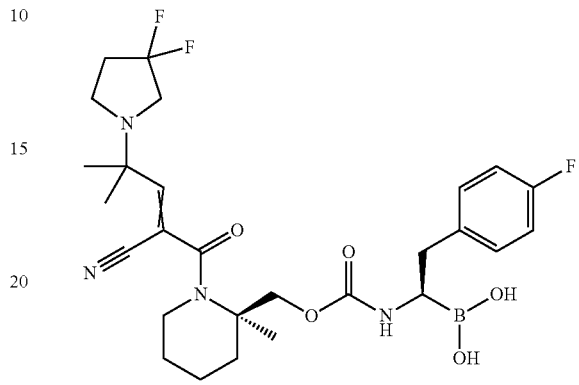

Using the method in example 82 and replacing (R)-tert-butyl 2-(hydroxymethyl)piperidine-1-carboxylate with (R)-tert-butyl 2-(hydroxymethyl)-2-methylpiperidine-1-carboxylate affords the title compound.

Example 162

((R)-1-(((((R)-1-(2-cyano-4-methyl-4-morpholinopent-2-enoyl)-2-methylpiperidin-2-yl)methoxy)carbonyl)amino)-2-(4-fluorophenyl)ethyl)boronic acid

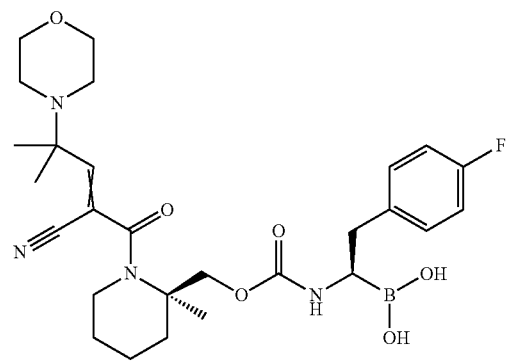 [SMILES: CC(C)(C=C(C#N)C(=O)N1CCCC[C@]1(C)COC(=O)N[C@@H](Cc1ccc(F)cc1)B(O)O)N1CCOCC1]

Using the method in example 161 and replacing 2-(3,3-difluoropyrrolidin-1-yl)-2-methylpropanal with 2-methyl-2-morpholinopropanal affords the title compound.

BIOLOGICAL EXAMPLES

Example 1

Immunoproteasome and Constitutive Proteasome Enzymatic Activity Assays

A Caliper-based proteasome assay (Caliper Life Sciences, Hopkinton, Mass.) was used to measure inhibition of the immunoproteasome LMP7/B5i subunit, the immunoproteasome LPM2/β1i subunit, and the constitutive proteasome β5c unit for a compound of Formula (I). For LMP7 and β5c, serial dilutions of test compounds were incubated with either human recombinant immunoprotcasome or constitutive proteasome (0.3 nM enzyme) and a carboxyfluorescein (FAM)-labeled peptide substrate FAM-TYETFKSIMKKSPF-NH$_2$ (1 μM) at it for 3 h. The reaction was then terminated with a buffer containing the known proteasome inhibitor carfilzomib at a concentration of 5 uM. For LMP2, serial dilutions of test compounds were incubated with human recombinant immunoproteasome proteasome (0.3 nM enzyme) and a carboxyfluorescein (FAM)-labeled peptide substrate FAM-GLTNIKTEEISEVNLDAEFRK-NH$_2$ (1 μM) at rt for 2 h. The reaction was then terminated with a buffer containing the known proteasome inhibitor ixazomib at a concentration of 6.7 uM. The reaction buffer was 20 mM Hepes pH 7.4, 0.01% bovine serum albumin, 0.015% SDS, 0.5 mM EDTA, 1%0/DMSO. The peptide cleavage reaction product was quantified on a Caliper LabChip 3000. Percent inhibition was calculated for each compound dilution and the concentration that produced 50% inhibition was calculated. This value is presented as the IC$_{50}$. The IC$_{50}$ values for a representative no. of compounds are provided below.

| Synthetic Ex # | LMP7 subunit IC$_{50}$ (nM) | β5c subunit IC$_{50}$ (nM) | LMP2 subunit IC$_{50}$ (nM) |
|---|---|---|---|
| 1 | 79 | 1457.5 | nd |
| 2 | 55 | >5000 | >5000 |
| 3 | 60 | >5000 | 3428 |
| 4 | 4.0 | 637 | 2438 |
| 5 | 7.6 | 1041 | 448 |
| 6 | 57 | >5000 | 964.5 |
| 7 | 2.6 | >5000 | >5000 |
| 8 | >5000 | >5000 | >5000 |
| 9 | 14 | >5000 | 3653 |
| 10 | 1.8 | 3414 | >5000 |
| 11 | 957 | >5000 | 3235 |
| 12 | 39 | >5000 | >5000 |
| 13 | 38 | >5000 | 4043 |
| 14 | 123 | 4847 | >5000 |
| 15 | 5.5 | 4194.7 | >5000 |
| 16 | 2.5 | 444 | >5000 |
| 17 | 1.9 | 2950 | >5000 |
| 18 | 2.0 | 1540 | >5000 |
| 19 | 60 | 3260 | >5000 |
| 20 | 3.6 | 4540 | >5000 |
| 21 | 1.4 | 1943 | 4782 |
| 22 | 1.8 | >5000 | >5000 |
| 23 | 2.6 | >5000 | >5000 |
| 24 | 3.7 | 1392 | >5000 |
| 25 | 0.6 | 172 | >5000 |
| 26 | 1.2 | 2109 | >5000 |
| 27 | 11 | 3479 | >5000 |
| 28 | 1.5 | 2192 | >5000 |
| 29 | 2.9 | 3401 | >5000 |
| 30 | 16 | >5000 | >5000 |
| 31 | 12 | 2386 | >5000 |
| 32 | 9.2 | 713 | >5000 |
| 33 | 41 | >5000 | >5000 |
| 34 | 14 | 3370 | >5000 |
| 35 | 2 | 3024 | >5000 |
| 36 | 6.9 | 397 | >5000 |
| 37 | 4 | 1957 | >5000 |
| 38 | 7 | >5000 | >5000 |
| 39 | 1.2 | 187 | >5000 |
| 40 | 1.3 | 228 | >5000 |
| 41 | 1.6 | 518 | >5000 |
| 42 | 0.5 | 141 | nd |
| 43 | 2 | 34 | nd |
| 44 | 2.3 | 396 | nd |
| 45 | 4 | 854 | nd |
| 46 | 1 | 187 | nd |
| 47 | 1.1 | 128 | nd |
| 48 | 0.6 | 115 | nd |
| 49 | 1.3 | 149 | nd |
| 50 | 9.8 | >5000 | nd |
| 51 | 0.5 | 356 | nd |
| 52 | 1.3 | 336 | nd |
| 53 | 1.8 | 205 | nd |
| 54 | 1.6 | 192 | nd |
| 55 | 2.5 | 225 | nd |
| 56 | 1.7 | 148 | nd |
| 57 | 1.4 | 176 | nd |
| 58 | 0.8 | 23 | nd |
| 59 | 2.8 | 372 | >5000 |
| 60 | 0.9 | 232 | nd |
| 61 | 1.4 | 1490 | nd |
| 62 | 1.6 | 205 | nd |
| 63 | 1.4 | 230 | nd |
| 64 | 3.3 | 645 | nd |
| 65 | 2.3 | 60 | nd |
| 66 | 2.1 | 217 | nd |
| 67 | 1 | 2310 | >5000 |
| 68 | 2.5 | 447 | nd |
| 69 | 3.2 | 670 | nd |
| 70 | 6.5 | 1840 | nd |
| 71 | 4.5 | 1660 | nd |
| 72 | 2.5 | 225 | nd |
| 73 | 2.7 | 288 | nd |
| 74 | 1.2 | 925 | 3360 |
| 75 | 1.1 | 1015 | nd |
| 76 | 1.2 | 677 | nd |
| 77 | 13 | >5000 | nd |
| 78 | 4.8 | 1266 | nd |
| 79 | 2 | 578 | nd |
| 80 | 2 | 1505 | nd |
| 81 | 4.4 | 3840 | nd |
| 82 | 1.4 | 2150 | >5000 |
| 83 | 4.4 | 1220 | >5000 |
| 84 | 2.9 | 445 | nd |
| 85 | 2 | 4890 | >5000 |
| 86 | 2.7 | 566 | >5000 |
| 87 | 13 | 1010 | nd |
| 88 | 7.1 | 263 | nd |
| 89 | 73 | 1850 | nd |
| 90 | 1 | 1960 | 4500 |
| 91 | 2.5 | 320 | nd |
| 92 | 1.9 | 2240 | nd |
| 93 | 3.0 | 165 | nd |
| 94 | 2.0 | 1760 | nd |
| 95 | 37 | 3390 | nd |
| 96 | 2.7 | >5000 | nd |
| 97 | 5.0 | 3970 | nd |
| 98 | 3.5 | 3270 | nd |
| 99 | 68 | 1990 | nd |
| 100 | 21 | 530 | nd |
| 101 | 1.7 | >5000 | nd |
| 102 | 0.7 | 1130 | 4492.7 |
| 103 | 5.3 | 2310 | nd |
| 104 | 1.4 | >5000 | nd |
| 105 | 2.7 | 1450 | 2162.2 |
| 106 | 5.2 | 2240 | nd |
| 107 | 111 | >5000 | Nd |
| 108 | 0.9 | 830 | Nd |
| 109 | 6.4 | 3320 | Nd |
| 110 | 22 | >5000 | Nd |
| 111 | 4.2 | 90 | nd |
| 112 | 2.5 | 95 | nd |
| 113 | >5000 | >5000 | nd |
| 114 | 2.3 | 2540 | nd |
| 115 | 2.6 | 2930 | nd |
| 116 | 62 | >5000 | nd |
| 117 | 0.8 | 640 | nd |
| 118 | 1.5 | 570 | nd |
| 119 | >5000 | >5000 | nd |
| 120 | 530 | >5000 | nd |
| 121 | 1.9 | 1750 | nd |
| 122 | 1.5 | 4180 | nd |
| 123 | 550 | >5000 | nd |
| 124 | 2.2 | 550 | nd |

| Synthetic Ex # | LMP7 subunit IC$_{50}$ (nM) | β5c subunit IC$_{50}$ (nM) | LMP2 subunit IC$_{50}$ (nM) |
|---|---|---|---|
| 125 | 1.6 | 2860 | nd |
| 126 | 21 | >5000 | nd |
| 127 | 5.0 | 900 | nd |
| 128 | 2.3 | 2730 | nd |
| 129 | 2.0 | 1940 | nd | nd = not determined

Example 2

Inhibition of Proteasome Activity Cells

The cell-based effects of a compound described herein on the immunoproteasome are determined by measuring inhibition of proteasome activity in cells using the Proteasome-Glo™ Cell-Based Reagent (Promega, Madison Wis.). The Proteasome-Glo™ assay contains a specific luminogenic proteasome substrate in a buffer optimized for cell permeabilization, proteasome activity, and luciferase activity. For the chymotrypsin-like activity (LMP7 and β5c), the peptide substrate is Suc-LLVY-aminoluciferin (Succinyl-leucine-leucine-valine-tyrosine-aminoluciferin). Cleavage of the substrate by proteasome results in luminescent signal which is proportional to the proteasome activity. The cell line THP-1 (a monocytic leukemia cell line enriched in immunoproteasome), the cell line HT-29 (a colorectal adenocarcinoma cell line enriched in constitutive proteasome), and primary human peripheral blood mononuclear cells (PBMC) are used to assess proteasome activity. Cells are seeded in a 96-well plate at 10,000 cells per well in RPMI 1640 high glucose medium with 10% fetal bovine serum (FBS). Compound dilutions are added to cells starting at a concentration of 5 uM and decreasing in tripling dilutions. The final DMSO concentration is 1%. The concentration range is adjusted as needed for compounds of different potencies. The cells treated with compounds are incubated for 2 h at 37° C. in 5% CO$_2$. At the end of the 2 h incubation period, cells are transferred to white 384 well assay plates. 20 uL of Proteasome-Glo™ Reagent is added to each well and incubated for 10 min at rt. The plate is read in the Analyst HT instrument (Molecular Devices, Sunnyvale, Calif.) using luminescence mode. The percent inhibition of activity is plotted as a function of log compound concentration. The IC$_{50}$ is then calculated for each compound using Prism software from GraphPad Software Inc. (San Diego, Calif.).

| Synthetic Ex # | PBMC/LMP7 IC$_{50}$ (nM) |
|---|---|
| 1 | 190 |
| 2 | 420 |
| 3 | 130 |
| 4 | 39 |
| 5 | 23 |
| 6 | 140 |
| 7 | 9.4 |
| 10 | 7.1 |
| 15 | 3.3 |

Example 3

IL-2 Production in Anti-CD3 and Anti-CD28 Stimulated Human PBMCs

Peripheral blood mononuclear cells (PBMCs) isolated from human whole blood are preincubated with or without the test compounds in RPMI 1640+10% fetal bovine serum at 37° C. for 30 min. PBMCs are stimulated with 2.5 ug/mL plate bound anti-CD3 and 1 ug/mL soluble anti-CD28 overnight and supernatant is collected for AlphaLISA IL2 assay. The IL-2 production is measured as AlphaLISA (Perkin Elmer) signal counts using Envision plate reader. Human Blood is obtained from healthy volunteer through Stanford Blood Center. Blood was collected by venipuncture into sodium heparin tubes. Blood was layered over Ficoll-Histopaque in 50 mL conical tube and centrifuged at 2000 rpm for 20 min at t. Mononuclear cells are collected into 50 mL conical tubes, pooled and diluted with 1×PBS to make up final volume to 50 mL in each tube. Cells are pelleted at 1500 rpm for 5 min and cells are washed two times. The cells are counted in Vi-Cell using trypan blue to determine cell number and viability. PBMCs are then resuspended in RPMI 1640 with 10% fetal bovine serum at a concentration 1×106 cells/mL.

A 96-well polystyrene plate is coated with 2.5 μg/mL anti-CD3 in PBS overnight at 4° C. The wells in column one are coated with PBS only for unstimulated controls. Test compounds are dissolved at 10 mM in 100% DMSO and 1:3 serial dilutions of compounds are prepared in DMSO. The compounds are further diluted in RPMI with 10% fetal bovine serum medium to make final DMSO 0.2% in 96-well polypropylene plate. To treat PBMC with compounds, 100 uL of 1×105 cells are cultured in 96-well polypropylene plate. Then 8 uL of each diluted compound is added in the corresponding wells in duplicate and 8 uL of medium with 2.5% DMSO is added to control wells. The plates are incubated at 37° C. incubator for 30 min. The anti-CD3 coated plates are washed with PBS twice. 92 uL of media containing 1 ug/mL anti-CD28 are added to all wells except unstimulated controls. In unstimulated wells, 92 uL medium is added. Plates are incubated overnight at 37° C., 5% CO$_2$ incubator.

The next day, 150 uL of supernatant is removed from each well for AlphaLISA IL2 assay. According to manufacturer's protocol (Perkin Elmer), 1× buffer. IL2 standards (10 conc.), 2.5× acceptor plus biotinylated beads mixture, 2× streptavidin donor beads are prepared. To each well, 2.5 uL standards or samples are added and then 10 uL of 2.5× beads are added to each well. The plate is sealed with aluminum plate sealer and incubated at room temp on shaker for 1 hr. 12.5 uL of streptavidin donor beads are added to each well in dark room. The plate is sealed with aluminum plate sealer and incubated at room temp on shaker for 30 min. The plate is read in an Envision plate reader.

The IC$_{50}$ for each compound is determined from a ten-point dose response curve for all compounds, each dose being tested in duplicate wells. The IC$_{50}$ represents the concentration of a compound that shows 50% inhibition of IL-2 production in response to anti-CD3+anti-CD28 stimulated PBMCs with compound to 50% of that in control wells without compounds, and is calculated using curve fitting software (Graphpad Prism, San Diego, Calif.).

Example 4

Recovery of Enzymatic Activity Upon Dialysis

The dialysis assay is done to determine if a compound binds reversibly or irreversibly to immunoproteasome thereby resulting in reversible or irreversible inhibition of proteasome activity. Compounds exhibiting an irreversible mode of binding will demonstrate no significant return of enzymatic activity following extensive dialysis. Partial or complete recovery of proteasome activity over extended periods of time during dialysis is indicative of slow off-rate kinetics due to formation of a reversible covalent bond. For rapidly reversible compounds complete recovery of proteasome activity upon dialysis should be observed.

A solution containing immunoproteasome is incubated with a compound described herein (test compound) or (S)-4-methyl-N—((S)-1-(((S)-4-methyl-1-((R)-2-methyl-oxiran-2-yl)-1-oxopentan-2-yl)amino)-1-oxo-3-phenylpropan-2-yl)-2-((S)-2-(2-morpholino-acetamido)-4-phenylbutanamido)-pentanamide (reference compound), an irreversible covalent inhibitor of the immunoproteasome which targets the catalytic threonine of the immunoproteasome subunits (see Kuhn, D. J., et al. 2007. Potent activity of carfilzomib, a novel, irreversible inhibitor of the ubiquitin-proteasome pathway, against preclinical models of multiple myeloma. Blood, 110(9), 3281-3290). Following pre-incubation, the solution containing immunoproteasome and the test compound or reference compound is dialyzed at rt in a buffer of 50 mM Hepes pH 7.5, 0.1% bovine serum albumin, 5 mM magnesium chloride, 1 mM dithiothreitol, and 0.01% Triton X-100 for 1 day, 2 days, and 3 days with a change of dialysis buffer twice daily. Following dialysis, enzymatic activity is measured using the Caliper-based proteasome activity assay (Caliper Life Sciences, Hopkinton, Mass.). The level of activity of solution with test or reference compound is compared to control samples (i.e., proteasome solution with no inhibitor) also dialyzed for 1 day, 2 days, and 3 days with a change of dialysis buffer twice daily.

Example 5

Durability of Binding in Cells

The durability of binding of proteasome inhibitors is assessed in cells using wash-out assays and the Proteasome-Glo™ Reagent kit. THP-1 cells, HT-29 cells, or PBMC were incubated with an 8-fold dilution series of inhibitor for 2 hours. Following 2 hours of incubation, cells are washed using 3 occasions of centrifugation followed by resuspension in culture medium. Following inhibitor washout, cells are returned to culture for either 30 min, 4 hours, or 18 hours. Cells are then transferred to white 384 plates, and 20 uL of Proteasome-Glo™ Reagent is added to each well for 10 min. Plates are then read on an Analyst HT plate reader using luminescence mode. The percent inhibition of activity is plotted as a function of log compound concentration. The $IC_{50}$ is then calculated for each compound using Prism software from GraphPad.

Example 6

Biochemical Durability of Binding

The durability of binding of proteasome inhibitors is assessed in cells using purified constitutive and immune proteasome and an ELISA-based active site occupancy assay called Pro-CISE. Here, occupancy of a test compound within the active site is measured in a time dependent fashion by blocking binding of a high affinity probe to the proteasome. A buffer of 20 mM Tris-HCl pH 8, 0.5 mM EDTA, 0.03% SDS is utilized for initial steps. 200 nM test compound is incubated with 60 nM proteasome for 1 h at rt to facilitate compound binding. The mixture is then diluted 50-fold, and a high concentration of 5 uM biotinylated proteasome active binding probe (PABP) is added (See Kirk et al. Meth Mol Biol 1172:114 (2014)) at 1, 3, 6, and 24 h following dilution. The probe will bind irreversibly to any proteasome sites that become available following dissociation of the test molecule, providing a read-out of the test compound's durability. The ELISA steps of the procedure utilize a buffer of phosphate buffered saline, 1% bovine serum albumin, 0.1% Tween-20. Streptavidin coated ELISA plates are pre-blocked with ELISA buffer, buffer is removed, and the following are added: 20 uL ELISA buffer, 70 uL 8M guanidine HCl in 20 mM Tris HCl pH 8.0 with 0.5 mM EDTA, and 10 uL of PABP-treated proteasome samples. Mixture is incubated for 1 h at rt. Plates are washed, incubated with subunit selective immune or constitutive primary antibody overnight at 4 deg C., washed, incubated with secondary antibody for 2 h at rt, washed, and detected using SuperSignal ELISA Pico Kit solution and luminescence is detected on a Perkin Elmer Envision. The % occupancy at each time point is determined by normalization to conditions with no test compound (maximum signal) or no proteasome (minimum signal) and the compound dissociation half-life ($t_{1/2}$) is determined by fitting the time course to a one-phase exponential decay.

| Synthetic Ex # | LMP7 subunit $t_{1/2}$ (hrs) | β5c subunit $t_{1/2}$ (hrs) | LMP2 subunit $t_{1/2}$ (hrs) |
|---|---|---|---|
| 1 | 9.2 | nd | nd |
| 2 | 1.1 | nd | <0.5 |
| 3 | 1.6 | nd | <0.5 |
| 4 | 3.6 | <0.5 | nd |
| 5 | <0.5 | <0.5 | nd |
| 7 | 13 | <0.5 | <0.5 |
| 9 | 4.7 | 1.8 | nd |
| 10 | 18 | <0.5 | nd |
| 12 | 0.51 | <0.5 | nd |
| 13 | 1.4 | 0.74 | nd |
| 14 | 2.4 | <0.5 | nd |
| 15 | 3.1 | <0.5 | nd |
| 16 | >40 | nd | nd |
| 17 | 22 | nd | nd |
| 18 | >40 | nd | nd |
| 19 | 11 | nd | nd |
| 20 | 25 | nd | nd |
| 21 | >40 | nd | nd |
| 22 | 35 | nd | nd |
| 23 | 35 | nd | nd |
| 24 | 19 | nd | nd |
| 25 | >40 | nd | nd |
| 26 | >40 | nd | nd |
| 27 | 0.89 | nd | nd |
| 28 | >40 | nd | nd |
| 29 | 16 | nd | nd |
| 30 | 13 | nd | nd |
| 31 | 20 | nd | nd |
| 32 | >40 | nd | nd |
| 33 | 4.0 | nd | nd |
| 34 | 7.4 | nd | nd |
| 35 | >40 | nd | nd |
| 36 | 12 | nd | nd |
| 37 | <0.5 | nd | nd |
| 38 | <0.5 | nd | nd |
| 39 | >40 | nd | nd |
| 40 | >40 | nd | nd |
| 41 | >40 | nd | nd |
| 42 | >40 | nd | nd |
| 43 | >40 | nd | nd |
| 44 | >40 | nd | nd |
| 45 | >40 | nd | nd |
| 46 | >40 | nd | nd |
| 47 | >40 | nd | nd |

-continued

| Synthetic Ex # | LMP7 subunit $t_{1/2}$ (hrs) | β5c subunit $t_{1/2}$ (hrs) | LMP2 subunit $t_{1/2}$ (hrs) |
|---|---|---|---|
| 48 | >40 | nd | nd |
| 49 | 25 | nd | nd |
| 50 | 12 | nd | nd |
| 51 | >40 | nd | nd |
| 52 | 39 | nd | nd |
| 53 | >40 | nd | nd |
| 55 | 25 | nd | nd |
| 56 | >40 | nd | nd |
| 57 | >40 | nd | nd |
| 59 | 31 | nd | nd |
| 61 | 21 | nd | nd |
| 62 | >40 | nd | nd |
| 63 | >40 | nd | nd |
| 65 | >40 | nd | nd |
| 67 | >40 | nd | nd |
| 69 | 22 | nd | nd |
| 70 | 14 | nd | nd |
| 71 | 0.60 | nd | nd |
| 73 | 0.53 | nd | nd |
| 74 | >40 | nd | nd |
| 75 | >40 | nd | nd |
| 76 | >40 | nd | nd |
| 77 | 2.0 | nd | nd |
| 78 | 39 | nd | nd |
| 79 | >40 | nd | nd |
| 80 | 24 | nd | nd |
| 81 | 6.6 | nd | nd |
| 82 | >40 | nd | nd |
| 83 | >40 | nd | nd |
| 84 | >40 | nd | nd |
| 85 | >40 | nd | nd |
| 86 | 39 | nd | nd |
| 87 | 4.6 | nd | nd |
| 88 | <0.5 | nd | nd |
| 89 | 2.7 | nd | nd |
| 90 | 36 | nd | nd |
| 91 | >40 | nd | nd |
| 92 | >40 | nd | nd |
| 93 | 32 | nd | nd |
| 94 | >40 | nd | nd |
| 95 | 4.9 | nd | nd |
| 96 | >40 | nd | nd |
| 97 | 11 | nd | nd |
| 98 | 4.2 | nd | nd |
| 99 | 11 | nd | nd |
| 100 | >40 | nd | nd |
| 101 | 2.5 | nd | nd |
| 102 | 27 | nd | nd |
| 103 | <0.5 | nd | nd |
| 104 | 32 | nd | nd |
| 105 | 6.5 | nd | nd |
| 106 | 39 | nd | nd |
| 107 | 2.8 | nd | nd |
| 108 | >40 | nd | nd |
| 109 | >40 | nd | nd |
| 110 | 5.9 | nd | nd |
| 113 | >40 | nd | nd |
| 114 | 6.5 | nd | nd |
| 116 | >40 | nd | nd |
| 117 | >40 | nd | nd |
| 118 | <0.5 | nd | nd |
| 119 | >40 | nd | nd |
| 120 | >40 | nd | nd |
| 121 | <0.5 | nd | nd |
| 122 | >40 | nd | nd |
| 123 | >40 | nd | nd |
| 124 | 35 | nd | nd |
| 125 | 2.5 | nd | nd |
| 126 | 3.6 | nd | nd |
| 127 | 5.1 | nd | nd | nd = not determined

The foregoing disclosure has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the disclosure should, therefore, be determined not with reference to the above description, but should instead be determined with reference to the following appended claims, along with the full scope of eq.alents to which such claims are entitled.

What is claimed is:

1. A compound of Formula (I):

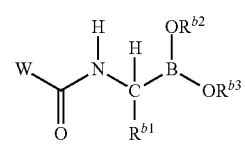

or a pharmaceutically acceptable salt thereof, wherein:

W is —O—P—Q—C($R^{8a}$)=C($R^{8b}$)($R^{8c}$) or a group of formula

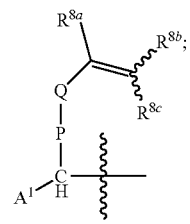

$A^1$ is hydrogen, hydroxy, alkyl, optionally substituted aryl, optionally substituted heteroaryl, optionally substituted heterocyclyl, or —S(=O)$_2$-alkyl, wherein said alkyl of said —S(=O)$_2$-alkyl is unsubstituted;

P is -alkyl-N(R)—, -alkyl-($C_3$-$C_6$)cycloalkyl-N(R)—, -alkyl-O-alkyl-N(R)—,

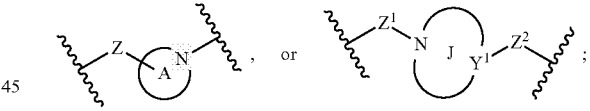

Z and $Z^1$ are independently a covalent bond, -alkyl-, -alkyl-O—, -alkyl-N(R)—, or -alkyl-O-alkyl-, with the proviso that Z is connected to ring A at a carbon atom adjacent to the ring nitrogen atom;

ring A with the ring nitrogen atom shown is an optionally substituted saturated mono- or multicyclic 4 to 10 membered heterocyclyl;

ring J with the ring nitrogen atom and ring $Y^1$ atom shown is a saturated 4 to 10 membered heterocyclyl;

$Y^1$ is C or N;

$Z^2$ is a covalent bond or N(R), with the proviso that when $Y^1$ in ring J is nitrogen, then $Z^2$ is a covalent bond;

each R is independently hydrogen, or alkyl;

Q is —C(=O)— or —S(=O)$_2$—;

$R^{8a}$ is hydrogen, halogen, or cyano;

$R^{8b}$ is hydrogen, optionally substituted alkyl, optionally substituted cycloalkyl, optionally substituted heteroaryl, or optionally substituted heterocyclyl, wherein when $R^{8b}$ is alkyl, the alkyl is optionally substituted with 1-2 substituents chosen from a —N(alkyl)(haloalkyl), —N(alkyl)2, and heterocyclyl, wherein the heterocyclyl is optionally substituted with 1-3 substituents chosen from halo, alkyl, and —C(=O)-alkyl; and the heterocyclyl is optionally substituted with 1-2 substituents chosen from halo, alkyl, alkoxy, haloalkyl, cyano and —S(=O)$_2$-alkyl; or $R^{8a}$ and $R^{8b}$ are taken together to form a bond; and $R^{8c}$ is hydrogen or alkyl;

$R^{b1}$ is optionally substituted alkyl, optionally substituted aryl, optionally substituted heteroaryl, optionally substituted cycloalkyl, or optionally substituted heterocyclyl, wherein when $R^{b1}$ is alkyl, the alkyl is optionally substituted with 1-2 substituents chosen from aryl and heteroaryl, each of which is optionally substituted with 1-3 substituents independently chosen from halo, alkyl, alkoxy, haloalkyl, cyano and —S(=O)$_2$-alkyl; and $R^{b2}$ and $R^{b3}$ are independently hydrogen or optionally substituted alkyl; or $R^{b2}$ and $R^{b3}$ together with the boron atom to which they are shown attached form a cyclic boronic ester;

wherein when the optionally substituted aryl, the optionally substituted heteroaryl, the optionally substituted heterocyclyl and the optionally substituted cycloalkyl is substituted, the optionally substituted aryl, the optionally substituted heteroaryl, the optionally substituted heterocyclyl and the optionally substituted cycloalkyl are substituted with one or more ring system substituents each independently selected from alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, alkoxyalkyl, aryloxy, aralkoxy, acyl, aroyl, halo, haloalkyl, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —SH, —SF$_5$, —OSF$_5$ (for aryl), —O-alkyl-O-alkyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), oxime (e.g., =N—OH), —NY$_1$Y$_2$, -alkyl-NY$_1$Y$_2$, —C(O)NY$_1$Y$_2$, —SO$_2$NY$_1$Y$_2$ and —SO$_2$NY$_1$Y$_2$, wherein Y$_1$ and Y$_2$ are the same or different and are independently chosen from hydrogen, alkyl, -alkyl-O-alkyl, aryl, cycloalkyl, heterocyclyl and aralkyl; or two available hydrogens on two adjacent carbon atoms of the optionally substituted aryl, the optionally substituted heteroaryl, the optionally substituted heterocyclyl and the optionally substituted cycloalkyl are taken together to form methylenedioxy, ethylenedioxy and —C(CH$_3$)$_2$—.

2. A compound or a pharmaceutically acceptable salt of claim 1, wherein:

W is —O—P—Q—C(R$^{8a}$)=C(R$^{8b}$)(R$^{8c}$) or a group of formula

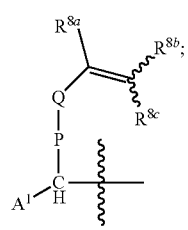

$A^1$ is hydrogen;

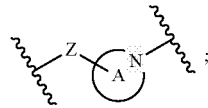

P is

Z is -alkyl- or -alkyl-O-alkyl-, with the proviso that Z is connected to ring A at a carbon atom adjacent to the ring nitrogen atom;

ring A with the ring nitrogen atom shown is an optionally substituted saturated mono- or multicyclic 4 to 10 membered heterocyclyl;

Q is —C(=O)—;

$R^{8a}$ is hydrogen, halogen, or cyano;

$R^{8b}$ is hydrogen; alkyl which is optionally substituted with 1-2 substituents chosen from a —N(alkyl)(haloalkyl), —N(alkyl)$_2$, and optionally substituted heterocyclyl; and heterocyclyl which is optionally substituted with 1-2 substituents chosen from halo, alkyl, alkoxy, haloalkyl, cyano, and —S(=O)$_2$-alkyl; or $R^{8a}$ and $R^{8b}$ are taken together to form a bond; and $R^{8c}$ is hydrogen or alkyl;

$R^{b1}$ is alkyl which is optionally substituted with 1-2 substituents chosen from aryl and heteroaryl, each of which is optionally substituted with 1-3 substituents independently chosen from halo, alkyl, alkoxy, haloalkyl, cyano, and —S(=O)$_2$-alkyl; and $R^{b2}$ and $R^{b3}$ are each hydrogen.

3. The compound or a pharmaceutically acceptable salt of claim 1, wherein W is

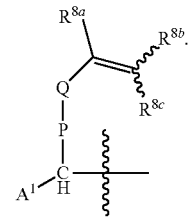

4. The compound or a pharmaceutically acceptable salt of claim 3, wherein $A^1$ is H.

5. The compound or a pharmaceutically acceptable salt of claim 1, wherein W is —O—P—Q—C(R$^{8a}$)=C(R$^{8b}$)(R$^{8c}$).

6. The compound or a pharmaceutically acceptable salt of claim 1, wherein:

said -alkyl-N(R)— of P is:

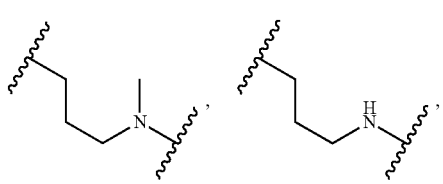

-continued
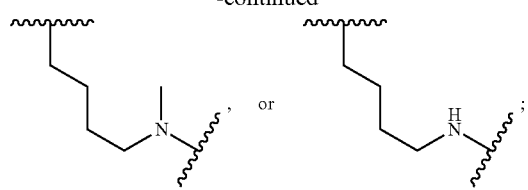, or
said -alkyl-O-alkyl-N(R)— of P is:
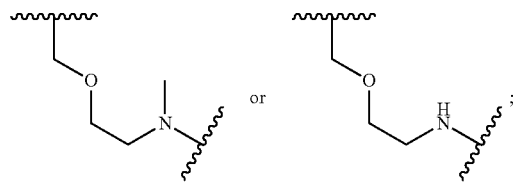, or
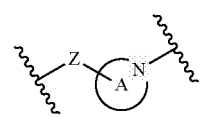
said of P is:
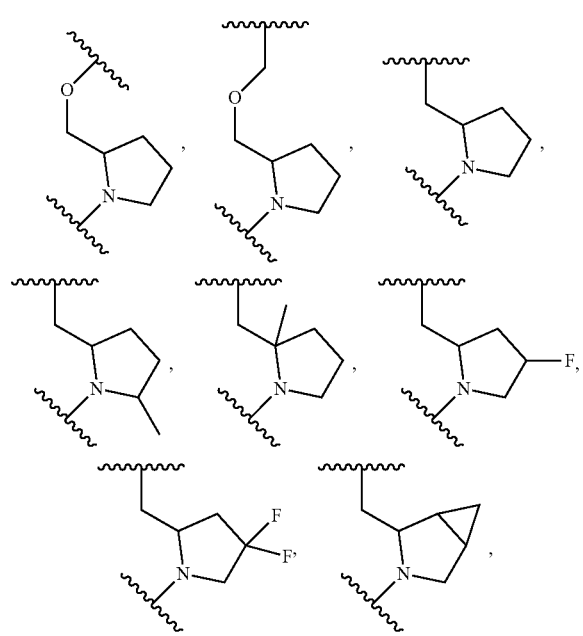
-continued
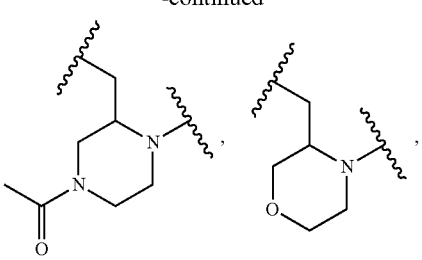,
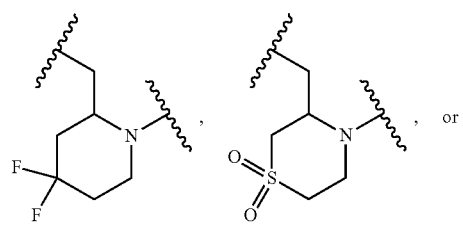, or
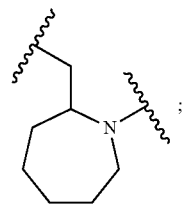;
and
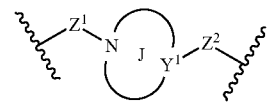
said of P is:
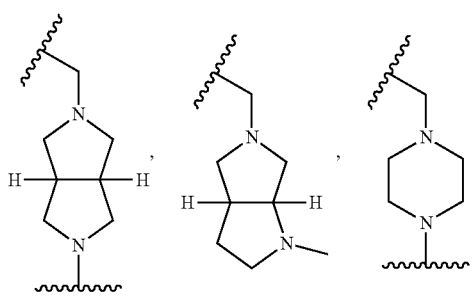
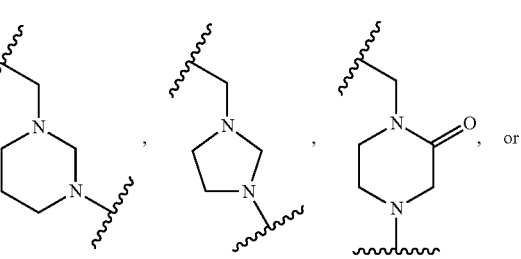

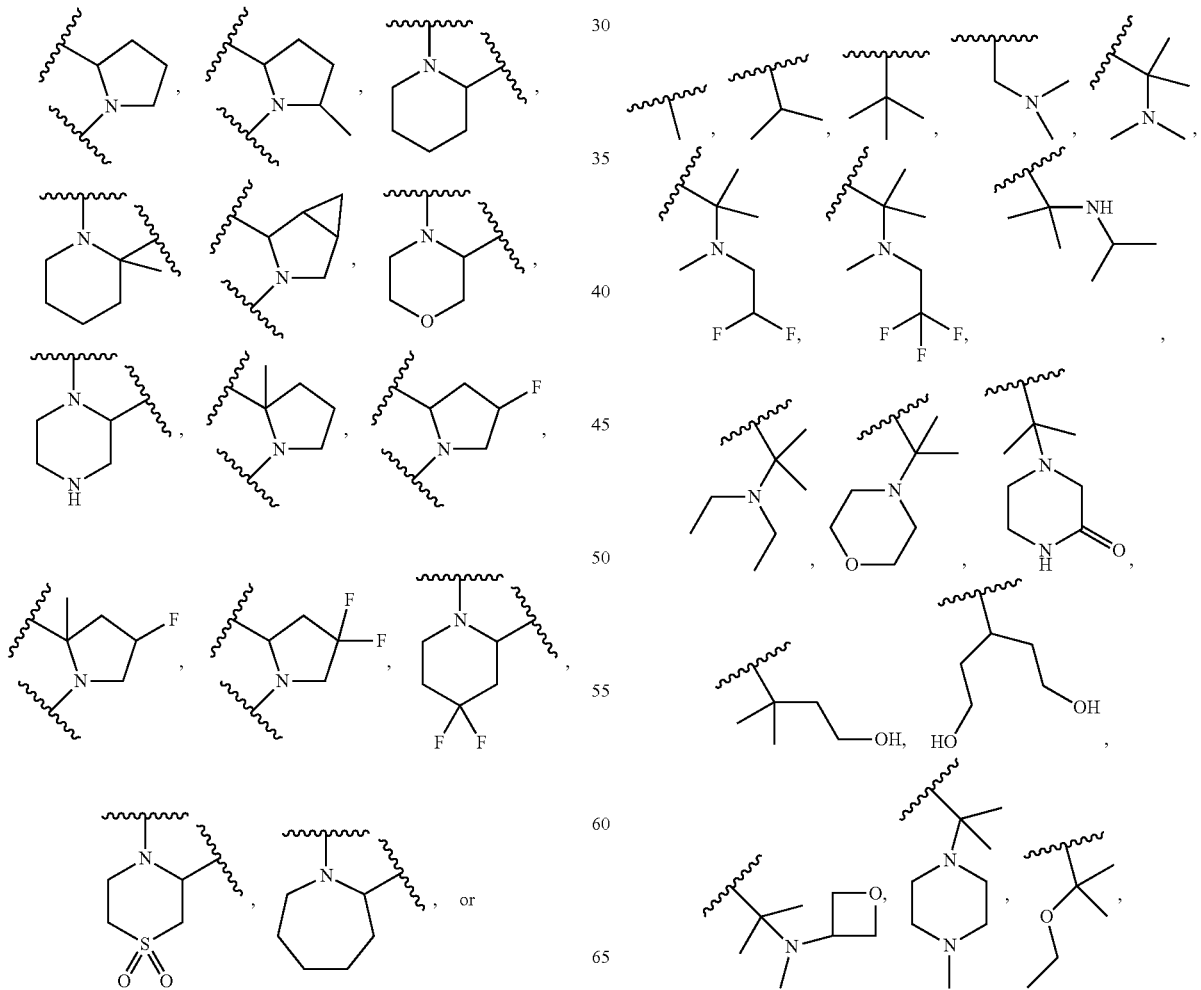

7. The compound or a pharmaceutically acceptable salt of claim 1, wherein P is

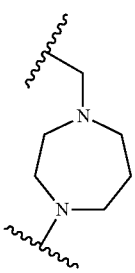

8. The compound or a pharmaceutically acceptable salt of claim 7, wherein ring A of P with the ring nitrogen atom shown is:

9. The compound or a pharmaceutically acceptable salt of claim 3, wherein Z of P is -alkyl-O-alkyl- or -alkyl-.

10. The compound or a pharmaceutically acceptable salt of claim 9, wherein:

said -alkyl-O-alkyl- of Z is —(CH$_2$)$_{1-4}$—O—(CH$_2$)$_{1-4}$—; and said -alkyl- of Z is —(CH$_2$)$_{1-4}$—.

11. The compound or a pharmaceutically acceptable salt of claim 5, wherein Z of P is -alkyl-; and said -alkyl- of Z is —(CH$_2$)—.

12. The compound or a pharmaceutically acceptable salt of claim 1, wherein Q is —C(=O)—.

13. The compound or a pharmaceutically acceptable salt of claim 1, wherein R$^{8a}$ is hydrogen or cyano; and said optionally substituted alkyl of R$^{ab}$ is chosen from:

251
-continued
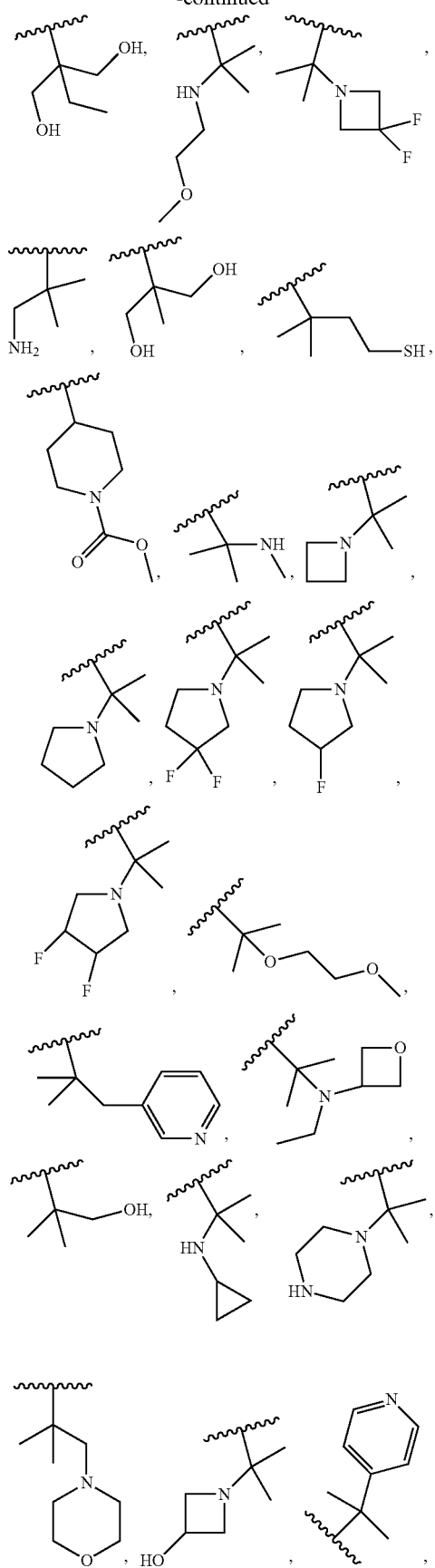
252
-continued
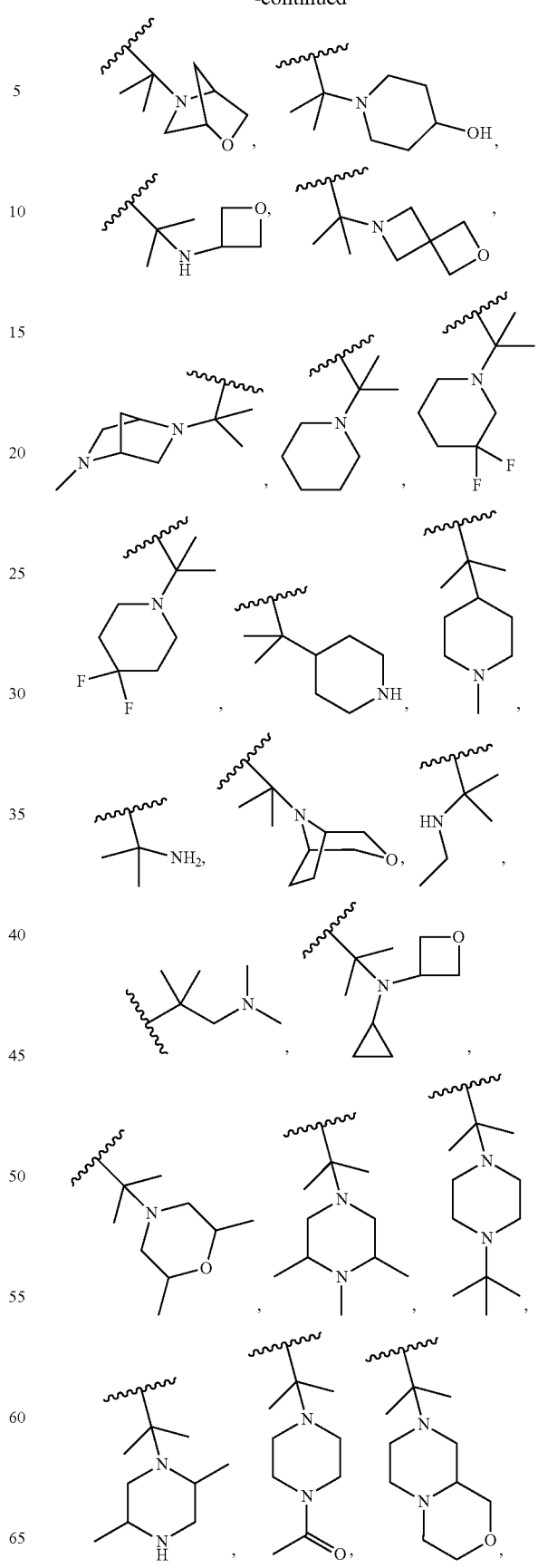

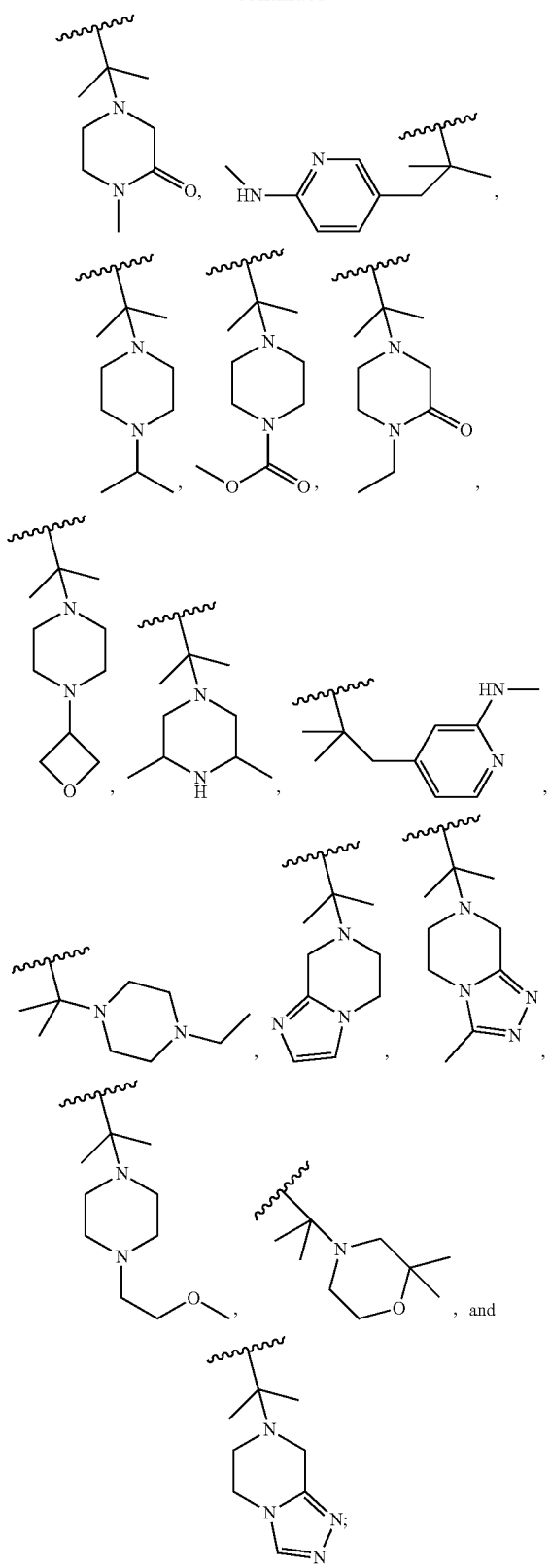

and
said optionally substituted heterocyclyl of $R^{ab}$ is chosen from:

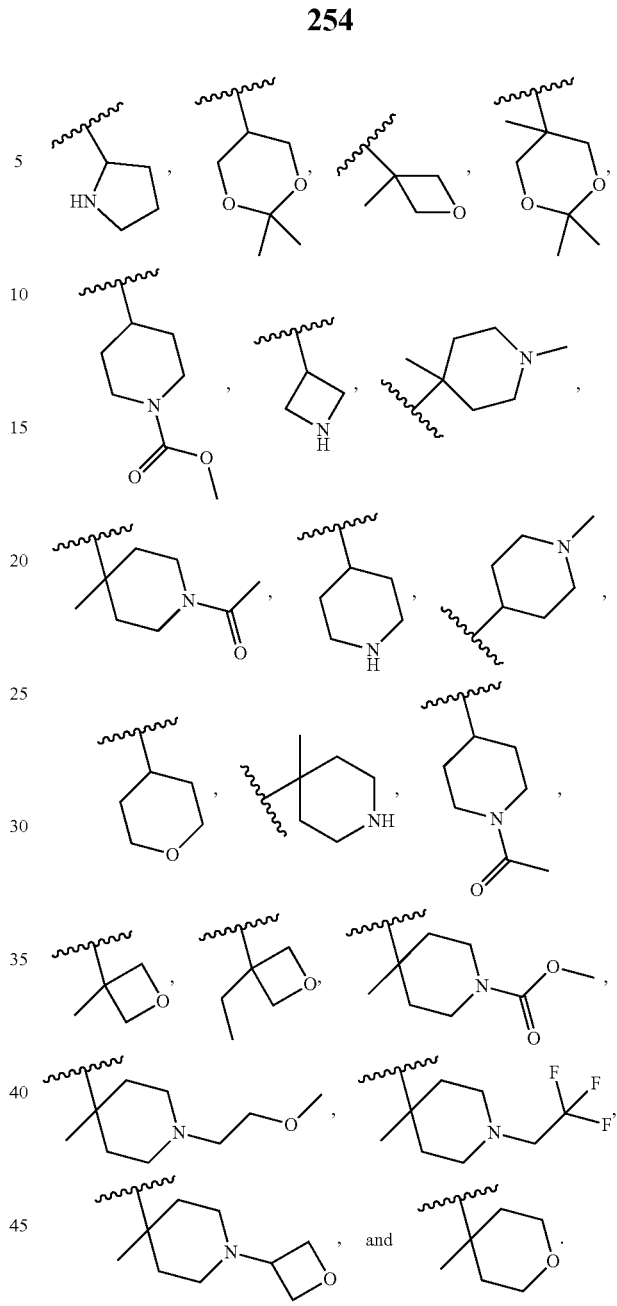

14. The compound or a pharmaceutically acceptable salt of claim 1, wherein:

$R^{8b}$ is H, or an alkyl which is optionally substituted with 1-2 substituents chosen from —N(alkyl)(haloalkyl), —N(alkyl)$_2$, and optionally substituted heterocyclyl; and $R^{8c}$ is H.

15. The compound or a pharmaceutically acceptable salt of claim 14, wherein $R^{8b}$ is an unsubstituted or substituted alkyl chosen from isopropyl, t-butyl, —C(CH$_3$)$_2$—N(CH$_3$)—CH$_2$CF$_3$, —CH$_2$—N(CH$_3$)$_2$, —C(CH$_3$)$_2$—N(CH$_3$)—CH$_2$—CHF$_2$,

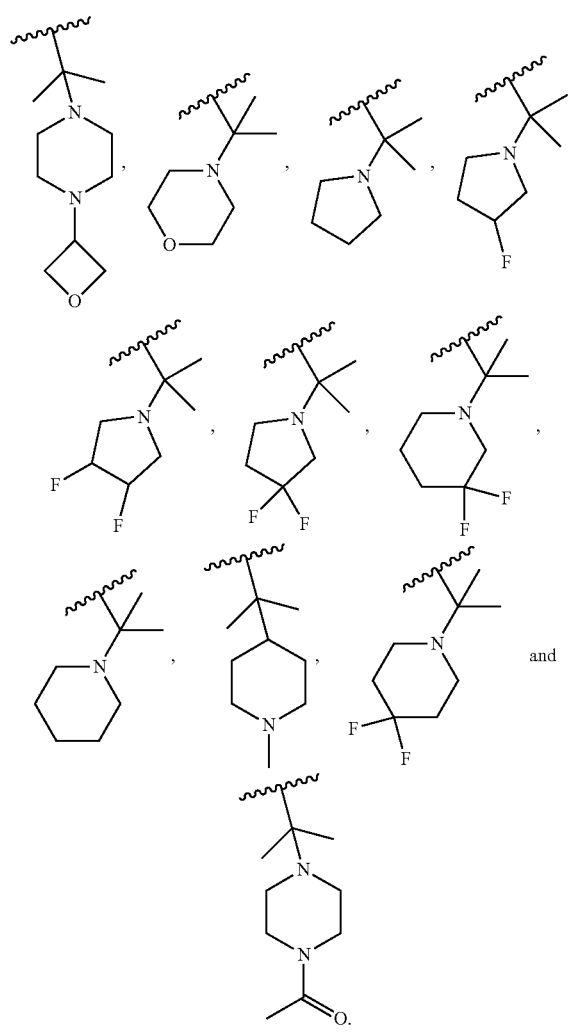

16. The compound or a pharmaceutically acceptable salt of claim 14,
wherein $R^{8b}$ is an optionally substituted heterocyclyl chosen from

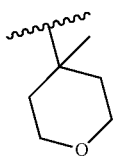

17. The compound or a pharmaceutically acceptable salt of claim 1, wherein $R^{b1}$ is an unsubstituted alkyl or a substituted alkyl, wherein the substituents are 1-2 substituents chosen from aryl and heteroaryl, each of which is optionally substituted with 1-3 substituents independently chosen from halo, alkyl, alkoxy, haloalkyl, cyano, and —S(=O)$_2$-alkyl.

18. The compound or a pharmaceutically acceptable salt of claim 17, wherein $R^{b1}$ is chosen from —CH$_2$CH(CH$_3$)$_2$, —CH$_2$C(CH$_3$)$_3$, —CH$_2$-phenyl, —CH$_2$CH$_2$-phenyl, —CH$_2$-tolyl, —CH$_2$-methoxyphenyl, —CH$_2$-chlorophenyl, —CH$_2$-fluorophenyl, —CH$_2$-trifluoromethylphenyl, —CH$_2$-benzofuranyl, —CH$_2$-naphthyl, —CH$_2$-cyanophenyl, —CH$_2$-difluorophenyl, and —CH$_2$-phenyl-S(=O)$_2$—CH$_3$.

19. The compound or a pharmaceutically acceptable salt of claim 1, wherein $R^{b2}$ and $R^{b3}$ are each H.

20. The compound or a pharmaceutically acceptable salt of claim 3, wherein the compound is chosen from:
  ((R)-1-(3-(((R)-1-(2-cyano-4-methylpent-2-enoyl)pyrrolidin-2-yl)methoxy)propanamido)-2-phenylethyl)boronic acid;
  ((1R)-1-(3-(1-(2-cyano-4-methylpent-2-enoyl)pyrrolidin-2-yl)propanamido)-2-phenylethyl)boronic acid; and
  ((1R)-1-(3-(1-(2-cyano-4-methylpent-2-enoyl)piperidin-2-yl)propanamido)-2-phenylethyl)boronic acid;
  an individual E or Z isomer thereof; and/or
  a pharmaceutically acceptable salt of any of the foregoing compounds.

21. The compound or a pharmaceutically acceptable salt of claim 5, wherein the compound is chosen from:
  ((R)-1-(((((R)-1-(2-cyano-4-methylpent-2-enoyl)piperidin-2-yl)methoxy)carbonyl)amino)-2-phenylethyl)boronic acid;
  ((R)-1-(((((R)-1-(2-cyano-4-methylpent-2-enoyl)pyrrolidin-2-yl)methoxy)carbonyl)amino)-2-phenylethyl)boronic acid;
  ((R)-1-(((((R)-1-acryloylpiperidin-2-yl)methoxy)carbonyl)amino)-2-phenylethyl)boronic acid;
  ((R)-1-(((((S)-1-((E)-2-cyano-4,4-dimethylpent-2-enoyl)piperidin-2-yl)methoxy)carbonyl)amino)-2-phenylethyl)boronic acid;
  ((R)-1-(((((R)-1-(2-cyano-4,4-dimethylpent-2-enoyl)pyrrolidin-2-yl)methoxy)carbonyl)amino)-2-phenylethyl)boronic acid;
  ((R)-1-(((((S)-1-acryloylpiperidin-2-yl)methoxy)carbonyl)amino)-2-phenylethyl)boronic acid;
  ((R)-1-(((((S)-1-(2-cyano-4-methylpent-2-enoyl)pyrrolidin-2-yl)methoxy)carbonyl)amino)-2-phenylethyl)boronic acid;
  ((R)-1-(((((S)-1-(2-cyano-4-methylpent-2-enoyl)piperidin-2-yl)methoxy)carbonyl)amino)-2-phenylethyl)boronic acid;
  ((R)-1-(((((R)-1-acryloylpyrrolidin-2-yl)methoxy)carbonyl)amino)-2-phenylethyl)boronic acid;
  ((R)-1-(((((R)-1-(2-cyano-4,4-dimethylpent-2-enoyl)piperidin-2-yl)methoxy)carbonyl)amino)-2-phenylethyl)boronic acid;
  ((R)-2-(benzofuran-3-yl)-1-(((((R)-1-(2-cyano-4-methylpent-2-enoyl)pyrrolidin-2-yl)methoxy)carbonyl)amino)ethyl)boronic acid;
  ((R)-1-(((((R)-1-(2-cyano-4-methyl-4-(4-(oxetan-3-yl)piperazin-1-yl)pent-2-enoyl)pyrrolidin-2-yl)methoxy)carbonyl)amino)-2-phenylethyl)boronic acid;
  ((R)-1-(((((R)-1-(2-cyano-4,4-dimethylpent-2-enoyl)pyrrolidin-2-yl)methoxy)carbonyl)amino)-2-(p-tolyl)ethyl)boronic acid;
  ((R)-1-(((((R)-1-acryloylpyrrolidin-2-yl)methoxy)carbonyl)amino)-2-(p-tolyl)ethyl)boronic acid;
  ((R)-1-(((((R)-1-(2-cyano-4-methyl-4-(piperidin-1-yl)pent-2-enoyl)pyrrolidin-2-yl)methoxy)carbonyl)amino)-2-phenylethyl)boronic acid;
  ((R)-1-(((((R)-1-(2-cyano-4-(4,4-difluoropiperidin-1-yl)-4-methylpent-2-enoyl)pyrrolidin-2-yl)methoxy)carbonyl)amino)-2-phenylethyl)boronic acid
  ((R)-1-(((((1R,2S,5S)-3-(2-cyano-4,4-dimethylpent-2-enoyl)-3-azabicyclo[3.1.0]hexan-2-yl)methoxy)carbonyl)amino)-2-phenylethyl)boronic acid;

((R)-1-(((((R)-1-(2-cyano-4-methyl-4-morpholinopent-2-enoyl)pyrrolidin-2-yl)methoxy)carbonyl)amino)-2-phenylethyl)boronic acid;

((R)-1-(((((R)-1-(2-cyano-4,4-dimethylpent-2-enoyl)piperidin-2-yl)methoxy)carbonyl)amino)-2-(p-tolyl)ethyl)boronic acid;

((R)-2-(benzofuran-3-yl)- 1-(((((R)-1-(2-cyano-4,4-dimethylpent-2-enoyl)piperidin-2-yl)methoxy)carbonyl)amino)ethyl)boronic acid;

((R)-1-(((((1S,2R,5R)-3-(2-cyano-4,4-dimethylpent-2-enoyl)-3-azabicyclo[3.1.0]hexan-2-yl)methoxy)carbonyl)amino)-2-phenylethyl)boronic acid;

((R)-1-(((((R)-1-(2-cyano-4-methyl-4-(pyrrolidin-1-yl)pent-2-enoyl)piperidin-2-yl)methoxy)carbonyl)amino)-2-phenylethyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-2-phenylethyl)boronic acid;

((R)-1-(((((R)-1-(2-cyano-4-methyl-4-morpholinopent-2-enoyl)piperidin-2-yl)methoxy)carbonyl)amino)-2-phenylethyl)boronic acid;

((R)-1-(((((R)-1-(2-cyano-4-methyl-4-(piperidin-1-yl)pent-2-enoyl)piperidin-2-yl)methoxy)carbonyl)amino)-2-phenylethyl)boronic acid;

((R)-1-(((((R)-1-(2-cyano-4-(4,4-difluoropiperidin-1-yl)-4-methylpent-2-enoyl)piperidin-2-yl)methoxy)carbonyl)amino)-2-phenylethyl)boronic acid;

((R)-1-(((((R)-1-(2-cyano-4,4-dimethylpent-2-enoyl)azepan-2-yl)methoxy)carbonyl)amino)-2-(p-tolyl)ethyl)boronic acid;

((R)-1-(((((S)-1-(2-cyano-4,4-dimethylpent-2-enoyl)azepan-2-yl)methoxy)carbonyl)amino)-2-(p-tolyl)ethyl)boronic acid;

((R)-1-(((((R)-1-(2-cyano-4-methyl-4-(pyrrolidin-1-yl)pent-2-enoyl)pyrrolidin-2-yl)methoxy)carbonyl)amino)-2-phenylethyl)boronic acid;

((R)-1-(((((R)-1-(2-cyano-4-(3,3-difluoropyrrolidin-1-yl)-4-methylpent-2-enoyl)pyrrolidin-2-yl)methoxy)carbonyl)amino)-2-phenylethyl)boronic acid;

((R)-1-(((((R)-1-acryloylpyrrolidin-2-yl)methoxy)carbonyl)amino)-2-(benzofuran-3-yl)ethyl)boronic acid;

((R)- 1-(((((1R,2R,5S)-3-(2-cyano-4,4-dimethylpent-2-enoyl)-3-azabicyclo[3.1.0]hexan-2-yl)methoxy)carbonyl)amino)-2-phenylethyl)boronic acid;

((R)-1-(((((1 S,2S,5R)-3-(2-cyano-4,4-dimethylpent-2-enoyl)-3-azabicyclo [3.1.0]hexan-2-yl)methoxy)carbonyl)amino)-2-phenylethyl)boronic acid;

((R)-2-(benzofuran-3-yl)- 1-(((((R)-1-(2-cyano-4,4-dimethylpent-2-enoyl)pyrrolidin-2-yl)methoxy)carbonyl)amino)ethyl)boronic acid;

((R)-2-(benzofuran-3-yl)- 1-(((((R)-1-(2-cyano-4-methyl-4-morpholinopent-2-enoyl)pyrrolidin-2-yl)methoxy)carbonyl)amino)ethyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-2-(p-tolyl)ethyl)boronic acid;

((R)-2-(benzofuran-3-yl)- 1-(((((R)-1-(2-cyano-4-(3,3-difluoropyrrolidin-1-yl)-4-methylpent-2-enoyl)pyrrolidin-2-yl)methoxy)carbonyl)amino)ethyl)boronic acid;

((R)-2-(benzofuran-3-yl)- 1-(((((R)-4-(2-cyano-4,4-dimethylpent-2-enoyl)morpholin-3-yl)methoxy)carbonyl)amino)ethyl)boronic acid;

((R)-2-(benzofuran-3-yl)- 1-(((((R)-1-(2-cyano-4-methyl-4-(4-(oxetan-3-yl)piperazin-1-yl)pent-2-enoyl)pyrrolidin-2-yl)methoxy)carbonyl)amino)ethyl)boronic acid;

((R)-1-(((((R)-1-(2-cyano-4-methyl-4-morpholinopent-2-enoyl)piperidin-2-yl)methoxy)carbonyl)amino)-2-(p-tolyl)ethyl)boronic acid;

((R)-2-(benzofuran-3-yl)-1-(((((R)-1-(2-cyano-4-methyl-4-morpholinopent-2-enoyl)piperidin-2-yl)methoxy)carbonyl)amino)ethyl)boronic acid;

((R)-2-(benzofuran-3-yl)-1-(((((R)-1-(2-cyano-4-(3,3-difluoropyrrolidin-1-yl)-4-methylpent-2-enoyl)piperidin-2-yl)methoxy)carbonyl)amino)ethyl)boronic acid;

((R)-2-(benzofuran-3-yl)- 1-(((((1S,2R,5R)-3-(2-cyano-4,4-dimethylpent-2-enoyl)-3-azabicyclo [3.1.0]hexan-2-yl)methoxy)carbonyl)amino)ethyl)boronic acid;

((R)-2-(benzofuran-3-yl)- 1-(((((R)- 1-((E)-4-(dimethylamino)but-2-enoyl)pyrrolidin-2-yl)methoxy)carbonyl)amino)ethyl)boronic acid;

((R)-1-(((((R)-1-(2-cyano-4,4-dimethylpent-2-enoyl)piperidin-2-yl)methoxy)carbonyl)amino)-3-phenylpropyl)boronic acid;

((R)-2-(benzofuran-3-yl)- 1-(((((1s,2R,5R)-3-(2-cyano-4-methyl-4-morpholinopent-2-enoyl)-3-azabicyclo [3.1.0]hexan-2-yl)methoxy)carbonyl)amino)ethyl)boronic acid;

((R)-1-(((((1s,2R,5R)-3-acryloyl-3-azabicyclo [3.1.0] hexan-2-yl)methoxy)carbonyl)amino)-2-(benzofuran-3-yl)ethyl)boronic acid;

((R)-1-(((((R)- 1-(4-(4-acetylpiperazin-1-yl)-2-cyano-4-methylpent-2-enoyl)pyrrolidin-2-yl)methoxy)carbonyl)amino)-2-(benzofuran-3-yl)ethyl)boronic acid;

((R)-2-(benzofuran-3-yl)- 1-(((((1s,2R,5R)-3-(2-cyano-4-(3,3-difluoropyrrolidin-1-yl)-4-methylpent-2-enoyl)-3-azabicyclo [3.1.0]hexan-2-yl)methoxy)carbonyl)amino)ethyl)boronic acid;

((R)-2-(benzofuran-3-yl)- 1-(((((R)-1-(2-cyano-4-methyl-4-(4-methylpiperazin-1-yl)pent-2-enoyl)pyrrolidin-2-yl)methoxy)carbonyl)amino)ethyl)boronic acid;

((R)-2-(benzofuran-3-yl)- 1-(((((R)-1-(2-cyano-4-methyl-4-morpholinopent-2-enoyl)-4,4-difluoropyrrolidin-2-yl)methoxy)carbonyl)amino)ethyl)boronic acid;

((R)-2-(benzofuran-3-yl)- 1-(((((2R,5S)-1-(2-cyano-4-methyl-4-morpholinopent-2-enoyl)-5-methylpyrrolidin-2-yl)methoxy)carbonyl)amino)ethyl)boronic acid;

((R)-2-(benzofuran-3-yl)-1-(((((R)-4-(2-cyano-4-methyl-4-morpholinopent-2-enoyl)morpholin-3-yl)methoxy)carbonyl)amino)ethyl)boronic acid;

((R)-2-(benzofuran-3-yl)-1-(((((R)-1-(2-cyano-3-(4-methyltetrahydro-2H-pyran-4-yl)acryloyl)piperidin-2-yl)methoxy)carbonyl)amino)ethyl)boronic acid;

((R)-2-(benzofuran-3-yl)-1-(((((R)-1-(2-cyano-4-methyl-4-(4-(oxetan-3-yl)piperazin-1-yl)pent-2-enoyl)piperidin-2-yl)methoxy)carbonyl)amino)ethyl)boronic acid;

((R)-1-(((((R)- 1-((E)-2-cyano-4,4-dimethylpent-2-enoyl)-4,4-difluoropyrrolidin-2-yl)methoxy)carbonyl)amino)-2-phenylethyl)boronic acid;

((R)-2-(benzofuran-3-yl)-1-(((((R)-1-(2-cyano-4-(3,3-difluoropiperidin-1-yl)-4-methylpent-2-enoyl)piperidin-2-yl)methoxy)carbonyl)amino)ethyl)boronic acid;

((R)-2-(benzofuran-3-yl)-1-(((((R)-1-(2-cyano-4-methyl-4-morpholinopent-2-enoyl)azepan-2-yl)methoxy)carbonyl)amino)ethyl)boronic acid;

((R)-2-(benzofuran-3-yl)-1-(((((S)-1-(2-cyano-4-methyl-4-morpholinopent-2-enoyl)azepan-2-yl)methoxy)carbonyl)amino)ethyl)boronic acid;

((R)-2-(benzofuran-3-yl)-1-(((((R)-4-(2-cyano-4-(3,3-difluoropyrrolidin-1-yl)-4-methylpent-2-enoyl)morpholin-3-yl)methoxy)carbonyl)amino)ethyl)boronic acid;

((R)-2-(benzofuran-3-yl)-1-(((((R)-1-(2-cyano-4-(4,4-difluoropiperidin-1-yl)-4-methylpent-2-enoyl)piperidin-2-yl)methoxy)carbonyl)amino)ethyl)boronic acid;

((R)-1-(((((1S,2R,5R)-3-(2-cyano-4-methyl-4-morpholinopent-2-enoyl)-3-azabicyclo[3.1.0]hexan-2-yl)methoxy)carbonyl)amino)-2-phenylethyl)boronic acid;

((R)-2-(benzofuran-3-yl)- 1-(((((S)-1-(2-cyano-4-(3,3-difluoropyrrolidin-1-yl)-4-methylpent-2-enoyl)azepan-2-yl)methoxy)carbonyl)amino)ethyl)boronic acid;

((R)-1-(((((R)-4-(2-cyano-4,4-dimethylpent-2-enoyl)morpholin-3-yl)methoxy)carbonyl)amino)-2-phenylethyl)boronic acid;

((R)-1-(((((R)-1-(2-cyano-4,4-dimethylpent-2-enoyl)piperidin-2-yl)methoxy)carbonyl)amino)-2-(4-methoxyphenyl)ethyl)boronic acid;

((R)-2-(benzofuran-3-yl)-1-(((((R)-1-(2-cyano-4-methyl-4-morpholinopent-2-enoyl)-2-methylpyrrolidin-2-yl)methoxy)carbonyl)amino)ethyl)boronic acid;

((R)-2-(benzofuran-3-yl)-1-(((((R)-1-(2-cyano-4-(3,3-difluoropyrrolidin-1-yl)-4-methylpent-2-enoyl)azepan-2-yl)methoxy)carbonyl)amino)ethyl)boronic acid;

((R)-1-(((((R)-4-(2-cyano-4,4-dimethylpent-2-enoyl)morpholin-3-yl)methoxy)carbonyl)amino)-2-(p-tolyl)ethyl)boronic acid;

((R)-1-(((((1S,2R,5R)-3-(2-cyano-4-(3,3-difluoropyrrolidin-1-yl)-4-methylpent-2-enoyl)-3-azabicyclo [3.1.0]hexan-2-yl)methoxy)carbonyl)amino)-2-phenylethyl)boronic acid;

((R)- 1-(((((1S,2R,5R)-3-(2-cyano-4-methyl-4-morpholinopent-2-enoyl)-3-azabicyclo [3.1.0]hexan-2-yl)methoxy)carbonyl)amino)-2-(p-tolyl)ethyl)boronic acid;

((R)-1-(((((1 S,2R,5R)-3-(2-cyano-4,4-dimethylpent-2-enoyl)-3-azabicyclo [3.1.0]hexan-2-yl)methoxy)carbonyl)amino)-2-(p-tolyl)ethyl)boronic acid;

((R)-1-(((((R)-1-(2-cyano-4,4-dimethylpent-2-enoyl)piperidin-2-yl)methoxy)carbonyl)amino)-2-(3-methoxyphenyl)ethyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-2-(4-methoxyphenyl)ethyl)boronic acid;

((R)-2-(4-chlorophenyl)- 1-(((((R)-1-(2-cyano-4-(3,3-difluoropyrrolidin-1-yl)-4-methylpent-2-enoyl)piperidin-2-yl)methoxy)carbonyl)amino)ethyl)boronic acid;

((R)-1-(((((R)-1-(2-cyano-4-((2,2-difluoroethyl)(methyl)amino)-4-methylpent-2-enoyl)piperidin-2-yl)methoxy)carbonyl)amino)-2-phenylethyl)boronic acid;

((R)- 1-(((((S)-1-(2-cyano-4-(3,3-difluoropyrrolidin-1-yl)-4-methylpent-2-enoyl)azepan-2-yl)methoxy)carbonyl)amino)-2-(p-tolyl)ethyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-2-(4-fluorophenyl)ethyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-2-(4-(trifluoromethyl)phenyl)ethyl)boronic acid;

((R)-1-(((((R)-1-(2-cyano-4-(3,3-difluoropyrrolidin-1-yl)-4-methylpent-2-enoyl)azepan-2-yl)methoxy)carbonyl)amino)-2-(p-tolyl)ethyl)boronic acid;

((R)-1-(((((R)-1-(2-cyano-4-(3,3-difluoropyrrolidin-1-yl)-4-methylpent-2-enoyl)-2-methylpyrrolidin-2-yl)methoxy)carbonyl)amino)-2-phenylethyl)boronic acid;

((R)-1-(((((R)-4-(2-cyano-4-(3,3-difluoropyrrolidin-1-yl)-4-methylpent-2-enoyl)morpholin-3-yl)methoxy)carbonyl)amino)-2-(p-tolyl)ethyl)boronic acid;

((R)-2-(benzofuran-3-yl)- 1-(((((1S ,2R,5R)-3-((E)-4-(dimethylamino)but-2-enoyl)-3-azabicyclo [3.1.0]hexan-2-yl)methoxy)carbonyl)amino)ethyl)boronic acid;

((R)-2-(benzofuran-3-yl)- 1-(((((1S,2R,5R)-3-(but-2-ynoyl)-3-azabicyclo [3.1.0]hexan-2-yl)methoxy)carbonyl)amino)ethyl)boronic acid;

((R)-1-(((((2R,4R)-1-acryloyl-4-fluoropyrrolidin-2-yl)methoxy)carbonyl)amino)-2-phenylethyl)boronic acid;

((R)-1-(((((2R,4R)- 1-((E)-2-cyano-4,4-dimethylpent-2-enoyl)-4-fluoropyrrolidin-2-yl)methoxy)carbonyl)amino)-2-phenylethyl)boronic acid;

((R)-1-(((((R)-1-acryloyl-4,4-difluoropyrrolidin-2-yl)methoxy)carbonyl)amino)-2-(benzofuran-3-yl)ethyl)boronic acid;

((R)-1-(((((1s,2R,5R)-3-(2-cyano-3-(4-methyltetrahydro-2H-pyran-4-yl)acryloyl)-3-azabicyclo [3.1.0]hexan-2-yl)methoxy)carbonyl)amino)-2-(p-tolyl)ethyl)boronic acid;

((R)-1-(((((R)-4-acryloylmorpholin-3-yl)methoxy)carbonyl)amino)-2-(benzofuran-3-yl)ethyl)boronic acid;

((R)-1-(((((R)-4-(2-cyano-4-(3,3-difluoropyrrolidin-1-yl)-4-methylpent-2-enoyl)morpholin-3-yl)methoxy)carbonyl)amino)-2-phenylethyl)boronic acid;

((R)-1-(((((1 S,2R,5R)-3-acryloyl-3-azabicyclo [3.1.0]hexan-2-yl)methoxy)carbonyl)amino)-2-(p-tolyl)ethyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-2-(3-methoxyphenyl)ethyl)boronic acid;

((R)-1-(((((R)-1-(2-cyano-4-methyl-4-(methyl(2,2,2-trifluoroethyl)amino)pent-2-enoyl)piperidin-2-yl)methoxy)carbonyl)amino)-2-phenylethyl)boronic acid;

((R)-1-(((((R)-4-(2-cyano-4-(3,3-difluoropyrrolidin-1-yl)-4-methylpent-2-enoyl)morpholin-3-yl)methoxy)carbonyl)amino)-3-phenylpropyl)boronic acid;

((R)-1-(((((1 S,2R,5R)-3-acryloyl-3-azabicyclo [3.1.0]hexan-2-yl)methoxy)carbonyl)amino)-2-phenylethyl)boronic acid;

((R)-1-(((((2R,4S)-1-acryloyl-4-fluoropyrrolidin-2-yl)methoxy)carbonyl)amino)-2-phenylethyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-3-phenylpropyl)boronic acid;

((R)-1-(((((2R,4S)-1-((E)-2-cyano-4,4-dimethylpent-2-enoyl)-4-fluoropyrrolidin-2-yl)methoxy)carbonyl)amino)-2-phenylethyl)boronic acid;

((R)-1-(((((R)- 1-((Z)-2-cyano-4-(3,3-difluoropyrrolidin-1-yl)-4-methylpent-2-enoyl)piperidin-2-yl)methoxy)carbonyl)amino)-2-phenylethyl)boronic acid;

((R)-1-(((((1S,2R,5R)-3-(2-cyano-4-(3,3-difluoropyrrolidin-1-yl)-4-methylpent-2-enoyl)-3-azabicyclo [3.1.0]hexan-2-yl)methoxy)carbonyl)amino)-3-phenylpropyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-3-methylbutyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-2-(2-cyanophenyl)ethyl)boronic acid;

((R)- 1-(((((1S,2R,5R)-3-(2-cyano-4-(3,3-difluoropyrrolidin-1-yl)-4-methylpent-2-enoyl)-3-azabicyclo [3.1.0]hexan-2-yl)methoxy)carbonyl)amino)-2-(4-fluorophenyl)ethyl)boronic acid;

((R)-1-(((((1 S,2R,5R)-3-acryloyl-3-azabicyclo [3.1.0]hexan-2-yl)methoxy)carbonyl)amino)-2-(4-fluorophenyl)ethyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-2-(2-(trifluoromethyl)phenyl)ethyl)boronic acid;

((R)-1-(((((S)-4-acryloyl-1,1-dioxidothiomorpholin-3-yl)methoxy)carbonyl)amino)-2-(benzofuran-3-yl)ethyl)boronic acid;

((R)-1-(((((R)-1-acryloyl-4,4-difluoropiperidin-2-yl)methoxy)carbonyl)amino)-2-(benzofuran-3-yl)ethyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-2-(2,4-difluorophenyl)ethyl)boronic acid;

((R)-1-(((((1S,2R,5R)-3-(2-cyano-4-methyl-4-morpholinopent-2-enoyl)-3-azabicyclo [3.1.0]hexan-2-yl)methoxy)carbonyl)amino)-2-(4-(trifluoromethyl)phenyl)ethyl)boronic acid;

((R)-1-(((((1 S,2R,5R)-3-acryloyl-3-azabicyclo [3.1.0]hexan-2-yl)methoxy)carbonyl)amino)-2-(4-(trifluoromethyl)phenyl)ethyl)boronic acid;

((R)-1-(((((1S,2R,5R)-3-(2-cyano-4-(3,3-difluoropyrrolidin-1-yl)-4-methylpent-2-enoyl)-3-azabicyclo [3.1.0]hexan-2-yl)methoxy)carbonyl)amino)-2-(p-tolyl)ethyl)boronic acid;

((R)-2-(benzofuran-3-yl)- 1-(((((R)-1-(2-cyano-4-(3,3-difluoropyrrolidin-1-yl)-4-methylpent-2-enoyl)-2-methylpyrrolidin-2-yl)methoxy)carbonyl)amino)ethyl)boronic acid;

((R)-1-(((((R)-1-(2-cyano-4-(3,3-difluoropyrrolidin-1-yl)-4-methylpent-2-enoyl)-2-methylpyrrolidin-2-yl)methoxy)carbonyl)amino)-3,3-dimethylbutyl)boronic acid;

((R)- 1-(((((1S,2R,5R)-3-(2-cyano-3-(4-methyltetrahydro-2H-pyran-4-yl)acryloyl)-3-azabicyclo [3.1.0]hexan-2-yl)methoxy)carbonyl)amino)-2-(4-fluorophenyl)ethyl)boronic acid;

((R)-1-(((((R)-1-(2-cyano-4-(3,3-difluoropyrrolidin-1-yl)-4-methylpent-2-enoyl)-2-methylpyrrolidin-2-yl)methoxy)carbonyl)amino)-2-(4-fluorophenyl)ethyl)boronic acid;

((R)-1-(((((R)- 1-(2-fluoroacryloyl)-2-methylpyrrolidin-2-yl)methoxy)carbonyl)amino)-2-(4-fluorophenyl)ethyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-2-(4-cyanophenyl)ethyl)boronic acid;

((R)- 1-(((((1S,2R,5R)-3-(2-cyano-4-methyl-4-morpholinopent-2-enoyl)-3-azabicyclo [3.1.0]hexan-2-yl)methoxy)carbonyl)amino)-2-(4-fluorophenyl)ethyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-2-(4-(methylsulfonyl)phenyl)ethyl)boronic acid;

((R)-1-(((((R)-1-(2-cyano-4-(4-(methoxycarbonyl)piperazin- 1-yl)-4-methylpent-2-enoyl)piperidin-2-yl)methoxy)carbonyl)amino)-2-phenylethyl)boronic acid;

((R)-1-(((((R)-1-(2-cyano-4-methyl-4-(4-(oxetan-3-yl)piperazin-1-yl)pent-2-enoyl)piperidin-2-yl)methoxy)carbonyl)amino)-2-phenylethyl)boronic acid;

((R)-1-(((((R)-1-(2-cyano-4-methyl-4-(4-(oxetan-3-yl)piperazin-1-yl)pent-2-enoyl)piperidin-2-yl)methoxy)carbonyl)amino)-2-(4-fluorophenyl)ethyl)boronic acid;

((R)-1-(((((R)- 1-((E)-2-cyano-4,4-dimethylpent-2-enoyl)piperazin-2-yl)methoxy)carbonyl)amino)-2-phenylethyl)boronic acid;

((R)- 1-(((((R)-1-(2-cyano-4-(3,3-difluoropyrrolidin-1-yl)-4-methylpent-2-enoyl)-2-methylpiperidin-2-yl)methoxy)carbonyl)amino)-2-phenylethyl)boronic acid;

((R)-1-(((((R)-1-(2-cyano-4-methyl-4-morpholinopent-2-enoyl)-2-methylpiperidin-2-yl)methoxy)carbonyl)amino)-2-phenylethyl)boronic acid;

((R)-1-(((((2R,4S)-1-(2-cyano-4-methyl-4-morpholinopent-2-enoyl)-4-fluoropyrrolidin-2-yl)methoxy)carbonyl)amino)-2-phenylethyl)boronic acid;

((R)-1-(((((2R,4S)-1-(2-cyano-4-(3,3-difluoropyrrolidin-1-yl)-4-methylpent-2-enoyl)-4-fluoropyrrolidin-2-yl)methoxy)carbonyl)amino)-2-phenylethyl)boronic acid;

((R)-1-(((((2R,4S)-1-acryloyl-4-fluoropyrrolidin-2-yl)methoxy)carbonyl)amino)-2-(benzofuran-3-yl)ethyl)boronic acid;

((R)-2-(benzofuran-3-yl)-1-(((((2R,4S)-1-(2-cyano-4-(3,3-difluoropyrrolidin-1-yl)-4-methylpent-2-enoyl)-4-fluoropyrrolidin-2-yl)methoxy)carbonyl)amino)ethyl)boronic acid;

((R)-1-(((((2R,4S)-1-(2-cyano-4-(3,3-difluoropyrrolidin-1-yl)-4-methylpent-2-enoyl)-4-fluoropyrrolidin-2-yl)methoxy)carbonyl)amino)-2-(4-fluorophenyl)ethyl)boronic acid;

((R)-2-(benzofuran-3-yl)-1-(((((2R,4S)-1-(2-cyano-4-methyl-4-morpholinopent-2-enoyl)-4-fluoropyrrolidin-2-yl)methoxy)carbonyl)amino)ethyl)boronic acid;

((R)-1-(((((2R,4S)-1-(2-cyano-4-methyl-4-morpholinopent-2-enoyl)-4-fluoropyrrolidin-2-yl)methoxy)carbonyl)amino)-2-(4-fluorophenyl)ethyl)boronic acid;

((R)-1-(((((2R,4S)-1-acryloyl-4-fluoropyrrolidin-2-yl)methoxy)carbonyl)amino)-2-(4-fluorophenyl)ethyl)boronic acid;

((R)-1-(((((R)-1-(2-cyano-4-((R)-3-fluoropyrrolidin-1-yl)-4-methylpent-2-enoyl)-2-methylpyrrolidin-2-yl)methoxy)carbonyl)amino)-2-phenylethyl)boronic acid;

((R)-1-(((((R)-1-(2-cyano-4-((S)-3-fluoropyrrolidin-1-yl)-4-methylpent-2-enoyl)-2-methylpyrrolidin-2-yl)methoxy)carbonyl)amino)-2-phenylethyl)boronic acid;

((R)-1-(((((R)-1-(2-cyano-4-((3S,4R)-3,4-difluoropyrrolidin-1-yl)-4-methylpent-2-enoyl)-2-methylpyrrolidin-2-yl)methoxy)carbonyl)amino)-2-phenylethyl)boronic acid;

((R)-1-(((((R)-1-(2-cyano-4-((R)-3-fluoropyrrolidin-1-yl)-4-methylpent-2-enoyl)-2-methylpyrrolidin-2-yl)methoxy)carbonyl)amino)-2-(4-fluorophenyl)ethyl)boronic acid;

((R)-1-(((((R)-1-(2-cyano-4-((S)-3-fluoropyrrolidin-1-yl)-4-methylpent-2-enoyl)-2-methylpyrrolidin-2-yl)methoxy)carbonyl)amino)-2-(4-fluorophenyl)ethyl)boronic acid;

((R)-1-(((((R)-1-(2-cyano-4-((3S,4R)-3,4-difluoropyrrolidin-1-yl)-4-methylpent-2-enoyl)-2-methylpyrrolidin-2-yl)methoxy)carbonyl)amino)-2-(4-fluorophenyl)ethyl)boronic acid;

((R)-1-(((((R)-1-(2-cyano-4-((R)-3-fluoropyrrolidin-1-yl)-4-methylpent-2-enoyl)piperidin-2-yl)methoxy)carbonyl)amino)-2-phenylethyl)boronic acid;

((R)-1-(((((R)-1-(2-cyano-4-((S)-3-fluoropyrrolidin-1-yl)-4-methylpent-2-enoyl)piperidin-2-yl)methoxy)carbonyl)amino)-2-phenylethyl)boronic acid;

((R)-1-(((((R)-1-(2-cyano-4-((3S,4R)-3,4-difluoropyrrolidin-1-yl)-4-methylpent-2-enoyl)piperidin-2-yl)methoxy)carbonyl)amino)-2-phenylethyl)boronic acid;

((R)-1-(((((R)-1-(2-cyano-4-((R)-3-fluoropyrrolidin-1-yl)-4-methylpent-2-enoyl)piperidin-2-yl)methoxy)carbonyl)amino)-2-(4-fluorophenyl)ethyl)boronic acid;

((R)-1-(((((R)-1-(2-cyano-4-((S)-3-fluoropyrrolidin-1-yl)-4-methylpent-2-enoyl)piperidin-2-yl)methoxy)carbonyl)amino)-2-(4-fluorophenyl)ethyl)boronic acid;

((R)-1-(((((R)-1-(2-cyano-4-((3S,4R)-3,4-difluoropyrrolidin-1-yl)-4-methylpent-2-enoyl)piperidin-2-yl)methoxy)carbonyl)amino)-2-(4-fluorophenyl)ethyl)boronic acid;

((R)-1-(((((R)-1-(2-cyano-4-methyl-4-morpholinopent-2-enoyl)-2-methylpyrrolidin-2-yl)methoxy)carbonyl)amino)-2-(4-fluorophenyl)ethyl)boronic acid;

((R)-1-(((((R)-1-(2-cyano-4-methyl-4-morpholinopent-2-enoyl)-2-methylpyrrolidin-2-yl)methoxy)carbonyl)amino)-2-phenylethyl)boronic acid;

((R)-1-((((((2R,4S)-1-(2-cyano-4-(3,3-difluoropyrrolidin-1-yl)-4-methylpent-2-enoyl)-4-fluoro-2-methylpyrrolidin-2-yl)methoxy)carbonyl)amino)-2-(4-fluorophenyl)ethyl)boronic acid;

((R)-1-((((((2R,4S)-1-(2-cyano-4-((S)-3-fluoropyrrolidin-1-yl)-4-methylpent-2-enoyl)-4-fluoro-2-methylpyrrolidin-2-yl)methoxy)carbonyl)amino)-2-(4-fluorophenyl)ethyl)boronic acid;

((R)-1-((((((2R,4S)-1-(2-cyano-4-((R)-3-fluoropyrrolidin-1-yl)-4-methylpent-2-enoyl)-4-fluoro-2-methylpyrrolidin-2-yl)methoxy)carbonyl)amino)-2-(4-fluorophenyl)ethyl)boronic acid;

((R)-1-((((((2R,4S)-1-acryloyl-4-fluoro-2-methylpyrrolidin-2-yl)methoxy)carbonyl)amino)-2-(4-fluorophenyl)ethyl)boronic acid;

((R)-1-((((((2R,4S)-1-(2-cyano-4-(3,3-difluoropyrrolidin-1-yl)-4-methylpent-2-enoyl)-4-fluoro-2-methylpyrrolidin-2-yl)methoxy)carbonyl)amino)-2-phenylethyl)boronic acid;

((R)-1-((((((2R,4S)-1-(2-cyano-4-((S)-3-fluoropyrrolidin-1-yl)-4-methylpent-2-enoyl)-4-fluoro-2-methylpyrrolidin-2-yl)methoxy)carbonyl)amino)-2-phenylethyl)boronic acid;

((R)-1-((((((2R,4S)-1-(2-cyano-4-((R)-3-fluoropyrrolidin-1-yl)-4-methylpent-2-enoyl)-4-fluoro-2-methylpyrrolidin-2-yl)methoxy)carbonyl)amino)-2-phenylethyl)boronic acid;

((R)-1-((((((2R,4S)-1-acryloyl-4-fluoro-2-methylpyrrolidin-2-yl)methoxy)carbonyl)amino)-2-phenylethyl)boronic acid;

((R)-1-(((((R)-1-(2-cyano-4-(3,3-difluoropyrrolidin-1-yl)-4-methylpent-2-enoyl)-2-methylpiperidin-2-yl)methoxy)carbonyl)amino)-2-(4-fluorophenyl)ethyl)boronic acid; and ((R)-1-(((((R)-1-(2-cyano-4-methyl-4-morpholinopent-2-enoyl)-2-methylpiperidin-2-yl)methoxy)carbonyl)amino)-2-(4-fluorophenyl)ethyl)boronic acid;

an individual E or Z isomer thereof; and/or a pharmaceutically acceptable salt of any of the foregoing compounds.

22. A pharmaceutical composition comprising at least one compound of claim 1 or a pharmaceutical acceptable salt thereof, and a pharmaceutically acceptable excipient.

23. A method of inhibiting Large Multifunctional Protease 2 (LMP2) and/or Large Multifunctional Protease 7 (LMP7) in a subject comprising administering to said subject in need of said inhibition a therapeutically effective amount of a compound of claim 1 or a pharmaceutically acceptable salt thereof, and thereby inhibiting Large Multifunctional Protease 2 (LMP2) and/or Large Multifunctional Protease 7 (LMP7).

24. A method of treating a disease in a patient in need of such treatment, comprising administering to the patient a therapeutically effective amount of a compound of claim 1 or a pharmaceutically acceptable salt thereof, wherein the disease is chosen from lupus, rheumatoid arthritis, scleroderma, ankylosing spondylitis, Duchene muscular dystrophy (DMD), Becker muscular dystrophy (BMD), idiopathic inflammatory myopathies (IIMs), polymyositis, sporadic inclusion body myositis, dermatomyositis, immune-mediated necrotizing myopathies (IMNM), psoriasis, multiple sclerosis, inflammatory bowel disease, Behcet's disease, ulcerative colitis, Crohn's disease, Sjogren's Syndrome, bronchitis, conjunctivitis, pancreatitis, cholecstitis, bronchiectasis, aortic valve stenosis, restenosis, fibrosis, infection, ischemia, cardiovascular disease, hepatitis, cirrhosis, steatohepatitis, chronic liver inflammation, Alzheimer's Disease (AD), amyotrophic lateral sclerosis (ALS), Huntington's disease, body myositis, myofibrilar myopathy, GVHD, and multiple myeloma.

25. A compound or a pharmaceutically acceptable salt thereof, wherein the compound is chosen from:

((R)-1-(3-(((R)-1-(2-cyano-4-methylpent-2-enoyl)pyrrolidin-2-yl)methoxy)propanamido)-2-phenylethyl)boronic acid;

((1R)-1-(3-(1-(2-cyano-4-methylpent-2-enoyl)pyrrolidin-2-yl)propanamido)-2-phenylethyl)boronic acid;

((1R)-1-(3-(1-(2-cyano-4-methylpent-2-enoyl)piperidin-2-yl)propanamido)-2-phenylethyl)boronic acid;

((R)-1-(((((R)-1-(2-cyano-4-methylpent-2-enoyl)piperidin-2-yl)methoxy)carbonyl)amino)-2-phenylethyl)boronic acid;

((R)-1-(((((R)-1-(2-cyano-4-methylpent-2-enoyl)pyrrolidin-2-yl)methoxy)carbonyl)amino)-2-phenylethyl)boronic acid;

((R)-1-(((((R)-1-acryloylpiperidin-2-yl)methoxy)carbonyl)amino)-2-phenylethyl)boronic acid;

((R)-1-(((((S)-1-((E)-2-cyano-4,4-dimethylpent-2-enoyl)piperidin-2-yl)methoxy)carbonyl)amino)-2-phenylethyl)boronic acid;

((R)-1-(((((R)-1-(2-cyano-4,4-dimethylpent-2-enoyl)pyrrolidin-2-yl)methoxy)carbonyl)amino)-2-phenylethyl)boronic acid;

((R)-1-(((((S)-1-acryloylpiperidin-2-yl)methoxy)carbonyl)amino)-2-phenylethyl)boronic acid;

((R)-1-(((((S)-1-(2-cyano-4-methylpent-2-enoyl)pyrrolidin-2-yl)methoxy)carbonyl)amino)-2-phenylethyl)boronic acid;

((R)-1-(((((S)-1-(2-cyano-4-methylpent-2-enoyl)piperidin-2-yl)methoxy)carbonyl)amino)-2-phenylethyl)boronic acid;

((R)-1-(((((R)-1-acryloylpyrrolidin-2-yl)methoxy)carbonyl) amino)-2-phenylethyl)boronic acid;

((R)-1-(((((R)-1-(2-cyano-4,4-dimethylpent-2-enoyl)piperidin-2-yl)methoxy)carbonyl)amino)-2-phenylethyl)boronic acid;

((R)-2-(benzofuran-3-yl)-1-(((((R)-1-(2-cyano-4-methylpent-2-enoyl)pyrrolidin-2-yl)methoxy)carbonyl)amino)ethyl)boronic acid;

((R)-1-(((((R)-1-(2-cyano-4-methyl-4-(4-(oxetan-3-yl)piperazin-1-yl)pent-2-enoyl)pyrrolidin-2-yl)methoxy)carbonyl)amino)-2-phenylethyl)boronic acid;

((R)-1-(((((R)-1-(2-cyano-4,4-dimethylpent-2-enoyl)pyrrolidin-2-yl)methoxy)carbonyl)amino)-2-(p-tolyl)ethyl)boronic acid;

((R)-1-(((((R)-1-acryloylpyrrolidin-2-yl)methoxy)carbonyl)amino)-2-(p-tolyl)ethyl)boronic acid;

((R)-1-(((((R)-1-(2-cyano-4-methyl-4-(piperidin-1-yl)pent-2-enoyl)pyrrolidin-2-yl)methoxy)carbonyl)amino)-2-phenylethyl)boronic acid;

((R)-1-(((((R)-1-(2-cyano-4-(4,4-difluoropiperidin-1-yl)-4-methylpent-2-enoyl)pyrrolidin-2-yl)methoxy)carbonyl)amino)-2-phenylethyl)boronic acid ((R)-1-(((((1R,2S,5S)-3-(2-cyano-4,4-dimethylpent-2-enoyl)-3-azabicyclo [3 0.1.0]hexan-2-yl)methoxy)carbonyl)amino)-2-phenylethyl)boronic acid;

((R)-1-(((((R)-1-(2-cyano-4-methyl-4-morpholinopent-2-enoyl)pyrrolidin-2-yl)methoxy)carbonyl)amino)-2-phenylethyl)boronic acid;

((R)-1-(((((R)-1-(2-cyano-4,4-dimethylpent-2-enoyl)piperidin-2-yl)methoxy)carbonyl)amino)-2-(p-tolyl)ethyl)boronic acid;

((R)-2-(benzofuran-3-yl)-1-(((((R)-1-(2-cyano-4,4-dimethylpent-2-enoyl)piperidin-2-yl)methoxy)carbonyl)amino)ethyl)boronic acid;

((R)- 1-(((((1S,2R,5R)-3-(2-cyano-4,4-dimethylpent-2-enoyl)-3-azabicyclo [3.1.0]hexan-2-yl)methoxy)carbonyl)amino)-2-phenylethyl)boronic acid;

((R)-1-(((((R)-1-(2-cyano-4-methyl-4-(pyrrolidin-1-yl)pent-2-enoyl)piperidin-2-yl)methoxy)carbonyl)amino)-2-phenylethyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-2-phenylethyl)boronic acid;

((R)-1-(((((R)-1-(2-cyano-4-methyl-4-morpholinopent-2-enoyl)piperidin-2-yl)methoxy)carbonyl)amino)-2-phenylethyl)boronic acid;

((R)-1-(((((R)-1-(2-cyano-4-methyl-4-(piperidin-1-yl)pent-2-enoyl)piperidin-2-yl)methoxy)carbonyl)amino)-2-phenylethyl)boronic acid;

((R)-1-(((((R)-1-(2-cyano-4-(4,4-difluoropiperidin-1-yl)-4-methylpent-2-enoyl)piperidin-2-yl)methoxy)carbonyl)amino)-2-phenylethyl)boronic acid;

((R)-1-(((((R)-1-(2-cyano-4,4-dimethylpent-2-enoyl)azepan-2-yl)methoxy)carbonyl)amino)-2-(p-tolyl)ethyl)boronic acid;

((R)-1-(((((S)-1-(2-cyano-4,4-dimethylpent-2-enoyl)azepan-2-yl)methoxy)carbonyl)amino)-2-(p-tolyl)ethyl)boronic acid;

((R)-1-(((((R)-1-(2-cyano-4-methyl-4-(pyrrolidin-1-yl)pent-2-enoyl)pyrrolidin-2-yl)methoxy)carbonyl)amino)-2-phenylethyl)boronic acid;

((R)-1-(((((R)-1-(2-cyano-4-(3,3-difluoropyrrolidin-1-yl)-4-methylpent-2-enoyl)pyrrolidin-2-yl)methoxy)carbonyl)amino)-2-phenylethyl)boronic acid;

((R)-1-(((((R)-1-acryloylpyrrolidin-2-yl)methoxy)carbonyl)amino)-2-(benzofuran-3-yl)ethyl)boronic acid;

((R)- 1-(((((1R,2R,5S)-3-(2-cyano-4,4-dimethylpent-2-enoyl)-3-azabicyclo [3.1.0]hexan-2-yl)methoxy)carbonyl)amino)-2-phenylethyl)boronic acid;

((R)-1-(((((1 S,2S,5R)-3-(2-cyano-4,4-dimethylpent-2-enoyl)-3-azabicyclo [3 0.1.0]hexan-2-yl)methoxy)carbonyl)amino)-2-phenylethyl)boronic acid;

((R)-2-(benzofuran-3-yl)- 1-(((((R)-1-(2-cyano-4,4-dimethylpent-2-enoyl)pyrrolidin-2-yl)methoxy)carbonyl)amino)ethyl)boronic acid;

((R)-2-(benzofuran-3-yl)- 1-(((((R)-1-(2-cyano-4-methyl-4-morpholinopent-2-enoyl)pyrrolidin-2-yl)methoxy)carbonyl)amino)ethyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-2-(p-tolyl)ethyl)boronic acid;

((R)-2-(benzofuran-3-yl)- 1-(((((R)-1-(2-cyano-4-(3,3-difluoropyrrolidin-1-yl)-4-methylpent-2-enoyl)pyrrolidin-2-yl)methoxy)carbonyl)amino)ethyl)boronic acid;

((R)-2-(benzofuran-3-yl)- 1-(((((R)-4-(2-cyano-4,4-dimethylpent-2-enoyl)morpholin-3-yl)methoxy)carbonyl)amino)ethyl)boronic acid;

((R)-2-(benzofuran-3-yl)- 1-(((((R)-1-(2-cyano-4-methyl-4-(4-(oxetan-3-yl)piperazin-1-yl)pent-2-enoyl)pyrrolidin-2-yl)methoxy)carbonyl)amino)ethyl)boronic acid;

((R)-1-(((((R)-1-(2-cyano-4-methyl-4-morpholinopent-2-enoyl)piperidin-2-yl)methoxy)carbonyl)amino)-2-(p-tolyl)ethyl)boronic acid;

((R)-2-(benzofuran-3-yl)- 1-(((((R)-1-(2-cyano-4-methyl-4-morpholinopent-2-enoyl)piperidin-2-yl)methoxy)carbonyl)amino)ethyl)boronic acid;

((R)-2-(benzofuran-3-yl)-1-(((((R)-1-(2-cyano-4-(3,3-difluoropyrrolidin-1-yl)-4-methylpent-2-enoyl)piperidin-2-yl)methoxy)carbonyl)amino)ethyl)boronic acid;

((R)-2-(benzofuran-3-yl)-1-(((((1S,2R,5R)-3-(2-cyano-4,4-dimethylpent-2-enoyl)-3-azabicyclo [3.1.0]hexan-2-yl)methoxy)carbonyl)amino)ethyl)boronic acid;

((R)-2-(benzofuran-3-yl)-1-(((((R)- 1-((E)-4-(dimethylamino)but-2-enoyl)pyrrolidin-2-yl)methoxy)carbonyl)amino)ethyl)boronic acid;

((R)-1-(((((R)-1-(2-cyano-4,4-dimethylpent-2-enoyl)piperidin-2-yl)methoxy)carbonyl)amino)-3-phenylpropyl)boronic acid;

((R)-2-(benzofuran-3-yl)-1-(((((1S,2R,5R)-3-(2-cyano-4-methyl-4-morpholinopent-2-enoyl)-3-azabicyclo [3.1.0]hexan-2-yl)methoxy)carbonyl)amino)ethyl)boronic acid;

((R)- 1-(((((1S,2R,5R)-3-acryloyl-3-azabicyclo [3.1.0] hexan-2-yl)methoxy)carbonyl)amino)-2-(benzofuran-3-yl)ethyl)boronic acid;

((R)-1-(((((R)- 1-(4-(4-acetylpiperazin-1-yl)-2-cyano-4-methylpent-2-enoyl)pyrrolidin-2-yl)methoxy)carbonyl)amino)-2-(benzofuran-3-yl)ethyl)boronic acid;

((R)-2-(benzofuran-3-yl)- 1-(((((1S ,2R,5R)-3-(2-cyano-4-(3,3-difluoropyrrolidin-1-yl)-4-methylpent-2-enoyl)-3-azabicyclo [3.1.0]hexan-2-yl)methoxy)carbonyl)amino)ethyl)boronic acid;

((R)-2-(benzofuran-3-yl)-1-(((((R)-1-(2-cyano-4-methyl-4-(4-methylpiperazin-1-yl)pent-2-enoyl)pyrrolidin-2-yl)methoxy)carbonyl)amino)ethyl)boronic acid;

((R)-2-(benzofuran-3-yl)-1-(((((R)-1-(2-cyano-4-methyl-4-morpholinopent-2-enoyl)-4,4-difluoropyrrolidin-2-yl)methoxy)carbonyl)amino)ethyl)boronic acid;

((R)-2-(benzofuran-3-yl)-1-(((((2R,5S)-1-(2-cyano-4-methyl-4-morpholinopent-2-enoyl)-5-methylpyrrolidin-2-yl)methoxy)carbonyl)amino)ethyl)boronic acid;

((R)-2-(benzofuran-3-yl)-1-(((((R)-4-(2-cyano-4-methyl-4-morpholinopent-2-enoyl)morpholin-3-yl)methoxy)carbonyl)amino)ethyl)boronic acid;

((R)-2-(benzofuran-3-yl)-1-(((((R)-1-(2-cyano-3-(4-methyltetrahydro-2H-pyran-4-yl)acryloyl)piperidin-2-yl)methoxy)carbonyl)amino)ethyl)boronic acid;

((R)-2-(benzofuran-3-yl)- 1-(((((R)-1-(2-cyano-4-methyl-4-(4-(oxetan-3-yl)piperazin-1-yl)pent-2-enoyl)piperidin-2-yl)methoxy)carbonyl)amino)ethyl)boronic acid;

((R)-1-(((((R)- 1-((E)-2-cyano-4,4-dimethylpent-2-enoyl)-4,4-difluoropyrrolidin-2-yl)methoxy)carbonyl)amino)-2-phenylethyl)boronic acid;

((R)-2-(benzofuran-3-yl)-1-(((((R)-1-(2-cyano-4-(3,3-difluoropiperidin-1-yl)-4-methylpent-2-enoyl)piperidin-2-yl)methoxy)carbonyl)amino)ethyl)boronic acid;

((R)-2-(benzofuran-3-yl)-1-(((((R)-1-(2-cyano-4-methyl-4-morpholinopent-2-enoyl)azepan-2-yl)methoxy)carbonyl)amino)ethyl)boronic acid;

((R)-2-(benzofuran-3-yl)-1-(((((S)-1-(2-cyano-4-methyl-4-morpholinopent-2-enoyl)azepan-2-yl)methoxy)carbonyl)amino)ethyl)boronic acid;

((R)-2-(benzofuran-3-yl)-1-(((((R)-4-(2-cyano-4-(3,3-difluoropyrrolidin-1-yl)-4-methylpent-2-enoyl)morpholin-3-yl)methoxy)carbonyl)amino)ethyl)boronic acid;

((R)-2-(benzofuran-3-yl)-1-(((((R)-1-(2-cyano-4-(4,4-difluoropiperidin-1-yl)-4-methylpent-2-enoyl)piperidin-2-yl)methoxy)carbonyl)amino)ethyl)boronic acid;

((R)-1-(((((1S,2R,5R)-3-(2-cyano-4-methyl-4-morpholinopent-2-enoyl)-3-azabicyclo[3.1.0]hexan-2-yl)methoxy)carbonyl)amino)-2-phenylethyl)boronic acid;

((R)-2-(benzofuran-3-yl)- 1-(((((S)-1-(2-cyano-4-(3,3-difluoropyrrolidin-1-yl)-4-methylpent-2-enoyl)azepan-2-yl)methoxy)carbonyl)amino)ethyl)boronic acid;

((R)-1-(((((R)-4-(2-cyano-4,4-dimethylpent-2-enoyl)morpholin-3-yl)methoxy)carbonyl)amino)-2-phenylethyl)boronic acid;

((R)-1-(((((R)-1-(2-cyano-4,4-dimethylpent-2-enoyl)piperidin-2-yl)methoxy)carbonyl)amino)-2-(4-methoxyphenyl)ethyl)boronic acid;

((R)-2-(benzofuran-3-yl)-1-(((((R)-1-(2-cyano-4-methyl-4-morpholinopent-2-enoyl)-2-methylpyrrolidin-2-yl)methoxy)carbonyl)amino)ethyl)boronic acid;

((R)-2-(benzofuran-3-yl)-1-(((((R)-1-(2-cyano-4-(3,3-difluoropyrrolidin-1-yl)-4-methylpent-2-enoyl)azepan-2-yl)methoxy)carbonyl)amino)ethyl)boronic acid;

((R)-1-(((((R)-4-(2-cyano-4,4-dimethylpent-2-enoyl)morpholin-3-yl)methoxy)carbonyl)amino)-2-(p-tolyl)ethyl)boronic acid;

((R)-1-(((((1S,2R,5R)-3-(2-cyano-4-(3,3-difluoropyrrolidin-1-yl)-4-methylpent-2-enoyl)-3-azabicyclo [3.1.0]hexan-2-yl)methoxy)carbonyl)amino)-2-phenylethyl)boronic acid;

((R)- 1-(((((1S,2R,5R)-3-(2-cyano-4-methyl-4-morpholinopent-2-enoyl)-3-azabicyclo [3.1.0]hexan-2-yl)methoxy)carbonyl)amino)-2-(p-tolyl)ethyl)boronic acid;

((R)-1-(((((1 S,2R,5R)-3-(2-cyano-4,4-dimethylpent-2-enoyl)-3-azabicyclo [3.1.0]hexan-2-yl)methoxy)carbonyl)amino)-2-(p-tolyl)ethyl)boronic acid;

((R)-1-(((((R)-1-(2-cyano-4,4-dimethylpent-2-enoyl)piperidin-2-yl)methoxy)carbonyl)amino)-2-(3-methoxyphenyl)ethyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-2-(4-methoxyphenyl)ethyl)boronic acid;

((R)-2-(4-chlorophenyl)- 1-(((((R)-1-(2-cyano-4-(3,3-difluoropyrrolidin-1-yl)-4-methylpent-2-enoyl)piperidin-2-yl)methoxy)carbonyl)amino)ethyl)boronic acid;

((R)-1-(((((R)-1-(2-cyano-4-((2,2-difluoroethyl)(methyl)amino)-4-methylpent-2-enoyl)piperidin-2-yl)methoxy)carbonyl)amino)-2-phenylethyl)boronic acid;

((R)-1-(((((S)-1-(2-cyano-4-(3,3-difluoropyrrolidin-1-yl)-4-methylpent-2-enoyl)azepan-2-yl)methoxy)carbonyl)amino)-2-(p-tolyl)ethyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-2-(4-fluorophenyl)ethyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-2-(4-(trifluoromethyl)phenyl)ethyl)boronic acid;

((R)-1-(((((R)-1-(2-cyano-4-(3,3-difluoropyrrolidin-1-yl)-4-methylpent-2-enoyl)azepan-2-yl)methoxy)carbonyl)amino)-2-(p-tolyl)ethyl)boronic acid;

((R)-1-(((((R)-1-(2-cyano-4-(3,3-difluoropyrrolidin-1-yl)-4-methylpent-2-enoyl)-2-methylpyrrolidin-2-yl)methoxy)carbonyl)amino)-2-phenylethyl)boronic acid;

((R)-1-(((((R)-4-(2-cyano-4-(3,3-difluoropyrrolidin-1-yl)-4-methylpent-2-enoyl)morpholin-3-yl)methoxy)carbonyl)amino)-2-(p-tolyl)ethyl)boronic acid;

((R)-2-(benzofuran-3-yl)- 1-(((((1S,2R,5R)-3-((E)-4-(dimethylamino)but-2-enoyl)-3-azabicyclo [3.1.0]hexan-2-yl)methoxy)carbonyl)amino)ethyl)boronic acid;

((R)-2-(benzofuran-3-yl)- 1-(((((1S,2R,5R)-3-(but-2-ynoyl)-3-azabicyclo [3.1.0]hexan-2-yl)methoxy)carbonyl)amino)ethyl)boronic acid;

((R)-1-(((((2R,4R)-1-acryloyl-4-fluoropyrrolidin-2-yl)methoxy)carbonyl)amino)-2-phenylethyl)boronic acid;

((R)-1-(((((2R,4R)- 1-((E)-2-cyano-4,4-dimethylpent-2-enoyl)-4-fluoropyrrolidin-2-yl)methoxy)carbonyl)amino)-2-phenylethyl)boronic acid;

((R)-1-(((((R)-1-acryloyl-4,4-difluoropyrrolidin-2-yl)methoxy)carbonyl)amino)-2-(benzofuran-3-yl)ethyl)boronic acid;

((R)-1-(((((1S,2R,5R)-3-(2-cyano-3-(4-methyltetrahydro-2H-pyran-4-yl)acryloyl)-3-azabicyclo [3.1.0]hexan-2-yl)methoxy)carbonyl)amino)-2-(p-tolyl)ethyl)boronic acid;

((R)-1-(((((R)-4-acryloylmorpholin-3-yl)methoxy)carbonyl)amino)-2-(benzofuran-3-yl)ethyl)boronic acid;

((R)-1-(((((R)-4-(2-cyano-4-(3,3-difluoropyrrolidin-1-yl)-4-methylpent-2-enoyl)morpholin-3-yl)methoxy)carbonyl)amino)-2-phenylethyl)boronic acid;

((R)-1-(((((1 S,2R,5R)-3-acryloyl-3-azabicyclo [3.1.0]hexan-2-yl)methoxy)carbonyl)amino)-2-(p-tolyl)ethyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-2-(3-methoxyphenyl)ethyl)boronic acid;

((R)-1-(((((R)-1-(2-cyano-4-methyl-4-(methyl(2,2,2-trifluoroethyl)amino)pent-2-enoyl)piperidin-2-yl)methoxy)carbonyl)amino)-2-phenylethyl)boronic acid;

((R)-1-(((((R)-4-(2-cyano-4-(3,3-difluoropyrrolidin-1-yl)-4-methylpent-2-enoyl)morpholin-3-yl)methoxy)carbonyl)amino)-3-phenylpropyl)boronic acid;

((R)-1-(((((1 S,2R,5R)-3-acryloyl-3-azabicyclo [3.1.0]hexan-2-yl)methoxy)carbonyl)amino)-2-phenylethyl)boronic acid;

((R)-1-(((((2R,4S)-1-acryloyl-4-fluoropyrrolidin-2-yl)methoxy)carbonyl)amino)-2-phenylethyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-3-phenylpropyl)boronic acid;

((R)-1-(((((2R,4S)-1-((E)-2-cyano-4,4-dimethylpent-2-enoyl)-4-fluoropyrrolidin-2-yl)methoxy)carbonyl)amino)-2-phenylethyl)boronic acid;

((R)-1-(((((R)- 1-((Z)-2-cyano-4-(3,3-difluoropyrrolidin-1-yl)-4-methylpent-2-enoyl)piperidin-2-yl)methoxy)carbonyl)amino)-2-phenylethyl)boronic acid;

((R)-1-(((((1S,2R,5R)-3-(2-cyano-4-(3,3-difluoropyrrolidin-1-yl)-4-methylpent-2-enoyl)-3-azabicyclo [3.1.0]hexan-2-yl)methoxy)carbonyl)amino)-3-phenylpropyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-3-methylbutyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-2-(2-cyanophenyl)ethyl)boronic acid;

((R)-1-(((((1S,2R,5R)-3-(2-cyano-4-(3,3-difluoropyrrolidin-1-yl)-4-methylpent-2-enoyl)-3-azabicyclo [3.1.0] hexan-2-yl)methoxy)carbonyl)amino)-2-(4-fluorophenyl)ethyl)boronic acid;

((R)-1-(((((1 S,2R,5R)-3-acryloyl-3-azabicyclo [3.1.0] hexan-2-yl)methoxy)carbonyl)amino)-2-(4-fluorophenyl)ethyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-2-(2-(trifluoromethyl)phenyl)ethyl)boronic acid;

((R)-1-(((((S)-4-acryloyl-1,1-dioxidothiomorpholin-3-yl)methoxy)carbonyl)amino)-2-(benzofuran-3-yl)ethyl)boronic acid;

((R)-1-(((((R)-1-acryloyl-4,4-difluoropiperidin-2-yl)methoxy)carbonyl)amino)-2-(benzofuran-3-yl)ethyl)boronic acid;

((R)- 1-(((((R)-1-(2-cyano-4-(3,3-difluoropyrrolidin-1-yl)-4-methylpent-2-enoyl)piperidin-2-yl)methoxy)carbonyl)amino)-2-(2,4-difluorophenyl)ethyl)boronic acid;

((R)-1-(((((1S,2R,5R)-3-(2-cyano-4-methyl-4-morpholinopent-2-enoyl)-3-azabicyclo [3.1.0]hexan-2-yl)methoxy)carbonyl)amino)-2-(4-(trifluoromethyl)phenyl)ethyl)boronic acid;

((R)-1-(((((1 S,2R,5R)-3-acryloyl-3-azabicyclo [3.1.0] hexan-2-yl)methoxy)carbonyl)amino)-2-(4-(trifluoromethyl)phenyl)ethyl)boronic acid;

((R)-1-(((((1S,2R,5R)-3-(2-cyano-4-(3,3-difluoropyrrolidin-1-yl)-4-methylpent-2-enoyl)-3-azabicyclo [3.1.0] hexan-2-yl)methoxy)carbonyl)amino)-2-(p-tolyl)ethyl)boronic acid;

((R)-2-(benzofuran-3-yl)- 1-(((((R)-1-(2-cyano-4-(3,3-difluoropyrrolidin-1-yl)-4-methylpent-2-enoyl)-2-methylpyrrolidin-2-yl)methoxy)carbonyl)amino)ethyl)boronic acid;

((R)-1-(((((R)-1-(2-cyano-4-(3,3-difluoropyrrolidin-1-yl)-4-methylpent-2-enoyl)-2-methylpyrrolidin-2-yl)methoxy)carbonyl)amino)-3,3-dimethylbutyl)boronic acid;

((R)- 1-(((((1S ,2R,5R)-3-(2-cyano-3-(4-methyltetrahydro-2H-pyran-4-yl)acryloyl)-3-azabicyclo [3.1.0] hexan-2-yl)methoxy)carbonyl)amino)-2-(4-fluorophenyl)ethyl)boronic acid;

((R)-1-(((((R)-1-(2-cyano-4-(3,3-difluoropyrrolidin-1-yl)-4-methylpent-2-enoyl)-2-methylpyrrolidin-2-yl)methoxy)carbonyl)amino)-2-(4-fluorophenyl)ethyl)boronic acid;

((R)-1-(((((R)- 1-(2-fluoroacryloyl)-2-methylpyrrolidin-2-yl)methoxy)carbonyl)amino)-2-(4-fluorophenyl)ethyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-2-(4-cyanophenyl)ethyl)boronic acid;

((R)- 1-(((((1S,2R,5R)-3-(2-cyano-4-methyl-4-morpholinopent-2-enoyl)-3-azabicyclo [3.1.0]hexan-2-yl)methoxy)carbonyl)amino)-2-(4-fluorophenyl)ethyl)boronic acid;

((R)-1-(((((R)-1-(2-cyano-4-(3,3-difluoropyrrolidin-1-yl)-4-methylpent-2-enoyl)piperidin-2-yl)methoxy)carbonyl)amino)-2-(4-(methylsulfonyl)phenyl)ethyl)boronic acid;

((R)-1-(((((R)-1-(2-cyano-4-(4-(methoxycarbonyl)piperazin-1-yl)-4-methylpent-2-enoyl)piperidin-2-yl)methoxy)carbonyl)amino)-2-phenylethyl)boronic acid;

((R)-1-(((((R)-1-(2-cyano-4-methyl-4-(4-(oxetan-3-yl)piperazin-1-yl)pent-2-enoyl)piperidin-2-yl)methoxy)carbonyl)amino)-2-phenylethyl)boronic acid;

((R)-1-(((((R)-1-(2-cyano-4-methyl-4-(4-(oxetan-3-yl)piperazin-1-yl)pent-2-enoyl)piperidin-2-yl)methoxy)carbonyl)amino)-2-(4-fluorophenyl)ethyl)boronic acid;

((R)-1-(((((R)- 1-((E)-2-cyano-4,4-dimethylpent-2-enoyl)piperazin-2-yl)methoxy)carbonyl)amino)-2-phenylethyl)boronic acid;

((R)- 1-(((((R)-1-(2-cyano-4-(3,3-difluoropyrrolidin-1-yl)-4-methylpent-2-enoyl)-2-methylpiperidin-2-yl)methoxy)carbonyl)amino)-2-phenylethyl)boronic acid;

((R)-1-(((((R)-1-(2-cyano-4-methyl-4-morpholinopent-2-enoyl)-2-methylpiperidin-2-yl)methoxy)carbonyl)amino)-2-phenylethyl)boronic acid;

((R)-1-(((((2R,4S)-1-(2-cyano-4-methyl-4-morpholinopent-2-enoyl)-4-fluoropyrrolidin-2-yl)methoxy)carbonyl)amino)-2-phenylethyl)boronic acid;

((R)-1-(((((2R,4S)-1-(2-cyano-4-(3,3-difluoropyrrolidin-1-yl)-4-methylpent-2-enoyl)-4-fluoropyrrolidin-2-yl)methoxy)carbonyl)amino)-2-phenylethyl)boronic acid;

((R)-1-(((((2R,4S)-1-acryloyl-4-fluoropyrrolidin-2-yl)methoxy)carbonyl)amino)-2-(benzofuran-3-yl)ethyl)boronic acid;

((R)-2-(benzofuran-3-yl)- 1-(((((2R,4S)-1-(2-cyano-4-(3,3-difluoropyrrolidin-1-yl)-4-methylpent-2-enoyl)-4-fluoropyrrolidin-2-yl)methoxy)carbonyl)amino)ethyl)boronic acid;

((R)-1-(((((2R,4S)-1-(2-cyano-4-(3,3-difluoropyrrolidin-1-yl)-4-methylpent-2-enoyl)-4-fluoropyrrolidin-2-yl)methoxy)carbonyl)amino)-2-(4-fluorophenyl)ethyl)boronic acid;

((R)-2-(benzofuran-3-yl)- 1-(((((2R,4S)-1-(2-cyano-4-methyl-4-morpholinopent-2-enoyl)-4-fluoropyrrolidin-2-yl)methoxy)carbonyl)amino)ethyl)boronic acid;

((R)-1-(((((2R,4S)-1-(2-cyano-4-methyl-4-morpholinopent-2-enoyl)-4-fluoropyrrolidin-2-yl)methoxy)carbonyl)amino)-2-(4-fluorophenyl)ethyl)boronic acid;

((R)-1-(((((2R,4S)-1-acryloyl-4-fluoropyrrolidin-2-yl)methoxy)carbonyl)amino)-2-(4-fluorophenyl)ethyl)boronic acid;

((R)-1-(((((R)-1-(2-cyano-4-((R)-3-fluoropyrrolidin-1-yl)-4-methylpent-2-enoyl)-2-methylpyrrolidin-2-yl)methoxy)carbonyl)amino)-2-phenylethyl)boronic acid;

((R)-1-(((((R)-1-(2-cyano-4-((S)-3-fluoropyrrolidin-1-yl)-4-methylpent-2-enoyl)-2-methylpyrrolidin-2-yl)methoxy)carbonyl)amino)-2-phenylethyl)boronic acid;

((R)-1-(((((R)-1-(2-cyano-4-((3S,4R)-3,4-difluoropyrrolidin-1-yl)-4-methylpent-2-enoyl)-2-methylpyrrolidin-2-yl)methoxy)carbonyl)amino)-2-phenylethyl)boronic acid;

((R)-1-(((((R)-1-(2-cyano-4-((R)-3-fluoropyrrolidin-1-yl)-4-methylpent-2-enoyl)-2-methylpyrrolidin-2-yl)methoxy)carbonyl)amino)-2-(4-fluorophenyl)ethyl)boronic acid;

((R)-1-(((((R)-1-(2-cyano-4-((S)-3-fluoropyrrolidin-1-yl)-4-methylpent-2-enoyl)-2-methylpyrrolidin-2-yl)methoxy)carbonyl)amino)-2-(4-fluorophenyl)ethyl)boronic acid;

((R)-1-(((((R)-1-(2-cyano-4-((3S,4R)-3,4-difluoropyrrolidin-1-yl)-4-methylpent-2-enoyl)-2-methylpyrrolidin-2-yl)methoxy)carbonyl)amino)-2-(4-fluorophenyl)ethyl)boronic acid;

((R)-1-(((((R)-1-(2-cyano-4-((R)-3-fluoropyrrolidin-1-yl)-4-methylpent-2-enoyl)piperidin-2-yl)methoxy)carbonyl)amino)-2-phenylethyl)boronic acid;

((R)-1-(((((R)-1-(2-cyano-4-((S)-3-fluoropyrrolidin-1-yl)-4-methylpent-2-enoyl)piperidin-2-yl)methoxy)carbonyl)amino)-2-phenylethyl)boronic acid;

((R)-1-(((((R)-1-(2-cyano-4-((3S,4R)-3,4-difluoropyrrolidin-1-yl)-4-methylpent-2-enoyl)piperidin-2-yl)methoxy)carbonyl)amino)-2-phenylethyl)boronic acid;

((R)-1-(((((R)-1-(2-cyano-4-((R)-3-fluoropyrrolidin-1-yl)-4-methylpent-2-enoyl)piperidin-2-yl)methoxy)carbonyl)amino)-2-(4-fluorophenyl)ethyl)boronic acid;

((R)-1-(((((R)-1-(2-cyano-4-((S)-3-fluoropyrrolidin-1-yl)-4-methylpent-2-enoyl)piperidin-2-yl)methoxy)carbonyl)amino)-2-(4-fluorophenyl)ethyl)boronic acid;

((R)-1-(((((R)-1-(2-cyano-4-((3S,4R)-3,4-difluoropyrrolidin-1-yl)-4-methylpent-2-enoyl)piperidin-2-yl)methoxy)carbonyl)amino)-2-(4-fluorophenyl)ethyl)boronic acid;

((R)-1-(((((R)-1-(2-cyano-4-methyl-4-morpholinopent-2-enoyl)-2-methylpyrrolidin-2-yl)methoxy)carbonyl)amino)-2-(4-fluorophenyl)ethyl)boronic acid;

((R)-1-(((((R)-1-(2-cyano-4-methyl-4-morpholinopent-2-enoyl)-2-methylpyrrolidin-2-yl)methoxy)carbonyl)amino)-2-phenylethyl)boronic acid;

((R)-1-((((((2R,4S)-1-(2-cyano-4-(3,3-difluoropyrrolidin-1-yl)-4-methylpent-2-enoyl)-4-fluoro-2-methylpyrrolidin-2-yl)methoxy)carbonyl)amino)-2-(4-fluorophenyl)ethyl)boronic acid;

((R)-1-((((((2R,4S)-1-(2-cyano-4-((S)-3-fluoropyrrolidin-1-yl)-4-methylpent-2-enoyl)-4-fluoro-2-methylpyrrolidin-2-yl)methoxy)carbonyl)amino)-2-(4-fluorophenyl)ethyl)boronic acid;

((R)-1-((((((2R,4S)-1-(2-cyano-4-((R)-3-fluoropyrrolidin-1-yl)-4-methylpent-2-enoyl)-4-fluoro-2-methylpyrrolidin-2-yl)methoxy)carbonyl)amino)-2-(4-fluorophenyl)ethyl)boronic acid;

((R)-1-((((((2R,4S)-1-acryloyl-4-fluoro-2-methylpyrrolidin-2-yl)methoxy)carbonyl)amino)-2-(4-fluorophenyl)ethyl)boronic acid;

((R)-1-((((((2R,4S)-1-(2-cyano-4-(3,3-difluoropyrrolidin-1-yl)-4-methylpent-2-enoyl)-4-fluoro-2-methylpyrrolidin-2-yl)methoxy)carbonyl)amino)-2-phenylethyl)boronic acid;

((R)-1-((((((2R,4S)-1-(2-cyano-4-((S)-3-fluoropyrrolidin-1-yl)-4-methylpent-2-enoyl)-4-fluoro-2-methylpyrrolidin-2-yl)methoxy)carbonyl)amino)-2-phenylethyl)boronic acid;

((R)-1-((((((2R,4S)-1-(2-cyano-4-((R)-3-fluoropyrrolidin-1-yl)-4-methylpent-2-enoyl)-4-fluoro-2-methylpyrrolidin-2-yl)methoxy)carbonyl)amino)-2-phenylethyl)boronic acid;

((R)-1-((((((2R,4S)-1-acryloyl-4-fluoro-2-methylpyrrolidin-2-yl)methoxy)carbonyl)amino)-2-phenylethyl)boronic acid;

((R)-1-(((((R)-1-(2-cyano-4-(3,3-difluoropyrrolidin-1-yl)-4-methylpent-2-enoyl)-2-methylpiperidin-2-yl)methoxy)carbonyl)amino)-2-(4-fluorophenyl)ethyl)boronic acid; and ((R)-1-(((((R)-1-(2-cyano-4-methyl-4-morpholinopent-2-enoyl)-2-methylpiperidin-2-yl)methoxy)carbonyl)amino)-2-(4-fluorophenyl)ethyl)boronic acid;

an individual E or Z isomer thereof; and/or a pharmaceutically acceptable salt of any of the foregoing compounds.

26. A pharmaceutical composition comprising at least one compound of claim 25 or a pharmaceutical acceptable salt thereof, and a pharmaceutically acceptable excipient.

27. A method of inhibiting Large Multifunctional Protease 2 (LMP2) and/or Large Multifunctional Protease 7 (LMP7) in a subject comprising administering to said subject in need of said inhibition a therapeutically effective amount of a compound of claim 25 or a pharmaceutically acceptable salt thereof, and thereby inhibiting Large Multifunctional Protease 2 (LMP2) and/or Large Multifunctional Protease 7 (LMP7).

28. A method of treating a disease in a patient in need of such treatment, comprising administering to the patient a therapeutically effective amount of a compound of claim 25 or a pharmaceutically acceptable salt thereof, wherein the disease is chosen from lupus, rheumatoid arthritis, scleroderma, ankylosing spondylitis, Duchene muscular dystrophy (DMD), Becker muscular dystrophy (BMD), idiopathic inflammatory myopathies (IIMs), polymyositis, sporadic inclusion body myositis, dermatomyositis, immune-mediated necrotizing myopathies (IMNM), psoriasis, multiple sclerosis, inflammatory bowel disease, Behcet's disease, ulcerative colitis, Crohn's disease, Sjogren's Syndrome, bronchitis, conjunctivitis, pancreatitis, cholecstitis, bronchiectasis, aortic valve stenosis, restenosis, fibrosis, infection, ischemia, cardiovascular disease, hepatitis, cirrhosis, steatohepatitis, chronic liver inflammation, Alzheimer's Disease (AD), amyotrophic lateral sclerosis (ALS), Huntington's disease, body myositis, myofibrilar myopathy, GVHD, and multiple myeloma.

\* \* \* \* \*

UNITED STATES PATENT AND TRADEMARK OFFICE
CERTIFICATE OF CORRECTION

PATENT NO. : 11,154,563 B2
APPLICATION NO. : 16/478788
DATED : October 26, 2021
INVENTOR(S) : Lou et al.

Page 1 of 1

It is certified that error appears in the above-identified patent and that said Letters Patent is hereby corrected as shown below:

In the Claims

In Column 253, Line 66, please change "Rab" to --R8b--.
In Column 255, Line 43, please change "claim 14" to --claim 1--.
In Column 256, Line 16, please change "and/or" to --or--.

Signed and Sealed this
Third Day of May, 2022

Katherine Kelly Vidal
*Director of the United States Patent and Trademark Office*